US007638275B2

(12) United States Patent
Lewin et al.

(10) Patent No.: US 7,638,275 B2
(45) Date of Patent: Dec. 29, 2009

(54) GENE EXPRESSION PROFILES THAT IDENTIFY GENETICALLY ELITE CATTLE

(75) Inventors: Harris A. Lewin, Urbana, IL (US); Zonglin Liu, Peoria, IL (US); Sandra Rodriguez-Zas, Savoy, IL (US); Robin E. Everts, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 355 days.

(21) Appl. No.: 10/857,294

(22) Filed: May 27, 2004

(65) Prior Publication Data

US 2005/0137805 A1 Jun. 23, 2005

Related U.S. Application Data

(60) Provisional application No. 60/474,577, filed on May 30, 2003.

(51) Int. Cl.
*C12Q 1/68* (2006.01)
*C07H 21/02* (2006.01)
*C07H 21/04* (2006.01)

(52) U.S. Cl. .......................... 435/6; 435/7.1; 536/23.1; 536/23.5

(58) Field of Classification Search ..................... None
See application file for complete search history.

(56) References Cited

U.S. PATENT DOCUMENTS

| | | | |
|---|---|---|---|
| 5,041,371 A | 8/1991 | Cowan et al. | |
| 5,374,523 A | 12/1994 | Collier et al. | |
| 5,614,364 A | 3/1997 | Tuggle et al. | |
| 5,645,834 A | 7/1997 | Cockrum et al. | |
| 5,767,080 A | 6/1998 | Beck et al. | |
| 5,850,804 A | 12/1998 | Hill et al. | |
| 5,939,264 A | 8/1999 | Rothschild et al. | |
| 5,981,187 A * | 11/1999 | Cook et al. .................. | 435/6 |
| 6,013,857 A | 1/2000 | Deboer et al. | |
| 6,017,563 A | 1/2000 | Knight et al. | |
| 6,183,786 B1 | 2/2001 | Knight et al. | |
| 6,319,525 B1 | 11/2001 | Knight et al. | |
| 6,492,142 B2 | 12/2002 | Renaville et al. | |
| 6,548,740 B1 | 4/2003 | Bremel et al. | |
| 2001/0053849 A1 | 12/2001 | Kreek et al. | |
| 2002/0058085 A1 | 5/2002 | Knight et al. | |
| 2002/0124803 A1 | 9/2002 | Chen et al. | |
| 2002/0169302 A1 | 11/2002 | Havukkala et al. | |

FOREIGN PATENT DOCUMENTS

| WO | WO 01/49879 | 7/2001 |
|---|---|---|
| WO | WO 02/36824 | 5/2002 |

OTHER PUBLICATIONS

Coleman et al. Drug Discovery Today. 2003. 8: 233-235.*
Liu et al. Clinical Immunology. 2004. 112: 225-230.*
Singh et al. Proceedings of the New Zealand Society of Animal Production. 2004. 64: 8-10.*
Ashburner et al. (2000) Gene ontology: tool for the unification of biology. The Gene Ontology Consortium. *Nature Genetics* 25(1):25-9.
Band et al., (2002) A 3800 gene microarray for cattle functional genomics: comparison of gene expression in spleen, placenta, and brain. *Anim Biotechnol.* 13(1):163-72.
Benjamini, Y. and Hochberg, Y. (1995), "Controlling the False Discovery Rate: a practical and powerful approach to multiple testing," *Journal of the Royal Statistical Society.* B, 57, 289 -300.
Brown and Botstein (1999) Exploring the new world of the genome with DNA microarrays. *Nature Genetics* 21, 33-37.
Diehl et al., (2000) Manufacturing DNA microarrays of high spot homogeneity and reduced background signal. *Nucleic Acids Research* 29(7).
Eisen et al. (1998) Cluster analysis and display of genome—wide expression patters. *PNAS (USA)* 95: 14863-14868.
Hegde et al. (2000) A concise guide to cDNA microarray analysis. *Biotechniques* 29(3):548-50.
Huang and Madan (1999) CAP3: A DNA sequence assembly program. *Genome Research* 9(9):868-77.
Rosenwald A, et al. (2002) The use of molecular profiling to predict survival after chemotherapy for diffuse large-B-cell lymphoma. N Engl J Med. 346(25):1937-47.
Rosenwald and Staudt (2002) Clinical translation of gene expression profiling in lymphomas and leukemias. Semin Oncol. 29(3):258-63.
Smith and Green (1999) (*Unpublished*) Repeatmasker, http://ftp.genome.washington.edu/RM/RepeatMasker.html.
Cox et al., (2002) Identification of candidate genes regulating HDL cholesterol using a chromosomal region expression array. Genome Res. 12(11):1693-702.
Yao, J. et al. (2001) Generation of EST and cDNA microarray resources for the study of bovine immunobiology. *Acta Vet. Scand.* 42(3): 391-405.
Wayne et al., (2002) Combining mapping and arraying: An approach to candidate gene identification. Proc Natl Acad Sci U S A. 99(23):14903-6.
Burton et al., "An Immunogenomics Approach to Understanding Periparturient Immunosuppression and Mastitis Susceptibility in Dairy Cows," *Acta vet. scand. (suppl.)*, 98: 71-88 (2003).
Ishiwata et al., "Characterization of Gene Expression Profiles in Early Bovine Pregnancy Using a Custom cDNA Microarray," *Mol. Reprod. and Dev.*, 65: 9-18 (2003).

* cited by examiner

*Primary Examiner*—Carla Myers
(74) *Attorney, Agent, or Firm*—Barnes & Thornburg LLP; Alice O. Martin

(57) ABSTRACT

Genetically elite ungulate mammals are identified on the basis of gene expression profiles from biological samples such as liver and blood. Methods and compositions are presented to select genetically elite animals with a desired phenotype such as high milk production for breeding to improve production levels. A method to select an animal with a specific phenotype, e.g. milk production and health traits, includes creating a Gene Expression Index for a specific phenotype and using the index to identify candidate animals for breeding by comparing the index to gene expression profiles of the animals.

7 Claims, 3 Drawing Sheets

SEQUENCE LISTING

<160> NUMBER OF SEQ ID NOS: 408

<210> SEQ ID NO 1
<211> LENGTH: 385
<212> TYPE: DNA
<213> ORGANISM: Bos Taurus

<400> SEQUENCE: 1

```
gcacgaggcg ggatcgaggg gcagcagcgt acggtgaagg acacaggccg tggagtttga    60
```

```
accccttgaa agattgaaat catggcaggt ccagaagctg atgcccagtt ccatttcact      120
ggtatcaaaa aatatttcaa ctcttacact ctcacaggga gaatgaattg tgtgctggcc     180
acatacggaa gtattgcttt gatagtctta tacttcaagt taaggtctaa aaaaactcca     240
gctgtgaaag caacataaac agattctgag ctgtacatta tctgttaagt tcccatgcct     300
gaagaagcta atgtcaactc atcatgtgat actcaatttg tacaataaat tatgaacctg     360
gaaaaaaaaa aaaaaaaaa aaaaa                                            385

<210> SEQ ID NO 2
<211> LENGTH: 565
<212> TYPE: DNA
<213> ORGANISM: Bos Taurus
<220> FEATURE:
<221> NAME/KEY: modified_base
<222> LOCATION: (114)..(117)
<223> OTHER INFORMATION: a, c, g, t, unknown, or other
<220> FEATURE:
<221> NAME/KEY: modified_base
<222> LOCATION: (311)..(312)
<223> OTHER INFORMATION: a, c, g, t, unknown, or other
<220> FEATURE:
<221> NAME/KEY: modified_base
<222> LOCATION: (392)..(393)
<223> OTHER INFORMATION: a, c, g, t, unknown, or other
<220> FEATURE:
<221> NAME/KEY: modified_base
<222> LOCATION: (484)..(485)
<223> OTHER INFORMATION: a, c, g, t, unknown, or other

<400> SEQUENCE: 2
tttttttttt tttttttgac tatctacaaa aatttattgt ctatttacag aagaaaagca      60
tgcgtatcat taaaacaaat aaaatgtgtt ttctcacagc gcagtacatt tttnnnnaaa     120 aaaattttt taagctgtat cacagaaaca agacacaagg atttttaaa agagctaaac       180 actcatcatt cgaggtgcaa tactcatgga catgagttcc tgaaacaaca gtttgcacgc     240
ataaggcatt cgaaccaaag agatctgggt tttatttcgg cagcccctgc attcgtatgt     300
atgggtcctg nngttcgcaa ttgccattat tccacaaaga ttgcaaacgt gaacctgata     360
cggatctgac gcctcaaaca acctctccct tnnaaactgg gctgctccat gcgcgatctg     420
acagtctcgt tccatctctc caaaacgcaa gccaccatca cgagatctac cctccatcgg     480
ctgnntattt agaatctgaa taggtccccg agcacgagaa tgaatcttat catccaccat     540
atgcttcaaa cgctggtagt aagta                                           565

<210> SEQ ID NO 3
<211> LENGTH: 478
<212> TYPE: DNA
<213> ORGANISM: Bos Taurus

<400> SEQUENCE: 3
gcacgagagc cggcgtctca gaggagtgca gacgctgctg gtgaccctgt ggcgcgtctc      60
tgtggggcca ggaactgaaa gagagccaaa atggctgaaa atggtgataa tgaaaaaatg     120
gctgctctgg aggccaaaat ctgtcatcaa attgagtatt attttggaga cttcaatttg     180
ccacgggaca aatttttaaa ggaacagatc aaactggatg aaggctgggt acctttggag     240
ataatgataa agtttaatag gttaaaccgt ttaacgacag actttaatgt aatagtagag     300
gccctgagca aatcaaaggc agaactcatg gaaataagtg aagataaaac taaaattaga     360
agatctccaa gcaaacctct ccctgaagtg actgatgagt ataaaaatga tgtaaaaaac     420
agatctgttt atattaaagg cttcccgaca gatgcagctc ttgatgacat aaaagaat      478
```

<210> SEQ ID NO 4
<211> LENGTH: 566
<212> TYPE: DNA
<213> ORGANISM: Bos Taurus

<400> SEQUENCE: 4

| | | | | | |
|---|---|---|---|---|---|
| gcacgagcgg | cggagagcgg | cacccacacc | gtgtgtcggc | ggtgagtccc | ggccagcccg | 60 |
| agctgcacgt | cccagccccg | gggagacgcc | ggaaaaaacg | gaaggacctg | ggattccaga | 120 |
| gcagtcgccg | ctgactgctg | ctctcctgcc | gttgccgcgg | cggaggcttc | cgcactcgcc | 180 |
| gctgaagacg | cggccctgac | aggcctagag | gcctaggcgc | ggccctccga | gcccgacgtg | 240 |
| ttgccgccgg | tgcagctgtg | agtaatccga | gcgctctctc | cacggccgtt | tacagattaa | 300 |
| aatggaggaa | atttccttgg | ctaacctgga | tactaacaag | ctggaggcca | tcgctcagga | 360 |
| gatatacgta | gacctgatag | aggattcttg | tttgggcttc | tgctttgagg | tgcaccgggc | 420 |
| agtcaagtgt | ggctacttct | acctggaatt | cgcagagact | ggtaacgtga | aggattttgg | 480 |
| cattcagcca | gttgaagata | aaggagcgtg | tcgcctcccg | ctttgctccc | ttcctggaga | 540 |
| atctgggaat | gggcctgatc | agcagc | | | | 566 |

<210> SEQ ID NO 5
<211> LENGTH: 465
<212> TYPE: DNA
<213> ORGANISM: Bos Taurus

<400> SEQUENCE: 5

| | | | | | |
|---|---|---|---|---|---|
| gcacgagatg | gcgcctgtga | aaaagcttgt | ggcgaagggg | ggcaaaaaaa | aagaagcaag | 60 |
| tcctaaaatt | cactctggac | tgtacccacc | ctgtagaaga | tggaatcatg | gatgctgcca | 120 |
| attttgagca | gtttcttcag | gagaggatca | aggtgaatgg | aaaagctggc | aacctgggcg | 180 |
| gcggtgttgt | aacaattgaa | agaagcaaga | gcaagattac | tgtaacttcc | gaggtgccct | 240 |
| tttccaaaag | gtatttgaaa | tatcttacca | aaaaatattt | gaagaagaat | aatctacgag | 300 |
| attggttacg | cgtagtcgct | aacagcaaag | aaagttacga | attgcgttac | ttccagatta | 360 |
| atcaagatga | agaagaggag | gaagatgagg | attaaaactc | aatctggaat | atttgtataa | 420 |
| gttcttaaat | aaaatttatc | aactgaaaaa | aaaaaaaaa | aaaaa | | 465 |

<210> SEQ ID NO 6
<211> LENGTH: 375
<212> TYPE: DNA
<213> ORGANISM: Bos Taurus

<400> SEQUENCE: 6

| | | | | | |
|---|---|---|---|---|---|
| gcacgaggtt | gatgtcctgt | atctgatgcc | ttgttgcggt | cgaaagtaag | cgagctccag | 60 |
| aggagtgcgg | agaaattcaa | gtctttcctg | ctgtaacttc | atcagcccgc | caagatggcg | 120 |
| atgcaagcgg | ccaagagggc | gaacattcga | cttccaccag | aagtaaatcg | gattttgtat | 180 |
| ataagaaatt | tgccttacaa | aatcacagct | gaagaaatgt | atgatatatt | tgggaaatat | 240 |
| ggacctattc | gtcaaatcag | agtggggaac | acacctgaaa | ctagaggaac | agcttatgtg | 300 |
| gtctatgagg | acatctttga | tgccaagaat | gcatgtgatc | acctgtcagg | attcaatgtt | 360 |
| tgtaacagat | acctt | | | | | 375 |

<210> SEQ ID NO 7
<211> LENGTH: 374
<212> TYPE: DNA

```
<213> ORGANISM: Bos Taurus
<220> FEATURE:
<221> NAME/KEY: modified_base
<222> LOCATION: (329)..(331)
<223> OTHER INFORMATION: a, c, g, t, unknown, or other

<400> SEQUENCE: 7
gcacgaggga cgccatggcg accaacatcg agcagatttt taggtctttc gtggtcagta    60
aattccggga aattcaacag gaactatcaa gtggaaggag tgaaggacag ctcaatggtg   120
aaacaaacac acctattgaa ggaaaccagg caggtgatgc agctgcctct gccaggaacc   180
taccaaatga agacatagtt cagaagatag aggaagtact ttctggggtc ttagatacag   240
aattacgata taagccagac ttgaaggagg catccagaaa aagtagatgt gtgtctgtcc   300
aaacagatcc tactgatgaa attcctacnn naaagtcgaa gaagcataaa aagcacaaaa   360
aaaaaaaaaa aaaa                                                     374

<210> SEQ ID NO 8
<211> LENGTH: 546
<212> TYPE: DNA
<213> ORGANISM: Bos Taurus

<400> SEQUENCE: 8
tctctgtctg cagtggtcca cacccatcct ccgccatacc cggcctcagc ctggctgcca    60
cgggcgccgc acctgccggg gctgcctcta gaggcggcaa gatgttgagc gcggcacgga   120
ggatccaggc ctactggcct agtcgggccg agagccggaa ggccacgtgg ttctcaggcg   180
cagtggaaga agccggaccc tgtgtgggcc acgccctgct ccacgcgcag gccctcgcgg   240
ccctgtgctg cggtgtgacg gtttccagaa tgtcccagta gatgagtcct gacacacagg   300
atttagttgt gccagaagat tccaggatga ctgaagctaa cctttctggt gagtgaagag   360
gacatgacag ggatggaacg aaagcctcag gacccggttg ccccccgttt tttaactggc   420
agtgcctgac actgaagtaa ctgaaaatac caccttgtca ctggagccgt cctttagaat   480
aagacctgtt gccagtaaag ctgtcttcat ctgtgcggat ctacagagtt gggagagaac   540
caaaaa                                                              546

<210> SEQ ID NO 9
<211> LENGTH: 272
<212> TYPE: DNA
<213> ORGANISM: Bos Taurus
<220> FEATURE:
<221> NAME/KEY: modified_base
<222> LOCATION: (126)..(126)
<223> OTHER INFORMATION: a, c, g, t, unknown, or other

<400> SEQUENCE: 9
tttttttttt ttcttcttct tgtccccgtc cttcttctct tcctcctctt catctgagcc    60
aacatcttct atctcgggct tgtcatcaaa ctccttttct tctttctcct tctcttcctc   120
tttgtnttcc ttctcttctg cttcatcatc actaacttct ttatcacgtt ccttttccac   180
cttcaaagga ggacaaatct tgtcacctct ccatcacaaa accgggggaa aaaagctaaa   240
ggagactgca gcacttacac caacgccacc tg                                 272

<210> SEQ ID NO 10
<211> LENGTH: 605
<212> TYPE: DNA
<213> ORGANISM: Bos Taurus
<220> FEATURE:
<221> NAME/KEY: modified_base
```

```
<222> LOCATION: (507)..(507)
<223> OTHER INFORMATION: a, c, g, t, unknown, or other

<400> SEQUENCE: 10
tttttttttt ttttaaggca acaaaaagct tcaatctctt ctccaagtaa acagaactag    60
tacagtatat tattttctgg aacatgtacc cccggagaag taacacaaga gttaaagggg   120
gccctctctg aacacactca cactccccc cctaccccaa tgaaccagtc tctctctcac    180
acccacgcac acacagagct attcacaggc gcaaatgtat actatgtaca aacacacaga   240
tccgggtttc ccctcaagtc tcctggcaga ctgcccacca gagaggaggg atgggctaag   300
gcaaggggaa gaaacaagga accagtctct ggaaggaaac cagctgagcc gtgagttgtg   360
aggtgcttag gggcgtgtct cttctcgtat tccaagatgc agcattgtag agttggggtt   420
gggcggtttg gaatcaacaa aggaaaaca aaagaacccg aggagaatgg tcgggatgga    480
tacgagtgca cagggtttgg gcccagngac agagatgtct gagcgttcac acagagacta   540
ggcgaggagg aaaaagtgca aatcgaggca acgtgtttgc agtctttctt gtttgatttg   600
ggtgc                                                               605

<210> SEQ ID NO 11
<211> LENGTH: 452
<212> TYPE: DNA
<213> ORGANISM: Bos Taurus
<220> FEATURE:
<221> NAME/KEY: modified_base
<222> LOCATION: (397)..(398)
<223> OTHER INFORMATION: a, c, g, t, unknown, or other

<400> SEQUENCE: 11
gcatttgttt tttttttttt ttttaagag gcagtctgtt ccttccatga accgtgttct    60
ctccttaaag ctctgggggt tgggggacc gatcatggct tgcagcgctg gacaaaccga   120
gggtacaaac acacatctcg gatgtggtat ctgtccagaa tccaggttaa gaatcgttcc   180
aagcccaggc catagccgcc atgtggacac gtgccatatt ttctctgatc cgtgtaccag   240
taatagggag tgggatcaat cccttctctt ttgtaacctg ccaggatctc ttcattatcc   300
cagatacgca tggagccacc cacgatctca ccaacattgg gcatcaacac gtcgacagat   360
tcggtgagcc gggggtgatg acggagcgcg ccttcannat tttggacatg ttctccccgc   420
ggatcatcat gtgtctgttg ttgagctgga cg                                452

<210> SEQ ID NO 12
<211> LENGTH: 251
<212> TYPE: DNA
<213> ORGANISM: Bos Taurus

<400> SEQUENCE: 12
tttttttttt tttttttttt tgagggaaac ataagcagag tggcgtcact tggtttattg    60
tattctgaag tgtcatgggg ggccggggag gggtgctgaa aacaagcctg ctttatcagc   120
agttctaaag ccttatcacc tgagatttgc attctggaaa caaaatcatg attgcagtat   180
cagcacatat gtcctgtgag atctgggttc cagccctggt ggatggctgg actaacctga   240
cgtgaggtca c                                                       251

<210> SEQ ID NO 13
<211> LENGTH: 339
<212> TYPE: DNA
<213> ORGANISM: Bos Taurus
<220> FEATURE:
```

```
<221> NAME/KEY: modified_base
<222> LOCATION: (120)..(121)
<223> OTHER INFORMATION: a, c, g, t, unknown, or other
<220> FEATURE:
<221> NAME/KEY: modified_base
<222> LOCATION: (132)..(133)
<223> OTHER INFORMATION: a, c, g, t, unknown, or other
<220> FEATURE:
<221> NAME/KEY: modified_base
<222> LOCATION: (149)..(151)
<223> OTHER INFORMATION: a, c, g, t, unknown, or other
<220> FEATURE:
<221> NAME/KEY: modified_base
<222> LOCATION: (184)..(185)
<223> OTHER INFORMATION: a, c, g, t, unknown, or other
<220> FEATURE:
<221> NAME/KEY: modified_base
<222> LOCATION: (266)..(266)
<223> OTHER INFORMATION: a, c, g, t, unknown, or other

<400> SEQUENCE: 13
atccgaccac gtgacgactg gcatcctcgg ctcaagcccc agagtcctgg gcgggacacc      60
ggactggccc agcccagctt gggggccccg tcgtagctgc caaaggagaa ggaaacacgn     120
nccgtggagc tnncaccaag cgggtgcgnn nccgccccac cgaaaccggc agagtctgct    180 tctnnnnccag tgaggagcag cgtctgtgag gtgcagccaa acggggacaa agtgaacaac    240
gcccgctgcc cgcagtcaca ctcagnccgt agtacacctc ccagaacaag cagctcccca    300
gggacagacg agcagccttg tgccggaagc tcgtgggca                           339

<210> SEQ ID NO 14
<211> LENGTH: 400
<212> TYPE: DNA
<213> ORGANISM: Bos Taurus
<220> FEATURE:
<221> NAME/KEY: modified_base
<222> LOCATION: (319)..(319)
<223> OTHER INFORMATION: a, c, g, t, unknown, or other
<220> FEATURE:
<221> NAME/KEY: modified_base
<222> LOCATION: (321)..(323)
<223> OTHER INFORMATION: a, c, g, t, unknown, or other

<400> SEQUENCE: 14
gttacagaat aatatgcaga aatgccacta tctagttact tggctctaca taagcaaaga      60
ctatcctgtc tttgtggtga ctgaacttag aatgtcctcc tctggaaatg gaaaagtacc    120
tgtattagga gctaagtgac agaaggagtt atcaaacttg actccatata gataatgaac    180
agtttagggg aagcattttt cttggaacta agaaggactt acctgacatt ggcctcattc    240
tggccttcac ttgttcataa gaatcatgga accagagttt gagttaagaa acttggaaaa    300
agcagctgaa acatctcng nnnccactta acaatttaaa aattccactt aagatgctaa    360
ataatccatt gcttatgtag caactcaacg atgttctcaa                          400

<210> SEQ ID NO 15
<211> LENGTH: 523
<212> TYPE: DNA
<213> ORGANISM: Bos Taurus

<400> SEQUENCE: 15
tttatgagca gctagaatgt gctgcaacag aagaagctgc gacacgccag tggggccaac      60
atcactaacg cagccactgc tgctaccaca gcggccacgg ccactgccac caccaccagc    120
accgagggca gcaacagcga gagcgaggct gagagcaccg agaacagccc taccccgtct    180
cctctgcaga agaaggtcac tgaggatttg tccaaaaccc tcttgatgta cactgtccct    240
```

```
gctgtccagg gcttcttccg ttccatctcc ttgtcacgag gcaacaacct ccaggacacg      300
ctcagagtcc tcaccttatg gtttgattat ggtcactggc cagatgtaaa tgaagcctta      360
gtggaagggg tgaaagcaat ccagattgac acttggttac aggttatacc acagctcatt      420
gcaagaattg atacgccaag gcccctggtg ggacgtctta tccaccagct tctcacagac      480
attggtcggt accaccccca ggccctcatc tacccactga cag                        523

<210> SEQ ID NO 16
<211> LENGTH: 383
<212> TYPE: DNA
<213> ORGANISM: Bos Taurus

<400> SEQUENCE: 16
ggggttcagg atcaccaggg ccggtctgac tttcaacccc atgtgtccgg tggggatctc       60
tgcagtgtgt gtctctggca ctcctacca ggggagcagg cttgacttct ccctctctgt      120
gggcttcgtg acagtcgagg tcacggccca ggcagggcct gggcccccct ctctggaagc      180
cgagctgtgg ccgtcacgta ctcgcctccc cctgcctcca ggacggagag tctgttttcc      240
ctgctcagcg ggtcggatac aaaggtcagg cctgtaggcc gcacgcgctg ccccacgaac      300
ttcctgggag gctttctaaa gacgttgaac agctgccccg agcccgcagg ccccgctctg      360 ggacacccctt gggccctgaa gct                                              383

<210> SEQ ID NO 17
<211> LENGTH: 512
<212> TYPE: DNA
<213> ORGANISM: Bos Taurus

<400> SEQUENCE: 17
cgctcggaag gtccccggtg tgcactcctt cagcaggcct tgggggaaga tggcggccct       60
gggggacggt caggagcccc ctcatgtcct gtccccggtc agtttcgagt cacccgggac      120
acctggagcc caccaccatg aagcccaact tcacctccac ctccatggtc atcaacatgc      180
agcagccctg aggtgccctc ccagccccca caggagccgt cagacctgga cttccaagag      240
gtggcagagg tccagatctg cagagacacc tgctggtcag gttctgagtc ggagccggag      300
caggccccgt cgtctcccag cccgcacggt cctaagacga ggtgcaccag gccggaggcg      360
tgctgaggac cctgctgagg agccttcccc gcagacccgg gggtggggac cgctttgggc      420
aggagcccag cctggagcgg tcagcaggcc agacaccgag ggctgggccc cgttcccaga      480
agagagacac ctggctcggg tcgcaggggg cc                                    512

<210> SEQ ID NO 18
<211> LENGTH: 635
<212> TYPE: DNA
<213> ORGANISM: Bos Taurus

<400> SEQUENCE: 18
gccccggtct actctggggt ggtgctaagc cggcgccaga tcgaccctcg actgaggaga       60
ggcagtgcgg ttcctctagg cgcttctccg ttggttcctc cggcttcctc agcctcctca      120
ccacccgcgg ggaccccgaga gctcggtgta tgccccaccc ctgaccccgc tagagacatg      180
tccaccccgg ctcggcggcg tctcatgagg gacttcaaga ggttgcagga ggatcctcca      240
gccgagtcca gcggggctcc gtctgagaac aacatcatgg tttggaacgc ggtcattttt      300
gggcctgaag ggaccccgtt tgaggatgga acctttaagc ttacaataga attcactgag      360
```

```
gaatatccaa ataagccacc aacggttaga tttgtctcta agatgttcca tccaaatgtc    420
tatgcagatg gtagcatatg tctggacata cttcagaacc gttggagtcc aacctatgat    480
gtgtcttcca ttttaacatc catacagtct ctactggatg aacccaatcc caatagtcca    540
gcaaatagcc aggctgctca gctgtaccag gagaacaagc gggagtatga aaaacgtgtt    600
tctgcgatag tagaacagag ctggcgtgac tgttg                               635
```

<210> SEQ ID NO 19
<211> LENGTH: 617
<212> TYPE: DNA
<213> ORGANISM: Bos Taurus

<400> SEQUENCE: 19

```
ggaggagtag gacggggaaa acactttctc ccccacaaat tcatcaaaag agcatttaaa     60
cgtcgagtaa attccacaaa acaacttctg aatgccggca gaggacatca ggcacccaga    120
aaagcaaccc aactcttcga aaggagtttt taccaacgct tcagacccga gtttctggtg    180
agaaatggct tcactgatgc gtcatctcct gccgtgtgca aaagtgctgg gcacagcacc    240
caattccgca gacagtggag ccaagtgggc tgtgcgcagt ggcggtataa acagcagctc    300
tacaggtggc cttctttaag caatctgctg gaagcatgtt cggcctgtcc accagtctgt    360
caactgaagt tatgttcaag aatttccaac tctagggaga ataaatcaca caagttctac    420
ctaccttaaa gacgactgtg agatttgaga ggtactgaag atgaaagcac ttccaatgtg    480
tgaggagtta aaaaaaatgt tactcatcat tatgataaaa ataaccataa tgatgaagat    540
gttggtaact gctctaattg gttttctttt tgttttatct cacacagacc atatgcaatt    600
aaagctctta ttaaatc                                                   617
```

<210> SEQ ID NO 20
<211> LENGTH: 572
<212> TYPE: DNA
<213> ORGANISM: Bos Taurus
<220> FEATURE:
<221> NAME/KEY: modified_base
<222> LOCATION: (481)..(481)
<223> OTHER INFORMATION: a, c, g, t, unknown, or other

<400> SEQUENCE: 20

```
gcacgagccc aatcctcctc ccaccctagt tgccaatgac cacacggctg ttatcaggta     60
aatgaccttt aatccagccc ctgcctcgcc cacaaggctt cggggggtgac agccaggccc    120 caggggacag gccggggcag ggccggggac cctcagcggc acgattcccc agcgcgccta    180
ggtgttgcgt acgaccagcg actgctccag ctcctgcctg cgctgctgga tctgtaagga    240
aaggagagca ggcgcaggtg accagttgct gcgcccccg aggcccccctt cacccttgagg    300 tcccgactct gggagcggag gaggtcctgg atgtagccct tggggtctct ggagaagctc    360
agcatgaagt ccctctggat cttgagctgg ttgatggact caatcgtctc gtggatctgc    420
agtgccaggc tccagcccca ccttactgtc cagagcgctg atctcctgct ggttggccgt    480
ngacagcagg aagctgctca tctgtccctt caggggctcc tccacttcca cgtcaatgtc    540
gtagcacgcc gtcttcttct ggtccgacgg gt                                  572
```

<210> SEQ ID NO 21
<211> LENGTH: 420
<212> TYPE: DNA
<213> ORGANISM: Bos Taurus

<400> SEQUENCE: 21

```
gcacgaggtc gcaatggtga agctgagcaa agaggccaag cagaggctgc agcagctttt      60
caagggagga caatttgcca tccgctgggg ttttattcct ctcgtgattt acctgggatt     120 taagagggt gcagatcctg gaatgcctga accaactgtt ttgagcttac tttggggata      180
aaggactgtt tggtcatctg gttttggaag cagtcaatgc agaggaacaa catggaaggt     240
gtgctctctg gctgggataa agatgggac atcgttcaga cggtcaccag ttggatggca      300
cagggctctt acttctcaga tgcatctgtt gcagagtgga acctctactg acttatttat     360
gatagactgt attaaaataa atgtttttaa caatgttaaa aaaaaaaaaa aaaaaaaact     420
```

<210> SEQ ID NO 22
<211> LENGTH: 274
<212> TYPE: DNA
<213> ORGANISM: Bos Taurus

<400> SEQUENCE: 22

```
gcacgaggtc gcctggcccg ccgtggtggt gttaaacgga tttctgggct catctacgag      60
gagacccgcg gggtgctgaa ggtgttcctg gagaacgtga tccggacgc ggtcacctac      120 accgagcacg ccaagcgcaa aactgtcacc gccatggacg tggtctacgc gctgaagcgc     180
cagggacgca ctctctacgg cttcggcggt taagttccag gcagccattt ggcatagtct     240
aataaaacca aaggcccttt tcagggccac acaa                                  274
```

<210> SEQ ID NO 23
<211> LENGTH: 439
<212> TYPE: DNA
<213> ORGANISM: Bos Taurus

<400> SEQUENCE: 23

```
tgtaactttg acccagtctg acttggtttt gttttgttct gttcttttc ccctggaat       60 acaggacggg accagggccc ttgtactcgg agccaagctg ctctccaggc attgtgtaag     120
cctcttgtgt tgtgctctct tcaggtagg ataattgcgg actgaaccct cgggctgcgg      180
tcatatatga gaacttgctc cgcgcggtcc cctttgccgg gatgtttcca ttgcttcatg     240
tttcagtaaa caaaggagtt tgtgaccaac tatgttttct ttcttaattt aattcttcta     300
cattcacttt tctctcctcc tggtactagt ctctgtagcc tttctgttcc tctcgttccc     360
agcctctgag cagccctagg taaggattat gttggcgtcc cctttctcct gtacagggg      420 atccctctta tcttgctttt                                                  439
```

<210> SEQ ID NO 24
<211> LENGTH: 239
<212> TYPE: DNA
<213> ORGANISM: Bos Taurus

<400> SEQUENCE: 24

```
atgatgctct tcaatgatgg cacctttcag gtgaatttct accatgatca tacaaaaata     60
atcatctgta gccaaaatga agaataccttt ctcacctaca tcaatgagga caggatatct    120 acaacttttta gactgacaac tcttctgatg tctggctgtt cgttagaatt aaaaaatcga    180
atggaatacg ctctgaacat gctcttacag aggtgtaact aggagatttc ttgaacgga      239
```

<210> SEQ ID NO 25
<211> LENGTH: 524
<212> TYPE: DNA
<213> ORGANISM: Bos Taurus

<400> SEQUENCE: 25

```
ttgatcaacc tgccaatttg ctacggatgt tttttgattg cctgtatgac gaggaggtga      60
tctctgagga tgccttctac aagtgggaga gcagcaagga cccggcagag cagaatggga     120
agggtgtggc cctgaagtct gtcacggcgt tcttcacatg gctgcgggaa gcagaagagg     180
agtctgagga taactaaaac ttcaaataca caaaacgaaa gaaaagaaac aatttaagta     240
ttttttttaaa aagtttcacg tcttcgccaa tcacagtgca gcaaggccaa ttctcgcaga     300
aaccccacg tgtgcacgag tgggaaaggg gaaagagaaa aaaaaaggtg atcatggagg      360
aaaaaggtac tggaaaaaaa gtaaacttca aacctgaggg cggagcact aaaaccaaaa     420
tacatgtatt atttatagaa aatatttct gttttaatct tttctttta aatgaggact       480
catactttaa aaaaaaacac atctgtttag caaaaaaaaa aaaa                      524
```

<210> SEQ ID NO 26
<211> LENGTH: 519
<212> TYPE: DNA
<213> ORGANISM: Bos Taurus

<400> SEQUENCE: 26

```
agggtcccctt ccaccaccta ggcctttggg tgggggtctt ggtcctggca ccccatgcac    60
gtctgcttcc tatgaggctg agcagggacc agggcctgag agggaggcgt ggcccaggtg     120
agaggtgagg ccttgctcag ggccctgggc ctcagtttcc ctctgtgaaa tggggtgatg     180
caggtctgcg gggccggca gggttggagc ttctgttgtt tggagctgcc cacccctcca     240
cacgcccagg gatgacgagg gtgggcagtc tcacctcccg gctccccagc caaacctggg    300
gggcccatct gtaccctcc tcgttttctg gtgctggttt cctgaccctg aggtcaagct     360
acctgatctg actggatgtt cagggccctt tatgtcactt ctgacccctg aaccctcagt    420
cccttccatg gtctgggga gggggccacc tgcttccaca cccgcttgtg acagccccag    480
caggtagatg cgtatcagcc aataaaggcc cccgcctga                            519
```

<210> SEQ ID NO 27
<211> LENGTH: 534
<212> TYPE: DNA
<213> ORGANISM: Bos Taurus

<400> SEQUENCE: 27

```
tgtggtgtgg cggcgaggtg acctcgaggc tgcggtgacc atgggccgcc agtttgggca     60
tctgacacgg gtgcggcatg tgatcaccta cagcttgtcg cccttcgagc agcgcgcctt    120
cccgcactac ttcagcaagg gcatccccaa cgttctgcgc cgaactcggg cgtgcatcct    180
tcgcgtcgcg ccgcgtgagt gccctggccg ggcggagagg ctagactccc atccacagag    240
ggtattgcgg gtcccctcag tgagcactct gcagctcgcc ataaacacgc tttctctttc    300
agtagtcctg aatgccgttg aactggtcat gtcctccgca tcttacagat aaaggagttg    360
ggtcacagag aaatgactgg ctcaaggtca cttgtgtgat ccagggtct ccctctgagc     420
tcacctttac ccactctttt cctagcagtg aactgttttg tgttaaaggt gcagcagatt   480
gtgatgatag ttgcacattt cgactttgct aaaacccaca gaagtgtaca tttc           534
```

<210> SEQ ID NO 28
<211> LENGTH: 453
<212> TYPE: DNA
<213> ORGANISM: Bos Taurus

<400> SEQUENCE: 28

```
gcacgagctt ggttgggggc gtcccgcatc taaggcagga agatggtggc cgcaaagaag    60
acgaaaaagt cactggagtc gatcaactct aggctccagc tggttatgaa aagtggaaag   120
tacgtgctgg ggtacaaaca gactctgaaa atgatcagac aaggcaaagc gaaactggtc   180
attctcgcca caactgccca gccttgaggg aaatctgaaa tagagtatta cgccatgttg   240
gccaaaactg gtgtccatca ctacagtggc aataatattg aattgggcac agcatgtgga   300
aaatactaca gagtatgcac actggctatc attgatccag gtgattctga tattattaga   360
agcatgccag aacagactgg tgaaaagtaa atcatgtaca attttctttt aataaaactg   420
gccagagctt gttttaaaaa aaaaaaaaaa aaa                                453

<210> SEQ ID NO 29
<211> LENGTH: 374
<212> TYPE: DNA
<213> ORGANISM: Bos Taurus

<400> SEQUENCE: 29
ttgaagttgt ctgaagagtc ttcaatcact atgtcaagcg acacagatat ttctctttct    60
tcatatgatg aagatcaggg atctaaactt atccgaaaag ctagagaggc accatttgtc   120
cccattggaa tggcaggttt tgcagcaatt gttgcatatg gattatatag attgaagagc   180
aggggacata ctaaaatgtc tgttcacctg atccacatgc gtgtggcagc ccaaggcttt   240
gttgtgggag caatgactct tggtatgggc tattccctgt atcaagaatt ctgggggaaa   300
cctaaacctt agaagaggag atgctgtctt ggtcgtcttg gtggtgcttg ctttagttag   360
acatctcata ttga                                                    374

<210> SEQ ID NO 30
<211> LENGTH: 496
<212> TYPE: DNA
<213> ORGANISM: Bos Taurus

<400> SEQUENCE: 30
gcacgagagt ggagccgctg ggccgcagcc gggaagctta gatgtggagg cgctgagact    60
taggagacac ctggggccgt tagggagact caggtggcgg acactggtg ggatcccgac    120 ctgaccctgg gccagtctcg ttctcgcggc ccgcctcctc accccgcccc cacttggggc   180
tgaagtggct ccgcctcctg atctgagcct ggtccctctt caggcactga cccttgacct   240
cggggcgctc cccatccctt gggcgcgat ggctacaggc gcggatgtcc gggacattct   300
agaactcggg ggtccagagg gagacgcagc ctctgggacc atcagcaaga aggacattat   360
caatccggac aagaaaaagt ccaagaagtc ctcggagaca ctgaccttca agaggcccga   420
gggcatgcac cggaggtct atgcactgct ctactctgac aagaaggacg cgcccccact   480
gctacccagt gacact                                                  496

<210> SEQ ID NO 31
<211> LENGTH: 552
<212> TYPE: DNA
<213> ORGANISM: Bos Taurus

<400> SEQUENCE: 31
tgattcagaa atagaatcgc tctgatgtct gaaggtccca tcgtcctcaa aactaaaaag    60
ttcttattga accgtcttct ctccaggaag caaatggtct tggaagtcct ccacccaggc   120
caagccaatg tttccaagga aaagcttggt gaactcattg ctaagaagtt caaggctgac   180
```

```
gccaagaacg ttgtcacctt cggcttccac actcacttcg gtggtggcag aagtactgga    240
ttctgcttgg tatacgacaa ccgtgactac ttgttgaagt acgaacccaa atacagactc    300
agaagactga aaatcttgga accaaagctt aacaacagaa aggccagaaa ggaattgaga    360
accaagagaa agaaggtcag aggaaaggaa aagtccaaga tccaagccgg aaagaagaag    420
taaagtatca tatgctccct ttatatggct ggtcgactcg gaatattttc tgtcgtattt    480
gttcttttct atgtgcgcgt atagttcatg catgaatctg aaaactgaaa ccataattta    540
gcaaacaaaa ag                                                        552
```

<210> SEQ ID NO 32
<211> LENGTH: 453
<212> TYPE: DNA
<213> ORGANISM: Bos Taurus

<400> SEQUENCE: 32

```
gccgtccaga cagcaagaca gaaaaccggc gcatcacaca catctctgcg gagcagaaga     60
ggcgtttcaa catcaagctg ggctttgaca cgctgcacgg gctggtgagc acactcagca    120
cccagcccaa cctcaagatg agcaaggcca ccacgctgca gaagacggcc gagtacattg    180
ccatgctgca gcaggagcgc gcggccaagc aggaggaggc ccagcagctc cgggaccaga    240
tcgaggagct caatgctgcc attaacctgt gccagcagca gctgcctgct accggggtgc    300
ccatcacaca ccagcggttc gaccaaatgc gagacatgtt cgatgactat gtccggaccc    360
gcacgctgca caactggaag ttctgggtat tcagcattct catccggccc ctgtttgagt    420
ccttcaacgg gatggtgtct acagcaagcc tgc                                 453
```

<210> SEQ ID NO 33
<211> LENGTH: 454
<212> TYPE: DNA
<213> ORGANISM: Bos Taurus

<400> SEQUENCE: 33

```
ttgggagcag atcatagctg ctaggttaag aaattgattc tcccgcagaa acaatggatt     60
tcggtgtagc ggaactgtta cgtggagatg ctaagatgca aaggtacatt tcaaaacacg    120
ccggacaata ttggctggaa aatgacttgg ttaaaacctg atgatcttac cagcattctg    180
caggttgatg aatactaatg aagctgtgga tgtcactgag cagcttcatt ttaaatgagg    240
ggttgctgtc tgcctgctgt ctgcctggtg tgctgtgaca ttttgaaggt ggaaacattt    300
ctggctagtg ctgcgagatt tacttgtctg tcttatgaaa atctggtgat tgggaaaacc    360
tccaatggat gtgggaagaa agttcaagat gaattacatt tttacattgg tttgtaaata    420
gattctgaac cagcatcgag tctagataat gcat                                454
```

<210> SEQ ID NO 34
<211> LENGTH: 582
<212> TYPE: DNA
<213> ORGANISM: Bos Taurus
<220> FEATURE:
<221> NAME/KEY: modified_base
<222> LOCATION: (504)..(504)
<223> OTHER INFORMATION: a, c, g, t, unknown, or other

<400> SEQUENCE: 34

```
gagaccatgg ccttaaaata cctcttatta aacccagaac atggtcttaa gcagtaccat     60
attacttctt gataatagtg ttaaatcttt tatgctttca gtgaaggaaa ggaaaagtct    120
tggatcaatg aaacccatgt gtgacttgtc ttatcatctt tctccagggc cctcttcttt    180
```

```
gatgcagtta tgccgcctta gaattcggaa gtgctttggg atcaagcagc atcataagat      240
cactgagctc aacctccctg aggagctgaa acggtttctc ctccacattt aaatgtgtca      300
agcgaatggc gacacagaca acagacaaat gttattgagt gttgagacca ctgggatttt      360
caagttaagt caggtttata gagttcagct aagttttgt tgtttgcagt gagacgttta       420
ttgtagcttc gtactaggtt cttttgcgct gttggtttgg agggtatgaa aaattatctc      480
ccctgcctgg aagagggtgg ctangatatc catggtgttg aatatcttac ccagcactga      540
gctgggaacc ctttatgctt tgtctaattt agtcccactc tt                         582
```

<210> SEQ ID NO 35
<211> LENGTH: 515
<212> TYPE: DNA
<213> ORGANISM: Bos Taurus
<220> FEATURE:
<221> NAME/KEY: modified_base
<222> LOCATION: (405)..(405)
<223> OTHER INFORMATION: a, c, g, t, unknown, or other

<400> SEQUENCE: 35

```
ggcctcgggt gcctacccgg cggtgtgtcg ggtgaagatc cccgcggccc tgcccgtggc      60
cgccgccgcc ccctttcctg ggctggcgga ggccggcgtg gccgcgactc taggtggcgg      120
agccgctctg gggtcaggct tcctgggagc tgggtctgtg gcggggaccc cgggggggagt    180 cggactgtca gccggaggcg ctgccgccgg cgtggctggt gtcgccgccg ccgccgccgg     240
agccggcggg gagatggctt tcgccaaggg gaccacttcg ttgcctactg agaccttcgg     300
ggccggcggc ggattccctc ctctgccgcc gcctcctcct cagttgccca ctttgggcgc    360
tggcctggga acagtggacg aaggtgactc tctggatgga ccagnatacg aggaggaaga   420
ggtggccatc ccgctgaccg ctcctccgac taaccagtaa gtcaagaccg gcgttttggg    480
ggaagctgac tcgtcggaaa aaaaaaaaa aaaaa                                 515
```

<210> SEQ ID NO 36
<211> LENGTH: 489
<212> TYPE: DNA
<213> ORGANISM: Bos Taurus

<400> SEQUENCE: 36

```
gttggcctca gggttttttgc tcatggtttc ctcagtggtg ctgtccgaga agtattcagg     60
tggtgaccat cactggtatg agtttctcag cagggttagg gcatatcttt gcatggactt    120
cggtggaatc attactgatt aggaggacag ttgttggggg ccatctgccc tgcacaggaa    180
gagatcttgg actcatgaaa tgagataccc ctcaccccg aagggaccaa atggaaactg      240
acatcagaaa ctctgataca aaatcatttt aattgcatca aatggcctta attctgagtt     300
tggtaggctt atcaatatgt tgcttacagt tggggtaggg gaagtagagg gagagaaagc    360
aagacattta tttactaagc acctcttagg tgccagacgc taggctaagc actttacgtg     420
agctgggtca tataagcccct gtgagaaccc tgtaaggaat gttactagta tttacacttg   480
acagatgaa                                                              489
```

<210> SEQ ID NO 37
<211> LENGTH: 526
<212> TYPE: DNA
<213> ORGANISM: Bos Taurus

<400> SEQUENCE: 37

```
atgtgggcag actgccacag tcctcaatag aatggccctc ttgctcccga acgtcctgaa      60
gccaccagtc agaactgtaa cgtactgcag ttcgagaaaa ggcaagagga agactgtgaa     120
agctgtcatc tataggtttc ttcgacttca tagcggcctg tggctaagga ggaaggctgg    180
ttataagaaa aaattatgga aaaagacggt tgcaagaaaa agacgcttga gggaatttgt    240
cttctgcaat aagacccaga gtaagctctt agataaaatg acaacgtctt tctggaagag    300
gcgaaactgg tatgctgatg atccttatca gatgtatcat gatcgaacaa acttgaaagt    360
atagatcaga agatccatga tttctcagtt attaactgta tatctgtgtg tgtatggtgt    420
ctttgcaaag atgaagtggt ataagacatg atgtaaattg taccaactga tacttggaac    480
atggggtacc aacattaaac ttaacaatgt tttaaaactt aatgga                    526
```

<210> SEQ ID NO 38
<211> LENGTH: 602
<212> TYPE: DNA
<213> ORGANISM: Bos Taurus
<220> FEATURE:
<221> NAME/KEY: modified_base
<222> LOCATION: (418)..(418)
<223> OTHER INFORMATION: a, c, g, t, unknown, or other
<220> FEATURE:
<221> NAME/KEY: modified_base
<222> LOCATION: (523)..(525)
<223> OTHER INFORMATION: a, c, g, t, unknown, or other

<400> SEQUENCE: 38

```
tgggtcggca tagccatggc ggctcgtgtc ctttgcgcct gtgtccgccg acttcccacg      60
gccttcgcgc cgctgcccag ctccccacg ctagccgcgg cccggccgct cagcactacc     120
ctcttcgccg cggagacccg gacgaggcct ggggctccgc tgccggcctt ggtgctcgcg    180
caggttccag gcagagttac acagctgtgc cgccagtata gcgatgcacc acctttgaca    240
ttggagggaa tcaaggaccg tgttctttac gtcttgaaac tctatgacaa gattgaccca    300
gaaaagcttt cagtaaattc ccattttatg aaagacctgg gcttagacag tttggaccaa    360
gtggagatta tcatggccat ggaggacgaa tttgggtttg aaattcctga tatagatncg    420
gagaagttaa tgtgtccaca agaaattgta gattacattg cagataagaa ggatgtatat    480
gaataaaata tcagacccct tttcctcatt gagagaaggc ttnnnagatg ctggcgagtg    540
tctggcggtg agaacgcatt tctgcatcat tgctgacttt gcgagtaatt ctgtttagac    600
tt                                                                    602
```

<210> SEQ ID NO 39
<211> LENGTH: 333
<212> TYPE: DNA
<213> ORGANISM: Bos Taurus
<220> FEATURE:
<221> NAME/KEY: modified_base
<222> LOCATION: (141)..(141)
<223> OTHER INFORMATION: a, c, g, t, unknown, or other
<220> FEATURE:
<221> NAME/KEY: modified_base
<222> LOCATION: (143)..(143)
<223> OTHER INFORMATION: a, c, g, t, unknown, or other
<220> FEATURE:
<221> NAME/KEY: modified_base
<222> LOCATION: (157)..(160)
<223> OTHER INFORMATION: a, c, g, t, unknown, or other
<220> FEATURE:
<221> NAME/KEY: modified_base
<222> LOCATION: (306)..(306)
<223> OTHER INFORMATION: a, c, g, t, unknown, or other

<400> SEQUENCE: 39

```
atactggtgt ggtcaggccc ttttcctttg aagaggtaag gtgaatctgg cttatttga      60 ggctttcagg tttcagtttt tttgatcttt aaagtatcct tcaacctgtg gtgcaaaagc    120
agaaactatg gctggattag ntnatgaata tttacgnnnn ttgtaaatta acttttaca     180 ttgagaacag cactgattag ggagatgatc agattctttt ttaaatacac tgtaatgacc    240
tagtgaacat aggcatgtag tggttttgtg tgagggtaac cagacacaga tttacttttt    300
gccttnaaga caaagggaga taaaagcaac aag                                  333
```

<210> SEQ ID NO 40
<211> LENGTH: 565
<212> TYPE: DNA
<213> ORGANISM: Bos Taurus
<220> FEATURE:
<221> NAME/KEY: modified_base
<222> LOCATION: (505)..(506)
<223> OTHER INFORMATION: a, c, g, t, unknown, or other

<400> SEQUENCE: 40

```
gcacgaggtg aagctgagcg tgtacttgga ttacgccaag gctgtgggac tctggaccgc     60
tctggtcatc tgtctgctgt atgggggtca aagcgcagct gctattgggg ccaacgtgtg   120
gctcagtgcc tggactgatg aggctgcggt ggacagccag cagaacagca cctcctacag   180
actaggtgtc tacgccgcct tgggaattct gcaagtgact ccctgacccg ccctagcagt   240
ctacctgcct ctggacctgt ctggctcatc ctagctatgc cctgcctttg agtgacatgc   300
ccaaggtcat tgctaatatg aggcagagcc cagactagtc cccgggtctt ctgattccca   360
atgtggcgat atttccacac tgtactgctt ataatcattt caagggatga cctccctacc   420
cccatgattt tttgtatttt ctagtctgaa gtgttttcg ttttgttttt aaataaagct    480
ttctcctctt tgaacagaag actgnnaggt caggccatcc ctaggaactg agtccaatac   540
tcattaaaaa tggagcactg atgaa                                          565
```

<210> SEQ ID NO 41
<211> LENGTH: 539
<212> TYPE: DNA
<213> ORGANISM: Bos Taurus
<220> FEATURE:
<221> NAME/KEY: modified_base
<222> LOCATION: (472)..(472)
<223> OTHER INFORMATION: a, c, g, t, unknown, or other

<400> SEQUENCE: 41

```
ggcgctaagc cttttttttt aagatttttc aggtacccct cactaaaggc accaaaggct     60
taaagtagga caaccatgga gtcttcctgt ggcaagagag acaacaaagc gctattaact   120
aaggtcaatc aaaatggtgt cggcctcaca gccccatctt ctgttagaaa tgaggacttg   180
actcaacccc cttgacaatg tgcattgagg ctctctgggg gagcgagcat ttaaaggaat   240
gcttgagtac cttgtatata tatccctgtg cttgtcctaa tatttaattt ggctgttttc   300
atagcagctg ttaatgaagc ctgaacttca agtgatgctt gaaggggagg gaaaggggga   360
aagcgggcaa ccacttttcc ctagcttttc cagaagcctg ttaaaaagca aggtctcccc   420
acaagtgact tctctgccac atcgccaccc tgtgcctttg gctagcgca gnccctccac    480 ccctcacctc gatgctgctg gtagcttgga tccttgtggg catgatccat aatcgcttt    539
```

<210> SEQ ID NO 42
<211> LENGTH: 573
<212> TYPE: DNA

<213> ORGANISM: Bos Taurus

<400> SEQUENCE: 42

```
ggcgactatc cctactttga aacgagtgca aaagatgcca cgaatgtcgc tgcagccttt      60
gaggaagcag ttcgaagagt gctcgctacc gaggataggc cggatcccctt gattcagaca    120
gacacggtcc gtctgcaccg gaagcccaag cccagctcgt cttgctgtgg aagttagaga    180
ggtagccagt gcaacctgac cagctcaccc acatgcgcag atgggctctg gcggagaag     240
agggtacgcg tgtgcagcaa cgcatcacat actcaaccat taaccgtgct gctgcctgtc    300
agtgggtggg ggaagcgaca catcccctca tgggagaatc catttactca gtaatggcgc    360
ctgacacgta cccattgtaa cggctgtcta ataatgttta atttaaatat gtatgttaca    420
gagctaataa gtgaaatgac caagactta taattaaaac acttaagtat cctagaagtt     480
actgtctttt ccctgggaat atggagaact acttttctta tgtgtatatt tttatgtaat    540
tagcattctg ttcctggttc agggaaagca tgt                                 573
```

<210> SEQ ID NO 43
<211> LENGTH: 536
<212> TYPE: DNA
<213> ORGANISM: Bos Taurus
<220> FEATURE:
<221> NAME/KEY: modified_base
<222> LOCATION: (500)..(500)
<223> OTHER INFORMATION: a, c, g, t, unknown, or other

<400> SEQUENCE: 43

```
gcaaaaccct ctttcagcat ggcgcatctg gatagcaaca ctgagccagg acttacattg      60
ggaggctatt tctgcccccca gtgtcgggca aagtactgtg agcttcctgt cgaatgtaaa    120
atctgtggtc ttactttggt gtctgctccc cacttagcac gatcttacca tcatttattt    180
cctttggatg cttttcaaga aattccccta gaagaacata atggagaaag gttttgttat    240
gcctgtcagg gggaattgaa agaccaacat gtctatgttt gcagtgtgtg ccagaatgtg    300
ttctgtgtgg actgtgatgt ttttgttcat gactctcttc attgttgtcc tggctgtatt    360
cataagattc cagttccttc aggtatttga ttccagcatg taatacacat tgaatgtatt    420
aaaaagaaat ttgcaactgt aaataaaatg attctttagt agaaactcca gttaaaacac    480
gaagaacagt ttgaaaggan aaaaaaaaaa aaaaaaaaaa aaaaaaaaaa aaaaaa        536
```

<210> SEQ ID NO 44
<211> LENGTH: 546
<212> TYPE: DNA
<213> ORGANISM: Bos Taurus

<400> SEQUENCE: 44

```
tgttaccatt ctcttcatta gttgtatctg atcgactgtc ttcttcaata tcttgcattt      60
gtctggtttt acacttaagc tgtcaatgtc actgatgttg gcagacaata actcagctag    120
ctcttccaaa tatttatttt cttgctccct gcgcctcttt tcagtgcttg atgccagtgt    180
gtcacatggt gacccttttc tcttatgtga gtctgggtta gcagggtcag atgaactgtc    240
cccaaggcca ctcatgttga aaacttcac acctgggaga cttctttgtt cataatgagt     300
cctcaaaaca gatatggtca aatatggtgc tccgtagggt agtttccagt ggaatggggg    360
aacactcttt tccagagatg gctctagtaa gtctcttcac tcttacctca tttaaggcca    420
gttatgcaaa caacttgaat accttagagt aagtagaagt tataaatgtc ggtgtcttca    480
tttggaagca aaaattctta ctgcctgatc ttgtctggtg gtccgtgatt tttatcatca    540
```

```
                                             gagtcg                                               546

<210> SEQ ID NO 45
<211> LENGTH: 592
<212> TYPE: DNA
<213> ORGANISM: Bos Taurus
<220> FEATURE:
<221> NAME/KEY: modified_base
<222> LOCATION: (539)..(540)
<223> OTHER INFORMATION: a, c, g, t, unknown, or other

<400> SEQUENCE: 45
aggcgctgca gaaagtgaag attgaggtga atgagagcgg cacgctggcg tcctcctcca        60
cagcccttgt agtctcagcc cgaatggccc ccgaggagat catcatggac agacccttcc      120
tcttcgtggt gcggcacaat cccacaggaa ctgtcctgtt catgggccaa gtgatggaac      180
cctgaccatg gggaaggcag ccctcatctg gacagaatg gagatgtcca agaggaagaa       240
agtccggagc aaagaatttt tattaattca ttttttctgga aaaagagaag atgtttattt     300
atttattttt ccatggtaaa ttcttttgaa tctgcctctt agacctaact ctgggctctc      360
tcaggagggg caaagaggac ctttgagtta aaccctccaa tggagaccct gggaaagact      420
gggaggcata acacccagcc ggcctcccaa ctggactgta ggactcccag gaccgctggc      480
ccagctgctt ctgcccatcg ttctgcctgg ttgggttttg ggtcctggat cccaccgann      540
ccctggtagg atggcaccac aaggcctaca tgaaggagct tttgtgtgtt ca              592

<210> SEQ ID NO 46
<211> LENGTH: 314
<212> TYPE: DNA
<213> ORGANISM: Bos Taurus

<400> SEQUENCE: 46
cgtggccccc aacgtggccc tggccccgcc agcccagcac aaggcagtga gcagcccacc       60
ctgtgccacg gtcgtctccc gggcccctga gcccctcccc gcctgcatcc agccccggaa      120
gcggaagctg cctgcggaca cccctggagc cccggagaca ccagcacccg ggcctgcccc      180
cgaggaggac aaggactcgg aggccgaggt ggaggtggag agccgagagg agttcacctc      240
ctccctgtcc tcgctgtcct ctccatcctt tacctcatcc agctccgcca aggacctgag      300
ctccccaggc ctgc                                                        314

<210> SEQ ID NO 47
<211> LENGTH: 502
<212> TYPE: DNA
<213> ORGANISM: Bos Taurus
<220> FEATURE:
<221> NAME/KEY: modified_base
<222> LOCATION: (120)..(122)
<223> OTHER INFORMATION: a, c, g, t, unknown, or other

<400> SEQUENCE: 47 ttttttttt tttttttta agagtcatac catgttttat tggacatctt aacatgggtg        60
tgggtgggac ctatgggttg gacagggcac caatgacagc ctcagtgaag tcttggcagn     120
nngcataacc acccatgtca gaagttcgaa cctgtagggg agaattgtta tcatctctgt     180
ggcctgggcc ccatccctaa cccccacca cctaactgtt ccctaaggaa gccagctccc      240
aacaacctag gctctgccca gaaggtaatt atggtctaaa agtataggc tcttctctgg      300 tccacagtac tgaagggagg tgtatggtcc ttgtgaggtt ggagggaata aagggctcta     360
```

```
gcccccatag gggtgcaggt ggccgatgac agacttgatg aagtcggttg tggtgctgta    420
gccgcccatg tctcgagtcc gtaccttgcc aactttaatc accttcttca ctgcctctgc    480
aatcatgttg gagtgatgct cg                                              502
```

<210> SEQ ID NO 48
<211> LENGTH: 303
<212> TYPE: DNA
<213> ORGANISM: Bos Taurus

<400> SEQUENCE: 48

```
aggccctgcc ccatctgagt cgcaggagaa gaagccgctg aagccctgct gcgcctgccc     60
ggagaccaag aaggcgcgcg atgcgtgcat aattgagaaa ggagaagagc aatgtggaca    120
cctaattgaa gcccacaagg agtgcatgag agccctggga tttaagatat gaaatggtga    180
gcatggtggt ctgctctggg agtgaatagt tcctgaaaaa tgaagaagat tcagtaactt    240
tgggagttcc ttgctgaaaa ttgataaata aaaaattatt tataatttat taaaaaaaaa    300
aaa                                                                   303
```

<210> SEQ ID NO 49
<211> LENGTH: 319
<212> TYPE: DNA
<213> ORGANISM: Bos Taurus

<400> SEQUENCE: 49

```
tttttttttt tttttttttt ttgaatttt atacaagtct ttatttacaa cttgtttaac      60
aactgtacac ttttttgcagc cttgaaaaca tttttgtact tgaatgggaa aatatagttt   120
gaccaaatct taactttatt cttcatatac atatacatat attatatgca tacatataaa   180
catatacata taattaatac cataacaagt tggcagtcat aaaattaaaa tgaataagtg   240
acatcaaaag gaaatacaat ataagatttc aaaaaattaa aaatctgtct tctggggatt   300
tcttggactt catgttttt                                                  319
```

<210> SEQ ID NO 50
<211> LENGTH: 328
<212> TYPE: DNA
<213> ORGANISM: Bos Taurus

<400> SEQUENCE: 50

```
ctttagtgcc ccaagctctg tattaacatt ttgcctgaat tattctatta accattctaa     60
gtgtccttca agagcggaaa tggaggcatg agatgacat taagtgctat atttgcttct    120
taacatggca ggtccccact ctctcaggta aagccacttt gatgatattt tcctgctcct   180
gtctcaggga agatgtagga tggaggtact tatgaaaaca atatcttttt catgacagat   240
ggggaaagtg aggcatgggg acactgtaag cacagtatta taaaaaacaa gaacacagag   300
gatgctggtt ctgttactta tttccttc                                        328
```

<210> SEQ ID NO 51
<211> LENGTH: 323
<212> TYPE: DNA
<213> ORGANISM: Bos Taurus

<400> SEQUENCE: 51

```
tctttcccta agacgtaccc gggacatgtc tttggtgtgt ggtggaggca gtgagacgtg     60
ccttgtcctt gggtgcacgc cgcctcctct ccacctgtag ttgatcgtgg tttcatagtg   120
gaactctagc tagctgggga gaaagagaat ctctgcagca ggaatcccgt gtcttcagat   180
```

```
gcaggtcaaa ccgttaagga attcccggaa ttcccatcta aatactgaga caggaaggaa      240
gccagatggc taacgcacag tcactttgtt agttagggca gcattagaaa tcgagcttcc      300
taaagtgttt tcttcttcgt agc                                              323

<210> SEQ ID NO 52
<211> LENGTH: 448
<212> TYPE: DNA
<213> ORGANISM: Bos Taurus

<400> SEQUENCE: 52
gagcagcgtc aacgtaggca gcggctgtgc agaaaaaggg cccgaggaat tgtctcagga       60
acctgcgcgc cccggcacta acatttcgag ggtgaagctt ttcgacacca tggtggacac      120
tttcctccag aagttggtcg ctgccgggag cttccagagg ttcactgact gttacaagcg      180
cttctaccag ttgcagcctg agatgaccca gcgcatctat acaagtttg taactcagtt       240 gcagacttct atccaggagg aaatctctga atcaaagct gagggaaacc tggaagctgt       300
cctgattgca ttggacgcga ttgtggaaga agcaaagac cgcaaggagc aagcctggcg       360
ccccagtggg atcccggaga aggacctgcg cagcgccatg gcgccctact tgctgcagca      420
gcgggatgcc ctgcagcgtc gtgtgcag                                         448

<210> SEQ ID NO 53
<211> LENGTH: 235
<212> TYPE: DNA
<213> ORGANISM: Bos Taurus
<220> FEATURE:
<221> NAME/KEY: modified_base
<222> LOCATION: (76)..(78)
<223> OTHER INFORMATION: a, c, g, t, unknown, or other

<400> SEQUENCE: 53
agggtgtcgg tccgcagccc cttgggggcg agcgcggcac ccctgtggcc tctgcaagtg       60
tccgtggcgc ggcctnnngg gtgggtgggg gaggctttgc accaaagatg tccagactct      120
gcccctctcc caccagccgc tccccgcccc ccgcccaaa caactcagcg acatatccag       180
gccagtgtgg ggtggggagg cctcgtgtta acctgagcac tgtggggagg ccccc           235

<210> SEQ ID NO 54
<211> LENGTH: 370
<212> TYPE: DNA
<213> ORGANISM: Bos Taurus
<220> FEATURE:
<221> NAME/KEY: modified_base
<222> LOCATION: (250)..(252)
<223> OTHER INFORMATION: a, c, g, t, unknown, or other

<400> SEQUENCE: 54
acaaaatttt attgtagggt tgcttttat gggttattga aattacaaaa ataaatgaag        60
catgctttgt atcaccaagg ttattgactt tagtaagggt gatatacacg taaaaaagga      120
attacagttc agtaatcttg ctataataga ggtatgtaca cagcactgtt ggaatattga      180 aaaggtgtg actttaattg cagggtccct gaggaaggtt tcgcaaagta acatacccct      240
ggccccaaan nntcctttct cctcttcttc aaatgaaaac ctttttaagt tggaaaaatg      300
gcacctaagg caattctgga gtctaggaag gaccgattgc agtcagccac tgtttgggct      360
aagccactcc                                                             370

<210> SEQ ID NO 55
```

```
<211> LENGTH: 493
<212> TYPE: DNA
<213> ORGANISM: Bos Taurus
<220> FEATURE:
<221> NAME/KEY: modified_base
<222> LOCATION: (373)..(373)
<223> OTHER INFORMATION: a, c, g, t, unknown, or other

<400> SEQUENCE: 55
gaagtgctga cccgggttct ctcaagcccc caggtgcccc gggtctccca cccgccttca      60
ccatggactc gggcccctg gggcccccag ctccagttcc cacaactcag gcaggctggt     120
ccaggccctg gctgcctca gtcaccagcc ccccagggag gaaccggccc ctcccaggga     180
gccacttccg agttttttag aaaaagttat ctcccatttc ttttcagcca agatgttcag     240
taaatatttt tagtacagca cttagtggac cacttcctaa ctgtgctttc ttgccacaca     300
agtgtcctgg caagagcccc ttctctttaa gacatcagga agccagccag accctttgg      360 gtcaggagcg ctntgcagcc ccaatagcaa ggctgtctgt gtctgagctg ccggccccc      420 ggaagcccag gaccccaga ggaaggagcc aggagagcac aagtctctgg agctgcagcc     480
ccacccatgg ttg                                                        493

<210> SEQ ID NO 56
<211> LENGTH: 558
<212> TYPE: DNA
<213> ORGANISM: Bos Taurus
<220> FEATURE:
<221> NAME/KEY: modified_base
<222> LOCATION: (528)..(528)
<223> OTHER INFORMATION: a, c, g, t, unknown, or other

<400> SEQUENCE: 56
gttctagaat ttttaaatta tggaacatta gtcaagtttt aatttggaca tatgttgaaa      60
ttcttcacat acacattttg tcctcatata tatgaagttg gggcttaaat atcagtattc     120
tcagaatatc attaattaat gaaattaatt aattgattaa ttggatttgt gtacctattt     180
gtcatgcaaa aaattccttc aggtcttcag aattctcaac tacctatgat ttttttttt      240 actgtcaact cttttgacag caactggtta aagaaattga tccaaagact taagaggcaa     300
cttcttcctt ggtttatgag tgcactttca tttataccag aataagcatg tacatatagg     360
cactatttaa ggtatttagc aggtagtaat atctagcttg gaccttagtt ctctgacaga     420
gtaggttctg catgtcaggt gttgtctctg tagttttttgt ggagcatgaa atatataaac     480
tctgacacct cggctagtat acatattgga agttaactca ctttcagntg ttgagagtta     540
aataacaatg tttgtaag                                                   558

<210> SEQ ID NO 57
<211> LENGTH: 603
<212> TYPE: DNA
<213> ORGANISM: Bos Taurus

<400> SEQUENCE: 57
agatttcaaa aggaactgct cgagttctga aggtgagccc agcctttcta aacctcttct      60
cagaaaaggg aaactgacac ttgaattttt gtcaccccctt tcctcattgg aagggaagga    120
gccttagaag attttttcttt ctaactctgg tcttaggtaa atatattcta ataaaacata    180
ggctactcta acaacataga atttagatgc ctcacgtacg tgagaaaatc ttgaatatag     240
gacaagggtc ctgcttttta aaaacagact caactgagct gattagatga cgtgaggccg     300
ctttgccttc aataacatga agttttggac agttcctact cctatttgca gaaggaaatt     360
```

```
ggctgaaaca tactttaacc atttcaaaga aggtaaaatt ggaccttaaa aggtatcaag    420
aagccagcat ggtacttaat tacaacataa cattttgacc ttaatgggaa ctcattttat    480
ttgcactaaa ggccttgctt gctgaagtct cttaactctt atctgtagaa ctttatttct    540
tccactagta caaggagaga aagagttct tataattgaa tgttatcata agagggaat     600 gga                                                                 603

<210> SEQ ID NO 58
<211> LENGTH: 504
<212> TYPE: DNA
<213> ORGANISM: Bos Taurus

<400> SEQUENCE: 58 ttttttttt tttttttaa atcaaagact aagaacaagt caggagctaa gtgacttctg      60
agttcaatga ctgacccatc agagattagc caaggcctct cagatggtct gccaagcctt   120
gcgttgtaac actgatctta taatgtggca cacttgtcct tttctcacag aaatataggt   180
atgggaagtg gatcatatat ggcagtatc cagcccagaa gtaactcaac aaagacattg    240
taaacttctt acttatatgt ttaatgagaa ccatatgtat ctgcagtaga acctaccaaa   300
taagagcacc tttgttttct tctttctaga gaggtaattc ggggatctg acggtggaac    360 tgcacacatg accaatgtag aagatctaga caagtaccct aggggtcacg tggccccaag   420
agtcggctct gaagagcctc aggtgaccct tcttactttg aatgtgtaaa ttctactcct   480
cagtcctagg gggtggagca atca                                         504

<210> SEQ ID NO 59
<211> LENGTH: 427
<212> TYPE: DNA
<213> ORGANISM: Bos Taurus

<400> SEQUENCE: 59
gcacgagggc cgatgctctc aagagtatca acaatgccga aaagagaggc aaacgccagg    60
tccttattag gccgtgctcc aaagtcatcg tcaggtttct aacagtgatg atgaagcatg   120
gttacattgg cgaatttgaa atcattgatg atcacagggc tgggaaaatt gttgtgaacc   180
tcacaggcag gctaaataag tgtggagtga tcagccctag attgatgtg caactcaaag    240 atctagaaaa atgcagaat aacctgctcc catcccgtca gtttggtttc attgtactga    300
caacctcagc tggcatcatg gaccatgaag aagcaagacg aaaacataca ggagggaaaa   360
tccttggatt cttttctag ggatgtaata catacaaata aatgcctca gaggactctg     420 atgcttc                                                            427

<210> SEQ ID NO 60
<211> LENGTH: 212
<212> TYPE: DNA
<213> ORGANISM: Bos Taurus

<400> SEQUENCE: 60
tgtctccgtt cgggagcctc acagacatat ctaggtaaaa agatcgttaa ataaacgccg     60
tcagccatcg caatgcaaaa ataaatatca atcctccggc cacagcgcca gctgcgctgc   120
gccccaagtc ccatcggccg cgcctaacaa ttataaaagt gttcagcgag agtgggtcgg   180
cgtgagtgtg aacgggtgtg cgcgcggggg gt                                212

<210> SEQ ID NO 61
```

```
<211> LENGTH: 530
<212> TYPE: DNA
<213> ORGANISM: Bos Taurus
<220> FEATURE:
<221> NAME/KEY: modified_base
<222> LOCATION: (328)..(328)
<223> OTHER INFORMATION: a, c, g, t, unknown, or other
<220> FEATURE:
<221> NAME/KEY: modified_base
<222> LOCATION: (383)..(385)
<223> OTHER INFORMATION: a, c, g, t, unknown, or other
<220> FEATURE:
<221> NAME/KEY: modified_base
<222> LOCATION: (422)..(422)
<223> OTHER INFORMATION: a, c, g, t, unknown, or other

<400> SEQUENCE: 61
agtgttcttg cctaggaaat cccatggaca gaggagtctg ctgggctaca gtccatgggg    60
tcacaaaaga atcagacaca actaagtgac taaacaataa cattaagatg acagagaagt   120
tcatcagact cctcataatg ttgggcctgg agtactgagc tctggcgtta agcactgagc   180
tgtggtgtaa cagccagaga ctaagtggaa ccttaagacc tgaaaagtga aagtgccctc   240
ctctaactag ctaatttagt gcacaggcac atcttagagt gtggagagaa tgcaagccca   300
ttataagtga agagctcttg ctgccctnga ggggaataag ttaaagagat tccatcaaat   360
gaatttgctc aactgcagca agnnntccat tttataaata tcaaatctag gctaataatg   420
tngctgaatt gctctctgaa ataaccgtgc caaccaacag caatacttta tcagtgatga   480
ggaatagcta ctgcacataa agtagaataa atgcacataa agtagaataa               530

<210> SEQ ID NO 62
<211> LENGTH: 341
<212> TYPE: DNA
<213> ORGANISM: Bos Taurus
<220> FEATURE:
<221> NAME/KEY: modified_base
<222> LOCATION: (104)..(106)
<223> OTHER INFORMATION: a, c, g, t, unknown, or other
<220> FEATURE:
<221> NAME/KEY: modified_base
<222> LOCATION: (159)..(161)
<223> OTHER INFORMATION: a, c, g, t, unknown, or other

<400> SEQUENCE: 62
aattacttct tagaagtttg ggaattacct tccatcaatt cagctaagaa cggaatggat    60
tctggtaaca agacgatata attctctctc agttttcag ccannnctaa cacagttatc   120
agagcagcaa atcgaacctg aaaagatgaa gaatcattnn ntaaaaacca aagaactatt   180
atagctctgt ttgttaattt atgatctaac ttgagacatg ctctgaatct taaactggta   240
tttcactctc cattcaagct tcatcttagc ataccagttc atttaacagt ttgagatctg   300
tttaataaca cgggcaacct tgtaagtcac agcctttcaa t                       341

<210> SEQ ID NO 63
<211> LENGTH: 341
<212> TYPE: DNA
<213> ORGANISM: Bos Taurus
<220> FEATURE:
<221> NAME/KEY: modified_base
<222> LOCATION: (199)..(201)
<223> OTHER INFORMATION: a, c, g, t, unknown, or other
<220> FEATURE:
<221> NAME/KEY: modified_base
<222> LOCATION: (237)..(237)
<223> OTHER INFORMATION: a, c, g, t, unknown, or other

<400> SEQUENCE: 63
```

```
atgcacctcc taataccatc actttgtgtg tgtgtgtgtg tgtgtaagca cgcgcacacg    60
cacgcatgtg tatgctcagt catgtccaac tctctgcagt cctatggact gtagcccacc   120
aggcttttct gttaatggaa ttttccaggc aatactgagt gggttgccat ttcctacgcc   180
agggtatctt cctgacccnn naatcgagcc tgcatctcct gtgtctcctg cattagnggc   240
agattcttta ccactgagcc acctgggaag ccccattttt ggaatttaga atttccacat   300
aggaatttta aagggacaca atattcaaa tcatggaccc t                       341
```

<210> SEQ ID NO 64

<400> SEQUENCE: 64

000

<210> SEQ ID NO 65

<400> SEQUENCE: 65

000

<210> SEQ ID NO 66
<211> LENGTH: 441
<212> TYPE: DNA
<213> ORGANISM: Bos Taurus

<400> SEQUENCE: 66

```
cagtgtccgc gcagctgaag tgtggatgga tgaatttaaa gagctctact accatcgcaa    60
tccccaggcc cgcctggagc cttttgggga cgtgacagag aggagacaac tccgtgcaag   120
gcttgggtgt aaggacttca agtggttctt gaataccgtg tatccagagc tgcacgtgcc   180
tgaggacagg cctggcttct ttgggatgct ccagaacaaa ggactgagag attactgctt   240
tgactacaat cctcccaatg agcacgagat cacaggacac caggtcattc tgtaccgctg   300
tcacgggatg ggtcagaacc agttttttcga atacacatcc cagaatgaaa tacgctacaa   360
cacccaccag ccagaaggct gcgtggcagt ggtggaagga acagacgtcc tcatcatgca   420
tctgtgtgag aacaccaccc c                                             441
```

<210> SEQ ID NO 67
<211> LENGTH: 476
<212> TYPE: DNA
<213> ORGANISM: Bos Taurus
<220> FEATURE:
<221> NAME/KEY: modified_base
<222> LOCATION: (96)..(96)
<223> OTHER INFORMATION: a, c, g, t, unknown, or other
<220> FEATURE:
<221> NAME/KEY: modified_base
<222> LOCATION: (442)..(442)
<223> OTHER INFORMATION: a, c, g, t, unknown, or other

<400> SEQUENCE: 67

```
agcagagacc cacatcagac agctcctaca cgtgcccgat gaacagggtc ttctcctggg    60
ctgggaggtt tgactgctga cctgtcccct ctcagnggta gccccaccc ccatctctcc    120 agtggaagtc tgttgcaaca agcttccgtc ccactcaggg atgcaaaatg cccacgaga   180 tcaagctgct gggggaagtg tttacgtctc tctaaacata cccctaaaca tactctctgt   240
tagtgttaac gttaggcaaa tggaagaaag accaggtcga attctgaaat aattattcag   300
cctcccctcc ttgtccactt catacaccac catgctgcag aatgttcctt atttcttaag   360
```

```
gatgagtgtg cctgttgaat acaaatgtac tgctgctgct taacttgcga gatgcatggc    420
gtatgttacc gtgctgggcc antgtcgttt cttaaatgcc catcgtaaat accatg         476
```

<210> SEQ ID NO 68
<211> LENGTH: 481
<212> TYPE: DNA
<213> ORGANISM: Bos Taurus

<400> SEQUENCE: 68

```
acaaacctag acagcgtatt aaaaagcaga gacattactt tgccaacaaa gagtccacca     60
cccccacctc tggcctggac gacccctctc ctgccagcct ggggaacctt tcggtgcagc    120
cagagtgtgg gccagggtcc tgcagtatca gagagctgcc tgaatccgag gggcagccgc    180
ctgcggcccc cctgcccctc ttcttcctga cgctggaggc cgactgggca gaggccaagg    240
ctcgctgggg tctggcctgg gaggcccacg tgtacggggt aggcgcgctc ttcggcctgg    300
tggccttgct ggcgctgctg gcgctagccc tcctgccctg gcgctgcccg ccggcgctc    360 cctgcctggc gctgctggac atgctcctgc tctcggctgg gaccacgcgg gccttcccgc    420
tcttctacga cgcctacggg caccgcgacc ggctgccggc gctggcctgg ctgctgctgc    480
a                                                                    481
```

<210> SEQ ID NO 69
<211> LENGTH: 436
<212> TYPE: DNA
<213> ORGANISM: Bos Taurus

<400> SEQUENCE: 69

```
tggttcttcc ggtcgtcttt gaaactgaga agttacagat ggagcaacag cagcagctgc     60
agcaacggca gatacttcta gggcctaata cagggctgtc aggaggaatg ccggggctc    120 taccttcact tcctggaaaa atctagattg ctactgctat atttgacctg tcttggtgaa    180
gaagtttgaa aattcaatag tgtttgaact gctgattatt ggattttttt tttttttaa    240 actttggcac atggctctat aaacctggtg gcaggaattc tccccacatt ggctcatgga    300
gagactcctc acttgcagct gtgcccttcca ctgtcctgac ttatttcttc tctcctcaat    360
gctgatacca gagagcagca acgcagacgg ttactccagc tctggccacc cacccccct    420 cactaaaatta ctcctg                                                    436
```

<210> SEQ ID NO 70
<211> LENGTH: 475
<212> TYPE: DNA
<213> ORGANISM: Bos Taurus

<400> SEQUENCE: 70

```
gtaattcatg ggactggagc atttggagca acaaagtgcc ccggtgctac gttctcacct     60
ttggttatga gatttcaagt tattttatcc ccttttcagt ggcaataaga acctttgttg    120
gacttcttgt ttaattcgta cataatgtgt aaaacacttt ctttgaaagc aaattcaagg    180
cactgaatct gtatgtctgt gtgggtgctg tgtccatgtg ctgtccatt ggcaggcaga    240 cttgatccct gacgccctgt acaccacact gcatgagtca ggcccttgat cgggtgttct    300
ctgcttggat ggtaggaacc acagagctta tgaaagaaca cttgtcacct gctccatcgg    360
ttacagtgct agctgaggaa aacagttcct cacatgtatt cttttaacag gactcgtgtt    420
ctagtttcct gtaatttatg ttcctttaat tttaataaaa gctgaactgt gaaaa          475
```

```
<210> SEQ ID NO 71
<211> LENGTH: 504
<212> TYPE: DNA
<213> ORGANISM: Bos Taurus
<220> FEATURE:
<221> NAME/KEY: modified_base
<222> LOCATION: (4)..(5)
<223> OTHER INFORMATION: a, c, g, t, unknown, or other
<220> FEATURE:
<221> NAME/KEY: modified_base
<222> LOCATION: (354)..(354)
<223> OTHER INFORMATION: a, c, g, t, unknown, or other

<400> SEQUENCE: 71
agcnnaatga aagttaagtc tgtgatccct ggtgccccca gcccgctgag tgtgcctcca      60
ggctcagagc cttggttccg aagctggtct ctgacaaggg ccagtgtctc ccacccaggt     120
ggagagcagg tcctgcttgc ggcgaaggcc gcagggtttg aaaagtttaa tgtgaaagac     180
cctccccaga gccctggctt gtctgggagg gccgtcagtc catggctatg ttgagacccc     240
cgaaaccctc ccctgttcct ctaagtgagg agctggtctt gtgcaggatt tgtgtgtgtg     300
tgtaaagagg atctgatgtg tttgtcttac tgtccgagcc ctgtgcagaa gagnctggaa     360
gggcaggggt gggcttggaa aggggacacc cttcctaggg agagcccagg gccctatgag     420
gtgtcagagc tggagacttg ggctgggcct ggcggggtct gagtgcgggc tccgtctcac     480
cggttcgggg ctgactgggt ctta                                            504

<210> SEQ ID NO 72
<211> LENGTH: 392
<212> TYPE: DNA
<213> ORGANISM: Bos Taurus

<400> SEQUENCE: 72
ggggaatgag cagcggctac agagggaggc agccggcact gctggcccct ccttcctgca      60
tctccaggaa cccaggacca gccactgcaa ctaacggctt aactcatgat acaccttccc     120
ttcattccaa agggaagatc gatgtctgct tatctatcac cacttgcttc atctgctctt     180
gctttgtttg ccttctcagt acttctgcct gctgtttccc tggtctgcgt ttattgcgac     240
gatgctccct tgactaaacg tggttactga caactgacgt taactctgca ccttgttggc     300
acctggagtt cagccactgg ctcacagacc gcagctctgg ctgaggaccc tcatccccag     360
ggatgctttc tgatcctgtg cattcctcca tg                                   392

<210> SEQ ID NO 73
<211> LENGTH: 529
<212> TYPE: DNA
<213> ORGANISM: Bos Taurus

<400> SEQUENCE: 73
gaggttactt cacaggaacc aggggcaaag ggccacatct tttttgaac aaggttaatc       60 ctttcctgca aagtagggcc acacagaatg ttgcaactac cggaggtttt tttgataaga     120
atttgacttc cagccttaag cttctaaatt tctgatttag ttgaatcttg gtgagaacca     180
gaggccggaa ctcagctgcc ccaggactgt ccaaggagca ggagcaagtg gtggccctga     240
actgatgcgg tgcccggaaa gcatctgtgg ccagcgtgct ggggttaaca agaccttggt     300
catccaccga ggaaagcagg aagttgtttc caaaacaagg aggaaaaaat agatgctgaa     360
gaatcagaag ctacagctgt gcagcacagg ctgccctcag acctggatgg acatagccca     420
agccccaaga cgaaaagctt ctgtgataca ctgacatgtt tataactgtc cgtgatcttg     480
```

```
ggggcaggca ccagaattcc tctgtctgtt ggagaaaata ggcatagag        529
```

<210> SEQ ID NO 74
<211> LENGTH: 341
<212> TYPE: DNA
<213> ORGANISM: Bos Taurus
<220> FEATURE:
<221> NAME/KEY: modified_base
<222> LOCATION: (185)..(185)
<223> OTHER INFORMATION: a, c, g, t, unknown, or other

<400> SEQUENCE: 74

```
tgtgtgattc ctatttaaca acaaaaaaag aagcctttag gaagagacag gtagaggggt     60
cccttcactt tgaacttggt ggaaagcagt gaggggactc cgggtgggca gctctggggt    120
cggctttggg gctggtctgt gcggccgag aggaagaccc cagccccttt tctgctccaa    180
gaagncctgg acgtttcttt cttcccagtg cattggacca aacagcgga caaggggtg    240
ccctcgaacc caagaagcgt tcccagatcc agcatcgctg aagggggcc gtcggaacca    300
tcccgctcca cgacaccaat gccgccttgt ttgagactcg t                       341
```

<210> SEQ ID NO 75
<211> LENGTH: 514
<212> TYPE: DNA
<213> ORGANISM: Bos Taurus

<400> SEQUENCE: 75

```
gggatctcca aagagttagg ggtccctgag gaggtcagag tgctaccaac cactaggata     60
ttcctaatgg gggctccttg gtgccagagc tccttggttg ggtgccctca gcatcccatc    120
atcctcccc aggtgggctc ccccatcccc gggggatggt tcctgagcga ctgccaccat    180
ggctccagcg ctacgtggac aaagtgtctg acctcagcct ttttgggggt ctcccagcca    240
accacgtcct tgtaaaccag tatctgcctg ggagggcat catgcccac gaggatgggc    300
cactgtacta cccgaccgtc agcactatca gcttgggctc tcacaccatg ctggacctct    360
acgagcctcg gcagccagag gatgataacc cgacagagca gccccggccc cgcccggc    420
cggccacctc tctgctgctt gaaccgcgca gcctgctggt gctccgtggc accgcctaca    480
cgcgcctcct ccatggcatc gcggcagcca gcgt                                514
```

<210> SEQ ID NO 76
<211> LENGTH: 561
<212> TYPE: DNA
<213> ORGANISM: Bos Taurus

<400> SEQUENCE: 76

```
ggcgagctct gacggcaaat aggtctttga aattgagggc ctgcccctga ggtgtggcaa     60
ggggtcagca cccccgatcc ccccggctgg cctctttccc tgtccaggcc cctgctccca    120
ccacagtcca aaggctgctg tcagcagaca cctgggctga gcgtgtccc ttcaggagcc    180
cgggaggcag ggaccccctc ctgctctcgt cccacccctc actagcatca tctctgtaac    240
caggtgagcc agggtgggag agggacttgg agagtccagg catctgcttc cagtctgcct    300
tgagggcctc agctccctcg agcggccagg ggctgcgagt tctgggcatt gggtgacagg    360
ccagtagact gccttcagcc tttgtgctac tgtgtccctc ctcttctgct gctccgggcc    420
ctccaccaag agatcctgtt ggacttggcc gctggaccgg ggcctatgag cttcccttcc    480
tgcccttgaa aatgaggatc ctctggtccc tgcctgccct gttgctatcc attgaggaaa    540
gggcagtgga gaactttccc a                                              561
```

<210> SEQ ID NO 77
<211> LENGTH: 505
<212> TYPE: DNA
<213> ORGANISM: Bos Taurus

<400> SEQUENCE: 77

```
cctcaaaccg caggcccgat tgtcccagg cggggctcc actctgggtt tggggtcacc      60
ccgtcccctc tggggagggg ctggagcttt gtttcatttt aatgacccttt gagcgttgta  120
gggaaactga ggcagggaag aagtcttgac tgcctaaacg gtcaactcct cctctaaact   180
tgaaggtggc accctctctt ctgtttaagt tgtgtgtgtg tgtgtgtgtg tgtctgtgcg   240
tgcgaacagt cggtcacttt tgtcccactg ttggaccctg ctgccctggg gctgtggttt   300
tcccgggtcc agggcgcgcc ctttctccca ggagctggca ttgaagactt gtcacttctg   360
gcagggtcct gatgaccccc tctgcccgcc agtatttggg ttatgtccag agggaactag   420
gtatcatggt ttccttggac ttgtaagctt caggattgct cagtaatgaa tgaaaacatc   480
acgggagaca tggggaagag cagtg                                         505
```

<210> SEQ ID NO 78
<211> LENGTH: 516
<212> TYPE: DNA
<213> ORGANISM: Bos Taurus
<220> FEATURE:
<221> NAME/KEY: modified_base
<222> LOCATION: (404)..(405)
<223> OTHER INFORMATION: a, c, g, t, unknown, or other

<400> SEQUENCE: 78

```
gcacgagcgg agccgcgcgg aggcggaggc tcgggtgcat tcaagattcg gctccacccg    60
taacccaccg ccatggccga ggaaggcatt gctgctggag gtgtaatgga cgttaatact   120
gctctgcaag aggtactgaa gaccgccctc atccacgatg gcttagcacg tggaattcgc   180
gaagctgcga aagctttaga caagcgccaa gcccatctgt gtgtgctcgc atccaactgt   240
gatgagccta tgtatgtcaa gttggtggag gcccttttgt ctgagcatca aatcaacctg   300
attaaggttg atgacaacaa gaaactaggg gaatgggtag gcctctgtaa aattgacaga   360
gaggggaaac tcgtaaagt ggttggttgc agttgtgtgg tggnnaagga ctatggcaaa    420
gaatctcagg ccaaggatgt catcgaggag tacttcaaat gcaagaaatg atgaaataaa   480
ctgatttctt gttttccaaa aaaaaaaaaa aaaaaa                             516
```

<210> SEQ ID NO 79
<211> LENGTH: 557
<212> TYPE: DNA
<213> ORGANISM: Bos Taurus

<400> SEQUENCE: 79

```
gcacgagccg tggcgcaatg aaggtgaagg ccgccctcgc cggcggccga ggtggtcaag    60
gcgaaggccg gagcgggctc tgccaccctg tccatggcat acgctggagc ccgctttgtc  120
ttctcccctcg tggacgcgat gaatggaaag gaaggagtcg tcgaatgttc cttcgttaag  180
tcccaagaaa cggactgtcc gtatttctcc acaccgttgc tgctggggaa aagggcatc    240
gagaagaatc taggcatcgg caaggtctcc cctttcgaag agaagatgat tgctgaggcc   300
atccctgagc tgaaagcctc catcaagaaa ggagaggagt ttgtcaagaa catgaaatga   360
gaaggcgctt agcgagcagt cggtctccctt aacttattaa ggcatcatgt cactgtaaag   420
```

```
ccgtttcaga tacttttgtc gtttcaattt gcttcgttga ggaggattgt attaacgaac    480 caccccttg caatcttggt cagtctgtcg gtgcatcaat aaaagcaggc tttgattttc     540
aaaaaaaaaa aaaaaaa                                                   557
```

<210> SEQ ID NO 80
<211> LENGTH: 265
<212> TYPE: DNA
<213> ORGANISM: Bos Taurus
<220> FEATURE:
<221> NAME/KEY: modified_base
<222> LOCATION: (99)..(101)
<223> OTHER INFORMATION: a, c, g, t, unknown, or other
<220> FEATURE:
<221> NAME/KEY: modified_base
<222> LOCATION: (128)..(128)
<223> OTHER INFORMATION: a, c, g, t, unknown, or other

<400> SEQUENCE: 80

```
tttttttttt tttttttaat ggatgcgtgg taccacctgc tagggctgtc catcctcaca     60
aagctgggat tcttggccac agtgcccctc gcgcggagnn nacagaccct ccagccacac    120
acgcagcngg agaaacagga agggacaggc cgtcccttc gcaggcgagc aaaggacaaa    180
actccatttt aagataaagt cattgcagaa gaaaaaaaaa aagtctttta agagacaatc    240
cttcacaaag ggggaaacga gcacc                                          265
```

<210> SEQ ID NO 81
<211> LENGTH: 425
<212> TYPE: DNA
<213> ORGANISM: Bos Taurus

<400> SEQUENCE: 81

```
ttcattggaa aaaagatttt tatttacca taaaaatgca aactggaata aacaccatct     60
ctcctaaggt ggacgttaca gctattttta agtatttcca agcttccctt ggagaagctg    120
acaattataa aatttaacaa gtttgcagcc ttaaatctga aacgttccaa gtaaaaataa    180
tttagcaaaa cggcttctta aaaaaaccac acaggctaac cttgactaga aaccaaagct    240
aattttaaac cagcctgctt ttttgtttta tgctgaatga cttgagtttg taaaaagtga    300
atgtctggga ccctgtgta ccacctgacg ctcttctgtt gtatgctgaa tgacttgaat    360
tcgtacaaag tgaatgtttg ggactcttct gtatcccgtc tgcaccagcc cacgcccgta    420
aagag                                                                425
```

<210> SEQ ID NO 82
<211> LENGTH: 504
<212> TYPE: DNA
<213> ORGANISM: Bos Taurus

<400> SEQUENCE: 82

```
aggagtcctc accctgggat cattccacaa tccccatggc tccagctccc agcttccgtg     60
gacaccagtg gacttacaac cctgtccgag ggtcctgcct gctgctgctg ctgctcatgt    120
ctaatctgct cctgtgccaa ggcaaatcat gcccgtcctg cggtcctgac gtgtttgttt    180
ccttacggaa atcctttaca gacaggttta tgaatgccgc cagcctctcc catgacttct    240
ataacctttc cacaataatg ttcaatgagt ttgatgaaaa atatgcccag gcaaactat    300 actatatcaa tgtcaccaag agctgccaca ccaattcctt ccatgctccc gaagaaagag    360
atatagtcca gcagacgaac attgaagacc ttagtaagtg gacactcgtg ttgctgtact    420
cctggaataa tcctctgcat catctagtca cggagctgca gcatatgaaa gaactgtcaa    480
```

```
acgccttcct atcaagcgcc acaa                                              504

<210> SEQ ID NO 83
<211> LENGTH: 483
<212> TYPE: DNA
<213> ORGANISM: Bos Taurus

<400> SEQUENCE: 83
gggaccaacg ggatcccctc taccccacca acccgggagg acgagttggg gtcggagttg        60
ggtggactag ctttcctggt cctctcccca cagagctgac gtgtcctggg ttccaggcga       120
tgggcatttc cacggggcgg gagggttcgg gtggtgggta caggcacgtc gctggcgctt       180
tcctccctcc tgtccctgct gctcttcgct gggatgcaga tgtatagtcg ccagctggcc       240
tccaccgagt ggctcaccat ccagggcggc ctgcttggtt ccggccttt cgtcttctct        300 ctcactgcct tcaataatct ggagaatctt gtctttggca aggattcca agcaaagatc        360 ttccctgaga ttctcctctg cctcctgttg gctctctttg catcaggcct catccacaga       420
gtctgtgtca ccacttgctt catcttctcc atggttggtc tgtactacat caacaagatc       480
tct                                                                     483

<210> SEQ ID NO 84
<211> LENGTH: 508
<212> TYPE: DNA
<213> ORGANISM: Bos Taurus
<220> FEATURE:
<221> NAME/KEY: modified_base
<222> LOCATION: (383)..(384)
<223> OTHER INFORMATION: a, c, g, t, unknown, or other

<400> SEQUENCE: 84
attttttctt ttttaaatt ttcaaacact actggggaaa ttattcttgt ccaataatta        60
ttaaaagtct tttcgacttg agcacatgga caaatgaact tgatttgaaa ctagagccat       120
aggccatgca tgttagtact ttattatttg gcttcctgcc atgttaggaa aacaaaatat       180
gaaaaaggtc attttcttta aaccatggaa ttttctca actaagatga atcaaatttc         240
cttatgtatg taaattcata cattaacaca aagttttata tcatgccagt tcacatagca       300
tagtggagtc accattctct agaatgtgtg tttctgcgaa acttaacttg ctttagaatt       360
ttaaatttta accttgcgca gannccagct cccgaaagct atgaaaaatt cccagtggct       420
gatgtggaaa cctcttttcca ctgctgccca gccctcagga tgtgcaactt agtgaaagga     480
gagaatcttt ttctaggaaa aatgagcc                                          508

<210> SEQ ID NO 85
<211> LENGTH: 545
<212> TYPE: DNA
<213> ORGANISM: Bos Taurus

<400> SEQUENCE: 85
gcacgagcag cagccggact tccagaccca gatgccaagc agtcttgtgc tggactgctc        60
catcgctgac tgcctgaggt tccgctgtga catcccctcc ttcggcgtcc aggaggaact       120
tgacttcatc ttgaagggca acctcagctt cggctgggcc agccagttgc tgcagaagaa       180
gacattggtc gtgagtatgg ctgaagtcac attcaacaga tctgtgtaca cccagatttc       240
aggacaggag gcattttga gagcccaggt agagatggtg ctagaagagt atgaggtcta        300
cagccccatg cccctccttg tgagcagctc catgggagga ctgctgctcc tggccctcat       360
```

| | |
|---|---|
| cacagcctta ctgtacaagt gtggcttctt caaacgtcaa tacaaagaaa tgatggataa | 420 |
| caagcctgaa aacactgcac tcaatgggga agatatccac catgagaccc cagatctacc | 480 |
| tttgtccgaa taatccactt tctcatttat gtctattccc attggctgac cttggcttca | 540 |
| cctac | 545 |

<210> SEQ ID NO 86
<211> LENGTH: 239
<212> TYPE: DNA
<213> ORGANISM: Bos Taurus

<400> SEQUENCE: 86

| | |
|---|---|
| acaagaaaat gttatcaacc acacggacga agaaggattt acccctctga tgtgggctgc | 60 |
| agcacacggg caaatagctg tggtagagtt tctacttcag aatggcgctg atcctcagct | 120 |
| tttaggaaaa ggtcgagaaa gtgctctgtc attggcctgt agcaagggct acacagatat | 180 |
| tgtcaaaatg ctgctggatt gtggagttga tgtaaatgaa tatgattgga atggagggga | 239 |

<210> SEQ ID NO 87
<211> LENGTH: 426
<212> TYPE: DNA
<213> ORGANISM: Bos Taurus

<400> SEQUENCE: 87

| | |
|---|---|
| ttctagcagt gggaccaggc agcaggacga ggagatgctt gaactcccag ctcctgctgc | 60 |
| agtggctgcg aagagtcagg ccttagagga cgatgcaaca atgagggctg cagacctggc | 120 |
| cgagaagaga gggcccctct tccagccccga gaaccccaga aagagacctc gggaagactc | 180 |
| tgatgtggaa atggtggagg atgcatcccg aaaggagatg acagccgctt gtaccccccg | 240 |
| gagaaggatc atcaacctta ccagtgttct gagtctccag gaggagatca acgagcgggg | 300 |
| ccatgagagt acctctccgg gagatgctgc ataaccactc ctttgtgggc tgcgtgaatc | 360 |
| ctcagtgggc cttggcacag catcagacca agttatacct tctcaacacc accagactta | 420 |
| gtgaag | 426 |

<210> SEQ ID NO 88
<211> LENGTH: 517
<212> TYPE: DNA
<213> ORGANISM: Bos Taurus

<400> SEQUENCE: 88

| | |
|---|---|
| tgcccaattc caaatgtaca gaactctccc attcctacaa agctccctga accagtgaaa | 60 |
| gccagtgagg cagctgcaaa gaagacccag ccaaaggcca gactgacaga tcccattccc | 120 |
| actacagaga cgtcaattgc accccgccag aggcctaaag ctgggcagac tcagcccaac | 180 |
| ccaggaatcc tccccatcca accagccctg acccctcgga gagggccac agttcagccc | 240 |
| ccgcctcagg ccgcaggatc cagcaatcag cctggtcttt tagccagtgt tcctcaacca | 300 |
| aaaaacccag ccccccaccca gtcaaccccct accacagtct cagcccaagc agcctcaggc | 360 |
| tccgcccacc tcacagcagc cgccttccgc gccggcccag gctctgccca cccaggccca | 420 |
| ggccacgccc cagcaccagc agcaactctt cctcaagcag cagcagcagc agcagacagc | 480 |
| gccgcccgca cagcagccag cgggcacgtt ctaccag | 517 |

<210> SEQ ID NO 89
<211> LENGTH: 274
<212> TYPE: DNA
<213> ORGANISM: Bos Taurus

<400> SEQUENCE: 89

```
ggtatccgcc cccagatcat gaacggcccc ctgcaccccc gcccctggt ggcgctgctc      60
gacggcagag actgcaccgt agagatgccc atcctgaagg acctggccac cgtggccttc    120
tgcgacgcac agtccaccca ggagatccac gagaaggttt taaacgaggc agtcggtgcc    180
atgatgtatc acaccatcac gctcaccagg gaggacctgg agaagttcaa ggccctgaga    240
gtgatcgtgc ggataggcag cggctatgac aacg                                274
```

<210> SEQ ID NO 90
<211> LENGTH: 247
<212> TYPE: DNA
<213> ORGANISM: Bos Taurus

<400> SEQUENCE: 90

```
gtctggctga gcctgacacc cccaggggaa agcagtgcag aaaccactgg tttcccagcc     60
gcggagggat ctgcactttt gtttgttttt gaccaaaaaa aaaaggttag cagtgagggg    120
ctaaggagac atccagcctc tgatacctaa gaggagaagt ccctggactt ggaccctcct    180
attgtgtgac ctcagcccag ggtgggaact gctaccgtga gtacctgggg aggagggat    240
gggagtt                                                              247
```

<210> SEQ ID NO 91
<211> LENGTH: 478
<212> TYPE: DNA
<213> ORGANISM: Bos Taurus

<400> SEQUENCE: 91

```
tggagagtgg gaaccccgcc atctttgcct ccgggatcat catggactcc agcatctcga     60
agcaggccct gagtgagatt gagacacgcc acagcgagat catcaagctg gagaacagca    120
tccgggagct gcacgacatg ttcatggaca tggccatgct cgtggagagc caggcgctgt    180
cttcccaaaa tccctcctcg ggccccctcg ccgcctggag ggggcccctc tggagctggg    240
gtgcccctgg ccctgcaggg ggagatgatt gacaggattg agtacaacgt ggaacattcg    300
gtggactacg tggagagggc cgtgtctgac accaagaagg ccgtcaagta ccagagcaag    360
gctcgccgga gaagatcat gatcgtcatc tgctgtgtgg ttctgggcat cgtgatcgcc    420
tccaccttcg ggggcatctt cggatagaaa ccaccccgcc tgccactctg ctctggac     478
```

<210> SEQ ID NO 92
<211> LENGTH: 430
<212> TYPE: DNA
<213> ORGANISM: Bos Taurus
<220> FEATURE:
<221> NAME/KEY: modified_base
<222> LOCATION: (146)..(148)
<223> OTHER INFORMATION: a, c, g, t, unknown, or other
<220> FEATURE:
<221> NAME/KEY: modified_base
<222> LOCATION: (345)..(347)
<223> OTHER INFORMATION: a, c, g, t, unknown, or other

<400> SEQUENCE: 92

```
tttttttttt tttttttttt tggcaggaga caaaagcagg tttatttggg ctctggggcc     60
agggatgcct aaggtgtgag ttaaggcaac tcagctggtt gtcaatgccc aaagggcagg    120
ccaggggagg gagaagggt gactcnnnat tgaagccaaa tctctgcatt tcaagtccct    180
ggccggagac ctcgggagtc agttctggga gggcatgggt ttctagtgtt ccctgggtc    240
```

```
tctgtgctttt tgctaggatt gggggaatgg tctgggggca ggagccttga atgcacagcc    300
ttcatttcag taacgaccat ttaatttgtt ccttggcaga ctgannnacc tgggccacac    360
tgtgttccgt caagccgctg tcatccgccc taaaattcac ttctggatc acttgctggg     420 ggtcactttc                                                            430
```

<210> SEQ ID NO 93
<211> LENGTH: 213
<212> TYPE: DNA
<213> ORGANISM: Bos Taurus

<400> SEQUENCE: 93

```
actgcgccct caagcctaca tcatcaagat tcaaaacagc tgccgcagcg tctttcaagg    60
aggcacagaa aatagctctc taaacacctg gatccttggt gatatcttcc tgaggcagta   120
cttctcggtt tttgatcgta aaaatagaag gattggcctg gctccggcag tgtaaatgct   180
tggactatca gcaagcattt gactaaatca gtc                                213
```

<210> SEQ ID NO 94
<211> LENGTH: 225
<212> TYPE: DNA
<213> ORGANISM: Bos Taurus

<400> SEQUENCE: 94

```
tgccgcgccg gtcgccaggc gcctcgcctc cccacgcctt ccggcctcg ggctttctc      60 ccgcccgtc ccccaccccc cacgcctccc gcggccgtct gtccggttct cccgccctgt    120
tctcgcctct cccgtacctc tgacgcgtgt cccctgcccg cttggcgccc agctcccgt    180 cggagcccct tccctccgcc ctcggtggtg gtgtgtgggg ggggg                    225
```

<210> SEQ ID NO 95
<211> LENGTH: 418
<212> TYPE: DNA
<213> ORGANISM: Bos Taurus

<400> SEQUENCE: 95

```
ccggcctcgg gcgggaggga agagagcata ggaggcgagg ctgaaggcgc agctgttgcc    60
tggacgatgg cggggacggc actcaagagg ctgatggccg agtacaaaca actaacgctg   120
aatcctccag aaggaattgt ggcaggcccc atgaatgaag agaattttt tgaatgggag    180 gcattgatca tgggcccaga agacacctgt tttgagtttg gggtgttcc tgccatcctg    240 agtttcccac ttgattaccc gttaagtccc ccaaagatga gatttacctg cgagatgttt   300
caccccaaca tctacccaga tggcagagtc tgcatctcca tcctgcacgc tcctggcgac   360
gaccccatgg gctacgagag cagcgccgag cgctggagcc ccgtgcagag cgtggaga     418
```

<210> SEQ ID NO 96
<211> LENGTH: 460
<212> TYPE: DNA
<213> ORGANISM: Bos Taurus

<400> SEQUENCE: 96

```
ctcgcgcagt cgtctgggcg agcgaagatg gcggccgaga gggagcctcc tccgctaggg    60
gacgggaagc ccaccgactt tgaagagctg aggacggag aggacctgtt caccagcact    120
gtctccaccc tggagtcaag tccatcatct ccggatccag ctagctttct tgcagaagat   180
attagtacaa actccaatgg tccaaaacct gcagaagttg cgctagatga tgacagaaa    240 gatcttttg cagaagctac agaggaagtt tctctggaca gtccagaaag ggaacctata   300
```

```
ctctcctccg aaccttctcc tgcagtcaca cctgtgaccc ccacaacact cattgctccc    360
agaattgaat caaagagtat gtctgctcct gtgatctttg atagatccag ggatgagatt    420
gaagaagaag caaatggaga tgtttttgat atagaaattg                          460
```

<210> SEQ ID NO 97
<211> LENGTH: 466
<212> TYPE: DNA
<213> ORGANISM: Bos Taurus

<400> SEQUENCE: 97

```
gcgtccctgc gaccctcttt ccggaagcgt ggatagtgcc cgtgggattt gtggccgtag     60
tttaggaact cacatccggg acaatggtgt gcattccctg catcgtcatt ccagttctgc    120
tctgggtcta caaaaagttc ctggagccat atatataccc tctgatctcc cccttttgtta   180 gccgtatgtg gcctcggaaa gctatacgag aaaccaatga taaaaacaaa ggcaaagtag    240
actataaggg tgcagacata aatggattac caacaagagg accaacagaa atgtgtgata    300
aaaagaaaga ctaaactgat tgtcccgaag gatctcattg ttataaaaat ggacctgata    360
ctatgaagca ccttctttgt aattgtctct gatcttttc caagaccaga atttgggtta    420
gatattaaca gtttagacat ttacctatgc taatcaggga ataccct                 466
```

<210> SEQ ID NO 98
<211> LENGTH: 363
<212> TYPE: DNA
<213> ORGANISM: Bos Taurus

<400> SEQUENCE: 98

```
gtggtctcaa ggcaggggg caggcagggg tggcctgttc agcccttcac agatcagtgg     60
tcttggcagg tctgagagct gccccactgg ccagactcct ctccagcagc agagccagcc    120
tggggcttgc atgtccagcc tgagcaagct taacaggatg aagctgaggc tttctcccca    180
ctgtgactgg agtgcatgtt tacaccagca cctttctgc acatgtatct tcaatcccac     240
cacagggagc tcgtcacccc tgcacaatga cattccaacc accaccagcc agaagttaca    300
gccaaccttg ctgactgtca caagcaggac cttgggtcca ttggcacggt cagtgatgta    360
agc                                                                  363
```

<210> SEQ ID NO 99
<211> LENGTH: 566
<212> TYPE: DNA
<213> ORGANISM: Bos Taurus
<220> FEATURE:
<221> NAME/KEY: modified_base
<222> LOCATION: (481)..(482)
<223> OTHER INFORMATION: a, c, g, t, unknown, or other

<400> SEQUENCE: 99

```
gaacttgagg gcccaagcct tatctcagcc tttcctcaat acggggttcc gttggactgg     60
ggctcctcca tgcctagtga gaattccatg tgggctcaga agactgggc atgcaggtgc    120 cgctgctgat gtgctgcctg tgtgtcggac acacagtgga agctggaatt gatggtccat    180
gaaggcttac cccacacaca cctgcagcct ccccagatca gtaggtgta ttcccctggc    240 agtctgggca acggagacca acaagaaaca tttttaggtt gttttaaatt ccttttttta   300
aacttgcagt ttattgcgta ctgagagttg atcacaacct ccatgcttca taagcggacg    360
ccatgttagg gtcaaacgtg ggcaccatga gtcctccgtg gctcctggac agagacccac    420
```

```
ctcaagatca gaagcccttt ggatggcgtt gcagatctca ttgctcaatt agcctcgaag    480
nntctaattc tcatcccact ctcagttgga ttttctggca ctcttcctgc atcgagtctt    540
ctgggactga accaagctct gtggtt                                         566
```

```
<210> SEQ ID NO 100
<211> LENGTH: 391
<212> TYPE: DNA
<213> ORGANISM: Bos Taurus

<400> SEQUENCE: 100
gtactcgggc ggccatggcg gggttggcag gcaggtttgc caggcgctgg ttctctgggc     60
ttctcggcag cccctgcag gtcccagccc ttgggttaca cgtgcgcggc cccgccatgc    120
tagccagcca gaaggacttt aacaacgcgg tgagccaggt gaagctcctg aaggaggatc    180
cgggcaatga ggtgaagctg aaactctacg cgctctacaa gcaggccact gaaggacctt    240
gtaacgtgcc caaaccaggt atgctggact ttatcaataa gaccaaatgg gatgcatgga    300
acgctcttgg cagtctgtcc aaggaagctg cccgacagaa ctacgtggac ttggtgtcca    360
ggctgagtgc ttcctctgag tcccccagcc c                                  391
```

```
<210> SEQ ID NO 101
<211> LENGTH: 368
<212> TYPE: DNA
<213> ORGANISM: Bos Taurus
<220> FEATURE:
<221> NAME/KEY: modified_base
<222> LOCATION: (162)..(162)
<223> OTHER INFORMATION: a, c, g, t, unknown, or other

<400> SEQUENCE: 101
acgcctttcc tttcctaccc agaagtagaa gcccagtggc agggcagcag cctgcataga     60
ctcaagtctg cccactggtc actgggcgct tggtggctcc tgggttcgat gctacctctt    120
ttccccaagt ttaattttag ataaattaca ctgcctgaag tngggcacc cctttctttc     180 cctgaggagc cccaagacca gagacaaggc caggacagct tggggacaca ctcctgggag    240
aggtgcagtc ccttccctgt tgggggaag cccagaccca tgccaatcag ctcgcagcca    300
ggctttgaca atctcgcagc cctcacgatt tggtcccact ggccacttgg gttctctcct    360
gggcaggc                                                             368
```

```
<210> SEQ ID NO 102
<211> LENGTH: 311
<212> TYPE: DNA
<213> ORGANISM: Bos Taurus

<400> SEQUENCE: 102
caccacgctg tggcgccgga acgccaacgg ggaccccgtg tgcaacgcct gcggcctcta     60
ctacaagctt cacaacgtga acaggccgct gaccatgaag aaggaaggca tccagacccg    120
gaaccggaag atgtccagca agtccaagaa gagcaagaag gggtccgagt gcttcgagga    180
gctgtccagg tgtgtgcagg acaaggcctc cccattcagc gccgccgccc tggcggggca    240
catggcgcct gtgggccacc tgccgccctt cagccactcc ggtcacatcc tgcccacccc    300
gacgcccatc c                                                         311
```

```
<210> SEQ ID NO 103
<211> LENGTH: 609
<212> TYPE: DNA
```

<213> ORGANISM: Bos Taurus

<400> SEQUENCE: 103

```
gatgcgaata cctgccctca acgcctacat gaagcacctc ctcagcctgc ccatctgggt    60
gctgatggac gaggacgttc gcatcttctt ctaccagtcg tcctacgacg ccgagcaggt   120
gcctcaagcg ctccggcggc tccgcccgcg caccggcga gtaaaaagcg agtccccaca   180
agctgctggc attgaccgca tggcagctcc acgagcagag gccctgtttg atttcactgg   240
gaacagcaaa catgagctga atttcaaagt tggagatgtg atcttccttc tcagtcggat   300
caataaagac tggctggagg gcactgtccg gggaaccaca ggcatcttcc cagtgtcctt   360
tgtgaagatc ctcaaggact tcccagagga ggaagacccc accaactggc tacgctgcta   420
ttactatgag gacaccatca gcaccatcaa ggacatttca gtggaggagg acctcagcag   480
cacccccactc ttcaaggact tgctggagct catgaggcct aaaggctgct ggacctttcc   540
cgaactctga tctctcccac ccaggcggga gttccagaga ggacatcg ccctcaacta   600
ccgacgctg                                                           609
```

<210> SEQ ID NO 104
<211> LENGTH: 296
<212> TYPE: DNA
<213> ORGANISM: Bos Taurus

<400> SEQUENCE: 104

```
ggatcccggg aagtggagac ccggggtccc ggcagcgggg cggcccgcgg gccacgccgg    60
ggatgcaccg tcgtggggtg ggagctggcg ccatcgccaa gaagaagctt gccgaggcca   120
agtacaagga gcgagggact gtcttggctg aggaccagct ggcccagatg tcaaagcagt   180
tggacatgtt caagaccaac ctggaagaat ttgccagcaa acacaagcag gagatccgga   240
agaatcctga gttccgggtg cagtttcaag acatgtgtgc caccattggc gtggat       296
```

<210> SEQ ID NO 105
<211> LENGTH: 525
<212> TYPE: DNA
<213> ORGANISM: Bos Taurus

<400> SEQUENCE: 105

```
agccctttag atttcctgga gtggaccggc accacttctg acttccctca gagacctgga    60
atctgagctc ttacagccaa ggatcttggt gggctcaagc ctggggaggg accagggatg   120
ggaagataga aactggtatc agtgggacat ttctggaatc tgccgaagag ggaccacaga   180
gaacatcttc agtctctcct tgtgtctctc ttacccttc ccagagatag ttccaccccg    240
agtttcttaa ccctctcttc agaggcatcc agaagctgat agcctaggct ggatgtgccc   300
taaggaagtg ggattccaag tctatacttg attctgactg tgtgtaatcc ctgccccttc   360
cataacctgt ggaggttctc ttcccccttca tagaggagga agtgatcagg tctgaaggtg   420
gaaaaaatga ccatacagcc aagcaaaacc caggatctta cagaggcaat ggcactggtt   480
gaggcctcca tacctcctca tttcaaattc cctcctattt ggatc                    525
```

<210> SEQ ID NO 106
<211> LENGTH: 585
<212> TYPE: DNA
<213> ORGANISM: Bos Taurus
<220> FEATURE:
<221> NAME/KEY: modified_base
<222> LOCATION: (495)..(496)
<223> OTHER INFORMATION: a, c, g, t, unknown, or other -continued

<400> SEQUENCE: 106

```
gaattcacct tatgccatcc atgaatcctg atgggtatga aaaggcccag gaaggagatc     60
tagtaagtgt aatcggcaga acaacagca acaactttga cctgaaccgg aatttcccgg    120
accagttcgt tcagatcaca gagcccaccc aaccagaaac tattgctgtg atgagctgga    180
tgaagaccta tccatttgtg ctgtcagcaa acctgcatgg aggtactttg gtggttaact    240
acccttttga tgatgatgaa caaggcattg ccacatatag taaatcacca gatgatgctg    300
tgtttcaaca aatagcactt tcttattcca aggaaaactc acagatgttt caaggtagac    360
cttgtaagaa catgtaccct aatgagtatt ttcctcatgg aataacaaat ggagccagtt    420
ggtacaatgt cccaggtggt atgcaggact ggaactattt gcaaacaaat tgctttgaag    480
tgactattga actannttgt gtgaaatacc catttgagaa agacctgcca aaattttggg    540
cacagaatcg aagatcccta atccagttta tgaaacaggt gacta                   585
```

<210> SEQ ID NO 107
<211> LENGTH: 578
<212> TYPE: DNA
<213> ORGANISM: Bos Taurus
<220> FEATURE:
<221> NAME/KEY: modified_base
<222> LOCATION: (496)..(496)
<223> OTHER INFORMATION: a, c, g, t, unknown, or other

<400> SEQUENCE: 107

```
ggagtgagtc cggcccggct ccctcgcccg ccgagtcaac ccaggcctca gtgacacttg     60
cgcagctcct gcagctggtc cagcagggcc aggagctccc cggcctggag aggcgccagg    120
tcgctgcgac ccttgacgaa cccacggcgt cccgactccc gcggatacccc aagccctggg   180
aggccgcgcg ctccgcggag cacccagcgc cacagttcca gactggggac cgcgggctcg    240
ccgaccctcc gagtgggcag aggaaccgcc tggaggagcc tggctcggcc gtttctgagg    300
ctccaggtcc tttgcagctg tgaatgaaaa atttttgctgc cctgtcggca aaggacactg    360
cagccccaag ggacaccccc agaatggagg aaggcctgac tactactgaa ccctcagcca    420
ctgcggacac tcccaaccgt gcaccctgag gtgcctccgg atgggataga ataagatact    480
ggccttggac agctanggtt catagcaaag gaatgatatt agtgagcccg gactcttatg    540
acttcctatg catgagaaaa gctaaattct ttgatgtg                           578
```

<210> SEQ ID NO 108
<211> LENGTH: 382
<212> TYPE: DNA
<213> ORGANISM: Bos Taurus

<400> SEQUENCE: 108

```
ggtccttatc atctgttcca tcaacatgta ctttgtcgtg gtttatgtcc aggatgtagg     60
gcatatggta ttgtatgtgg tggctgcagt ggtcagcgta gcttatctga gctttgtgtt    120
ttacttgggt tggcagtgtt tcattgcact gggcatgtcc ttcctggact ctggacacac    180
acgcttatga acctatctct ctgatggatg gaggtgtcag tgccattgaa ggatacgaga    240
agagattgtt ccacgttgct ctctttccgt actccaacat gactacaatt ttgattattg    300
taaagagttt gtttcaggat tcctcaaaat ctacgactct ggtttcaaa gccattgtgc     360
aagtttagtg ttgaaatcta ct                                            382
```

<210> SEQ ID NO 109
<211> LENGTH: 570

```
<212> TYPE: DNA
<213> ORGANISM: Bos Taurus
<220> FEATURE:
<221> NAME/KEY: modified_base
<222> LOCATION: (456)..(458)
<223> OTHER INFORMATION: a, c, g, t, unknown, or other

<400> SEQUENCE: 109
gggttcttgg aagacctggc acctctggag cgcagtggcc taatccagga ctgggaaaca      60
tctgggcttg tttacctgga ctacattagg gtcattgaaa tgctccgtca tatacagcag     120
gtggattgct caggttatga actcgagcag ttgcacacca aagtgacctc actgtgcaac     180
aggatagagc aaatccagtg ttacaatgcc aaggaccgcc tggctcagtc agacatggcc     240
aaacgtgtag ccaacctgct gcgggtggta ctgagccttc agcatgcctc tgatacaacc     300
tccgactcaa cgccagaccc tcagcgagtc cctttgcgcc tgttggctcc ccacattggc     360
cggcccccca tgcctgagga ctatgccttg gaggaactgc gcagcctcac acagtcctac     420
ctgcgggaac tgactgtcgg gagccagtga gccctnnnct cctcccacca cactcacatg     480
cttgttcaca ctcaccacac agagggctcc tgcatcaagt tgattgccct gtttgccgtt     540
ctctggcttg gccatggaat ctcccctccc                                       570

<210> SEQ ID NO 110
<211> LENGTH: 405
<212> TYPE: DNA
<213> ORGANISM: Bos Taurus

<400> SEQUENCE: 110
tttctttccc cctcacaagg ctcccagaag ccctagttgg ccttgacctg acacttcctt      60
tttattaggc gtcctgttgg ggtggctgag aatcatgaaa acagatcct ctgctagcct      120 ccatgatgaa gttgttagac accagctttc tgggaactcg tgtttgattt ttaaatggca     180
tgtgacccct ctgtgttctg gggactcaat cagaaaggta aaagccatta acaaagtta      240 gtaagagttt tattcatctc atatcttcct gcctgggttc acggccttac tgactgaaat     300
aaaatcattt ctgattggac gcagacctgc gtttctttgg acttctgaat ccatgttcat     360
attttctctg gccactgaac accttggaga ttccgtttag ggact                      405

<210> SEQ ID NO 111
<211> LENGTH: 515
<212> TYPE: DNA
<213> ORGANISM: Bos Taurus

<400> SEQUENCE: 111
agtttcttgg aaatcttgac agcttcaaat atttagaccc atttagttct aatacaagtt      60
catctttatt gtcaaagtaa aagcaatatt cttgtaatac ttaactatgt aaatgcaaat     120
gagaaccttc ttctcagagt acttctcacg ctctaggatt tactaattct tcctcctttc     180
ctcttaaata gggttaattg ttcaaggcca acaaagagca gttcttttgg attttgataa     240
agagaaaatt tggggataca ttagcaagtg tgcctgatgt aagcagctaa acacaatagc     300
cagcatagtc attaacactg cctgacatat tcaagaaaga actggcatag ctaaatgtga     360
ttgatgtgtg tttattgtca gaatcaaaac ttcttagagt ccacggttgt gtgtgaacac     420
actggatgtt ttcatcatca gctcaattaa atgggttcac tgtagaaagg gaaaaaagcc     480
aatgaaaggt atctacaggc agacctcatt ttact                                 515

<210> SEQ ID NO 112
```

<211> LENGTH: 432
<212> TYPE: DNA
<213> ORGANISM: Bos Taurus

<400> SEQUENCE: 112

| | | |
|---|---|---|
| gaaaaaatgg cgccgacgtg agcgcgagcc cgcggccacc gaaggagtcg ccgcagcctt | 60 | |
| agttggagcc gctgaagccg cgggaacaag aggctgaacc aagctgagga tggatgagga | 120 | |
| accctcgggg cccagcctgg acatgccggc tactgcagag cccagctcca gtgagaccga | 180 | |
| caaggggtg tccccagttc tggctgctat agacaaatcc tcttctatgg aggaggagcc | 240 | |
| gggccctgac cgggcaacca cacccccagt gtgggaacgt ggagggccca ccggagggac | 300 | |
| ccagcagggt gcctccccag ccccagacag tggccattcc ggacctggac acacccttgg | 360 | |
| cccaaccagc actgtctccg ggaccagtga ggacctgcgg cctcccagac gacgcccacc | 420 | |
| accagggaag ca | 432 | |

<210> SEQ ID NO 113
<211> LENGTH: 536
<212> TYPE: DNA
<213> ORGANISM: Bos Taurus

<400> SEQUENCE: 113

| | | |
|---|---|---|
| ttttttttag aaagacaaac tgctttattt taaaacactg gaaaaaacat taaaaggcaa | 60 | |
| atgtccatta tataaccaag aatgttaagc atttggaaaa tgttaatctt ctaaattgtg | 120 | |
| gtaggcactt ccagagagct aaatattgca aattatccta ccagatgtct tctgtaatac | 180 | |
| caaaaatact tgatatgatg aaacacacaa ctaattaccc aaagtcacca tgttaggttt | 240 | |
| caatttaatt acaagtaaaa gttttgtcca agatgttcct gacacatgaa gcgtccagtt | 300 | |
| gaatttcaga atgttaaca aaagtatctt ccttttttgc ctgtgaatgt ttgggtattg | 360 | |
| ctgtattgtt ggcttatatc cactacagat actggttcta ggccagccca agggtcttca | 420 | |
| agcattgaag gcttgaaata actctccaac tcattagaca ttctcttttc tctaccacgc | 480 | |
| cctgatccaa atggtgtaga tgtccttgga gaaccctggg ggtgggtctg ctgctg | 536 | |

<210> SEQ ID NO 114
<211> LENGTH: 406
<212> TYPE: DNA
<213> ORGANISM: Bos Taurus

<400> SEQUENCE: 114

| | | |
|---|---|---|
| gcacgaggcc agggtcaccc tgagcaggga aagcaccgcg atgctgacca ggttcctggg | 60 | |
| cccgcgctat cgccagctgg ccagaaactg ggtccccacg gcgagcctgt ggggcgctgt | 120 | |
| gggtgccgtg gggctggtat gggccactga ctggcggctg attctggact gggtgcccta | 180 | |
| catcaacggc aagttcaaga aggatgacta gactcacaac ctcaggcccc tctgatgtct | 240 | |
| gctgtgctgc ctcctgccat ctgcatctgg aactgcccag gctctctgga tggactctag | 300 | |
| gaagtccctg gcacgagttc atttcctctt ttggtggaaa taacttttgt gtgtggacac | 360 | |
| acagcattaa acctcactct gaaacctgaa aaaaaaaaa aaaaaa | 406 | |

<210> SEQ ID NO 115
<211> LENGTH: 237
<212> TYPE: DNA
<213> ORGANISM: Bos Taurus

<400> SEQUENCE: 115

| | | |
|---|---|---|
| acattttaat acatatttac gtgcaacgtt gttagaagcc taagttggtg aaaaactttt | 60 | |

```
catttcagtg ggctgttagt acattaaaag tctcagagtt taaaggtata ctttgtttat    120
ccgattcagt aatcttcaag aactcatagg gaagtcagta tcagcaggaa agtggttagc    180
ttggctgaaa catacccaca aaaccccag aggtgaggga aggcatttta atgctta        237

<210> SEQ ID NO 116
<211> LENGTH: 482
<212> TYPE: DNA
<213> ORGANISM: Bos Taurus

<400> SEQUENCE: 116
atttttttca ggccttcttc caggagcatg tgttcccagt gtaccgcaaa gtactaacag     60
tatataactg acatcgtgtc atagtttgca aggcactccg gatgggcaaa ctgtcttatt    120
catataccta atgtccagta tggtgcctgg cacattatgg caccctcaaaa tatgttcatg   180 gttaaaaatg gtaggctgta tgtttgtcag ctaggaaaac agtacatcag cactttatac    240
ttgggtccct ttctggtcag tggcacatat ctcgtgttag acttgtacct aaatggataa    300
gcactcccca gtggttcacg aacactgcga aaacagaagt atggggaggt gcaaccctgg    360
caggcaaatg ctgcctgaca atacccttg gtagcaaagg cctgcacttg gatgatcctg    420
atccctctgg tttgtcacga agaataggat gggataaata gagcatacat tgacattaac   480
ct                                                                   482

<210> SEQ ID NO 117
<211> LENGTH: 401
<212> TYPE: DNA
<213> ORGANISM: Bos Taurus

<400> SEQUENCE: 117
accatttgtg ttttttgttg ttttttaatt tagacaaaac cgctttggaa aggggaagtc     60
tcatgcaggt tataggtctt tctctgtcta ggtttcaggt gcttgcaact ggactgcaga    120
ctcttaccaa tcacgggcat tttacctttt ctgaacactg cagtttgtta ggctagagct    180
gaagttggag gagcctgtag tgctttcaac agtgatgcat gttttaatgg ataaaaatag    240
ctggtttcta ttaactgtat agacagtaaa caaaaaatcc ttaatactta actagcttct    300
tttcagaatg cgttttattt ttgtcagtta cagtcctaga tatacttact gctggtacag    360
ttgtactcta agatttgtat ttgatatcca cgttactccc t                        401

<210> SEQ ID NO 118
<211> LENGTH: 446
<212> TYPE: DNA
<213> ORGANISM: Bos Taurus

<400> SEQUENCE: 118
aatatattac aatctttcaa agtcgtacac tcctcagttt ctattgtgtg atcagtttgt     60
gttttatttt gtatttgtct cccccatctt gcccttcttc taagaaaccc tatcttctct    120
tttgccatct caaattgaga atctcaactc tggttgctga actgcctggc cagctcccac    180
aagcaatacc tcccttgttc cagcaggacc aagggagccg gccttcactg agtgagtaac    240
ttgtgcaact gcctctccct caagggtcgg ggacccttggc tggagtcctg accctgggct    300
cccagacaga gatcttcgcc ttcctttgct gtgaggcaat cttttggcac acctgggatt    360
tccccatgac ccaggtcatt tttttttgt tcaacggact ctggactctc aaaaggatct    420 gatcctttg aattttgcac agccct                                          446
```

<210> SEQ ID NO 119
<211> LENGTH: 552
<212> TYPE: DNA
<213> ORGANISM: Bos Taurus

<400> SEQUENCE: 119

| | | | | | |
|---|---|---|---|---|---|
| gcacgcctta | acagtgctgt | tgctcagact | attctctagg | acttgaattt | ggagcagaaa | 60 |
| caaaacagca | cctggtcctc | agttacagag | tggggccttg | gttaggataa | atcaaattat | 120 |
| tgagtttact | gagggaaca | agcatctggc | ttctttcatc | ttagcatctt | taaatctgag | 180 |
| aatgctagct | gagggtgaaa | agcctgggga | taggcctgcc | tgaacactcc | tctgctgctt | 240 |
| attacaatct | tagctgagca | ccttcaaacc | ctggttcctg | tatatgcaaa | tagttcccaa | 300 |
| taatagcatt | atcttataag | acttgacagg | aagctaaatt | atgaagcatc | tcgcccaggt | 360 |
| cctgacacct | gggaggtgct | gaatactggt | cagcttcttc | cgtaggtacc | cgccagaaaa | 420 |
| ggtggcaggg | gactgaacca | tatatctgac | ctctgcgagc | ctttccagtt | cttagattat | 480 |
| gggggtcagt | ggtataattt | aggtttgtta | acagcagtag | ccagtattgg | agttatttac | 540 |
| cacataatcg | ag | | | | | 552 |

<210> SEQ ID NO 120
<211> LENGTH: 546
<212> TYPE: DNA
<213> ORGANISM: Bos Taurus

<400> SEQUENCE: 120

| | | | | | |
|---|---|---|---|---|---|
| ttttgttgaa | ttgatttaaa | tattttattt | aaggaaatat | tctgaagact | atagttcatt | 60 |
| atttatagga | aaaatataaa | gcatacatgt | ttaaagatca | ttttgtagtg | acattatagg | 120 |
| aaatagattt | ctccaaataa | cataattagt | tttgtagtgc | taccagtgga | atgcattctg | 180 |
| cagaaacatg | gttttacctt | cagatctgag | cacactgccc | ttacatcaaa | aaagaaaaa | 240 |
| aggataataa | aaaaaaaaa | cacaactttg | attagtttaa | attttagta | gaccacatct | 300 |
| gatttgttga | agagcaagtt | cttttatta | cctcttcaag | gaagtgctta | ttttttcac | 360 |
| ctctttctga | gcatctttat | cctctttggt | aatacaagga | agcaacaccg | ccaaattaca | 420 |
| gaacttcata | gcactgtcga | tttgattaag | atcggcataa | cacttggcca | tgaacatgta | 480 |
| attggactta | gaaaacccag | gctgtagttc | ttcaacctta | aggaaatttt | gcaaagcttc | 540 |
| ttgtac | | | | | | 546 |

<210> SEQ ID NO 121
<211> LENGTH: 394
<212> TYPE: DNA
<213> ORGANISM: Bos Taurus

<400> SEQUENCE: 121

| | | | | | |
|---|---|---|---|---|---|
| ggcttcttgg | ggctgcggcc | cacgtcagtg | gatccagcgc | tgaggaggcg | gcgacgaggc | 60 |
| ccaagaaata | agaagcgagg | ctggaggcgg | ctcgctcaag | agcctctggg | actggaagtc | 120 |
| gatcagttct | tggaggacgt | gcggctgcag | gagcgcacga | gtggccccct | ccgatctatg | 180 |
| gctgacattc | tgcatttcca | tctcccagtg | gcttgtatc | agaggccccc | gatgagaaac | 240 |
| ttttcttcgt | ggacactggc | ttcaaggata | agaactgaa | caagaagagg | accaaaggcc | 300 |
| agaagaggtc | actgcttctc | aagaagcccc | tccggagcga | cctcatccta | gagaacacct | 360 |
| ccaaggtccc | tgttcccaaa | gacgtcctcg | ccca | | | 394 |

<210> SEQ ID NO 122
<211> LENGTH: 392
<212> TYPE: DNA
<213> ORGANISM: Bos Taurus

<400> SEQUENCE: 122

| tggacggccg agtgcagctg atcaaggccc tcctggccct gcccattcgg gctcagacac | 60 |
| gtcggtggag aacccgatc cccttccccg agacgtttga cggcgacacc gaccggctcc | 120 |
| cggagtttat cgtgcagacg ggcgcctaca tgctagtgga cgagaacctg ttcaccaacg | 180 |
| atgccctgaa ggtgacgttc ctcatcaccc gcatgaccgg ccagctctg cagtgggtga | 240 |
| tccctacat caggaagcag agccccctcc tcaacgatta ccggggcttc ctggccgaga | 300 |
| tgaagcgggt gtttggatgg gtggaagacg aggacttcta ggccgggagc gcctcgggtc | 360 |
| tgggggcggg tgctcggggg agggtccgcc gc | 392 |

<210> SEQ ID NO 123
<211> LENGTH: 408
<212> TYPE: DNA
<213> ORGANISM: Bos Taurus

<400> SEQUENCE: 123

| catttttca gcggatcaat tttcagatcc tcaacttcct gttgcactct atccaaagat | 60 |
| tcatcagtgt gagaaaatgc cctttctcc ccttacagaa ggaagtaggt cttctcccca | 120 |
| cattcagtct tactctagag caggactcaa gatacaattg agtatagtgt ctggaaagtg | 180 |
| caagcctctt aacaggatac gggtcctcct ccagtgctgg tggtttccag ttccttgctt | 240 |
| tcaacaaaac tgaaggaata cccagatttc tgagtatcct gagattaccc tgctaccact | 300 |
| aactccttct gttctcattt gtctgtgtga aaaaggatc attcgcattt ccatttgtaa | 360 |
| aactgaaaat ggagaacaga atcgacactg tatcgctgcc gttctgcc | 408 |

<210> SEQ ID NO 124
<211> LENGTH: 239
<212> TYPE: DNA
<213> ORGANISM: Bos Taurus

<400> SEQUENCE: 124

| ttttttttt ttttcctgat aacgtgcttt taattacgtc cattccaaag atacctcctt | 60 |
| tcccagttaa agacgacgcg tggtgaggcc tggctgtgtg tctgcagagg gggcggcgag | 120 |
| ctccacacgg gggccagctc ctcccaggcc tcactggccg tcacgccaca gcggctggcc | 180 |
| tggggcgctg ctccctgctg gcagccccag gccctctggg ccccgacccc cttgggggg | 239 |

<210> SEQ ID NO 125
<211> LENGTH: 227
<212> TYPE: DNA
<213> ORGANISM: Bos Taurus

<400> SEQUENCE: 125

| gaaagaacaa atgctcggaa gaaaacaat cacagtgaaa ggaagtacta ctactatgaa | 60 |
| aggcatagat caaggagcct atctagtaat agatcaaaga ctgcatctac agggcctgac | 120 |
| cgggtgagaa atgaaaagcc tggtgggaaa cgaaaataca aaacacggca tttggagggt | 180 |
| actaatgatg ttgctcaacc atgtcatgaa tttgcttcta agtaaa | 227 |

<210> SEQ ID NO 126
<211> LENGTH: 631

```
<212> TYPE: DNA
<213> ORGANISM: Bos Taurus
<220> FEATURE:
<221> NAME/KEY: modified_base
<222> LOCATION: (490)..(491)
<223> OTHER INFORMATION: a, c, g, t, unknown, or other

<400> SEQUENCE: 126
tacagatgag gaaattaagg cgagagaaac tagggaattt gcctgaggtc acgtaggtct      60
cgtgtcaaaa ccagtttata ttaataaaac cttattttca tttaatgatg atatagggggg   120 aaaaaaaaaa cagtcctagt aacatcatta gctcagagag gagtgggcag tgtccttctg   180
aaatggattt tcacataatg gcattttaga aggtatttaa atcatacaga tctgacccgt   240
tctgggtatg gttttatgca aagaaatctt aatgaagttt tcaacatggc tcctaatttg   300
ggggcatttc atggttcaaa ttttggtcc cttctggaac ttcaaggtgc ttccaattaa    360
caataacttt gaacactgac tcctgcagta tggtatgcct cccctgccag gtgggctttc   420
tgtggatact catggcactc tacgtgcccg caaccaagac aagcagaggt tcaccactgt   480
attccccagn ngaggtatgg cattgattta aaacttcaac attatttttcc aggttgagaa   540 actgaaaca tcgagcaag taagcctaaa aatagccttg tgtttttctg gttactatat    600
ctttcatata gaactcaaaa ttagtgaaaa g                                   631

<210> SEQ ID NO 127
<211> LENGTH: 498
<212> TYPE: DNA
<213> ORGANISM: Bos Taurus
<220> FEATURE:
<221> NAME/KEY: modified_base
<222> LOCATION: (225)..(228)
<223> OTHER INFORMATION: a, c, g, t, unknown, or other
<220> FEATURE:
<221> NAME/KEY: modified_base
<222> LOCATION: (440)..(441)
<223> OTHER INFORMATION: a, c, g, t, unknown, or other

<400> SEQUENCE: 127
tttttttttt tttttttgag cagcgcttga tttattagca ttaaaaaaac ccagttcata    60
tatacaaaac aagctgattt ttgttgtcaa gtgttaaaag cactcctta aaattaaata   120 caatttaaag catggattaa tgagttgatt tcctgggaag cacttcagtg aatgaatatt   180
tgccaatgga aacatcagat gcacaccacg cgggcaccag ggggnnnngg gatccacagg   240
gctgctcatc acagcgtctg acccagaca ctgtaggtgc cacacacgtc cccggtgggt    300
attcccgcta agacccaggg cggggggcacg acctgtgaaa attcacttgc acgttagaat   360
aacgaccaac ttcagctgca acttaaacct cgccccaggc ccaccgcagc tgcaccgatg   420
agccgtgaca ctcggggcgn ncagtgaaag ttcgctggac aatgttgtgt gaacgtccat    480
gctcggctgt gggcccg                                                  498

<210> SEQ ID NO 128
<211> LENGTH: 534
<212> TYPE: DNA
<213> ORGANISM: Bos Taurus

<400> SEQUENCE: 128
attcatatga agctacagag ggttctggac tgttagtggg tttaggaacc agcccatcaa    60
cgtcagtcag ccctctgagg atgggcgtat ggccggaagt gtccattctt cactgtggct   120
ggtctgtggt gaagtggctg gtctacggtg aacgtgctct aaggcatctg ctcaggagga   180
```

| | | |
|---|---|---|
| aagggctctg atcagtatca cattaattaa gataattaga aaaatggagt aactggcaga | 240 | |
| gaaagaggaa agcggtaatt tactactata tatgggatct aaaaacagac ccaacagaag | 300 | |
| ttcattattt gccaggagcc agtgtgagga gctccgcccg tggcaaaggt catgaggaag | 360 | |
| gaggctcggc acacgcaaag gcgggatcaa gcctcaggag tcccctgga aattctcgag | 420 | |
| cttctacccc caaaccagag tctgcctact ttctgctttg tgctctcacc tacacctctg | 480 | |
| actttacggg gggctgtccc ctaccacctc tctctgaaaa gagttaaatt acag | 534 | |

<210> SEQ ID NO 129
<211> LENGTH: 562
<212> TYPE: DNA
<213> ORGANISM: Bos Taurus
<220> FEATURE:
<221> NAME/KEY: modified_base
<222> LOCATION: (454)..(454)
<223> OTHER INFORMATION: a, c, g, t, unknown, or other

<400> SEQUENCE: 129

| | | |
|---|---|---|
| tattttgcca ggttcccggt ctcaaatgca caggcttgga ttgctttaca tcatggtatc | 60 | |
| ttcccatcct gggtggacaa accggcaatg agttaagatt acagccccctt aatcctaccc | 120 | |
| agcactagtc acactggaga ccttggggtc acccaacttc aatctgggga tcccagaagg | 180 | |
| ttgacctgcc tcaacctgcc tagggatctg gtccccctgga ggttgtcacg cctcagcctg | 240 | |
| ctcggagatc tgccagtcca ggggtcccag gaggttgacg tgcctcgacc tgcctgagga | 300 | |
| tctgcaccct gacccaggga agcccagctc tcaggttgca acagtactgg gtaggataag | 360 | |
| cttcagaaag actcacccct aagtaagtcc acccatggaa atagaaggaa gcctattagt | 420 | |
| tgtgggactg tgcccagttt caacaataac tcangagtcc aacaagaacc ccattgccct | 480 | |
| tctggaaagt ctaaagagg ccctcccaaa gtttgccaat ctggacttag actcttacga | 540 | |
| gggacaggtg attttaaagg ac | 562 | |

<210> SEQ ID NO 130
<211> LENGTH: 556
<212> TYPE: DNA
<213> ORGANISM: Bos Taurus

<400> SEQUENCE: 130

| | | |
|---|---|---|
| tttttttttt tttttaaat atgaagcaga aacataaggt ttggggaggg atagcaggaa | 60 | |
| agaaatgaca tcaattttat ctttacatat tcccctcctc taggcagttc tccagacatc | 120 | |
| agatctctta acttggggtg tggatcagct ttcatactca taaaggggac cagttcttta | 180 | |
| aacatgcata agcctggaga ctccaggatg gttctcctcc ctctctttaa atgctgtgga | 240 | |
| ctagaaaggc gcccactttg ctaaaaactc tacatcagtg tccctggagc cccgaggctc | 300 | |
| ctcaggttcc tcctgaagac ttaaaggata gcacagaaaa acttcttctc cctaaatggg | 360 | |
| ttttctgaag ccggaacagg tgtcaggagg ggatcttcct tggcatgcgc ttcacagtag | 420 | |
| gccatcaaat ctgcagctgc cttggacacc tttatcctat cgatgttggc ttccatcttc | 480 | |
| agctgttcta ccagtttcct ggcttgtgct atgctggcgg tgttgttgct ggccattgga | 540 | |
| atgctgggta ggtttc | 556 | |

<210> SEQ ID NO 131
<211> LENGTH: 248
<212> TYPE: DNA
<213> ORGANISM: Bos Taurus

<400> SEQUENCE: 131

```
aagagtacca gactcgggag cagcttcgag cccgctccct gcagggctgg gtctgctacg    60
tcacctttat ctgcaacatc tttgactacc tgagggtgaa caacatgcct atgatggccc   120
tggtgaaccc tgtctacgac tgcctcttcc ggctggccca gcccgacagc ctgagcaagg   180
aggaggaggt ggactgcctg gggctgcagc tgcatcgggt cggggagcag ctggagaaga   240
tgaatggg                                                             248

<210> SEQ ID NO 132
<211> LENGTH: 426
<212> TYPE: DNA
<213> ORGANISM: Bos Taurus
<220> FEATURE:
<221> NAME/KEY: modified_base
<222> LOCATION: (59)..(61)
<223> OTHER INFORMATION: a, c, g, t, unknown, or other
<220> FEATURE:
<221> NAME/KEY: modified_base
<222> LOCATION: (356)..(357)
<223> OTHER INFORMATION: a, c, g, t, unknown, or other

<400> SEQUENCE: 132
ggcaccaaac ccaaaaccgc agtgcccaag tcacaagcca cggaggagtc tatgaagcnn    60
natgtaaagg agaaacaatc gcagaagata tctagatcaa acaaaataga caaagaaagc   120
caaaagccac ttgaagttaa aaaagtcttg tctgaccgta caccgtgggg attgtccaca   180
catcctgctg gcggtctggc gcccacccca tcaacaggaa ccagagccgg ggggcagcct   240
ccagcccctc ctcctgaggc cagagggagc cttttggaga acaagtacc agaagcagat   300 ggggagctgg ctcttcccct gttcaaaaca gaaaaattgg aaaagcaggc agcagnngga   360
atcttaaagg ctgaggaaga gattttggaa gatcagctgc ccatgcaaaa tttgaagcca   420
gccccct                                                              426

<210> SEQ ID NO 133
<211> LENGTH: 453
<212> TYPE: DNA
<213> ORGANISM: Bos Taurus

<400> SEQUENCE: 133
tgaattgcta caccctcctt caggtgatct tccgaaccca gggatcaaac ccacggctcc    60
tgcagctcct gcactgcagg cagattcttt actgctgagc caccagggaa gccctagagt   120
acataggctg agtataaatg tcatagatca gaaggggcct gcttctttga cattccctag   180
atcctgcctt gaactgccat ttggtcatta attccacatt ctagtcatct acacaaatct   240
taaaggtatc acatcttctg tgtttgtttt aaagcgacca gtgaagacta taagctcctg   300
gaaaatatga ataaactaac cagcctgaag tatcttgaaa tgaaagatat tgctataaac   360
attagtagaa acttaaagga cttaaaccag aagtgtaagt aataaatttta caattaaaca   420 tatttgtttg tatttaatgt tcatttgtgc ttg                                  453

<210> SEQ ID NO 134
<211> LENGTH: 552
<212> TYPE: DNA
<213> ORGANISM: Bos Taurus

<400> SEQUENCE: 134
ggaaaatggc ggattcctcg ggcgggggcg ctgggaagcc tcctgcagtg ggccccagta    60
ctgctagggg tgctaggagc aaaggaagaa cacaaggtgg aagaatagtg gagtcgcggt   120
```

| | |
|---|---|
| acttgcagta tgaaaagaaa gcccccagaa aggctcctgc agcagatgca ttaaaggccg | 180 |
| gtgggacgat gcctgcaggt ggaacaaaat ccagccagct ccaaaagagc aaagatggca | 240 |
| gtgggcttga caaaggcaac ctgcagtcta ccttgctgga ggggcatgac actgccttgt | 300 |
| ctgacctgga tctctcagcc attcatgata aaagtgtggt ccgaaagact ccacaactaa | 360 |
| aaaaaaagtc aaagaaagcc gagttgtcat cctcttctgc tgtgagtgaa aagagcccag | 420 |
| atctgttaca agcaatggaa atgatggagt cccagactct ccttctgacc ctgctgaccg | 480 |
| tgaagatgga gaatggcctg tctgcattcg aagaacaggc agaaaagaac ctagaaatat | 540 |
| tgtgtaaaga ga | 552 |

<210> SEQ ID NO 135
<211> LENGTH: 437
<212> TYPE: DNA
<213> ORGANISM: Bos Taurus

<400> SEQUENCE: 135

| | |
|---|---|
| tttattgagt cagctcatga tcagaagtct actcatacct tgatcattgc aaaggaagta | 60 |
| gacccctgtc ctttatctct tccctttct gtaagctcca ggccctggcc atgcaattgt | 120 |
| cttcatcctc tcctagtcca gttagtgaac cacttctcca cataaccata gcctccgctc | 180 |
| tgctggcttt ttttgttcct tgccatggga gtatgtgcaa ggccagtgca tggatgtgaa | 240 |
| aacctgtcac ttgccaggtc acaaaaagga gtcatcacta cccttactgt ccgaagccct | 300 |
| gagctgtatt ctggcctcac tctaaaatgg tcctgtccta gagctgatgg ccaagcagta | 360 |
| agctgcaggt gtgggtgcca caggtaattc tggaaggagc acaggggat ggtcgagcca | 420 |
| gcttggacca ccatcta | 437 |

<210> SEQ ID NO 136
<211> LENGTH: 524
<212> TYPE: DNA
<213> ORGANISM: Bos Taurus
<220> FEATURE:
<221> NAME/KEY: modified_base
<222> LOCATION: (291)..(293)
<223> OTHER INFORMATION: a, c, g, t, unknown, or other

<400> SEQUENCE: 136

| | |
|---|---|
| atgttcctca ccatgtttgg ggagaagctg aacggcacag accctgagga cgtgatccgt | 60 |
| aacgccttcg cctgcttcga cgaggaggcc tcaggtttca tccatgagga ccaccttcgg | 120 |
| gagctgctca ccaccatggg tgaccgcttc acagacgagg aggtggacga gatgtaccga | 180 |
| gaggcgccca ttgataagaa aggcaacttc aactatgtgg agttcaccg catcctcaaa | 240 |
| cacggcgcca aggacaagga tgactaggcc atcccagcgc ccctgcccg nnncctgtcc | 300 |
| cagccacctg ctcccacata taccgtatgc accagctcca tgcccatgag cccagagccc | 360 |
| cctctcagag gactctcccc ctgaggggcc ggggcccag ctccgagtga aggaaacggg | 420 |
| ctgagaaagc acagcaccag gccaggggca gagccagcgg gaggccggtg accctccaag | 480 |
| gaaaccccat cttctcggga gctgggccag ggggctggac cggg | 524 |

<210> SEQ ID NO 137
<211> LENGTH: 561
<212> TYPE: DNA
<213> ORGANISM: Bos Taurus

<400> SEQUENCE: 137

| | |
|---|---|
| aagcccatca cctttcctga tggacgctcc ttacctgcag gaatcttagt ctccctctcc | 60 |

```
ttttatggac ttcatcacaa cccaaacgtg tggccgaatc cagaggtgtt tgacccaacc      120
cggttctcac caggttctac tcaacacagc tatgccttcc tgcccttctc aggaggatcc      180
aggaactgca tcgggaagca gtttgccatg aatgagttga aggtggccgt ggccctgacc      240
ttgcttcgct ttgagctgtc accagatccc tccagggtcc ctgtgcccac tccaatcatg      300
gtgctgagat ccaaaaatgg gatccacttg cagctcagga aactgtctga tccaggactt      360
ttgtgattag atgaacaact catataagac agacttgttc tcctgtctgg tgattaggat      420
gaggacacct gggcagccat tgctggacat gttaagtctt gtgtgaccac catcagcctg      480
tctccggctc tctccagtgc ctacccatgt gtcagtcatg tggcttcccc tctcttgctc      540
tcccttaata aagtttgcat g                                                561
```

<210> SEQ ID NO 138
<211> LENGTH: 515
<212> TYPE: DNA
<213> ORGANISM: Bos Taurus
<220> FEATURE:
<221> NAME/KEY: modified_base
<222> LOCATION: (232)..(234)
<223> OTHER INFORMATION: a, c, g, t, unknown, or other
<220> FEATURE:
<221> NAME/KEY: modified_base
<222> LOCATION: (428)..(429)
<223> OTHER INFORMATION: a, c, g, t, unknown, or other

<400> SEQUENCE: 138

```
gctcacaata tatgccgcat tgcccttttgt caggcaggct ggcctgtact ccatcagttt      60
acctaacaaa tacaatttct cctttgatta ttatgcattc ctaattctga taatgatctc      120
ttacattcca cttttccccc agttatactt ccacatgata caccagagaa gaaagatcct      180
ttctcatact gaagaacaca agaaatttga atagttcctt cttcctgcac annnccagaa      240
acaaactttc caatgacaaa aaatgctgca gacttttca gttcccaata cgtttcatag       300
aaaataagta agaactattt ttaaatacta aaaaaataaa taaataaacc aaaatccagt      360
gtcatgtggg cctggggttt tctaaaaaac aaaacaaaaa aacgaaagct gttacataaa      420
acatcctnnc cggtccattt cagcatgctc tttcaaccag aagttcccaa tatttatgat      480
ggcgctggaa agggatttgg cattttatat cctcc                                515
```

<210> SEQ ID NO 139
<211> LENGTH: 658
<212> TYPE: DNA
<213> ORGANISM: Bos Taurus

<400> SEQUENCE: 139

```
gttatctgta cctggacttg ctgctatggg aaccagctgt tgtttgtaca acaccttga       60 aaactttgaa acctgacccct ttgaaacctt acccttatc accttttacc gcgtgccagg     120 cccttctga ctttcactgg ttgactctgc cccttcctt cccagagctg gctggaccat      180
cgctctctgg tgacccgtgg aagttaggcg cacagcagct tccagctgcc atgcagagac      240
ctccagctca gaacaggctc gtctccgcca cgcccagacc ccctcctgtt cctcaaccag      300
tttctctctg cgactcggaa gcgatgcaac caggaagaa accttttatc aacatgggcc       360
cttgtccaca tgtctggtct taagacttca aggggccctt gaaagccaca ttttgatgag      420
tttggtgtaa aatgagttgg gcacacaggg atttaatttt ccttgaaaac tgcacagcct      480
tagaaattag cagagtaaaa attaatggtg aaatgggtgc ttaatcctcg tcaaccccct      540
```

```
aagttttttta ttgaaaatgg gcaagattgt taattcaagt gctctttggc tttggtgctt    600
gagcaaaagg atggactctc tccaagtctc cattaactcg tgggaagatg gggctttg      658

<210> SEQ ID NO 140
<211> LENGTH: 374
<212> TYPE: DNA
<213> ORGANISM: Bos Taurus
<220> FEATURE:
<221> NAME/KEY: modified_base
<222> LOCATION: (193)..(193)
<223> OTHER INFORMATION: a, c, g, t, unknown, or other
<220> FEATURE:
<221> NAME/KEY: modified_base
<222> LOCATION: (219)..(221)
<223> OTHER INFORMATION: a, c, g, t, unknown, or other
<220> FEATURE:
<221> NAME/KEY: modified_base
<222> LOCATION: (328)..(328)
<223> OTHER INFORMATION: a, c, g, t, unknown, or other

<400> SEQUENCE: 140 ttttttttt tttttgcagc aatgacattt aatacttctg gaatgattgg gtatctgaga     60
acacgctgtg ggcggctatg ctgggctccc ggatgtggga gctgggcccc gcctcccgaa   120
ggggtccctg cccgggtggg aggagcgggc ggcgcggcgg gccctgaccg gcaggcgggc   180
agcccgggcg gcngcggagc ttccagaatg gcacagcann nggcccatgg agaggcttca   240
aggaccggag ggtcgacacg ctcggccggg gccaaactcc atgccctcga cgtccacttc   300
ttgctccgag tcgtcggtgg agacggcnga gcccgtgctg tcggtgcgca cgcgctccag   360
gctctgcgcc gaca                                                     374

<210> SEQ ID NO 141
<211> LENGTH: 531
<212> TYPE: DNA
<213> ORGANISM: Bos Taurus

<400> SEQUENCE: 141
gcacgagccc agttgagcgt ggggaagggg atgaacagcg gttacaggag gttactcagg    60
aacaaggaac cctctgagat cttcagaacc tgcactgtga aagacagac agacaaacaa    120 acctaaggat taaaggcaca ctgcttatca tcaggcttta caactcacac aggcaatgcc   180
aagactttgg tatggatcag ctgccatgtt tgcccatgca ggaagagagg ggtttggtta   240
caccaatgta cgcatttctc aacaggccaa accatctgct tgggatgtgt ttctcactgt   300
atgcaaatgt cctcagaaga aacaggagct acaaacacac actgtactct agttaaggac   360
tggccagctg gagggtctac tggtgacgtg aactggaact ttctctgcaa tgcatctccc   420
aaaataagat gggctggtgg acggacagag gcagagacag ctgtgtgatg tcggtgacaa   480
aagccacggg taggtgttca ggcgttcatg gctctttcga cttctctgca t            531

<210> SEQ ID NO 142
<211> LENGTH: 544
<212> TYPE: DNA
<213> ORGANISM: Bos Taurus

<400> SEQUENCE: 142
gctgatggac ctggtggagc gccagctcgg gcctggcctc acggagcctc gagccttgca    60
gctctgcggt ggacgcgctg caggccgtgc ttgtccgcgg tggcaatgag gatgtggtcc   120
agtgcatgga gctggacggg ggctggcagt tgctcaggac ctcggctggg cacgaggaag   180
gtgtcacccg gctggccagt gccatggcaa agttcgcagg cccccggctg ccctggtga    240
```

```
tgaagctgct cttcaccaca cagagtagca tgtatgaggt ccagagggtc acctccacag    300
ccttcctggc tgagctgctc agcagcaatg tggtgaacga cctgatgctc ctggagtcac    360
tgctgtacaa cctgatggca cggcagaagg acacgagcgc ccgcgtgcgg aggctggtgc    420
tccacggcct ggccaacatc accttgggct ccccagataa ggtacagacc cacagccccc    480
aactcctgac agccatgatc ggtgggctgg acgacgggga cgacccacac agcctggtgg    540
cgct                                                                 544

<210> SEQ ID NO 143
<211> LENGTH: 464
<212> TYPE: DNA
<213> ORGANISM: Bos Taurus

<400> SEQUENCE: 143
gcacgagccg acccctgcct ttctcctttg gggtggtcgg acctagcatg atggggactg     60
aggccgaggg gagacaggcc cccgtcccaa gctgctgctt cctcttggct gtttgcgggg    120
agttggaagc ctggacaccg ttcttagggt ctccggcttc tcccctccct gcccctctc    180 tcttgcttgt gatcgcccag gctctgtcac agcccagcct tctccaagca gcaggaggcc    240
tccactgctc taggcagctt cgtttgctgc tgcagcctgg aaacgagttg tccacgccag    300
tggcagagac caaaaccccg gttttaggcc gggtgttggg aggacagact ggccaaagcg    360
ggggatagac gaggggggccc ggtgtccttc aggatagcgg gcatgtgcag gacccggggt    420
ctggggcaca gggaatgcaa ccccgctggc cagccctggg gcac                    464

<210> SEQ ID NO 144
<211> LENGTH: 599
<212> TYPE: DNA
<213> ORGANISM: Bos Taurus

<400> SEQUENCE: 144
acctgaggtt ctccgagatg agccctacaa tgaaaaggcg gacgtgttct cttatggtat     60
catcctctgt gagatcatcg cccgcatcca ggctgatcca gactatcttc cccgaacaga    120
gaatttcggg ctagactatg atgctttcca gcacatggtg ggagactgtc ccccagactt    180
tctgcagctc accttcaact gctgtaatat ggacccaaaa ctacgcccat cctttgtgga    240
gattgggaag accttggagg aaattctgag ccgcctacag gaggaagagc tggagagaga    300
caggaagctg cagcccacag ccaagggact cttggagaaa ggacctgggg tgaagcgact    360
gagcttactg gatgacaaga taccgcccaa gtccccacgc ccaagacgta ccatctggct    420
gtctcgaagc cagtcagaca ttttctccaa taagcccca cgtacagtga acgtctttct    480
gattaactcc ctgagtaaac tgttataata atgaaaaatg tgctactcat ggcagtagta    540
ggtcacagag atgccttttc tgtgatgtta ctggctctga ttcttcattc agtattttt    599

<210> SEQ ID NO 145
<211> LENGTH: 492
<212> TYPE: DNA
<213> ORGANISM: Bos Taurus

<400> SEQUENCE: 145 ggaggggggcc tcagggtgga agagcaagag cgggaccaca cctgcctcct cactcactgc     60
ccctctccct gtcccatgca gggcgactcc cacaagcttg actttcggaa cgacctcctg    120
ccctgccttc cggggcccta tggggccctg ccccctgggc aggagctctc ccaccggcc    180
```

```
gcctccctct tcactgcgac tggtgccgtc catgctgcag ccaacccttt cacggcagct    240 cccgggccc  atggacccctt tctgagtccc agcacccaca ttgatccctt tgggcgtccc    300
acaagcttcg cctccttggc tgccctctcc aacggggcct ttggaggcct gggcagcccc    360
acattcaact ccggcgccgt ctttgcccag aaagaaagtc caggggcccc accagccttc    420 gcctccccc  cagacccatg gggccgcctg caccgcagtc ctctggcctt tcctgcctgg    480
gtccggcccc ct                                                        492

<210> SEQ ID NO 146
<211> LENGTH: 397
<212> TYPE: DNA
<213> ORGANISM: Bos Taurus

<400> SEQUENCE: 146
cggggtggtg tacgccctct gggactacag tgcggagttt ggggacgagc tgtccttccg     60
agagggcgat tcggtcaccg tgctgcggag ggacggacta gaggagacgg actggtggtg    120
ggccacgctg catggccagg agggttacgt gccccgtaac tacttcgggc tcttccccag    180
ggtgaagcct cagaggagta aggtgtagct ggagagaagg acgtttccaa gggagacagg    240
atgaagcagc agctgccttc gctccagacc tcctcctcct cttccgctgc atatctctgt    300
acccccaagc ccttgcagcg gtggggtcct tgccaacagc tctccggaaa ccctggggag    360
aacgagaacc ccagccttaa acttagaagc ctgcctt                             397

<210> SEQ ID NO 147
<211> LENGTH: 486
<212> TYPE: DNA
<213> ORGANISM: Bos Taurus
<220> FEATURE:
<221> NAME/KEY: modified_base
<222> LOCATION: (458)..(458)
<223> OTHER INFORMATION: a, c, g, t, unknown, or other

<400> SEQUENCE: 147
gcttcctgaa tggaggcgag atgaaggtag aacagctatt tcaagacttc agcaacagaa     60
gagctgacaa ccttcagtcg gatggtgtca acgactctga aaaatgctct cccaccgctt    120
ctcaggagct ccggagatca tcctgggaag ccgctacagc acacccatcg acatatggag    180
ttttggctgc atccttgcag aactttaac  aggacagccg ctcttccctg gagaggatga    240
aggagaccag ctggcctgta tgatggaact tctggggatg ccaccagcaa aacttctgga    300
acaatccaaa cgtgccaagt actttattaa ctccaagggc ctgcctcgct actgttctgt    360
gaccacgcag gccgatggga gggctgtgct tgtgggaggt cgttcgcgga ggggtaagaa    420
gcggggtccc ccaggcagca aagattgggt gacggcantg aaagggtgtg aggactactt    480
atttat                                                                486

<210> SEQ ID NO 148
<211> LENGTH: 380
<212> TYPE: DNA
<213> ORGANISM: Bos Taurus
<220> FEATURE:
<221> NAME/KEY: modified_base
<222> LOCATION: (288)..(290)
<223> OTHER INFORMATION: a, c, g, t, unknown, or other

<400> SEQUENCE: 148
atttctgttt tatctttaag gtcttttttgg ttcatcacgg gtacagtatg ttgtagatca     60
tgcaatgaaa attgtctttc tccacaccga tccctccatt gtcatgacct acgacactgt    120
```

```
tcaaggtctg cactctgtgt gggctctccg gagagtcaaa acagaggtaa gggtgaaggc    180
aagtcacttc ttaacagaag aagatagtta atactgaaaa cttgcatatt tttttttttt    240
ttgctactca ttaaaaatta ttttaaaat ttgtttattt ttaattgnnn gataattgct     300
ttacagtatt ctcttggttt ctgccataca tcaatatgaa tcagccatag gtatacatat    360
gtcccctccc ccttgaacct                                                380

<210> SEQ ID NO 149
<211> LENGTH: 328
<212> TYPE: DNA
<213> ORGANISM: Bos Taurus
<220> FEATURE:
<221> NAME/KEY: modified_base
<222> LOCATION: (34)..(35)
<223> OTHER INFORMATION: a, c, g, t, unknown, or other

<400> SEQUENCE: 149
acagccaggt gccgctgaga gaggtgaaga accnnagaca gcaggagaga cacagtgggg    60
atctcggagc aggagtgtgg gtggccagga gcctggggcc gcccgaggga cgtgcttaca    120
tgggatactg tctgtgaggc gcttggaacc gtacctgatg gtgggaagca atcagtaaag    180
accgttactg ccacctgctg aagtcttgcc ttttccagtc cccactgctc agggtctccc    240
gccccggcac cgttcaggct ggacgatcgc tctcctgctc ccgtctcacc cctacatctc    300
ctctccacgt gctgcccgat ggagcctt                                       328

<210> SEQ ID NO 150
<211> LENGTH: 255
<212> TYPE: DNA
<213> ORGANISM: Bos Taurus
<220> FEATURE:
<221> NAME/KEY: modified_base
<222> LOCATION: (52)..(53)
<223> OTHER INFORMATION: a, c, g, t, unknown, or other
<220> FEATURE:
<221> NAME/KEY: modified_base
<222> LOCATION: (180)..(182)
<223> OTHER INFORMATION: a, c, g, t, unknown, or other

<400> SEQUENCE: 150
agattaaaca ttttatataa atgactctta aagctttaca ccttggggcc anngtactcc    60 tgggcagaa tacatttaga tataaaagac gttattaata cattgcacag ttgtcaaact     120
ttaaacacga aaccgaacgc tgctcgcggc agctgccgcg ggttgctgct acatggacgn    180
nnccagccga ggcccagcgc tcctctcctg tccactgccc aacgggctcc gtcagggctc    240
tttgagcacg aggct                                                     255

<210> SEQ ID NO 151
<211> LENGTH: 552
<212> TYPE: DNA
<213> ORGANISM: Bos Taurus

<400> SEQUENCE: 151
gcacgaggta aaagcaaca atcaactagc cgaaaacgag cctctaaatt ccgtctcact     60
ccagtgccgt cttctctaaa gtttgctcca cggtccagtc acagttctca ggggtcctgg    120
cggtctccca acgctgtgtt ccacaggaaa acagggtcca caggaaggca ggtcatgcgg    180
gacgccctgg gtaagcacct gtacagcggg gataccgcgg ggtctcagtt ctcctccggc    240
ttgtcggctg gtgggccgca aggctgcagc atcttctcca tcaagttgaa gcggactcgc    300
```

```
gctttgctct cattctcggc aatggcgaag tagttgagaa gatcgaagtg gcccatgtag      360
gagcagtagg agtcgcggtg ctggttcacc agccattccc acttcgtggt gtccgcgtgg      420
ccggtgccga tgtacttgga ctgcagatgc tctagctggc tgtgaatggt gtagcggtcc      480
gtcatctcac cgcttttccc tttgctccca ggtgaaaggc agccgactac aggcactcgc      540
tctggaactt ca                                                          552
```

<210> SEQ ID NO 152
<211> LENGTH: 511
<212> TYPE: DNA
<213> ORGANISM: Bos Taurus

<400> SEQUENCE: 152

```
ttgatgaggg ccagaaccag gcctggcgtc acccctgggc cccacctgct tctcgcccac       60
cccagggctg gagcgaccca tagaggtgcc acctcccctt ctgatggcag ccccagccac      120
gctcccccag ccaagtgctc tccctcagac agccagagac acctggaagc ctccctgctc      180
ccaccattcc tgctgggaac cctgaaggtc tctcagaggc ttgcaccctg tggccttgct      240
ccctccggtc ctgggacccc cagtgctgtc cctgacgtct gtctggggct cacctgcgag      300
gagccgtttc ctgagctgcc ccattacccc tccccccaac taccccaggt ggtggtcctc      360
ctgcttcaag ccttgcaggg cctgggcaca ggtaggcagg cagatcctgc tgctctgcca      420
accgccccgc tggcacctag tggtgtttag ctgtgctggt tgaatgtcag caccctctgc      480
aggcactttt aaaggagtgt ttatgttgct g                                     511
```

<210> SEQ ID NO 153
<211> LENGTH: 355
<212> TYPE: DNA
<213> ORGANISM: Bos Taurus
<220> FEATURE:
<221> NAME/KEY: modified_base
<222> LOCATION: (116)..(118)
<223> OTHER INFORMATION: a, c, g, t, unknown, or other

<400> SEQUENCE: 153

```
gcacgaggaa gaagatcctt tgcgagaggc atgttctcgt gaggatcttc ttcatccctc       60
tccagaagag gagaagagga aacacaagaa gaagcgcctg gtgcagagcc ccaatnnnta      120
tttcatggat gtaaaatgcc caggatgcta taaaatcacc accgtctttta gccatgcaca      180 aacagtagtc ttgtgtgttg gctgctctac tgtcctctgc cagcctacag gaggaaaagc      240
gaggcttaca caaggatgct cttcagacg gaagcagcac taaaagtacc ctgtatcaag       300
atgaacggga aaccatccca ataaacacgt tttggataaa aaaaaaaaaa aaaaa           355
```

<210> SEQ ID NO 154
<211> LENGTH: 337
<212> TYPE: DNA
<213> ORGANISM: Bos Taurus

<400> SEQUENCE: 154

```
tgtaaaagtg ccaaagacag gacgtcgatg tccgtgacgc ttgaacagtg ctcaatcctg       60
agagatgagc atcagttaca caaggacttc tttatccgag cactggattg tatgagaaga      120
gaaggatgcc gcatagaaaa tgtactgaag aatatcaaat gcaggaagta tgctttcaac      180
atgctacagc tgatggcttt ccccaagtac tacagacctc cagaggggac ttatggaaaa      240
gctgacacct aagtttacca acatgtaaat aaacaggaac acaaatacgc ttccgttgga      300
aaatctccac cgttttttgt tttcattgtc atgaatt                               337
```

<210> SEQ ID NO 155
<211> LENGTH: 546
<212> TYPE: DNA
<213> ORGANISM: Bos Taurus

<400> SEQUENCE: 155

| | | | | | |
|---|---|---|---|---|---|
| gatgaatcat | ctgaccgaag | atggcttgct | acctgacatt | ctttgttgaa | ccaggaagca | 60 |
| cacagaattg | actcaagtta | tagcaacacc | agcaagcaca | gtgcagacat | cctggtgttg | 120 |
| gaggagcctg | accacaattg | aaccccgatc | cttactcatc | acgcctgtta | ccttgggcag | 180 |
| gcacagaagc | ccgcacttct | atgtaaggac | tcattggaaa | agtccctgat | gctgggaaag | 240 |
| attgacggca | ggaggagaag | agggcgtcag | aggacaagat | ggctggatag | catcattggt | 300 |
| gcaatggata | tgaacttggg | caaacttcgg | gagatggtga | gggacagaga | ggcctggcgt | 360 |
| gctgaagtcc | atggggtcat | cacagagcat | caagccgagt | ccctgtgtt | atatagcagc | 420 |
| ttcccagtgg | ctatctattt | tacacaagaa | gccgaagcct | gctctcctcc | accctgcagt | 480 |
| agaggctctt | ggaagacggg | taagcagatt | gttccagctg | tttaaactac | gctcctgatc | 540 |
| ccgtga | | | | | | 546 |

<210> SEQ ID NO 156
<211> LENGTH: 521
<212> TYPE: DNA
<213> ORGANISM: Bos Taurus

<400> SEQUENCE: 156

| | | | | | |
|---|---|---|---|---|---|
| gcacgagcgg | ggatgggggg | ggctgggcag | cctcttcaca | aggctcgggg | tcgcaggaga | 60 |
| gcctggcacc | agcgggcttc | tccccacagc | ctccagcagt | ggaagcagct | cagggccagc | 120 |
| atctcagctc | caggcagacc | catgggtacc | ctccatggcc | catcgagcag | ctggcccagg | 180 |
| ttttcaaccc | cttcctcagc | agtgccttgc | tggcaggag | tggctctctc | ctgagggaac | 240 |
| acgggtgccc | ctcttggcct | accagttaat | gcccgggcac | cccaggaacc | cggaatagag | 300 |
| gccagggctc | tgggccaagt | agatcagaag | gaaaagacag | ggggagcgt | ggggtcctg | 360 |
| ggtccagggc | actttcctca | tgaccaccct | gctcccatga | aggcccctg | gatgtcactg | 420 |
| cagcagggag | agccaagggg | ccgtgttggt | gggtctggct | tcctcccaca | gaaggagact | 480 |
| agggatacc | aaccagacag | gcctgataag | aggcactcaa | c | | 521 |

<210> SEQ ID NO 157
<211> LENGTH: 410
<212> TYPE: DNA
<213> ORGANISM: Bos Taurus
<220> FEATURE:
<221> NAME/KEY: modified_base
<222> LOCATION: (317)..(317)
<223> OTHER INFORMATION: a, c, g, t, unknown, or other
<220> FEATURE:
<221> NAME/KEY: modified_base
<222> LOCATION: (320)..(320)
<223> OTHER INFORMATION: a, c, g, t, unknown, or other

<400> SEQUENCE: 157

| | | | | | |
|---|---|---|---|---|---|
| gcacgagggt | tactccgtgg | agttggagct | ttggcctccc | aggccctgag | ggcccggggt | 60 |
| ccaaatggag | tctccgtggt | gcgctctatg | gcgtctggag | gtactcgccg | gcaacgtgcg | 120 |
| ccgttgccct | cccgcggtgg | tgttcctact | gatgaagagc | aggcgactgg | gctagagagg | 180 |
| gaggtcatgc | tggctgctcg | caagggacag | gacccataca | atatacttgc | cccaaaggca | 240 |

```
acctcaggta ccaaggagga ccctaattta gtccccctcca tcaccaacaa gcggatagtg    300
ggctgcatct gtgaagnagn caacagtact gtcatctggt tctggctgca caaaggcgag    360
gcccagcgat gccccagctg tggaacccat tacaagctgg tgccacacca              410
```

<210> SEQ ID NO 158
<211> LENGTH: 443
<212> TYPE: DNA
<213> ORGANISM: Bos Taurus

<400> SEQUENCE: 158

```
gtgaccggcc gatgcgtgtc ggccctgggc cgccgcttcc acccggacca cttcacctgc     60
accttctgcc tgcgcccgct caccaagggc tccttccagg agcgcgcggg caagccctac    120 tgccagcccct gcttcctcaa gctcttcggc tgaccgcctg ccgggctcgc ccctccggga   180
aagcggagcc acaaagacct cgcctttccc ccacccccct caaaagatcg ggctctctag    240
accccaaggc cttgctgttg gagcttcggg ctccaccagc ccggcttctt gaggcctcac    300
cccactgcag ggactggccc tgaagatact gtacgttctc cgtgggcgag ttcagaaaag    360
gctccgtgaa cccttaaggc cacacgcctc ccgaagtggg tccgtacact gaccgatccc    420
acgtgagccc ttcactttgt tcc                                           443
```

<210> SEQ ID NO 159
<211> LENGTH: 376
<212> TYPE: DNA
<213> ORGANISM: Bos Taurus

<400> SEQUENCE: 159

```
aggctgagag gaaggacggt agccaccccg tccacgtgga caactgcatc ctgaatgccg     60
aggccctcgt gtgcatcaag gagcccccctg cctacacttt ccgggacttc agcgccattc   120
tttatctgaa cgaagacttt gatggaggaa acttttatttt cactgaacta gatgccaaga   180
ccgtgatggc agaggtgcag ccccagtgcg gaagggctgt gggattctct tccggcacgg    240
aaaacccgca tggagtaaag gccgtcacca gagggcagcg ctgtgccatc gccctctggt    300
tcactttgga tgctcgacac agcgagaggg agcgagtgca ggcggacgac ctggtaaaga    360
tgctctttag cccaga                                                   376
```

<210> SEQ ID NO 160
<211> LENGTH: 564
<212> TYPE: DNA
<213> ORGANISM: Bos Taurus

<400> SEQUENCE: 160

```
tgaataagga aactgttgga aagttttttcc aaacagacat tgcagaaaat gctttgaaaa     60
atgccttaga aacagaaatt cctactgtca gtgttttagc tgacgaagaa tttcttccct    120
tcagagaaaa tacgtttgac ctggtggtta gcagtttaag tttgcactgg gtgaatgacc    180
ttcctagagc acttgaacag attcattatg ttttaaaacc agatggcgtg ttcattggtg    240
caatgtttgg aggtgacacg ctctttgaac tccggtgttc cttacagtta gcggaaacag    300
agagggaagg gggctttttct ccgcacgtct ccccttttcac tgctgtcaat gacttaggac    360
atctgcttgg gagagctggc tttaatactc tgactgtgga cactgatgaa attcaagtta    420
actatcctgg gatgtttgaa ttgatggaag atttacaaga agaaagtcca gaacattgac    480 ctaatttgc aaaacgcgta tcagctgagg aacacatgag aagttttgga ggctttcaca    540
gtagttttaa gggatgggtg agag                                          564
```

<210> SEQ ID NO 161
<211> LENGTH: 537
<212> TYPE: DNA
<213> ORGANISM: Bos Taurus
<220> FEATURE:
<221> NAME/KEY: modified_base
<222> LOCATION: (285)..(285)
<223> OTHER INFORMATION: a, c, g, t, unknown, or other
<220> FEATURE:
<221> NAME/KEY: modified_base
<222> LOCATION: (372)..(372)
<223> OTHER INFORMATION: a, c, g, t, unknown, or other

<400> SEQUENCE: 161

| | | | | | | |
|---|---|---|---|---|---|---|
| gccccgaggg | agccagaggc | tcccacctcg | gccaacggct | cggcgggagg | ctgccagccg | 60 |
| cggcgggaca | tcgtgttcat | gaagacgcac | aagacggcca | gcagcacgct | gctcaacatc | 120 |
| ctgttccgct | tcggccagaa | gcacgggctc | aagttcgcct | tccccaacgg | ccgcaacgac | 180 |
| ttcgactatc | ccgccttctt | cgcgcgcagc | ctggtgcagg | actaccggcc | cggggcctgc | 240 |
| ttcaacatca | tctgcaacca | catgcgcttc | cactacgacg | aggtncgggg | ccctggtggc | 300 |
| gcccaacgcc | accttcatca | ccgtgctgcg | cgaccccgcc | cgcctcttcg | agtcctcctt | 360 |
| ccactacttc | gnctccgtgg | tgcccttcac | gtggaagctc | tcgggccgcg | acaagctggc | 420 |
| cgagttcctg | caggaccccg | accgctacta | cgaccccgc | ggctacaacg | cccactacct | 480 |
| ccgcaacctg | ctcttcttcg | acctgggcta | cgacagcgac | ctggacccca | gcagccc | 537 |

<210> SEQ ID NO 162
<211> LENGTH: 529
<212> TYPE: DNA
<213> ORGANISM: Bos Taurus

<400> SEQUENCE: 162

| | | | | | | |
|---|---|---|---|---|---|---|
| ggtgagaagt | gacgattcgg | aacacaagta | cagctccacg | ccgctggact | gggtcatgct | 60 |
| ggacaccaac | atcgcttact | ggctgcaccc | caggaccagt | gcgcagatcc | acctgcttgg | 120 |
| gaacgtcgtg | atctgggcct | ccgccagcct | tgccaccctg | gtgtacgccc | tgctgttcat | 180 |
| ctggtacctg | ctcagacgca | gaaggagagt | ctgcgacctc | cctgaagacc | gctggctgcg | 240 |
| ctgggtgctg | gccggggctc | tgtgcgccgg | ggctgggct | gtgaactacc | tgcctttctt | 300 |
| cctgatggag | aagacgctct | tcctctacca | ctacctgccg | gcgctcacct | tccagatcct | 360 |
| gctgctgccc | gtggtcctgg | agcacatcag | cgacccctg | tgcaggtccc | agctccaaag | 420 |
| gagcctcttc | acggccctgg | tcgtcgcatg | gttcacctct | gcctgtcacg | tgtcgaacat | 480 |
| gctgcgcccg | ctgacctatg | ggtacaggtc | gctgtcaccc | agtgagctc | | 529 |

<210> SEQ ID NO 163
<211> LENGTH: 530
<212> TYPE: DNA
<213> ORGANISM: Bos Taurus

<400> SEQUENCE: 163

| | | | | | | |
|---|---|---|---|---|---|---|
| gcacgaggta | ctagccgaga | tggcggcggc | tgcagcgatt | cgtggggtcc | gaggcaaatt | 60 |
| gggtcttcgt | gaaattcgta | tccatttgtg | ccagcgctcg | cccggcagcc | agggcgtcag | 120 |
| ggacttcatt | gagaaacgct | atgtggagct | gaagaaagcg | aatcccgacc | tgcccatcct | 180 |
| aatccgcgag | tgctcggatg | tgcagcccaa | gctctgggcc | cgctacgcat | ttggccaaga | 240 |
| gaagaatgtc | tctctgaaca | atttcagtgc | tgatcaggta | actagagccc | tggagaacgt | 300 |

```
gctaagtagc aaagcctgaa gtctccactg aggattaaaa acaacagccc cagagtctgg    360
gctctgctgg actgagaaca atgtggagaa atgtattttg ttctgtataa agattgtgct    420
gaaaatgctg tctaaaaatg atctgattcg catcccacca actacccatt attgtgcaac    480
catctgaggg aaagcagttg aatataaaaa taaaacttat tttattctgt              530

<210> SEQ ID NO 164
<211> LENGTH: 459
<212> TYPE: DNA
<213> ORGANISM: Bos Taurus

<400> SEQUENCE: 164
ctctttgtta agcagagatt taactctgtg gtatttgtga caaaatggga agaagagaca     60
tagtgattaa ggccaagttg gtggcttagc taaactgaga aagaaatttt cacagtggaa    120
ggcctggggc gtggtcacaa ctcagaccag gcctcacaca gctgtccctt gtggagacct    180
cttgccgtgg actttgcttg gtctctcgct taaagccaag gcagcactct ggaatttctg    240
taaagccaca aacaagcaat tcagtggtgg gagcaccaca caaattatgg gaaaaggggg    300
cagtcctaca gcaggattat atcagggtta tgttattagg aacctctctc tgtgcaatca    360
tgttgtataa gatgtgagag atggacat agatccttgc aactcaatct gttactcttc     420
ccctaaatta tacccttttg aggaagtttt atctaatta                          459

<210> SEQ ID NO 165
<211> LENGTH: 551
<212> TYPE: DNA
<213> ORGANISM: Bos Taurus

<400> SEQUENCE: 165 caacccctc aacgccatgc agatcctgtg gatcaacatc atcatggacg ggccgccggc     60
gcagagcctg ggtgtggagc cggtggacaa ggacacactc cggcagccgc cgcggaacgt    120
caaggaccag atcctgagcc gagcccttgt cctgcggatc ctcctctcgg ccaccaccat    180
catcagcggg accctcttca tcttctggaa ggagatgccc gaggacaggg caagcacccc    240
tcgcaccaca accatggcct tcacctgctt cgtgttcttc gacctcttca acgccttgac    300
ctgccgctcc cagaccaagc tgatcttcga gatcggcttc ctccggaacc gcacgttcct    360
ctactctgtg ctcggctcca tcctgggaca gctggctgtc atttacacgc cgcccctgca    420
gagggtcttc cagacagaga gcctgggggc gctggattta ttgcttttaa ccggattggc    480
ctcgtctgtg ttcatcttgt cagagctctt caagctgtgt gaaaagttct gctgcagagc    540
ccagaaagcc c                                                        551

<210> SEQ ID NO 166
<211> LENGTH: 253
<212> TYPE: DNA
<213> ORGANISM: Bos Taurus

<400> SEQUENCE: 166
gctctctcaa cctaaagaag actgggcgcc cacgaccttc ctgggtccct tcccgcccct     60
attaggtcgc tgcagatctg tgaacggtgc gggcgcaaaa gtcagactct ttccagggag    120
tttcccgccc agttgaggat gcaccgggga gggctgtccc ggcctggaac cagagatttg    180
aaagcagcag gaaaaccgga acgacctgac cgcagaagga atgcagagta ggggcagtaa    240
atagagtgtg ttt                                                      253
```

<210> SEQ ID NO 167
<211> LENGTH: 650
<212> TYPE: DNA
<213> ORGANISM: Bos Taurus
<220> FEATURE:
<221> NAME/KEY: modified_base
<222> LOCATION: (547)..(547)
<223> OTHER INFORMATION: a, c, g, t, unknown, or other
<220> FEATURE:
<221> NAME/KEY: modified_base
<222> LOCATION: (622)..(622)
<223> OTHER INFORMATION: a, c, g, t, unknown, or other

<400> SEQUENCE: 167

| | | | | | |
|---|---|---|---|---|---|
| atttgttctg | tcttcacctg | ccttcattaa | aagccctgac | tcaattttgg | tgttgagaag | 60 |
| gaacaaaacc | caggcccatc | ccagtgcttc | tgcccctcag | caccagggcc | cagcatggac | 120 |
| ctggtaagga | gggcacagtg | gatatccacc | caagacaggg | aaatgaggat | tatgaggaac | 180 |
| tatgaatgta | gtggataaac | tagacccctc | tgatgcctca | gctcccagca | tgtcctcaaa | 240 |
| agcagttcaa | tgtctgggga | ggaacagggc | tgtcatagct | caaaaccacc | aacctctacc | 300 |
| ctatttattc | ctggttcctc | cagaagcagt | gctggggaga | acatgaata | ttcattggtt | 360 |
| tgagattacc | aaaaaaatgc | aaggcaagtg | ttttgtgggg | gaagctggtt | ttgtgattga | 420 |
| ggcggtggat | taattctgag | ttgagtccac | agggtcggaa | ctggatacaa | ctgagcgact | 480 |
| aaccgtttca | ctgagctcct | gtggtagctc | agatggtaaa | gaatctgcct | gcagtgcaag | 540 |
| agaccanggt | tcaatccctg | agttgggagg | atccctgga | gaagataatg | gcaacctatc | 600 |
| cagtattctt | gcctgggaaa | tnccatggag | ctgtagtctg | atgggctaca | | 650 |

<210> SEQ ID NO 168

<400> SEQUENCE: 168

000

<210> SEQ ID NO 169

<400> SEQUENCE: 169

000

<210> SEQ ID NO 170
<211> LENGTH: 432
<212> TYPE: DNA
<213> ORGANISM: Bos Taurus

<400> SEQUENCE: 170

| | | | | | |
|---|---|---|---|---|---|
| gcacgaggag | gccttcagga | tggtgcagcg | tctgacgtac | cgtcgtaggc | tgtcctacaa | 60 |
| tacagcctct | aacaaaacca | ggctgtcccg | gaccctggt | aacagaattg | tttacctta | 120 |
| taccaagaag | gttgggaaag | caccaaaatc | tgcatgtggt | gtgtgcccag | gccgactgag | 180 |
| aggcgttcgt | gctgtgagac | caaaagttct | catgaggttg | tctaaaacga | agaaacacgt | 240 |
| cagccgagcc | tatggtggtt | ccatgtgtgc | taaatgtgtc | cgcgacagga | tcaagcgcgc | 300 |
| tttccttatt | gaagagcaga | agatcgttgt | gaaagtattg | aaagcacaag | cacagagtca | 360 |
| gaaagctaaa | taaaaaatga | accgttttg | agtaataaat | caaaaaaaaa | aaaaaaaac | 420 |
| tcgaggggg | gc | | | | | 432 |

<210> SEQ ID NO 171
<211> LENGTH: 391
<212> TYPE: DNA

<213> ORGANISM: Bos Taurus

<400> SEQUENCE: 171

```
gcacgagcct gggctggggg cggggagcag gtgggctgga ggggaccctg ccctgggtgt      60
tgggcgccag ggccgcactc ccgctgggat cttcctgtga aaaacctcgg gtggcagcgt     120
gctcggttgg cctccagcct ctgacagtgt ttacagacaa ggccgtcacc ctgggaaggg     180
gtcgcctccc tccagcgtcc cctgggctct tgaaccgcta cttgaattaa ccgtaggcgc     240
tgcttgtaga gtccacttgt tatttgaaac aaggcatgtt tcaatccaaa gtgttatcgt     300
caaaggtact aacttgagta gaagaattca cagatgactt ctctttaata aataaattct     360
cctttttccaa aaaaaaaaaa aaaaaaaaa a                                   391
```

<210> SEQ ID NO 172
<211> LENGTH: 414
<212> TYPE: DNA
<213> ORGANISM: Bos Taurus
<220> FEATURE:
<221> NAME/KEY: modified_base
<222> LOCATION: (350)..(351)
<223> OTHER INFORMATION: a, c, g, t, unknown, or other

<400> SEQUENCE: 172

```
agtatatggt gatgtacatc gagtgaagat aatgtttaat aagaaagaaa atgcattgtt      60
tcagatggca gatgcaaatc aagctcaact agcaatgaat catctgagcg gtcaaagact     120
ttatgggaaa gtgcttcgtg ctacactgtc caagcatcaa gcggttcagc ttcctcgaga     180
gggacaagaa gaccaaggtc tgactaagga ttttagcaat agtccttgc atcgctttaa      240
aaaacctggc tctaaaaact tccagaatat ttttcccccg tcagctactc tgcatctttc     300
caacatcccc ccctctgtta cagtagatga cctgaagaat cttttcacan nagctggatg     360
ttcagtgaag gcttttaaat tcttccagaa agatcgcaaa atggcactca ttca           414
```

<210> SEQ ID NO 173
<211> LENGTH: 416
<212> TYPE: DNA
<213> ORGANISM: Bos Taurus

<400> SEQUENCE: 173

```
ggagatgatg aattttttga ccttgatgac tactaggtag tcgacatggg tccggcaaaa      60
cgtgcctcac cctccagcat ccaacccaag gagcataccc gtggtggaat ccaaacagat     120
ccctgcctta caattggaac atttccgaa cttaatccat gagcattgga tattgaaaag      180
aaaaccgaaa caaaaccaga cccaacccta cactttggtt tgtcatggtg tcagcgcagc     240
agcctacaac tagttcctaa atgccacttt ggactaattt aaaaaagaat cccagttttt     300
acttttactc gatggtgaaa ttggttgctc ttgtatttta tggggaaaaa acaaaaagat     360
ttttttaacc ttcatacata gaagcaaaaa tactttaact gctgtaaacc ttcaaa         416
```

<210> SEQ ID NO 174
<211> LENGTH: 291
<212> TYPE: DNA
<213> ORGANISM: Bos Taurus

<400> SEQUENCE: 174

```
ggaagggtgt ggtccaggag ctcctgggcg gtggctctct cctgggggtc ccgcaccagc      60
atccggtcca ggaagtctcg cagcaccggg gagaccttgt aggagttctt cagcttgggt     120
gggggggctgt cccgaagcct cttcatggct tgcacagggg agtcactgaa gtaaggtggt     180
```

| | |
|---|---|
| tctccatcca ccatctcaat caccatgatg cccagagacc agatatctac ctcagttgca | 240 |
| tacagagacc tggagatcac ttctggagcc atccagtatg gggttcccac c | 291 |

<210> SEQ ID NO 175
<211> LENGTH: 570
<212> TYPE: DNA
<213> ORGANISM: Bos Taurus

<400> SEQUENCE: 175

| | |
|---|---|
| gagttggaca cgactgagtg actgtctgaa ctgaactgaa ctgaatgcag tggatactgt | 60 |
| tttggggatc tgattggaca cttttccatgg gaatctttat aactgaggga ggagggaact | 120 |
| ggggctggag agcaacagtg ggaagagctg ataaacacca ccagtacaac agtgttggct | 180 |
| ttcttgccag gatggaaaac acatgcatcc gcagtgtgca aatcaccatc ctcttcacac | 240 |
| ccagacaggt ggtgggtact gcaaataccc tggggcccac tgaggacact ggagaggaca | 300 |
| ctactcttgc aggaatgtta ctcattagaa ctgtttcaac tgtcatgata acagtcattt | 360 |
| gggagtgaac ctcacaccaa ttgtgaagat gtgtgtaaaa tgaatttatg taaattggat | 420 |
| cccagttttc ctttgcatat ataaaggaag cttttttccc tcccctgaaa tagttcctgg | 480 |
| catgtggtag gcactcaaat atttattgaa tgaatcaatg aaagaatatt tgtctttaaa | 540 |
| aaaaaaaaaa aaaaaaaaaa aaaaaaaaaa | 570 |

<210> SEQ ID NO 176
<211> LENGTH: 266
<212> TYPE: DNA
<213> ORGANISM: Bos Taurus

<400> SEQUENCE: 176

| | |
|---|---|
| gaatgacagc agtgctcttc tgtttttttt tttttaaat tttaacagac cagccttaac | 60 |
| tgtgggtttg aatcctaaaa ggacatttgc cacagtgtga ctcaaggaag tatttggttg | 120 |
| gcaggtgagc accagtgaca gccaaatgga gggacatact tgcatggtca gtttattctc | 180 |
| taattccagg aagttctttg ctttcagaat gaagaaaaca ttttctcccc ctttcccca | 240 |
| cccacccgtt gttttttttt ttttta | 266 |

<210> SEQ ID NO 177
<211> LENGTH: 509
<212> TYPE: DNA
<213> ORGANISM: Bos Taurus
<220> FEATURE:
<221> NAME/KEY: modified_base
<222> LOCATION: (318)..(320)
<223> OTHER INFORMATION: a, c, g, t, unknown, or other

<400> SEQUENCE: 177

| | |
|---|---|
| atcaggacaa ggaacttgtg gtcatcaata agccctacgg tctccctgtg cacggtggcc | 60 |
| ctggggtcaa gctctgcatc agtgatgtac tgcctgtcct ggcaaagata ctccatggcc | 120 |
| ccaaggcaaa gccgctgcac ctgtgccatc ggctggacaa ggaaaccaca ggtgtaatgg | 180 |
| tgttggcttg ggaaaaagaa gtggcgcatc aagtccaaga gctgtttaga acccgtcagg | 240 |
| tgacaaagaa gtactgggcc atcaccgtgc gcgtcccggt gcctgaagcg ggagtcgtgg | 300 |
| acatccccat cgtcgagnnn gaggcgcagg gccagcagca tcaccacaag atgacgctgt | 360 |
| ccccgagcta ccgcatggac gacgggaaga tggtgagggt gcggagcagc cggaacgcac | 420 |
| agctggcagt gactcagtac cgggtgctga gcagcagcct gtccgccgcc ctcttggagc | 480 |

```
tccagcctat cacgggaata aaacatcag                                      509
```

<210> SEQ ID NO 178
<211> LENGTH: 624
<212> TYPE: DNA
<213> ORGANISM: Bos Taurus

<400> SEQUENCE: 178

```
aagatttaaa aattttctac atttaaaaca aaactcgaaa gaattttttt ggaatgttga     60
ggaggacttc aaacctgttc cagagtgctg gataccagcg aaggaaatag aacagataaa    120
tgggaatccg atacctgatg aaaatggaca cattcctggt tgggtcccag tggagaaaaa    180
cagcaaacag cactgctggc attcgtccgt agtcgattac gagtctgaga tcgccctggt    240
cctgaggcat catcctgacg accctgggct tttggaaatc agtgcagtgc cgctctcaga    300
tcttctagaa caaacactgg agcttatagg aaccaatatt aatggaaatc cttatgggtt    360
aggaagcaaa aagcatccat tacatcttct tataccacat ggagcgtttc aaataagaaa    420
tctacctacc ttgaagcaca gtgatctgtt gtcctggttt gatggttgca gagagggtaa    480
aattgaagga atagtatggc attgcaatga tggttgttta atcaaggtcc atcgccacca    540
tcttggttta tgttggccga tcccagatac ttatatgaat tcaaaaccag ttattatcaa    600
catgaatctg aacaaatatg agta                                          624
```

<210> SEQ ID NO 179
<211> LENGTH: 457
<212> TYPE: DNA
<213> ORGANISM: Bos Taurus

<400> SEQUENCE: 179

```
gacagacatt atggccacct tcccaagagc agccagcccg tccaggcagc ccccaggccc     60
agaggatgaa gatgccgtcc tagacgagta cgacctctac agcctggctc attcttaccc    120
gggagtggga ggccggaaag gtcgcagcaa gagagaagcc gccatcaaca ccaaccgcca    180
cagccctggt gggcatgaga ggaagctggt gaccaagctt cagaacacgg agcggaaaaa    240
gcgaggggca cggccctgag acaggactgg agatgaggcc agaggacgga cacccacagc    300
aatggaaata ggactgagga agagccagcc cctgggggcg ggatccaggc ctgcttgccc    360
cacccccaacc ccaggactta tccccacctg actgagactc tggggggcacc acggaggaag    420
cacccccggc cccagagaaa ggacaagatg agaagca                             457
```

<210> SEQ ID NO 180
<211> LENGTH: 457
<212> TYPE: DNA
<213> ORGANISM: Bos Taurus

<400> SEQUENCE: 180

```
atgaaagtat ctgctgaatt ggttggtgat cattacattc aatgatccac tgaagaaagg     60
aattgacttg gggcctttag caatatcaga agaggcacca tcctaagacc ctatagcatt    120
atcaaggaag ggaatccagg ccccattctt gggtctgttt tcacacatca gcacttagtg    180
ttcaatttga cctgatgaat agcatatcca tagagatgca gatgatacag aaggttgaaa    240
aaactaattc agttccaccc ttctgcctgt tggcattgtc caaccagaac tctgtttgct    300
attatctccc tagctaccaa gtgaacatgt ttatgttaat gtctgagaaa aagctcgtgt    360
ccttaagtct aagtatcctg caaagagttg gtaatctact cacatgaact tgcatttgat    420
ggaccatagg gtgatcaaca cgctttcctg gcatctc                             457
```

<210> SEQ ID NO 181
<211> LENGTH: 470
<212> TYPE: DNA
<213> ORGANISM: Bos Taurus

<400> SEQUENCE: 181

```
ggcagcccgc ggctcaccga ggtgtccccg gagctgaagg atcgcaaaga ggatgcaaag      60
gggatggagg acgaaggcca gaccaaaatc aagcagaggc gaagtcggac caatttcacc     120
ctggaacaac tcaacgagct ggaaaggctt tttgatgaga ctcactaccc ggacgccttt     180
atgcgtgaag aactgagcca acggctgggg ctgtccgagg cccgagtgca ggtttggttt     240
caaaatcgaa gagctaaatg tagaaagcaa gaaaatcaac ttcataaagg cgtcctcata     300
ggagctgcca gccaatttga agcttgtaga gtagcaccct atgtcaatgt aggtgcttta     360
aggatgccat ttcagcaggt tcaggcgcag ctgcagctgg acagcgccgt ggcgcacgcg     420
caccaccacc tgcacccgca cctggccgcg cacgcgccct acatgatgtt                470
```

<210> SEQ ID NO 182
<211> LENGTH: 202
<212> TYPE: DNA
<213> ORGANISM: Bos Taurus

<400> SEQUENCE: 182

```
atggctgcag gcagtcttcc aagcccccaa caaatccact ccagcctgtc ctgaggtcca      60
ctcagacaga cagatttcct gtggctaaaa ccagccagga tatagaaagc ccagtccatc     120
cccagcatcc tcaggagccc tcctgaaggc cacgaagatg agccggctct gcctctctgc     180
agcccttctc cttctcctgg gc                                              202
```

<210> SEQ ID NO 183
<211> LENGTH: 279
<212> TYPE: DNA
<213> ORGANISM: Bos Taurus

<400> SEQUENCE: 183

```
gtcattggca tgagatcttt cattaaagct gaaaacacga ctcacgctac gtccatcaaa      60
atcctttgct gtgcggactg cctgatgggt gtgtatctgt tcttcattgg cctttgcgat     120
ctaaagtacc gagggcagta tcagaagtac gcgctgctgt ggatggagag cttgcagtgc     180
cgcctcctgg gcttcctggc catgctgtcc actgaggtct ctgtcctctt gctcacatac     240
ttgaccctgg agaagttcct ggccgttgtc tttcccttc                            279
```

<210> SEQ ID NO 184
<211> LENGTH: 488
<212> TYPE: DNA
<213> ORGANISM: Bos Taurus

<400> SEQUENCE: 184

```
tgtgtggtgt cagatgcccc agcctccagg aagccagtca agagggatg tggccacaga       60
aaagaaaca ccgaaaacac aagcacaaag gcaagcaaaa gaataaaaaa tcagagaaaa      120
gtagtagttc tgagagtaca gacagcagcg acagccagag tgaagaaggg cccacagacc     180
tgtcacccca ggagttgctg agacggctga agcgtcttcc actaaggagg cagtaattga     240
attctgcccc tgcccgtccc aataccagac ctcctccagg atggaagttc attgatcact     300
cagttaatac attgtataga ttgtatttat atgtaaattc atgctgtgaa ataatttttt     360
```

```
tttaaaaacct tgacatttca aagcctgcct tggaagtttg ctgaaattga tttctatttt    420
taacttctgt tagtgtcaga gaaagaaatt cagactgtac agtttaatta aaatggcatt    480
tttgtaaa                                                              488
```

<210> SEQ ID NO 185
<211> LENGTH: 476
<212> TYPE: DNA
<213> ORGANISM: Bos Taurus
<220> FEATURE:
<221> NAME/KEY: modified_base
<222> LOCATION: (153)..(153)
<223> OTHER INFORMATION: a, c, g, t, unknown, or other

<400> SEQUENCE: 185

```
tgtaaagcta tagtttcata agaacagggg tcttatttgc ctgaatcctt ccctccctga     60
gttcataatt ggtgctgggc acatagtagg tagcttggga gaaatttgta agtaagaaaa    120
gaaggtcagt gctaggccaa ggtttccatc agnatgcact ccgcctgctg tgtttcaaca    180
accccaaagg gcctataagc tgtattctgt tcccttgccc cccagaggtt ccaatgctga    240
ataatcagca ccttcccaag gcctgaccct cacccattgg tcgttttaga accctgctc     300 cttctctaaa ggaatagccc attgctatag gactgttcca tgctcctcca cacttgcta    360 atttagtaac cataaattcc tataacaagt catgggcact aaatagcctc cttacagaga    420
aatgaaatgt ttgaaccctg aagcacttaa ccaaaggatc aatctactgt ggagtt       476
```

<210> SEQ ID NO 186
<211> LENGTH: 381
<212> TYPE: DNA
<213> ORGANISM: Bos Taurus
<220> FEATURE:
<221> NAME/KEY: modified_base
<222> LOCATION: (270)..(271)
<223> OTHER INFORMATION: a, c, g, t, unknown, or other

<400> SEQUENCE: 186

```
gggcttcgca cttgttcatc ccaacacatc acttccctta agacctctgg aagcactgcc     60
tggacacatc cgcccatggt ctctaccaca cctgccgccc gcatcccggc tgttctcggt    120
ggttctctca attgccttgc cctgtcctgt cattgcacta aagcccagac gaacgagata    180
ctacgagccc caccctagct gaaactcgcc tcatcgcttt taccctcagt aagaaataat    240
caactgcctg ctgtaaacac tgaggatccn ncactgaaaa aatggacaga agccccagcc    300
ttcagggagt tattctagga caggagaaca aaccgctgac agaataagta agcagaatat    360
ctagtacatg gaagcactat g                                              381
```

<210> SEQ ID NO 187
<211> LENGTH: 453
<212> TYPE: DNA
<213> ORGANISM: Bos Taurus

<400> SEQUENCE: 187

```
gctatttctg accttgtggg gcgtgtggct tctgggtggc taggcgatgc tgtcccaggg     60
cctgtggcaa gactcctgat gctctggacc accctgactg gggtgatact ggccctgtac    120
cctgtggctg aggcgcccac tggcttggtg gccctgacta tggcctacgg cttcacatca    180
ggggccctga ccccagtggc cttctccgtg ctgcctgaac tggtggggac tggaaagata    240
tactgtggcc tggactggt acagatggta gaaagcatcg gggggctgct ggggctcct     300 ctgtcaggtt acctccggga tgtgacaggc aactacacag cttcttttgt ggtagctggg    360
```

| | |
|---|---|
| gccttccttc tggcaggaag tggagttctc atcactttgc cccacttctt ctgcttctca | 420 |
| gctcctacct ccaagcccca ggatcttgta aca | 453 |

<210> SEQ ID NO 188
<211> LENGTH: 543
<212> TYPE: DNA
<213> ORGANISM: Bos Taurus

<400> SEQUENCE: 188

| | |
|---|---|
| gtggccatgg cttttacgtt gtactcgctg ctgcaggcgg cccttctctg cgtcaatgcc | 60 |
| atcgccgtgc ttcacgagga gcgtttcctc aagaacattg gctggggaac agaccaggga | 120 |
| attggaggat tcggagaaga gccaggaatt aaatctcagc taatgaacct tattcgatct | 180 |
| gtaagaaccg tgatgagagt gccattgata atagtaaact caattgcaat tgtattactt | 240 |
| ttactgtttg ggtgaagatc agtgggggaa acggagactc caagaagag ctgccagcag | 300 |
| aagttattac ttcagtcttt attgaagtat acatatctta gctggctctc cttggacttg | 360 |
| acaaaaatgt aaacctgaca ataaaaccag agtccctatt tatctgattt ttaaaaaatg | 420 |
| ttgtacttac agttttattg taaaaagatc gtatcatcag aggccataac tgtcgaggat | 480 |
| tggaatacat tggattgctg actgctgata aagttcatg ctatggaaaa gattgttaaa | 540 |
| agg | 543 |

<210> SEQ ID NO 189
<211> LENGTH: 464
<212> TYPE: DNA
<213> ORGANISM: Bos Taurus

<400> SEQUENCE: 189

| | |
|---|---|
| ggccctgctg tctccacaca gtggaggtac catgacctca acggtcagga caccagacgt | 60 |
| cgccagaagc cctgcagcac tggctgggac aactccctga cactcggagg ggagcccagg | 120 |
| ctgggcaagc cacatctgtc acctacagtc atttcccagg aaaggccggt tgctagctgc | 180 |
| tagcctggtg cggacgtcaa gtttatgggc tggaagtcct acccggaggc tgctcactga | 240 |
| agtgtaacca gccacaaggc ggatggaagg catgcctgct gctgctccag gtctcccccg | 300 |
| tccccaggcc caagatgaca tccaacagca ccagggaggt gcccagcccc gttcctgcag | 360 |
| gggccctggg gctctcccctg gccctggcaa gcctcatcgt cgctgccaac ctgctcctgg | 420 |
| ccgtgggtat cgccggggac cgccgcctgc gcagcccgcc cgct | 464 |

<210> SEQ ID NO 190
<211> LENGTH: 446
<212> TYPE: DNA
<213> ORGANISM: Bos Taurus
<220> FEATURE:
<221> NAME/KEY: modified_base
<222> LOCATION: (380)..(382)
<223> OTHER INFORMATION: a, c, g, t, unknown, or other

<400> SEQUENCE: 190

| | |
|---|---|
| tgaaacagtt cagtctcctt gcatttcttc tctcccctac cttcctcagc agagcctgcc | 60 |
| tatttccttt cctctatgat gctgagagac ttccctggtg gcacagatgg taaaagcgtc | 120 |
| tgactacaat gtgggagacc cgggttcaat ccctgggtca ggaagatctc ctggagaagg | 180 |
| aaatagcaac ccactccagt gttcttgcct ggaaaatccc atggacagag gagcctggta | 240 |
| ggctacagtc catggggtcg caaagagtag gacactactg agcaacttca cttcacttta | 300 |

| | |
|---|---|
| tgatgctggg gaagattgag agcaggagga gaagggggaca gcagaagatg agatggttgg | 360 |
| gtggcatcac caacttaatn nncatgagtt tgagcaagct ctgaaacaca gtaaagacag | 420 |
| ggaagtctgg catgctgaag cccatt | 446 |

<210> SEQ ID NO 191
<211> LENGTH: 480
<212> TYPE: DNA
<213> ORGANISM: Bos Taurus

<400> SEQUENCE: 191

| | |
|---|---|
| tgcaggcctg caaaaatcag gcagcaagcc agaccggccc acagaccaag tttgccaacc | 60 |
| ccttgtctag atgaccgcaa agggcctaac cctcaagaga atgctagcc aatcaccagg | 120 |
| ctcctttgtg tttcggcgct gatcacgtga ccagccctgg gcacacagat ccaaaggatg | 180 |
| ggctctgtcc caggcgagag gctgctcggg cgtaaaccac tgacccgagt cctgtcctcc | 240 |
| tagacctctg aaaagtcagt ggccgagcag gtctgttagg tggggctgag ctgagaggtc | 300 |
| agaccggtgt tgtggccaga gttcacgcag gtcaggatag tcaggtgtca gagtgaacag | 360 |
| cccgtgagtg aagcccgaga cgggagccgc tgccgtcagt cagtcgtctg tcccggagca | 420 |
| gcccggggtg ctggtgacac gcatcgccgt ggggctcgtg cagccgctga cttgagtcca | 480 |

<210> SEQ ID NO 192
<211> LENGTH: 501
<212> TYPE: DNA
<213> ORGANISM: Bos Taurus

<400> SEQUENCE: 192

| | |
|---|---|
| acagcttgaa ggatgagatg ggcaacctca ggtgggggca gacaggacaa ggtaggggca | 60 |
| ggggtccggg aggggggccgg acagagcaca ggaagtgtgg ggtgtgggca cctagtgggg | 120 |
| tcctccccag gatttgctga gggctggaat caaggtctag cccacgagga tccttctgac | 180 |
| cctcctttgt cactctggct caggacccat gcccctgttc cctacagga agctgctaga | 240 |
| cactacccca tcaccagtgg tcttttgcca caatgatatc caagaaggga acatcttact | 300 |
| gctctcagag cctaaaaaca ccgacagcct catgctggtg gacttcgagt acagcagtta | 360 |
| taactcagg ggctttgaca tcgggaacca ttttttgtgag tgggtttacg attatactca | 420 |
| cgaggagtgg cctttctaca aagcgcagcc tgcaaactac cccactgagg acagcagct | 480 |
| ccatttttctt cgccactacc t | 501 |

<210> SEQ ID NO 193
<211> LENGTH: 484
<212> TYPE: DNA
<213> ORGANISM: Bos Taurus

<400> SEQUENCE: 193

| | |
|---|---|
| gcataacaac tgaccagctg agaccgtatt gcctgttgca tcaatagtgg aaggcagaag | 60 |
| tgttgacaca atttctcctt gtcctttctg atttttatat aagaaacact ggaaacagta | 120 |
| gagaacagca cagcgtaata caaatggctg cctttcatta accatggaca taagaagtac | 180 |
| tacgatggct ggtcttggtg ggtttgaagg tgcatttaca gaagcaaagt agtcttggtt | 240 |
| tacttggcag cctcgaataa cttctgatac agtattaatg gtctcagtca ggatatcagc | 300 |
| aggaactcca gtagtctctc aaaagcattt tcaaaagcaa caatttttctg gattgctcca | 360 |
| ttgcttcttg ttagtgcctg cagtagtaag acgccatcat tacgtataac ttccctggaa | 420 |
| tctgctaata agtccatcaa tcttgaaaca cccatgggac tgactaaaat aatttgctga | 480 |

```
acct                                                                484
```

<210> SEQ ID NO 194
<211> LENGTH: 512
<212> TYPE: DNA
<213> ORGANISM: Bos Taurus
<220> FEATURE:
<221> NAME/KEY: modified_base
<222> LOCATION: (416)..(418)
<223> OTHER INFORMATION: a, c, g, t, unknown, or other

<400> SEQUENCE: 194

```
gagggggttt ggctgtcagg gccccaggag ccgttcttga aggggtcctg gtgagggtcc      60
caggtccagg atcgggtgag gttatagcct cctccgtctt cggagggtct gcccctgggg     120
cctgaggcac ggacatctcg gctccagcca cagcctcggg caccaagggc tccgggccgg     180
agacctgcgc cctgggggca tcgggtgagg cctccagagt cagtcccacc tccgtgctgg     240
ctgtgaccgt cgggccgggg accgagtctg aggtctgggt cagacccggt acccatgcgg     300
gccgcgcctc cccgggggcc accagggtga ccggggccga agtggccgta gtcactggcg     360
gccccggagc caccaccagg acgggcccgg cccgagagcc gcggggcggc ggcgannngg     420
ccgcgggggc gccatgacgg cgcggcgggg ccaccagggg cgccgggccc gtctccatgt     480
ccgcgggccg cccctcacat cccccgcag cg                                    512
```

<210> SEQ ID NO 195
<211> LENGTH: 431
<212> TYPE: DNA
<213> ORGANISM: Bos Taurus
<220> FEATURE:
<221> NAME/KEY: modified_base
<222> LOCATION: (11)..(11)
<223> OTHER INFORMATION: a, c, g, t, unknown, or other

<400> SEQUENCE: 195

```
aaaccctcag ngaacagcag acagagatgt cagaggtatc aattcttctc cagtgaccct      60
tcagttgagt tgggtcagta ggaaaggatg actggacagt atctcatgct ctgtcctcaa     120
ggaatccttc cctagtcgtg ccagcttgct gctcattaga atgaacaact cttcatcagc     180
atctaattgc cattctctga taacatagcc aagaactgca gacttcatct gtgttttgga     240
atgtccattg tcaatggtga atacactaac gtggtttttc aggataataa gtggtcttta     300
attgctaatt tagagaagat tggttggtgt gtatctctgt aaagagatga tagcctgaaa     360
ctatcattag gataattccc attaaacatt atgcagacat tatcagactg ataagctccc     420
aagctgggct g                                                          431
```

<210> SEQ ID NO 196
<211> LENGTH: 463
<212> TYPE: DNA
<213> ORGANISM: Bos Taurus

<400> SEQUENCE: 196

```
gaaattgaca gctgagagct cctcagtaat taaacgtttt aactcggcag ttgattagct      60
gtgggagaga ggtcgatcct gagcgatgct agtttagcca cctgaaatct ctggtggttc     120
tgtttatatg gtgagaaaaa ccagaagggg aggaacaacc tgtgctcgaa ggaagatgga     180
ggtggtctct gaagatggct gtttgggttt ggaagcatgc ttttgttatt ttctgtcagg     240
ctggtcagta aatatttact gagtatatac tatgctttac aacctaggc aaagacaagc      300
```

```
catctaagcc tcagtgtctc ctttgtttga aagtttatct tggtacggaa gagcatttag    360
agagtaaaat tagtttgcaa agtgcttaac cattgtaagc atgctggtgg tagctgctca    420
tctccacatg ggctaaaatg agactggtca gtagtcggag gtc                      463

<210> SEQ ID NO 197
<211> LENGTH: 347
<212> TYPE: DNA
<213> ORGANISM: Bos Taurus

<400> SEQUENCE: 197
tcaaggactc aaaccttatt aaaacgcagg atgtgtttac agtcattcag tacatctcat     60
acaacagcta tgggaagact atggcctgga attggataca actcaactgg gaatatctag    120
tcaacaggta tacactcaat aacagaaacc ttggccggat tgtcactata gcagagccat    180
tcaacactga actcaactc tggcagatca agagcttttt cgaaagatat cctgaagctg     240
gagcgggaca gaaacctagg gagcaagtac tggaaacagt gaaaaacaat atcgagtggc    300
taaaacaaaa cagggacacc ataagaaact ggtttcttga tttgaat                  347

<210> SEQ ID NO 198
<211> LENGTH: 508
<212> TYPE: DNA
<213> ORGANISM: Bos Taurus

<400> SEQUENCE: 198
cagccggcca ggaagcgcag gccctcaggc tccgaacagt cggacaacga atccctgcag     60
tctgggcgga gccgctccgc aggctctgag atggactccc ggcccgcgtc cccaagtgct    120
gagtcggacc acgactccga aagagcatct gacaatgagg ctccggccc aggttccgga    180 aatgaatctg aacccgaggg atccaacaac gaggcctcgg ataggggctc agaacgtggt    240
tcagatgata gcgactaggc tttatttcat gaatatgctt catctctgca ggaaactttt    300
tttttacata tgaaagctgt gataaaaaca tttcaggtgt ttggtcagtg gtgaaatttt    360
tgctaaggca attttttttcc ctatccattc gtacattact atgaccgcaa gagatatttc    420
ccgtgttaga gtctaatatt tgagtctctt gagcaaaagg tgactattct tcattatggt    480
acaattccac ctattacatg tgaaaacc                                       508

<210> SEQ ID NO 199
<211> LENGTH: 590
<212> TYPE: DNA
<213> ORGANISM: Bos Taurus
<220> FEATURE:
<221> NAME/KEY: modified_base
<222> LOCATION: (285)..(287)
<223> OTHER INFORMATION: a, c, g, t, unknown, or other

<400> SEQUENCE: 199
ggaataaaca acagaaccgt ggctcctaaa gagcaggaag acttctcttc ctgcaaccat     60
ggtcaccata aaatttatcg tcccaaccgg ggcatttctg ggcgtgaaaa ggaatggtat    120
tgacaaacac cccgagacaa aaggcatcac tggacgtctt cggtgaacca ggagcacgct    180 cacccctaaac aggacccgac atctctgact gtgcttgcac taaggggtg aggcgcacgg    240 taggacgccc accgcagcgc aggagaggcc gtgggctgcg gctcnnnacc ccgccacctc    300
ttcttccaaa tccctcactg gtgtccggcc gcgccgtgcg gtgatgggat cacagccccc    360
ggccagggct gaagctgggc cccgcaggga cagcgcagcc tactacctgc tgggctgcca    420
gggaacccgt cgggctctcc tgagtcacgg agatgccaag caaagtgctg aacaccccac    480
```

```
agcctcagtg caagaaggac tggtatttat ctcacagggc tgtgctgagg actgaacagt    540
ttcatatatg tgaaacagct aacacagtgc caggcataaa caataataaa              590

<210> SEQ ID NO 200
<211> LENGTH: 594
<212> TYPE: DNA
<213> ORGANISM: Bos Taurus

<400> SEQUENCE: 200
ggttcttttg ctggagatat ctggggagaa attgatacaa gattctcttt ttgtgcagtg     60
gcaactttgg cactattggg gaagttggat gctattaatg tggaaaaggc aatcgaattt    120
gttttatcat gtatgaactt tgatggtgga tttggttgca gaccaggttc tgaatcccat    180
gctgggcaga tctattgttg cacaggattc ttggctatta ctagtcagtt gcaccaagta    240
aattctgatt tactcggttg gtggctttgt gaacgacagc ttccatcagg tggactcaat    300
ggaaggccag agaagttacc agatgtatgc tattcatggt gggtgttggc ttccctaaag    360
ataattggaa ggcttcattg gattgataga gaaaaactcc gcagtttcat cctagcatgt    420
caagatgaat aaacaggagg atttgcagat aggccaggag atatggtaga tccttttcat    480
actctgtttg gaattgctgg attgtcactt ttgggagaag aacagattaa acctgttagc    540
cctgtttttt gcatgcctga agaagtactt cggagagtga atgttcagcc tgaa          594

<210> SEQ ID NO 201
<211> LENGTH: 430
<212> TYPE: DNA
<213> ORGANISM: Bos Taurus

<400> SEQUENCE: 201
tcattcatgc ccggggtcca gcgacccatc ccagggagcc caagaggtgg cagctgtagc     60
accagggact taggtcggaa gtcagcggga cttcctcaga cttccctctc tccgtgaagg    120
ggagggcccc agtgcccaga ggccgggat gcacccgaag aagcccaccc cttgtcactg    180
atcagaagca ataaggccct ccatgtgcct gaaagcccag agggagcgcg ggcagggtcc    240
ccagcggcgg ggacggcatc tccccggaac ggcccctctc gcctccgcag ggacagcgct    300 ggccccgtg ggcgccccgg ccctccgcac ccgccgcagc cggagccctg cgccgccgcc    360
accgccgcca acaccaatgc ctcggccccc gacgccccc gcgggctgct ggcagtggga    420
tgggccgtgg                                                          430

<210> SEQ ID NO 202
<211> LENGTH: 637
<212> TYPE: DNA
<213> ORGANISM: Bos Taurus

<400> SEQUENCE: 202
agaaggagaa gatgattttt ctcctcctta ggataaatga aaccttgttt ttatgtaaga     60
atcagatgac caaatttgac ctcggtctga atggccccac aggttgtgct atgatgtaga    120
gccctcaagt aaagcctacc caggaagaga gtgagaaaga gaaccacttc tttgtctttg    180
cttttgcagt tcatctttaa ccttcttggg aagaaaaagg actctcccct tagagatgag    240
gggaaaagaa ggtttacatt ttaagacagg gaaaaaagtg gaatcaaatc ctaaaagtgt    300
gactggggag aagtcagtca tttctgtgtc ttttgaccct tgtgataatt aaccccgcgc    360
aataccatgt ttaagatgca tttagaataa caaaattaaa aacttgacat aagatctcat    420
```

| | |
|---|---|
| tttcagaaag cagattacag accaccagag ggaaatcatg ggggccgtat tgcacaggca | 480 |
| actctgagaa agttgtgctg aaaatgtaat tccttctaac caggtttcct ttttctcctt | 540 |
| tgaaagaaga acattccact ttgtttagaa ttctgagttt ttgttaaatc atcccactta | 600 |
| aaagctctct tccaacccaa cttatacagt ttgaaat | 637 |

<210> SEQ ID NO 203
<211> LENGTH: 477
<212> TYPE: DNA
<213> ORGANISM: Bos Taurus

<400> SEQUENCE: 203

| | |
|---|---|
| gcacgaggtc gctcagctgc ggtaccgctg tctgcgttgt ctgtttggag aaacccaaat | 60 |
| accgctgccc cgcctgccgc gtgccctact gctccttgcc ctgcttccgg aagcacaaag | 120 |
| agcagtgcag gcctgcagct ggtcctgtcg agaaaaaaat aagatcagct ctgactgcaa | 180 |
| aaactaaaaa gcctgtggaa aacgaaggtt ccttagatga tgatgactct gtggctgatt | 240 |
| ttctcaatag tgatgaggaa gaggacagag tgtctttgca gaatttaaag aatttagggg | 300 |
| agtctgcagc actgaggagc ttactgctca atccacacct cagacagctg atggtcgacc | 360 |
| tcgatcaggc ggacgacaag gccaagctta tgcgagcctg catgcaggag cccttgtttg | 420 |
| tggagtttgc tgactgctgc ttgagtatcg tggagccgtc tcagaacgag gatcctt | 477 |

<210> SEQ ID NO 204
<211> LENGTH: 484
<212> TYPE: DNA
<213> ORGANISM: Bos Taurus

<400> SEQUENCE: 204

| | |
|---|---|
| gcacgaggat gatgcaaaca gaaattccac cggcctccag atactatcat gtgtcatgtt | 60 |
| tcaccaggct ccacaagctt gagcttcaga ctgtctcggt cacttgcagg tgagcaggct | 120 |
| caagactctg ctccccagcc aggagaagat gactgacact gagtttggct acgttcacgg | 180 |
| gctggctgag gactatctga atatgtgtt gcagatacag caacctggat ccaagccaag | 240 |
| cagaaaattg ccaagaggtc aaagatcaag tcttttgtga agtttataa ttataatcac | 300 |
| ctcatgccca caaggtactc tgtggatatc cccttggaca aaactgttgt caacaaggat | 360 |
| gtcttcagag accctgctct caaacgcaag gcccgacgag aggcaaaggt caagtttgag | 420 |
| gagagataca agacgggcaa gaacaaatgg ttcttccaga agctgcggtt ttaggtctgt | 480 |
| ctca | 484 |

<210> SEQ ID NO 205
<211> LENGTH: 481
<212> TYPE: DNA
<213> ORGANISM: Bos Taurus

<400> SEQUENCE: 205

| | |
|---|---|
| tacagtgtgc ctttcggagt gctatggtcg gtaggttgct gttcgcagca gaggcccgta | 60 |
| ccacgagcca gcgcagggaa actacaccac tacactaaaa tttaccatat tttatatggt | 120 |
| cagaaatctg ttcaaagcaa aagataattt gagagggact tggatcaaga atggattctc | 180 |
| ttaactatac aacagcatgt gattcagctg tggaaactga aatcaaagt gacaactctt | 240 |
| cctctggtag cagcttattt aaaactcagt gtgttcctgt cccacctaaa cggaggcaaa | 300 |
| gaaacactat tagaaaattc gttcacatac ccaaaaatac tcaagcaaca gagtcatcta | 360 |
| gtgactcatc tatagagcca agaccactga ctttaaaggc tattttgaa agattcaaaa | 420 |

```
ataagaaacg taaacgtaaa aagaagaaat acaagccaac gggaagatca gtgggaagac    480
c                                                                   481
```

<210> SEQ ID NO 206
<211> LENGTH: 333
<212> TYPE: DNA
<213> ORGANISM: Bos Taurus

<400> SEQUENCE: 206

```
gattggatac acggctgcca cggggctggt ggggcctctc ctggtgtgga tcatgggtat    60
tcccagcgtt accagctctc aaaggatggg aactgagcaa ccctcggccc tgtgtttgtt    120
cacagaccct gtgggctcgt gtgtacagtg ttagagatcc tctttcatca caaaaggact    180
gtgggtggag gagtaaggtc atagctcaaa gggctttgca aaattttaat atattaaaac    240
aagaggcatc tgctagaaaa ccttctattg tataaaaccc gagcttttaa aaaaaaaaa    300
aaaaaaaaaa aaaaaaaaa aaaaaaaaac caa                                 333
```

<210> SEQ ID NO 207
<211> LENGTH: 349
<212> TYPE: DNA
<213> ORGANISM: Bos Taurus
<220> FEATURE:
<221> NAME/KEY: modified_base
<222> LOCATION: (148)..(150)
<223> OTHER INFORMATION: a, c, g, t, unknown, or other
<220> FEATURE:
<221> NAME/KEY: modified_base
<222> LOCATION: (152)..(154)
<223> OTHER INFORMATION: a, c, g, t, unknown, or other
<220> FEATURE:
<221> NAME/KEY: modified_base
<222> LOCATION: (279)..(280)
<223> OTHER INFORMATION: a, c, g, t, unknown, or other

<400> SEQUENCE: 207

```
ccagactcac ttccgctgcc cgggatgtgg gcggggcttc cgccggaaac cgcacttgct    60
tagcccctg gcggtccggg ctgaggagag ccgcccgctg ggcctcgaaa gtgaagaaac     120
gtgtggccac cgtgtgacac cgccaagnnn cnnntccata ctccggttgc gacgagggtg    180
cctcccgggg cccccggc atggagaggc cagtctcccc gagagagggc gccggggcgg      240
cctctgagca ggacgagctc cctccgagct cgaacctann tggtcagaag tgtggccgct    300
gggctggggg gccggaggcc ctcaagcctg gccccggagg ggagagacc                349
```

<210> SEQ ID NO 208
<211> LENGTH: 539
<212> TYPE: DNA
<213> ORGANISM: Bos Taurus

<400> SEQUENCE: 208

```
gcacgagaag gaaaagactg tgaaataaga gctgtggtga acaggactgc ctagacctat    60
gggccagtag tggactttga cccctgccag cacggtatga tgtgaagctc tcagtcaata    120
gaatccacag ccttcttcag agtcctggta accaggtctt gcttcaagtt ggtgtcttga    180
gtttgggatt tctgaaatca gctttctcaa gactttggaa ggctcagacc tctgtgctca    240
cagagctggg cacatagctg cctttttatgc agaggtgaca cagggcaaga acagtagta    300
gaggtggtgt agagccccag aagtttctgg aactgccctc tcccaagaag cactattaca    360
aaatcctcta cagagaaaca agttgtcgcc caaatgttgt ttcttcacat ataaacagag    420
```

```
gtctgtggac atgtgaggat aagaataaag acaaaaatct tgctctttac atgtgtatct    480
ctggcttcca ctgtggagag ataaccagca aaacaaggca agagatgtga gaataaact     539

<210> SEQ ID NO 209
<211> LENGTH: 456
<212> TYPE: DNA
<213> ORGANISM: Bos Taurus
<220> FEATURE:
<221> NAME/KEY: modified_base
<222> LOCATION: (16)..(16)
<223> OTHER INFORMATION: a, c, g, t, unknown, or other
<220> FEATURE:
<221> NAME/KEY: modified_base
<222> LOCATION: (47)..(47)
<223> OTHER INFORMATION: a, c, g, t, unknown, or other
<220> FEATURE:
<221> NAME/KEY: modified_base
<222> LOCATION: (63)..(63)
<223> OTHER INFORMATION: a, c, g, t, unknown, or other
<220> FEATURE:
<221> NAME/KEY: modified_base
<222> LOCATION: (74)..(74)
<223> OTHER INFORMATION: a, c, g, t, unknown, or other
<220> FEATURE:
<221> NAME/KEY: modified_base
<222> LOCATION: (103)..(103)
<223> OTHER INFORMATION: a, c, g, t, unknown, or other
<220> FEATURE:
<221> NAME/KEY: modified_base
<222> LOCATION: (134)..(134)
<223> OTHER INFORMATION: a, c, g, t, unknown, or other
<220> FEATURE:
<221> NAME/KEY: modified_base
<222> LOCATION: (230)..(230)
<223> OTHER INFORMATION: a, c, g, t, unknown, or other
<220> FEATURE:
<221> NAME/KEY: modified_base
<222> LOCATION: (236)..(236)
<223> OTHER INFORMATION: a, c, g, t, unknown, or other
<220> FEATURE:
<221> NAME/KEY: modified_base
<222> LOCATION: (254)..(254)
<223> OTHER INFORMATION: a, c, g, t, unknown, or other
<220> FEATURE:
<221> NAME/KEY: modified_base
<222> LOCATION: (274)..(274)
<223> OTHER INFORMATION: a, c, g, t, unknown, or other
<220> FEATURE:
<221> NAME/KEY: modified_base
<222> LOCATION: (281)..(281)
<223> OTHER INFORMATION: a, c, g, t, unknown, or other
<220> FEATURE:
<221> NAME/KEY: modified_base
<222> LOCATION: (317)..(317)
<223> OTHER INFORMATION: a, c, g, t, unknown, or other
<220> FEATURE:
<221> NAME/KEY: modified_base
<222> LOCATION: (332)..(332)
<223> OTHER INFORMATION: a, c, g, t, unknown, or other
<220> FEATURE:
<221> NAME/KEY: modified_base
<222> LOCATION: (345)..(345)
<223> OTHER INFORMATION: a, c, g, t, unknown, or other
<220> FEATURE:
<221> NAME/KEY: modified_base
<222> LOCATION: (351)..(351)
<223> OTHER INFORMATION: a, c, g, t, unknown, or other
<220> FEATURE:
<221> NAME/KEY: modified_base
<222> LOCATION: (358)..(358)
<223> OTHER INFORMATION: a, c, g, t, unknown, or other
<220> FEATURE:
<221> NAME/KEY: modified_base
<222> LOCATION: (412)..(413)
<223> OTHER INFORMATION: a, c, g, t, unknown, or other
<220> FEATURE:
<221> NAME/KEY: modified_base
```

<222> LOCATION: (417)..(417)
<223> OTHER INFORMATION: a, c, g, t, unknown, or other
<220> FEATURE:
<221> NAME/KEY: modified_base
<222> LOCATION: (452)..(452)
<223> OTHER INFORMATION: a, c, g, t, unknown, or other

<400> SEQUENCE: 209
aggacttggg gagtcnttat ctgctccatc tcagccactc gccacantca gaggatatgc    60
canggaggtc aggnggactg cttccagatc ctcctagaag canttacttg gaaggtccaa   120
gaggcccaag attngatggt cctcgaagat ttgaggattt agggtcaagg tgtgaaggac   180
cgagacccaa agggccttgt tttgaaggaa atcgcccga tgggccaagn acccanattt    240
gaaggtcacc cacnagcagg gcactaaaag caanatgggg naatgtattc ccgggggcc    300
aagcatctta aagtttncta tattaccccc antacatccc ttcanccctc ngacagantt   360
ggaccacagg tggaaaggcc ccaaacccaa cttttggac aagcaacatc anncaancaa    420
cctaaagttc acaagccagt aaccaaggaa anaaaa                             456

<210> SEQ ID NO 210
<211> LENGTH: 464
<212> TYPE: DNA
<213> ORGANISM: Bos Taurus

<400> SEQUENCE: 210
gtcatcgacg atcactttca aaagcagtgt acgtcacagg aatgtcagtc cccagatcag    60
aagagtgttt attttgaaaa gctgagggaa ggttggagtg taagtggatg gattggagga   120
tgtatacaag gggggcttca acttaaaata ttttctttct tttaaagaaa agagaaaaat   180
tcaaaacgtg gaaaactgtt aagagtagat aagctatgag gtgatgggga tattcatcat   240
attgttttt ctactttct gtaggcttca gatattttt aaaaaaccat tgagtgactt      300
tgttgtggtg atgcaaacag tgctacgtat cagacatttt ggaaacagtt aattgacctg   360
ggaaactaca cgtgtacata ggcttgtgta agaggaagag agcgccttct agatctgatc   420
gccacgtttc tagtgctgca gttccttcgc accaagttga aaca                    464

<210> SEQ ID NO 211
<211> LENGTH: 314
<212> TYPE: DNA
<213> ORGANISM: Bos Taurus

<400> SEQUENCE: 211
tttttttttt ttttttata gatacatatt taatataata aatgtgattg tggttacaga     60
tacatatttg gtgctttatc aagtagtatg aattccagag tacacaacac gtgggataca   120
aaatttgaag ataaacacaa ttgttcctaa atgaaaaaca tgggatacat gctgatgaat   180
ggatttccaa acttcatttt ccactctttt ctccaggctg gtctcctgaa gatgagttgc   240
aagttgtagc agtcttaaaa aaaaactcag tcccccaaat tctaataaca tgtaatatga   300
aaagaacttt tggc                                                     314

<210> SEQ ID NO 212
<211> LENGTH: 409
<212> TYPE: DNA
<213> ORGANISM: Bos Taurus

<400> SEQUENCE: 212
attttcgaag attgtggcaa cgtgcccagc gaactcaaag atcgaggaga attgaacaac    60

```
gaacaaggag agcgaaaagt ctgcaggttc aagcttgaat ggctgggaaa ttgctctgga      120
ataaatgatg aaacttacgg ctacaaagat ggcaaaccat gtgtcattat aaagctcaac      180
cgagttctgg gcttcaaacc taagcctccc aagaatgagt ccttggagac ttacccagtg      240
atgaagtata atccgtatgt cctgcctgtt cagtgcactg gcaagcgaga cgaagataag      300
gagaaagttg gaagcataga gtactttgga ctgggcggct accctggttt ccctctgcag      360
tattatccct actacggcaa gcttctgcag cccaagtacc tgcagcctc                  409

<210> SEQ ID NO 213
<211> LENGTH: 470
<212> TYPE: DNA
<213> ORGANISM: Bos Taurus
<220> FEATURE:
<221> NAME/KEY: modified_base
<222> LOCATION: (433)..(433)
<223> OTHER INFORMATION: a, c, g, t, unknown, or other

<400> SEQUENCE: 213
gcaacaatgc tttctgatcc agtgaaggct ttaaaaaaaa aaaaaatcc aagaacagaa       60 ttcattttca tcatctctgg ttttcagagg atttaaaaaa aaagtgtgtt tcctgggacg      120
cccgttaaaa tccttttctt tgtcgaaggc tgccatgagc tgcactttt ggggtgggaa      180 gggtgaatgc cgcgtgggga taggggggac aggggcaggg gcctgtcgtg gatgagggcc     240
tgtggctgcg gggggaggag tcctgtctcg caaacctcac cccaccagcc aggggggactt   300 attctaagac ccgtgcatga ggaatggtgg ccagtgttgt tctagatcga caaggtgttg    360
gtttctctgt aggctgtaac ttttaaaaat aaacagttat ttaagggtta tgctgcacta    420
gtatttctta agnggaaact gttccttaca gctaggaaag ggagtgggca                 470

<210> SEQ ID NO 214
<211> LENGTH: 435
<212> TYPE: DNA
<213> ORGANISM: Bos Taurus

<400> SEQUENCE: 214
atcacacacg atattgagga aagggcgtc cgcatgaagc tgacagtcat cgacacgccg       60
ggcttcgggg atcacatcaa caatgagaac tgctggcagc ccatcatgca gttcatcaac     120
gaccagtacg agaagtacct gcaagaggag gtcaacatca accggaagaa gcgcatcccg     180
gacacccgcg ttcactgctg cctgtacttc atccccgcca ccggccactc cctcaggccc     240
ctggacatcg agttcatgaa gcgcctgagc aaagtggtca acatcgtccc agtcatcgcc    300
aaggctgaca cgctgaccct ggaggagagg gtctacttca acagcggat cactgcggac     360 ctgctgtcca atggcattga cgtgtacccc cagaaggagt ttgacgagga ctctgaggac    420
cggctggtga atgag                                                      435

<210> SEQ ID NO 215
<211> LENGTH: 329
<212> TYPE: DNA
<213> ORGANISM: Bos Taurus

<400> SEQUENCE: 215
gcacgaggtt gtcttgcact gtttggaaat ctgcccccgc tcctccctgc cctcacttcc      60
tgaatgaaat gcttctgagg ttgttatga aaggagtgat ccttgggcag gcaggaggca    120
gtgggcttta tggctccttg gagttactgt tgatcttgac cttctctttg gctaccttga     180
gacaaagaat atgccaatac ttggggctct gagtttata gtcaatattt atttgtatca     240
```

```
tctctttgtc taggaatgta aaagtgactc taaactaaga tgtgtaataa aaatcagatt    300
tattgtacct ccaaaaaaaa aaaaaaaaa                                      329
```

<210> SEQ ID NO 216
<211> LENGTH: 516
<212> TYPE: DNA
<213> ORGANISM: Bos Taurus

<400> SEQUENCE: 216

```
gcacgaggac cttcgcaccc ccatcccagt ttctgtccct tctcggttgc ttttaggtgg     60
atcccttgga ggcagaagca gccaaggact gatcccaggt actctgtgta gcaaacaaac    120
tgtgaattct gactcccctt gcccttcttc cagctgtagg tgcctcccct ctgatcgcct    180
gggaggggac tgaagaaagg caagggccaa gatgctgcta cttctgaccc tcctctctgg    240
ggcagggcag gagaggagcc tggttcattg tgccacattt catacccgtg caggcatggg    300
cgagcgactg gcaccccttt ccggcctcaa agccctccct gcagtgaagc agggcaggag    360
ggaagaggcc ccagcattgg ggtttggatt ctagagggga catgatgacc gtcagggtca    420
agtgcagaaa tctttgcctt tgctaccatt tctgtatgat gagaaataaa agttcaccaa    480
ggttttgttt tgtaaaaaaa aaaaaaaaa aaaaaa                               516
```

<210> SEQ ID NO 217
<211> LENGTH: 510
<212> TYPE: DNA
<213> ORGANISM: Bos Taurus

<400> SEQUENCE: 217

```
agctcagctc gctcgtgtga attttgtcac gcccctttgc ctctctgagt ctgcttcctc     60
atccataatc aagggaatc tttgacatct cataaagcgt ggatgagcct tcacgtttct    120
gaaagaatag tgctcggcgc atagaaagtg ctggtagatg tcatctgtta aagatctttt    180
cttcatgtgg tgtaggctgc gagggacagg aaaatatctg aagccataaa atagtttcat    240
cagctattcc taaggcgaa tggttttctt ttctgttttt cctgaaatgg caaaggtacg    300
ggatggggag agatgacagg aggagatgaa gagataggac aagactggtt tctacgcttc    360
atttgtatca tgttatcgtt cggtgcatt ttttttagcc accgtcccat tttaaagcag    420
aaggtcagtc ataacaggga actctgttca atgttatggg cagcctggaa gggaagggag    480
tttgggggag aatggataca tgtatgtata                                    510
```

<210> SEQ ID NO 218
<211> LENGTH: 541
<212> TYPE: DNA
<213> ORGANISM: Bos Taurus

<400> SEQUENCE: 218

```
gtggggagcc aggacgacac agaccttagc acatacgggg acagcctgtc tggctggtgg     60
cttctgtgga agcggctgaa tccctgggca gacaagatca aggttccaga tatggcagag    120
atccagtctc gcctggccta cgtgtcctgc gtgcgacagc tggaggttgt gaagtccagc    180
tcctactgtg agtacctgcg cccacccatc gactgcttca agaccatgga cttcgggaag    240
ttcgaccaga tctatgatgt gggctaccag tatggatcga ccgtctttgg gggctggagc    300
cggggcgaca tcattgaaaa gattctcaca gaccggtggt ctgccgacct gaacgagagc    360
cgccgtgcag acgtgctcgc cttccccagc tctggcttca ccgacttggc ggagatagtg    420
```

```
tcccggatcg agccgcccac cacgagctac gtttcggttt ccgacggttg tgctgatggg     480
gaggagtcgg actgtctgac ggagtatgag gaggacgcgg ccctgagtg ctcacgggac     540 g                                                                    541

<210> SEQ ID NO 219
<211> LENGTH: 495
<212> TYPE: DNA
<213> ORGANISM: Bos Taurus

<400> SEQUENCE: 219
gcacgaggga cgaagccaga gatggtatat ccagcatgaa ggtgtcagac catgaggtcc     60
tcgcaggttc cgtagatggc cgggtgaggc gctatgacct gaggatgggg cagctcttct    120
cagactacgt gggcagcccc atcacctgca tctgcttcag ccgggatggc cagtgcaccc    180
tggtgtccag cctagactct accttgcggc ttctggacaa ggacacaggg gagctgctgg    240
gcgagtacac gggccataag aacaaggagt ataagctgga ctgctgcctg agcgagcgcg    300
atacacatgt ggtcagctgt tctgaggacg ggaaggtgtt cttctgggac ctggtggaag    360
gtgccctggc gctggccctg cctgtaggtc tggtgtggt gcaatcgctg acctaccacc    420
ccacagagcc ctgcctgctg actgccatgg ggggcagcat ccagtgctgg cgggaggaga    480
cctacgaggc tgaag                                                     495

<210> SEQ ID NO 220
<211> LENGTH: 489
<212> TYPE: DNA
<213> ORGANISM: Bos Taurus

<400> SEQUENCE: 220
ggttcactgc cctggtcatt ctcctgcatc ttctgtcgct ctggtggctg tctctgggag     60
ggactcagac agtcccagga gacctggaaa tggactcatt ggcctttgag gatgtggctg    120
taaacttcac cctggatgag tgggttttac tggattcctc acagaggaaa ctctacagag    180
atgtgatgcg ggaaaacttc aggaatgtag tctcagtaga agcaaaacag gaagatcagg    240
acattgacga tcaggacaaa aaccaggaga gaaaattacg aaatcccaag gcagagagac    300
actccgaaaa gaaagatatt aattcctctg aagaaagctt caaccttatt ccaactccca    360
atgtgaagag aactcgtgat ataaaaccat gggaatgcag agcatgtggg aaagtcttca    420
tgtatcattc atcccttact agacacatga aatgtcacat tgaaaacaga tcagatcgcc    480
gaaagtacc                                                            489

<210> SEQ ID NO 221
<211> LENGTH: 290
<212> TYPE: DNA
<213> ORGANISM: Bos Taurus

<400> SEQUENCE: 221
agccagctac ctcggtaact ccaattcagg ttaacttccc tagggaacag tgcaggtgtc     60
cacggacacc gcctcctcgg tggggtgggg gctgccactt cggagggggtg gcacggacct    120 gcctggcctc tccatttggg gtggttcctc ccccatcttc ttgctcttgg gttttccgac    180
gggtacaagg cctgccggc tccccctcc ccgggagc tcactctggt cttccaacag        240
gactgggcgt cagctcccg cccggctcca ccgccccc agtggctccc                  290

<210> SEQ ID NO 222
<211> LENGTH: 475
```

<212> TYPE: DNA
<213> ORGANISM: Bos Taurus

<400> SEQUENCE: 222

```
agaagcttta aatattagtg tttcatcaaa ttgggcttaa tttaagagaa tccattgaca      60
cgaaaatgaa agagaatgat cttagggttt caagcttctt aaacgaacac cccagtcagt     120
ccttcagacg cagctgttca gagctctaaa gccgaccagg ttcagtcact ggttgggctt     180
ccatgatgta actcggcctt ttctggtttt aatatttaca gggtattgca cataggagac     240
agatgaccag aacccgaaag gctctattgc acacacagat aatcacacgt gaaaataaaa     300
atccacagga ccaatagcgc atcttaaact tcttcatact tagaaaaata tattttttaaa    360
tagcagtctg cataatttcc agtcctcagg aaactagaga gaagctaaat aggaagttcc     420
tgaatggcaa gtactgatct ttggcagcat ttaaagggaa caggagtaaa gacct          475
```

<210> SEQ ID NO 223
<211> LENGTH: 408
<212> TYPE: DNA
<213> ORGANISM: Bos Taurus

<400> SEQUENCE: 223

```
gatactacat tctgggtttt gcttgaccac cagtgtcatt ctgactggca gtcagggtcc      60
tgacggacgc tgcagtgtgc acgtctttta aatacgatgg attgttttag tgctgtcagt     120
gataatgcta gcctacttct attttgactt tagtacagag tttataattg tgtaactcct     180
agaacattac atggagccct ggtcccttttt ccctacttga tgatttgact ttattctttt    240
tctcgatcgc tcactttcct gattctccaa ggaccaaatt ctccagtgag cactggagcg     300
tgtctccagg gtaagccaaa ggctgcgctc ctcagcctct aattgttctg cagctgcctc     360
tggcaggcac aagtagcccc actgtgtgca ggaacacatg ccaaggaa                  408
```

<210> SEQ ID NO 224
<211> LENGTH: 439
<212> TYPE: DNA
<213> ORGANISM: Bos Taurus
<220> FEATURE:
<221> NAME/KEY: modified_base
<222> LOCATION: (373)..(373)
<223> OTHER INFORMATION: a, c, g, t, unknown, or other

<400> SEQUENCE: 224

```
acctgccctc ttgctggctc gggcccagcc gtggtccctg gaaccctcaa gttgggggct      60
gcggccttgg gatgggggt cgcaggggg ctgctgcttc ccaggcgttg cccaccggtg       120
cctggtccag ctgcgggtca gagccccgag cagggtgccg cacaccggcc ctgaggatgc     180
cgccccgcg ggtccccgtg ctggttcctg ctgaggcccc gcttcgcccc gcacctggtc      240
ggtcatcaca gaagtctcca gaatcctgct cgcagcgttt ctcctgcaga cttaacaact     300
ctggacgcat tggcagttgg gacccagggg cgggcttggt gttctgttcc gggggggacgg   360
tttccagagg canctggtcc cctctcactc tgccttgccc tgccccgggc atcactggtc    420
acttgcctct gccagggac                                                  439
```

<210> SEQ ID NO 225
<211> LENGTH: 670
<212> TYPE: DNA
<213> ORGANISM: Bos Taurus
<220> FEATURE:
<221> NAME/KEY: modified_base
<222> LOCATION: (606)..(606)

<223> OTHER INFORMATION: a, c, g, t, unknown, or other

<400> SEQUENCE: 225

```
gcgctctctc gggcaacatg gcgggtgtgg aggaggcagc gtcctgcggg agccacctga      60
atggcgacct ggatccagac gaaagagagg agggagctgc ctctacggct gaggaagcgg     120
ccaagaaaaa aaaacggaag aagaagaaga gtaaaggggc tgccacaggg caacaggaac     180
ctgataaaga agcaggagcc tcagttgatg aggtgacaag acaattggaa agacaagcat     240
tggaagagaa agaaaaagat gatgatgatg aaggtaggat tatcgattgt gcttttactg     300
tcacttttaa tcccaaatat gatacattat taaaagctgt caaagatgcc actaacactg     360
gaataaagtg tgccggaatt gatgttcgtc tctgtgatgt tggtgaggct atccaagaag     420
ttatggaatc ctatgaagtt gaaatagatg gaagacata tcaaggcttc caagaacaaa      480
acacttgtta aatgtcatca atgaaaactt tggcactctt gccttctgcc gcagatggct     540
ggatcgtttg ggagaaagta atacttgat ggctctgaag aatctgtgtg acttgggcat      600
tgtagnccca tatccaccat tatgtgacat taaaggatca tatacagcac agtttgaaca     660
caccatactt                                                            670
```

<210> SEQ ID NO 226
<211> LENGTH: 484
<212> TYPE: DNA
<213> ORGANISM: Bos Taurus
<220> FEATURE:
<221> NAME/KEY: modified_base
<222> LOCATION: (169)..(169)
<223> OTHER INFORMATION: a, c, g, t, unknown, or other
<220> FEATURE:
<221> NAME/KEY: modified_base
<222> LOCATION: (415)..(415)
<223> OTHER INFORMATION: a, c, g, t, unknown, or other
<220> FEATURE:
<221> NAME/KEY: modified_base
<222> LOCATION: (417)..(418)
<223> OTHER INFORMATION: a, c, g, t, unknown, or other

<400> SEQUENCE: 226

```
tttgttttt tttttttttt ttgcttttt gttgcagcct ttagtccttg ccatggcagg       60
ctggttctat taaatacat caaaacatat cctaatgatt ccatgtcatc tcggcgactt      120
tgttcaatac caagatgtgc attgatgcta gcataccgag cagtgccant gagattttta     180
tcttctctgt atgggatgtg ttgccttgtc ctgttgtctc tgtacttttt ggccaaacca     240
aaatcaataa ggaataactt attacagtga cgcccaatac ccattaggaa gttatctggt     300
ttaatgtctc tgtgtataaa attctttgta tgcacatatt cgattctact gatcatctgg     360
tcagctaaca taagtacagt tttcattgtg aaccttcttg aacagaaatt gaagngnnct     420
tcaaggctgg gtccaagaag atccataact agcacgttat agtcttttc ctgaccatac      480
cacc                                                                  484
```

<210> SEQ ID NO 227
<211> LENGTH: 252
<212> TYPE: DNA
<213> ORGANISM: Bos Taurus

<400> SEQUENCE: 227

```
agagagagag aaaaatccat gatgcttacc tgtaaccccc tagaacccaa gtgccagaat      60
taattcctag atgctgcttc tgtttgaata aaaagtcact gcttttacac ttgaaaaaca     120
ctcaaaaaat gttcaactcc atgaaaactg ttttttggctt taagaaactg tttgatgttt    180
```

```
aactgtttcc tttgattgcc attccaccag taaattgttg gttgatttgc actgcacact    240
ggggttgggg ga                                                        252

<210> SEQ ID NO 228
<211> LENGTH: 612
<212> TYPE: DNA
<213> ORGANISM: Bos Taurus

<400> SEQUENCE: 228
gaggacaaca tggcttcttc tttggcatgt ttaattgtga tgtttaacgg acatccttgc     60
agtttaagat gacactttta aaataaaatt ctctcctaat gatgacttga gccctgccac    120
tcgatgggag aatcagcaga acctgtagga tcttatttgc aattgacatt ctctattgta    180
attttgttcc tgtttatttt taaattttc tttttgtttc actggaaagg aaagatgatg     240 ctcagttta acgttaaaa gtgtacaagt tgctttgtta caataaaact aaatgtgtac      300
acaaaggatt tgatgctttt ctctcagata aacttaatat gactttccaa gtttgacttg    360
tgtaatgtta ttgtcaaact ttttgtcacc ctatcttcgt attttttgat acgcactttg    420
caggatgacc tcagggctat attgattgag taaagggatt tgaatcaatg tattaatgtc    480
tccatagctg ggaacccatc atgggtataa tttgccatta gtttctgaaa tctttcacat    540
cattgaggat accagattgc tgaaaactcg gttctgaatg tgttgtactt ttgatttgta    600
tctcaaatca tt                                                        612

<210> SEQ ID NO 229
<211> LENGTH: 524
<212> TYPE: DNA
<213> ORGANISM: Bos Taurus
<220> FEATURE:
<221> NAME/KEY: modified_base
<222> LOCATION: (149)..(149)
<223> OTHER INFORMATION: a, c, g, t, unknown, or other
<220> FEATURE:
<221> NAME/KEY: modified_base
<222> LOCATION: (344)..(345)
<223> OTHER INFORMATION: a, c, g, t, unknown, or other
<220> FEATURE:
<221> NAME/KEY: modified_base
<222> LOCATION: (409)..(409)
<223> OTHER INFORMATION: a, c, g, t, unknown, or other
<220> FEATURE:
<221> NAME/KEY: modified_base
<222> LOCATION: (471)..(471)
<223> OTHER INFORMATION: a, c, g, t, unknown, or other

<400> SEQUENCE: 229
aactgctggg gtctgctctc gccgcccgcc cggcagtcag tcagcctcgc tgccgctgtc     60
gccgcctcag cggttccggt agtcttaagc ccgccccacc acctttccc cgcgcctccc     120 ggagcctccg ggtgtttcct gtccgcccnc acaggccggc cgcgaccgtc tgcgtcttct    180
cggcgcccct cgccgctccg gccgacatga gtggggacca tctccacaac gattcccaga    240
tcgaggcgga tttccgactg aatgattctc ataaacacaa agataagcat aaagatcgag    300
aacaccggca caaagagcac aagaaggaca aggagaaaga ccgnnaaaag tccaagcaca    360
gcaacagtga acataaagat tctgaaaaga aacacaaaga gaaggagang accaaacaca    420
aagatggaag ttcagagaag cataaagaca aacacaaaga cagagacaag naaaacgaa     480 aggaagagaa gattaaagct tctggggatg caaaaataaa aaag                     524

<210> SEQ ID NO 230
```

<211> LENGTH: 492
<212> TYPE: DNA
<213> ORGANISM: Bos Taurus

<400> SEQUENCE: 230

| gcacgagaaa agatcagtga ggatgagatc ccgcctccag tggccttggg caggaggccc | 60 |
| ctggtccccc aggaaacaac taacaggagc cctgaagcag aacccccagc tgcccctcc | 120 |
| gtggagccag ataacccctc ccagcctgag acaagcctct tgggcagccc tggtatttct | 180 |
| gccccacccg actcagaccc ggacccacgg gccctgctgt tggcccggca gagagagtac | 240 |
| aaagtggctg ctctgaatgc caagcgggct ggagacctag accgtgcccg agagctcatg | 300 |
| agggttggga agagatttgc tgctgtcctg gaggccctgg agaaggggca gcctgtggac | 360 |
| ctgagtgcca tgcccccatc accagaggac ctgaagcccc ttccacaggc ttcccaagcc | 420 |
| ccgacagcgc cctccgatgc accccggca gtggagcgaa tgcacccagt gatggcctct | 480 |
| gacatcccag ca | 492 |

<210> SEQ ID NO 231
<211> LENGTH: 460
<212> TYPE: DNA
<213> ORGANISM: Bos Taurus
<220> FEATURE:
<221> NAME/KEY: modified_base
<222> LOCATION: (355)..(355)
<223> OTHER INFORMATION: a, c, g, t, unknown, or other
<220> FEATURE:
<221> NAME/KEY: modified_base
<222> LOCATION: (391)..(393)
<223> OTHER INFORMATION: a, c, g, t, unknown, or other
<220> FEATURE:
<221> NAME/KEY: modified_base
<222> LOCATION: (421)..(421)
<223> OTHER INFORMATION: a, c, g, t, unknown, or other

<400> SEQUENCE: 231

| agaatttagt gttctgcagt tatgagtaat ataaactgct agctgttaaa gacagattgt | 60 |
| tcatgttaaa attctcttca ttttgttgtt cactgaggtt ggatatattt gacactgtag | 120 |
| atttctatat gtaaaaatat ctcccagtaa aaaaatgcct ttcttttctc tcctcctttc | 180 |
| tttttccttc ctaactgaag aacattttat catcactcag gttgaattaa attaacatct | 240 |
| caagctaaaa gctctgtaat tgaggttgcc tctggagaag ataggaaaca ttgcacaatg | 300 |
| caaactccta atgtctgttg agcttttacg tatgagtaat tccctttgat gtagntaaaa | 360 |
| gctttacctg tttacttttta aggacacact nnnatcattt gaatcagttc ttaaaatcca | 420 |
| ntttatacta tggatatcac aaccctatgc ataaattaac | 460 |

<210> SEQ ID NO 232
<211> LENGTH: 333
<212> TYPE: DNA
<213> ORGANISM: Bos Taurus

<400> SEQUENCE: 232

| aaaaatgtct ggagggatgg gaccttcagg atttattcat atttaagatg tagcttttg | 60 |
| ttgtttccgg cattatgtat aaagcgacga ttatttatg gaccaagttt taatgtaact | 120 |
| gttgcagtga aagtgcaata tctaaccccc tgctcccagc gggaaacgct cggcccgaca | 180 |
| atcacagccc cagccagggg ccccgtggcc agtgcctcct cctgtcggtc ccacctcacc | 240 |
| ccatctcgcc tgtcgcctcg gtgagcagcc atcggatgg aggagcacct acaagagtct | 300 |
| cggcccgcct gcaataaagg cctggaggct gcc | 333 |

<210> SEQ ID NO 233
<211> LENGTH: 611
<212> TYPE: DNA
<213> ORGANISM: Bos Taurus

<400> SEQUENCE: 233

| gccagggcca | gacccagcc | cgcgggcccg | agtccagcca | ctgcccctgc | cccaacccctt | 60 |
| tctcctgtct | cttgaaatct | gaggcacagc | ccagggcccg | ctccctcccc | gggggggaagg | 120 |
| gctggaggtg | ggaggaagcg | tcttgcttgt | ttaaattcgt | ggtagttcca | ggacgtgttt | 180 |
| gcaaactttt | cttcttgtaa | tgttttaagt | cattttgatt | ctaaactttt | atttagaggg | 240 |
| tgacttgttt | tgttttgctt | cagtgtctgt | gttttttggt | gtaaccttgt | taggtttgta | 300 |
| aagcgaattg | gaaaacttcc | taccctgatc | tggaactgcc | aaggaaatat | aagcgaactg | 360 |
| gcccttgtcc | ggcctttgaa | ctgccccact | ctgtaaagga | aaagtcttta | taaattgaaa | 420 |
| acgaaaatgt | aattgcctat | attccctttt | actttaacgc | aactatttaa | aaaatctgtt | 480 |
| ttctatgcat | ataagcattt | tgagtcattc | taagtaatgt | gcgtattgta | gttttccaa | 540 |
| ataatttttt | acattgataa | ttactatgct | gtgtggctga | ccattttgtt | caattttttt | 600 |
| tgctactata | g | | | | | 611 |

<210> SEQ ID NO 234
<211> LENGTH: 538
<212> TYPE: DNA
<213> ORGANISM: Bos Taurus

<400> SEQUENCE: 234

| tgcaccctga | gtgccccagc | cccatctgca | gtcctgcacc | atctccctga | gcagtaggct | 60 |
| tcccactgac | ggggaggctg | tgggaccaaa | gtccactttg | acccttgggt | tgggtggaac | 120 |
| acttgctggg | gggcctggaa | cagacaaggg | agcctcgaca | ggtcttccca | catattattt | 180 |
| attcacttct | ttcctcaacc | cgtgagacct | ggaaccccaa | gtgcgctgtt | ggcaatgacc | 240 |
| agaaaatgcc | tcgcaccaag | tatactggtc | agcttaacag | accttcccag | tgacagaagt | 300 |
| gattcctaca | gtctggaga | gaaggtggtg | acacctatgg | gttctcagcc | ataaggaaga | 360 |
| caccagacct | tcgtgccctg | ttcagggaaa | cccctagtt | ttctccagga | gcagcttgct | 420 |
| cttcgcgtcc | acatgggggc | ttgcagtgcg | gttttcctgg | ggcctgagtg | ctgcctgagc | 480 |
| ccacccactg | cccgaaccta | gtgtttgtgt | gtgaagtcca | tggagcaggt | acacacac | 538 |

<210> SEQ ID NO 235
<211> LENGTH: 301
<212> TYPE: DNA
<213> ORGANISM: Bos Taurus
<220> FEATURE:
<221> NAME/KEY: modified_base
<222> LOCATION: (78)..(80)
<223> OTHER INFORMATION: a, c, g, t, unknown, or other
<220> FEATURE:
<221> NAME/KEY: modified_base
<222> LOCATION: (112)..(112)
<223> OTHER INFORMATION: a, c, g, t, unknown, or other
<220> FEATURE:
<221> NAME/KEY: modified_base
<222> LOCATION: (142)..(142)
<223> OTHER INFORMATION: a, c, g, t, unknown, or other
<220> FEATURE:
<221> NAME/KEY: modified_base
<222> LOCATION: (223)..(225)
<223> OTHER INFORMATION: a, c, g, t, unknown, or other -continued

```
<400> SEQUENCE: 235
catccgggat gatgccaacc ccagctcccg ccagcgagga ctcaagcgct tccaggccaa      60
ccctgaggcc aactgggnnn cccggccccg tgcccggcca ggaggcaagg cngcaggaga     120
aactgtggaa gagagacgta gnctgctcca aaataagcga aaagagccgg tggaggaccc     180
agctgagcgg gctgcctggc tcaaaacatt tccctgcaag agnnncaagt aggtgaacca     240 aaccacccc caaccgaagt acccatgggt tctcccagct acaggactgg gccaatgggc     300
c                                                                     301

<210> SEQ ID NO 236
<211> LENGTH: 477
<212> TYPE: DNA
<213> ORGANISM: Bos Taurus

<400> SEQUENCE: 236
tgcctgcagt cccgggcccg gcggcgactg cgtgctctgc cccaacaagg gtggcgcctt      60
caagaagacg gacgacgacc gctggggcca cgtggtgtgc gccctgtgga tccccgaggt     120
gggcttcgcc aacaccgtgt tcatcgagcc catcgacggc gtgcggaaca tcccgcccgc     180
gcgctggaag ctgacctgct acctctgcaa gcagaagggc gtgggcgcct gcatccagtg     240
ccacaaggcc aactgctaca ccgccttcca cgtgacgtgc gcccagcgcg ccggcctcta     300
catgaagatg gagcccgtgc gcgagctggc cggcggcgcc gccaccttct ccgtcaggaa     360
gaccgcttac tgtgacgtcc acacgccccc cggctgcacc cgcaggcctc tgaacattta     420
cggggacgtg gagatgaaaa acggcgtctg tcggaaggag agttcggtca aagcggt       477

<210> SEQ ID NO 237
<211> LENGTH: 467
<212> TYPE: DNA
<213> ORGANISM: Bos Taurus
<220> FEATURE:
<221> NAME/KEY: modified_base
<222> LOCATION: (292)..(293)
<223> OTHER INFORMATION: a, c, g, t, unknown, or other
<220> FEATURE:
<221> NAME/KEY: modified_base
<222> LOCATION: (299)..(301)
<223> OTHER INFORMATION: a, c, g, t, unknown, or other
<220> FEATURE:
<221> NAME/KEY: modified_base
<222> LOCATION: (364)..(365)
<223> OTHER INFORMATION: a, c, g, t, unknown, or other

<400> SEQUENCE: 237
gcacgaggtt ttctgtaatc ctgtttggca agattttctt tatttgatgg taacaacaaa      60
ggttacagtt tagtacttaa accagcagtt aatagtgatt ttctccccag gcagagtaac     120
taaaagcacc tgtgaaaact gcaaagaaaa ctagggacag gacaagaggc agcggaagcc     180
tggctgctgt aaactggtgt gcaccccgc attccagcaa gggcagggga gccagaatca     240
ccgactgctt tcctcaggga cttgaattga cagttttttc ccaactatct tnntactgnn     300
ngcattccac tgtacccagt taaatataaa gaattagtct tcttaataaa atcacctttt     360
cagnngaact atacacatta aaaaaaaaat cactgattgt gtttccttcg tcttttttc     420 tttgaacttg caggtgattg agtctcctgt gtttcttctt ttacacc                  467

<210> SEQ ID NO 238
<211> LENGTH: 591
<212> TYPE: DNA
<213> ORGANISM: Bos Taurus
```

```
<220> FEATURE:
<221> NAME/KEY: modified_base
<222> LOCATION: (504)..(505)
<223> OTHER INFORMATION: a, c, g, t, unknown, or other

<400> SEQUENCE: 238
cagtgcaggt ggacggagaa gcatgggttc agcctccagg gattatcaag atcgtgcaca        60
agaacagagc tcagatgctc accagggaca gggcctttga aagcaccctg aagtcttggg       120
aagataagca gaaatgtgat tcgggtaagc cagttctccg aacgcacttg tacatccagc       180
acgcggcgga cctggccacg gaggaagtgt ctcagatgca gctgtgctcg caggcggccg       240
aggagctcat caccaggatc tgcgatgcgg ccaccatcca ctgtctattg gagcaggagc       300
tggcccacgc ggtgaacgcc tgctcccacg ccctgaacaa agccaaccca cgcttcccag       360
agagtcttac aagagacact gccactgaaa tagccatcaa tgtgaaggcc ctatataacg       420
aaacagaatc tttactagtg ggcagggttc ctttgcaatt ggaatctcca catgaagagc       480
gagtatccaa tgccttacat tccnnggaag tggagctaca gaagttaaca gagattccat       540
ggctttatta tatcttacac ccgaatgagg atgaggagcc ccccatggat t                591

<210> SEQ ID NO 239
<211> LENGTH: 287
<212> TYPE: DNA
<213> ORGANISM: Bos Taurus

<400> SEQUENCE: 239
ggccaggtgg tggcctggga ctcccaacac agtgtgcatc tgtttccctg tgcagtgaat        60
gtcagtccga ccagtacatc tgctcgctaa gaggatggtc caatttgaca atgttactcc       120
cattcggatt ctgtactgcc ttttggtaga tgaaaactac caggaaaaga agggaaggga       180
agttcccagt taaagttccc aaaagatcga ggctgtgaga cgcatagagg tatacagaaa       240
gctgaggcca gaacgctctg gtggtgggc gtgcagatgg aggcagc                      287

<210> SEQ ID NO 240
<211> LENGTH: 562
<212> TYPE: DNA
<213> ORGANISM: Bos Taurus
<220> FEATURE:
<221> NAME/KEY: modified_base
<222> LOCATION: (501)..(502)
<223> OTHER INFORMATION: a, c, g, t, unknown, or other

<400> SEQUENCE: 240 gttttaata ttcctgaga gatgtctctg gaaggaaaag tgttttgaaa actaatgact          60
atttttgagg acaaaaatga caacttaagc taatttctta aatacagtag gataactttc       120
aggacaatat tgcctcacaa ccctgctcac attgagaagt cttttttttcg tttccccctta      180 gctgttctga ctggatttt ctacagaagc tatggaagat tatctttgtt ctcgtttgct         240
gctatttcct gtcctacttt aagaaatata aatacataga aatggtgcat ctttaacatt       300
tgtttgtaca tgtataaatg tcttgtattt taattcgttt ttagcatgta gcaacacgaa       360
ttgttcaagg gtaagccaca acatctaaaa atcactccta gatacgaaca ataaaggaaa       420
aaaaatggta ccgatttagg aggaaacaaa gccgctgtcg ctgggttttc tgtgcagcct       480
gcagtgactt ccgacacacg nngagaagct gtcactgtaa accaagtcat ccttgttggg       540
agagcgccac agcctgctgc tt                                                 562

<210> SEQ ID NO 241
```

<211> LENGTH: 558
<212> TYPE: DNA
<213> ORGANISM: Bos Taurus

<400> SEQUENCE: 241

```
gcacgagcca actacaaaaa gcctcgcacc ccgacccttc tccacctctg tgcatcttct      60
cccgactcga cgtcgtcgtt acagggaaga agaagcgggt gagaaaaact tctgtttcca     120
ccgttttgcc catttctgca gatttgttcc gaggccgagg agcctttgtt ggaagagatg     180
gtcatggtcc tgagccccct gttttttggtc ttcatactgg gtctgggtct gaccccagtg    240
gccccggctc aagatgacta cagatacata cacttcctga cccagcacta cgatgccaaa     300
ccaaagggcc ggaatgacga atattgtttt aacatgatga aaaatcgacg cctgaccaga     360
ccttgcaaag accgcaacac ctttattcat ggcaacaaga atgacattaa ggccatctgt     420
gaggacagaa atggacagcc ttacagaggc gatctcagaa taagcaagtc tgaattccag     480
atcaccatct gcaagcataa aggaggttcc tcccggcctc catgccggta cggagccaca     540
gaagactcca gagtcatt                                                    558
```

<210> SEQ ID NO 242
<211> LENGTH: 390
<212> TYPE: DNA
<213> ORGANISM: Bos Taurus

<400> SEQUENCE: 242

```
ttgaccgccg tggcccagag cgaagaggtg ggaagcgtgg ccgagggcaa gcaggtgcat      60
cccagccccg caccctggc accccgcag gccgcgtgct ctcagagctc aagaccaagc      120
agcagatcct gaagcagcgg cgccgagccc agaagatgcg cttcctgcag cgtgggggcc     180
tgaagcagct ctctgcccgc aaccggcgcc gagcccagga gctgcagcag ggcgcctttg     240
gccggggtgc cccttccaag aagggcaaga tgaggaagag gatgtaagaa ggtgacacag     300
ccccgcgatt cctccgttgg tccaggcgtg ggcatcagca gcgttcccca tgtaccgctg     360
tgtccctggc cctgagttgg gtgctggggg                                       390
```

<210> SEQ ID NO 243
<211> LENGTH: 389
<212> TYPE: DNA
<213> ORGANISM: Bos Taurus
<220> FEATURE:
<221> NAME/KEY: modified_base
<222> LOCATION: (30)..(32)
<223> OTHER INFORMATION: a, c, g, t, unknown, or other

<400> SEQUENCE: 243

```
tttttttttt tttttttttt cttccaaggn nnggtttatt tcaaaattat gaagatttat      60
atattatttt ttattacata caataaaggg gtttagctta aagtaaaagc tttcacattt     120
aaagttttta ttttaaaaag atattttaaa aatgtagacc cttaaaaacc accaaaaaag     180
ctgaatatat cttgcagcgt aggtttatcc ttaaatattc acatctcaaa tgctgtttag     240
aaaaaagatt taaaaactgg ctaaaaatca tttacacttg gcaatgatta aaatctcatc     300
tctgacagag catattaatg gcacataatg aatttactgt cacaagcatt taacagttta     360
atgggtacgt agtttttatca gtatacaaa                                       389
```

<210> SEQ ID NO 244
<211> LENGTH: 641
<212> TYPE: DNA
<213> ORGANISM: Bos Taurus

```
<220> FEATURE:
<221> NAME/KEY: modified_base
<222> LOCATION: (591)..(591)
<223> OTHER INFORMATION: a, c, g, t, unknown, or other

<400> SEQUENCE: 244
aggacctgac cagctgagct tccagcgagg ggaagtgctg cgtgtcatcg ccactgtgga      60
tgaggactgg ctccgctgtg ggagggatgg agcggagggg ctggtacccg tggggtatac     120
ctcccttgtt ctctaggcct agcacctgtt cctttcctgc acctctctct cccttctgtc     180
acctgggaat ggaatggcct gtgaatactc acccatgtat actgactgtc cccaaagtat     240
cttccctgtc tgcaaaatga cactttcctc ccatagccat ttctgctaat acctaaaata     300
aactttttc cttccttcct atacccatct ataaggtgaa atctgctctt cgaaaatata     360
taaaaacgaa tttccctcca tgccatctct ttcctctttc caatctgtat tctgcaaaat     420
ggaaatctag cccctgtat cttcttcctc cataagtgga ctgcacctct atatacgcct      480
cagttcccaa gacttgaagg gcctctatag tcttcttcct gtgtatggaa ccttccccca     540
cctcacccat cccgcattgc ctgtatttat gatgtactca tgctggacta ngtgctgaag     600
tctggacacc cctggtgggt gggcctgtgg ggtcagtctg t                          641

<210> SEQ ID NO 245
<211> LENGTH: 627
<212> TYPE: DNA
<213> ORGANISM: Bos Taurus

<400> SEQUENCE: 245
tttaaggtgg aacaggtcat ttttttgttt ctctgctttt aaatctaatg cttataaaag      60
aggtgtgttt atccctagac cacagtgcct tgcaccccac caccaccatt tggtaaatgg     120
gcattagatg ctgcacaagc ctttagggca ctattttggt agctataaaa gtttatccag     180
aaactgtacc tggtgtctca gtttattgtc attcaacttg ttcatgaata ttaactattt     240
ccagggtttg tttagaagga agaattgatc tgttctttag tttactatat ttttttttc      300
tggtgtaaaa atgagccaga ataagccctt attgctaagt aattatataa acccacataa     360
tccctgcata agattccctc cacacacttc actatatgta tgtggatttg gatagaaaat     420
gatgttgcca gcattaccag ttttaaatac ttgactatac agattgatgg aataaaatta     480
ttaaagtgtt ttcagggaac ttaatccata tgtcaccacc aaagatttct acagtgttat     540
aaggtatgta aatattccaa atttctgtaa acattggtta gataaagagt ttttctcttt     600
tttttggaat aacacagttt gtactct                                          627

<210> SEQ ID NO 246
<211> LENGTH: 516
<212> TYPE: DNA
<213> ORGANISM: Bos Taurus

<400> SEQUENCE: 246
ttttttttct tttatctttt aaaatggaag caagtgtttc gacagaatac gatggctgct      60
ctataagagc cgatctagga gtaattcact gggtcttctc tcggatagct cggatttaaa     120
aaagaaaaa agacaaaaca agaaaaataa cccacagagc gtcaaacacc aactctgagc     180
ctggtgggga atccgttcat taaataagcc ataagctaca cattcaggtc agaataactg     240
gctcctgcct ccttatgtct ccaagccata ttccctatgg tgtttcacca ccaacaacaa     300
ttttgctcac ttaattaatt gggtatcaga accttagaac atttctgaat cttaataatg     360
```

```
aaggtcttca gcagattgtg ttgataaaga aacacataca ggcttgaata taaaccactg    420
taattattgg tttctttata tctcattatc cacttgagta tttaaagcac acacgtacac    480
acaaaaccac accaaacatt caaatacccct gaaact                             516
```

<210> SEQ ID NO 247
<211> LENGTH: 238
<212> TYPE: DNA
<213> ORGANISM: Bos Taurus

<400> SEQUENCE: 247

```
aggcttataa ggaacaaata aaagagaga gtgtcttgac tgctacaagc attttaaata     60
atccaatagt gaaggcacga tacgaacgtt ttattaaggg tgagaatccc tttgaaattc    120
aagatcattc tcaagatcaa caaatagaag gagatgagga gggagaggaa aagattgacg    180
aacctgtgga agaagaggag gaagaggagg aagaagagga ggaagtgggg aaggggga     238
```

<210> SEQ ID NO 248
<211> LENGTH: 558
<212> TYPE: DNA
<213> ORGANISM: Bos Taurus

<400> SEQUENCE: 248

```
acggcagctc aaaggaaggc acttctgtct gagtctcctg cagaaaatga aattactgtt     60
caacttacca aaatgcctta cacattcctt acaaataaac caaccgacac agcgttatcc    120
gggcccaact tcggtagctc tgagaagcca taaagacaag agtttcttag caccagaagt    180
agatcttcca gacccagttt gtacaagaag aacctttgtc acattcgaga aacactatcg    240
ccctggcccg gccctggacc accagccagc agacgccaaa gccctcgtca gccgtgcgac    300
agacccaggg cttgttctgg gaggcgggcc cggggtctgt atgtcagtca gtgcaattgt    360
gtctttcgcg gggttgggg tcgggtggtt ctagtgctga gtccctaagg ctgcagagca    420
gactggaagg tcacagccag cgaggcagca gccccagtcc ccggaagatg ctgcccccag    480
aaccgacgcg tgactcctgg gtgttaatgc cattaaaacc cgcgtgtcgc ccggcaaaaa    540 aaaaaaaaa aaacaaat                                                  558
```

<210> SEQ ID NO 249
<211> LENGTH: 478
<212> TYPE: DNA
<213> ORGANISM: Bos Taurus

<400> SEQUENCE: 249

```
ttgaaaaagc tgtaatttgg cctcagtatg tgaaggatag aattcattcc acttacatgt     60
acttagcagg aagtattggc ttaacagctt tgtctgctgt ggcagtgagc agaactcctg    120
ctctcatgaa cttcatgatg agaggctctt ggataaccat tggtgcaacc tttgcagcca    180
tgattggagc tggaatgctg gtacagtcaa tcatacga gcagagtcca ggcccaaagc     240
accttgcttg gttactacat tctggtgtaa tgggtgctgt ggtggctcct ctgacgatcc    300
taggggggcc tcttctcctc agagctgcgt ggtacacggc tggcatcgtg ggaggtctct    360
ccaccgtggc catgtgtgcg cccagtgaga agtttctgaa catgggggcc cccctgggtg    420
tgggcctcgg tgtcgtcttt tgtgtcctcac taggatcgat gtttcttcca cctaccac     478
```

<210> SEQ ID NO 250
<211> LENGTH: 393
<212> TYPE: DNA
<213> ORGANISM: Bos Taurus

<400> SEQUENCE: 250

```
tcctctaaaa ctatttcctt gtggtccgag ggcaagttgc tactcatctt gagtaatctt      60
tgcctctctt tccatggcat tttgacccta agtccattga agcattctga tcttccacct     120
tcctaatggg gatatgggaa gacatctacc ttccttatgg agatatgatt ctcctagttg     180
agagaatatg cgaatggagc tctcccccat attaaaccag ctctaatgga tttattctga     240
cctcgagtca ctgttgccat gatttcccag gtgtttgctt catgttctcg ctttgagaac     300
catttccctt tgttttcttt cctccaccac ctccgtatga ggtaatggca ccttgccatt     360
ggatggttgg actctgccct ttcctccgtg cag                                  393
```

<210> SEQ ID NO 251
<211> LENGTH: 393
<212> TYPE: DNA
<213> ORGANISM: Bos Taurus

<400> SEQUENCE: 251

```
taaagatcta actcaagact gactctgcta gtgtagcatt tccctggggg attttggttt      60
taattagacg gttcactgct actgtgtagt gccgggatgg ccggacatgg ttaggggta     120
acccagcgac accagcactg attggacggc ccttcaccaa tcagaagctc agtgcccagt     180
gggccgctgt gtgacttgga atcatgttgt gcactatagt cacatgtact gtaaagtgaa     240
aagggatgtg caaaaacaga aagcgagacc tgctactaga aaagtgggaa ggggaatgag     300
taaacttctt ttcttgcgga cagatgtgca catagccgct agtaaaacca gcctcaaaca     360
gaatgctcat agcttaataa taaaagctgt gca                                  393
```

<210> SEQ ID NO 252
<211> LENGTH: 446
<212> TYPE: DNA
<213> ORGANISM: Bos Taurus

<400> SEQUENCE: 252

```
tttatcctct ctctttcagg gtagatttct ggatagctag tagtgatggc atctgaaata      60
gccattgagg ggtgggtggt attcatttag taacccgagc ttttgcctga agagcttctg     120
cttaactctt ctttgctgtt tcaataggtc tttatttggt tttcttcctg ctaggttgat     180
gcatattagc ttaagaactt ttaaattgtg ggggcagtaa gaaaactttg aatgcctggg     240
gccctgcact tctctcttag aagcagccag agggtttagt gtgtatctgt tagcaggaga     300
gtcttctaga aggtccattt ggtacctctc acacccacag ctttgtgcta tggtttggcc     360
ctcctcctct cctgatgaat ccatgccatg acccagtgta gctgaatctc atgtgctctg     420
aaagccattg gaaaggcacg tgttgc                                          446
```

<210> SEQ ID NO 253
<211> LENGTH: 476
<212> TYPE: DNA
<213> ORGANISM: Bos Taurus
<220> FEATURE:
<221> NAME/KEY: modified_base
<222> LOCATION: (344)..(344)
<223> OTHER INFORMATION: a, c, g, t, unknown, or other

<400> SEQUENCE: 253

```
gcagaatgga tttgttgatt taatccagag gcactttata taatgtgttc tctgttttag      60
tttatcaaag actcctcaga gataagaacc cttttaacag tgagcaaggc tcggggagtg     120
```

| | |
|---|---|
| aaatggagtc agaggtggag cgtcaaggcc agggtgtggc cccaggtctg cctgtccctc | 180 |
| ccagcctcag tttcctcaga tgtagaggga agaccaccac tccccgcccg ccacatgttt | 240 |
| ttctaggagg aaaactctgt gtccccattt ttgcacatta gttctttttt cggtcctgac | 300 |
| ttttacatat atatatactt ttttttttc ttttgtctgt gctntgcggg attttattcc | 360 |
| ccaactaggg atcgaatctg tgcccctgc atttgaagca cgcacttaac cactggaccg | 420 |
| ctagaaaagt cccctttatc tgttttatta ttttgttaca tttactttgt gggatg | 476 |

<210> SEQ ID NO 254
<211> LENGTH: 495
<212> TYPE: DNA
<213> ORGANISM: Bos Taurus

<400> SEQUENCE: 254

| | |
|---|---|
| tttgaaaatt aattttgtat tatgcattct tgatttggtt catcagtagg tgctattatt | 60 |
| catcctgtga ttccagtaga ttaggggaat tgatacctt ttgcagtttt gaataaaagt | 120 |
| gttgataatt tctaaattat catttataaa attcttagag cttcaacatt tgcgtcatc | 180 |
| acaggctgat ttagtattgt tttgtattaa aatagtcctt ttccctttcg tgctgccatt | 240 |
| cattccgtgc cattagtcct taaaatgcgt ttaaagaaga aatagccaag ttgactgtta | 300 |
| cacctcatcc aaacagacac atcacaaaca tacgagggcg acagtgcctg ggatggacgt | 360 |
| ggtacttctc agtctgcctg ttctgagaga agagcaatta gcatggccac gtcaccttgt | 420 |
| gcttgaagtg gaaaacttta agatcggaaa aatttaaagt cagatcaggg atttacagct | 480 |
| atctactttg gtagt | 495 |

<210> SEQ ID NO 255
<211> LENGTH: 566
<212> TYPE: DNA
<213> ORGANISM: Bos Taurus

<400> SEQUENCE: 255

| | |
|---|---|
| ggtaagatca tagtggatgt ggggtcacaa atatgtagat ggccacatga agataggcag | 60 |
| agactggagt tatgatgctg aaagtcaagg aatatgtggg gccatcagaa gcaagaagag | 120 |
| tcaaggaagg ttggaaggat tcttccttgg agtgcagagg gtacatggcc ctgctgacac | 180 |
| cttaattttg ggtttctaag caccagaatg gtgagaaaat caatttctgt agttttaagc | 240 |
| cacacagtta gtggtaattt attacagcaa ttctaggaaa ctaacacagt caccaaactg | 300 |
| attatctttg ctaatttatg ataaatttat gttttttatca tgttacataa gcagatgaaa | 360 |
| tgagtgtgaa gagttgtagt ttctgtgaaa accaagttga atactttgga aaagctagat | 420 |
| gaaagtgtgt tgctttcccc atgcccaatt taaatgtatt ggttaattat tggtaaaaca | 480 |
| gttgtaaaag actggccagc aatgtactaa aaatccacag gtattcatta ccagtgtaca | 540 |
| actatataac gtaacacata tgattt | 566 |

<210> SEQ ID NO 256
<211> LENGTH: 526
<212> TYPE: DNA
<213> ORGANISM: Bos Taurus

<400> SEQUENCE: 256

| | |
|---|---|
| gcaactagag agtaaccct gctctccaca actagagaaa agcccatgca gcaacgaaga | 60 |
| cccagcacag ccaaaaataa attaataaat aaataaaatt ttttttaaaa gaaggtccct | 120 |
| ctaggagaaa gcccttcaaa atacctcctg aatccagact ataacctgcc ccagtgaaag | 180 |

```
aagagtagct tattcatttc tgtgtctgct gtgtggatcg caaggccagg catggagcag    240
gactcccagt gatgctggct gaatggacaa gtggagaatt ttgagaggag tgctccggat    300
cagggtatca gaggagctgg agcttgcctt gtaaatatca tctattggta ttttgcggca    360
agtcacttaa cctctagcct cagcctattt ggctgtcaga tggagctgag aagacttgct    420
tcaaggattg ttttcgagca gcctgaagaa gctgatgaaa gcagatcct caggagccta    480 taaaacaact acacggattg gtgcaaccgc atgtcagtca ccgcgt                   526

<210> SEQ ID NO 257
<211> LENGTH: 225
<212> TYPE: DNA
<213> ORGANISM: Bos Taurus

<400> SEQUENCE: 257
gcatttgttt ttttttttt ttttttttaa atgactctga aactttaatt acagatactt     60
atcaacatct gaaagtgtgg attcgttctc tttctgcgga aaggctggca cggttgttcc   120
cttacaccca tgtcttttcc tgctcccgt ctcttcttta tgtaaaaaaa aaaatgtctg    180
gatcacagtc ccaaccaact ctgctctgca tcccttgctg ggaac                   225

<210> SEQ ID NO 258
<211> LENGTH: 558
<212> TYPE: DNA
<213> ORGANISM: Bos Taurus

<400> SEQUENCE: 258
gcacgaggac atactggacc tgaacgagat ggtcagacaa gtgacgggga agatccccat    60
cttcttctat tcacactatg gctgttactg cagaaaaggt ggccaaggcc aacccagaga   120
tgccacagac aggtgctgcc gtgaacatga ctgctgctac cgtcacctga atctgacaa    180 ctgtgacatc agcttcgacc actatgacta ccctttttc caggggaaag tccagtgttc    240
caccaagggg agctggtgtg agcagcagct gtgcgcctgt gacaagacgt tggccttctg    300
cctgcagcgg aacctgaaca cctacaagaa tcacctgcga cgtctgtcca gatgcgaggg   360
cgagactcta gcctgtcccc ctgcatcttg agctctgggg aaggccccc aggaccactg    420 gccacagccc cgacctctgc ctggagcctt taaagcactc ctggaagagg aaggggcttg    480
gcctcgcccc tagctaccac ttgcctcttg gaccttctga atctcccagg ctgtctgttc   540
cgagggtgga ttgagatc                                                  558

<210> SEQ ID NO 259
<211> LENGTH: 439
<212> TYPE: DNA
<213> ORGANISM: Bos Taurus

<400> SEQUENCE: 259
agatgtttca cttataacaa atgcaaaaac ttaagacaaa agtgatatgt gaagaagtct    60
tttacagtaa aatatatcct gaatccatat aggttcgttc ataattgagt ctcttcttga   120
gctacctttt ctaacacgta gacaatgtga agacagtgac agcgtccttt tctagaggtg   180
tttaacctgt tcttacaaac tgtgaaaaca aagaattttc tactttacta atgtttgtgg   240
ttttaaacag ttatttcat tctaatcagt tctctaccct ctaatttcta ctaaaactgt    300
aaatacattt agaaatgata tttgtaaata cagtatatga agtcaagtta attttgggga    360
cagtggagaa cctcccaatt ggctctgcct tggcagtttt gttttttgtt gttgctggtt   420
```

```
ttttttttttt ttaaacagc                                              439

<210> SEQ ID NO 260
<211> LENGTH: 481
<212> TYPE: DNA
<213> ORGANISM: Bos Taurus
<220> FEATURE:
<221> NAME/KEY: modified_base
<222> LOCATION: (384)..(384)
<223> OTHER INFORMATION: a, c, g, t, unknown, or other

<400> SEQUENCE: 260
tcatttccta ttgcagctgg ggggaccgcc acaaacgcag cgacgtaaac ccgcaggagc     60
gtgtgctgac agtccagggg tgtttcctcg gcagagccca gggagggtca gcgtcctgtc    120
tcccggggtg tcagcagagc tcagcccctg cggtagggcc aggtcctgct cctgccgct    180 gtgagctgaa gcccttattg gcttctggaa gcctctgggc tggccgctcg gccccttcc    240 tcttccaagc tggcagctcc tctcccatgt tgggccttca cacgtcccct gctgcttcca    300
agggctgtgc aattaggggt cccacgaaga tccaggtcg cccgtccgcc tgtgtccgtg     360
tccctgcgct taccggcccg cagnggccgg ctcgggcccc ggcggccagg cctccttgcg    420
gcaggagggg cagagctggc tctgcgcggc tcggcgcagc tgtgcacgtt ccgccctga    480 c                                                                  481

<210> SEQ ID NO 261
<211> LENGTH: 597
<212> TYPE: DNA
<213> ORGANISM: Bos Taurus

<400> SEQUENCE: 261
gtgtaactca gtcttgtctt ccttctggga gctctaggtt tgctcccagc tcagaccatg     60
gttgcctcta gccactacta tggggctgcc tcctgtactt ctcttcctcc tctggttctg    120
ccatctctga ctctcttgag gattcttccc ctattgctca tgccttcagg gtccctgtat    180
tccatcattg gtccacttct ctttcctctc tatttactcc caaaatagaa tcatccatcc    240
tgatgtcaac tgccattgat atgctggtga ttcccaaata tatatctcaa gccctaactg    300
ccctttatct ttagatctgt attttttatca cctgctggat atctccttgg acatgtccag    360
atggactcaa ctctttctgt ccctactgcc aagtatgttc ctcctgaatt ccaatcctgg    420
ttacattcat cactcttcat aggctcacca gctagaaaca ttttatgggc ttaaattcct    480
tcccatattt tactagtcag tatatcatat ccattccact ccaagttttc ttgtttttgg    540
cccttcttct cccctctgcc tctactctag ttcacaggag cttgggattt ggagtca       597

<210> SEQ ID NO 262
<211> LENGTH: 563
<212> TYPE: DNA
<213> ORGANISM: Bos Taurus

<400> SEQUENCE: 262
ggaaagagaa cagccaccac gttttgctca gcctgggaca tttgaatttg agtatgcatc     60
tcgatggaag gctctggatg aaatggagaa gcagcagcgc gagcaggttg acagaaacat    120
ccgagaagcc aaagagaaac tggaggcgga gatggaagcg gcccggcacg agcaccagct    180
gatgctcatg cggcaagatt taatgaggcg tcaagaggaa ctcagacgtt tggaagaact    240
cagaaatcaa gagctacaaa aacgaaagca aatacagctg aggcatgagg aagagcaccg    300
tcgtcgtgaa gaggaaatga tccgacacag agaacaggag gagctgaggc gacagcagga    360
```

```
gggctttaag ccaaactata tggaaaatga gaaaaggaaa catggatgaa gctacctgaa    420
atttggcttc ctgtgtgagc ccaaagttga gagctgagga aaacctgcca gagtttcctt    480
tcagtggtct tggggagcag gaacctcagc cttttcttgat tatcgcttgt gagatgagac   540
tgatgacatc agagcactgg ctt                                            563
```

```
<210> SEQ ID NO 263
<211> LENGTH: 470
<212> TYPE: DNA
<213> ORGANISM: Bos Taurus
<220> FEATURE:
<221> NAME/KEY: modified_base
<222> LOCATION: (48)..(50)
<223> OTHER INFORMATION: a, c, g, t, unknown, or other
<220> FEATURE:
<221> NAME/KEY: modified_base
<222> LOCATION: (382)..(382)
<223> OTHER INFORMATION: a, c, g, t, unknown, or other
<220> FEATURE:
<221> NAME/KEY: modified_base
<222> LOCATION: (388)..(388)
<223> OTHER INFORMATION: a, c, g, t, unknown, or other
<220> FEATURE:
<221> NAME/KEY: modified_base
<222> LOCATION: (390)..(390)
<223> OTHER INFORMATION: a, c, g, t, unknown, or other

<400> SEQUENCE: 263
cgcaactttt taaaagattc agttacagct cttttgaaga ggttttcnnn ttttatttaa    60
actactaatg gatcaaagaa caattgttta tttttttctc tttggtttta gatattaatg   120
ataaccttgt tggaattttt ttccaaagaa aatattttta taattccgta atttaatgtg   180
ttccttttca tcatccactc ttggcagtgt taggctatgt ttaccttaaa ataaatctga   240
ctcaagattt tttatgtatg tataaagaag tattttgtgt gctacaaaag ccttttcaaa   300
ttatcagtaa tttttttttt ttaaagaatg agccagtatt tgctcagtgc tctgtaaggg   360
aacatgcaga tggaagctca gntcttangn aagggctggg gagatgggtt tattttccc    420 acctgtgaat atgtaaaaca taaaaccatt atctctgagg gacttctcac               470
```

```
<210> SEQ ID NO 264
<211> LENGTH: 630
<212> TYPE: DNA
<213> ORGANISM: Bos Taurus
<220> FEATURE:
<221> NAME/KEY: modified_base
<222> LOCATION: (278)..(280)
<223> OTHER INFORMATION: a, c, g, t, unknown, or other

<400> SEQUENCE: 264
ctcttacctt ttcctcttgt tccaccaaat ggttgctctt ttccagagca gaaactggcg    60
gatatgcaat gatagccaga acccctgttc ctcacccacc tgggtctgta gctgaatgtg   120
ggctggcaga acagggacac caagagatgg agaaggggc ttcccagcct cccagcaact    180
tcctagccca taagcaagca caaagatgag gcagagatct gtcagagctg aaagttcatt   240
tggttgctca caactcaggt atgcacaccg tgtggcannn gggcagcaga gccctacttg   300
accgcaagtc ccgtgcaccc agacctgtgg ccagatcgtg gactctggct gcctcaggcg   360
ccgcctcttt gcatagggtt ctcctccatt agtaactaca gccgactcag acatcctcca   420
cattgtgcac actggttctg cctttgtcct cgcaagttga tacttggcat tagcatgaaa   480
cttgtgggtg tgggagggtt tagagagaat tctaacacaa aacatcctat taaattgtac   540
```

```
ttgagagatg aaaaaactcc tgttgtattt tgacagaatt atttttatta aaatatacat        600
ccatgagcaa aaaaaaaaaa aaaaaaaaca                                         630

<210> SEQ ID NO 265
<211> LENGTH: 419
<212> TYPE: DNA
<213> ORGANISM: Bos Taurus

<400> SEQUENCE: 265
gcaaatcgaa ctcctgcttc agctccggct gcagctctag ctccagcccc ggctccggca         60
ggctctggga ccactgtacc agctccatca cagactcccg gttcagctcc cctgcctcag        120
gcccagggac ccccgtaccc cacctatcca gggtatcccg ggtattgcca aatgcccatg        180
cccatgggct acaatcctta tgcgtatggc cagtataata tgccgtatcc accagtgtat        240
caccagagcc ctgggcaggc tccatacccg gaccccagc agccttcata ccccttccct         300 cagccccac agcagtctta ctatccacag cagtaatatg tcagctcaga agctcagctg         360
gttcagttca aagggaaaga ataccaacc ctgcaataag tgtactaaac tctacgctc          419

<210> SEQ ID NO 266
<211> LENGTH: 212
<212> TYPE: DNA
<213> ORGANISM: Bos Taurus

<400> SEQUENCE: 266
gtggccgtgg ctaccatctc aacgaggagg gaacccgctg cgttgatgtg gacgagtgct         60 ctccccctc tgagccctgt gggccggggc acctgtgtgt gaactcccct ggaagtttcc        120
gctgtgagtg caaagccggg tactacttcg acggcatcag caggacatgt gtggacatca        180
acgagtgccg gcggtaccca gggcgcctgt gc                                      212

<210> SEQ ID NO 267
<211> LENGTH: 352
<212> TYPE: DNA
<213> ORGANISM: Bos Taurus
<220> FEATURE:
<221> NAME/KEY: modified_base
<222> LOCATION: (82)..(82)
<223> OTHER INFORMATION: a, c, g, t, unknown, or other
<220> FEATURE:
<221> NAME/KEY: modified_base
<222> LOCATION: (226)..(226)
<223> OTHER INFORMATION: a, c, g, t, unknown, or other
<220> FEATURE:
<221> NAME/KEY: modified_base
<222> LOCATION: (249)..(251)
<223> OTHER INFORMATION: a, c, g, t, unknown, or other

<400> SEQUENCE: 267
ccccgacacc accacccat ggagagtacc tgccagatat ggggctggga atcgagggag          60
cgaaaccccc gcacgcctac gntgctaaga aggcaagaa tggaggaggg ccggcctacg        120
agatgcccgc gttcaccgct gagctgacgg cgcctttccc gcccgtgggg gccccggtga        180
agttcgacaa actgctctat aacggcagac agaactacaa cccgcngacg ggcatcttca        240
cctgcgagnn nnctggggtc tactactttg tataccacgt tcactgcaag gggggcaacg        300
tgtgggttgc tctgtttaag aacaacgagc ccgtaatgta cacgtacgac ga                352

<210> SEQ ID NO 268
<211> LENGTH: 251
<212> TYPE: DNA
<213> ORGANISM: Bos Taurus
```

<400> SEQUENCE: 268

```
aagggaaagc agtttgattt gttttaaaaa cacttttttat cagctttgga gaaaaccgaa    60
atgcaaacga gaacagctgc tctgaagccc cttccttgtg cagggagaag aaaaaaaaaa   120
aaacaaaacc aaaactcaga aagccgttca gcagcgtgaa atgccttttc agaagctaac   180
ccggggattt tgaaagcctg gctccgtgtc tcagtttgaa aaaagattc caggctgtaa   240
aaggctttca t                                                        251
```

<210> SEQ ID NO 269
<211> LENGTH: 489
<212> TYPE: DNA
<213> ORGANISM: Bos Taurus

<400> SEQUENCE: 269

```
acaaagtagc gttttaataa aaaaaaaaac actcacagac ataaagatcc cgtcactacc    60
cccaaagctg aataagttaa gttgtgtccc tgctgccctg tgacggaggc gggcccgtgc   120
gctcagggct cgccccttct ccagatggcg acaatgttgg agtcagtcag cgcagtgagg   180
taggtaaagg cggggttggc caccaccgtg ttcaccatcg tcttggtcac cgtctggccc   240
attgcctggg gctggggcca cttaaggatc tgcgtggggg cctgcggggc ggtctgtggt   300
ggggagcgct gcgccaggag gggcctgacg tcatagatcc acacgctgcc ctgctcatcc   360
ccgcagagca caagccccctt gtcaggacag gtgctgaggg agaagtaggc caggatggtg   420
ggcgaccact gcagccaagc caggactacc acagccactg tgggctggct gccccgaccc   480
tgccacgtc                                                           489
```

<210> SEQ ID NO 270
<211> LENGTH: 558
<212> TYPE: DNA
<213> ORGANISM: Bos Taurus
<220> FEATURE:
<221> NAME/KEY: modified_base
<222> LOCATION: (470)..(471)
<223> OTHER INFORMATION: a, c, g, t, unknown, or other

<400> SEQUENCE: 270

```
tgtttaagtc ctttgggtgt ggtgtgtgtg tgcttaacca tgtctgactc ttcgatcccc    60
ctggactgta gcccatcagg cttctctctc catgggattc ttccagcaag aatattggag   120
tggagtgcta tttcctctcc agatcaggga ttgaacctac atctcatatg cctcctgcat   180
tggagagatc cagtgagcct gggtctgtct ggaaaattct tggatcctgt ggggacacac   240
cctgagtgtg aacctggata ccggaccttg gtggcaaaat tcatcttctc ctcactgggg   300
tgtaattttt aaaacacagc aacatcatct cattgatctc tccatttgtc tttggtctca   360
gctcagtaaa ctgaatgaat gaagcttaaa tgcaatcatt ttctaaacat tttacatctg   420
tcagtataaa caactgccct gagcctcaca tatcttcgc taccatgaan nacccatgtc   480
agctgaagtg tacagcggca tgctttctcc aaacttatca agtttactgc accctctctc   540
ctctggcctg ctactcat                                                 558
```

<210> SEQ ID NO 271
<211> LENGTH: 447
<212> TYPE: DNA
<213> ORGANISM: Bos Taurus

<400> SEQUENCE: 271

| gcggcttgct gccccggcgt cggctgcggc ggagctgcgg ctcagctctt cggcccgccg | 60 |
| caccccctaag gtgcccttgg cccgtgctcc cattcacacg ctcgggtgag gtggctttga | 120 |
| ccccggcttg cctggctagc acgaccgagg aggtggctgg acggctggag aatgaacgga | 180 |
| gaagccgact gccccacaga cctggaaatg gccgccccta aaggccaaga ccgctggtcc | 240 |
| caggaagaca tgttgacttt gttggaatgc atgaagaaca acattccatc caatgacagc | 300 |
| tccaagttca aaaccaccga gtcacatatg gactgggaaa agtagcatt taaagacttt | 360 |
| tctggagaca tgtgcaagct gaaatgggtg gagatttcta cgaggtgag aaagttccgt | 420 |
| acattgacag aattgatcct cgatgct | 447 |

<210> SEQ ID NO 272
<211> LENGTH: 533
<212> TYPE: DNA
<213> ORGANISM: Bos Taurus

<400> SEQUENCE: 272

| gtcatcacct ccatcttgga gaaaatggat atattcttgt tgccggtggc caatcctgat | 60 |
| ggatatgtgt acactcatac tcacaaccga ttatggagga agacacggtc tgtaaatcct | 120 |
| agaagcacct gcattggtgc tgatccaaat agaaattggg attctcattt tggaggagtg | 180 |
| ggaaccagta acgacccttg ctctgatacg tatcatggac tccatgccca ttcagaagtg | 240 |
| gaggtgaaat cggtggcaga tttcattaca aatcatgggg acttcaaatg cctcatcgac | 300 |
| ctgcacagct actcgcagct ggtgatgtat ccatatggct acacaactag cagagtcccg | 360 |
| gatgctgatg aactggatat ggtggcacgg aatgcatcca agctatggc ttccttgtcg | 420 |
| ggcactcagt accaagtggg ttctgtcggc tccactgtct atacagctag tgggaacact | 480 |
| attgactggg catatgataa tggcatcaag tatgcgttct cttttgagtt gag | 533 |

<210> SEQ ID NO 273
<211> LENGTH: 491
<212> TYPE: DNA
<213> ORGANISM: Bos Taurus

<400> SEQUENCE: 273

| agagctgcta aaggcgaccc tctaccccgg ccgagggaca cacagacca gtgctgaagg | 60 |
| ctaatgtgtg gcttttacta ccctccccac cccctatttt ccaggggtt taggctacat | 120 |
| ttaaaatcta aacctgcagt ccgtgacttc ctatcaagcc caaatgcatt ttggttttgg | 180 |
| ttttctgctt ctctgcccct ttccacttct ttcgtatttg ctttatgtgc gagtgctgaa | 240 |
| atggccctgg aattgagaat ttggctctcc accaagcacc ttatcttgcc accttagcct | 300 |
| taagaatgag tatgaagaaa aatgcacagc ccctctctgtc cagggcagtg agaagccctg | 360 |
| caaggaagag gtcggagaca aggaaaggaa cagacagtca ctcccacagt tccgaggcta | 420 |
| ccatgcctca gggggcccca gggattgcag aaggggata tcctggaagt tcgatttctg | 480 |
| cagtttgtgc c | 491 |

<210> SEQ ID NO 274
<211> LENGTH: 591
<212> TYPE: DNA
<213> ORGANISM: Bos Taurus
<220> FEATURE:
<221> NAME/KEY: modified_base
<222> LOCATION: (107)..(109)
<223> OTHER INFORMATION: a, c, g, t, unknown, or other

<400> SEQUENCE: 274

```
gcttggggct attttttgtgt atattgatga tgaagacatg tgcaatgtag aattacagtg      60
aaactctggt gactgtgggt agtcattctt actgaaaact gcactgnnnt tcccacacca     120
tgaactggct ggtcgcctct attttcggga ttctttgaca cttggtggta cttcattctt     180
gccaggcata ccttctaact gagtaggaag gagccttgta agatccttca caggcagtgc     240
atgtgaagca tgctttgctg ctataaaaat gagcatcaga aagtgtgtat catgttatt      300 tattatgttc ttgcttttgg tgtagaattc agcaaatttt catcaaaatc tagccagagc     360
ccttcactgc catgatagct ggggcttcac cagtctgtct actgtgatga tttgtagact     420
tctggttgta tttctgtatt tattttaaa tctaccgtgt ggatatttag tgctatgtct      480
ctttaagttt ggattagtgt ttctaaaatg gtggagttgc tctgaatgtt acaaatggat     540
caaggcatta aaatgaatga gatctacctt tcaccaagta ctgatgctat t              591

<210> SEQ ID NO 275
<211> LENGTH: 255
<212> TYPE: DNA
<213> ORGANISM: Bos Taurus

<400> SEQUENCE: 275
gcctgaccca agggcctttc ctggggcttc tggggcccat cctgaaccca gatccacatg      60
gaccttcgtg ttgagccagg gtgaggggag caacccccac cccgacccac tcaagcccct     120
ggccagcttc acagggcagg gggaggctgg ctcttactca ctggagctgc tagaaccttc     180
cctacagtct ggacccagct aacctgaggg gagccattgc cacctttcca gcaccaccca     240 tgtgcccca cccac                                                       255

<210> SEQ ID NO 276
<211> LENGTH: 406
<212> TYPE: DNA
<213> ORGANISM: Bos Taurus
<220> FEATURE:
<221> NAME/KEY: modified_base
<222> LOCATION: (104)..(104)
<223> OTHER INFORMATION: a, c, g, t, unknown, or other

<400> SEQUENCE: 276
tgttaccatt ctgatgttgg agtggccgca tttgttttt ttttttttt taatgatgaa       60 agtagttaat atttggtcaa tatgtccatt gtaaccataa ggtngaaaat gaaacacagg     120
tctgttttct ttcctgtaaa ctggagatcc tctgcactgg ccaccttgtt agaggagagc     180
attagtgcct ccctgcaacc ctatcatccc cctcagagca aaactcgata aaggtgact      240 gccaggtatg ggaagaactg gtcttgggag tcaatttctt aaagaattta tttccagtac     300
tgctttagct aaacagatgg ctacttatat ctcttgaatg atttaattac cccagatcct     360
atagccagtc agaaacgagc ttattcacag aagtacagca taaccc                    406

<210> SEQ ID NO 277
<211> LENGTH: 443
<212> TYPE: DNA
<213> ORGANISM: Bos Taurus

<400> SEQUENCE: 277
gcttccgggt aggaattagg tgaccccggc tgccgctgga acctgcggtg acagcagcca      60
tgggggctca cctggcccgg agatacctgg gcgatgcatc ggtggagccc gatcccctgc     120
ggatgcccac tttcccgccc gactacggct tccccgagcg caaggaacgc gagatggtgg     180
```

| | |
|---|---|
| ccactcagca ggagatgaac gacgcccagc tggtgctcca gcaacgcgac tactgcgccc | 240 |
| actacctcat ccggtttctc aagtgcaagc gcgacagctt ccccaacttc ctggcctgca | 300 |
| agcacgagcg gcacgactgg gactactgcg agcacctcga ctatgtgaag cgcatgaagg | 360 |
| agtttgagcg cgagcggcgg ctgctccagc ggaagaagag acgggagcag agggaggcgg | 420 |
| acatggccaa aggcctgggg ccc | 443 |

<210> SEQ ID NO 278
<211> LENGTH: 573
<212> TYPE: DNA
<213> ORGANISM: Bos Taurus
<220> FEATURE:
<221> NAME/KEY: modified_base
<222> LOCATION: (406)..(410)
<223> OTHER INFORMATION: a, c, g, t, unknown, or other

<400> SEQUENCE: 278

| | |
|---|---|
| gcacgaggta tcccgggcat cctggcgccg gcggcggcta ctacgcaggc gggtacggag | 60 |
| gggctcccgg agggcctgcg tttcccgggc aaactcagga tccgctgtat ggttactttg | 120 |
| ctgctgtagc tggacaggat ggacaaatag atgctgatga actgcaaaga tgcctgacac | 180 |
| agtcgggcat tgctggagga tacaaacctt ttaacctgga gacttgccgg cttatggttt | 240 |
| caatgctgga tagagacatg tcaggcacaa tgggtttcaa tgaatttaaa gaactctggg | 300 |
| ctgtactgaa tggctggaga caacacttta tcagtttcga cagtgatagg agtggaacag | 360 |
| tggatcccca agaattgcag aaggccctga caacaatggg atttannnnn gagtccccag | 420 |
| gctgtgaatt caattgcaaa acgatacagt accaatggaa agatcacctt cgatgattac | 480 |
| atcgcctgtt gcgtcaagct gcgagctcta acagacagct ttcgaagacg agatactgct | 540 |
| cagcaaggtg tagtaaattt cccatatgat gat | 573 |

<210> SEQ ID NO 279
<211> LENGTH: 561
<212> TYPE: DNA
<213> ORGANISM: Bos Taurus

<400> SEQUENCE: 279

| | |
|---|---|
| gcacgaggaa ggttgtagct gcccgtgtga agtccagaga gcgtaagccc tgtcactgga | 60 |
| cccagtctga cctcctttc tgacggctgc ctggtgtaat cactaggaga tctctcactg | 120 |
| ggagttacca ccttccccg gtggtacccc cttttgtagc tggatgagaa ctgtggggtc | 180 |
| ctgatccctc tgcatcttcg ctgggaaatt tccatccct tggaaatatc ccttagaaaa | 240 |
| accttcatgt cccctaagga gaccactgac attgccaagt tgaaaaatcc catagattgt | 300 |
| aatcctgcaa cctcgctgga ctctcagcct ctgagcagtg atgggttcag tgttaaatgt | 360 |
| gataaatact gtattttgta ttgtttaaat ggcatctccc acaaaatgtg aaaatggtcc | 420 |
| cggagaaggc agcttcctgt atgcagtgtg cttttaaaa aaaaaaaaa aaaacaagta | 480 |
| acaactcctt ttgagaaaca atttctactt tgaaatcata tcaatgaaaa gatgtatatg | 540 |
| cacttataat tttcctaata a | 561 |

<210> SEQ ID NO 280
<211> LENGTH: 344
<212> TYPE: DNA
<213> ORGANISM: Bos Taurus

<400> SEQUENCE: 280

| | |
|---|---|
| gagatcagct ccctcaagga cgagttacag acagctttac gggataagaa gtacgccagt | 60 |

```
gacaagtaca aagacatcta cacagagctc agcatcgtga gggcgaaggc cgactgcgac    120
gtcagcaggt tgaaggagca gctgaaagcc gccacggaag cactgggtga aagtccccg    180 gagaacccac ctgtgtccgg atatgacatc atgaagtcca agagcaaccc cgatttcctg    240
aagacagaca ggtcatgtgt cggccggcag ctcagaggcc tcaggtccaa gagtctgaag    300
gaaggcctga cggtgcaaga tcgcctgaag ctctttgagt cccg                     344
```

<210> SEQ ID NO 281
<211> LENGTH: 479
<212> TYPE: DNA
<213> ORGANISM: Bos Taurus
<220> FEATURE:
<221> NAME/KEY: modified_base
<222> LOCATION: (202)..(205)
<223> OTHER INFORMATION: a, c, g, t, unknown, or other

<400> SEQUENCE: 281

```
ggcccagaag ctgctgaact ccgacctggg ggagctcatc aacaagatga aactggccca     60
gcagtacgtc atgaccagcc tgcagcagga gtacaagaag cagatgctga cagccgcgca    120
cgcgctggcc gtggacgcca agaacctgct cgacgtcatc gaccaggcca gactgaaggc    180
cctggggcag ccgaggccgc annnngcacg acccgccctt gccccacccg ccacgaggcc    240
acccggcgca ggcacaccca cgccaacgt tttgactgac ggctgcttgg aaatctcaca    300
taagtttaac tgcgttttga tttggttgt tgttgtttca gctctttaat catggtgttc    360
agaaaagtcc gggatccaca gtgcagcatt tttctgagag taaaagttgt atgtgagaag    420
ctcttaaaga acgatgaagg ataggctgtg ctcacgtcag gatacgcttt cgtggaaat    479
```

<210> SEQ ID NO 282
<211> LENGTH: 524
<212> TYPE: DNA
<213> ORGANISM: Bos Taurus
<220> FEATURE:
<221> NAME/KEY: modified_base
<222> LOCATION: (119)..(120)
<223> OTHER INFORMATION: a, c, g, t, unknown, or other

<400> SEQUENCE: 282

```
gcacgagcct agtccattgg ccagagaaga aggcctttcc ctccctgtgt ccagccctcc     60
cccagatggg gacaggcagg tcatcgattc aagtatagat ggcccagttg tgaatctgnn    120
ggctacagag gtgacagcag gcgccctggg cacacacttg tcacagccgg agttggaaga    180
gactcctgag gaccgagaac ccacccagga agacgcagag cccaggtctg ccgcaggctc    240
cttgaaggag ctcagaaatt tgctgacggt gaccgccgaa gtaacagggg agtccgctgt    300
gcttgaggtt gagaaagata cacatgagga ggcccttgtt ccccaagata ttgaaaaaga    360
agaggaagca acccaaatcg acacagaggc cagtcaagca tctgcttcgg gtcaggacaa    420
ctgtgaagaa agtgaagtcg gtgaggggga ggcccatggt ccaactccca aggccgaggc    480
cagcggggtg gagctgggag aatttccaga tgctcagcca acct                     524
```

<210> SEQ ID NO 283
<211> LENGTH: 462
<212> TYPE: DNA
<213> ORGANISM: Bos Taurus

<400> SEQUENCE: 283

```
gaattggaac gttctgcttt ggtgtgatca tgtttctcca gtattacctc aacgagcaag     60
```

| | |
|---|---:|
| gagagcgggt ctacacgctg aagaagcttg atcctttggg acaacagacg tgctcggccc | 120 |
| accctgctcg attctcccca gacgacaaat actctcgaca ccgaatcacc atcaagaaac | 180 |
| gcttcaaggt gctcatgacc cagcagccgc gccccgtcct ctgaggatgt cttaacattt | 240 |
| cgtgtgtctt ctgctgcctg ccagccccca agagactttg tgcagccagg ctcttcagtc | 300 |
| tgtgagcctg gaagcttgct ccgacccta ctcctcgaat ccggtctcat ctttgccttt | 360 |
| gattatgctt gttgtgaagc agtcatggta gcatccccgt ccaaggggag atatttgaat | 420 |
| cttttcgtac cttgaatcac tgccaggtta ttaaaatgat tt | 462 |

<210> SEQ ID NO 284
<211> LENGTH: 410
<212> TYPE: DNA
<213> ORGANISM: Bos Taurus

<400> SEQUENCE: 284

| | |
|---|---:|
| tttctctacc ttgcccctag gagcgaatcc gtttagctcg acagattgaa aaagcggagt | 60 |
| atcggaactt ccaggcttgt ctgcacaact cttggatcga gcaggccgcg gctgccctgg | 120 |
| agattgagct ggaagaagaa atgtataggg aggaaaagt tgatgagcag gaagagcgtc | 180 |
| ggagacaaaa gcagatgaag atcctgaaga aggagctgcg ccatttactt tcgcagccgc | 240 |
| tgtttaaaga tgacctgaaa accaagtatc ccactcagtc aggcaagctg ccctgctca | 300 |
| cgtctgcccc aagaaagggt gagtccgcgc tgagctgcct ttccaaacag aagaagaaga | 360 |
| agaagaaaaa gcagcagccg caggagcagc cgcagccgag cacaagtgca | 410 |

<210> SEQ ID NO 285
<211> LENGTH: 445
<212> TYPE: DNA
<213> ORGANISM: Bos Taurus

<400> SEQUENCE: 285

| | |
|---|---:|
| ccctcgcccg gcctgccggc gccgctctcc gccgcagctt cagcacctcg gcccagaaca | 60 |
| atgctaaagt agccgtgctg ggggcctctg gaggaattgg gcagcctctt tcgcttcttc | 120 |
| tgaagaacag cccgttggtg agccgcctga ccctctacga tatcgctcac acgcccggag | 180 |
| tggccgccga cctgagccac atcgagacca gagcgaccgt gaaaggctat ctcggacctg | 240 |
| agcagctgcc agattgcctg aagggctgtg atgtggtggt cattccggca ggagtcccaa | 300 |
| gaaaaccagg tatgcccga gatgactgt tcaataccaa tgccacgatc gtggccaccc | 360 |
| tgaccgctgc ctgtgcccag cactgcccgg aagccatgat ctgcatcatc tcaaatccag | 420 |
| ttaactccac catcccaatc acagc | 445 |

<210> SEQ ID NO 286
<211> LENGTH: 404
<212> TYPE: DNA
<213> ORGANISM: Bos Taurus

<400> SEQUENCE: 286

| | |
|---|---:|
| tttttttca ccgtccaaat cttgacttta ttttttttat ataaaaatg caattttgga | 60 |
| aacccaccct acctttccc ctaacataat gcttttacct cttaaaaata aaaataaagt | 120 |
| actaatccta tgtacatcac atgtaccata aaaaatgtat ccaagtttc tattgctacc | 180 |
| aaagtgttct aaatcaaaac gagttacaga aagcccctca ttgtaaacaa aagattacaa | 240 |
| gttacaaaat caaagcacac acagccagag tcatttatac aacaaccaac atcctgctcc | 300 |
| caaagcaagt tgaattttta tgtgcctgta taaaaatgca tatcaatata cttctgcaaa | 360 | tttattttc attataaagc aaatgaatac actttctaca ataa        404

<210> SEQ ID NO 287
<211> LENGTH: 468
<212> TYPE: DNA
<213> ORGANISM: Bos Taurus

<400> SEQUENCE: 287
gctccttagg tataaaggta atctttctg attaagtggt tattgaagtg ttttgagttt        60
gtacattttt gccacacgtg ttctgcagat ggttgattat aaacatactt tacctctcat       120
actagtaagt gtttagtttc agaatcataa gtatatttt aggtaagagc ccctgattc         180
aaagaatgct cttgttgctg cagtttttaa aacatgggtt tttctgtgta cacacttaaa       240
tctctttatt catctttta ggtcctacag ctctgctggc tcatgaaata ggttttggaa        300
gcaaagttac aacacaccca cttgctaaag acaaaatgat gaacgaagt cattacagct        360
actccgagaa ccgtgtggaa aaggatggcc tgatccttac cagccgaggg ccaggaacca      420
gctttgagtt tgctctgaag atcgtcgagg tgctggttgg caaggagg                    468

<210> SEQ ID NO 288
<211> LENGTH: 467
<212> TYPE: DNA
<213> ORGANISM: Bos Taurus

<400> SEQUENCE: 288
gcttgagaga gattttatc tggtgcaatc tccctgcagt gtgtgtgaca acttaacctg         60
gctactgaaa aagagtgcca tgcccaacac cactgccagg acctttcctt cacctaatag       120
caggagtttc tctcatcaat tggaatctcc aggccccaca aaatggtatt gttttggaa        180
caataggact gtagaatctt tcatcattta acttggtgga ggcagggctg gaggggaat       240
ataaatcagc aagcctttga gttaggggcc aggaaataca gctttagatc cattttaat       300
gattcatttc cttttggtc atataactgc acaacgggag atgaaagggg aaaatagaaa       360
atttgacttt taggtgccaa tagtacattg cactacactg atcgaagaag ttatccaaag      420
tactgtataa catcttgttt attatttaat gttttctaaa agtgaaa                    467

<210> SEQ ID NO 289
<211> LENGTH: 535
<212> TYPE: DNA
<213> ORGANISM: Bos Taurus

<400> SEQUENCE: 289
gcacgagggc caacgaaggc ttgatcacca agcttcaggc ttgctgccgg gggtacttag       60
tccgacagga gttccgatcc aggatgaatt tcctgaagaa acagatcccg gccatcacct      120
gcattcagtc tcagtggaga ggatacaagc agaagaaggc gtaccaagac cgcttggctt      180
acctgcgctc ccacaaagat gaagttataa agatccagtc tctggcaagg atgcaccaag      240
ctagaaagcg ctatagagaa cgcctgcagt atttccgaga tcatataaat gacattatca      300
aaatccaggc ttttatccgg gcaaacaaag ctcgtgatga ctacaagact ctcatcaacg      360
ccgaggatcc gcctatgatt gtggtccgga aatttgtcca cctgctcgac caaagtgacc      420
aggattttca ggaggagctc gatcttatga aaatgcggga agaggttatt acccttatcc      480
gttctaacca gcagctggag aacgacctca atctcatgga tatcaaaatc ggact           535

<210> SEQ ID NO 290

<211> LENGTH: 538
<212> TYPE: DNA
<213> ORGANISM: Bos Taurus

<400> SEQUENCE: 290

```
atcactccca tctgactgct aatacacatg caggctgcag ctgggttta gcccacagtc      60
agagttgcca gcccatgaac tacagcataa gaaacagtaa taatgcaatt acagaatttt     120
gaagttaaag gagactttag agataattta accgaattcc tttatttcag ggatacaaag     180
atattcaaca atttgttcaa gttttaaacc taaccttatc actgatccac tctccacaga     240
cctggaaatt tcacaccaga aaaccaaaa acacatagcc ataaaaaac tcatacacga       300
ctatttagag cagcattagt caaggaaatg gcaacccact ccagtgttct tgcctggaga     360
atcccaggga cggggggagcc tggtgggctg ccgtctatgg ggtcccacag agaaggacac    420
gactgaatcg acttagcagt agcagtcaca acagtcagaa agtggaaaag tccacacgtc     480
catccactaa tgggataaac aagttgtggt ccatccatat aatggagcgt tatttagc       538
```

<210> SEQ ID NO 291
<211> LENGTH: 562
<212> TYPE: DNA
<213> ORGANISM: Bos Taurus

<400> SEQUENCE: 291

```
gcacgagatc aaagagggct cacaactgaa gcagcagatc cagtccatcc agcagtccat      60
tgaaaggctc ttagtctaaa ctggtggcct cagccacact cccagctgac tcctctccac     120
cccccgccc ccgcagagtt atgtatcata ttgtctgtta gcatgtagtg tttccagcta      180
ccttctattg ttataaaata ttttaatgct caatctgatt tttgcatttt tgtactgttg     240
tcttgtttta taggttgtca gccctccc taatctcccc ttcctctctg ccatcttatc       300
ctccctttta gaaaaatgaa ctaacgccaa gaacaggtgg aacaggctgg atgacaccac     360
ttaaaggcag ggaagagccg agagagtaga gaattggttc cagcttcag gggcctgctt      420
cctactgtgc agggcatgat ggcataactg tctgcttgta ccctcattc ccatgtacag      480
gatcgttgca cgtgtgtctg aatcatcgag gggtttcctt tgctctgcag ggcataatgt     540
atcatttggg gaggaagcat gt                                              562
```

<210> SEQ ID NO 292
<211> LENGTH: 549
<212> TYPE: DNA
<213> ORGANISM: Bos Taurus

<400> SEQUENCE: 292

```
gcgtcaacgt tttaagtccc atcttttacc tccacaagct acagaaaaat caggacatgt      60
tttccctacc cgtgaaattg ccacaccttg tactaatgag aaaatgttct ttttaaaaaa     120
atcccccct ccacctatgt tactgttccc catttcctaa aagggcacag atctcccttc      180
caggctcttt atgttcagtt tttcatcacg ctcggtttct gtcttccgct tgccatgcat     240
cactggtggg tctcaggctc caggggggact tgagcacgtt ttggccacgt ggacagtatt    300
gaagcagcat tgcgctgcca cagtcaggac tgtccaggca ctcggaacgt gcatcttgct     360
tggccagcac agtgttttaac aaaattgagc cacttttttaa atatctggag attttgcaaa   420
caaattttgg atccccgagt gagactagat agctgatggc ttacagttct cgctgtgcca    480
cgtcattcac agatgatggt gtagacacac ttagaaaagct gctctcttcc cctgtgaaca    540
ttcgtgttt                                                             549
```

<210> SEQ ID NO 293
<211> LENGTH: 443
<212> TYPE: DNA
<213> ORGANISM: Bos Taurus

<400> SEQUENCE: 293

| | | | | | |
|---|---|---|---|---|---|
| aagagttcca | tgctgatagc | ccagcagact | gacacgtctg | acccggagaa | ggtggtctcc | 60 |
| gccttcctga | aggtgtcctc | cgtgttcaag | gatgaagcct | cggtgcggac | agctgtgcag | 120 |
| gacgctgtag | atgctttgat | gaagaaggcc | ttcagctcgt | ccgccttcaa | ctccaacgcc | 180 |
| ttcctcaccc | ggctgctcat | ccacatgggg | ctgctcaaga | gtgaagacaa | gatcaaggcc | 240 |
| gttgccaacc | tgtacggccc | cctgatgcg | ctgacccacg | tggtgcagca | ggactacttc | 300 |
| cccaaggccc | ttgcccccct | gctgctagcg | ttcatgacca | agcccaacgg | cgccctggaa | 360 |
| tcctgctcct | tgcccgcca | caatctactg | cagacgctgt | acaaggtcta | gatgccaagc | 420 |
| tggcctctgc | ccatccctcg | cct | | | | 443 |

<210> SEQ ID NO 294
<211> LENGTH: 585
<212> TYPE: DNA
<213> ORGANISM: Bos Taurus

<400> SEQUENCE: 294

| | | | | | |
|---|---|---|---|---|---|
| tttattttaa | gattgaaaag | ggagcgcatg | ttccttggaa | gggagagcat | tgctcgccga | 60 |
| gacgaagctt | cgtggcatac | aaaggggcg | gttcgtgagt | tctcccatgc | accctgctcc | 120 |
| agcttcaccc | agtggggctg | cttttgcttg | atccatccag | cctttacag | ccttgtcata | 180 |
| gatgtcctag | atattggatg | cttttcttct | tttttggtag | taaatgctta | agtattaact | 240 |
| ttttgttgtc | cctctatgtt | atagaggggt | ttcgggtttg | tttgtttgtt | tgtttctgta | 300 |
| ttcttaatca | tgttttcca | ctcccacttg | ggaattttgg | acgctggtca | gcttgtgggt | 360 |
| tttctaggat | gttgggaaac | ctagatgacc | ttactgggtg | caatactagc | tacgttaaag | 420 |
| ctagaaacct | acactgtcac | tttactgaga | tttctgagta | tactttccat | attgccttaa | 480 |
| tgtagcagta | atgtgtttat | gcatttgttt | ctttgcacag | acattttgtc | aaatattaaa | 540 |
| actctacttt | tttatggcac | atattagcat | ataagccttt | attcc | | 585 |

<210> SEQ ID NO 295
<211> LENGTH: 603
<212> TYPE: DNA
<213> ORGANISM: Bos Taurus

<400> SEQUENCE: 295

| | | | | | |
|---|---|---|---|---|---|
| tctccacagg | tgttaaagtt | cctcgtaatt | ttcgtttgtt | ggaagaactt | gaagaaggac | 60 |
| agaaaggagt | gggcgacggt | acggtcagct | ggggcctgga | agatgatgaa | gacatgacac | 120 |
| tcacaaggtg | gacaggcatg | atcattgggc | caccacggac | aaattacgaa | aacagaatat | 180 |
| atagcctgaa | agtagaatgt | ggacctaaat | acccagaagc | tcctccatca | gttagatttg | 240 |
| taaccaaaat | taatatgaat | ggaataaata | attccagtgg | aatggtggat | gcacgaagca | 300 |
| taccagtgtt | agcaaaatgg | caaaattcat | atagcattaa | agttgtactt | caagagctaa | 360 |
| gacgtctaat | gatgtccaaa | gaaaatatga | agcttccaca | gccaccagaa | ggacaaacat | 420 |
| acaacaatta | attttagtgg | atctcaaact | tgtcttaaat | cagcaaccett | ctactcatgt | 480 |
| taatgtcttg | attaaatatc | acaatgcaaa | atacccacac | attaaagtaa | gataattcca | 540 |

```
gctggtaaac atgacctgga cgtttgtaag aatatattta atatatgtac acccattatg      600
ttt                                                                    603

<210> SEQ ID NO 296
<211> LENGTH: 403
<212> TYPE: DNA
<213> ORGANISM: Bos Taurus

<400> SEQUENCE: 296
tgagtggtgg gcagtgtgca agcttgcaga cctcacttag tggcagcgat gtggtcttga       60
tttgtgcttc ttcattttaa catggctgtt agagagtgta ctgagtggtg ggcagtgtgc      120
aagcttgcag acctcactta gtggcagcga tgtggtcttg atttgtgctt cttcatttta      180
acatggctgt tagagagtgt actgagtggt gggcagtgtg caagcttgca gacctcactt      240
ggtggcagcg atgtggtctt ccccagacaa agcctttctt acaagagaat tcccttgttg      300
ctgttggttg agcactctca cagatagacc ttttggtttt taatatttat ttatttggct      360
gcatcggatc ctagttgtgg cacgtgggat ctagttccct gac                       403

<210> SEQ ID NO 297
<211> LENGTH: 274
<212> TYPE: DNA
<213> ORGANISM: Bos Taurus

<400> SEQUENCE: 297
gcggtacctt cttcatggtt tggagtgtgt ggtagcaatg catcaagctc agctcatttc       60
caagattcca catatcttga aggagatgta tgacgcagac cttttggagg aagaggtcat      120
cattagctgg tcggaaaaga cctctaagaa atatgtctca aaagagcttg ccaaagagat      180
tcgtgtcaaa gcggaacctt ttataaaatg gttgaaggaa gcagaggaag aatcttccgg      240
tggtgaagat gatgatgaag atgagaatat tgag                                  274

<210> SEQ ID NO 298
<211> LENGTH: 447
<212> TYPE: DNA
<213> ORGANISM: Bos Taurus

<400> SEQUENCE: 298
ggaagcagca cgagctgttc tgctgcaagc tgtgcctcag gcacctgcag atcttcacac       60
acgagcggaa gtggtactca cgcaaggacc tggctcggca ccgcatgcag ggtgaccccg      120
acgacacttc acaccgcgga cacccctct gcaagttctg tgacgagcgc tacctggaca      180
acgacgagct gctcaagcac ctgcgtcgtg accactactt ctgccacttc tgcgacgcgg      240
atggggccca ggactactac agtgactatg cgtatctgcg tgagcacttc cgcgagaagc      300
acttcctgtg tgaggagggc cgctgcagca ccgagcagtt cacgcacgcc ttccgcacgg      360
aaatcgacct gaaggcccac aggacggcct gccacagccg cagccgcgcc gaggcccgcc      420
agaaccgcca gatcgacctg cagttca                                          447

<210> SEQ ID NO 299
<211> LENGTH: 456
<212> TYPE: DNA
<213> ORGANISM: Bos Taurus

<400> SEQUENCE: 299 gccttgcac cagcgacggg aacctgtccc atcacaccca ccccttgagg gtgcacgggg       60
accccagccc ccctgccccg tgccctccc cagatgggcc gtggccaagc ctgtgccacc      120
```

```
agccaggccc tacgcggctc cccatgtgcg ctcacacgtg tgcgtgtccg tgtgtgtgcg      180
tgtctgtgtc cgttgctgtg tcgtgaagct gtgcccgtcc cccagtccaa acaagtgaat      240
ggccgccgag gccacagtta tgcaactttc cgtgtgtgtt gtgacagcgt cactgctttt      300
taaacttgat aattctttat tttagtaaga tgccccaaga gtccacacaa cttgtgttgg      360
acttgcagag gttttatttt tttggcctta gaatctgcag gaattaggag gtaccgaccc      420
ccgtgcagca gcctcggccc tggattgcgt ttgcct                               456

<210> SEQ ID NO 300
<211> LENGTH: 334
<212> TYPE: DNA
<213> ORGANISM: Bos Taurus
<220> FEATURE:
<221> NAME/KEY: modified_base
<222> LOCATION: (293)..(293)
<223> OTHER INFORMATION: a, c, g, t, unknown, or other

<400> SEQUENCE: 300
cctgcgtcca agtccaggtg tctgtggccg ccgatctgga cgtcaggggc tcagcttccc      60
ttcttcggac cagccagccc cctgttttgc ctttgccaat tggtgcccat atttaggtcg     120
gctttggcga ggctgagaag gccgccggca agatgttcaa aaacacgttc cagagcggct     180
tcctctccat cctctacagc atcggcagca aaccctgcga gatctgggac aaaaaggtac     240
gaaatggcca catcaaaaga atcactgata atgacatcca gtccctggtg ctngagattg     300
aaggaacaaa tgtcagcacc acgtatatca catg                                 334

<210> SEQ ID NO 301
<211> LENGTH: 592
<212> TYPE: DNA
<213> ORGANISM: Bos Taurus

<400> SEQUENCE: 301
tttttttttt ttttttttata agacaaaaat ttaatgaaaa ttggtaagta ataatccaag     60
gggctaaata gttacatggg actgtattag aaatttaata tacaaatgtt acatgttatc    120
atcatctgat tcatcttctt ccttcaaaga ttccttggca tatttctctg cctcttccct    180
tacatcttta ggaactattt catgtcttcc attagttatt tcaccaaccc agctgagctc    240
tagttcaaaa gctttatcct taacttcatc gtgtactatg taaattatct ttgcaacttc    300
tttaacaaca tcacggcagg tcatttcttt catctgaagc ttttcaattt ctgtctttgc    360
agcctgcctt gctttgccaa tggcacagcc ccaataacca tatgaaacac ccgatgggtc    420
aatcatgtag agctgtgcac cgtcattcac actgtaagac cctaacatga aactgcagcc    480
aaaaggtcta acagcactgt agagtgtata cgcgtgtaca tacatggcca ctctatctgc    540
aagatgtttt agtggaatgt tatatccaaa gttagatcta agttggaag cc              592

<210> SEQ ID NO 302
<211> LENGTH: 241
<212> TYPE: DNA
<213> ORGANISM: Bos Taurus
<220> FEATURE:
<221> NAME/KEY: modified_base
<222> LOCATION: (85)..(87)
<223> OTHER INFORMATION: a, c, g, t, unknown, or other

<400> SEQUENCE: 302
tggagatgtg tgttgtgggt ttcttttttt ttttttttcc ctcccctatt ttagttgcat      60
```

| | |
|---|---|
| atgaataaac aaatacaaca caagnnnggc cttgtgttgc ctggttcctc ttcagtattt | 120 |
| cctgggatt atttgctttc taagtaaaac ccttctgacc aacagcccag tatgtcttaa | 180 |
| gaccggaggt catgtcacct actttggaag ctctcacagc aggctgctcc gctcggatct | 240 |
| g | 241 |

<210> SEQ ID NO 303
<211> LENGTH: 458
<212> TYPE: DNA
<213> ORGANISM: Bos Taurus

<400> SEQUENCE: 303

| | |
|---|---|
| gcagctgcag gggaaacttc tgcagagccg accaggtttt tccagtcctc catggggacc | 60 |
| agcgttagcg gtccaaggtc cagctatatt ttcagaacca acaaatgata ccagtggaag | 120 |
| tacggagacg tccagccttt tggatagtat attttggatg gcagctccta aaaacaggcg | 180 |
| cagcattgaa gtgaaccggt gtaggagaag aaaccctcat aagcttatta agttaagaa | 240 |
| caatatagac ttttgtcctg agtgtggtca cctgaaacag aaacatgtcc tctgtggcta | 300 |
| ttgctatgag aaggtgcgca aggaaacggc agaaatcaga agacagatag ggaagcaaga | 360 |
| gggggggccct ttcaaggctc ctactgtgga gactgtggtg ctgtactcgg gggagacacc | 420 |
| ctctgagcac gatcaaggca agaggatcat tgagcgag | 458 |

<210> SEQ ID NO 304
<211> LENGTH: 391
<212> TYPE: DNA
<213> ORGANISM: Bos Taurus

<400> SEQUENCE: 304

| | |
|---|---|
| tgcttttgga agagggtgc ggggctggga ccttgctttt tctcccctcg gttccagaca | 60 |
| cgcattcagt tcctgttgtt gaagggccac ttgtatttcc acgcatgccc acacccaggc | 120 |
| gtccaaggcc ccgtgtcttg agcagaggc ctggctgagg ggagtgggct gagccaggcc | 180 |
| tgtggcatga gggtgtccgc gctgcgtccg gggaaggtga cggccgcgcg aggggaccca | 240 |
| gagcccatgg tctgccaggg cgttgcttga aaagaatacg ttctgtgggt ttttctggtt | 300 |
| ggaggaacaa aagagccttt cttcctgaga tgctcgcaca tctgtctgtg aaagtagtgt | 360 |
| ttccacaggg agtggccttt gggagggtga g | 391 |

<210> SEQ ID NO 305
<211> LENGTH: 603
<212> TYPE: DNA
<213> ORGANISM: Bos Taurus

<400> SEQUENCE: 305

| | |
|---|---|
| agccgccctg cggtagttct cgcggtattt gctgccgcca gtctgctgga gaggttgctg | 60 |
| tttcctggcg gtccttttcta gctcatctgg tcgccgcggc tgttgtgttt ccagttgcca | 120 |
| ggtcgcgtat catgacgtcc gccttggaga actacatcaa ccgaactgtt gctgtcatta | 180 |
| cttctgatgg gagaatgatt gtgggaacat gaaaggttt tgaccagacc attaatttga | 240 |
| tactggatga aagccatgaa cgagtgttca gctcttcaca gggagtagaa caagtggtac | 300 |
| tagggttata catcgtaaga ggcgacaatg ttttctggagg tccgaagtcc agatggattt | 360 |
| cacgaggcta aaagcaagga ctgatgctaa agctaaagtt ccaacacttt ggccaggtga | 420 |
| tgcaaagagc caactcactg gaaaagacct tgatgctggg aaagactgaa agcaaaagga | 480 |
| gaaggcggca ggagaggatg agatggttaa tagcataatc aacacgatgg acatgaatct | 540 |

```
gagcaaacac caggagatag tgaaggacag gggagcctgg tgtgctgcag tccatgggtt    600
cac                                                                  603
```

```
<210> SEQ ID NO 306
<211> LENGTH: 635
<212> TYPE: DNA
<213> ORGANISM: Bos Taurus

<400> SEQUENCE: 306
agaagaacca agcattaata cagcactttt tttttttataa taaagtatat ctttgttttt    60
ccctagttgg ccaaaacttt tttagtttta ggtgttaatc ttcccatagc tatttagtt    120 tatctcctta tattatagta cttaacatga actctgatga gaagtgagct gctgcagcag    180
cttaaacata caatggctct gccacagtaa ggaaaaccaa tatcctgaga ttaggttaat    240
ttattgaact gttaatactt agggctccct gttttggagg gttaaacttg agaaatagct    300
tataattggc tgacttgtac aaaattaata ctgagcatta gctgatcagg cagaattagt    360
aactagtttc ttatgtgaca taacttcatg acaacatgtc aacggtacaa aatttccaaa    420
atcacctatt tttagaagtt actgtaacgg tatccctcat gcaactttaa atcttgctgt    480
tctcttttgt gtttgatgtc agatgacctt cagtaattac taattgtgaa aattgaagca    540
tacaatgaaa tttcaaagcc aagacttgct tttaaaccag tctttgggaa atttagttac    600
atattcaggt ttttgcataa gttcaatttg ctttg                               635
```

```
<210> SEQ ID NO 307
<211> LENGTH: 206
<212> TYPE: DNA
<213> ORGANISM: Bos Taurus

<400> SEQUENCE: 307
tatttcacca ttaatagtga gggaaacatg ctctcttatg caaagacgac aaactcgagt    60
gttgaatgag taactggtac ccacaaaaga acatcaggac tcttattctc ttaattcacc    120
ctattttggg tttgtcttaa gaactccaat ataacctcag attgtcgggc ctctttcagc    180
agtgtgagcc cccggagatg ctgacc                                         206
```

```
<210> SEQ ID NO 308
<211> LENGTH: 382
<212> TYPE: DNA
<213> ORGANISM: Bos Taurus

<400> SEQUENCE: 308
gcgctgtgag aaaacacatt ttatttgttt taatgatacg catgcttttc ttctgtaaat    60
agacaataaa ttttttgtaga tagtcttggt gtgttatctt aatttcgtat ttcactgtgt    120
aaaatcagtg aatatagctc aagtgttagt ggactggatg aaaagaaact ggttactagg    180
caagaacagg aggctgtagt tacccatgac tactttagc tatgcagact aatacattct    240
gcaggtttac agctcagcac cttcaccttt tttcactggt atttcatgta aggcatcaac    300
cactgtaatt tttgctgatg ctgaagcctg tccttgggaa ttggatgcat ggcactcata    360
ttctccggca tcttccttac ta                                             382
```

```
<210> SEQ ID NO 309
<211> LENGTH: 506
<212> TYPE: DNA
<213> ORGANISM: Bos Taurus
```

```
<400> SEQUENCE: 309
attattagct catgtatttg aggaagagca gctgtcttt tatatgtttt ttgacaaatc      60
atattgtaat tcttttgtac aaaaaagaac tacttgtatt ctagaagaaa tatgaaatgc    120
ttaatttata agcgggctgg agattttttc caatattgtt ttctttgaaa atgaaagggg    180
atcatctatt ttagtttcgg ggtctgggaa cttttttgaaa atttaatttg tggaccaatg   240
ttatgtgaaa gctaaggaag ggcaggggta aaataggggct tgattttctc attctgtaca   300
gaccagcaaa cttccctctg caaggcaggc tcaaatcaca cacccaagag tgttggcgtc    360
ataaaacgct agtttgcttc agcccctagt aacctcagga cttggtttga atataaaagg    420
tagacaactg atatgttttc acgagtaaaa tattgtcagc cagaaacagc tggtgtcagg    480 taaactttt tttttttta agcttt                                           506

<210> SEQ ID NO 310
<211> LENGTH: 473
<212> TYPE: DNA
<213> ORGANISM: Bos Taurus
<220> FEATURE:
<221> NAME/KEY: modified_base
<222> LOCATION: (423)..(423)
<223> OTHER INFORMATION: a, c, g, t, unknown, or other

<400> SEQUENCE: 310
ttgaatctga agcctgggga gggggccccg aacctgccct tctccagggc tcagctgcag    60
gtcctagcca gccagccctt cctgctcgcc cggcctcccc gccaatcctg tagctgaatg    120
tgcatggtcg tcatgggccc ccagccctag agttcaggac tgaggagggg gccggggcag   180
ccgtggcatg tgtcccctg ggctctggcc gcaccaggtc tctctcttga gttgggggtc    240
cgcgggctgg accctcct ccaggatgcc ctcctcctcc tgggactaca tccagctccc     300
ccgccccacc tttgcgggcg ggggcctgcc caccgccaag ggcccctggc tgggaacctc    360
caggggacct gcaggcctca cctttcccag ctccacctcg ctcctcctct atctggcagc    420
tcntctctgg cttccccccg cccccccggc tctgcttgcc agatccgacc tgt           473

<210> SEQ ID NO 311
<211> LENGTH: 572
<212> TYPE: DNA
<213> ORGANISM: Bos Taurus
<220> FEATURE:
<221> NAME/KEY: modified_base
<222> LOCATION: (432)..(434)
<223> OTHER INFORMATION: a, c, g, t, unknown, or other

<400> SEQUENCE: 311
gctccctaag catgtgatgt ttcagggact ggtagagctt ctttctggca actcttgcta    60
gagccagaag tacatcccca aatggtggca gggtcctcca tttactcctc taggacctct   120
tgggtgggca cttctgactt cacagggctt ccccaagagg ccaggcccca aagtgcaagg   180
aggactgggt tcccttacct gcaggctgcc tcagtgctgg gccatccagg tgctcccgtg   240
agtgagaacc aggtaactgc aagtcaggga tgactagact tctggtcaac gttgcaacct   300
tctctgcctt gggccaggca tgaccttcat tttccctgct ccccagact gtccagtgga    360 ggctgcaagg ccactctgct gagctgagtt gttgggaaca ggaagggcag cggtctccac    420
tccacttgta tnnntggctg ggggctgccc aggtcccag gcttacaaaa tgctacaccc    480
ctgcgtaggc cacctacgg atagtaggca gcaggctgga agttctctgc cttgtctgga    540
tacacaactg tgcccagact gccatgagtc ca                                  572
```

<210> SEQ ID NO 312
<211> LENGTH: 569
<212> TYPE: DNA
<213> ORGANISM: Bos Taurus

<400> SEQUENCE: 312

| tatagttcat | ttcactcagc | atatccaaaa | tattatcatt | tcaacatgta | atttatataa | 60 |
| atcttttaag | atagcttgca | ttcttttgta | ctaattttt | ttatttctgg | tgtatatttt | 120 |
| actaatttgg | gctagccaca | tttcaagtta | attttaataa | cttaataata | cacagttctg | 180 |
| tattaatcta | catattaatt | tgttgttcta | taagatgttg | tagggaattt | cctagaatca | 240 |
| ctctcttaag | tacaaaatct | tttctggtct | ctgaagcctt | cagtgcttgc | ttttagtgtg | 300 |
| ccctaagaag | tgtgaacttc | ttaacattag | aaataaatca | gttagaaata | aatatcaatt | 360 |
| gtcaataaaa | taaaaatgat | agcccaaaat | atttcccttt | aaagataaca | aacttttcat | 420 |
| aggactgttg | atggaatgaa | agaatataat | ctgccttgtg | gcaatatgat | tgattatttt | 480 |
| ctctggctta | tagctagttt | gtattagaaa | cacatgtatg | taggagatat | ttggcatagt | 540 |
| actgttttca | gtacataccct | attttttttt | | | | 569 |

<210> SEQ ID NO 313
<211> LENGTH: 426
<212> TYPE: DNA
<213> ORGANISM: Bos Taurus

<400> SEQUENCE: 313

| gcacgaggct | gagacttgtc | ccaccgcgcg | tgggaggaat | tcatacaagt | gtccagttca | 60 |
| agctgcagta | tggcccgttg | gcgtacatac | ttggtgaaaa | agcaaccaaa | aagatgacag | 120 |
| aaaagagcaa | actgataact | gtagatggca | atatatgttc | tggaaaaagc | aagcttgcga | 180 |
| aagaaatagc | agagaaacta | ggcctgaagc | actttcccga | ggcgggaatc | cactatgtgg | 240 |
| acagcaccac | aggggacggg | aagcccctgc | ctgtgcagtt | cagtggcaac | tgcagtttgg | 300 |
| agaagtttta | cgacgacccg | aaaagcaacg | atggcaacag | ctaccgcctg | cagtcctggc | 360 |
| tgtacgccag | ccgcctgctg | cagtacgcgg | atgccctgga | gcacctgctg | agcacaggac | 420 |
| agggtg | | | | | | 426 |

<210> SEQ ID NO 314
<211> LENGTH: 511
<212> TYPE: DNA
<213> ORGANISM: Bos Taurus

<400> SEQUENCE: 314

| gcacgagata | tctgaacacc | tctaacagag | aagtgaaggt | acgcatttgt | aaatctggac | 60 |
| aagtgaccgc | cattccattt | tggtatcata | tgtacctcga | cgatgagatt | aggttagata | 120 |
| cttcgagtga | agcctctcac | tggaagcagg | ccgcagttgt | tttagataat | cccatccaag | 180 |
| tggaaatggg | agacgaactt | gtactcagca | tccagcacca | caaaagcaac | gtcagcatca | 240 |
| ccataaagca | atgaagagca | gatttctaat | gaaaaagtgt | ggaagtagag | cagtgggttt | 300 |
| ccagttctag | tctgaattag | tagtgggatt | gtaaccataa | aatgcaggtg | tatttaagtc | 360 |
| cttgaaatgg | tcaaatgttt | ttaaaacatt | gacattaata | aagtgtattt | aaacacccta | 420 |
| actaaagagt | agcattatta | caaaaatctt | actgcagact | tcctttctgg | caaaggctgt | 480 |
| cattaatttt | tcaaattaag | aactttttat | t | | | 511 |

<210> SEQ ID NO 315
<211> LENGTH: 469
<212> TYPE: DNA
<213> ORGANISM: Bos Taurus

<400> SEQUENCE: 315

| | | | | | | |
|---|---|---|---|---|---|---|
| ggagagggct | ggaccactca | gggaggggga | aaggatcagg | ggaatggaca | ggcgtcttgc | 60 |
| cgctccagaa | tctgaggcct | tcaccttgag | cgattcctcc | ctccaactca | cgaaagcccg | 120 |
| ctcaaacttc | cagctggact | cgaccaaagg | aataaggtta | ccagaaacta | cagaagaagc | 180 |
| caaccctctt | accatcggtt | ctgaggggga | aatgcgaaag | ggccgcctcg | agagccgacg | 240 |
| tgcgcccacc | gctgtacctc | caggcgcgcg | cgtccagcag | ggagttcgcg | gagcagtggg | 300 |
| ttcagaaggc | ccgaggaggg | cagcaagccc | agaggccaag | agcctagagg | tgccctggag | 360 |
| gccggaggat | cgcggctgcg | ctcggaacgg | ccccgccgcg | cgcggcccgg | gtccctgccg | 420 |
| gccctgggcg | acaggtgcag | ccgcagcctc | cgccgcccgc | tgggccggg | | 469 |

<210> SEQ ID NO 316
<211> LENGTH: 667
<212> TYPE: DNA
<213> ORGANISM: Bos Taurus
<220> FEATURE:
<221> NAME/KEY: modified_base
<222> LOCATION: (606)..(607)
<223> OTHER INFORMATION: a, c, g, t, unknown, or other

<400> SEQUENCE: 316

| | | | | | | |
|---|---|---|---|---|---|---|
| aaacttggac | tccagataaa | tgcatttaac | ttggttacag | gacctcaaga | tgtgtatgtc | 60 |
| agcctcattt | tttacagatt | gatggtcctg | aaccatgata | gtttgttgat | ccatgaacac | 120 |
| agctttaccc | agtcatagga | gttttcactg | aacttaaaga | aacaaagttt | ccattcagga | 180 |
| ggttgatatt | tttcttttaa | caccagtttt | ctcaaatacc | acaaatttct | cttggatact | 240 |
| acactctgtt | taagaatatt | gtacatctgt | acagaaactc | atgatagatt | tttgaaatgg | 300 |
| tagttccaag | tatttgtcca | gtcttagact | gatagggcat | tttggacagt | tttagcccct | 360 |
| tcctagccta | ccttcaaagg | tgctcagaag | gtatttaagg | aaattattcc | cgtggactaa | 420 |
| ttggtgtaaa | tgtgtttgct | tttattaaga | tcccggtcca | ggtcgagatc | aagatccagg | 480 |
| tctcttttcac | ggcctagaag | cagccgatca | aagtccagat | ctccatctcc | aaaaagaagg | 540 |
| taagctaaat | aatttgttgc | catatcttaa | ctgtcaagtg | tggcctctgc | agaattttgc | 600 |
| ttactnncta | cttccctgag | ctctttggag | aattggtgct | atatgttaaa | atactaaata | 660 |
| gagtttc | | | | | | 667 |

<210> SEQ ID NO 317
<211> LENGTH: 371
<212> TYPE: DNA
<213> ORGANISM: Bos Taurus

<400> SEQUENCE: 317

| | | | | | | |
|---|---|---|---|---|---|---|
| aagtgatgtg | cgcaagacac | cgcggcagca | ccggagcgcg | cggcgagcgc | tgccgtgccg | 60 |
| ttcggcctgg | ctgcacaccg | caggagaagc | tgtcacgtgt | gggtcaaagc | cctctgccct | 120 |
| cctccgctgt | ctcccgtggc | gctgagagag | tgtgcgagtg | agcgaggcgt | cagatgggaa | 180 |
| gcggccgggc | ccgtgctcac | cgctctgctg | ttgctttgca | gccgcatctg | ggacaccgcc | 240 |
| tcgggccagt | gcctgaagac | gctcatcgat | gacgacaacc | ccccgtgtc | cttcgtgaag | 300 |
| ttctctccga | acggcaagta | catcctggcc | gccaccttgg | acaacacgct | gaagctctgg | 360 |

```
gactacagca a                                                            371

<210> SEQ ID NO 318
<211> LENGTH: 220
<212> TYPE: DNA
<213> ORGANISM: Bos Taurus

<400> SEQUENCE: 318
tttttttttt tttttttcag catttacact ttatttgtga cataaagaag ccgtatttac      60
acaatacatt catatttta aatatgttac acagctctcc tagaaaacca ctccatcaca      120
gaacagcagc atgtagcttg ggttccgtct ttaaaatatt aaatcaagta gaaatactct    180
ttaatttcat agcccatcac agagggagac tctgagggag                            220

<210> SEQ ID NO 319
<211> LENGTH: 455
<212> TYPE: DNA
<213> ORGANISM: Bos Taurus
<220> FEATURE:
<221> NAME/KEY: modified_base
<222> LOCATION: (83)..(84)
<223> OTHER INFORMATION: a, c, g, t, unknown, or other
<220> FEATURE:
<221> NAME/KEY: modified_base
<222> LOCATION: (287)..(289)
<223> OTHER INFORMATION: a, c, g, t, unknown, or other

<400> SEQUENCE: 319
cctggacctg ggcagcaacc ggctgggcga cgcgggcctt gcggagctgt gccccgggct      60
gctgagcccc agctcccagc tcnngaccct gtggctctgg gagtgtgacc tcaccgtcag    120
cggctgcaga gagctctgcc gcgtcctcca ggccaaggag gccctgaagg agctgagtct    180
ggcgggcaac agcctggggg acgagggcgc ccagctgctg tgcgagagcc tgctgcagcc    240
cggctgccag ctggagtccc tgtgggtgaa gtcctgcggg tttacgnnng cctgctgcca    300
gcacttcagc tctatgctga cccagaacaa gcatctcttg gagctgcagc tgagcagcaa    360
cccgctgggc gacgcgggcg tccacgtgct gtgccaggcc ctgggccagc cgggcactgt    420
gctgcgggtg ctctgggtgg gcgactgtga gctga                                455

<210> SEQ ID NO 320
<211> LENGTH: 393
<212> TYPE: DNA
<213> ORGANISM: Bos Taurus

<400> SEQUENCE: 320
gccgtgggcc tgcggttggg aagtgctggt gtcaggccgg ggttcggaga cccccacata      60
ccgccggcgg cagaacaggc ccgaggcagc ccggggtttg ctttaggaag agcggcttta    120
aaacctgcgc gccccggctcc tctggcagat accattgtgt agtttgaatc aggaatgaaa    180
ttttctgaaa gctaagagta gaagtcttgg tcagcatgga ggacaaaaga cggcgagccc    240
gagtgcaggg agcctgggct ggtcctgcta agagccaggc cactgctcag ccagctccca    300
ctgctgagaa caatctccaa cagagacctg gtaaagcctg gatgaacaag gagcagcatc    360
tgtctgacag acagtttgtg ttcaaagaac ccc                                   393

<210> SEQ ID NO 321
<211> LENGTH: 412
<212> TYPE: DNA
<213> ORGANISM: Bos Taurus
```

<400> SEQUENCE: 321

```
ggtgaacctg gcatctttcc actttccagt agtcagtgaa acgcagtttg attttctcg      60
ttgcttccta taaaatact tgtaagctca agcacggtgc agccgtaagc tcatgctgcc     120
ctgggacccct ccccacccat tcaccgcagc caaccctcca cttcatgcct tagcaacgcg    180
tgtggctcat gtagacgcgc ttcgtctgca cttgtaagac gagacaaggc ctcatcaaga    240
agaggaacgc cctgtccttt aatgcctgca catcccgaca cacccaccg gggctaccgg      300
ggccagggtc cctggaccaa ggagatattt tgtatcttca aggggcctgc actgcttgga    360
aacaagtgga gagaatcaag tggaatcttg tttggaaaaa aaaaaaat ga              412
```

<210> SEQ ID NO 322
<211> LENGTH: 493
<212> TYPE: DNA
<213> ORGANISM: Bos Taurus

<400> SEQUENCE: 322

```
gcctacatcg gcctttgttt gccaaagctg ctcaaccccc tcataaggct gcagcttctc      60
acctggactc cgcttgaggc aaaatgtcgt gactttgaga acatgctgtg gtttgaatct    120
ttgctgtttt atggttgtga agagcgagag caagaaaagg acgatgtcga tgtcgcactg    180
ttgcctacca ttgttgaaaa ggtgattctt cctaaactaa cagtgattgc tgaaaatatg    240
tgggacccct tttctacaac acagacttca agaatggttg gaattactct aaaattaata    300
aatggatatc cttcagtggt gaatgcagaa aataaaaata cacaggtata cctaaaagca    360
cttctattga gaatgaggag aactttagat gatgatgtat tcatgcccctt gtatcccaaa    420
aatgtcttgg aaaataaaaa ttctgggcct tacttgtttt ttcaacgaca gttttggtct    480
tcagttaagc tct                                                        493
```

<210> SEQ ID NO 323
<211> LENGTH: 501
<212> TYPE: DNA
<213> ORGANISM: Bos Taurus
<220> FEATURE:
<221> NAME/KEY: modified_base
<222> LOCATION: (324)..(326)
<223> OTHER INFORMATION: a, c, g, t, unknown, or other
<220> FEATURE:
<221> NAME/KEY: modified_base
<222> LOCATION: (328)..(328)
<223> OTHER INFORMATION: a, c, g, t, unknown, or other

<400> SEQUENCE: 323

```
tttttttttt tttttttccca tctcgaaaca tttttattca acaacaggtt gattcctctc      60
tttgctcttt tcctcactgg gtttcaggac acagttcacg taatccttga tacttcatca    120
gtctaacaag ttgtggcttg cttttcttgat cagttcatgc tgtgtgacgt cttgagaact    180
tatatccact tcaagtgaat gagcactcca gttctcagcc aacatcaatc attcttacca    240
tgtcgcttcc catcatggaa ccactcattg ttgccggtgg aacgccagga ttagcttcat    300
aacctatgcc agcaccacca cctnnngntg gaaatttctg gcctcctgag ccatagggat    360
ctcccatgtt cattgctcct ccaccaccca ttctcatgtc tctttctctt ggatccatat    420
agcccatccg actataactt tcctctcttt ggcgtctcat ctgttcttcc atctcacgtt    480
gacgaatcat catctcttct t                                              501
```

<210> SEQ ID NO 324
<211> LENGTH: 490

```
<212> TYPE: DNA
<213> ORGANISM: Bos Taurus
<220> FEATURE:
<221> NAME/KEY: modified_base
<222> LOCATION: (447)..(448)
<223> OTHER INFORMATION: a, c, g, t, unknown, or other

<400> SEQUENCE: 324
actgtccatc ctgagcaata tgctaagcga ttcctggatt ttattaccaa catctttgcc      60
taagagactg cctgagttca tgaggaggag ctggggaag ggggttgttg gccatcttca     120
agacctgact ggacagatcc cttcagtggg ggtgtggtca gttctggagg ctggacggat    180
gagccaaggg agtaaggttc actccctgtg ttgaatttcc tttcttcatg tctagccatc    240
ccggaggttt tagtcccagc agaagggaat acctctactt gggttaaccc tggtcatctc    300
aagagaatgg aagtctcaca tggggagcg tcctccactc cctgaaagta tgccccttcc    360
tccctgccc cttctcaaac ccttttccca gttggatttg ttattctgtt cttttctgtc    420
catcttaact gctactgtgt ctcccanngg acagatggcc ctctttgtca tcttcactct    480
ccaccccag                                                             490

<210> SEQ ID NO 325
<211> LENGTH: 480
<212> TYPE: DNA
<213> ORGANISM: Bos Taurus

<400> SEQUENCE: 325
ggatcttctg cgagcacttg gagccgggaa agaagcatga agtggcttgt gctccttggg      60
ctggtggccc tctcagagtg catagtcata tggcctatgt gggcaacatc accattggaa    120
cacccccta ggagttccgg gttgtctttg acacaggctc atctgacttg tgggtgccct    180
ccatcaagtg catcagtcct gcctgtcata cacatattac cttcgaccat cacaaatctt    240
ccaccttccg gcttacgcgc aggcccttcc acatcctcta cggatctggg atgatgaacg    300
gagttcttgc ctatgacact gttcgggtaa catggaaaca aagctgaat cagatctgca    360
ctaaccaacc ccctcgtggt ccccatagat ggcctatgtt agatcgggaa acttgtcagc    420
actgaccagc cgtttggcct aagcctgcag caattcgggt ttgataacgc acccttgat    480

<210> SEQ ID NO 326
<211> LENGTH: 456
<212> TYPE: DNA
<213> ORGANISM: Bos Taurus

<400> SEQUENCE: 326
agatttcctc cattcagtcc tgttgggcca tctccccatc agcagcagtc ctcatcctgg      60
gatttctctc caatcctcat ggctccagca tctagccatc gtgggcacca gtggatttgt    120
gaccttgttc gagggtcctg cctgctcctg ctgctggtgg tgtcaaatct actcttgtgc    180
cagggtgcgg aggattatgc accatactgt aaaaaccaac ctggcaactg ccggattccc    240
cttcaaagcc tgtttgagag agcaacattg gtggctagca acaactatag gctcgccagg    300
gaaatgttca atgaatttga cgaagccctg ttgaggttgg ttatcagttt gctccactcg    360
tgggatgaac ctctgcatca ggcagtcaca gagttgttgc acaggaatgg agcctcacct    420
gatatcttgg caagggctaa agagattgag gacaag                               456

<210> SEQ ID NO 327
<211> LENGTH: 336
<212> TYPE: DNA
```

<213> ORGANISM: Bos Taurus

<400> SEQUENCE: 327

| | |
|---|---|
| agagccaggc tgtgaagttt gcattggaca tggcaagggg catggccttc ctacacacac | 60 |
| tagagcccct catcccacga catgcactca acagccgtag tgtaatgatt gatgaggaca | 120 |
| tgactgctcg aatcagtatg gccgacgtca agttctcctt ccagtgcccc gggcgcatgt | 180 |
| atgcacctgc ctgggtggct cctgaagctc tgcaaaagaa gcctgaagac acaaacagac | 240 |
| gctcagcaga tatgtggagt tttgcagtgc ttctatggga actggcgaca cgggaggtac | 300 |
| cctttgctga cctctccaac atggaaattg aatga | 336 |

<210> SEQ ID NO 328
<211> LENGTH: 337
<212> TYPE: DNA
<213> ORGANISM: Bos Taurus

<400> SEQUENCE: 328

| | |
|---|---|
| ttgcggcgtc gaaggggaat gggggcggcg ggggccgtgc cggggccggc gaagccagca | 60 |
| gctcgcggag gaagaagggc ccagggcctc tggccacggc atacctggtc atctacaatg | 120 |
| tggtgatgac cgcggggtgg cgttatagca gttggtctgg tcagagcata cctggctaag | 180 |
| ggtagctatc atagccttta ttattccatt gaaaagcctt tgaaattctt ccaaactgga | 240 |
| gccttattgg agattttaca ctgtgcaata ggaattgttc cgtcttctgt tgtcctgact | 300 |
| tctttccagg tgatgtcaag agtttttcta atatggg | 337 |

<210> SEQ ID NO 329
<211> LENGTH: 490
<212> TYPE: DNA
<213> ORGANISM: Bos Taurus

<400> SEQUENCE: 329

| | |
|---|---|
| gtcacagtga agaaagagga agaaaagaag ccccacgtga agaagcctct taatgccttc | 60 |
| atgttatata tgaaggagat gagggccaag gtggtggctg agtgcaccct gaaggagagt | 120 |
| gcagccatca accagatcct ggggaggaag tggcacaacc tgtcccgaga agaacaggcc | 180 |
| aagtactacg aattggcccg gaaggagcgg cagcttcact cacagctcta cccgacctgg | 240 |
| tcagcccggg acaactacgt acgtgcccac tcaggcaccg ggggccgcct ccaaggtaag | 300 |
| aaaaagaaga ggaagcgaga aaagcagctg tcccagacgc agtcccagca gcagcaagtc | 360 |
| caagagacag acggtgctct ggcctccaaa agcaagaagc catgtgtcca gtacctgccc | 420 |
| cccgagaagc cctgtgacag ccctgcttcc tcgcatggca gcatgctgga ctccccagct | 480 |
| accccctccg | 490 |

<210> SEQ ID NO 330
<211> LENGTH: 265
<212> TYPE: DNA
<213> ORGANISM: Bos Taurus
<220> FEATURE:
<221> NAME/KEY: modified_base
<222> LOCATION: (136)..(138)
<223> OTHER INFORMATION: a, c, g, t, unknown, or other
<220> FEATURE:
<221> NAME/KEY: modified_base
<222> LOCATION: (144)..(144)
<223> OTHER INFORMATION: a, c, g, t, unknown, or other
<220> FEATURE:
<221> NAME/KEY: modified_base
<222> LOCATION: (252)..(252)
<223> OTHER INFORMATION: a, c, g, t, unknown, or other

<400> SEQUENCE: 330

```
attgaagata gtgcggcggt cggggtggca gtggcagcgt tcgtgtgctc gggtgtgaat      60
cgccggggga ggaggcggtg gaggaagagg tggcggcggt ggcggtggtc gtagcggtgg     120
cggaggaggc gggtannnat cagntgcggg cggagacatg gccaacattg cggtgcagcg     180
aatcaagcgg gagctcaagg aggtgctgaa gagcgaggag acgagcaaaa atcaaattaa     240
agtagatctt gnagatgaga atttt                                           265
```

<210> SEQ ID NO 331
<211> LENGTH: 425
<212> TYPE: DNA
<213> ORGANISM: Bos Taurus

<400> SEQUENCE: 331

```
gtgaattcag ttttactttt aagaaagtag aatttatcct gaaaaatatg aattaaagtg      60
ctaacttgat tttgttatgt gtgaatatat tatacagtaa cttttgtaaa atgttactct     120
acatgaaggt ttcactttgg gcaatcactg ggatatgtta ctactaactg ggtattattt     180
atggaactaa gagcctctcg ttgaatgact aatgactatt cagattttga gacagatttc     240
ttgaattgtt tacgtaatct ttgcctgaag gatgtagatt ctgctttcta atagtgaaac     300
taatttatat ggtggccaga gtgtaatata tgctaatact ttggcatggg agatatttat     360
catgagtttt tactattaaa aaatgttata catttgccta ctagttttat aaatgatgtt     420
gcctt                                                                 425
```

<210> SEQ ID NO 332
<211> LENGTH: 395
<212> TYPE: DNA
<213> ORGANISM: Bos Taurus
<220> FEATURE:
<221> NAME/KEY: modified_base
<222> LOCATION: (278)..(280)
<223> OTHER INFORMATION: a, c, g, t, unknown, or other
<220> FEATURE:
<221> NAME/KEY: modified_base
<222> LOCATION: (311)..(311)
<223> OTHER INFORMATION: a, c, g, t, unknown, or other

<400> SEQUENCE: 332

```
attatctctt cccttatcag ggtgagcacg gccgtcttat ctgattcgct gaggcagatg      60
ccatccaggg ggctctccac cccgcaggcc acggacacgg gggtcttctc caccggggac     120
tccagcagtg cgggcacagt ggatccatcc ttctccatct tctgacatgg atccttctcg     180
gagcctttcc cctcggcccc agtgggtttc tgaaccgatg atgtggacgc cagcttctcc     240
tcatcagtag catgaccgtc cctgttaaaa atgtctgnnn tctgggagat cactgctcct     300
tcatcctgag nacacccatc caaagcaaga gactgggctt catatttctt caccttacag     360
ccactcctga aactcaagga tttggtctcg gcttg                                395
```

<210> SEQ ID NO 333
<211> LENGTH: 453
<212> TYPE: DNA
<213> ORGANISM: Bos Taurus
<220> FEATURE:
<221> NAME/KEY: modified_base
<222> LOCATION: (19)..(19)
<223> OTHER INFORMATION: a, c, g, t, unknown, or other

<400> SEQUENCE: 333

```
ggatcagcca ggggccagna tgagccggag ggagggcagt ctggttggaa tgggacagag    60
cctgcctggc ttaaaaattg gagaattcag agtggagcct ctgggttcag gaagagcgag   120
cctggaagaa gtggtcaaga agcaaggggt tggggtgctc tcattcctcc cctgcttttc   180
ccaccagagg accccaggc tgactcctca gcctcacccc ttccccactt ggaggccaag   240
atccaacaga cacacagcct tgcccgcctc ctcaccaaat atgctgagca gcttctccag   300
gaatatgtgc agcaccaggg agaccccttc gggctgcccg gcttctcgcc cccgcggctg   360
ccggtggccg atctgagcga cccggccccg ggccacgctg gcctgccagt gcccgagcgc   420
ctgcggctgg acgccgcggc gctggccgcg ctt                                453

<210> SEQ ID NO 334
<211> LENGTH: 604
<212> TYPE: DNA
<213> ORGANISM: Bos Taurus

<400> SEQUENCE: 334
gggaactgct ccggaagccc ctggcgtcgc tgtctgctgg gtggaaacgt gtaccgtcat    60
ccgtgggcct ggccatggcg ctgcagctct cccgggagca aggcatcacc ttgcgcggga   120
gcgccgagat cgtggccgag ttcttctcat ttggcatcaa cagtatttta tatcagcgtg   180
gcttatatcc atcggaaacc tttactcggg tgcagaaata tggactcacc ttgcttgtaa   240
ctactgatcc tgagctcata aaatacctaa ataatgtgga tcaactaaaa gaatagttat   300
acaagtgttc agttcagaaa ctggtggtag tcatctcaaa cattgaaagt ggagaggtcc   360
ttgaaagatg gcagtttgat attgagttca taagatgtaa aagatgatag tgcacccaga   420
gaaaagtttc agaaagctat ccaagatgaa atctgttcag tggtcagaca gatcacagct   480
acagtaacat ttctgccact gttggaagtt tcttgttcat ttgatctcct tatttgtaca   540
gacaaagatc tggttgtacc tgaaaaatgg gaagagtcgg gaccacagtt cattaccaat   600
tctg                                                                604

<210> SEQ ID NO 335
<211> LENGTH: 463
<212> TYPE: DNA
<213> ORGANISM: Bos Taurus

<400> SEQUENCE: 335
gtctctgctc cacttcttta tctcgtggac tttctatgcc atcaagggaa gtatctaaag    60
ttttagatga aattatttct ttgctggtgg tagaaagtaa aacatcagac tgtcctttca   120
caggagaaga aagttcagca gtgatgtctt tatcgttact attttaatg gacttaaagc   180 ttgtaaggct atctacattt tctgagaaat catgaattgg cataaaatgg tttgaaggta   240
caaactcttc cttgggacga gtgtaatctg gtgtatcaaa atcaacaaac cctacaccag   300
aagggctaac ttcagaaaac ccaccaaatt ccccaaattc atcgtcatca tcatcctcag   360
ctccgttgtc tagtggtggt ggggacgaag agtacattcg aatgatgtct ggctccattg   420
ttcaattgct ttcaatactt aatttatacc tggttcgtcc ggg                     463

<210> SEQ ID NO 336
<211> LENGTH: 632
<212> TYPE: DNA
<213> ORGANISM: Bos Taurus

<400> SEQUENCE: 336
gctcaacaac ctgcttctgc ggaaggacgt ctgctcctgg agcacaggca tgcagctcag    60
```

```
gtacaacatt agtcagctgg aggaatggct tcggggaaga aacctgcacc agagcggagc    120
tgttgagacc atggaacccc tgattcaggc tgcccagctc ctgcagttaa agaagaaaag    180
ccccgaggat gctgaggcca tctgctccct gtgcaccgcc ctcagcaccc agcagattgt    240
caaaattttg aacctttata cccctctgaa tgaatttgaa gaacgggtga cagtggcttt    300
tatacgaaca atccaggcac aactgcaaga tcggaatgac cctcagcagc tgctattaga    360
cttcaagcac atgtttcctg ttttgttccc gtttaatcca tcttctctga ccatggactc    420
aatccacatc ccagcatgtc tcaatctgga gttcctcaac gaagtctgaa aatgcacatg    480
ccagagcttg attgccagtg agagcacgaa ggaagtacat aggacagtga agtgaattta    540
agaatctgtt aaaatctgta aaggagatc agatcaaagt ttgagagcct gtgcagagtg     600
aactatacag aataagacac atctgtcatt at                                  632
```

```
<210> SEQ ID NO 337
<211> LENGTH: 349
<212> TYPE: DNA
<213> ORGANISM: Bos Taurus
<220> FEATURE:
<221> NAME/KEY: modified_base
<222> LOCATION: (190)..(192)
<223> OTHER INFORMATION: a, c, g, t, unknown, or other

<400> SEQUENCE: 337
```

```
gtgcccaca tgggcccggg cgacggcact gcaggtgctc atggacctgc ctctgagcgc     60 cgtgccccc gccaggagg agaggccggg ccctgccccc gccagcctgt cccgcccacc     120
tccgcccagg aacaagccct acgtctcgtg gccctcgtca gggggatctg aacccggagt    180
gtctgtgccn nnaaggagta tgtctgaccc tgaccaggac tttgacaaag aggtgaggtt    240
cgcctggcga aggcggaggc ctggggtctg aggctctgtc tgccctggag tggccacctc    300
gggcctccgt ggtccccagc cccccagaac cgccttctct ggactgctc                349
```

```
<210> SEQ ID NO 338
<211> LENGTH: 476
<212> TYPE: DNA
<213> ORGANISM: Bos Taurus
<220> FEATURE:
<221> NAME/KEY: modified_base
<222> LOCATION: (218)..(221)
<223> OTHER INFORMATION: a, c, g, t, unknown, or other
<220> FEATURE:
<221> NAME/KEY: modified_base
<222> LOCATION: (236)..(238)
<223> OTHER INFORMATION: a, c, g, t, unknown, or other

<400> SEQUENCE: 338
```

```
gtgattgccc tgaagaagaa tacaaggcgt acttgtatct agatgaagct cacagcatcg    60
gggctctggg ccctacagga cgaggcgtgg tggactactt tggcctggat cctgaggatg    120
tggacatcat gatgggaaca ttcacaaaaa gctttggtgc ttctggagga tacatcggag    180
gcaagaaggc gctgatcgac tacctgcgga cgcattcnnn ngcgcggtgt acgctnnntc    240
gctgtccccg cctgtggcag agcagatcat cactgccatg aagtgcatca tggggcagga    300
tggcaccacc cttggcaaag agtgtattca gcagttagcc gaaaacgtca ggtatttcag    360
gagacgtctg aaaagcatgg gcttcatcat ctatggaaat gaagattctc cagtggtgcc    420
tctgatgctc tacatgccag ccaaaattgg cgcctttgga cgggagatgc tgaagc        476
```

```
<210> SEQ ID NO 339
```

```
<211> LENGTH: 317
<212> TYPE: DNA
<213> ORGANISM: Bos Taurus

<400> SEQUENCE: 339
gaggaaactg aggtccggag acaggaaatg acgcactccc ggggatgccc tgagtcatct      60
ggtttctacg ccatcctcaa agtcctccca caggttcagt tctgggctgt tcatcttccc     120
tttcaacttt ctgaaagatg ctggagattc cggtcaactg caaaatgaat gcgctctcag     180
tctcatacac cttatgccag tctggagagt gactggagtg tccaccttct ctggcacaaa     240
gagggacttg gcaaagtggt tggtgggcag tttagccaga gggtagccag ccgccacggg     300
ttggggttga gaggaga                                                    317

<210> SEQ ID NO 340
<211> LENGTH: 520
<212> TYPE: DNA
<213> ORGANISM: Bos Taurus

<400> SEQUENCE: 340
gaaacgctta acagccagtt tgtggaaaat tgcaaggggg tgattcagcg gctgacgctt      60
caggagcaca agatggtttg aaccggaca  acccacctct ggaacgactg ttccaagatc     120
attcaccaga ggacgaacac ggtgcccttt gacctggtgc cccacgagga cggcgcgggc     180
gtggccgtgc gcgtgctgaa gccctggac gcggtggacc tgggcctgga gactgtgtac      240
gagaggttcc accctccac gccgtccttc accgacgtcg tcggccacta cctcagcggg      300
gagcggccca agggcgtcca ggagacggag agatgctga aggtggggc gccactcacg       360 ggggtgggcg agctggtgct ggaccacagc tgcgtgcgcc tgcagccccc caaggggccg     420
ggcatgcagt actacctgag cagccaggac ttcgacagcc tgctgcagcg gcaggagtcc     480
agcgtccggc tctggaaggt cctggcgctg gtcttcggct                           520

<210> SEQ ID NO 341
<211> LENGTH: 333
<212> TYPE: DNA
<213> ORGANISM: Bos Taurus

<400> SEQUENCE: 341
tgtttcacca agtatatttt gagttggttt ccacacattt ccagagtgca gcagtacagt      60
tctctgttca ttgcacgctg gcaaacttct gtagctatgt gggatggtat gtcaatgaaa     120
aattagataa attctttttt cttataatta atataacact tctggacttg aactttgaca     180
ggagatgcca aaaggcagtg gtaccgtgtt atttgtttat atgaattact ttttaacaag     240
gaatgattca tattcattaa atgaattcaa tattttccct gtaaaaacaa tagaatttca     300
gtacatgaac tatagaaaaa atatatatat aat                                  333

<210> SEQ ID NO 342
<211> LENGTH: 432
<212> TYPE: DNA
<213> ORGANISM: Bos Taurus
<220> FEATURE:
<221> NAME/KEY: modified_base
<222> LOCATION: (318)..(318)
<223> OTHER INFORMATION: a, c, g, t, unknown, or other

<400> SEQUENCE: 342
cccaccgggc cccactgcgc cgtcgtctgc aactctacct ctctgacgcc tggaaccagt      60
gcgacctggt ggccctcgcc tgcttcgttc tgggcgtggg ctgcaggctg accccgggcc     120
```

```
tgtatgacct gggccgcact gtcctctgcc ttgacttcat gatcttcacg ctgaggctgc    180
tgcacatctt cacagtcaac aaacagctgg ggcccaagat cgtcatcgtg agcaagatgg    240
tgaaggatgt gttcttcttc ctcttcttcc tcggcgtgtg gctggttgcc tacggggtgg    300
ccactgaggg gctccttngg ccccaggacc gtagcctccc gaatatcctg cgccgtgtct    360
tctaccggcc ctacctgcag atctttgggc agatccctca ggggagatg gacgtggccc     420 tcatggagca cg                                                        432

<210> SEQ ID NO 343
<211> LENGTH: 494
<212> TYPE: DNA
<213> ORGANISM: Bos Taurus

<400> SEQUENCE: 343
gccattcagc ccagcagtgg ttgaccatcg agaagtatat gacggggag ttccggaagt      60 acaacaacaa caacggtgat gaaattgccc ccagcaacac cttggaggag ctgatgttgg    120
ctttctctca ctggacctat gagtatactc ggggagagct gctggtttta gatttgcaag    180
gtgttggaga aaatttgacg gatccatctg taataaaacc tgaatacaaa caatcaagag    240
gaatggtgtt tggaccagcc aatttagggg aagatgcaat tagaaacttc attgcaaaac    300
atcgttgcaa ctcctgctgc cggaagctca aactcccgga cttaaaaaga aatgactact    360
ctcctggaag gataaaattct gcctttggac ttgaaatcaa aatagaacca gctgaggaga    420
ttccagcggg ggaagagggt agtaattctc cagaagatct cacacgattg taaaaaaaaa    480
aaaaaaaaac aaat                                                      494

<210> SEQ ID NO 344
<211> LENGTH: 332
<212> TYPE: DNA
<213> ORGANISM: Bos Taurus

<400> SEQUENCE: 344
gctaaacata gctggggatt tgggtcagag ttgaaagaaa tggctatatt aaaaacgcgt     60
tgtatcaagc tgagcttaac attgtcaagc ttagcttaac aatatcgtgt taagtgatat    120
tgggtgagaa ctctattagc tttcttatta aaacatgttt cccactctaa gagtagtaga    180
gagagagtga ttgggagttt aaatattggt atatgacgtt catgaagttt cagtttattt    240
tacaggttgt tttgcaaaaa cactcataga acgtgttggt gtgaagaacc tgaagtcctg    300
ggctagtgtc aatcgaggag ccattattct ct                                  332

<210> SEQ ID NO 345
<211> LENGTH: 471
<212> TYPE: DNA
<213> ORGANISM: Bos Taurus

<400> SEQUENCE: 345
tgtgttgcca tagcaaaggc ctttgcctgg gaaaaccaaa aacaaaaaat ttaaaaacac     60
accctcagtt gtttattttt gtatagtaat ttatttaaaa gtgaacaaaa tggtcattca    120
aatccaaaga gaatcttaaa acagtccatt tctttgaaag tattacgtgt gctcaaattt    180
tcattcaagt ttgagaatgc tttgagacca tttagattgt tttaaaaact gcttggtcct    240
tacatgaaaa gtgttatggt tttgtgtcat tatttgaggt gtcaagtatt gatgttgaag    300
gtttattcag tctatagtca ggtgatacta aattttattt tgggctggca aggccatcgg    360
```

```
cgtgctgacc agtggcggtg atgcgcaagg catgaatgcc gctgtcagag ccgtgactcg    420
tatgggcatt tacgtgggg ccaaggtctt cctcatctac gagggctatg a              471
```

<210> SEQ ID NO 346
<211> LENGTH: 553
<212> TYPE: DNA
<213> ORGANISM: Bos Taurus
<220> FEATURE:
<221> NAME/KEY: modified_base
<222> LOCATION: (451)..(453)
<223> OTHER INFORMATION: a, c, g, t, unknown, or other

<400> SEQUENCE: 346

```
tgcttcctca ccccaagggg ttcagcaaga tacagtttca caatctctgg atcaagaagt    60
tttattaaaa gttaaaactg aaattgaaga agagctcaaa tccctggaca aagaaatttc   120
tgaagccttc gccagcacag gcttcgaccg ccacacctgc caggactcgg acccaggag    180 aaagaaggag ggttttagtt gtctcgactg aatccgaatg gcagcagct ggttggacat    240 ccgcaggacg ctctggggtg aggagctggg tcagcagggc aggggcggcc cacctgccgg    300
ggcttgaggt agaggctgtg cacgcggtct gctgggcggt ccctggcctg ggttcctctg    360
agattcaggg tctagggtgt caagtgcttc ctcagtcttg tctgtggcat ctgggcaacc    420
ccggctgtga gcacctgtgc ccccgagggt nnntagcctc ccccatcagc ccccgtagca    480
ccttcccctt tggtgacagc accccccgat gtgccaaacg tccccggggt aatgggtccc    540
gtgagagcct cag                                                      553
```

<210> SEQ ID NO 347
<211> LENGTH: 500
<212> TYPE: DNA
<213> ORGANISM: Bos Taurus
<220> FEATURE:
<221> NAME/KEY: modified_base
<222> LOCATION: (237)..(244)
<223> OTHER INFORMATION: a, c, g, t, unknown, or other

<400> SEQUENCE: 347

```
gatgttccca ttcgaagacg ccgctgctct cgcctgtttt agcaagcctc tgctgatgga    60
agccctggga tgaatctagg cttttaaatg gatgtctcga taatgtcaat aactaaactg   120
ttctcagctt atattaatag caggaagact agcatgaaat actgtgccag gccctgggtt   180
ctgtgcgatg ctcctttagg aattggattg tttgggtttg ttttgtggtt ttgaggnnnn    240
nnnngaaacg ggaatctttt tttctcttct aggagttaat gggagaatag ttatctagct    300
aaggaacaga cattacttta tttaaaaata ttttatactt ataaaaatat ggaaacggaa    360
gggaattggt ttgaaagaag atttaaaatg aatcagaaat acctacacaa ggatagagag    420
gaactatgtg actgaatggt tctgtgaaaa gacgtataag ttatttagaa atgaacagaa    480
tttgtaatta ggctaatcca                                               500
```

<210> SEQ ID NO 348
<211> LENGTH: 570
<212> TYPE: DNA
<213> ORGANISM: Bos Taurus
<220> FEATURE:
<221> NAME/KEY: modified_base
<222> LOCATION: (504)..(504)
<223> OTHER INFORMATION: a, c, g, t, unknown, or other

<400> SEQUENCE: 348

```
gcaggggggc ggtcttgaag acgcgtcgtt tggtttgacc tcagtgacgg agttctccgt    60
```

```
cttcaaccgc tgggcggaag gcgtttgtta ggggcccggc caagaaagag gccctcgagg      120
ttcctgatgg tgtccatgac tttcaagcgg agccgcagcg accggttcta cagcacccgg      180
tgctgcggct gttgccatgt tcgcaccggg acgatcatcc tggggacctg gtacatggtg      240
gtcaacctgt tgatggcaat tctgctgact gtggaggtaa cacacccaaa ctcaatgcca      300
gctgtcaaca ttcagtatga agtcattggc aattactatt cgtctgagag aatggctgat      360
aatgcctgtg ttcttttttgc cgtctctgtt cttatgttta taatcagttc aatgctggta      420
tacggagcaa tttcttatca agtgggttgg ctgattccgt tcttctgtta ccggcttttt      480
gactttgttc tcagctgcct ggtngctatc agttctctga cttacttgcc aagaatcaaa      540
gaatatctgg atcagttacc tgattttccc                                      570

<210> SEQ ID NO 349
<211> LENGTH: 401
<212> TYPE: DNA
<213> ORGANISM: Bos Taurus

<400> SEQUENCE: 349
tgaggtgcac tgggtgggat aaaaatggaa gcaggaaaaa aaggaagta gaaggtccaa       60 tcatgaggtg gggtggacct agccccattc ttctccttct ccaggtccaa tgaagcgcca      120
agtggcagta aaatccaccc ggggttttgc tttgaaatca acccatggca ttgccattaa      180
atcaaccaac atggcatctg tggaaaaggg ggagagtgca cccattcgta agaacacacg      240
ccagttctat gatggggagg agtcttgcta catcatcgat gccaagcttg aaggcaacct      300
gggccgctac ctcaatgtga gaccccttttc gctcacctgt atgtgctggt tatcccctag      360
tcctcacatt tctagttctt ttaaatacaa ctccataaac c                         401

<210> SEQ ID NO 350
<211> LENGTH: 600
<212> TYPE: DNA
<213> ORGANISM: Bos Taurus

<400> SEQUENCE: 350
gataaagtga ctagtccaga gaaagctgaa gaagcaaaat taaaagcaag gtatcctcat       60
ctgggacaaa agcctggagg ttccgatttt taaggaaac gattgcagaa agggcaaaaa      120
tattttgatt ctgggattaa caacatggct aaagcaaaaa tgaagaacaa gcaacttcct      180
actgcaaccc cggataagac agaggtcact ggtgaccaca ttcccactcc acaggacctt      240
cctcaacgga aaccatctct tgttgctagc aaactggctg gctgattaaa aagagctgaa      300
ctgcatgaat cttctaatgc ccattatttc tccttaatat gttactcctc tgcttttttat      360 ttcctttttac tccctgtgtc atttgagagt gatggctttg caggtagcgg tagtgtgtgc      420
tgctatttta agggaatata catgtgtaga gttttttgatt agtttaacag tgcactgatg      480
aaaagaacat gttagagcaa cataaagtaa tctacttgaa aataattgta tatattacct      540
aactcctagt gtagggctgg atccaacaag taactaacaa gttttgcagt ttaaatgttg      600

<210> SEQ ID NO 351
<211> LENGTH: 437
<212> TYPE: DNA
<213> ORGANISM: Bos Taurus
<220> FEATURE:
<221> NAME/KEY: modified_base
<222> LOCATION: (312)..(313)
<223> OTHER INFORMATION: a, c, g, t, unknown, or other
<220> FEATURE:
```

```
<221> NAME/KEY: modified_base
<222> LOCATION: (318)..(320)
<223> OTHER INFORMATION: a, c, g, t, unknown, or other

<400> SEQUENCE: 351
tttttttttt tttttttttt taaacttgca gaagcctctt tattttcatc catcagaggg      60
cagacagaat gaaaaccaca attacagaaa actaaccaaa atgatcacat ggatcacagc     120
cttgtgtaac tcagtgaaac tatgagccat gccgtgtaag gccagccgag acagacaggt    180
catggtggcg ggttctgaca aaccgtggtc cattggagaa ggaaatggca aaccacttca    240
gcattcttgc cgtgagaacc ccatgaatgt atgaaaagtg tgagaagcag agagcaaaag    300
ctagtgactg gnnggccnnn tctgccccac agataaactt caatttacat gtcattattt    360
acaactttag gggcggttta aacaaaacag ttggggagaa aaaatggcat ttctgacttg    420
cgttaaaaaa tcgtcaa                                                    437

<210> SEQ ID NO 352
<211> LENGTH: 526
<212> TYPE: DNA
<213> ORGANISM: Bos Taurus

<400> SEQUENCE: 352
agacaggact ctaaagttag actctcctga ttttcacaa gatgctggac tggagattag       60
caagtgcaca tttatcctg ctatgacac tgatgctctg gagctcagga aaagtgttct     120
cagtgggtgt cacaacagag gcctttgatt ctggagtctt aggtgttcag tcatcaccca    180
cagtcagaga agcgaagtcg gccactgacc tggcagcaaa actcttactt cttgatgaac    240
ttgtgtctct ggagaatgac gtgattgaaa caaagaagaa aagaagcttc tctgggtttg    300
gttctcccct ggacagactc tcagctggct ctgtaagtca taaaggtaaa cagaggaaag    360
tagtagatca tccaaaaagg cgatttggta tccctatgga tcggattgga agaaaccggc    420
tttcaaattc cagaggctaa tggattccaa tcacacaact tccttgggtg aaatgtcaca    480
gaaacatgga agatattttg gtgaagttct tcacacttct taatga                   526

<210> SEQ ID NO 353
<211> LENGTH: 477
<212> TYPE: DNA
<213> ORGANISM: Bos Taurus

<400> SEQUENCE: 353
gcacgagccc atctctaggg tggtgaacta ccctgaaatc tctgggactg gaatttgttc       60
cccaaagtct tgagtggctc tggcttattt gtgtctccac cctggttctg tgaaccaccc    120
cactccagat gccagagcca ctggggttgg ggcctggaac agggataggc ctgtcagaag    180
gagctggagc cagtatgcga agcagctgta atggtctgag tggatttatt gacagtgaat    240
aaagggcaca aagcccgagc caggcagact cacctcacac accccctgct ccccgtggtg    300 ggacacctg agagagagga ggggtggaca atgagagaac aggagatggg tcataccagt     360
ggcctcgcag agcaggggca ataagagctc agcccattgc agtgctggcc atgtcttcat    420
acctggtgat ctgaggtgtc ctgtttgctt ggctgtccgt ttgcttcttt tctggct       477

<210> SEQ ID NO 354
<211> LENGTH: 504
<212> TYPE: DNA
<213> ORGANISM: Bos Taurus

<400> SEQUENCE: 354
```

```
gcacgaggct ggcggggaa catgtcggag tcagagctcg gccggaagtg ggaccggtgc    60
ttggcggacg ccgtcgtgaa gataggtact ggctttggat taggacttgt tttctcactt   120 accctctttta aaagaagaat gtggccatta gcctttggct ctggaatggg atttggaatg   180
gcctactcca attgtcagca tgatttccag gctccgtacc ttctacacgg aaaatacgtc   240
aaagagcagg agcagtgact cacgcctgag agcaccccag ggggagggca ggagaaacca   300
cgttcattcc tcaggaacgc tgaagcgccc gagtgagccg cactctccgt gagcgtcgcc   360
agtaatgctc aactccagca cactgtgcac gtgtttgaaa ccaagtccgt ttcttgtttt   420
gtattttctc tctggaaatt gcagggcggt ggtcttaaaa taaataaact aaactcggca   480
gcccagaaaa aaaaaaaaaa aaaa                                         504
```

<210> SEQ ID NO 355
<211> LENGTH: 529
<212> TYPE: DNA
<213> ORGANISM: Bos Taurus

<400> SEQUENCE: 355

```
gcacgagctg gcctcagtca gtgatgaaaa caagggaagg gacagggagg ggcagtctcc    60
taggtcaacc ctcggggagg gccctgggcc aggattcacc cttcctagtg cctctgagtc   120
aggatccgcg ggaccccag ccttgacccc acctgtattc tgtagtccct ctcctgccc    180 actcaggact tagaggcact catccattgc acatgtttat aagcacctgt taccagccaa   240
tactgaaaag gacagactca tggaattag agtctagtgg ggaattcaga ccctggtgat   300
gaatgttggg aaagaggaag ctatgaggtg actgcattgc aatcctgggg gcctaactgg   360
gcccaagact gggcaagagt cctgcagaag actttgaaaa acctcaagtg ggaaggtctg   420
ggggctgttg gaggctggag ccagtatgag ctccccatgg ctcctctgac ccgtaatcaa   480
ggacccaagg agctgacttg acgacagttt ttgaggaagt ggagcaggt              529
```

<210> SEQ ID NO 356
<211> LENGTH: 361
<212> TYPE: DNA
<213> ORGANISM: Bos Taurus

<400> SEQUENCE: 356

```
gcacgaggtc acggacagta tggttccgcc ggtgcaggtc tctccgctca tcaagctcgg    60
ccgttactcc gccctgttcc tcggcatggc ctacggcgcc aagcgctaca attacctgaa   120
acctcgggca gaagaggaga ggaggcttgc agccgaggag aagaagaagc gggatgagca   180
gaagcgcatc gagcgggagc tggcggaagg tggtcatgcg tttggctctc ctagattttc   240
ccccgccccg cggggttttc agaaacagct gctgcttcat acggagcagc aagtggagag   300
gaaaggctgc cttctccatt tccactggcc cctgggccat cctctgctga gtggggtagg   360
g                                                                 361
```

<210> SEQ ID NO 357
<211> LENGTH: 572
<212> TYPE: DNA
<213> ORGANISM: Bos Taurus

<400> SEQUENCE: 357

```
ccacagtctg tctcaccatc cacaaaagct cacaggatcg cctaggtgac atccgaagct    60
ctgtcacata cgatctggcg ttggatccag gtcggctgat ttctcgtgct gttttggtg   120
```

| | | |
|---|---|---|
| agaccaggaa ctggactttg actcgaagaa aaaccctgga gctgggagag cactgtgact | 180 | |
| ccatgaagct gcttatacca gactgtgtgg aggacatggt gaacccccatt atcctgcgac | 240 | |
| tcaacttctc cctggttggg gagcccattg cctcatctca gaacctccgc ccgtgctgg | 300 | |
| ctgtgggctc ccaggacctc ttcacggcct ctctccccct tgagaagaac tgtgggcaag | 360 | |
| atcacctttg tgaaggggac ctcagtgtca acctgagctt cttagggctg gagaccctgg | 420 | |
| tggtggggag ctccctggag ctcaatgttg cagtgatggt gtccaatgag ggcgaggatt | 480 | |
| cctatggaac ggtgatcagc ttctactatc cagcagggct gtcctatcga cgcacgttag | 540 | |
| caatccagca acctggtcag cgtcccctgc gc | 572 | |

<210> SEQ ID NO 358
<211> LENGTH: 303
<212> TYPE: DNA
<213> ORGANISM: Bos Taurus

<400> SEQUENCE: 358

| | | |
|---|---|---|
| ataatcctgg cgtagggcgg ctcgggctgc gccccagcta tcagaacag gccccagact | 60 | |
| gtggcagcac ttccccaggg gtcttgctgg gaacttgaca tctcgggccc cacccggacc | 120 | |
| tgctgattca gggcccacct ttcacatgat cccctgggaa ttctgaacat tccaaggca | 180 | |
| gccttccttg cacagccctt ggctctggcc acacccagg attcctgggg aggcagagaa | 240 | |
| aaccctgatg ctgccccac tccagaggct ctgacttaat gggggtaggc cgggtgtggg | 300 | |
| ctc | 303 | |

<210> SEQ ID NO 359
<211> LENGTH: 454
<212> TYPE: DNA
<213> ORGANISM: Bos Taurus

<400> SEQUENCE: 359

| | | |
|---|---|---|
| tttttaaaaa aaaaaataat tacctttatt acaaaactca tggtaaacct agggatttat | 60 | |
| gtccggttaa gctctttcac ctgaaattag tgggtggctc tgaaaagagc ctttgaggtt | 120 | |
| ttcaaagcag gaggtgccgc tgaagattta cttcttcttg agaccgcct tcttggcctt | 180 | |
| tgtagccttg ggtttggcag ctttaggttt ggctgccttg gcttggggg ctttggcctt | 240 | |
| ggccggactc ttagtcggct tcttcggctt ggctgccttc gccttcttcg gactcttggc | 300 | |
| tactttcttg gtcccagcag ccgcagccgg cttcttaact ttcttagggg tcttcttggc | 360 | |
| agccttcttc ggagtggccg caccgtgga tttcttgggt ttcttagccg ccccagcagc | 420 | |
| cttcttgggc ttggccgcgc ccgccttctt cccc | 454 | |

<210> SEQ ID NO 360
<211> LENGTH: 586
<212> TYPE: DNA
<213> ORGANISM: Bos Taurus

<400> SEQUENCE: 360

| | | |
|---|---|---|
| tggaagctga agatttccca gaacaagaac ccaagataag ctggagttaa tggaagcttt | 60 | |
| tctttggctt tttcggttgt gacctacctt ccaaccagtg ctgcagtata taaccaccta | 120 | |
| gaccagcaac gttcctctgg agccagcata gggcccttct tgagcaaata ccaccagact | 180 | |
| cacaaacagc tctgttacta aggttttatt taatttcaga gtgcaaatat ttttcaaatg | 240 | |
| ctcactaggt tttatatact aagaagctat atttttgccc ttaaacactc cttgtggatt | 300 | |
| atgatttata ttcacatata ctggcctcaa atgagataaa aaccaaactg tctgttatgt | 360 | |

-continued

```
ttactttgat atattaattt ctttagagca gcgttttagc tactaaagtt aacatgttta    420
ttctttcctt ctcacatgct tgattaaaag gtgagctaat tctttcaaga gttttgatta    480
attaacagaa aatcctaaat tcaaactgct aaagaacagt ttgattttta tggctctcct    540
taagtatgag acacatctta ttttattgaa tttctttcaa tacccct                 586

<210> SEQ ID NO 361
<211> LENGTH: 371
<212> TYPE: DNA
<213> ORGANISM: Bos Taurus

<400> SEQUENCE: 361
gactaatcct ctcctgcttc agctgttcaa attttcgctt taactcggcc tgccgctcca     60 cttcttttg tgcacggcca acgaaaatga ccttcccagt gatttctttt ccattcatct    120
cttccacagc caaactggct aaatagctct ttcagattct catcatcaac ctcttcccca    180 aagttttga tgtaaacatt ggtgaattcc ttggctttgg ctccaagttc ggcttcccgc    240
tcttttcgag acttgaatct gcccacaaac cagccctgga gtggagaggt aggagcaggc    300
cacacttggg ccgagagaac cagtagccgc cttgtgtgtg ccagtttata ccgaggtggg    360
gccacggctg g                                                         371

<210> SEQ ID NO 362
<211> LENGTH: 800
<212> TYPE: DNA
<213> ORGANISM: Bos Taurus
<220> FEATURE:
<221> NAME/KEY: modified_base
<222> LOCATION: (7)..(7)
<223> OTHER INFORMATION: a, c, g, t, unknown, or other
<220> FEATURE:
<221> NAME/KEY: modified_base
<222> LOCATION: (21)..(21)
<223> OTHER INFORMATION: a, c, g, t, unknown, or other
<220> FEATURE:
<221> NAME/KEY: modified_base
<222> LOCATION: (39)..(39)
<223> OTHER INFORMATION: a, c, g, t, unknown, or other
<220> FEATURE:
<221> NAME/KEY: modified_base
<222> LOCATION: (87)..(87)
<223> OTHER INFORMATION: a, c, g, t, unknown, or other
<220> FEATURE:
<221> NAME/KEY: modified_base
<222> LOCATION: (92)..(92)
<223> OTHER INFORMATION: a, c, g, t, unknown, or other
<220> FEATURE:
<221> NAME/KEY: modified_base
<222> LOCATION: (102)..(102)
<223> OTHER INFORMATION: a, c, g, t, unknown, or other
<220> FEATURE:
<221> NAME/KEY: modified_base
<222> LOCATION: (272)..(272)
<223> OTHER INFORMATION: a, c, g, t, unknown, or other
<220> FEATURE:
<221> NAME/KEY: modified_base
<222> LOCATION: (293)..(293)
<223> OTHER INFORMATION: a, c, g, t, unknown, or other
<220> FEATURE:
<221> NAME/KEY: modified_base
<222> LOCATION: (299)..(299)
<223> OTHER INFORMATION: a, c, g, t, unknown, or other
<220> FEATURE:
<221> NAME/KEY: modified_base
<222> LOCATION: (365)..(365)
<223> OTHER INFORMATION: a, c, g, t, unknown, or other
<220> FEATURE:
<221> NAME/KEY: modified_base
<222> LOCATION: (454)..(454)
```

```
<223> OTHER INFORMATION: a, c, g, t, unknown, or other
<220> FEATURE:
<221> NAME/KEY: modified_base
<222> LOCATION: (498)..(498)
<223> OTHER INFORMATION: a, c, g, t, unknown, or other
<220> FEATURE:
<221> NAME/KEY: modified_base
<222> LOCATION: (510)..(510)
<223> OTHER INFORMATION: a, c, g, t, unknown, or other
<220> FEATURE:
<221> NAME/KEY: modified_base
<222> LOCATION: (543)..(543)
<223> OTHER INFORMATION: a, c, g, t, unknown, or other
<220> FEATURE:
<221> NAME/KEY: modified_base
<222> LOCATION: (569)..(569)
<223> OTHER INFORMATION: a, c, g, t, unknown, or other
<220> FEATURE:
<221> NAME/KEY: modified_base
<222> LOCATION: (579)..(579)
<223> OTHER INFORMATION: a, c, g, t, unknown, or other
<220> FEATURE:
<221> NAME/KEY: modified_base
<222> LOCATION: (623)..(623)
<223> OTHER INFORMATION: a, c, g, t, unknown, or other
<220> FEATURE:
<221> NAME/KEY: modified_base
<222> LOCATION: (633)..(633)
<223> OTHER INFORMATION: a, c, g, t, unknown, or other
<220> FEATURE:
<221> NAME/KEY: modified_base
<222> LOCATION: (672)..(672)
<223> OTHER INFORMATION: a, c, g, t, unknown, or other
<220> FEATURE:
<221> NAME/KEY: modified_base
<222> LOCATION: (695)..(695)
<223> OTHER INFORMATION: a, c, g, t, unknown, or other
<220> FEATURE:
<221> NAME/KEY: modified_base
<222> LOCATION: (785)..(785)
<223> OTHER INFORMATION: a, c, g, t, unknown, or other
<220> FEATURE:
<221> NAME/KEY: modified_base
<222> LOCATION: (792)..(792)
<223> OTHER INFORMATION: a, c, g, t, unknown, or other
<220> FEATURE:
<221> NAME/KEY: modified_base
<222> LOCATION: (795)..(795)
<223> OTHER INFORMATION: a, c, g, t, unknown, or other
<220> FEATURE:
<221> NAME/KEY: modified_base
<222> LOCATION: (798)..(798)
<223> OTHER INFORMATION: a, c, g, t, unknown, or other

<400> SEQUENCE: 362
aaccctntta aaaccccca nacttttact atagggaant tggccctcga ggccaagaat      60
tcggcacgag gcgcaaagat gtcagtnttt tnggggggtg gngtacaata cctgcagtga    120
ggccagggcg ggccctgcag cgaaagggca cctctcacag gtgctctagc tactgccct    180 ttgggaagcc aaatcctcca gccgggaccc ttgggtatgt gttctggaac atcctgacct    240
ctgataccct gcctgtgacc ctgacttgct gngcaaggca tccttccccc tanagctttnt    300 tgcaaattac tggcttcctt gagccctgcc ttggagccac ccaatccagc tgtaaaatga    360
acacncagga aaccacacat cttgactcaa cttatccagg tcattcctgg agtgggcctg    420
gggctataaa taggcatcat gagttgatca caanaagggc ttgagaaaag ctgaaaggag    480
agtaggggag gaagccantg ttagacccan aactataggc acacacacct tcaggccagc    540
ttntgagctg tgggaaccgt gttctctant taaggcacnt gatggtgttt ggaagagggg    600
acggggtttc ttccttgtct gcntgatggg acnactcatc catacttgat ggcggtctt    660 tgcaagcggg tncccttcca ccccccaggg ccaanaaaca tgtcccccctt cacttcccat    720
```

| | |
|---|---:|
| ggaattttttt cttttattat cccccccacc ctttgcaggg aaacccctttt gcaaagaaaa | 780 |
| aaggnccttg anacnagnga | 800 |

<210> SEQ ID NO 363
<211> LENGTH: 548
<212> TYPE: DNA
<213> ORGANISM: Bos Taurus

<400> SEQUENCE: 363

| | |
|---|---:|
| ttaagatggc tgccgggcgg caccgtccgg actgaaaaga tgtggagtgg gctgttacct | 60 |
| cctggcctaa atgaaagtga tgttgaattg aattctgacg atgataccac attagagagc | 120 |
| tctgaactta acttcaaga gggtaaagaa gatgggacct ttgaaaagac agagatggta | 180 |
| gatattccta cagatggacc aagcactgaa gcagaggcaa atataaatgc atatgaagag | 240 |
| tgtccctctg gaattccctt aaatatgtgg aataaatttc aagaattgca taaaaagcat | 300 |
| tctgaacaga aaacttcagc ttctagatcc gaaaagaaaa aagaaaacg ctccagaaaa | 360 |
| ggtaaattga gaatgaaga gaatctcat agtgaacaat cttcaagtga aacccagtgg | 420 |
| aaggagctta cccagtattt tggagtcaat gagaggtttg acccccctgt taaaggaaaa | 480 |
| aaagttgaaa agtcgggact tgaaaagagg atagaccaag ctgtggaaga gtggaacatt | 540 |
| gagaaggc | 548 |

<210> SEQ ID NO 364
<211> LENGTH: 222
<212> TYPE: DNA
<213> ORGANISM: Bos Taurus

<400> SEQUENCE: 364

| | |
|---|---:|
| ttttaataag gatggggtag aaggctggtt ggttgagatg tcctggcgag ggtctcccgg | 60 |
| agccagggca atctgagcca attcattcct cttccctctc ttcccctggc cttacgcgaa | 120 |
| gcctcgggct ccttgaagca gcgccagggc tcctgacacc cccatggtca aggcagaacg | 180 |
| cgcacaggct gggaccacgc cggagatcat cgggtcattt tg | 222 |

<210> SEQ ID NO 365
<211> LENGTH: 609
<212> TYPE: DNA
<213> ORGANISM: Bos Taurus

<400> SEQUENCE: 365

| | |
|---|---:|
| gaattctctt ccaagtttga aaattcaagt tggataacca gtattatcct cgttggtcct | 60 |
| gttgctgtta aggcattgac atatatgtgg aggaatgaaa tacttaacta gaattctta | 120 |
| atagggttta tggtttaact ttagagagca cctttgtatt tttcttatca gctaggacaa | 180 |
| aatattgtat taagcatatg tagcacttca taaaatggct attgtgtaag ctacaggtaa | 240 |
| aagcaaagct atagggtaga tttataatac agtgaaggca cgaggacttc aaacgtgccg | 300 |
| gcagtttggc catagaaact ggaagttaaa agtcacatga aggtcaagat ccagacttaa | 360 |
| ctcatgccac tgtccttcag gatctctgtc ttggagcatg agggagttgg caagttaaat | 420 |
| gtagaaagca ggcccaaact tggaaaggtt ttgttttttgt aaatcatttg acttactttt | 480 |
| aacatgctca gtagaacgtt tttactttta ctgttttgta cccaggagtt attttttacct | 540 |
| agccgtagag caaactgtt cataaatgta tcccttttcaa atgtctttga gaaaatgga | 600 |
| gggaaaaac | 609 |

<210> SEQ ID NO 366
<211> LENGTH: 453
<212> TYPE: DNA
<213> ORGANISM: Bos Taurus

<400> SEQUENCE: 366

| | | | | | |
|---|---|---|---|---|---|
| gaatgaaaga | tatacctaga | acaccatcca | gggggagaag | tgaatgtgat | tcctctccag | 60 |
| aaccaaaagc | tttgcctcag | actcctaggc | caaggagtcg | ttctccatct | tccccggagc | 120 |
| tcaacaataa | gtgtcttacc | cctcagagag | agagaagtgg | gtcagagtca | tcagttgaac | 180 |
| agaagactgt | ggctaggaca | cctcttgggc | agagacgtcg | gtctggatct | tctcaggaac | 240 |
| tcgatgggaa | acccagtgca | tccccctcagg | agagaagtga | gtcagactct | tctccagatt | 300 |
| ctaaagctaa | gatacgaatg | ccactcaggc | agaggagtca | ctctggatcc | tctccggagg | 360 |
| tggacagcaa | atcccggcct | tctcctcggc | gtagcaggtc | tggctcatcc | cctgaggtta | 420 |
| aagagaagcc | aagagcagca | cccagggcac | aga | | | 453 |

<210> SEQ ID NO 367
<211> LENGTH: 447
<212> TYPE: DNA
<213> ORGANISM: Bos Taurus

<400> SEQUENCE: 367

| | | | | | |
|---|---|---|---|---|---|
| gcggtgccgc | ccgccctgcg | ctctcggagc | ccggagccgc | cgcccagggg | gatgcgggag | 60 |
| ccccggtttt | gggggaacag | agaggcaggc | ggggagccga | ggacggcatg | tcccaggccc | 120 |
| caggagctca | gccaagcccg | ccctccgtgt | accacgaacg | gcaacgcctg | gagctctgtg | 180 |
| ccgtgcacgc | cctcaacaac | gtcttgcagc | agcagctctt | cagccaggag | gctgccgatg | 240 |
| agatctgcaa | gaggttggcc | ccagactccc | ggctgaaccc | ccatcgcagc | ctcctgggca | 300 |
| ccggcaacta | cgacgtcaac | gtgatcatgg | ctgccctgca | ggggcagggc | ctggctgccg | 360 |
| tgtggtggga | ccgaaggagg | cccctgtccc | agctggcgct | gccccgggta | ctggggctga | 420 |
| tcctgaacct | gccgtcgccc | gtctcgc | | | | 447 |

<210> SEQ ID NO 368
<211> LENGTH: 445
<212> TYPE: DNA
<213> ORGANISM: Bos Taurus
<220> FEATURE:
<221> NAME/KEY: modified_base
<222> LOCATION: (151)..(152)
<223> OTHER INFORMATION: a, c, g, t, unknown, or other
<220> FEATURE:
<221> NAME/KEY: modified_base
<222> LOCATION: (209)..(211)
<223> OTHER INFORMATION: a, c, g, t, unknown, or other
<220> FEATURE:
<221> NAME/KEY: modified_base
<222> LOCATION: (284)..(286)
<223> OTHER INFORMATION: a, c, g, t, unknown, or other

<400> SEQUENCE: 368

| | | | | | |
|---|---|---|---|---|---|
| tgcaggggtt | acgtttgcag | tcagtccggt | gtttgcaaat | attgtgcggg | ctcgcgagcg | 60 |
| cgtctccggg | ctccggccag | gacccgaacc | cgcggcgcct | aatcgctgcg | cacttgagtt | 120 |
| tgcatgaact | tccccggcgc | tgcaggcacg | nncgcgcgc | tcccgactgc | agaccgcaag | 180 |
| cctccctgtt | tttacagcag | cggggacgnn | ntcttccaac | ccgacatgga | tgtgctccca | 240 |
| atgtgcagca | tcttccagga | actccagatt | gtgcacgaga | ctgnnnactt | ctcggcgctg | 300 |
| ccctccctgg | aggaatactg | gcaacagacc | tgcctggagt | tggaacgtta | cctgcagagc | 360 |

```
gagccctgct acgtgtcagc ctccgagatc aaattcgaca gccaggaaga tctgtggacc      420
aaaatcatct tggctcggga gaaaa                                           445

<210> SEQ ID NO 369
<211> LENGTH: 384
<212> TYPE: DNA
<213> ORGANISM: Bos Taurus

<400> SEQUENCE: 369
gagtacagca tcttcgctcc cctctcccgg atggaggccg agattgtgca gcagcaggcg       60
cctccctcct acgggcagct cattgcccag ggcgccatcc ctcctgtaga ggacttccct      120
acagagaacc ctaatgataa ctctgttctg ggcaatctgc gttctctgct acagatcctg      180
cgccaggaca tgactccagg gagcacctct ggtgcccgcc gccgccagcg gggccgctct      240
atgcgccgcc tggtgcgccg tcttcgccgc tggggcttgc ttccccgaac caacccccca      300
gcccggaccc ctgaaaccag atcccaggcc acaccatcca ctgctcctcc tgagaccttg      360
gatggcagca caggtccagc ccat                                            384

<210> SEQ ID NO 370
<211> LENGTH: 485
<212> TYPE: DNA
<213> ORGANISM: Bos Taurus

<400> SEQUENCE: 370
ggaggctgat gaaggagctt gaagaaatcc gcaagtgtgg gatgaaaaac ttccgtaaca       60
tccaggtcga tgaagctaat ttgctgactt ggcaagggct cattgttccc gacaaccctc      120
cctatgataa gggggccttc agaatcgaaa tcaactttcc agcagagtac cccttcaaac      180
caccgaagat cacgttcaaa acgaagatct accacccgaa catcgacgag aaggggcagg      240
tgtgtctgcc tgtaattagt gctgaaaact ggaagccagc aaccaaaacc gaccaagtca      300
tccagtccct catagcactg gtgaacgacc ccagccgga gcacccgctc cgggctgacc       360
tagccgaaga atactctaag gaccgtaaaa aattctgtaa gaatgctgaa gaatttacaa      420
agaaatatgg ggaaaagcga cctgtggact aaaatctgcc gcaatggatt ccagcgagtg      480
tgagc                                                                 485

<210> SEQ ID NO 371
<211> LENGTH: 431
<212> TYPE: DNA
<213> ORGANISM: Bos Taurus

<400> SEQUENCE: 371 tttttttta aaacaaaaca aaagtttatt aaaagtgttc ttaatgctcg aaacggaaaa        60
gattcccaaa tatacagatg cctcttttct catagaaata gattatttt tatgatacaa      120 aaaaaggcc aaaaaaaaa aaaaaaacca acaaaaacaa aaacaacat caacagcaac        180 aaccccgtag gaacatcttt aagcgattac tcagggcccg gctgacagtt acacgtgggt      240
tgcgtcagtc ccgtgtacac acgcgttcag ccatgtttaa accgattgca tcaacttcga      300
aaccggcccg cccgccggcg cccggagagg ggggtgggca ggaggagagg caagagttta      360
tcattcatct gtacacatag acatctcttc tttaataac accgcgggcg ggcgccccgt      420
ctgcacgtgc g                                                          431

<210> SEQ ID NO 372
```

<211> LENGTH: 465
<212> TYPE: DNA
<213> ORGANISM: Bos Taurus

<400> SEQUENCE: 372

```
agcaaggaca gcgagcaggg ctgagctggg ggtgcgtggg ctgctacggc ccgccacctc    60
catcacatgc acctctgcac ccctgctgc ctgactcagg agtgggggg ggggtcctgt    120
gcttccttca ctccagaccc acggtgctga cccagtgcac ccacctggtc ctctagtgcg    180
gacctggcca cagggctcct gtgggccac gctgatcccg ccctggtccc ttcataaaga    240
actcttgagc acatgcagcc caggggagcc aggaggctcc agtgtgctgt gtccatctgc    300
ctccctccag ccccttccga gacactgcgc atcatgcccc cctccacccc cacccacact    360
ggcaggagga acagacaggg agaccacaca cagagctcgt tgtttataaa tctctgcctg    420
gctcatcggt ctgtttgtcc atgtatatat ctgtatatct ctatg                   465
```

<210> SEQ ID NO 373
<211> LENGTH: 369
<212> TYPE: DNA
<213> ORGANISM: Bos Taurus
<220> FEATURE:
<221> NAME/KEY: modified_base
<222> LOCATION: (99)..(101)
<223> OTHER INFORMATION: a, c, g, t, unknown, or other
<220> FEATURE:
<221> NAME/KEY: modified_base
<222> LOCATION: (141)..(142)
<223> OTHER INFORMATION: a, c, g, t, unknown, or other

<400> SEQUENCE: 373

```
ctttgatttg agcatgcccc tcaagtagac agcatgctct ctggtccctt gggggcaaca    60
cctgatccag atggtgaggc tgtctgccta gaccccagnn ngtggtgaga acggggagca   120
gaacgcctgt cagtcagagg nngcctcctg gcagcctcag ctgagcaaag gccaaagaaa   180
gtagccagcg gaagcagccc aagagccgcc gggaggcccc acgtgggaga agcaagggggg  240
tcagacctga ccaggggcgc tcacgtgccc ccctcccctg catccactcc aaggttgact   300
gctggctccg gccagcactg tccgtggccc cagcatgctg agggtccttc tggtgaccca   360
tgtttgaaa                                                           369
```

<210> SEQ ID NO 374
<211> LENGTH: 372
<212> TYPE: DNA
<213> ORGANISM: Bos Taurus

<400> SEQUENCE: 374

```
tcctgagagc cccgaggaac ccctctcccc gccaacatgg ccaacaaggg tccttcctat    60
ggcatgagcc gggaagtgca gtcgaaaatc gagaagaagt atgacgagga gctggaggag   120
cggctggtgg agtggatcgt aatgcagtgc ggccccgatg tggggcgccc cgaccgcggg   180
cgcctgggct tccaggtctg gctgaagaat ggcgtgattc tgagcaagct ggtcaatagc   240
ctgtatcctg atggctccaa gccagtgaag gtgcccgaga acccgccctc catggtcttc   300
aagcagatgg agcaggtggc tcagttcctg aaggcagctg aggattatgg cgtcaccaag   360
actgacatgt tc                                                       372
```

<210> SEQ ID NO 375
<211> LENGTH: 409
<212> TYPE: DNA
<213> ORGANISM: Bos Taurus

<400> SEQUENCE: 375

```
cgggccccccg cgcgcagcgg ctggcccctc agcccgcgc cctgcccgca cccgccggcc      60
ctaaagctgt cacgatgcag ccgcccgcgc cctcccgcct ggggctgctc ctgctgctgc     120
tcctgagtcc ggcgcacgtc ggcggactgt ggtgacatcc gggagacggc cttcgtgttc     180
gctataacgg cggcaggcgc cagccatgcg gtcacgcagg cctgctccat gggcgagctg     240
ctgcagtgcg gctgccaggc gccccgaggc cgggccccac cccgaccccc cggcctgcca     300
ggcacccctg gccccccgg ccccgcggga tccccgacg gcagcgctgc ctgggagtgg       360
ggaggctgcg gcgacgacgt ggacttcggg gacgagaagt cgaggctct                409
```

<210> SEQ ID NO 376
<211> LENGTH: 437
<212> TYPE: DNA
<213> ORGANISM: Bos Taurus

<400> SEQUENCE: 376

```
tacaacctac gcggaagtct acctttgatg cagccagttt cattggagga attgtccttg      60
tcttgggtgt gcaggctgta attttctttc tctataaatt ctgcaaatct aaagaacgaa     120
actaccacac tctgtaaaga gacccactaa attaacaagg actggcgtgt aactcactga     180
aaccaaaata ttatctttca agatgtccca catggaagac gctattctag gatctttaat     240
ttttcaaagg atgcatatag gagcatcacc cttgaagaag aatcagttca gtcactttgc     300
tcaacgggcc tatttaaagt acgctgcatg agtccttgtg gctgtctttc attttacatg     360
gctgctgctg tgggattgtg ttctctctgc ttgacatgcc aaatgtaact ttaagtgatg     420
gaaaacattg tcctgcg                                                   437
```

<210> SEQ ID NO 377
<211> LENGTH: 275
<212> TYPE: DNA
<213> ORGANISM: Bos Taurus

<400> SEQUENCE: 377

```
attacttctg tttatatggc agcagtttca ttgactgaac aagtacacac tgctcaatat      60
gttgatgcta tgtccaaaaa tgtttcttta gcattggcaa cagaggaagc tatattcagg     120
aagctggaga tgaggataga tgccctagag gaagcaatat tgcatattgg aaatgaattg     180
caggctttaa aagtgagatt ggcactgtcc tgtcatgccg actatcggtg gatttgtgta     240
acaccctga aagtaaatga gacagattat gactg                                 275
```

<210> SEQ ID NO 378
<211> LENGTH: 499
<212> TYPE: DNA
<213> ORGANISM: Bos Taurus

<400> SEQUENCE: 378

```
ggaaaaccca ctgcacctcc tccacccatc cctcagcatg tggatctgca tttctgcact      60
cccggaaagc cagagcttgt ctgccaggcc caaggagctg ctgctcccca cctccacaga     120
attacattga ttgatctgtc cattatttag atttttccaga gttttagtaa ctttcggtag    180
aagtgcagga taagattctt taagatttgt tgataatgta atggattcat ggttttttt     240
ttcctttctg tttacttctg aatttaatac ttaaaaaaag agagagaaaa gggtgtagtg     300
tccacattct tgtctccttt tcttacctcc atggttcctc tagtgttcac agtggtgctg     360
```

```
atactctggg ggaggggggc gcgtgcctcc tgcgcgtgat aaaggcatgt tgggcaccgt    420
gggaacctgt ggcgacggtg ctcctctttc ccacaaacgt ttgaagttaa aatagaagc     480 taagcttccc gggattgcc                                                 499

<210> SEQ ID NO 379
<211> LENGTH: 484
<212> TYPE: DNA
<213> ORGANISM: Bos Taurus

<400> SEQUENCE: 379
tccttagatt tattatgcct gtaataagaa ataacctag caaatggttc actggatttt     60
cttctttgaa ttttcaagg tatctgcata taaaatcttc agcgggtaga tggtgacttc     120
tgaagaagaa aaggctttga taacagaaac aatttctggg tggcttggag acagtggtat    180
ttgctgagtc ttttgacctc ctaaacattg tctgttattc ttttcctgaa aagaaactga    240
atttgtctgg ttcacctgtg ttattctact gagtattgat aaactttaaa ttttaaaaa     300 ttgccttcag ttgggagaga aaggaacttt atatttctaa gagatacatt tgatagtttc    360
ttaaagcagc acacaaaaaa ggaaaaacct ttgcaaactt ttgcacattc tccccacagt    420
gcctgtaaat ctcattagta ttttcgattt gcacttattt ttgttgttag catttggaaa    480
acga                                                                 484

<210> SEQ ID NO 380
<211> LENGTH: 215
<212> TYPE: DNA
<213> ORGANISM: Bos Taurus

<400> SEQUENCE: 380
agctgctgca agactgtggt gcccggctgt gggcggcggg accacgcctc caacatctac    60
aaagtggagg gcggctgcat caccaagctg gagaccttca tccaggagca cctgaggatc    120
atcggggccg tgggcctggg cattgcctgt gtacaggtgt tcgggatgct cttcacctgc    180
tgcctgtaca agagcctgaa gctggagcac tactg                               215

<210> SEQ ID NO 381
<211> LENGTH: 444
<212> TYPE: DNA
<213> ORGANISM: Bos Taurus
<220> FEATURE:
<221> NAME/KEY: modified_base
<222> LOCATION: (115)..(116)
<223> OTHER INFORMATION: a, c, g, t, unknown, or other
<220> FEATURE:
<221> NAME/KEY: modified_base
<222> LOCATION: (202)..(203)
<223> OTHER INFORMATION: a, c, g, t, unknown, or other

<400> SEQUENCE: 381
tgctgaagcg gctcaaggag cgctcgctgg acacgctgct ggaggcggtg gagtcccgcg    60
gcggcgtgcc gggcggctgc gtgctggtgc cgcgcgccga cctccgcctg ggcgnncagc    120
ccgcgccgcc gtagctgctg ctcggacgcc tcttccgctg gcccgacctg cagcacgccg    180
tggagctcaa gcccctgtgc gnntgccaca gcttcgccgc cgccgccgac ggccccacag    240
tgtgctgcaa cccctaccac ttcagccggc tctgcgggcc agaatcaccg ccaccgccct    300
actctcggct gtctcctcgc gacgagtaca agccactgga tctatctgat tccacattgt    360
cttacactga aacagaggcc gccaactccc tcatcacagc tccgggtgaa ttctcagacg    420
ccagcatgtc tccggacgcc acca                                           444
```

<210> SEQ ID NO 382
<211> LENGTH: 347
<212> TYPE: DNA
<213> ORGANISM: Bos Taurus

<400> SEQUENCE: 382

```
tgagagactt cactttcatt tttcactttc actttcact ttcatgtatt ggagaaggaa      60
atggcaaccc actccagtat tcttgcctgg agaatcccag ggaccctgga gcctggtgag     120
ctgccgtcta tggggtcaca cagagtcgga cacaactgaa gcaacttagc agcagcggca    180
ttaagataag gccctcagct gaaacaacct gagctggctg ggaggtctgt gtactctgtc    240
gctgatgttg aagaggatt ttccttactg aactctcact gcacatccac ggtctgctgc     300
caggcttcat gactctgaat taagtccctc gtctgttgga gctcctc                  347
```

<210> SEQ ID NO 383
<211> LENGTH: 435
<212> TYPE: DNA
<213> ORGANISM: Bos Taurus
<220> FEATURE:
<221> NAME/KEY: modified_base
<222> LOCATION: (402)..(402)
<223> OTHER INFORMATION: a, c, g, t, unknown, or other

<400> SEQUENCE: 383

```
aaagaaacaa aggaaagaaa aagagaagtt tttacttcag aagcatgaaa tcgagtccaa     60
gttatttggg gatccagacg agttcccgct ggcccatctc ttgcagcctt ccggcagta    120
ttacctccaa gctgagcact ccctgccagc actcatccag ataaggcatg attgggatca   180
gtacctggtg ccatctgatc atcccaaagg cagctccatt cctcaaggat gggtccttcc   240
cccgctcccc agcaacgaca tctgggcaac cgctgttaag ctgcattagt aaaagacgtt   300
gcaggagtgt catccagcca aggctccttc cagctctgag tatcagcgat gctgccgtct   360
tgtacagtag accaaactct gtgtggcatt gccctgccca gnggtacac tttccttccg    420
tcctctgtct cagcc                                                    435
```

<210> SEQ ID NO 384
<211> LENGTH: 540
<212> TYPE: DNA
<213> ORGANISM: Bos Taurus
<220> FEATURE:
<221> NAME/KEY: modified_base
<222> LOCATION: (465)..(465)
<223> OTHER INFORMATION: a, c, g, t, unknown, or other
<220> FEATURE:
<221> NAME/KEY: modified_base
<222> LOCATION: (479)..(481)
<223> OTHER INFORMATION: a, c, g, t, unknown, or other

<400> SEQUENCE: 384

```
gagcgagtgg aagatgaatg ccagaggact tggatctcag ctaaaggaca gtattccagt     60
tactgagctg tcagcaagtg gacctttga aagtcatgat cttcttcgaa aaggtttctc    120
ttgtgtgaaa aatgaacttc tgcccagtca tcctcttgaa ttatcagaaa aaaatttcca   180
gctcaaccaa gacaagatga acttctccac actgagaaac atccagggtc ttttgcacc    240
actaaaactg cagatggaat tcaaggcagt gcagcaggtt cagcgtcttc catttcttcc   300
aagctcaaac ctttcactgg atattttgag gggtaacgat gagactattg gatttgaaga   360
tattcttaat gacccatcac aaagtgaact aatgggagaa ccgcatttga tggttgaata   420
```

```
taaacttggc ttactgtaat gccatgtgct gttcatggaa gtagngcggc tgcgtcttnn    480
ntatagttgt cttttcccta taatttgatg tgcacaacat taaaagtact aacacatgag    540

<210> SEQ ID NO 385
<211> LENGTH: 471
<212> TYPE: DNA
<213> ORGANISM: Bos Taurus

<400> SEQUENCE: 385
gggaagttta ttctcttcag ctattctacc atctgcagct ccttcctttt ctacccacc     60 caagaaaggt gcctggtgct ctctgggcct gtctgtggac actctgggt agtggagaaa    120 gtcttggctg gcctggcttc tagttactct gtttctcttg agggccacta gcgttccttc    180
tctgggcctt atagtgtgct tggattacaa atgaggacaa gaggcttgcc tgcttcagaa    240
tatattcccc atgtggcttc gggcaagtca gccctctttc tgaactttac ttttctgtca    300
agtgggcatt tggaggaat tagagctcac atttttaggg ctgtatgtga gggcaagtgg    360
ggctctggca gtgagaatgc actttagcaa atgattgagt tcccagaagt tgagaagaag    420
gagtggttaa tagttagagt ttcctagttg ccctagtgtt gaatcttgaa g             471

<210> SEQ ID NO 386
<211> LENGTH: 425
<212> TYPE: DNA
<213> ORGANISM: Bos Taurus

<400> SEQUENCE: 386
ccggcaaggc ggctttttc gcgatgccag gggcagccgc caagggctcg agctgtccg      60 agaggatcga gagtttcgtg gaggcgctga agcggggcgg cgggaggcgc agctccgagg   120
acatggcccg ggagactctg ggactgcttc gccgcatcat cacggaccac cgctggagca   180 atgcaggga gctgatggaa ctgatccgga gagaaggccg gaggatgacg gccgcgcaac   240
cctcagagac cacagtgggc aacatggtgc ggagagtgct caggatcatc cgggaggagt   300
atggcagact ccatggacgc agcgacgaga gcgatcagca ggagtctctg cacaaactct   360
tgacatccgg gggcctgagc gaggatttcc gttcccatta tgctcaactc cagtccaaca   420
tcatt                                                                425

<210> SEQ ID NO 387
<211> LENGTH: 495
<212> TYPE: DNA
<213> ORGANISM: Bos Taurus

<400> SEQUENCE: 387
gctttcggcc gcagtgccca tggagctgaa tgcttcccgg cctgccaccc tgaaaatgga    60
ttctgcgacg atgacagtgt gtgcaggtgc cagcctggct ggcagggtcc cctgtgtgac   120
cagtgcgtga ccttcccgg ctgtgtgaac ggcctctgcg tggagccatg gcagtgcatc    180
tgcaaggacg gctgggacgg acacctctgt gacctagaca tccgggcttg cacctcgacc   240
ccctgcgcca caacggcac ctgcctgaac ctcgatgacg ccagtacga gtgctcctgc    300 gcccccgggt tctcaggaaa ggattgtcag gaaatggatg ggccctgcgt ggtgaatggc   360
tcgccctgcc agcacggagg cagctgcgtg acgatgagg gccgggcccc ccacgctgtc   420
tgcctgtgcc ccctggcctt ctcgggcaac ttctgcgaga tcgtgaccaa cagctgcatc   480
cccaacccgt gcgag                                                    495
```

<210> SEQ ID NO 388
<211> LENGTH: 351
<212> TYPE: DNA
<213> ORGANISM: Bos Taurus
<220> FEATURE:
<221> NAME/KEY: modified_base
<222> LOCATION: (309)..(311)
<223> OTHER INFORMATION: a, c, g, t, unknown, or other

<400> SEQUENCE: 388

| | | | | | |
|---|---|---|---|---|---|
| agaagactca | aaagagcgtg | aagatcgcac | ctggagcagt | tgtgtgtgta | gagagcgaaa | 60
| tcagaggtga | tgtcactata | ggacccagga | cagtgatcca | ccctaaagca | cgaatcatcg | 120
| cagaagccgg | tccaatagtg | atcggcgaag | gcaacctaat | agaggagcag | gcgctcatca | 180
| taaatgctca | ccctgataat | atcactcctg | atgcagaaga | tccagaaccc | aaacctatga | 240
| tcattggcac | caataatgtg | tttgaagttg | gctgttactg | ccaagccatg | aaaataggag | 300
| ataataatnn | natcgagtca | aaagcgtatg | tgggcagaaa | tgtgatactg | a | 351

<210> SEQ ID NO 389
<211> LENGTH: 475
<212> TYPE: DNA
<213> ORGANISM: Bos Taurus

<400> SEQUENCE: 389

| | | | | | |
|---|---|---|---|---|---|
| gccacagacc | aaacctgcac | cataagccct | gactccttgc | ccataccacc | cacccatggc | 60
| ctccgaacca | ggcccagcgt | cttgctgaca | tggtaacaca | gtggaggacc | agcagatgaa | 120
| tggaaacctt | gaagcagagg | agcggcagga | ccagaggcca | gagcaggagc | tgacctggag | 180
| ctggggctac | cggcctagaa | gcgccctgga | cagggtcaag | gccatggccc | cccaccgcc | 240
| actggccccc | agcaccccac | tcctgcatgg | cgagtttggc | tcctacccag | accgcggccc | 300
| acgcttcgcc | ctcactctca | caccacaagc | cctgcacata | cagcggttgc | gcccaaagcc | 360
| cgaggcccgg | ccccggggtg | gcctggtcct | gctgaccgag | gtctcaggct | gctgcaccct | 420
| gcggagccga | agcccctgg | actcagcagc | ctacttctgc | gtctacacct | accc | 475

<210> SEQ ID NO 390
<211> LENGTH: 484
<212> TYPE: DNA
<213> ORGANISM: Bos Taurus

<400> SEQUENCE: 390

| | | | | | |
|---|---|---|---|---|---|
| gagcgggtga | gagggcagcg | atatggctcc | tccggctcct | ggtccggctt | ctggcggctc | 60
| cggggaggtg | gacgagctgt | tcgacgtgaa | gaacgccttc | tacattggca | gctaccagca | 120
| gtgcatcaac | gaggcgcagc | gggtgaagcc | atccagcccg | gagagagatg | tggagcggga | 180
| tgtcttcctg | tacagagcat | acctggccca | gaggaagtac | ggcgtggtgc | tggacgagat | 240
| caagccctcc | tccgcccegg | agctgcaggc | cgtgcgcatg | tttgctgagt | acctggccag | 300
| cgacagccgg | cgggatgcga | tcgtggccga | gctggaccga | gagatgagcc | ggagcgtgga | 360
| tgtgaccaac | accaccttcc | tgctcatggc | tgcctccatc | tatttctacg | accagaaccc | 420
| agatgcagcc | ctgcgcaccc | ttcaccaggg | ggacagcctg | gagtgcatgg | ccatgacagt | 480
| gcag | | | | | | 484

<210> SEQ ID NO 391
<211> LENGTH: 559
<212> TYPE: DNA
<213> ORGANISM: Bos Taurus

```
<400> SEQUENCE: 391 agggggcgg ccttccatcc tgggggcagc cccttggcgt cccggcgtcc tgacagatcc      60
gttccacccc cagatggatg gtctgttgag gtcactgtcg agctgtctca gaattcaggt    120
tccctcggtc tgtccaagta ctggccgcgt ggagccgatg gccgggccct cccggtggaa    180
ggatgggccg gcagccctgt cttccgacag ccccctccct ccaaagaaaa atgtcagtct    240
ttctgctccg tgtggtacta tgcagctgct cttgcagaaa tcacggattt cctgtggaat    300
aaaggtggtc cccaaagtag gcagaaagga aatatatata tattttagta atttatatag    360
atgtcagcaa ttaggcaggt caagctgtag tttcatttcc actgttaaaa taaagcttac    420
atagtttctt taaaagcctg tgttgtcctt taacagaggt tttttaaaca ctagggtgtc    480
gaatgtgaaa caccagtttt cattgttcac ctcgaaacca aaagttgtgt gttgccaaag    540
ccaaacccag gttcacgga                                                 559

<210> SEQ ID NO 392
<211> LENGTH: 509
<212> TYPE: DNA
<213> ORGANISM: Bos Taurus
<220> FEATURE:
<221> NAME/KEY: modified_base
<222> LOCATION: (421)..(422)
<223> OTHER INFORMATION: a, c, g, t, unknown, or other

<400> SEQUENCE: 392
aggcgtgcgt ggtgactctg gagaactcgg aacaggctca catcttctgg tggaaagctg     60
ctaggaacac gatgagtctg cagtggactg cagtcgccac cttcctctat gcggaggtct    120
tcgctgtgct gctgctctgc attcccttca tttctcccaa aagatggcag aagattttca    180
agtcccgcct tgtggagttg gtagtgacat atggcaacac cttctttgtg gttctcattg    240
tcatccttgt gctactggtc attgatgctg ttcgtgagat tcgaaagtat gatgatgtga    300
cagagaaggt gaacctccag aacaaccctg gggctgtgga gcacttccac atgaagcttt    360
tccgtgccca gaggaacctc tacattgctg gcttttcctt gctgctgtcc tttctgctta    420
nncgcctggt gactctcatc tcccagcagg ccacgctgtt ggcctccaac gaagccttta    480
aaaagcaggc agagagcgcc agtgatgca                                      509

<210> SEQ ID NO 393
<211> LENGTH: 489
<212> TYPE: DNA
<213> ORGANISM: Bos Taurus
<220> FEATURE:
<221> NAME/KEY: modified_base
<222> LOCATION: (49)..(49)
<223> OTHER INFORMATION: a, c, g, t, unknown, or other

<400> SEQUENCE: 393
gtcggctgtc ttccagtgcc tgggccacgg cggcggccct gggagcagng gtggagcatc     60
cccattgcgt caaagatgaa aggctggggt tggctggccc tgcttctggg agccctcttg    120
ggaactacct gggcccggag gagccaggat ctacactgtg gagcttgcag ggctctggtg    180
gatgaacttg agtgggaaat tgcccaggtg gatcccaaga agaccattca gatgggctct    240
ttccgaatca atccagatgg cagccagtca gtggtggagg tgccttatgc tcgctcagag    300
gcccacctca cagagctgct agaggaagta tgcgaccgga tgaaggagta tggggaacag    360 atcgacccctt ccacgcaccg caagaactat gtacgtgtcg tgggccgaaa tggagaatcc    420
agtgaactgg acctacaggg cattcgaatt gattcagaca tcagtggcac cctcaagttc    480
``` gcgtgtgag                                                                      489

<210> SEQ ID NO 394
<211> LENGTH: 444
<212> TYPE: DNA
<213> ORGANISM: Bos Taurus

<400> SEQUENCE: 394
ggatcggagg cgactgtgtg gccaagtggg cgcggccggt acgagctgag gggcagggtg    60
ccccgggcag gggggaggtg acccgggaca gtgcaggcgg gagaatagac ccgcggacct   120
ccgagggaaa tctgagcgtt cagaccgtga gcggatgtaa aattgaccaa gtctgggggc   180
cagaaactga tcagcgctgc ggggcttaac tacgcggccg gcgggagcgt tctccggtgg   240
cgcgggggag caggtgaaca ggtcctcact cccagctcca cgccctcacg cgctctcgcc   300
aggagccagg ttcccgccgg cagccatggg ccccggctcc agccgtgccg ccggcgtcct   360
acgcccgttg ctcggcatgc tcgccttgat ggtggccgca agcaaccgcg ccgcctccgc   420
cttcaacctg gacacccgat tcct                                          444

<210> SEQ ID NO 395
<211> LENGTH: 467
<212> TYPE: DNA
<213> ORGANISM: Bos Taurus
<220> FEATURE:
<221> NAME/KEY: modified_base
<222> LOCATION: (74)..(74)
<223> OTHER INFORMATION: a, c, g, t, unknown, or other
<220> FEATURE:
<221> NAME/KEY: modified_base
<222> LOCATION: (209)..(209)
<223> OTHER INFORMATION: a, c, g, t, unknown, or other

<400> SEQUENCE: 395
gcgccctgca ctctgtccct cactcgccgc cgacggcctg tctcgtcacc cgcacgtcgc    60
gccgctgccc cgcngaaatg cttcgattac ccgcagtcct tcgtcaaatg aggccagtgt   120
ccagggcact ggctcctcat ctcactcggg cttatgccaa agatgtaaaa ttcggtgcag   180
atgctcgagc cttaatgctt caaggtgtng accttttagc cgatgctgta gccgttacta   240
tggggccaaa gggaaggaca gtgattattg aacagagttg gggaagtccc aaagtgacaa   300
aagatggtgt gactgttgca aagtctattg atttaaaaga taaatataaa aatattggcg   360
ctaaacttgt tcaagatgtt gccaataaca caaatgaaga ggcgggggat ggcaccacta   420
ctgctactgt actggcacgc tctattgcca aggaaggctt cgagaag                467

<210> SEQ ID NO 396
<211> LENGTH: 288
<212> TYPE: DNA
<213> ORGANISM: Bos Taurus

<400> SEQUENCE: 396
agttggatgc ctacatggct cagacagatc ccgaaaccaa tgactgaagc ctgcccaccc    60
tcctggaaga ctcttgttca agtcacacat ctgtaaataa cttaggataa cagatgggaa   120
gaaagctgac tgatactgaa aggacctatc ataataggct ctggactgac ttgccaccag   180
tttgtgcatc tagtgtgttc cttttacttt ttgatactat gttgtatgaa acccttttt   240 tccctctga ctggggtttg gttttgtttt gttatttggg ggggaggg                288

<210> SEQ ID NO 397

<211> LENGTH: 576
<212> TYPE: DNA
<213> ORGANISM: Bos Taurus
<220> FEATURE:
<221> NAME/KEY: modified_base
<222> LOCATION: (546)..(546)
<223> OTHER INFORMATION: a, c, g, t, unknown, or other

<400> SEQUENCE: 397

```
cgcgagcggc tccagggtgc gaaccgccgg agcggttccc agaagatggg cctcgaagcg    60
caggccatcg gcagcacctt ccagggctcg ggctccgagg ccacgtggct gggccaggct   120
atcccgtgcg tggctgacat actgggcgag acttacaaag acgacatcgg gcggcacctg   180
gagacgctca tcagaagcta ccccgacatc aggcattgcg gcatcggcat cgcggccccc   240
tgctgcctcc ttcggtgcac taggtttccg gaacctctgc ctgggcctca gaggccgttc   300
ccatcaggct tgcttcttcc cgtctccgcc ggtctttgca cccttcaaga cccaggcacc   360
cccccaggaa cgctgggtgc cctaatgctt ccagtccgag ccccggggtc cccctcgccc   420
tagggtccag ggtgtcactg gagctgtcgc gtctacagca ggggcccgtg tgtctctgca   480
ggcgggacca cgtgcctgcc atcctggcgc tgctccgact gggccgccgt cggaaccagc   540
acttcntgcg ccacgcccag gccctgctga gggctg                             576
```

<210> SEQ ID NO 398
<211> LENGTH: 487
<212> TYPE: DNA
<213> ORGANISM: Bos Taurus

<400> SEQUENCE: 398

```
gttggagcgg ccgcatttgt tttttttttt ttttttttcc tttttttacaa aaacatgcat    60
acatacacag ggtatagtct tggggaagac acacgcactt gcacgcacac acactccctc   120
tctttcactc gcacacgcgt gcatgcacgc gcgcacacac acatacacac aaatactttc   180
cttcttggcc ccaggcctca accccagaag cctcgaagac tgtgccaggg tagcctcccc   240
ctcccccatg tcttccatcc actctcccac ccactctccc ctcagccaag ctagtcctat   300
gtagggcaag agtcagctgg ggtccaggag acccccaaaa gagagaaggc tcatggaggg   360
gggcatggtg actgagggag ccctgggggg gtcatgctgt gcttctgagg agagatgaag   420
ggtttggcac cattggatca ggaagcacgg aactccaaga gcacctgtct gctccaccag   480
ggcactg                                                             487
```

<210> SEQ ID NO 399
<211> LENGTH: 209
<212> TYPE: DNA
<213> ORGANISM: Bos Taurus

<400> SEQUENCE: 399

```
tgcggagact gctggggcac atcgttcccc tgtcctctcg gttccctgcg gccgaaaggc    60
ctgctaggat tcggggatct ggcctaggct tccgcggcgc cccgcggggg cggaatggcc   120
gcggaagaag aggacgaggt ggaatgggtg gtggagagca tcgcgggggtt cctgcggggc   180
ccggactggt ccatccccat cttggactt                                     209
```

<210> SEQ ID NO 400
<211> LENGTH: 361
<212> TYPE: DNA
<213> ORGANISM: Bos Taurus
<220> FEATURE:
<221> NAME/KEY: modified_base

```
<222> LOCATION: (191)..(193)
<223> OTHER INFORMATION: a, c, g, t, unknown, or other

<400> SEQUENCE: 400
gctggcctga tgcagtcaat cagcctcact ttccgcctgt gttgctgaag cctggtgagg      60
agtatgacca caccacttgg ttcaagtttt ctgtggccta aggaaatgta aagatatgtc     120
ctgctccaag gtcaggctgg gagccccttt aacagcctga ctctcctata aagagatgag     180
ttgaagattt nnnggctttc aaagtgatcc tgtgatttaa aatcatacaa atggtagcag     240
tcagggtagt caggtctgaa tattgatttc cttcccaaag actggctcca ggccaggtct     300
aatgaccagc tctcctctct gtgaagtgaa ggggactcaa ccaccaatgt cacccatcat     360
c                                                                    361

<210> SEQ ID NO 401
<211> LENGTH: 442
<212> TYPE: DNA
<213> ORGANISM: Bos Taurus

<400> SEQUENCE: 401
gacaccctac tatccagtgg gaatgggaaa tggacacctt gtagtttgaa acagaaccgg      60
cccagatcaa gtactgtgat gtacatatgt catcctgaat ctaagcatga aattctttca     120
gtagctgaag ttacaacttg tgaatatgaa gttgtcattt tgacaccact cttgtgcaat     180
catcctaaat atagattcag agcatctccc gtgaatgaca tattttgcca gtcactacca     240
ggatcgccgt ttaaacccct caccctgaga cagttggaac aacaggaaga aatactaagg     300
gtgcctttta ggagaaacaa agaggaagat ttgcaatcaa ctaaggaaga gagatttcca     360
gcaatccaca aacccattgc tgttggttct cagccaatgc tcactgttgg aacaacccac     420
atatccaaat tgacagatga cc                                             442

<210> SEQ ID NO 402
<211> LENGTH: 470
<212> TYPE: DNA
<213> ORGANISM: Bos Taurus
<220> FEATURE:
<221> NAME/KEY: modified_base
<222> LOCATION: (61)..(61)
<223> OTHER INFORMATION: a, c, g, t, unknown, or other
<220> FEATURE:
<221> NAME/KEY: modified_base
<222> LOCATION: (387)..(389)
<223> OTHER INFORMATION: a, c, g, t, unknown, or other

<400> SEQUENCE: 402
gcaatatggc aattttactg ggggtttaac cctacctagg atgattgctt gctggggctt      60
ngcaacaggg tccagttcac acttagcact aattaaatac tttattgaat aaatataata     120
ccaaacaaaa tgcattcaaa tgctaaaaaa aaaatcaatt ttaaaggcct ttctattcag     180
gctaatgaca aacacaataa aggcagatat gctagtttaa cataattggc tgattttata     240
cagcacttat atcttttagt ccacaagtat attattaaat gatagagaac atctaataca     300
accatttcta cagaactagg aaataaattt ctaagaaaga aagattttac agaccccatc     360
ttttataccc accccaacag tctaacnnna aagaggataa agccaatgcc tttcctcaca     420
agagctcacg actaatgtcg ctttgctatc aaaatctgta tttctgatcc                470

<210> SEQ ID NO 403
<211> LENGTH: 412
<212> TYPE: DNA
```

<213> ORGANISM: Bos Taurus

<400> SEQUENCE: 403

```
ttttttttttt ttttttttact gtttaaaaca tttatattta tatatataaa aaaattaaat      60
atatataata tatagtgtgt ttgagactaa aaatatagta cataatattt aaaaaaaagg      120
aaaatgaaaa aaggcagaat aggaaaagtg tgagggacac agatacacat tgctaaaaat      180
ctacgatggt ctgttctaac aaaaataata ttttttcct cttaattatc atcatggacc       240
catttattat tggggcttga gtggagaaaa tttaactgga gccagaaatg gtggttgtaa      300
tcccaagaag agtggggtta gaaaacgtga ccacagggag ccctggacct cattctggtg      360
tgactggagg cagccaaatc tcctgggtca ctattgctag caagattgtg tc             412
```

<210> SEQ ID NO 404
<211> LENGTH: 492
<212> TYPE: DNA
<213> ORGANISM: Bos Taurus
<220> FEATURE:
<221> NAME/KEY: modified_base
<222> LOCATION: (132)..(132)
<223> OTHER INFORMATION: a, c, g, t, unknown, or other
<220> FEATURE:
<221> NAME/KEY: modified_base
<222> LOCATION: (196)..(196)
<223> OTHER INFORMATION: a, c, g, t, unknown, or other
<220> FEATURE:
<221> NAME/KEY: modified_base
<222> LOCATION: (256)..(256)
<223> OTHER INFORMATION: a, c, g, t, unknown, or other
<220> FEATURE:
<221> NAME/KEY: modified_base
<222> LOCATION: (286)..(286)
<223> OTHER INFORMATION: a, c, g, t, unknown, or other
<220> FEATURE:
<221> NAME/KEY: modified_base
<222> LOCATION: (327)..(327)
<223> OTHER INFORMATION: a, c, g, t, unknown, or other
<220> FEATURE:
<221> NAME/KEY: modified_base
<222> LOCATION: (367)..(367)
<223> OTHER INFORMATION: a, c, g, t, unknown, or other
<220> FEATURE:
<221> NAME/KEY: modified_base
<222> LOCATION: (369)..(369)
<223> OTHER INFORMATION: a, c, g, t, unknown, or other
<220> FEATURE:
<221> NAME/KEY: modified_base
<222> LOCATION: (378)..(378)
<223> OTHER INFORMATION: a, c, g, t, unknown, or other
<220> FEATURE:
<221> NAME/KEY: modified_base
<222> LOCATION: (391)..(391)
<223> OTHER INFORMATION: a, c, g, t, unknown, or other
<220> FEATURE:
<221> NAME/KEY: modified_base
<222> LOCATION: (400)..(400)
<223> OTHER INFORMATION: a, c, g, t, unknown, or other
<220> FEATURE:
<221> NAME/KEY: modified_base
<222> LOCATION: (407)..(407)
<223> OTHER INFORMATION: a, c, g, t, unknown, or other
<220> FEATURE:
<221> NAME/KEY: modified_base
<222> LOCATION: (412)..(413)
<223> OTHER INFORMATION: a, c, g, t, unknown, or other
<220> FEATURE:
<221> NAME/KEY: modified_base
<222> LOCATION: (416)..(417)
<223> OTHER INFORMATION: a, c, g, t, unknown, or other
<220> FEATURE:
<221> NAME/KEY: modified_base
<222> LOCATION: (420)..(420)
<223> OTHER INFORMATION: a, c, g, t, unknown, or other

```
<220> FEATURE:
<221> NAME/KEY: modified_base
<222> LOCATION: (423)..(426)
<223> OTHER INFORMATION: a, c, g, t, unknown, or other
<220> FEATURE:
<221> NAME/KEY: modified_base
<222> LOCATION: (447)..(447)
<223> OTHER INFORMATION: a, c, g, t, unknown, or other
<220> FEATURE:
<221> NAME/KEY: modified_base
<222> LOCATION: (452)..(452)
<223> OTHER INFORMATION: a, c, g, t, unknown, or other
<220> FEATURE:
<221> NAME/KEY: modified_base
<222> LOCATION: (460)..(460)
<223> OTHER INFORMATION: a, c, g, t, unknown, or other
<220> FEATURE:
<221> NAME/KEY: modified_base
<222> LOCATION: (465)..(465)
<223> OTHER INFORMATION: a, c, g, t, unknown, or other

<400> SEQUENCE: 404
acgacgccaa caacgccaag gccgtggtga agaccttcca cgagacgctt aactgctgtg      60
gttccaacac gctgatgaca ctgaccacct ctgtgctcaa gaacagcctg tgtccctcca     120
gcggcaacgt cntcactaat ttgttcaagg aggactgcca tgggaagatc gacgagctct     180
tctcgggaaa actgtnccte attggcatcg cggccatcgt ggtcgctgtg atcatgatct     240
tcgagatgat cctgancatg gtgctctgct gtggcattcg gaacanctcg gtgttctgaa     300
gctgccgccg ctgaaggctc caggaanggc ctcagggaac cccgcagccc cccgaattta     360
tccaaanant tccaaaanng gccccccccac nttttttttn accccetnttt cnntgnnacn     420 ttnnnncttt tttttttaaag tttttttnttt cnaaaccccn tttanttcct ttgggggatt     480
ccttgggggt cc                                                         492

<210> SEQ ID NO 405
<211> LENGTH: 520
<212> TYPE: DNA
<213> ORGANISM: Bos Taurus
<220> FEATURE:
<221> NAME/KEY: modified_base
<222> LOCATION: (485)..(485)
<223> OTHER INFORMATION: a, c, g, t, unknown, or other

<400> SEQUENCE: 405
gcacgagggt ttgatagctc ctggagttcg tgtatcagga gatgatgtta ttataggcaa      60
aacagtcacc ttgcctgaaa atgaagatga attggagggc actaatagac gctatacaaa     120
gagagactgt agcactttc tcaggactag tgagacgggc attgtggatc aggttatggt     180
aactctcaac caagaaggat ataaattttg taaaataagg gtacgctctg ttagaattcc     240
acagattgga gacaaatttg ctagtcgaca tggtcaaaag ggtacttgtg gtattcagta     300
tagacaggag gatatgcctt tcacctgtga aggtatcacc cctgatatca tcataaatcc     360
ccatgccatc ccctctcgta tgaccattgg tcacttgatt gaatgtcttc aagggaaggt     420
```

<210> SEQ ID NO 406
<211> LENGTH: 455
<212> TYPE: DNA
<213> ORGANISM: Bos Taurus
<220> FEATURE:
<221> NAME/KEY: modified_base
<222> LOCATION: (119)..(120)
<223> OTHER INFORMATION: a, c, g, t, unknown, or other

<400> SEQUENCE: 406

```
gcacgagcgg cgacgcggag ctaccggatc ggttcgagat ggcagaggtg gaggagaccc      60
tgaagcgact ccagagccag aagggcgtgc agggaatcat cgtggtaaac acagaaggnn     120
ttcccatcaa gagcaccatg gacaatccca ccaccacaca gtacgccaac ctcatgcaca     180
acttcatctt gaaggcccgg agcaccgtgc gcgaaattga ccccagaat gacctcactt      240
tccttcgaat tcgctccaag aaaaatgaaa ttatggttgc accagataaa gactatttcc     300
tgattgtgat tcagaatcca actgaataag ctgctttctt ggctccctgc gtcattcctt     360
aatttaatgc ccctcaagaa taatagcgtt aatcatgtcc attgacgggc acgtggaagg     420
cacgttggag ccctcccagg ctggtccgtg acccg                                 455
```

<210> SEQ ID NO 407
<211> LENGTH: 546
<212> TYPE: DNA
<213> ORGANISM: Bos Taurus
<220> FEATURE:
<221> NAME/KEY: modified_base
<222> LOCATION: (516)..(516)
<223> OTHER INFORMATION: a, c, g, t, unknown, or other

<400> SEQUENCE: 407

```
gcacgaggag aagcagatga atatgagtcc acctccgggc aatgctggcc cagtgatcat      60
gtccattgag gagaagatgg aggctgatgc ccgttccatc tatgttggca atgtggacta     120
tggtgcaaca gcagaagagc tagaagcaca ctttcatggc tgtggttcag tcaaccgcgt     180
aactatactc tgtgacaaat ttagtggcca tccgaaaggg tttgcgtata tagagttctc     240
agacaaagag tcagtgagga cttccctggc cttagatgaa tccttattta gaggaagaca     300
gatcaaggtg atccctaaac gaaccaacag accaggcatc agcacaacag accgaggctt     360
cccacgagcc cgataccgtg cccgaaccac caactacaac agttcccgct ctcgattcta     420
cagtggtttt aacagcaggc cccggggtcg cgtctacagg ggccgggcta gagcgacatc     480
atggtattcc ccttactaaa aaaagtgtg tattangagg agagagagga aaaaagagg       540
aaagaa                                                                 546
```

<210> SEQ ID NO 408
<211> LENGTH: 463
<212> TYPE: DNA
<213> ORGANISM: Bos Taurus
<220> FEATURE:

-continued

```
<221> NAME/KEY: modified_base
<222> LOCATION: (449)..(449)
<223> OTHER INFORMATION: a, c, g, t, unknown, or other

<400> SEQUENCE: 408
ttttaaattg taatttgttt attggaaaac aaatatacaa cttggaatgg atttgaggca        60
aattgtgcca taagcagatt ttctttaagt ggctaaaaca aagtttaaaa agcaagttaa       120
caataaaaga aaatgtttct ggtataggac cagcagtaca aaaaaatagt gtacgagtac       180
ctggataaaa cacccgtttt gcaatagtgc aacttttaag tacatattgt tgactgtccg       240
tagtccacgc agagttacaa ctccacactt caacaacaac atgctgacag ttcctaaaga       300
aaactactca aaaaaaaaaa aaaaaggcat aacccagatg ttccctcatt tgaccaactc       360
catctaagtt taaatgtgca gaagggctta aatatatcca gagtaagcca catgcaacat       420
gttacttgat caattttcta aaataaggnt tcaggacaat gac                         463
```

GENE EXPRESSION PROFILES THAT IDENTIFY GENETICALLY ELITE CATTLE

This application claims priority from U.S. Ser. No. 60/474,577, filed May 30, 2003.

BACKGROUND OF DISCLOSURE

Animal improvement has been achieved through selective breeding since the beginning of animal agriculture. In recent times, animal breeding employs a quantitative genetics approach, where improvement is based on evaluation of production records of progeny and relatives, e.g. records of milk production and carcass quality, followed by breeding pedigreed animals whose phenotypes are closest to a desired phenotype. Most improvement in dairy cattle, for example, is made through use of sire lines selected in this manner.

Marker-assisted selection using genetic markers that identify chromosomal regions containing genes (genetic loci) that affect quantitative traits (QTL) is an approach that is currently being developed by the animal breeding industry, e.g. for cattle traits. For example, a polymorphism in the somatotropin gene causing a change at amino acid position 126 provides a marker that can be correlated to the trait of superior milk production, but does not necessarily identify the polymorphism as the cause of the trait. The actual cause of the increased milk production may be due to some other closely linked (i.e. in close proximity) genetic factor or gene in the cattle genome, and not to the existence of the somatotropin polymorphism. Consequently, these statistics-based animal breeding methods are generally slow, expensive and inaccurate because the genes themselves underlying the traits of interest have not been identified, so selection does not achieve completely successful or predictable outcomes.

Further, complex gene action and interactions among genes serve to complicate objectives of traditional breeding programs. Selection based purely on phenotypic characteristics does not efficiently take into account such genetic variability, and is therefore not optimal.

For example, these traditional approaches are used for the purpose of selecting and breeding dairy cows capable of superior milk production. Although such programs have improved milk production, there are disadvantages because of the significant costs and time involved before the success of the program can be determined. For example, a traditional breeding program requires the breeding of many cows with a particular bull and subsequent analysis of the milk production of the female-progeny of these cows to determine whether the bull is of superior genetic value. A particularly successful breeding family of cattle is the Holstein line derived from the bull Carlin-M Ivanhoe Bell.

Female progeny must be raised, become pregnant, allowed to give birth and milked for a minimum length of time before milk production capabilities can be analyzed. Although this type of improvement program has improved milk production, there are disadvantages because of the significant costs and time involved before the success of the program can be determined. A breeding program relying on traditional techniques and selection criteria typically requires the investment of 4 or more years in a group of cattle before significant analysis of the program can be undertaken. It would, therefore, be advantageous if additional methods or criteria were available that were quicker and cheaper to determine whether a bull, heifer or cow should be included in a breeding program designed for superior milk production.

Boosting the level of growth hormones via introduction of additional hormones can improve cattle performance. An example is the use of bovine growth hormone or somatotropin. This has been made possible by the cloning and isolation of genes that express such proteins and then adding the resulting products of these commercially produced proteins to animals via feeds, injections, drugs, and the like. This method of boosting production of essential proteins however is inherently limited by the underlying genetics of the animal and because the effects are not heritable, does not offer anything in the way of selection of genetically superior animals for optimum genetic capabilities.

Furthermore, qualified administration of multiple injections of growth hormone keep costs high, and sick animals cannot be given growth hormone injections. There is also a concern that animals that are treated with growth hormone are more susceptible to mastitis. In addition, public acceptance of growth hormone is still uncertain. The results of bovine growth hormone injection include an increase in overall milk production, with no change in milk composition. This is a significant disadvantage because a dairy producer is paid on the basis of three milk characteristics, total volume of milk, total pounds of fat in the milk, and total pounds of protein in the milk, thus quality is as important as quantity. Producers may be paid more for protein than fat. Thus it can be seen that there is a continuing need for means of efficiently selecting and breeding cattle for improved milk production without concomitant decrease in milk composition, particularly protein content. In general, better methods of identifying animals with desirable predicted transmitting ability (PTA) for desirable phenotypes, such as high milk production and yield of protein and fat, are needed for long term benefits.

Microarrays are being developed for many research applications in animals, e.g. to study responses of genes to external stimuli. Microarray technology is revolutionizing biology by permitting the simultaneous analysis of transcript levels of thousands of genes in different physiological states of an organism, tissue or cell. Construction of microarrays is most efficient when information is utilized from annotated genome or EST sequencing projects. Evaluation of transcript levels using microarray technology has led to new insights into animal development, cancer, infectious diseases and aging. Microarrays have recently been produced for studying the functions of cattle genes and gene expression changes in different physiological states, although results to date have been quite limited.

In summary, a need exists in the art for a method of genetically evaluating animals such as ungulate (hoofed) mammals to enable breeders to more accurately select those animals which not only phenotypically express desirable traits, but those which express favorable underlying genetic criteria leading to the desired phenotypes. Therefore, it would be advantageous to find ways to more accurately predict quantitative traits from genomic information.

SUMMARY OF DISCLOSURE

Methods and compositions to identify and select genetically elite animals, e.g. ungulate (hoofed) mammals, with a desired phenotype for breeding, in particular, a quantitative trait such as high milk production, carcass quality and resistance to disease, include creating gene expression profiles from individual animals, developing a Gene Expression Index for phenomic selection by comparing gene expression profiles of animals whose phenotypes are at the extreme ends of a continuous distribution of the phenotype, and using the index to identify and select elite animals for breeding to improve economically important traits.

A method of making a gene expression index for phenomic selection of elite ungulate mammals, e.g. cattle, sheep, goats, horses, and deer, includes the steps of defining and selecting a phenotype that has multiple levels, for example, quantitative complex traits, especially those that are economically important, such as milk production levels, and other traits such as high protein values, carcass quality, fertility and resistance to disease. A plurality of genes is selected for which gene expression can be determined to create gene expression profiles of individual animals. In an embodiment, the first group of animals differs from the second group of animals in predicted transmitting ability (PTA) for the desired phenotype, e.g. high milk production, fertility, disease, resistance. cDNA is prepared from RNA isolated from biological samples such as blood or liver from a first group of animals that has a first level of a defined phenotype (e.g., high genetic potential for milk production or fertility). The cDNAs are hybridized to the plurality of nucleic acids representing the genes. Hybridization can take place on a microarray which may be designated a DNA microchip or biochip. cDNAs from RNA isolated from biological samples from a second group of animals that has a second level of the phenotype (such as low genetic potential for milk production or fertility), are also hybridized to the plurality of nucleic acids, either on the same or a different array. The expression profiles of the two groups of animals are compared statistically and the genes that differ significantly between the two groups form the Gene Expression Index (FIG. 1) This index can be used for phenomic selection, a method that involves comparing gene expression profiles of candidate animals for animal breeding to the Gene Expression Index or to a Reference Expression Profile created from an optimal subset of genes in the Gene Expression Index.

The method of creating a Gene Expression Index that can be used to identify genetically elite ungulate mammals then includes the steps of:
  (a) comparing expression levels of genes in tissues (e.g., blood) of ungulate mammals classified according to multiple levels of a selected phenotype (e.g. genetic potential for milk production);
  (b) determining a set of genes that differ significantly in expression levels at different levels of the selected phenotype; and
  (c) using statistical criteria, creating a list of genes that are differentially expressed (Gene Expression Index) in animals classified according to the different level(s) of the phenotype (e.g., high and low genetic potential for milk production).

A Gene Expression Index that includes genes whose GenBank accession numbers are listed in Table I, Table II, Table III or a combination or a subset thereof is disclosed. In the Gene Expression Index, an optimal subset to create a Reference Expression Profile includes 1 to about 100 nucleic acid sequences, whose GenBank accession numbers are selected from Table I, Table II, or Table III.

A method of determining whether an ungulate mammal (candidate animal) is genetically elite for a phenotype/trait of interest includes the steps of:
  (a) determining a gene expression profile for the animal using RNA collected from one or more tissues;
  (b) comparing the expression profile with the gene expression index or a Reference Expression Profile for that tissue(s); and
  (c) identifying the animal as an elite animal if the gene expression profile is similar to expression levels of genes the Gene Expression Index.

For example, a method for predicting milk production or genetic potential for milk production in a cow (candidate animal) prior to her first lactation includes the steps of:
  (a) obtaining a gene expression profile of the candidate cow as a heifer; and
  (b) comparing the profile to a Gene Expression Index created from heifers or cows with known milk production levels, or known genetic potential for milk production; and
  (c) predicting milk production or genetic potential for milk production of the candidate animal by ranking similarity to the Gene Expression Index.

For example, a method for phenomic selection of a breeding bull predicted to transmit high genetic potential for milk production to his offspring includes the steps of:
  (a) selecting an optimal subset of nucleic acids from the Gene Expression Index representing genes whose sequences are designated by GenBank accession numbers listed in TABLE I, II, and III, to create a Reference Expression Profile, wherein the Reference Expression Profile accounts for a significant fraction of the variation in the phenotype of interest;
  (b) creating a gene expression profile of the subset of nucleic acids for the the candidate bull;
  (c) designating the candidate bull as genetically elite if the gene expression profile is similar to the Reference Expression Profile for the phenotype of interest, e.g., genetic potential for milk production (measured as predicted transmitting ability, or PTA).
  (d) selecting a bull for a breeding program if the Candidate Expression Profile shows has a high similarity to the Reference Expression Profile (FIG. 2).

A microarray that includes nucleic acids derived from cattle RNA, whose nucleic acid sequences are designated by GenBank accession numbers listed in TABLES I or II or III or a combination thereof is within the scope of this disclosure. Any other suitable gene expression detection methods such as PCR and Northern blots can also be used to test the expression levels of genes in the Gene Expression Index and is in the scope of the disclosure.

An optimal subset of nucleic acids whose expression levels in blood leukocytes are useful for predicting genetic potential for milk yield includes genes encoding for a factor upregulated during skeletal muscle growth (SEQ ID NO: 1), Sjogren syndrome antigen B (SEQ ID NO: 2), ribosomal protein L22 (SEQ ID NO: 4), pre-mRNA branch site protein p14 (SEQ ID NO: 5) and other genes represented by for example, SEQ ID NOS: 1-10 in TABLE I. New functions related to lactation are provided for these genes by this disclosure.

An optimal subset of nucleic acids whose expression levels in liver are useful for predicting genetic potential for milk yield includes genes encoding for histone 1 (SEQ ID NO: 359), epithelial v-like antigen 1 (SEQ ID NO: 360), poly (A) binding protein (SEQ ID NO: 361), and any other genes represented by SEQ ID NOS: 358-367 in TABLE II.

An optimal subset of nucleic acids whose expression levels in both liver and blood are useful for predicting genetic potential (TABLE III) includes genes encoding for a core promoter element binding protein (SEQ. ID. NO: 368), a low density lipo protein receptor-related protein (SEQ. ID. NO: 369), a ubiquitin conjugating enzyme E2L3 (SEQ. ID. NO: 370) and any other genes designated by SEQ ID NOS: 371-408.

A kit for detecting gene expression profile differences includes in discrete compartments:
  (a) at least one microchip comprising nucleic acids whose sequences are designated by genes having GenBank accession numbers listed in TABLE I, II or III;

(b) reagents to perform a microarray analysis; and optionally (c) a computer program that can compare expression profiles and identify genetically elite ungulate mammals for breeding or for production traits Kits may also include a subset of oligonucleotides, whose sequences represent a part of the sequences designated by GenBank accession numbers listed in TABLE I, II or III.

Reagents to perform quantitative PCR and other methods of detecting differences in Gene expression profiles, are also suitable in kits. A kit that utilizes any suitable method for detecting gene expression is within the scope of this disclosure. Such methods also include conventional reverse transcriptase (RT)-PCR, and Northern hybridizations.

The Gene Expression Index is created by statistical comparison of gene expression patterns in tissues collected from animals differing in a particular phenotype or trait, e.g., genetic potential for milk production (FIG. 1). A summary of the approach is given here, with details given in the Detailed Description of the Disclosure. Microarray gene expression data are processed for spot quality, and intensity values are normalized. Gene expression in the tissue (e.g. liver or blood) is measured relative to a standard reference control (pool of RNA from different sources) for all samples and all genes. The gene expression intensity values relative to the intensity values in the standard reference (the gene expression ratios) are calculated for all samples for all genes on the array. Ratios are compared for animals in each group, e.g., high and low for a trait, using ANOVA. The relative difference in gene expression between the two groups of samples is measured as a "ratio-of-ratios" (see Definitions) for each gene. The probabilities of the differences being due to chance are corrected for the number of comparisons made using the false discovery rate (FDR). The genes with the highest significance value falling below a certain FDR threshold are considered "significant" and used to create the Gene Expression Index (FIG. 1). A Gene Expression Index can be created for more than one trait, or a weighted index can be created for multiple traits simultaneously. More than two groups of animals may be compared. An optimal subset of genes can then be selected to streamline the testing of candidate animals for breeding or retention in a herd (FIG. 2). The optimal subset is created by selecting those genes with the highest significance for predicting the trait, i.e., those genes whose expression level account for a large amount of phenotypic variation in the trait among the animals tested. A gene expression pattern created using an optimal subset of genes is called the Reference Expression Profile (FIG. 2).

A method of determining whether an animal is a genetically elite ungulate mammal, suitable for phenomic selection of any trait, includes the steps of determining a candidate expression profile (see Definitions) for a candidate ungulate mammal and comparing the candidate expression profile to a Reference Expression Profile. The animal is designated an elite animal for purposes of breeding or production, if its gene expression profile is similar to the Reference Expression Profile. Similarity is determined by comparing the expression profile values using statistical methods. Phenomic selection may be for high milk production or other economically important traits, such as health traits, fertility, or carcass quality.

In an embodiment, a method for selecting a genetically elite animal predicted to have high genetic potential for milk production, includes the steps of selecting an optimal subset of nucleic acids from TABLE I-III, to create a Reference Expression Profile. Genes included are those encoding for a factor upregulated during skeletal muscle growth (SEQ ID NO: 1), Sjogren syndrome antigen B (SEQ ID NO: 2), ribosomal protein L22 (SEQ ID NO: 4), pre-mRNA branch site protein p14 (SEQ ID NO: 5). The Reference Expression Profile accounts for the greatest amount of variation in the phenotype or a predetermined amount of variation in the phenotype, for example in TABLE I, genetic potential for milk production. cDNA from RNA obtained from a biological sample from the animal is used to create a gene expression profile. For a specific phenotype, a trait for which gene expression profiles are derived from RNA from various tissues, the predictive set of genes for the phenotype may overlap among the tissues or be unique. For example, for genetic potential for milk production in cattle, TABLE I shows predictive genes identified from leukocytes, TABLE II shows predictive genes from liver. TABLE III shows predictive genes from blood and liver. The expression levels ranked by significant differences between high and low genetic potential for milk production (or PTA), may not be identical when RNA is derived from leukocytes versus liver.

The GenBank accession numbers of cattle DNA sequences whose expression profiles are predictive of cattle milk production, are listed as genes in TABLE I and include both unannotated e.g. BF040830 (SEQ ID NO: 139), BF041863 (SEQ ID NO: 127) and known genes e.g. BF040826 (SEQ ID NO: 10), BM366099 (SEQ ID NO: 22) in cattle and in other species. That is, the list in TABLE I includes those genes whose expression level in peripheral blood leukocytes is different between the high and low PTA groups of cattle at a significance level of less than or equal to an FDR adjusted p-value of 0.29 (see Materials and Methods). Significance level cut-offs vary, and that will alter the number of genes used for selection.

Nucleic acids whose GenBank accession numbers of cattle DNA are listed as genes in TABLE II, whose expression profiles in liver are predictive of genetic potential for milk production include both unannotated e.g. SEQ ID NO: 358 (AW464111) and known e.g. SEQ ID NO: 359 (AW464166) genes. The unannotated genes are of unknown specific function, but their utility is that their gene expression profile is predictive of milk production. "Gene" used herein refers to sequences which are derived from sequencing cattle cDNAs and/or ESTs. Gene quantity was determined by comparing sequences with the human and mouse UniGene databases and other GenBank resources.

A Gene Expression Index may include nucleic acids selected from the group consisting of genes in TABLE I, genes in TABLE II, genes in TABLE III, or a unique combination or a subset thereof.

A method of increasing milk production in cattle also includes selecting a gene or genes from TABLE I or TABLE II or TABLE III and modulating expression of the gene in the target cow, heifer or bull to increase milk production. Modulation indicates the variation in the level of the protein in the cattle or the level of gene expression of other genes that affect lactation as a result of transgenic and non-transgenic manipulation, e.g. somatotropin injection.

A gene expression profile-based phenotypic selection is not limited by the number of phenotypic markers, such as enzyme levels or blood groups. Gene expression data can be correlated with the expression of complex phenotypes. Also, gene expression profiling can be applied to any sex (e.g. identify elite bulls for milk production), life stage, including embryos, and targeted at specific tissues that determine particular phenotypes. In addition, correlations between expression profiles and phenotypes selected provide insights into metabolic and signaling pathways that affect complex traits.

Gene expression profile-based selection is useful to lower the high cost of progeny testing currently used to prove a sire's genetic merit, because young sires that are determined by genetic testing to have undesirable Gene Expression Index values would not have to be progeny tested, thus saving the seedstock industry millions of dollars and increasing the rate of genetic improvement for targeted traits. In addition to identification of genetically elite bulls, the gene expression profile of individual females can identify those animals that will have the highest lactation levels and also those that can serve as bull dams for the production of the next generation of elite dairy cows.

Thus, methods of the present disclosure for identifying genetically elite animals based on gene expression profiles using any tissue as a source of RNA greatly reduces the time and expense for identifying breeding animals and improves the accuracy of selection.

DEFINITIONS

Array, microarray: molecules connected to a matrix or support in a specific arrangement relative to each other.

Accession numbers: relate to sequences that represent cattle genes in GenBank. The UniGene database provides unique identification numbers of the corresponding genes in human or mouse databases. Cattle gene sequences are aligned to human or mouse sequences to determine "gene" identification and or similarity.

Biochip: also known as a chip, DNA chip, DNA microarray, DNA array, peptide chip or peptide array; includes array of biological molecules such as DNA fragments, peptides, proteins, lipids, and tissues connected to a matrix.

Biological sample: a biological material obtained from blood, liver, skin, tissues, saliva, tears, bodily fluids or bodily secretions.

Candidate animal: an animal that is screened for a desired molecular phenotype, e.g. expression profile, to determine if it is a genetically elite animal.

Candidate Expression Profile: an expression profile obtained from a biological sample of a candidate animal whose phenotype is to be predicted.

cDNA expression array: also known as cDNA array or gene expression array or gene expression microarray. The ordered alignment of different complementary DNAs (cDNAs), or fragments of cDNAs, or oligonucleotides immobilized on a support (e.g. a nylon-based membrane or a glass slide). Such arrays may contain tens of thousands of different cDNAs on a small space (e.g. 1×1 cm, or less), and are used to determine differential gene expression patterns. cDNA arrays can be produced by different techniques. For example, one method uses PCR amplified partial sequences of cDNAs.

Elite: an animal with desired or improved characteristics (traits).

Expression profile (gene expression profile): a gene expression dataset generated by simultaneous detection in a sample from an animal of expression of a plurality of genes, whose genomic DNA, cDNA or oligonucleotide fragments thereof are determined by methods including microarrays wherein the DNA is immobilized onto a matrix or support, to which labeled cDNA from a target sample(s) are hybridized.

Expression ratio: ratio of expression value of a gene from at least two biological sources or at least two different time points.

False Discovery Rate (FDR): an approach to statistically analyze false positives in multiple samples. Instead of controlling the chance of any false positives, FDR controls the expected percent of false predictions in a set of predictions. A FDR threshold is determined from the observed p-value distribution.

Gene: a specific sequence of nucleic acids that generally includes introns and exons and regulatory regions. A "gene" referred to herein also includes ESTs cDNAs or fragments thereof, which include exons.

Gene index: (Gene Expression Index): a selective list of genes based on their differential expression profiles that correlate to the genetic potential for a desired phenotype. A Gene Expression Index represents expression values arranged or ranked using a specific classifying scheme such as hierarchical clustering or p-value (probability level) sorting.

Genotype: the complete genetic complement at a locus or of an organism.

High PTA ratio: normalized fluorescence intensity level of a singe DNA sequence on the microarray for an individual or group of high genetic potential animals divided by the normalized fluorescence intensity value for the same DNA sequence expressed in the reference standard control. Fluorescence intensity is directly related to the level of sequence-specific mRNA in a cell, cells or tissues (other measures of relative expression are within the scope of the disclosure).

Hybridization: the formation of duplex molecules from complementary single strands (e.g., DNA-DNA, DNA-RNA, RNA-RNA). A single stranded nucleic acid molecule is generally labeled, e.g. with a detectable dye (radioactive or fluorescent) and used as a probe that may anneal to molecules with similar sequences that are single stranded. Conditions are varied to detect degrees of similarity, i.e. the more stringent the conditions, the greater the similarity needed for hybridization to occur.

Low PTA ratio: normalized gene expression ratio from a biological source with low predicted transmitting ability for a particular phenotype. (See also, High PTA Ratio.)

Marker: any specific DNA segment whose base sequence is polymorphic and is used as a diagnostic tool to identify a particular phenotype or a method of detecting the presence of a linked gene. Markers used herein refer to molecular markers and markers determined by expression profile analysis.

Matrix: a support such as glass slide, silicon, gold slide, gel pad, nylon membrane or other similar structures on which an array or microarray of molecules is formed. A matrix or support may contain functional groups to attach biomolecules.

Modulating: refers to a controlled increase or decrease of transcript or protein levels of any specific gene through genetic or non-genetic methods.

Nucleic acids: DNA, cDNA, mRNA and any other modified nucleic acids. Nucleic acids also include single stranded DNA, double stranded DNA, RNA-DNA hybrids, complements and reverse complements.

Optimal subset: a selective list of genes whose expression profiles account for the greatest amount of variation in a desired phenotype, or a predetermined amount of variation. An optimal subset may include as few as one gene.

P-value: represents the probability that a deviation as great as, or greater than, that obtained from the experiment will occur by chance alone. In other words, p-value is the probability of observing a test statistic that is as extreme or more extreme than currently observed, assuming that the null hypothesis ($H_O$) is true.

Phenomic selection: selection of animals for breeding or production on the basis of one or more phenotypic markers that directly contribute through molecular processes to a particular phenotype. Phenotypic markers can include profiles of RNA transcripts (transcriptome), protein profile (proteome) and metabolites (metabolome).

Phenotype: the observable structural and functional properties of an organism which results from interactions of both genotype and environment. The phenotype can be exhibited in multiple levels or degrees. The term phenotype also includes improved phenotype, desired phenotype, favorable phenotype, preferred phenotype and target phenotype.

Pleiotropy: multiple effects of a gene which can result in distinct, apparently unrelated phenotypes.

Polynucleotide: any single stranded or double stranded molecule with a sequence of more than ten nucleic acids. The cDNA spots on a microarray are all double stranded, but are denatured during the process of hybridization.

Predictive genes: a subset of genes from a gene index selected to account for a predetermined amount of variation in a phenotype, based on gene expression profiles.

Printing: a process by which a biomolecule such as DNA, RNA or peptides are immobilized or attached to a matrix.

Proteome: the complete set of proteins in a cell at a given time.

PTA: predicted transmitting ability of an animal in reference to phenotypic traits; a measure of genetic merit.

Quantitative trait locus (QTL): a genomic region controlling expression of a quantitative trait, the locus may have several alleles; or two or more separate genetic loci that contribute cooperatively to the establishment of a specific phenotype or trait.

Ratio-of-ratios: ratio of normalized gene expression ratio from a biological source with high predicted transmitting ability for a particular phenotype to the normalized gene expression ratio from a biological source with low predicted transmitting ability for the particular phenotype. The ratio-of-ratios gives the absolute difference in expression for a particular gene among the two sources or groups.

Reference Expression Profile: a gene expression profile obtained from an optimal subset of predictive genes from a Gene Expression Index. Variation in expression of genes in the Reference Expression Profile accounts for all, some or a predetermined amount of variation of a trait.

Similar: a measure is similar if the correlation between it and another measure is statistically significant.

Statistical significance: statistical methods allow an estimate to be made of the probability of the observed degree of association between variables, and from this statistical significance can be expressed, commonly in terms of the p value.

Target animal (candidate animal): an animal that is potentially an elite animal.

Traits: phenotypes, e.g., genetic potential for milk production.

Transcriptome: an entire set of mRNAs and non-coding RNAs expressed by a given cell, tissue or organism.

Weighted Gene Expression Index: a list of genes organized according to a weighting factor. A weighted index can be used for phenomic selection on the basis of its ability to predict a phenotype(s). One method to create a weighted index is to multiply the p-value for a given gene (in the comparison of two phenotype classes) by the percentage of correct predictions when the gene is used to identify high or low PTA animals at the population level.

DETAILED DESCRIPTION OF THE DISCLOSURE

Figure 1:
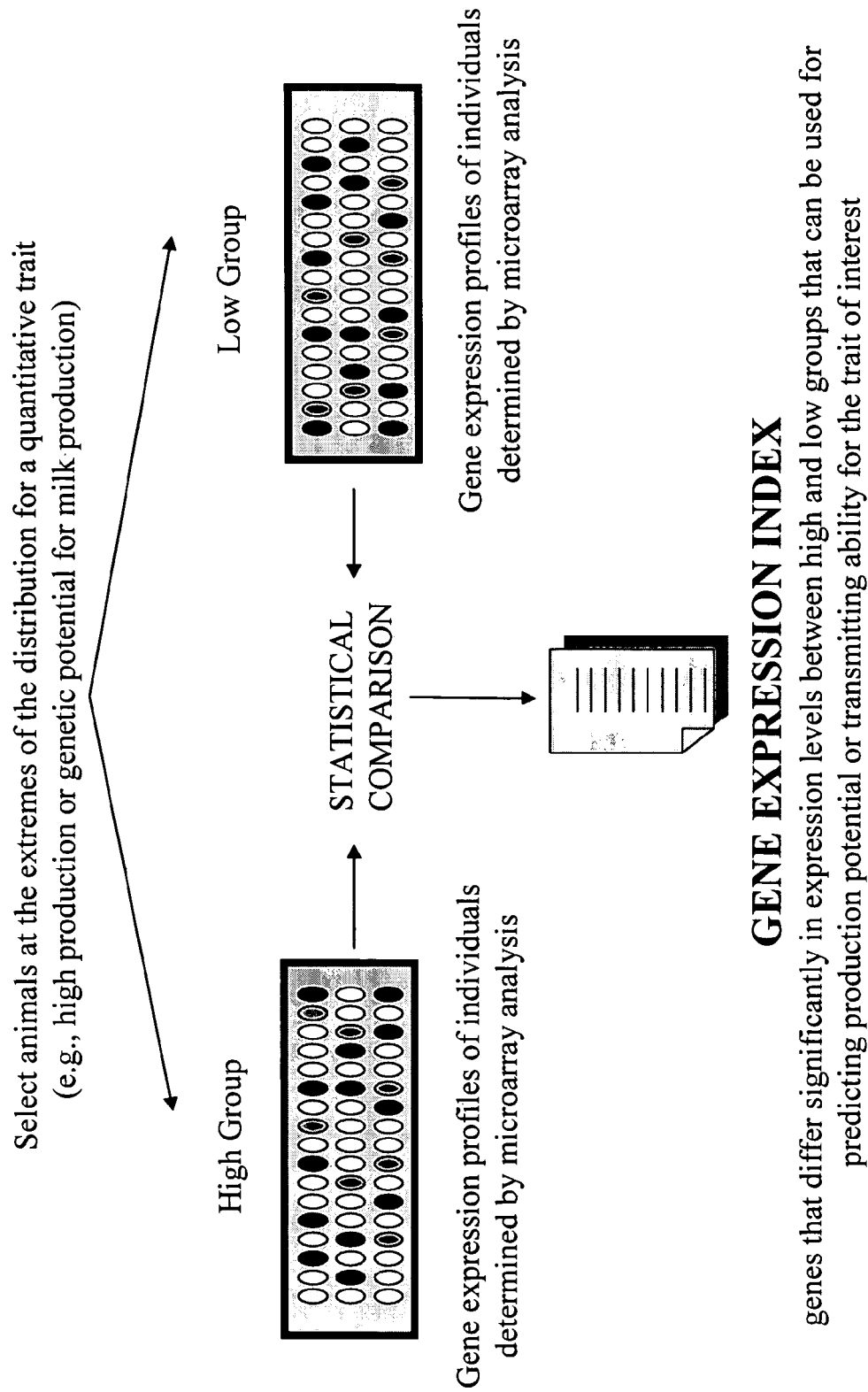
FIG. 1 shows a schematic illustration of creation of a Gene Expression Index for phenomic selection of an ungulate mammal.

Methods of the present disclosure ("phenomic selection") will enhance or replace progeny testing, significantly increasing the rate and efficiency of genetic improvement in animals. Multiple phenotypic traits may also simultaneously be improved by these methods. Quantitative traits may be controlled either by the action of a major gene, or by many genes interacting with environmental factors. Construction of a Gene Expression Index for a specific trait permits use of that index for selective breeding. The gene expression profile for a particular trait may be linked to a single gene with a major effect or associated with a number of genes with additive effects. Premises of the disclosure are that 1) the genes whose expression levels are under artificial selection include genes that directly affect the quantitative trait of interest, and/or 2) genes that might not physically be associated with a mapped quantitative trait locus (QTL; trans effects) can be used as a reliable predictor of the trait. In other words, using "polymorphism" in gene expression levels as a correlated indicator(s), alleles that control a particular trait, despite being present at a chromosomally distinct locus or loci, will also be selected. This represents an effective approach for "marker assisted selection," because of the possible roles of pleiotropy and epistasis in determining complex phenotypes. For example, an important predictor of a complex phenotype may be the expression level of a transcription factor that is regulated by five polymorphic QTL. Monitoring the expression level of the transcription factor directly controls for many favorable alleles at the QTL level. Because individual animals will have different expression patterns for the QTL identified by expression profiling, the Gene Expression Index can be used to identify genetically elite individuals. Using this scheme, the animals with the maximum number of QTL positively affecting a trait and the minimum number of QTL negatively affecting the trait would be selected for breeding. Values might range from +100, which would represent 100 percent positively associated expression levels of all genes positively affecting a trait, to −100, which would represent 100 percent negatively associated expression levels of all genes negatively affecting a trait. This is an example of a weighted index. Selection can be performed on either sex using indices that are common to the sexes or be sex-specific. Selection can be performed at any stage of development, depending on the trait. Even embryos may be tested.

Gene expression patterns that are associated with phenotypic variation in a quantitative trait may be part of upstream or downstream regulatory pathways and are thus potential candidates for drug targets or genetic modification. Expression patterns may vary both quantitatively or qualitatively to have value in predicting a specific phenotype.

The present methods can reduce the number of animals needed to achieve a production goal and reduce breeding costs. Gene expression profiles from young male calves can be tested before entry into sire evaluation programs. Young bulls whose expression profiles most closely match the "ideal" phenotype predicted by the gene index are advanced in breeding programs while those that have lower overall index values are culled from the program. The bulls' expression index value allows ranking of that bull for genetic merit, thus permitting prediction of milk yield (and other traits) among his daughters. For young female calves (heifers) the expression profile is used to predict milk production (and other traits) during the animal's individual future lactation or lifetime. Heifers that have a low expression index value are then culled from the herd. Animals may be tested in any life stage assuming tissues are available, but the index used may need to be matched to each specific life stage.

The Gene Expression Index provides information as a supplement to other traditional tools for selection. However, in cases of equal pedigree merit, the Gene Expression Index or Reference Expression Profile will help distinguish among the lines and thus lead to substantial improvements at much lower cost, and much more quickly. It is contemplated gene expression profiles could replace current statistical methods for animal breeding.

Extension of comparisons to more than two phenotypic levels is straightforward under the ANOVA approach or any other equivalent statistical method. Phenotypes for which these methods are useful are the basis of three milk characteristics, total volume of milk, total pounds and percentage of fat in the milk, and total pounds and percentage of protein in the milk. Thus, quality is as important as quantity. Producers may be paid more for protein than fat.

A suitable starting number of genes for an expression index is 10-300. The more stringent the p-value [or false discovery rate (FDR) adjusted p-value] used as a cut-off, the less number of genes that are included in the index. Sufficient number of genes need to be included to account for a large proportion of variation in each phenotype. The various factors that determine the number of genes included in the Gene Expression Index for trait analysis may depend on the technical and practical feasibility (e.g. handling of multiple genes in an array or multiple samples in a quantitative PCR), the robustness of the statistical significance of the expression data for a subset of genes that correlates with a particular trait, and nature of the trait (e.g., monogenic vs polygenic).

A method of making a Gene Expression Index for phenomic selection of elite animals such as ungulates, in an embodiment, cattle, includes the following steps: First, a phenotype to be improved is selected, such as high milk production, high milk protein levels, high milk fat, fertility, disease resistance, carcass quality. PTAs are available for these traits in many breeds of cattle and pigs. Next, a plurality of nucleic acids with measurable expression levels is selected, and hybridized to cDNAs created from RNAs of biological samples from a first group of animals expressing the phenotype at a first level, and compared to a reference standard or to other samples, directly (e.g., in a loop design). The same is done for a second group of animals expressing the phenotype at a second level. Expression ratios are then calculated for nucleic acids from each group. It is then determined whether there is a statistically significant difference between the expression ratios of the two groups (FIG. 1). A Gene Expression Index is created in which the nucleic acids (genes) are ranked according to their statistical significance. Multiple groups and multiple levels are within the scope of the disclosure. The methods are extendable to more than two groups using ANOVA.

Figure 2:
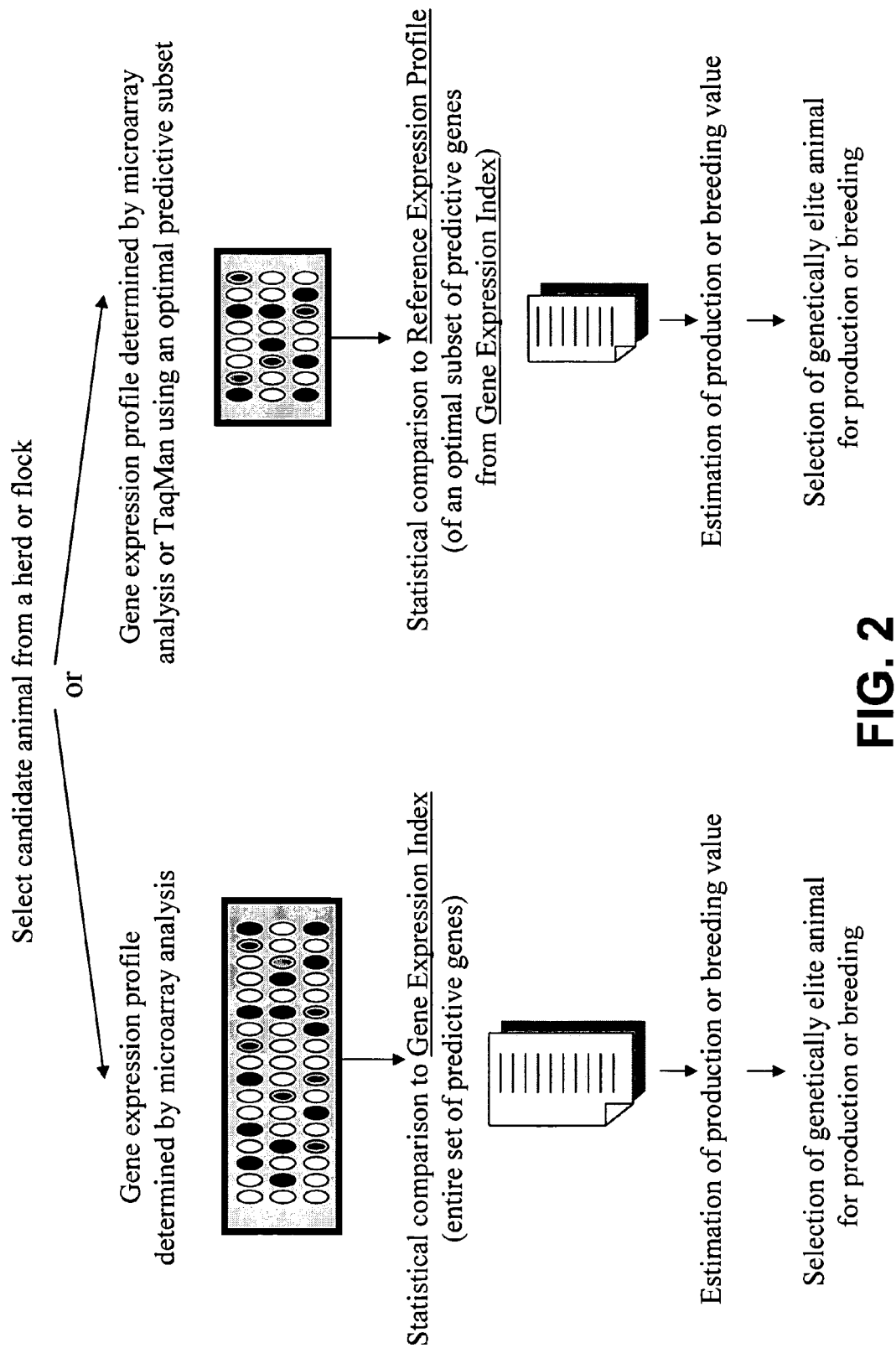
FIG. 2 shows a schematic illustration of phenomic selection of genetically elite ungulate mammals for production or breeding using a Gene Expression Index or Reference Expression Profile.

An optimal subset of nucleic acids from a Gene Expression Index is used to create a Reference Expression Profile that accounts for the greatest amount of variation in the phenotype, or for a predetermined amount of variation (FIG. 2). The Reference Expression Profile is compared to a gene expression profile created from a biological sample, such as blood or liver tissue, from a candidate (target) animal. Comparison is made by microarrays or relatively inexpensive assays such as quantitative real-time RT (reverse transcriptase) PCR, e.g. TaqMan®. An animal is selected for breeding if the two expression profiles are correlated.

A cDNA library was created using mRNA from bovine placenta. Approximately 17,000 clones were partially sequenced and are termed expressed sequence tags (ESTs). Using standard normalization and computational techniques, a collection of 12,620 ESTs was selected after eliminating redundant clones. Further refinement was performed by eliminating repeats, clones with bad sequence reads, clones having sequence length of less than 300 bp, and multiple ESTs representing the same gene by BLAST analysis against the human UniGene databases. This reduced the collection to 7,653 ESTs representing approximately 6,000 unique genes. These 7,653 ESTs, represent ~6,000 genes were printed in duplicate on a glass slide (microarray). The microarray was used in hybridization analysis of blood and liver RNA samples from cattle. Based on the microarray results from cattle blood samples, genes whose expression levels were significantly different among heifers grouped by PTA for milk production were included in TABLE I. Similarly, based on the microarray results from liver samples, genes whose expression levels were significantly different among the same heifers grouped by PTA for milk production were included in TABLE II. Based on the microarray results from liver and blood samples, genes whose expression levels were significantly different among the same heifers grouped by PTA for milk production were included in TABLE III. Thus, TABLES I-III do not contain all the genes present on the microarray. The tables contain genes whose expression levels have predictive values for the trait of interest.

An embodiment of the disclosure is a method for selecting genetically elite cattle predicted to have a phenotype of interest. This is accomplished by selecting an optimal subset of nucleic acids from TABLE I or TABLE II or TABLE III (a Reference Expression Profile) and comparing against a gene expression profile created from a biological sample of a candidate animal using a microarray, or quantitative PCR or another method for determining mRNA levels in a cell, tissue or organ. Afterward, the candidate cow or bull is designated as elite if the two expression profiles are statistically similar. The degree of similarity to the expression pattern obtained with Reference Expression Profile provides a relative measure of genetic merit of the candidate animal.

An embodiment of the disclosure is increasing milk production in target cattle or genetic potential for milk production (in bulls and cows). This method includes selecting a gene from TABLE I or TABLE II or TABLE III or a unique combination or subset thereof, for a Gene Expression Index. Furthermore, modulating expression of specific genes in the target animal is contemplated.

Subsets of genes whose GenBank accession numbers listed in TABLE I or II or III are also aspects of the disclosure. TABLES I-III show genes that differ significantly in expression levels for milk production in cattle. Another aspect is a group of polynucleotides (polydideoxynucleotides) selected from a group designated by GenBank accession numbers listed in TABLES I-III, for which there are no known functions. These include novel cattle genes, that is, genes with no existing human or mouse equivalent, or whose ortholog cannot yet be identified by sequence comparison.

A subset of approximately 1 to about 100 genes from the gene expression indices (TABLES I-III) can be used to predict a desired phenotype. The number in the subset is related to the contribution of any gene to the variations in the trait of interest. The greater the contribution, the fewer genes are needed.

EXAMPLES

Example 1

Development of Microarrays for Predicting Milk Production

A microarray printed with about 7,500 cattle genes was used to profile gene expression in liver and peripheral blood leukocyte samples collected from two groups of heifers selected for significant differences in predicted transmitting ability (PTA) for milk production. The equations ("animal model") for predictive PTAs are published and used by DHIA as part of their routine summaries. The PTAs of 20 heifers selected from the extremes of the PTA distributors were obtained from the DHIA records of milk yield (also correlated with fat and protein yields). The two groups of animals were age-matched (all heifers) and of the same breed (Holstein Friesian).

The microarray for gene expression profiling included a plurality of approximately 7,500 cDNAs spotted in duplicate representing a unique gene (cDNA) set of approximately 6,000 genes (see Materials and Methods). Creation of the arrays was performed essentially as described by Brown and Botstein (1999), although any microarray production method for expressing profiles is suitable for practice of the disclosure. The genes represent amplified inserts from a cattle placenta cDNA library referenced in Band et al. (2002) as disclosed herein. A cDNA library from which approximately 17,000 ESTs were sequenced and screened to reduce redundant gene sets through computational methods. The resulting unique gene set was amplified for printing on the microarray. Not all the genes that are on the array are shown in TABLE I. Only those genes that are significant between PTA groups in blood are shown in TABLE I. TABLE II shows genes expressed in liver that exhibit significant differences between PTA groups. Table III lists genes whose expression patterns differ in both blood leukocytes and liver.

Microarray Construction

A 7,653 gene cDNA microarray was created, representing an expansion of the 3,800 element microarray described by Band et al. (2002). The microarray was created according to the methods in Band et al. (2002). Briefly, a collection of 12,620 ESTs from a normalized and subtracted cattle placenta cDNA library were used as to select all new cDNA inserts that were added to the 3800 element array. Normalization equalizes the representation of the cDNAs in a cDNA library, thus reducing the over representation of genes, whose mRNAs are expressed to higher levels. Subtraction involves the reduction in the number of new cDNA clones to be sequenced by hybridizing the previously sequenced cDNA molecules against the cDNA library to eliminate duplicates. The placenta cDNA inserts were unidirectionally cloned and sequenced from the 5' end using the M13 reverse-48 primer (AGCGGATAACAATTTCACAC). Sequences were trimmed of vector, low-quality reads and minimum length of >300 bp using a local script and filtered for repeats using RepeatMasker (Smith and Green, 1999). Clusters of ESTs were then created using CAP3, (Huang and Madan, 1999) using default parameters, except that 40 bp was set as the minimum size of the overlap between clones. Sequences entering CAP3 had an average Phred score of 20. After CAP3 assembly, all clusters and singlets containing sequences present on the 3,800 gene array were removed from the data set. New sequences were selected for the array using an approach that combined BLAST with evaluation of clone position in the transcript. First, all sequences were analyzed by BLASTN against human UniGene database (build 155-Oct. 25, 2002) and mouse UniGene database (build 116-October 2002) and checked for duplicates on the basis of human UniGene identification numbers of the best BLAST hits. Second, a representative clone was picked from each cluster with a UniGene identification number not represented on the 3,800 gene array (clusters without UniGene hits were also used). Clones were selected from clusters with the longest and most 3' high quality read that were available. Third, singletons with and without a human UniGene hit were selected. With the few remaining places in the rearrayed grid of clones, a low level of redundancy (for intended control) was introduced by selecting clones with stronger similarity scores to human UniGene clusters than original clones used for the 3,800 set. The total number of selected sequences for the microarray was 7,653.

Amplification of clone inserts, clean-up of PCR products and spotting of the microarray were performed as described by Band et al. (2002) with some modifications. Amplification of inserts employed M13-FWD (GTTTTCCCAGTCAC-GACGTTG) and M13-REV (TGAGCGGATAA-CAATTTCACACAG) oligonucleotide primers (Hegde et al., 2000). After purification, PCR products were redissolved in 3×SSC supplemented with 1M betaine (Diehl et al., 2001). A row of 32 control spots was placed in every grid of the array. Controls include the endogenous housekeeping genes encoding beta actin (ACTB), glyceraldehyde-3-phosphate dehydrogenase (GAPDH) and hypoxanthine phosphoribosyltransferase (HPRT), BLV genes env and tax, exogenous soybean control genes chlorophyll ab binding protein (CAB), Rubisco small chain 1 (RBS1) and major latex protein (MSG). Negative controls are Cot1 DNA, genomic DNA, spotting buffer, poly-A and $H_2O$. Duplicate spots were placed in different blocks instead of adjacent to each other as in the 3,800 gene array. This layout permits identification of the true experimental variation over the entire slide, thus facilitating interpretation of statistical analyses. Spot and printing quality were assessed on one slide by hybridizing a Cy3-labeled random nonamer (Operon, Alameda, Ca). The accuracy of the reracking, spotting and clone annotation was evaluated by resequencing the entire set of clones of the original 3,800 gene microarray and sample sequencing 8 clones per plate of the new clone set. Analysis of the sequence data revealed an error rate of 2% for the first set and 0% for the second set. Mislabeled clones were reannotated on the basis of the sequences obtained.

Functional Annotation of Microarray Sequences

All sequences were masked for repeats using RepeatMasker prior to BLAST analysis. Similarity searches were conducted for all sequences against the human UniGene database (build 166) using BLASTN. The remaining sequences with no significant similarity to human UniGene sequences (E-value threshold of $e^{-5}$) were analyzed by TBLASTX against the human UniGene database followed by BLASTN against the human genome draft sequence (build 34.2, Jan. 12, 2004). In all searches, best hits were used to annotate the cattle sequences as putative orthologs. Previous comparative mapping studies have shown that such predictions are at least 95% accurate (Band et al., 2000). The GO annotations associated with human UniGene numbers were parsed from LocusLink (Mar. 1, 2004 release). GeneOntology (GO) terms (March, 2004 release) were downloaded (Ashburner et al., 2000) and used for GO annotation of the sequences. Many of the steps of the process, including BLAST and GO annotation, were automated with Perl computer programs.

Example 2

Hybridization Analysis for Predicting Milk Production cDNA samples from 10 heifers (see Materials and Methods) that were predicted to have high predicted transmitting ability for milk production based on breeding values of their parents, were tested 2 times (once with Cy3 dye and once with Cy5 dye) using a microarray slide printed with ~15,000 spots, or approximate 7500 cDNA molecules in duplicate. Cy3 and Cy5 dyes are used to label cDNAs. Similarly, cDNA samples from 10 heifers, that were predicted to have low predicted transmitting ability for milk production based on breeding values of their parents were tested 2 times (once with Cy3 dye and once with Cy5 dye) using microarray printed with 7,500 genes in duplicate. Therefore, every low PTA ratio (normalized gene expression ratio for heifers with low PTAs) or high PTAs (normalized gene expression ratio for heifers with high PTAs) shown in TABLE I or TABLE II (see Sequences for clones in Tables I and II) refers to an average of up to 40 data points. For example, every experiment involves isolating RNA from cow blood, synthesizing and labeling the cDNAs with a fluorescent dye (Cy3), and co-hybridizing on a microarray with Cy5-labeled cDNA prepared from the reference standard RNA. The experiment is replicated by dye-swapping (labeling sample with Cy5 and the reference standard with Cy3). The reference standard is produced by pooling RNA from brain tissue and three different bovine cell lines. Thus, the reference standard is the same for all comparisons. Following labeling, the cDNA samples (blood and reference standard) are hybridized to the same microarray containing approximately 7,500 gene spots in duplicates. Likewise, the experiments are repeated for other cows whose predicted transmitting ability (PTA) for milk production is known.

A "reference standard" RNA pool was created to enable comparison of expression profiles obtained using the 7,653 gene array. RNA collected from brain tissue of three cows (two Angus x Hereford and one Hereford) and the following cell lines were used to create the reference standard: B-lymphocyte cell line BL3⁰ (ATCC: CRL-8037), bovine tracheal epithelial cell line EBTr (ATCC: CCL-44; provided by Dr. M. Abrahamsen, University of Minnesota, St. Paul, Minn.) and bovine kidney cell line MDBK (ATCC: CCL-22). EBTr was grown in MEM whereas MDBK and BL3⁰ were grown in L-15. Both culture media were supplemented with 10% FBS, 100 U/ml penicillin and 0.1 mg/ml streptomycin (Sigma, St. Louis, Mo.). After checking the quality and quantity of RNA, 8 mg of total RNA from each source were mixed to create the pool and frozen at −80° C. until use. Labeling of the reference RNA with Cy3 and Cy5 and subsequent co-hybridization revealed 70% (Cy3) to 75% (Cy5) of spots were 3 standard deviations above background signal.

Analysis of the Data

Fluorescence intensity data were available in a total of 40 microarrays, 20 pertaining to 10 high PTA animals (including dye-swap) and 20 pertaining to 10 low PTA animals with dye-swap. Dye-swap refers to switching of the dyes used to label the cDNAs derived from mRNAs representing the high PTA and the low PTA groups. Dye-swap accounts and corrects for differences in the fluorescence intensity due to dye instability or labelling efficiency. The fluorescence intensities from half of the animals within each PTA level were obtained at the first stages of the experiment by one person and the remaining half were obtained at a later stage by another person. This potential variation was considered a sub-experiment effect and was accounted for in the model. Each sequence was available in duplicated spots within the microarray. The intensity record was the median of all pixels in the foreground subtracted from the associated median background intensity. A filtering process was implemented to remove suspicious observations and use only data that were reproducible. When the foreground minus background intensity was lower than one, the difference was set equal to one. All background-subtracted spot intensities lower than the mean plus 3 standard deviations of the corresponding slide-dye background intensities in both dye systems were removed from the analysis. The logarithmic transformation (base 2) of the background-subtracted intensities was used in the follow-up analysis. A spot intensity was removed from the data if the corresponding sample:reference ratio was extreme with respect to the rest of the ratios available for an animal, i.e. an outlier.

The Cook's Distance (a metric for deciding whether a particular point alone affects regression estimates), a well-known influence statistic that measures the change to the estimates that results from deleting each observation (Cook, 1977) was used to identify suspicious ratios. Sequences with less than 10 sample:universal control ratios per PTA-sub-experiment group (from a maximum of 20 ratios) and with less than two high or low PTA animals per sub-experiment were removed from the analysis. A global Loess normalization based on 20% of the data in the neighborhood of each spot average fluorescence intensity was applied within slide to the remaining sequences. In addition to the within-array normalization for fluorescence intensity effects, an across-array scaling of the normalized ratios for dye effects was implemented. The resulting normalized ratios were analyzed using a linear mixed effects models and an analysis of variance (ANOVA) approach for each sequence. The model included the fixed effects of sub-experiment and PTA group nested within sub-experiment and the random effect of cow. False-discovery-rate (FDR, Benjamini and Hochberg, 1995) adjusted significance p-values of the PTA effect were obtained for each sequence and the contrast between PTA estimates represented the adjusted ratio-of-ratios due to the logarithmic transformation of the fluorescence intensities. "Ratio-of-ratios" was used to estimate the absolute differences in gene expression between the two groups.

The statistical model used was conservative and powerful for detecting differences in gene expression levels between the highPTA and lowPTA groups. LOESS transformation of the data for normalization was used. The FDR was used to reduce the number of false positives. An FDR of ≦10% is reasonable, although higher FDR can also be used. Raw probabilities for the ANOVA are also given in TABLES I-III, in addition to FDR adjusted p-value. In TABLE I, the number of genes with effects at each FDR p-value cutoff is: <0.1 (number of genes ~50); <0.2 (number of genes ~200); and <0.3 (number of genes ~357).

The model used in calculating the difference in expression level of each gene on the array was $y_{ij}k_l = m + P_i + PTA(P)_{ij} + C(PTA)_{ijk} + e_{ijkl}$, where $y_{ij}k_l$ = log 2 transformed and LOESS normalized ratio of cow/reference intensities "l" for data set i (e.g., experiment 1 or experiment 2), PTA level "j" (high or low) nested within data set, and cow "k" nested within a PTA group and data set. m equals overall mean; $P_i$ equals fixed effect of data set i; PTA(P) equals fixed effect of PTA level j nested within data set; C(PTA) equals random effect of cow k nested within PTA level; eijkl=random residual associated with observations $y_{ij}k_l$.

TABLE I provides gene expression data from blood for approximately 357 DNA fragments representing approximately 357 genes that have varying levels of significance in predicting a desirable phenotype (e.g., milk production).

The "GenBank ID" column in TABLE I refers to GenBank accession numbers of cattle ESTs/DNA fragments representing a cDNA clone on the microarray. In TABLE 1, the data set was generated from two sets of separate experiments (e.g., first set of 10; animals; and a second set of 10 animals) and the data from the two experiments were combined to generate the gene expression profile from blood. ANOVA was performed on LOESS transformed fluorescence intensity values for the combined gene expression data (fluorescence intensity equates to expression level of a gene). The standard errors were calculated for expression data of each gene on the microarray. The "fold-change" ratio-of-ratios column in TABLE I shows the change of gene expression level of highPTA group relative to lowPTA group. The differences were transformed to a linear scale for easy comparison (a value of 1.5 means that expression level was 1.5 fold-greater in highPTA vs. lowPTA group). Comparisons are always for highPTA-to-lowPTA ratio-of-ratios. The "ratio-of-ratios" is calculated by dividing the "high-PTA-ratio" by "low-PTA-ratio". This quotient, referred to as the "ratio-of-ratios," represents the ratio of high-PTA-ratio to the low-PTA-ratio values. The normalized ratio is calculated as follows:

1) compute the log 2 (tissue/reference) (after background subtraction and removal of spots<3SD)
2) normalize the log 2 ratio using Ab binding gene
3) find the average of normalized log 2 ratio for all spots pertaining to the sequence The "raw_pvalue" column shows the probability estimate of ANOVA for difference between high and low PTA groups. The "FDR adjusted p value" column shows the FDR for ANOVA as disclosed herein. The FDR was calculated for the combined data (from experiment 1 and 2), unless a gene's expression data was absent in either experiment 1 or experiment 2.

In TABLE I, the "Gene Name" column provides a descriptive name of the gene associated with that particular GenBank accession number. Other details of the gene can be obtained from the GenBank database by using the appropriate GenBank accession numbers. The "gene symbol" column provides relevant gene symbols if available. The gene identification was determined by BLAST analysis of the cattle sequence on the microarray against the public domain DNA sequence databases. If a human gene was identified, the human gene name was given. If there was no similarity to a human gene, but significant similarity to a gene from another species (e.g., mouse), then gene name was given from the species with the highest significant BLAST score. The "GenBank ID best hit" column provides GenBank accession numbers of nucleic acid sequences that returned the best similarity when compared against the cattle sequences. A GenBank ID representing a cattle sequence will appear only if there was no hit in the human or mouse genomes. The "UniGene" column provides identification numbers for the best hit of cattle sequence on the microarray against human unigene databases. Human UniGene release 166 (Jan. 12, 2004); Mouse UniGene release 135 (Feb. 27, 2004); human genome Build #34.2 (January 2004); Cow UniGene Build 55 (Mar. 9, 2004); TIGR9 (Sep. 3, 2003); LocusLink of Mar. 1, 2004 were used to update the "UniGene" column.

In TABLE I, for genes differentiated expressed in blood samples, the list was sorted based on the FDR adjusted p-value. Presumably, the genes appearing on the top of the list have a higher predictive value compared to those appearing at the bottom of the list. The order of the genes in the list may vary depending upon the trait tested and tissue analyzed. However, the genes in the list provide a statistically robust method for milk yield using gene expression data.

TABLE II shows the data and calculations, based on liver samples, using similar column headings as used for TABLE I. Testing and analysis of gene expression ratios as described for blood samples in TABLE I were performed using liver samples. TABLE II provides a list of 10 genes, whose expression profile in liver is predictive of high milk production and associated traits in cattle.

TABLE III contains a list of genes expressed in both liver and blood that have significant effects on PTA. The analysis was done as described for the blood data in TABLE I. The gene expression levels from both blood and liver predict PTA across various tissue types. This provides confirming evidence that these genes are involved in regulating the traits of interest.

In TABLE III, the "contrast blood" and "contrast" test statistics column provides a comparison between two levels (i.e. transformed and normalized estimated ratio of cow:reference intensities) of an independent variable (PTA high and low) for blood and liver samples only. ANOVA was performed on LOESS transformed fluorescence intensity values. Standard errors were calculated. The "raw p-value blood" column represents an unadjusted p-value for ANOVA of blood data. The "contrast liver" column represents a comparison between two levels (transformed and normalized estimated ratio of cow:reference intensities) of an independent variable (PTA high and low) for liver samples. ANOVA was performed on LOESS transformed fluorescence intensity values. The "raw p-value liver" column provides an unadjusted p-value for ANOVA of liver data. The "Gene Name", "Gene Symbol", "GenBank Best hit" and the "UniGene" columns are as described for TABLE I.

The genes in the list provided in TABLE III are arranged based on the raw p-value for both blood and liver. For example, a listing in TABLE III was generated by comparing genes with raw p-values of ≦0.10 for both blood and liver. The genes appearing on the top of the list have a higher predictive value compared to those appearing at the bottom of the list. The order of the genes in the list may vary depending upon the trait tested and tissue analyzed. However, the genes in the list provide a statistically robust method (see peripheral blood).

Figure 3:
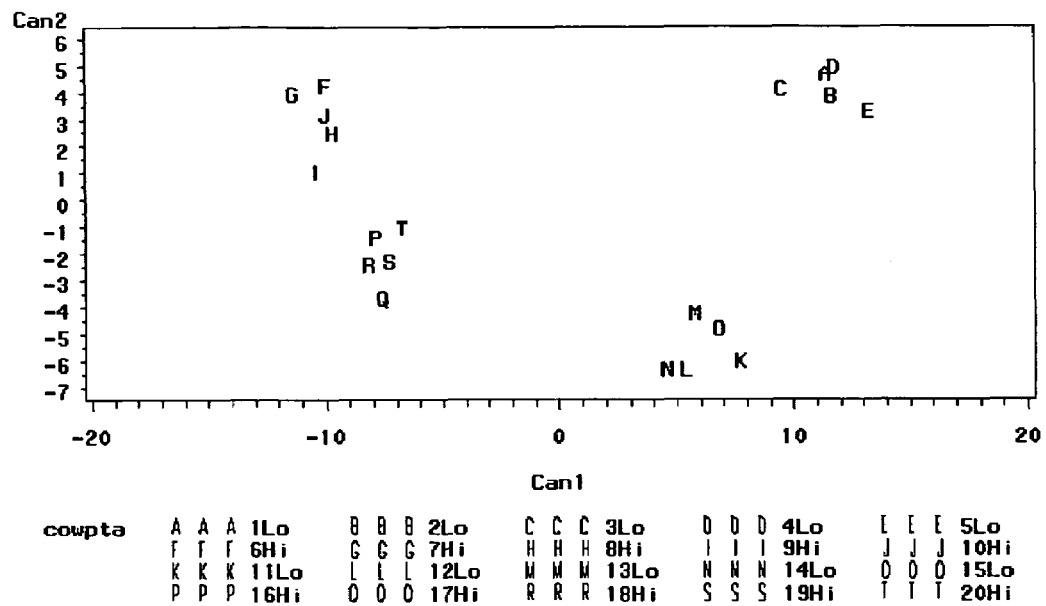
FIG. 3 shows that a scatter plot of the first two canonical discriminant functions (Can1 and Can2) of gene expression separates cows into high (Hi) and low (Lo) PTA groups number represent individual cow identification. Table IV shows the data for the cows.

Results from the analysis of fluorescence intensities collected from high and low PTA animals were used to identify the sequences with the highest potential as biomarker predictors of PTA level (FIG. 3). Only genes significant at FDR-adjusted p-value<0.1 (50 genes) and with information on all 20 animals (14 genes) were considered repeatable and highly likely to be true positives. The predicted values for the 20 animals from the linear mixed effects model corresponding to genes represented by the 14 sequences (AW461980, AW464526, AW465165, AW465571, AW466043, BF039168, BF044446, BF044893, BF046007, BF046202, BF440243, BF440261, AW466044, BF039212) were used in a discriminant analysis to identify the sequences that can most accurately classify animals into high and low PTA groups. These 14 genes define an optimal subset to create a Reference Expression Profile for a candidate mammal. A stepwise discriminant analysis (Klecka, 1980) further reduced the number of genes used to distinguish PTA groups to five represented by Gen Bank (AW466043, BF044446, BF039168, BF046202, AW461980). Stepwise selection started with no genes in the model and in an iterative process, the variable that contributed most to the discriminatory ability of the model was entered and the ones that contributed least and did not meet the statistical criterion (p-value<0.15) were removed. Disjoint cluster analysis using Euclidean distances, also known as k-means model, divided the animals into clusters with centers based on least-squares estimation. Canonical variables were used to depict the cluster of animals based on the selected sequences (FIG. 3). Canonical discriminant analysis was used for the purpose of graphical representation of the cluster of cows by PTA group. Canonical discriminant analysis is a dimension-reduction technique that finds the linear combinations of the quantitative variables that provide maximal separation between the classes or groups (SAS online manual 2002, The SAS Institute Inc.). This approach successfully discriminated animals by PTA.

Example 3

Developing a Gene Expression Index for Phenomic Selection

The expression profiles of the genes in high PTA cows and low PTA cows (TABLES I-III) were ranked according to their p-values or FDR-adjusted p-value, i.e. gene expression profiles represented in TABLES I-III were classified based on statistical significance. For example, in blood samples from cows with predicted transmitting ability for high and low milk production, a total of 357 genes (or partial DNA fragments representing those 357 genes) were found to differ significantly between the groups at <FDR adjusted p-value of 0.29 and approximately 25 genes at <0.051 FDR-adjusted p-value (TABLE I). Any other relevant statistical method can be used to rank the genes.

In liver samples from cows with predicted transmitting ability for high and low milk production, a total of 10 genes were found to differ significantly between the groups at $\leqq 0.4$ FDR-adjusted p-value (TABLE II). The genes listed in TABLES I-III are part of a Gene Expression Index useful for identifying a candidate animal as predicted to be elite, that is, to have increased (high) milk production.

These results demonstrate that genetically elite cows can be identified prior to their first lactation on the basis of gene expression profiles of liver or peripheral blood leukocyte RNA. When applied to bulls, this method may enhance or replace progeny testing, significantly increasing the rate and efficiency of genetic improvement by breeding. Multiple phenotype traits may be improved simultaneously using this method. This method is generally referred to as phenomic selection.

Example 4

Developing a Weighted Gene Expression Index for Phenomic Selection

Based on the expression profiles of all the genes in the microarray, a Gene Expression Index is developed, where the genes ranked higher in the index according to statistical significance between high and low PTA for milk production (or any 2 levels of a different trait) account for a greater fraction of the phenotypic variation in the trait. More levels could also be added. One method to further refine the Gene Expression Index is to create a weighted Gene Expression Index. This is accomplished by comparing actual milk production records from the high and low PTA cows from genetically distinct backgrounds and in different herds to their gene expression profiles for the genes in non-weighted index. Weighting of the index is accomplished by ranking the actual production values or PTAs of cows or bulls in the population and adjusting the p-value-based ranking of individual genes by a defined multiple. The weighted index can then be used to rank candidate animals in a breeding program. The genes with a greater weighted average will have the most predictive power for the trait, such as high milk production.

Example 5

Identifying a Candidate Animal for Selective Breeding

Expression profiles of genes selected from a gene index are evaluated in the cattle population for their ability to predict high milk production. The RNA isolation, synthesis of cDNA and labeling are performed as described in MATERIALS AND METHODS. Hybridization can be carried out with a microarray containing genes selected from the disclosed gene index. Alternatively, particularly useful at field level, quantitative PCR analysis for measuring gene expression or an equivalently sensitive method can be performed for a limited number of genes selected from the gene index. For example, quantitative real-time RT (reverse transcription) PCR analysis is less expensive for a limited number of genes and diagnosis is portable.

Following microarray hybridization or quantitative PCR, the expression profiles of tested genes are compared to the expression profiles of genes in the Gene Expression Index or Reference Expression Profile (FIG. 2). Similarity of the expression profile of a sample from the candidate animal to the Gene Expression Index indicates higher probability for increased milk production.

The Gene Expression Index and the weighted Gene Expression Index disclosed herein can also be used to identify bulls for predicted transmitting ability for high milk production. This is based on the premise that a strong selection pressure for increased milk production must have influenced the fundamental gene expression pattern, and this gene expression pattern that correlates with increased milk production must be present in bulls as well. Consequently, the gene expression indices disclosed herein can provide a basis to correlate expression profiles from cows at the population level, as well as a specific bull's daughters for increased milk production. Therefore, the need for expensive progeny testing can be minimized. An aspect of the disclosure is that blood, indeed any tissue for which expression profiles can be obtained, at any stage of development, can be used for creating the index. With complex traits such as lactation that involve hundreds of genes, many of which will be involved in intermediary metabolism, RNA levels of such genes are expected to be consistently different in animals of different PTA levels. That is, an animal with a high potential for milk

Example 6

Identification of Novel Genes Involved in Milk Production

Several genes with differential expression levels in high milk producing cows and low milk producing cows were identified through a microarray analysis. Based on the sequence information of these genes, several genes do not have counterparts or functional annotations in humans and may represent genes unique to milk production in cattle. The data provided in this disclosure presents an insight to analyzing functions of several unannotated genes.

Example 7

Genetic Manipulation of a Desired Gene

A method to manipulate gene expression in a ungulate mammals is through in vitro fertilization of a genetically altered egg followed by an embryo transfer. Methods to generate transgenic ungulate mammals include microinjection of DNA into the oocyte under conditions which permit the transfection of the oocyte, and contacting the transfected oocyte with sperm under conditions which permit the fertilization of the transfected oocyte to produce an embryo. Following the fertilization of the transfected oocyte, the embryo is transferred into a hormonally synchronized non-human recipient animal generally of the same species (i.e., a female animal hormonally synchronized to stimulate early pregnancy). The transferred embryo is allowed to develop to term. A transgenic offspring is then identified based on the expression of the desired gene or by detecting the presence of a recombinant protein. An altered gene expression or a difference in the amount of protein indicates a successful gene transfer to generate a transgenic offspring expressing a desired characteristic such as increased milk production. Genes suitable for manipulation through transgenesis are those disclosed herein.

Example 8

Selecting for Traits in Dairy Cattle and Beef Cattle Using a Gene Expression Index The following are traits other than milk production that are suitable for developing gene indices for cattle selection:

A. Dairy Cattle

1. Health Traits in Dairy Cattle

The primary problems are mastitis, digestive and reproductive disorders. Use of antibiotics and drugs is already limited for lactating cows. Therefore the ability to predict better health traits in breeding cows is valuable for the dairy industry to minimize economic losses due to diseases. Adequate evidence indicates that the variability in disease incidences and health disorders is under some degree of genetic control.

(a) Somatic Cell Score:

Somatic cell concentration is a quantitative trait in cattle with moderate heritability and is apparently affected by many different loci. Somatic cells in milk consist primarily of leukocytes and neutrophils secreted in response to invasion by an infectious pathogen. Somatic cell counts in milk serve as an indicator of udder health and are elevated during mastitis infections. Research has indicated that somatic cells in milk are elevated when heifers give birth to their first offspring, although clinical symptoms may or may not be present. The relative roles of pre-calving infections, or even calfhood infections, environmental stressors, or onset of lactation in causing elevated cells counts is not clear. Correlations between somatic cell score and mastitis infection and QTL are available. The methods to create gene expression indices disclosed herein can be used to predict somatic cell counts in cattle and to predict disease resistance for mastitis infections.

(b) Immunity:

Overall immunity is a measure of healthier and longer productive life for cattle. The methods for creating gene expression indices disclosed herein can be used to estimate the predictive transmitting ability for disease resistance in cattle.

(c) Fertility and Longevity:

Reproductive traits such as fertility can also be predicted using the methods of the present disclosure. Longevity of dairy cattle is a result of overall fitness and a Gene Expression Index can be used to predict longevity of the animal in a herd. Correlations between somatic cell score and fertility in dairy cattle have been detected and can be used with a gene according to the present discussion to predict longevity.

2. Type Traits in Dairy Cattle:

The standard type traits that can be used in methods for creating the gene expression indices disclosed herein include stature, chest, width, body depth, angularity, rump angle, rump width, rear legs set, rear legs rear view, foot angle, fore udder attachment, rear udder height, central ligament, and teat length.

B. Beef Cattle

In addition to some of the traits such as health, disease resistance, and reproductive fitness, beef cattle are selected for higher carcass and meat quality and growth traits. Beef cattle traits may also include customer satisfaction traits, such as marbling, tenderness and composition. These beef traits can also be predicted using methods of the present disclosure.

Example 9

Phenomic Selection for Traits in Swine Using a Gene Expression Index

Health traits including immunity or disease resistance (e.g., resistance to intestinal *E. coli* associated diarrhea), reproductive traits such as fertility, and meat quality (tenderness and intramuscular fat content) in swine (an ungulate mammal) can be predicted using the Gene Expression Index methods disclosed herein. The methods described herein for analyzing PTA for milk production in cattle can also be used to evaluate PTA for the above-mentioned traits in swine. These methods include isolating a suitable tissue sample such as blood from swine and comparing the expression profiles of genes from the swine samples with reference to a Gene Expression Index created by methods disclosed herein. Boars and sows with superior genetic merit as assessed by comparison to the relevant expression index, can be used for selective breeding.

Example 10

Analyzing Phenotypic Traits in Sheep/Goats Using a Gene Expression Index

Analyzing traits in sheep or goats (ungulate mammals) includes predicting traits for better meat quality, increased milk production, wool quantity and quality and other health traits such as immunity or disease resistance and fertility. The methods disclosed herein for analyzing PTA for milk production in cattle can also be used to evaluate PTAs or phenotypes of the above-mentioned traits in sheep or goats. These methods include isolating a suitable tissue sample such as blood from sheep or goats and comparing the expression profiles of genes from the sheep or goats samples with reference to a Gene Expression Index created by methods disclosed herein for a specific trait. A high correlation of the trait with the expression of genes present in a Gene Expression Index created by methods disclosed herein indicates superior genetic merit for the chosen trait. Sheep, goats, deer, horses and other ungulate mammals can be selected for breeding according to the methods of the disclosure to improve production efficiency, health and profitability.

Example 11

Race Horses

Racing ability in horses can be predicted by creating a Gene Expression Index and comparing gene expression levels in horses that have known racing ability, or phenotypes that are correlated with racing ability. Gene expression profiling is performed on RNA collected from muscle tissue collected from foals. When the horses reach racing age, the patterns established when they are foals is correlated with racing ability or racing-related traits (e.g., speed). An index associated with speed can therefore be established. Candidate foals are then tested at birth and the patterns most closely matching the patterns of horses with greater speed can be identified.

Materials and Methods

Experimental Animals. A total of 20 Holstein Friesian dairy heifers were selected for study, 10 with extreme low breeding values for milk production and/or composition traits and 10 with extreme high breeding values. All animals were housed at the University of Illinois Dairy Farm, operated by the Department of Animal Sciences. A cow's genetic merit is determined from the predicted transmitting ability (PTA) of her dam, and the daughter yield deviation (DYD) of the sire. Only offspring of sires and dams with high accuracy predictions (>0.80) were used. Blood and tissue (liver punch biopsy) samples were collected in pairs (one high potential, one low genetic potential). All samples were collected at the same time of day, in the same season, all prior to the heifer's first lactation. Animals were fed identical diet and housed under identical conditions.

Total RNA purification for gene expression analysis. Two tissues were sampled from each animal: peripheral blood leukocytes and liver. Liver tissue was collected using a standard approved biopsy procedure. Total RNA isolation was performed using optimized protocols developed for this project. Briefly, blood samples were collected in a 250 ml bottle containing 100 ml of 0.5M EDTA and mixed well. The sample was thoroughly mixed with an equal amount of a lysis buffer (8.9 g $NH_4Cl$, 0.1 g $KHCO_3$ in one liter of $H_2O$) and centrifuged at 3,500 rpm for 10 min at 4° C. to separate blood leukocytes. The procedure was repeated with one-third the amount of the lysis buffer until clean leukocytes were obtained. Liver biopsies were collected and stored in liquid nitrogen and/or RNALater (Ambion, Inc., Austin, Tex.). Frozen liver tissue was ground into fine powder in liquid nitrogen using a mortar and pestle. Tissue preserved in RNALater was cut into small pieces before being used for RNA isolation. Total RNA was extracted using TRIzol reagent (Life Technologies, Carlsbad, Calif.). Briefly, each sample of leukocytes or liver was homogenized in TRIzol using a mechanical homogenizer, debris was precipitated by centrifugation and discarded. The RNA was further purified by extractions using chloroform, acid phenol:chloroform, precipitated by adding isopropanol, and incubated at −20° C. The isolated RNA was cleaned using 75% ethanol, resuspended in RNA storage buffer, aliquoted and stored at −80° C. until use. The integrity of total RNA was examined by denaturing agarose gel electrophoresis. RNA concentrations and purity were measured by spectrophotometry.

RNA probe labeling. RNA labeling procedures were adapted from Hegde et al. (2000) with modifications. Based on the optimized protocol disclosed herein, 10 μg of total RNA for each sample were used for each labeling reaction. In a typical 30 μl reverse transcription reaction, 10 μg of total RNA in 7.5 μl is mixed with 1 μl of oligo (dT)s (2 μg/μl) and 1 μl of exogenous control gene mix, and incubated at 70° C. for 10 min. After cooling on ice, 15 μl of labeling buffer is added followed by 3 Ill of Cy3-dUTP or Cy5-dUTP, separately, 2 μl of SuperScriptII (200 U/μl) and 0.5 μl of RNasin (40 U/l). The mix is then incubated in the dark at 42° C. for 2 h. Each of the labeled Cy3- and Cy5-dUTP reactions are purified separately using a column purification system (QIAGEN, Valencia, Calif.).

The length of labeled cDNA and the quality of the paired probes was examined by electrophoresis. The probes incorporated with Cy3 and Cy5 are measured using spectrophotometry. Total dye incorporations are calculated using the following formula: Cy3-dUTP (pmol)=($OD_{550}$× volume)/($E_{550}$×$10^{-6}$); and Cy5-dUTP (pmol)=($OD_{650}$× volume)/($E_{650}$×$10^{-6}$), where $E_{550}$ is the molar extinction coefficient of Cy3 (150,000 $cm^{-1}$ $M^{-1}$) and $E_{650}$ is molar extinction coefficient of Cy5 (250,000 $cm^{-1}$ $M^{-1}$).

Hybridization to microarrays. Prior to hybridization, the arrays were treated with prehybridization buffer (5×SSC, 0.1% SDS and 0.1% BSA) by immersing into the prehybridization solution at 42° C. for 45 min. The prehybridized slide was then washed five times by sequential dipping in MilliQ water at room temperature with a final dip wash once in isopropanol. The washed slide was spun dry at 500 rpm for 1 min and used immediately for hybridization. The purified labeled probe was combined with 20 μg of bovine Hyblock DNA (Applied Genetics Laboratories Inc., Melbourne, Fla.) and 1 μg of poly (A) in μl volume. This hybridization mix was denatured in a water bath at 95° C. for 3 min and subsequently mixed with an equal amount of 2× hybridization buffer (50% formamide, 10×SSC and 0.2% SDS) and hybridized at 42° C. overnight in a CMT-hybridization chamber (Corning, Inc. Corning, N.Y.) using a LifterSlip (Erie Scientific Company, Portsmouth, N.H.) for each array slide. The hybridization chamber contained a small piece of moist filter paper next to the array to maintain proper moisture. The chamber was sealed and incubated at 42° C. in a water bath in the dark overnight. The hybridized slide was washed in a buffer containing 1×SSC and 0.2% SDS at 42° C. for 5 min with agitation. Then it was washed in a second buffer containing 0.1× SSC and 0.2% SDS at room temperature for 5 min with agitation, followed by a third wash in 0.1×SSC at room temperature for 5 min with agitation. The slides were spun dry at 2,000 rpm for one min after final wash before they were scanned. All samples were hybridized to duplicate slides and repeated with reverse labeling for a total of 2 slides, or 4 spots per gene per experiment. Slides were scanned for both dye channels using an Axon 4,000B Scanner (Axon Instruments, Inc., Union City, Calif.) and data acquisition was done using Gene Pix 3.5 and raw data saved in files of gpr format.

Spiking control using exogenous nucleic acids. Exogenous nucleic acids were spiked into labeling and hybridization reactions for use as a reference for normalization and validation. The spiking control consists of three soybean (*Glycine max*) genes, photo system I chlorophyll ab binding protein (Cab), major latex protein (MSG), and ribulose bisphosphate carboxylase small chain I precursor (RBS1). The polyadenylated RNA of the exogenous nucleic acids was prepared by in vitro transcription using MAXIscript (Ambion, Inc. Austin, Tex.) and quantified by spectrophotometry and gel electrophoresis. One microliter of spiking control contains 10, 100 and 1,000 μg of mRNA from MSG, Cab and RBS1, respectively.

TaqMan® Analysis. One microgram of total RNA from each sample was denatured at 70° C. for 10 min and reverse transcribed in 20 μL reactions containing 500 ng oligo-dT primer, 500 KM dNTP, 100 μM DTT, 40 U RNasin, 1× first strand buffer and 200 U reverse transcriptase (SuperScript II, GIBCO BRL, Rockville, Md.) at 42° C. for 1 hour. Quantitative PCR was carried out on an ABI7700 PRISM sequence detector in 25 μL reactions containing 1× Quantitative PCR Universal PCR Master Mix (Applied Biosystems, Foster City, Calif.) 1 μL cDNA, 200 nM each primer and 100 nM probe. The PCR protocol consisted of denaturation at 95° C. for 9 min followed by 40 cycles of 95° C. for 15 s and 60° C. for 1 min. All reactions were carried out in triplicate. Standard curves for both target and reference genes were constructed using 2-fold serial dilutions of adult spleen cDNA. Relative amounts of transcripts are calculated.

p-values. p-values represent the probability that a deviation as great as, or greater than, that obtained from the experiment will occur by chance alone. In other words, p-value is the probability of observing a test statistic that is as extreme or more extreme than currently observed, assuming that the null hypothesis ($H_0$) is true. This can be expressed as the conditional probability P(data/$H_0$ true), where "P" is read "the probability of" and "/" is read as "given" or "conditional upon." If the p-value is small, it is concluded that the deviations are not entirely due to chance, and the null hypothesis is rejected. If the p-value is greater than the predetermined value (e.g., 0.05), the data confirm reasonably well with the predictions of the hypothesis, and the null hypothesis is accepted.

False Discovery Rate: This method is used to adjust for multiple comparisons by setting an acceptable proportion of false positives for an experiment (Benjamini and Hochberg, 1995). In this case the p-values are ranked in increasing order of $p_i$ ($p_1 < p_2 < p_k \ldots < p_m$, m=total number of comparisons). The p-values for each comparison are then sequentially compared to an adjusted cutoff for each $p_k$ equals to (FDR)*(i/m), where FDR=the false discovery rate. The null hypothesis is rejected for any comparison in which $p_k$<(FDR)*(i/m), until a comparison is made in which the observed p-value is greater than the adjusted cut-off. All larger p-values ($p_k \ldots p_m$) are not statistically significant. If the smallest p-value yields a false discovery rate higher than the selected FDR, the null hypothesis cannot be rejected for any test.

```
SEQ. ID. NO:1      BM362588
GCACGAGGCGGGATCGAGGGGCAGCAGCGTACGGTGAAGGACACAGGCCGTGGAGTTTGAACCCCT

TGAAAGATTGAAATCATGGCAGGTGCAGAAGCTGATGCCCAGTTCCATTTCACTGGTATCAAAAAATATTTCA

ACTCTTACACTCTCACAGGGAGAATGAATTGTGTGCTGGCCACATACGGAAGTATTGCTTTGATAGTCTTATA

CTTTCAAGTTAAGGTCTAAAAAAACTCCAGCTGTGAAAGCAACATAAACAGATTCTGAGCTGTACATTATCTGT

TAAGTTCCCATGCCTGAAGAAGCTAATGTCAACTCATCATGTGATACTCAATTTGTACAATAAATTATGAACC

TGGAAAAAAAAAAAAAAAAAAAAAAAA

SEQ. ID. NO:2      BF440243
TTTTTTTTTTTTTTTTGACTATCTACAAAAATTTATTGTCTATTTACAGAAGAAAAGCATGCGTATCA

TTAAAACAAATAAAATGTGTTTTCTCACAGCGCAGTACATTTTTNNNNAAAAAAATTTTTTTAAGCTGTATCA

CAGAAACAAGACACAAGGATTTTTTAAAAGAGCTAAACACTCATCATTCGAGGTGCAATACTCATGGACATG

AGTTCCTGAAACAACAGTTTGCACGCATAAGGCATTCGAACCAAAGAGATCTGGGTTTTATTTCGGCAGCCCC

TGCATTCGTATGTATGGGTCCTGNNGTTCGCAATTGCCATTATTCCACAAAGATTGCAAACGTGAACCTGATA

CGGATCTGACGCCTCAAACAACCTCTCCCTTNNAAACTGGGCTGCTCCATGCGCGATCTGACAGTCTCGTTCC

ATCTCTCCAAAACGCAAGCCACCATCACGAGATCTACCCTCCATCGGCTGNNTATTTAGAATCTGAATAGGTC

CCCGAGCACGAGAATGAATCTTATCATCCACCATATGCTTCAAACGCTGGTAGTAAGTA

SEQ. ID. NO:3      BM361928
GCACGAGAGCCGGCGTCTCAGAGGAGTGCAGACGCTGCTGGTGACCCTGTGGCGCGTCTCTGTGGGG

CCAGGAACTGAAAGAGAGCCAAAATGGCTGAAAATGGTGATAATGAAAAAATGGCTGCTCTGGAGGCCAAA

ATCTGTGATCAAATTGAGTATTATTTTGGAGACTTCAATTTGCCACGGGACAAATTTTTAAAGGAACAGATCA

AACTGGATGAAGGCTGGGTACCTTTGGAGATAATGATAAAGTTTAATAGGTTAAACCGTTTAACGACAGACT

TTAATGTAATAGTAGAGGCCCTGAGCAAATCAAAGGCAGAACTCATGGAAATAAGTGAAGATAAAACTAAA
```

```
ATTAGAAGATCTCCAAGCAAACCTCTCCCTGAAGTGACTGATGAGTATAAAAATGATGTAAAAAACAGATCT
GTTTATATTAAAGGCTTCCCGACAGATGCAGCTCTTGATGACATAAAAGAAT
```

SEQ. ID. NO:4    BM364471
```
GCACGAGCGGCGGAGAGCGGCACCCACACCGTGTGTCGGCGGTGAGTCCCGGCCAGCCCGAGCTGC
ACGTCCCAGCCCCGGGGAGACGCCGGAAAAAACGGAAGGACCTGGGATTCCAGAGCAGTCGCCGCTGACTG
CTGCTCTCCTGCCGTTGCCGCGGCGGAGGCTTCCGCACTCGCCGCTGAAGACGCGGCCCTGACAGGCCTAGA
GGCCTAGGCGCGGCCCTCCGAGCCCGACGTGTTGCCGCCGGTGCAGCTGTGAGTAATCCGAGCGCTCTCTCC
ACGGCCGTTTACAGATTAAAATGGAGGAAATTTCCTTGGCTAACCTGGATACTAACAAGCTGGAGGCCATCG
CTCAGGAGATATACGTAGACCTGATAGAGGATTCTTGTTTGGGCTTCTGCTTTGAGGTGCACCGGGCAGTCAA
GTGTGGCTACTTCTACCTGGAATTCGCAGAGACTGGTAACGTGAAGGATTTTGGCATTCAGCCAGTTGAAGAT
AAAGGAGCGTGTCGCCTCCCGCTTTGCTCCCTTCCTGGAGAATCTGGGAATGGGCCTGATCAGCAGC
```

SEQ. ID. NO:5    BM365159
```
GCACGAGATGGCGCCTGTGAAAAAGCTTGTGGCGAAGGGGGCAAAAAAAAGAAGCAAGTCCTA
AAATTCACTCTGGACTGTACCCACCCTGTAGAAGATGGAATCATGGATGCTGCCAATTTTGAGCAGTTTCTTC
AGGAGAGGATCAAGGTGAATGAAAAGCTGGCAACCTGGGCGGCGGTGTTGTAACAATTGAAAGAAGCAAG
AGCAAGATTACTGTAACTTCCGAGGTGCCCTTTTCCAAAAGGTATTTGAAATATCTTACCAAAAAATATTTGA
AGAAGAATAATCTACGAGATTGGTTACGCGTAGTCGCTAACAGCAAAGAAAGTTACGAATTGCGTTACTTCC
AGATTAATCAAGATGAAGAAGAGGAGGAAGATGAGGATTAAAACTCAATCTGGAATATTTGTATAAGTTCTT
AAATAAAATTTATCAACTGAAAAAAAAAAAAAAAAAAA
```

SEQ. ID. NO:6    BM365446
```
GCACGAGGTTGATGTCCTGTATCTGATGCCTTGTTGCGGTCGAAAGTAAGCGAGCTCCAGAGGAGTG
CGGAGAAATTCAAGTCTTTCCTGCTGTAACTTCATCAGCCCGCCAAGATGGCGATGCAAGCGGCCAAGAGGG
CGAACATTCGACTTCCACCAGAAGTAAATCGGATTTTGTATATAAGAAATTTGCCTTACAAAATCACAGCTGA
AGAAATGTATGATATATTTGGGAAATATGGACCTATTCGTCAAATCAGAGTGGGGAACACACCTGAAACTAG
AGGAACAGCTTATGTGGTCTATGAGGACATCTTTGATGCCAAGAATGCATGTGATCACCTGTCAGGATTCAAT
GTTTGTAACAGATACCTT
```

SEQ. ID. NO:7    BM365732
```
GCACGAGGGACGCCATGGCGACCAACATCGAGCAGATTTTTAGGTCTTTCGTGGTCAGTAAATTCCG
GGAAATTCAACAGGAACTATCAAGTGGAAGGAGTGAAGGACAGCTCAATGGTGAAACAAACACACCTATTG
AAGGAAACCAGGCAGGTGATGCAGCTGCCTCTGCCAGGAACCTACCAAATGAAGACATAGTTCAGAAGATA
GAGGAAGTACTTTCTGGGGTCTTAGATACAGAATTACGATATAAGCCAGACTTGAAGGAGGCATCCAGAAAA
AGTAGATGTGTGTCTGTCCAAACAGATCCTACTGATGAAATTCCTACNNNAAAGTCGAAGAAGCATAAAAAG
CACAAAAAAAAAAAAAAAAA
```

SEQ. ID. NO:8    BF046007
```
TCTCTGTCTGCAGTGGTCCACACCCATCCTCCGCCATACCCGGCCTCAGCCTGGCTGCCACGGGCGCC
GCACCTGCCGGGGCTGCCTCTAGAGGCGGCAAGATGTTGAGCGCGGCACGGAGGATCCAGGCCTACTGGCCT
AGTCGGGCCGAGAGCCGGAAGGCCACGTGGTTCTCAGGCGCAGTGGAAGAAGCCGGACCCTGTGTGGGCGA
CGCCCTGCTGCACGCGCAGGCCCTCGCGGCCCTGTGCTGCGGTGTGACGGTTTCCAGAATGTCCCAGTAGATG
AGTCCTGACACACAGGATTTAGTTGTGCCAGAAGATTCCAGGATGACTGAAGCTAACCTTTCTGGTGAGTGA
AGAGGACATGACAGGGATGGAACGAAAGCCTCAGGACCCGGTTGCCCCCCGTTTTTTAACTGGCAGTGCCTG
```

-continued

ACACTGAAGTAACTGAAAATACCACCTTGTCACTGGAGCCGTCCTTTAGAATAAGACCTGTTGCCAGTAAAG

CTGTCTTCATCTGTGCGGATCTACAGAGTTGGGAGAGAACCAAAAA

```
    SEQ. ID. NO:9       BF044446
        TTTTTTTTTTTCTTCTTCTTGTCCCCGTCCTTCTTCTCTTCCTCCTCTTCATCTGAGCCAACATCTTCTA
```

TCTCGGGCTTGTCATCAAACTCCTTTTCTTCTTTCTCCTTCTCTTCCTCTTTTGTNTTCCTTCTCTTCTGCTTCATC

ATCACTAACTTCTTTATCACGTTCCTTTTCCACCTTCAAAGGAGGACAAATCTTGTCACCTCTCCATCACAAAA

CCGGGGGAAAAAAGCTAAAGGAGACTGCAGCACTTACACCAACGCCACCTG

```
    SEQ. ID. NO:10      BF040826
        TTTTTTTTTTTTTTAAGGCAACAAAAAGCTICAATCTCTTCTCCAAGTAAACAGAACTAGTACAGTAT
```

ATTATTTTCTGGAACATGTACCCCCGGAGAAGTAACACAAGAGTTAAAGGGGGCCTCTCTGAACACACTCA

CACACTCCCCCCTACCCCAATGAACCAGTCTCTCTCTCACACCCACGCACACACAGAGCTATTCACAGGCGCA

AATGTATACTATGTACAAACACACAGATCCGGGTTTCCCCTCAAGTCTCCTGGCAGACTGCCCACCAGAGAG

GAGGGATGGGCTAAGGCAAGGGGAAGAAACAAGGAACCAGTCTCTGGAAGGAAACCAGCTGAGCCGTGAGT

TGTGAGGTGCTTAGGGGCGTGTCTCTTCTCGTATTCCAAGATGCAGCATTGTAGAGTTGGGGTTGGGCGGTTT

GGAATCAACAAAAGGAAAACAAAAGAACCCGAGGAGAATGGTCGGGATGGATACGAGTGCACAGGGTTTGG

GCCCAGNGACAGAGATGTCTGAGCGTTCACACAGAGACTAGGCGAGGAGGAAAAAGTGCAAATCGAGGCAA

CGTGTTTGCAGTCTTTCTTGTTTGATTTGGGTGC

```
    SEQ. ID. NO:11      BF039212
        GCATTTGTTTTTTTTTTTTTTTTAAGAGGCAGTCTGTTCCTTCCATGAACCGTGTTCTCTCCTTAAAG
```

CTCTGGGGGTTGGGGGGACCGATCATGGCTTGCAGCGCTGGACAAACCGAGGGTACAAACACACATCTCGGA

TGTGGTATCTGTCCAGAATCCAGGTTAAGAATCGTTCCAAGCCCAGGCCATAGCCGCCATGTGGACACGTGC

CATATTTTCTCTGATCCGTGTACCAGTAATAGGGAGTGGGATCAATCCCTTCTCTTTTGTAACCTGCCAGGATC

TCTTCATTATCCCAGATACGCATGGAGCCACCCACGATCTCACCAACATTGGGCATCAACACGTCGACAGATT

CGGTGAGCCGGGGGTGATGACGGAGCGCGCCTTCANNATTTTGGACATGTTCTCCCCGCGGATCATCATGTGT

CTGTTGTTGAGCTGGACG

```
    SEQ. ID. NO:12      AW461477
        TTTTTTTTTTTTTTTTTTTGAGGGAAACATAAGCAGAGTGGCGTCACTTGGTTTATTGTATTCTGAA
```

GTGTCATGGGGGGCCGGGGAGGGGTGCTGAAAACAAGCCTGCTTTATCAGCAGTTCTAAAGCCTTATCACCT

GAGATTTGCATTCTGGAAACAAAATCATGATTGCAGTATCAGCACATATGTCCTGTGAGATCTGGGTTCCAGC

CCTGGTGGATGGCTGGACTAACCTGACGTGAGGTCAC

```
    SEQ. ID. NO:13      AW464361
        ATCCGACCACGTGAGGACTGGCATCCTCGGCTCAAGCCCCAGAGTCCTGGGCGGGACACCGGACTGG
```

CCCAGCCCAGCTTGGGGGCCCCGTCGTAGCTGCCAAAGGAGAAGGAAACACGNNCCGTGGAGCTNNCACCA

AGCGGGTGCGNNNCCGCCCCACCGAAACCGGCAGAGTCTGCTTCTNNCCCAGTGAGGAGCAGCGTCTGTGAG

GTGCAGCCAAACGGGGACAAAGTGAACAACGCCCGCTGCCCGCAGTCACACTCAGNCCGTAGTACACCTCCG

AGAACAAGGAGCTCCCCAGGGACAGACGAGCAGCCTTGTGCCGGAAGCTCGTGGGCA

```
    SEQ. ID. NO:14      AW466044
        GTTACAGAATAATATGCAGAAATGCCACTATCTAGTTAGTTGGCTCTACATAAGCAAAGACTATCCT
```

GTCTTTGTGGTGACTGAACTTAGAATGTCCTCCTCTGGAAATGGAAAAGTACCTGTATTAGGAGCTAAGTGAC

AGAAGGAGTTATCAAACTTGACTCCATATAGATAATGAACAGTTTAGGGGAAGCATTTTTCTTGGAACTAAG

AAGGACTTACCTGACATTGGCCTCATTCTGGCCTTCACTTGTTCATAAGAATCATGGAACCAGAGTTTGAGTT

AAGAAACTTGGAAAAAGCAGCTGAAAACATCTCNGNNNCCACTTAACAATTTAAAAATTCCACTTAAGATGC

TAAATAATCCATTGCTTATGTAGCAACTCAACGATGTTCTCAA

SEQ. ID. NO:15        BF039490
    TTTATGAGCAGCTAGAATGTGCTGCAACAGAAGAAGCTGCGACACGCCAGTGGGGCCAACATCACT

AACGCAGCCACTGCTGCTACCACAGCGGCCACGGCCACTGCCACCACCACCAGCACCGAGGGCAGCAACAG

CGAGAGCGAGGCTGAGAGCACCGAGAACAGCCCTACCCCGTCTCCTCTGCAGAAGAAGGTCACTGAGGATTT

GTCCAAAACCCTCTTGATGTACACTGTCCCTGCTGTCCAGGGCTTCTTCCGTTCCATCTCCTTGTCACGAGGCA

ACAACCTCCAGGACACGCTCAGAGTCCTCACCTTATGGTTTGATTATGGTCACTGGCCAGATGTAAATGAAGC

CTTAGTGGAAGGGGTGAAAGCAATCCAGATTGACACTTGGTTACAGGTTATACCACAGCTCATTGCAAGAAT

TGATACGCCAAGGCCCCTGGTGGGACGTCTTATCCACCAGCTTCTCACAGACATTGGTCGGTACCACCCCCAG

GCCCTCATCTACCCACTGACAG

SEQ. ID. NO:16        BF042320
    GGGGTTCAGGATCACCAGGGCCGGTCTGACTTTCAACCCCATGTGTCCGGTGGGGATCTCTGCAGTG

TGTGTCTCTGGCATCTCCTACCAGGGGAGCAGGCTTGACTTCTCCCTCTCTGTGGGCTTCGTGACAGTCGAGG

TCACGGCCCAGGCAGGGCCTTGGGCCCCCTCTCTGGAAGCCGAGCTGTGGCCGTCACGTACTCGCCTCCCCCT

GCCTCCAGGACGGAGAGTCTGTTTTCCCTGCTCAGCGGGTCGGATACAAAGGTCAGGCCTGTAGGCCGCACG

CGCTGGCCCACGAACTTCCTGGGAGGCTTTCTAAAGACGTTGAACAGCTGCCCCGAGCCCGCAGGCCCCGCT

CTGGGACACCCTTGGGCCCTGAAGCT

SEQ. ID. NO:17        BF043074
    CGCTCGGAAGGTCCCCGGTGTGCACTCCTTCAGCAGGCCTTGGGGGAAGATGGCGGCCCTGGGGGAC

GGTCAGGAGCCCCCTCATGTCCTGTCCCCGGTCAGTTTCGAGTCACCCGGGACACCTGGAGGCCACCACCATG

AAGCCCAACTTCACCTCCACCTCCATGGTCATCAACATGCAGCAGCCCTGAGGTGCCCTCCCAGCCCCCACAG

GAGCCGTCAGACCTGGACTTCCAAGAGGTGGCAGAGGTCCAGATCTGCAGAGACACCTGCTGGTCAGGTTCT

GAGTCGGAGCCGGAGCAGGCCCCGTCGTCTCCCAGCCCGCACGGTCCTAAGACGAGGTGCACCAGGCCGGA

GGCGTGCTGAGGACCCTGCTGAGGAGCCTTCCCCGCAGACCCGGGGGTGGGACCGCTTTGGGCAGGAGCCC

AGCCTGGAGCGGTCAGGAGGCCAGACACCGAGGGCTGGGCCCCGTTCCCAGAAGAGAGACACCTGGCTCGG

GTCGCAGGGGCC

SEQ. ID. NO:18        BF044776
    GCCCCGGTCTACTCTGGGGTGGTGCTAAGCCGGCGCCAGATCGACCCTCGACTGAGGAGAGGCAGTG

CGGTTCCTCTAGGCGCTTCTCCGTTGGTTCCTCCGGCTTCCTCAGCCTCCTCACCACCCGCGGGGACCCGAGA

GCTCGGTGTATGCCCCACCCCTGACCCCGCTAGAGACATGTCCACCCCGGCTCGGCGGCGTCTCATGAGGGA

CTTCAAGAGGTTGCAGGAGGATCCTCCAGCCGGAGTCAGCGGGGCTCCGTCTGAGAACAACATCATGGTTTG

GAACGCGGTCATTTTTGGGCCTGAAGGGACCCCGTTTGAGGATGGAACCTTTAAGCTTACAATAGAATTCACT

GAGGAATATCCAAATAAGCCACCAACGGTTAGATTTGTCTCTAAGATGTTCCATCCAAATGTCTATGCAGATG

GTAGCATATGTCTGGACATACTTCAGAACCGTTGGAGTCCAACCTATGATGTGTCTTCCATTTTAACATCCAT

ACAGTCTCTACTGGATGAACCCAATCCCAATAGTCCAGCAAATAGCCAGGCTGCTCAGCTGTACCAGGAGAA

CAAGCGGGAGTATGAAAAACGTGTTTCTGCGATAGTAGAACAGAGCTGGCGTGACTGTTG

SEQ. ID. NO:19        BF046287
    GGAGGAGTAGGACGGGGAAAACACTTTCTCCCCCACAAATTCATCAAAAGAGCATTTAAACGTCGA

GTAAATTCCACAAAACAACTTCTGAATGCCGGCAGAGGACATCAGGCACCGAGAAAAGCAACCCAACTCTTC

GAAAGGAGTTTTTACCAACGCTTCAGACCCGAGTTTCTGGTGAGAAATGGCTTCACTGATGCGTCATCTCCTG

CCGTGTGCAAAAGTGCTGGGCACAGCACCCAATTCCGCAGACAGTGGAGCCAAGTGGGCTGTGCGCAGTGGC

```
GGTATAAACAGCAGCTCTACAGGTGGCCTTCTTTAAGCAATCTGCTGGAAGCATGTTCGGCGTGTCCACCAGT
CTGTCAACTGAAGTTATGTTCAAGAATTTCCAACTCTAGGGAGAATAAATCACACAAGTTCTACCTACCTTAA
AGACGACTGTGAGATTTGAGAGGTACTGAAGATGAAAGCACTTCCAATGTGTGAGGAGTTAAAAAAAATGTT
ACTCATCATTATGATAAAAATAACCATAATGATGAAGATGTTGGTAACTGCTCTAATTGGTTTTCTTTTTGTTT
TATCTCACACAGACCATATGCAATTAAAGCTCTTATTAAATC

SEQ. ID. NO:20      BM362351
      GCACGAGCCCAATCCTCCTCCCACCCTAGTTGCCAATGACCACACGGCTGTTATCAGGTAAATGACC
TTTAATCCAGCCCCTGCCTCGCCCACAAGGCTTCGGGGGTGACAGCCAGGCCCCAGGGGACAGGCCGGGGCA
GGGCCGGGGACCCTCAGCGGCACGATTCCCCAGCGCGCCTAGGTGTTGCGTACGACCAGGGACTGCTCCAGC
TCCTGCCTGCGCTGCTGGATCTGTAAGGAAAGGAGAGCAGGCGCAGGTGACCAGTTGCTGCGCCCCCGGAGG
CCCCCTTCACCTTGAGGTCCCGACTCTGGGAGCGGAGGAGGTCCTGGATGTAGCCCTTGGGGTCTCTGGAGA
AGCTCAGCATGAAGTCCCTCTGGATCTTGAGCTGGTTGATGGACTCAATCGTCTCGTGGATCTGCAGTGCCAG
GCTCCAGCCCCACCTTACTGTCCAGAGCGCTGATCTCCTGCTGGTTGGCCGTNGACAGCAGGAAGCTGCTCAT
CTGTCCCTTCAGGGGCTCCTCCACTTCCACGTCAATGTCGTAGCACGCCGTCTTCTTCTGGTCCGACGGGT

SEQ. ID. NO:21      BM366715
GCACGAGGTCGCAATGGTGAAGCTGAGCAAAGAGGCCAAGCAGAGGCTGCAGCAGCTTTTCAAGGG
AGGACAATTTGCCATCCGCTGGGGTTTTATTCCTCTCGTGATTTACCTGGGATTTAAGAGGGGTGCAGATCCT
GGAATGCCTGAACCAACTGTTTTGAGCTTACTTTGGGGATAAAGGACTGTTTGGTCATCTGGTTTTGGAAGCA
GTCAATGCAGAGGAACAACATGGAAGGTGTGCTCTCTGGCTGGGATAAGAGATGGGACATCGTTCAGACGGT
CACCAGTTGGATGGCACAGGGCTCTTACTTCTCAGATGCATCTGTTGCAGAGTGGAACCTCTACTGACTTATT
TATGATAGACTGTATTAAAATAAATGTTTTTAACAATGTTAAAAAAAAAAAAAAAAAAAAACT

SEQ. ID. NO:22      BM366099
      GCACGAGGTCGCCTGGCCCGCCGTGGTGGTGTTAAACGGATTTCTGGGCTCATCTACGAGGAGACCC
GCGGGGTGCTGAAGGTGTTCCTGGAGAACGTGATCCGGGACGCGGTCACCTACACCGAGCACGCCAAGCGCA
AAACTGTCACCGCCATGGACGTGGTCTACGCGGTGAAGCGCCAGGGACGCACTCTCTACGGCTTCGGCGGTT
AAGTTCCAGGCAGCCATTTGGCATAGTCTAATAAAACCAAAGGCCCTTTTCAGGGCCACACAA

SEQ. ID. NO:23      AW464526
      TGTAACTTTGACCCAGTCTGACTTGGTTTTGTTTTGTTCTGTTCTTTTTCCCCCTGGAATACAGGACGG
GACCAGGGCCCTTGTACTCGGAGCCAAGCTGCTCTCCAGGCATTGTGTAAGCCTCTTGTGTTGTGCTCTCTTTC
AGGTAGGATAATTGCGGACTGAACCCCTCGGGCTGCGGTCATATATGAGAACTTGCTCCGCGCGGTCCCCTTTG
CCGGGATGTTTCCATTGCTTCATGTTTCAGTAAACAAAGGAGTTTGTGACCAACTATGTTTTCTTTCTTAATTT
AATTCTTCTACATTCACTTTTCTCTCCTCCTGGTACTAGTCTCTGTAGCCTTTCTGTTCCTCTCGTTCCCAGCCT
CTGAGCAGCCCTAGGTAAGGATTATGTTGGCGTCCCCTTTCTCCTGTAGAGGGGGATCCCTCTTATCTTGCTTT

SEQ. ID. NO:24      BF046202
      ATGATGCTCTTCAATGATGGCACCTTTCAGGTGAATTTCTACCATGATCATACAAAAATAATCATCTG
TAGCCAAAATGAAGAATACCTTCTCACCTACATCAATGAGGACAGGATATCTACAACTTTTAGACTGACAAG
TCTTCTGATGTCTGGCTGTTCGTTAGAATTAAAAAATCGAATGGAATACGCTCTGAACATGCTCTTACAGAGG
TGTAACTAGGAGATTTCTTGAACGGA

SEQ. ID. NO:25      AW466043
      TTGATCAACCTGCCAATTTGCTACGGATGTTTTTTGATTGCCTGTATGACGAGGAGGTGATCTCTGAG
GATGCCTTCTACAAGTGGGAGAGCAGCAAGGACCCGGCAGAGCAGAATGGGAAGGGTGTGGCCCTGAAGTC
TGTCACGGCGTTCTTCACATGGCTGCGGGAAGCAGAAGAGGAGTCTGAGGATAACTAAAACTTCAAATACAC
AAAACGAAAGAAAAGAAACAATTTAAGTATTTTTTAAAAAGTTTCACGTCTTCGCCAATCACAGTGCAGCA
```

-continued

AGGCCAATTCTCGCAGAAACCCCCACGTGTGCACGAGTGGGAAAGGGAAAGAGAAAAAAAAGGTGATCA

TGGAGGAAAAAGGTACTGGAAAAAAAGTAAACTTCAAACCTGAGGGCGGGAGCACTAAAACCAAAATACAT

GTATTATTTATAGAAAATATTTTCTGTTTTAATCTTTTCTTTTTAAATGAGGACTCATACTTTAAAAAAAACA

CATCTGTTTAGCAAAAAAAAAAAA

SEQ. ID. NO:26    BF040403
AGGGTCCCTTCCACCACCTAGGCCTTTGGGTGGGGGTCTTGGTCCTGGCACCCCATGCACGTCTGCTT

CCTATGAGGCTGAGCAGGGACCAGGGCCTGAGAGGGAGGCGTGGCCCAGGTGAGAGGTGAGGCCTTGCTCA

GGGCCCTGGGCCTCAGTTTCCCTCTGTGAAATGGGGTGATGCAGGTCTGCGGGGGCCGGCAGGGTTGGAGCT

TCTGTTGTTTGGAGCTGCCCACCCCTCCACACGCCCAGGGATGACGAGGGTGGGCAGTCTCACCTCCCGGCTC

CCCAGCCAAACCTGGGGGGCCCATCTGTACCCCTCCTCGTTTTCTGGTGCTGGTTTCCTGACCGTGAGGTCAA

GCTACCTGATCTGACTGGATGTTCAGGGCCTTTTATGTCACTTCTGACCCCTGAACCCTCAGTCCCTTCCATGG

TCTGGGGAGGGGCCACCTGCTTCCACACCCGCTTGTGACAGGCCCAGCAGCTAGATGCGTATCAGCCAAT

AAAGGCCCCCGCCTGA

SEQ. ID. NO:27    BF039168
TGTGGTGTGGCGGCGAGGTGACCTCGAGGCTGCGGTGACCATGGGCCGCCAGTTTGGGCATCTGACA

CGGGTGCGGGATGTGATCACCTACAGCTTGTCGCCCTTCGAGCAGCGCGCCTTCCCGCACTACTTCAGCAAGG

GCATCCCCAACGTTCTGCGCCGAACTCGGGCGTGCATCCTTCGCGTCGCGCCGCGTGAGTGCCCTGGCCGGGC

GGAGAGGCTAGACTCCCATCCACAGAGGGTATTGCGGGTCCCCTCAGTGAGCACTCTGCAGCTCGCCATAAA

CACGCTTTCTCTTTCAGTAGTCCTGAATGCCGTTGAACTGGTCATGTCCTCCGCATCTTACAGATAAAGGAGTT

GGGTCACAGAGAAATGACTGGCTCAAGGTCACTTGTGTGATTCCAGGGTCTCCCTCTGAGCTCACCTTTACCC

ACTTCTTTCCTAGCAGTGAACTGTTTTGTGTTAAAGGTGCAGCAGATTGTGATGATAGTTGCACATTTCGACTT

TGCTAAAACCCACAGAAGTGTAGATTTC

SEQ. ID. NO:28    BM362530
GCACGAGCTTGGTTGGGGGCGTCCCGCATCTAAGGCAGGAAGATGGTGGCCGCAAAGAAGACGAAA

AAGTCACTGGAGTCGATCAACTCTAGGCTCCAGCTGGTTATGAAAAGTGGAAAGTACGTGCTGGGGTACAAA

CAGACTCTGAAAATGATCAGACAAGGCAAAGCGAAACTGGTCATTCTCGCCAACAACTGCCCAGCCTTGAGG

AAATCTGAAATAGAGTATTACGCCATGTTGGCCAAAATGGTGTCCATCACTACAGTGGCAATAATATTGAA

TTGGGCACAGGATGTGAAAATACTACAGAGTATGCACACTGGCTATCATTGATCCAGGTGATTCTGATATTA

TTAGAAGCATGCCAGAACAGACTGGTGAAAAGTAAATCATGTACAATTTTTCTTTAATAAAACTGGCCAGAG

CTTGTTTTAAAAAAAAAAAAAAAAAAA

SEQ. ID. NO:29    AW461980
TTGAAGTTGTCTGAAGAGTCTTCAATCACTATGTCAAGCGACACAGATATTTCTCTTTCTTCATATGA

TGAAGATCAGGGATCTAAACTTATCCGAAAAGCTAGAGAGGCACCATTTGTCCCCATTGGAATGGCAGGTTT

TGCAGCAATTGTTGCATATGGATTATATAGATTGAAGAGCAGGGGACATACTAAAATGTCTGTTCACCTGATC

CACATGCGTGTGGCAGCCCAAGGCTTTGTTGTGGGAGCAATGACTCTTGGTATGGGCTATTCCCTGTATCAAG

AATTCTGGGGGAAACCTAAACCTTAGAAGAGGAGATGCTGTCTTGGTCGTCTTGGTGGTGCTTGCTTTAGTTA

GACATCTCATATTGA

SEQ. ID. NO:30    BM364411
GCACGAGAGTGGAGCCGCTGGGCCGCAGCCGGGAAGCTTAGATGTGGAGGCGCTGAGACTTAGGAG

ACACCTGGGGCCGTTAGGGAGACTCAGGTGGCGGGACACTGGTGGGATCCCGACCTGACCCTGGGCCAGTCT

CGTTCTCGCGGCCCGCCTCCTCACCCCGCCCCCACTTGGGGCTGAAGTGGCTCCGCCTCCTGATCTGAGCCTG

GTCCCTCTTCAGGCACTGACCCTTGACCTCGGGGCGCTCCCCCATCCTTTGGGCGCGATGGCTACAGGCGCGG

ATGTCCGGGACATTCTAGAACTCGGGGGTCCAGAGGGAGACGCAGCCTCTGGGACCATCAGCAAGAAGGAC

-continued

ATTATCAATCCGGACAAGAAAAAGTCCAAGAAGTCCTCGGAGACACTGACCTTCAAGAGGCCCGAGGGCAT
GCACCGGGAGGTCTATGCACTGCTCTACTCTGACAAGAAGGACGCGCCCCCACTGCTACCCAGTGACACT

SEQ. ID. NO:31  BF039456
TGATTCAGAAATAGAATCGCTCTGATGTCTGAAGGTCCCATCGTCCTCAAAACTAAAAAGTTCTTATT
GAACCGTCTTCTCTCCAGGAAGCAAATGGTCTTGGAAGTCCTCCACCCAGGCCAAGCCAATGTTTCCAAGGA
AAAGCTTGGTGAACTCATTGCTAAGAAGTTCAAGGCTGACGCCAAGAACGTTGTCACCTTCGGCTTCCACACT
CACTTCGGTGGTGGCAGAAGTACTGGATTCTGCTTGGTATACGACAACCGTGACTACTTGTTGAAGTACGAAC
CCAAATACAGACTCAGAAGACTGAAAATCTTGGAACCAAAGCTTAACAACAGAAAGGCCAGAAAGGAATTG
AGAACCAAGAGAAAGAAGGTCAGAGGAAAGGAAAAGTCCAAGATCCAAGCCGGAAAGAAGAAGTAAAGTA
TCATATGCTCCCTTTATATGGCTGGTCGACTCGGAATATTTTCTGTCGTATTTGTTCTTTTCTATGTGCGCGTAT
AGTTCATGCATGAATCTGAAAACTGAAACCATAATTTAGCAAACAAAAAG

SEQ. ID. NO:32  BF042632
GCCGTCCAGACAGCAAGACAGAAAACCGGCGCATCACACACATCTCTGCGGAGCAGAAGAGGCGTT
TCAACATCAAGCTGGGCTTTGACACGCTGCACGGGCTGGTGAGCACACTCAGCACCCAGCCCAACCTCAAGA
TGAGCAAGGCCACCACGCTGCAGAAGACGGCCGAGTACATTGCCATGCTGCAGCAGGAGCGCGCGGCCAAG
CAGGAGGAGGCCCAGCAGCTCCGGGACCAGATCGAGGAGCTCAATGCTGCCATTAACCTGTGCCAGCAGCA
GCTGCCTGCTACCGGGGTGCCCATCACACACCAGCGGTTCGACCAAATGCGAGACATGTTCGATGACTATGT
CCGGACCCGCACGCTGCACAACTGGAAGTTCTGGGTATTCAGCATTCTCATCCGGCCCCTGTTTGAGTCCTTC
AACGGGATGGTGTCTACAGCAAGCCTGC

SEQ. ID. NO:33  BF044457
TTGGGAGCAGATCATAGCTGCTAGGTTAAGAAATTGATTCTCCCGCAGAAACAATGGATTTCGGTGT
AGCGGAACTGTTACGTGGAGATGCTAAGATGCAAAGGTACATTTCAAAACACGCCGGACAATATTGGCTGGA
AAATGACTTGGTTAAAACCTGATGATCTTACCAGCATTCTGCAGGTTGATGAATACTAATGAAGCTGTGGATG
TCACTGAGCAGCTTCATTTTAAATGAGGGGTTGCTGTCTGCCTGCTGTCTGCCTGGTGTGCTGTGACATTTTGA
AGGTGGAAACATTTCTGGCTAGTGCTGCGAGATTTACTTGTCTGTCTTATGAAAATCTGGTGATTGGGAAAAC
CTCCAATGGATGTGGGAAGAAAGTTCAAGATGAATTACATTTTTACATTGGTTTGTAAATAGATTCTGAACCA
GCATCGAGTCTAGATAATGCAT

SEQ. ID. NO:34  BF040573
GAGACCATGGCCTTAAAATACCTCTTATTAAACCCAGAACATGGTCTTAAGCAGTACCATATTACTTC
TTGATAATAGTGTTAAATCTTTTATGCTTTCAGTGAAGGAAAGGAAAAGTCTTGGATCAATGAAACCCATGTG
TGACTTGTCTTATCATCTTTCTCCAGGGCCCTCTTCTTTGATGCAGTTATGCCGCCTTAGAATTCGGAAGTGCT
TTGGGATCAAGCAGCATCATAAGATCACTGAGCTCAACCTCCCTGAGGAGCTGAAACGGTTTCTCCTCCACAT
TTAAATGTGTCAAGCGAATGGCGACACAGACAACAGACAAATGTTATTGAGTGTTGAGACCACTGGGATTTT
CAAGTTAAGTCAGGTTTATAGAGTTCAGCTAAGTTTTTGTTGTTTGCAGTGAGACGTTTATTGTAGCTTCGTAC
TAGGTTCTTTTGCGCTGTTGGTTTGGAGGGTATGAAAAATTATCTCCCCTGCCTGGAAGAGGGTGGCTANGAT
ATCCATGGTGTTGAATATCTTACCCAGCACTGAGCTGGGAACCCTTTATGCTTTGTCTAATTTAGTCCCACTCTT

SEQ. ID. NO:35  BM364731
GGCCTCGGGTGCCTACCCGGCGGTGTGTCGGGTGAAGATCCCCGCGGCCCTGCCCGTGGCCGCCGCC
GCCCCCTTTCCTGGGCTGGCGGAGGCCGGCGTGGCCGCGACTCTAGGTGGCGGAGCCGCTCTGGGGTCAGGC
TTCCTGGGAGCTGGGTCTGTGGCGGGACCCCGGGGGGAGTCGGACTGTCAGCCGGAGGCGCTGCCGCCGGC
GTGGCTGGTGTCGCCGCCGCCGCCGGAGCCGGCGGGGAGATGGCTTTCGCCAAGGGGACCACTTCGTTG
CCTACTGAGACCTTCGGGGCCGGCGGCGGATTCCCTCCTCTGCCGCGGCCTCCTCCTCAGTTGCCCACTTTGG

-continued

GCGCTGGCCTGGGAACAGTGGACGAAGGTGACTCTCTGGATGGACCAGNATACGAGGAGGAAGAGGTGGCC

ATCCCGCTGACCGCTCCTCCGACTAACCAGTAAGTCAAGACCGGCGTTTTGGGGAAGCTGACTCGTCGGAA

AAAAAAAAAAAAAAAA

SEQ. ID. NO:36    BF042198
GTTGGCCTCAGGGTTTTTGCTCATGGTTTCCTCAGTGGTGCTGTCCGAGAAGTATTCAGGTGGTGACC

ATCACTGGTATGAGTTTCTCAGCAGGGTTAGGGCATATCTTTGCATGGACTTCGGTGGAATCATTACTGATTA

GGAGGACAGTTGTTGGGGGCCATCTGCCCTGCACAGGAAGAGATCTTGGACTCATGAAATGAGATACCCCTC

ACCCCCGAAGGGACCAAATGGAAACTGACATCAGAAACTCTGATACAAAATCATTTTAATTGCATCAAATGG

CCTTAATTCTGAGTTTGGTAGGCTTATCAATATGTTGCTTACAGTTGGGGTAGGGGAAGTAGAGGGAGAGAA

AGCAAGACATTTATTTACTAAGCACCTCTTAGGTGCCAGACGCTAGGCTAAGCACTTTACGTGAGCTGGGTCA

TATAAGCCCTGTGAGAACCCTGTAAGGAATGTTACTAGTATTTACACTTGACAGATGAA

SEQ. ID. NO:37    BF045424
ATGTGGGCAGACTGCCACAGTCCTCAATAGAATGGCCCTCTTGCTCCCGAACGTCCTGAAGCCACCA

GTCAGAACTGTAACGTACTGCAGTTCGAGAAAAGGCAAGAGGAAGACTGTGAAAGCTGTCATCTATAGGTTT

CTTCGACTTCATAGCGGCCTGTGGCTAAGGAGGAAGGCTGGTTATAAGAAAAAATTATGGAAAAAGACGGTT

GCAAGAAAAGACGCTTGAGGGAATTTGTCTTCTGCAATAAGACCCAGAGTAAGCTCTTAGATAAAATGACA

ACGTCTTTCTGGAAGAGGCGAAACTGGTATGCTGATGATCCTTATCAGATGTATCATGATCGAACAAACTTGA

AAGTATAGATCAGAAGATCCATGATTTCTCAGTTATTAACTGTATATCTGTGTGTATGGTGTCTTTGCAAA

GATGAAGTGGTATAAGACATGATGTAAATTGTACCAACTGATACTTGGAACATGGGGTACCAACATTAAACT

TAACAATGTTTTAAAACTTAATGGA

SEQ. ID. NO:38    BF039771
TGGGTCGGCATAGCCATGGCGGCTCGTGTCCTTTGCGCCTGTGTCCGCCGACTTCCCACGGCCTTCGC

GCCGCTGCCCAGGCTCCCCACGCTAGCCGCGGCCCGGCCGCTCAGCACTACCCTCTTCGCCGCGGAGACCCG

GACGAGGCCTGGGGCTCCGCTGCCGGCCTTGGTGCTCGCGCAGGTTCCAGGCAGAGTTACACAGCTGTGCCG

CCAGTATAGCGATGCACCACCTTTGACATTGGAGGGAATCAAGGACCGTGTTCTTTACGTCTTGAAACTCTAT

GACAAGATTGACCCAGAAAAGCTTTCAGTAAATTCCCATTTTATGAAAGACCTGGGCTTAGACAGTTTGGAC

CAAGTGGAGATTATCATGGCCATGGAGGACGAATTTGGGTTTGAAATTCCTGATATAGATNCGGAGAAGTTA

ATGTGTCCACAAGAAATTGTAGATTACATTGCAGATAAGAAGGATGTATATGAATAAAATATCAGACCCCTT

TTCCTCATTGAGAGAAGGCTTNNNAGATGCTGGCGAGTGTCTGGCGGTGAGAACGCATTTCTGCATCATTGCT

GACTTTGCGAGTAATTCTGTTTAGACTT

SEQ. ID. NO:39    BF041569
ATACTGGTGTGGTCAGGCCCTTTTCCTTTGAAGAGGTAAGGTGAATCTGGCTTATTTTGAGGCTTTCA

GGTTTCAGTTTTTTTGATCTTTAAAGTATCCTTCAACCTGTGGTGCAAAAGCAGAAACTATGGCTGGATTAGN

TNATGAATATTTACGNNNNTTGTAAATTAACTTTTTACATTGAGAACAGCACTGATTAGGGAGATGATCAGAT

TCTTTTTTAAATACACTGTAATGACCTAGTGAACATAGGCATGTAGTGGTTTTGTGTGAGGGTAACCAGACAC

AGATTTACTTTTTGCCTTNAAGACAAAGGGAGATAAAAGCAACAAG

SEQ. ID. NO:40    BM366529
GCACGAGGTGAAGCTGAGCGTGTACTTGGATTACGCCAAGGCTGTGGGACTCTGGACCGCTCTGGTC

ATCTGTCTGCTGTATGGGGGTCAAAGCGCAGCTGCTATTGGGGCCAACGTGTGGCTCAGTGCCTGGACTGATG

AGGCTGCGGTGGACAGCCAGCAGAACAGCACCTCCTACAGACTAGGTGTCTACGCCGCCTTGGGAATTCTGC

AAGTGACTCCCTGACCCGCCCTAGCAGTCTACCTGCCTCTGGACCTGTCTGGCTCATCCTAGCTATGCCCTGC

CTTTGAGTGACATGCCCAAGGTCATTGCTAATATGAGGCAGAGCCCAGACTAGTCCCCGGGTCTTCTGATTCC

CAATGTGGCGATATTTCCACACTGTACTGCTTATAATCATTTCAAGGGATGACCTCCCTACCCCCATGATTTTT

-continued

TGTATTTTCTAGTCTGAAGTGTTTTTCGTTTTGTTTTTAAATAAAGCTTTCTCCTCTTTGAACAGAAGACTGNN

AGGTCAGGCCATCCCTAGGAACTGAGTCCAATACTCATTAAAAATGGAGCACTGATGAA

SEQ. ID. NO:41    AW465571
GGCGCTAAGCCTTTTTTTTTAAGATTTTTCAGGTACCCCTCACTAAAGGCACCAAAGGCTTAAAGTAG

GACAACCATGGAGTCTTCCTGTGGCAAGAGAGACAACAAAGCGCTATTAACTAAGGTCAATCAAATGGTGT

CGGCGTCACAGCCCCATCTTCTGTTAGAAATGAGGACTTGACTCAACCCCCTTGACAATGTGCATTGAGGCTC

TCTGGGGGAGCGAGCATTTAAAGGAATGCTTGAGTACCTTGTATATATATCCCTGTGCTTGTCCTAATATTTA

ATTTGGCTGTTTTCATAGCAGCTGTTAATGAAGCCTGAACTTCAAGTGATGCTTGAAGGGGAGGGAAAGGGG

GAAAGCGGGCAACCACTTTTCCCTAGCTTTTCCAGAAGCCTGTTAAAAAGCAAGGTCTCCCCACAAGTGACTT

CTCTGCCACATCGCCACCCTGTGCCTTTGGCCTAGCGCAGNCCCTTCACCCCTCACCTCGATGCTGCTGGTAG

CTTGGATCCTTGTGGGCATGATCCATAATCGCTTT

SEQ. ID. NO:42    BF043043
GGCGACTATCCCTACTTTGAAACGAGTGCAAAAGATGCCACGAATGTCGCTGCAGCCTTTGAGGAAG

CAGTTCGAAGAGTGCTCGCTACCGAGGATAGGTCGGATCCCTTGATTCAGACAGACACGGTCCGTCTGCACC

GGAAGCCCAAGCCCAGCTCGTCTTGCTGTGGAAGTTAGAGAGGTAGCCAGTGCAACCTGACCAGCTCACCCA

CATGCGCAGATGGGCTCTGGGCGGAGAAGAGGGTACGCGTGTGCAGCAACGCATCACATACTCAACCATTAA

CCGTGCTGCTGCCTGTCAGTGGGTGGGGAAGCGACACATCCCCTCATGGGAGAATCCATTTACTCAGTAAT

GGCGCCTGACACGTACCCATTGTAACGGCTGTCTAATAATGTTTAATTTAAATATGTATGTTACAGAGCTAAT

AAGTGAAATGACCAAGACTTTATAATTAAAACACTTAAGTATCCTAGAAGTTACTGTCTTTTCCCTGGGAATA

TGGAGAACTACTTTTCTATGTGTATATTTTATGTAATTAGCATTCTGTTCCTGGTTCAGGGAAAGCATGT

SEQ. ID. NO:43    BF043765
GCAAAACCCTCTTTCAGCATGGCGCATCTGGATAGCAACACTGAGCCAGGACTTACATTGGGAGGCT

ATTTCTGCCCCCAGTGTCGGGCAAAGTACTGTGAGCTTCCTGTCGAATGTAAAATCTGTGGTCTTACTTTGGT

GTCTGCTCCCCACTTAGCACGATCTTACCATCATTTATTTCCTTTGGATGCTTTTCAAGAAATTCCCCTAGAAG

AACATAATGGAGAAAGGTTTTGTTATGCCTGTCAGGGGGAATTGAAAGACCAACATGTCTATGTTTGCAGTG

TGTGCCAGAATGTGTTCTGTGTGGACTGTGATGTTTTTGTTCATGACTCTCTTCATTGTTGTCCTGGGTGTATTC

ATAAGATTCCAGTTCCTTCAGGTATTTGATTCCAGCATGTAATACACATTGAATGTATTAAAAAGAAATTTGC

AACTGTAAATAAAATGATTCTTTAGTAGAAACTCCAGTTAAAACACGAAGAACAGTTTGAAAGGANAAAAA

AAAAAAAAAAAAAAAAAAAAAAAAAAAA

SEQ. ID. NO:44    BF044823
TGTTACCATTCTCTTCATTAGTTGTATCTGATCGACTGTCTTCTTCAATATCTTGCATTTGTCTGGTTTT

ACACTTAAGCTGTCAATGTCACTGATGTTGGCAGACAATAACTCAGCTAGCTCTTCCAAATATTTATTTTCTTG

CTCCCTGCGCGTCTTTTCAGTGCTTGATGCGAGTGTGTCACATGGTGACCCTTTTCTCTTATGTGAGTCTGGGT

TAGCAGGGTCAGATGAACTGTCCCCAAGGCCACTCATGTTGAAAAACTTCACACCTGGGAGACTTCTTTGTTC

ATAATGAGTCCTCAAAACAGATATGGTCAAATATGGTGCTCCGTAGGGTAGTTTCCAGTGGAATGGGGGAAC

ACTCTTTTCCAGAGATGGCTCTAGTAAGTCTCTTCACTCTTACCTCATTTAAGGCCAGTTATGCAAACAACTTG

AATACCTTAGAGTAAGTAGAAGTTATAAATGTCGGTGTCTTCATTTGGAAGCAAAAATTCTTACTGCCTGATG

TTGTCTGGTGGTCCGTGATTTTTATCATCAGAGTCG

SEQ. ID. NO:45    BF044893
AGGCGCTGCAGAAAGTGAAGATTGAGGTGAATGAGAGCGGCACGCTGGCGTCCTCCTCCACAGCCC

TTGTAGTCTCAGCCCGAATGGCCCCCGAGGAGATCATCATGGACAGACCCTTCCTCTTCGTGGTGCGGCACAA

TCCCACAGGAACTGTCCTGTTCATGGGCCAAGTGATGGAACCCTGACCATGGGGAAGGCAGCCCTCATCTGG

-continued

GACAGAATGGAGATGTCCAAGAGGAAGAAAGTCCGGAGCAAAGAATTTTTATTAATTCATTTTTCTGGAAAA

AGAGAAGATGTTTATTTATTTATTTTTCCATGGTAAATTCTTTTGAATCTGCCTCTTAGACCTAACTCTGGGCT

CTCTCAGGAGGGGCAAAGAGGACCTTTGAGTTAAACCCTCCAATGGAGACCCTGGGAAAGACTGGGAGGCA

TAACACCCAGCGGGCCTCCCAACTGGACTGTAGGACTCCCAGGACCGCTGGCCCAGCTGCTTCTGCCCATCGT

TCTGCCTGGTTGGGTTTTGGGTCCTGGATCCCACCGANNCCCTGGTAGGATGGCACCACAAGGCCTACATGAA

GGAGCTTTTGTGTGTTCA

SEQ. ID. NO:46     BF046610
CGTGGCCCCCAACGTGGCCCTGGCCCCGCCAGCCCAGCACAAGGCAGTGAGCAGCCCACCCTGTGCC

ACGGTCGTCTCCCGGGCCCCTGAGCCCCTCCCCGCCTGCATCCAGCCCCGGAAGCGGAAGCTGCCTGCGGAC

ACCCCTGGAGCCCCGGAGACACCAGCACCCGGGCCTGCCCCCGAGGAGGACAAGGACTCGGAGGCCGAGGT

GGAGGTGGAGAGCCGAGAGGAGTTCACCTCCTCCCTGTCCTCGCTGTCCTCTCCATCCTTTACCTCATCCAGC

TCCGCCAAGGACCTGAGCTCCCCAGGCCTGC

SEQ. ID. NO:47     BF440261
TTTTTTTTTTTTTTTTTAAGAGTCATACCATGTTTTATTGGACATCTTAACATGGGTGTGGGTGGGA

CCTATGGGTTGGACAGGGCACCAATGACAGCCTCAGTGAAGTCTTGGCAGNNNGCATAACCACCCATGTCAG

AAGTTCGAACCTGTAGGGGAGAATTGTTATCATCTCTGTGGCCTGGGCCCCATCCCTAACCCCCCACCACCTA

ACTGTTCCCTAAGGAAGCCAGCTCCCAACAACCTAGGCTCTGCCCAGAAGGTAATTATGGTCTAAAAGTATA

GGGCTCTTCTCTGGTCCACAGTACTGAAGGGAGGTGTATGGTCGTTGTGAGGTTGGAGGGAATAAAGGGCTC

TAGCCCCCATAGGGGTGCAGGTGGCCGATGACAGACTTGATGAAGTCGGTTGTGGTGCTGTAGCCGCCCATG

TCTCGAGTCCGTACCTTGCCAACTTTAATCACCTTCTTCACTGCCTCTGCAATCATGTTGGAGTGATGCTCG

SEQ. ID. NO:48     BM362515
AGGCCCTGCCCCATCTGAGTCGCAGGAGAAGAAGCCGCTGAAGCCCTGCTGCGCCTGCCCGGAGACC

AAGAAGGCGCGCGATGCGTGCATAATTGAGAAAGGAGAAGAGCAATGTGGACACCTAATTGAAGCCCACAA

GGAGTGCATGAGAGCCCTGGGATTTAAGATATGAAATGGTGAGCATGGTGGTCTGCTCTGGGAGTGAATAGT

TCCTGAAAAATGAAGAAGATTCAGTAACTTTGGGAGTTCCTTGCTGAAAATTGATAAATAAAAAATTATTTAT

AATTTATTAAAAAAAAAAA

SEQ. ID. NO:49     AW465165
TTTTTTTTTTTTTTTTTTTTGAATTTTTATACAAGTCTTTATTTACAACTTGTTTAACAACTGTACACT

TTTTGCAGCCTTGAAAACATTTTTGTACTTGAATGGGAAAATATAGTTTGACCAAATCTTAACTTTATTCTTCA

TATACATATACATATATTATATGCATACATATAAACATATACATATAATTAATACCATAACAAGTTGGCAGTC

ATAAAATTAAATGAATAAGTGACATCAAAAGGAAATACAATATAAGATTTCAAAAAATTAAAAATCTGTCT

TCTGGGATTTCTTGGACTTCATGTTTTT

SEQ. ID. NO:50     AW464987
CTTTAGTGCCCCAAGCTCTGTATTAACATTTTGCCTGAATTATTCTATTAACCATTCTAAGTGTCCTTC

AAGAGCGGAAATGGAGGCATGGAGATGACATTAAGTGCTATATTTGCTTCTTAACATGGCAGGTCCCCACTC

TCTCAGGTAAAGCCACTTTGATGATATTTTCCTGCTCCTGTCTCAGGGAAGATGTAGGATGGAGGTACTTATG

AAAACAATATCTTTTTCATGACAGATGGGAAAGTGAGGCATGGGGACACTGTAAGCACAGTATTATAAAAA

ACAAGAACACAGAGGATGCTGGTTCTGTTACTTATTTCCTTC

SEQ. ID. NO:51     AW462906
TCTTTCCCTAAGACGTACCCGGGACATGTCTTTGGTGTGTGGTGGAGGCAGTGAGACGTGCCTTGTCC

TTGGGTGCACGCCGCCTCCTGTCCACCTGTAGTTGATCGTGGTTTCATAGTGGAACTCTAGCTAGCTGGGGAG

AAAGAGAATCTCTGCAGCAGGAATCCCGTGTCTTCAGATGCAGGTCAAACCGTTAAGGAATTCCCGGAATTC

```
                         -continued
CCATCTAAATACTGAGACAGGAAGGAAGCCAGATGGCTAACGCACAGTCACTTTGTTAGTTAGGGCAGCATT

AGAAATCGAGCTTCCTAAAGTGTTTTCTTCTTCGTAGC

SEQ. ID. NO:52    AW463449
         GAGCAGCGTCAACGTAGGCAGCGGCTGTGCAGAAAAAGGGCCCGAGGAATTGTCTCAGGAACCTGC

GCGCCCCGGCACTAACATTTCGAGGGTGAAGCTTTTCGACACCATGGTGGACACTTTCCTCCAGAAGTTGGTC

GCTGCCGGGAGCTTCCAGAGGTTCACTGACTGTTACAAGCGCTTCTACCAGTTGCAGCCTGAGATGACCCAGC

GCATCTATGACAAGTTTGTAACTCAGTTGCAGACTTCTATCCAGGAGGAAATCTCTGAAATGAAAGCTGAGG

GAAACCTGGAAGCTGTCCTGATTGCATTGGACGCGATTGTGGAAGAAAGCAAAGACCGCAAGGAGCAAGCC

TGGCGCCCCAGTGGGATCCCGGAGAAGGACCTGCGCAGCGCCATGGCGCCCTACTTGCTGCAGCAGCGGGAT

GCCCTGCAGCGTCGTGTGCAG

SEQ. ID. NO:53    BF040406
         AGGGTGTCGGTCCGCAGCCCCTTGGGGGCGAGCGCGGCACCCCTGTGGCCTCTGCAAGTGTCCGTGG

CGCGGCCTNNNGGGTGGGTGGGGGAGGCTTTGCACGAAAGATGTCCAGACTCTGCCCCTGTCCCACCAGCCG

CTCCCCGCCCCCCGCCCCAAACAACTCAGCGACATATCCAGGCCAGTGTGGGGTGGGGAGGCCTCGTGTTAA

CCTGAGCACTGTGGGGAGGGCCCC

SEQ. ID. NO:54    BF042130
         ACAAAATTTTATTGTAGGGTTGCTTTTTATGGGTTATTGAAATTACAAAAATAAATGAAGCATGCTTT

GTATCACCAAGGTTATTGACTTTAGTAAGGGTGATATACACGTAAAAAAGGAATTACAGTTCAGTAATCTTGC

TATAATAGAGGTATGTACACAGCACTGTTGGAATATTGAAAAAGGTGTGACTTTAATTGCAGGGTCCCTGAG

GAAGGTTTCGCAAAGTAAACATACCCTGGCCCCAAANNNTCCTTTCTCCTCTTCTTCAAATGAAAACCTTTTT

AAGTTGGAAAAATGGCACCTAAGGCAATTCTGGAGTCTAGGAAGGACCGATTGCAGTCAGCCACTGTTTGGG

CTAAGCCACTCC

SEQ. ID. NO:55    BF043536
         GAAGTGCTGACCCGGGTTCTCTCAAGCCCCCAGGTGCCCCGGGTCTCCCACCCGCCTTCACCATGGA

CTCGGGCCCCCTGGGGCCCCCAGCTCCAGTTCCCACAACTCAGGCAGGCTGGTCCAGGCCCTGGGCTGCCTC

AGTCACCAGCCCCCAGGGAGGAACCGGCCCCTCCCAGGGAGCCACTTCCGAGTTTTTAGAAAAAGTTATC

TCCCATTTCTTTTCAGCCAAGATGTTCAGTAAATATTTTTAGTACAGCACTTAGTGGACCACTTCCTAACTGTG

CTTTCTTGCCACACAAGTGTCCTGGCAAGAGCCCCTTCTCTTTAAGACATCAGGAAGCCAGCCAGACCCTTTT

GGGTCAGGAGCGCTNTGCAGCCCCAATAGCAAGGCTGTCTGTGTCTGAGCTGCCGGCCCCCCGGAAGCCCAG

GACCCCCAGAGGAAGGAGCCAGGAGAGCACAAGTCTCTGGAGCTGCAGCCCCACCCATGGTTG

SEQ. ID. NO:56    AW464569
         GTTCTAGAATTTTTAAATTATGGAACATTAGTCAAGTTTTAATTTGGACATATGTTGAAATTCTTCAC

ATACACATTTTGTCCTCATATATATGAAGTTGGGGCTTAAATATCAGTATTCTCAGAATATCATTAATTAATG

AAATTAATTAATTGATTAATTGGATTTGTGTACCTATTTGTCATGCAAAAAATTCCTTCAGGTCTTCAGAATTC

TCAACTACCTATGATTTTTTTTTACTGTCAACTCTTTTGACAGCAACTGGTTAAAGAAATTGATCCAAAGAC

TTAAGAGGCAACTTCTTCCTTGGTTTATGAGTGCACTTTCATTTATACCAGAATAAGCATGTACATATAGGCA

CTATTTAAGGTATTTAGCAGGTAGTAATATCTAGCTTGGACCTTAGTTCTCTGACAGAGTAGGTTCTGCATGT

CAGGTGTTGTCTCTGTAGTTTTTGTGGAGCATGAAATATATAAACTCTGACACCTCGGCTAGTATACATATTG

GAAGTTAACTCACTTTCAGNTGTTGAGAGTTAAATAACAATGTTTGTAAG

SEQ. ID. NO:57    BF040351
         AGATTTCAAAAGGAACTGCTCGAGTTCTGAAGGTGAGCCCAGCCTTTCTAAACCTCTTCTCAGAAAA

GGGAAACTGACACTTGAATTTTTGTCACCCCTTTCCTCATTGGAAGGGAAGGAGCCTTAGAAGATTTTTCTTT

CTAACTCTGGTCTTAGGTAAATATATTCTAATAAAACATAGGCTACTCTAACAACATAGAATTTAGATGCCTC
```

ACGTACGTGAGAAAATCTTGAATATAGGACAAGGGTCCTGCTTTTTAAAAACAGACTCAACTGAGCTGATTA

GATGACGTGAGGCCGCTTTGCCTTCAATAACATGAAGTTTTGGACAGTTCCTACTCCTATTTGCAGAAGGAAA

TTGGCTGAAACATACTTTAACCATTTCAAAGAAGGTAAAATTGGACCTTAAAAGGTATCAAGAAGCCAGCAT

GGTACTTAATTACAACATAACATTTTGACCTTAATGGGAAGTCATTTTATTTGCACTAAAGGCCTTGCTTGCTG

AAGTCTCTTAACTCTTATCTGTAGAACTTTATTTCTTCCACTAGTACAAGGAGAGAGAAGAGTTCTTATAATT

GAATGTTATCATAAAGAGGGAATGGA

```
    SEQ. ID. NO:58    BF440195
        TTTTTTTTTTTTTTTTTAAATCAAAGACTAAGAACAAGTCAGGAGCTAAGTGACTTCTGAGTTCAATG
```

ACTGACCCATCAGAGATTAGCCAAGGCCTCTCAGATGGTCTGCCAAGCCTTGCGTTGTAACACTGATCTTATA

ATGTGGCACACTTGTCCTTTTCTCACAGAAATATAGGTATGGGAAGTGGATCATATATGGGCAGTATCCAGCC

CAGAAGTAACTCAACAAAGACATTGTAAACTTCTTACTTATATGTTTAATGAGAACCATATGTATCTGCAGTA

GAACCTACCAAATAAGAGCACCTTTGTTTTCTTCTTTCTAGAGAGGTAATTCGGGGGATCTGACGGTGGAACT

GCACACATGACCAATGTAGAAGATCTAGACAAGTACCCTAGGGGTCACGTGGCCCCAAGAGTCGGGTCTGAA

GAGCCTCAGGTGACCCTTCTTACTTTGAATGTGTAAATTCTACTCCTCAGTCCTAGGGGGTGGAGCAATCA

```
    SEQ. ID. NO:59    BM362654
        GCACGAGGGCCGATGCTCTCAAGAGTATCAACAATGCCGAAAAGAGAGGCAAACGCCAGGTCCTTA
```

TTAGGCCGTGCTCCAAAGTCATCGTGAGGTTTCTAACAGTGATGATGAAGCATGGTTACATTGGCGAATTTGA

AATGATTGATGATCACAGGGCTGGGAAAATTGTTGTGAACCTCACAGGCAGGCTAAATAAGTGTGGAGTGAT

CAGGCCTAGATTTGATGTGCAACTCAAAGATCTAGAAAAATGGCAGAATAACCTGCTCCCATCCCGTCAGTTT

GGTTTCATTGTACTGACAACCTCAGCTGGCATCATGGACCATGAAGAAGCAAGACGAAAACATACAGGAGGG

AAAATCCTTGGATTCTTTTTCTAGGGATGTAATACATACAAATAAAATGCCTCAGAGGACTCTGATGCTTC

```
    SEQ. ID. NO:60    AW462632
        TGTCTCCGTTCGGGAGCCTCACAGACATATCTAGGTAAGATCGTTAAATAAACGCCGTCAGCCA
```

TCGCAATGCAAAAATAAATATCAATCCTCCGGCCACAGCGCCAGCTGCGCTGCGCCCCAAGTCCCATCGGCC

GCGCCTAACAATTATAAAAGTGTTCAGCGAGAGTGGGTCGGCGTGAGTGTGAACGGGTGTGCGCGCGGGGGGT

```
    SEQ. ID. NO:61    BF040216
        AGTGTTCTTGCCTAGGAAATCCCATGGACAGAGGAGTCTGCTGGGCTACAGTCCATGGGGTCACAAA
```

AGAATCAGAGACAACTAAGTGACTAAACAATAACATTAAGATGACAGAGAAGTTCATCAGACTCCTCATAAT

GTTGGGCCTGGAGTACTGAGCTCTGGCGTTAAGCACTGAGCTGTGGTGTAACAGCCAGAGACTAAGTGGAAC

CTTAAGACCTGAAAAGTGAAAGTGCCCTCCTCTAACTAGCTAATTTAGTGCACAGGCACATCTTAGAGTGTGG

AGAGAATGCAAGCCCATTATAAGTGAAGAGCTCTTGCTGCCCTNGAGGGGAATAAGTTAAAGAGATTCCATC

AAATGAATTTGCTCAACTGCAGCAAGNNNTCCATTTTATAAATATCAAATCTAGGCTAATAATGTNGCTGAAT

TGCTCTCTGAAATAACCGTGCCAACCAACAGCAATACTTTTATCAGTGATGAGGAATAGCTACTGCACATAAA

GTAGAATAAATGCACATAAAGTAGAATAA

```
    SEQ. ID. NO:62    BF045874
        AATTACTTCTTAGAAGTTTGGGAATTACCTTCCATCAATTCAGCTAAGAACGGAATGGATTCTGGTAA
```

CAAGACGATATAATTCTCTCTCAGTTTTTCAGCCANNNCTAACACAGTTATCAGAGCAGCAAATCGAACCTGA

AAAGATGAAGAATCATTNNNTAAAAACCAAAGAACTATTATAGCTCTGTTTGTTAATTTATGATCTAACTTGA

GACATGCTCTGAATCTTAAACTGGTATTTCACTCTCCATTCAAGCTTCATCTTAGCATACCAGTTCATTTAACA

GTTTGAGATCTGTTTAATAACACGGGCAACCTTGTAAGTCACAGCCTTTCAAT

```
    SEQ. ID. NO:63    AW461973
        ATGCACCTCCTAATACCATCACTTTGTGTGTGTGTGTGTGTAAGGACGCGCACACGCACGCATG
```

TGTATGCTCAGTCATGTCCAACTCTCTGCAGTCCTATGGACTGTAGCCCACCAGGCTTTTCTGTTAATGGAATT

TTCCAGGCAATACTGAGTGGGTTGCCATTTCCTACGCCAGGGTATCTTCCTGACCCNNNAATCGAGCCTGCAT

CTCCTGTGTCTCCTGCATTAGNGGCAGATTCTTTACCACTGAGCCACCTGGGAAGCCCCATTTTTGGAATTTA

GAATTTCCACATAGGAATTTTAAAGGGACACAAATATTCAAATCATGGACCCT

```
SEQ. ID. NO:64      AW461973
ATGCACCTCCTAATACCATCACTTTGTGTGTGTGTGTGTGTGTAAGCACGCGCACACGCACGGATG
```

TGTATGCTCAGTGATGTCCAACTCTCTGCAGTCCTATGGACTGTAGCCCACCAGGCTTTTCTGTTAATGGAATT

TTCCAGGCAATACTGAGTGGGTTGCCATTTCCTACGCCAGGGTATCTTCCTGACCCNNNAATCGAGCCTGCAT

CTCCTGTGTCTCCTGCATTAGNGGCAGATTCTTTACCACTGAGCCACCTGGGAAGCCCCATTTTTGGAATTTA

GAATTTCCACATAGGAATTTTAAAGGGACACAAATATTCAAATCATGGACCCT

```
SEQ. ID. NO:65      AW461973
ATGCACCTCCTAATACCATCACTTTGTGTGTGTGTGTGTGTGTAAGCACGCGCACACGCACGCATG
```

TGTATGCTCAGTCATGTCCAACTCTCTGCAGTCCTATGGACTGTAGCCCACCAGGCTTTTGTGTTAATGGAATT

TTCCAGGCAATACTGAGTGGGTTGCCATTTCCTACGCCAGGGTATCTTCCTGACCCNNNAATCGAGCCTGCAT

CTCCTGTGTCTCCTGCATTAGNGGCAGATTCTTTACCACTGAGCCACCTGGGAAGCCCCATTTTTGGAATTTA

GAATTTCCACATAGGAATTTTAAAGGGACACAAATATTCAAATCATGGACCCT

```
SEQ. ID. NO:66      AW462202
CAGTGTCCGCGCAGCTGAAGTGTGGATGGATGAATTTAAAGAGCTCTACTACCATCGCAATCCCCAG
```

GCCCGCCTGGAGCCTTTTGGGGACGTGACAGAGAGGAGACAACTCCGTGCAAGGCTTGGGTGTAAGGACTTC

AAGTGGTTCTTGAATACCGTGTATCCAGAGCTGCACGTGCCTGAGGACAGGCCTGGCTTCTTTGGGATGCTCC

AGAACAAAGGACTGAGAGATTACTGCTTTGACTACAATCCTCCCAATGAGCACGAGATCACAGGACACCAGG

TCATTCTGTACCGCTGTCACGGGATGGGTCAGAACCAGTTTTTCGAATACACATCCCAGAATGAAATACGCTA

CAACACCCACCAGCCAGAAGGCTGCGTGGCAGTGGTGGAAGGAACAGACGTCCTCATCATGCATCTGTGTGA

GAACACCACCCC

```
SEQ. ID. NO:67      AW465524
AGCAGAGACCCACATCAGACAGCTCCTACACGTGCCCGATGAACAGGGTCTTCTCCTGGGCTGGGAG
```

GTTTGACTGCTGACCTGTCCCCTCTCAGNGGTAGCCCCCACCCCCATCTCTCCAGTGGAAGTCTGTTGCAACA

AGCTTCCGTCCCACTCAGGGATGCAAAATGCCCACGGAGATCAAGCTGCTGGGGGAAGTGTTTACGTCTCTCT

AAACATACCCCTAAACATACTCTCTGTTAGTGTTAACGTTAGGCAAATGGAAGAAAGACCAGGTCGAATTCT

GAAATAATTATTCAGCCTCCCCTCCTTGTCCACTTCATACACCACCATGCTGCAGAATGTTCCTTATTTCTTAA

GGATGAGTGTGCCTGTTGAATACAAATGTACTGCTGCTGCTTAACTTGCGAGATGCATGGCGTATGTTACCGT

GCTGGGCCANTGTCGTTCTTAAATGCCCATCGTAAATACCATG

```
SEQ. ID. NO:68      AW465958
ACAAACCTAGACAGCGTATTAAAAAGCAGAGACATTACTTTGCCAACAAAGAGTCCACCACCCCCAC
```

CTCTGGCCTGGACGACCCCTCTCCTGCCAGCCTTGGGAACCTTTCGGTGCAGCCAGAGTGTGGGCCAGGGTCC

TGCAGTATCAGAGAGCTGCCTGAATCCGAGGGGCAGCCGCCTGCGGCCCCCCTGCCCCTCTTCTTCGTGACGC

TGGAGGCGGACTGGGCAGAGGCCAAGGCTCGCTGGGGTCTGGCCTGGGAGGCCCACGTGTACGGGGTAGGC

GCGCTCTTCGGCCTGGTGGCCTTGCTGGCGCTGCTGGCGCTAGCCCTCCTGCCCTGGCGCTGCCCGCCCGGCG

CTCCCTGCCTGGCGCTGCTGGACATGCTCCTGCTCTCGGCTGGGACCACGCGGGCCTTCCCGCTCTTCTACGA

CGCCTACGGGACCGCGACCGGCTGCCGGCGCTGGCCTGGCTGCTGCTGCA

```
SEQ. ID. NO:69      BF041193
TGGTTCTTCCGGTCGTCTTTGAAACTGAGAAGTTACAGATGGAGCAACAGCAGCAGCTGCAGCAACG
```

GCAGATACTTCTAGGGCCTAATACAGGGCTGTCAGGAGGAATGCCGGGGGCTCTACCTTCACTTCCTGGAAA

AATCTAGATTGCTACTGCTATATTTGACCTGTCTTGGTGAAGAAGTTTGAAAATTCAATAGTGTTTGAACTGC

```
TGATTATTGGATTTTTTTTTTTTTTAAACTTTGGCACATGGCTCTATAAACCTGGTGGCAGGAATTCTCCCCA
CATTGGCTCATGGAGAGACTCCTCACTTGCAGCTGTGCCCTCCACTGTCCTGACTTATTTCTTCTCCTCAAT
GCTGATACCAGAGAGCAGCAACGCAGACGGTTACTCCAGCTCTGGCCACCCACCCCCCCTCACTAAATTACT
CCTG

SEQ. ID. NO:70      BF042630
        GTAATTCATGGGACTGGAGCATTTGGAGCAACAAAGTGCCCCGGTGCTACGTTCTCACCTTTGGTTAT
GAGATTTCAAGTTATTTTATCCCCTTTTCAGTGGCAATAAGAACCTTTGTTGGACTTCTTGTTTAATTCGTACA
TAATGTGTAAAACACTTTCTTTGAAAGCAAATTCAAGGCACTGAATCTGTATGTCTGTGTGGGTGCTGTGTCC
ATGTGGCTGTCCATTGGCAGGCAGACTTGATCCCTGACGCCCTGTACACCACACTGCATGAGTCAGGCCCTTG
ATCGGGTGTTCTCTGCTTGGATGGTAGGAACCACAGAGCTTATGAAAGAACACTTGTCACCTGCTCCATCGGT
TACAGTGCTAGCTGAGGAAAACAGTTCCTCACATGTATTCTTTTAACAGGACTCGTGTTCTAGTTTCCTGTAAT
TTATGTTCCTTTAATTTTAATAAAAGCTGAACTGTGAAAA

SEQ. ID. NO:71      BF043059
        AGCNNAATGAAAGTTAAGTCTGTGATCCCTGGTGCCCCCAGCCCGCTGAGTGTGCCTCCAGGCTCAG
AGCCTTGGTTCCGAAGCTGGTCTCTGACAAGGGCCAGTGTCTCCCACCCAGGTGGAGAGCAGGTCCTGCTTGC
GGCGAAGGCCGCAGGGTTTGAAAAGTTTAATGTGAAAGACCCTCCCCAGAGCCCTGGCTTGTCTGGGAGGGC
CGTCAGTCCATGGCTATGTTGAGACCCCCGAAACCCTCCCCTGTTCCTCTAAGTGAGGAGCTGGTCTTGTGCA
GGATTTGTGTGTGTGTAAAGAGGATCTGATGTGTTTGTCTTACTGTCCGAGCCCTGTGCAGAAGAGNCTGG
AAGGGCAGGGGTGGGCTTGGAAAGGGGACACCCTTCCTAGGGAGAGCCCAGGGCCCTATGAGGTGTCAGAG
CTGGAGACTTGGGCTGGGCCTGGCGGGGTCTGAGTGCGGGCTCCGTCTCACCGGTTCGGGGCTGACTGGGTC
TTA

SEQ. ID. NO:72      BF043236
        GGGGAATGAGCAGCGGCTACAGAGGGAGGCAGCCGGCACTGCTGGCCCCTCCTTCCTGCATCTCCAG
GAACCCAGGACCAGCCACTGCAACTAACGGCTTAACTCATGATACACCTTCCCTTCATTCCAAAGGGAAGAT
CGATGTCTGCTTATCTATCACCACTTGCTTCATCTGCTCTTGCTTTGTTTGCCTTCTCAGTACTTCTGCCTGCTG
TTTCCCTGGTCTGCGTTTATTGCGACGATGCTCCCTTGACTAAACGTGGTTACTGACAACTGACGTTAACTCTG
CACCYTTGTTGGCACCTGGAGTTCAGCCACTGGCTCACAGACCGCAGCTCTGGCTGAGGACCCTCATCCCCAGG
GATGCTTTCTGATCCTGTGCATTCCTCCATG

SEQ. ID. NO:73      BF043635
        GAGGTTACTTCACAGGAACCAGGGGCAAAGGGCCACATCTTTTTTTGAACAAGGTTAATCCTTTCCT
GCAAAGTAGGGCCACACAGAATGTTGCAACTACCGGAGGTTTTTTTGATAAGAATTTGACTTCCAGCCTTAAG
CTTCTAAATTTCTGATTTAGTTGAATCTTGGTGAGAACCAGAGGCCGGAACTCAGCTGCCCCAGGACTGTCCA
AGGAGCAGGAGCAAGTGGTGGCCCTGAACTGATGCGGTGCCCGGAAAGCATGTGTGGCCAGCGTGCTGGGG
TTAACAAGACCTTGGTCATCCACCGAGGAAAGCAGGAAGTTGTTTCCAAAACAAGGAGGAAAAAATAGATG
CTGAAGAATCAGAAGCTACAGCTGTGCAGCACAGGCTGCCCTCAGACCTGGATGGACATAGCCCAAGCCCCA
AGACGAAAAGCTTCTGTGATACACTGACATGTTTATAACTGTCCGTGATCTTGGGGGCAGGGACCAGAATTCC
TCTGTCTGTTGGAGAAAATAGGCATAGAG

SEQ. ID. NO:74      BF043736
        TGTGTGATTCCTATTTAACAACAAAAAAAGAAGCCTTTAGGAAGAGACAGGTAGAGGGGTCCCTTCA
CTTTGAACTTGGTGGAAAGCAGTGAGGGGACTCCGGGTGGGCAGCTCTGGGGTCGGCTTTGGGGCTGGTCTG
TGCGGCCGGAGAGGAAGACCCGAGCCCCTTTTCTGCTCCAAGAAGNCCTGGACGTTTCTTTCTTCCCAGTGCA
```

-continued

TTGGACCAGAACAGCGGACAAGGGGGTGCCCTCGAACCCAAGAAGCGTTCCCAGATCCAGCATCGCTGAAG

GGGGGCCGTCGGAACCATCCCGCTCCACGAGACCAATGCCGCCTTGTTTGAGACTCGT

SEQ. ID. NO:75      BF044851
    GGGATCTCCAAAGAGTTAGGGGTCCCTGAGGAGGTCAGAGTGCTACCAACCACTAGGATATTCCTAA

TGGGGGCTCCTTGGTGCCAGAGCTCCTTGGTTGGGTGCCCTCAGCATCCCATCATCCTCCCCCAGGTGGGCTC

CCCCATCCCCGGGGGATGGTTCCTGAGCGACTGCCACCATGGCTCCAGCGCTACGTGGAGAAAGTGTCTGAC

CTCAGCCTTTTTGGGGGTCTCCCAGCCAACCACGTCCTTGTAAACCAGTATCTGCCTGGGGAGGGCATCATGC

CCCACGAGGATGGGCCACTGTACTACCCGACCGTCAGCACTATCAGCTTGGGCTCTCACACCATGCTGGACCT

CTACGAGCCTCGGCAGCCAGAGGATGATAACCCGACAGAGCAGCCCCGGCCCCGCCCCGGCCGGCCACCTC

TCTGCTGCTTGAACCGCGCAGCCTGCTGGTGCTCCGTGGCACCGCCTACACGCGCCTCCTCCATGGCATCGCG

GCAGCCAGCGT

SEQ. ID. NO:76      BF045170
    GGCGAGCTCTGACGGCAAATAGGTCTTTGAAATTGAGGGCCTGCCCCTGAGGTGTGGCAAGGGGTCA

GCACCCCCGATCCCCCCGGCTGGCCTCTTTCCCTGTCCAGGGCGGTGCTCCCACCACAGTCCAAAGGCTGCTG

TCAGCAGACACCTGGGCTGAGCGGTGTCCCTTCAGGAGCCCGGGAGGCAGGGACCCCCTCCTGCTCTCGTCC

CACCCCTCACTAGCATCATCTCTGTAACCAGGTGAGCCAGGGTGGGAGAGGGACTTGGAGAGTCCAGGCATC

TGCTTCCAGTCTGCCTTGAGGGGCTCAGCTCCCTCGAGCGGCCAGGGGCTGCGAGTTCTGGGCATTGGGTGAC

AGGCCAGTAGACTGCCTTCAGCCTTTGTGCTACTGTGTCCCTCCTCTTCTGCTGCTCCGGGCCCTCCACCAAGA

GATCCTGTTGGACTTGGCCGCTGGACCGGGGCCTATGAGCTTCCCTTCCTGCCCTTGAAAATGAGGATCCTCT

GGTCCCTGCCTGCCCTGTTGCTATCCATTGAGGAAAGGGCAGTGGAGAACTTTCCCA

SEQ. ID. NO:77      BF045305
    CCTCAAACCGCAGGCCCGATTGTCCCCAGGCGGGGGCTCCACTCTGGGTTTGGGGTCACCCCGTCCC

CTCTGGGGAGGGGCTGGAGCTTTGTTTCATTTTAATGACCTTTGAGCGTTGTAGGGAAACTGAGGCAGGGAA

GAAGTCTTGACTGCCTAAACGGTCAACTCCTCCTCTAAACTTGAAGGTGGCACCCTCTCTTCTGTTTAAGTTGT

GTGTGTGTGTGTGTGTCTGTGCGTGCGAACAGTCGGTCACTTTTGTCCCACTGTTGGACCCTGCTGCCCT

GGGGCTGTGGTTTTCCCGGGTCCAGGGCGCGCCCTTTCTCCCAGGAGCTGGCATTGAAGACTTGTCACTTCTG

GCAGGGTCCTGATGACCCCCTCTGCCCGCCAGTATTTGGGTTATGTCCAGAGGGAACTAGGTATCATGGTTTC

CTTGGACTTGTAAGCTTCAGGATTGCTCAGTAATGAATGAAAACATCACGGGAGACATGGGGAAGAGCAGTG

SEQ. ID. NO:78      BM362735
    GCACGAGCGGAGCCGCGCGGAGGCGGAGGCTCGGGTGCATTCAAGATTCGGCTCCACCCGTAACCC

ACCGCCATGGCCGAGGAAGGCATTGCTGCTGGAGGTGTAATGGACGTTAATACTGCTCTGCAAGAGGTACTG

AAGACCGCCCTCATCCACGATGGCTTAGCACGTGGAATTCGCGAAGCTGCGAAAGCTTTAGACAAGCGCCAA

GCCCATCTGTGTGTGCTCGCATCCAACTGTGATGAGCCTATGTATGTCAAGTTGGTGGAGGCCCTTTGTGCTG

AGCATCAAATCAACCTGATTAAGGTTGATGACAACAAGAAACTAGGGGAATGGGTAGGCCTCTGTAAAATTG

ACAGAGAGGGGAAACCTCGTAAAGTGGTTGGTTGCAGTTGTGTGGTGGNNAAGGACTATGGCAAAGAATCTC

AGGCCAAGGATGTCATCGAGGAGTACTTCAAATGCAAGAAATGATGAAATAAACTGATTTCTTGTTTTCCAA

AAAAAAAAAAAAAAAA

SEQ. ID. NO:79      BM366522
    GCACGAGCCGTGGCGCAATGAAGGTGAAGGCCGCCCTCGCCGGCGGCCGAGGTGGTCAAGGCGAAG

GCCGGAGCGGGCTCTGCCACCCTGTCCATGGCATACGCTGGAGCCCGCTTTGTCTTCTCCCTCGTGGACGCGA

TGAATGGAAAGGAAGGAGTCGTCGAATGTTCCTTCGTTAAGTCCCAAGAAACGGACTGTCCGTATTTCTCCAC

ACCGTTGCTGCTGGGGAAAAAGGGCATCGAGAAGAATCTAGGCATCGGCAAGGTCTCCCCTTTCGAAGAGAA

-continued

```
GATGATTGCTGAGGCCATCCCTGAGCTGAAAGCCTCCATCAAGAAAGGAGAGGAGTTTGTCAAGAACATGAA

ATGAGAAGGCGCTTAGCGAGCAGTCGGTCTCCTTAACTTATTAAGGCATCATGTCACTGTAAAGCCGTTTCAG

ATACTTTTGTCGTTTCAATTTGCTTCGTTGAGGAGGATTGTATTAACGAACCACCCCTTTGCAATCTTGGTCAG

TCTGTCGGTGCATCAATAAAAGCAGGCTTTGATTTTCAAAAAAAAAAAAAAAAA

SEQ. ID. NO:80      AW461513
       TTTTTTTTTTTTTTTTTAATGGATGCGTGGTACCACCTGCTAGGGCTGTCCATCCTCACAAAGCTGGGA

TTCTTGGCCACAGTGCCCCTCGCGCGGAGNNNACAGACCCTCCAGGCACACACGCAGCNGGAGAAACAGGA

AGGGACAGGCCGTCCCCTTCGCAGGCGAGCAAAGGACAAAACTCCATTTTAAGATAAAGTCATTGCAGAAGA

AAAAAAAAAAGTCTTTTAAGAGACAATCCTTCACAAAGGGGGAAACGAGCACC

SEQ. ID. NO:81      AW462120
       TTCATTGGAAAAAAAGATTTTATTTTACCATAAAAATGCAAACTGGAATAAACACCATCTCTCCTAA

GGTGGACGTTACAGCTATTTTTAAGTATTTCCAAGCTTCCCTTGGAGAAGCTGACAATTATAAAATTTAACAA

GTTTGCAGCCTTAAATCTGAAACGTTCCAAGTAAAAATAATTTAGCAAAACGGCTTCTTAAAAAAACCACAC

AGGCTAACCTTGACTAGAAACCAAAGCTAATTTTAAACCAGCCTGCTTTTTGTTTTATGCTGAATGACTTGA

GTTTGTAAAAAGTGAATGTGTGGGACCCCTGTGTACCACCTGACGCTCTTCTGTTGTATGCTGAATGACTTGA

ATTCGTACAAAGTGAATGTTTGGGACTCTTCTGTATCCCGTCTGCACCAGCCCACGCCCGTAAAGAG

SEQ. ID. NO:82      AW463593
       AGGAGTCCTCACCCTGGGATCATTCCACAATCCCCATGGCTCCAGCTCCCAGCTTCCGTGGACACCA

GTGGACTTACAACCCTGTCCGAGGGTCCTGCCTGCTGCTGCTGCTCATGTCTAATCTGCTCCTGTGCCAA

GGCAAATCATGCCCGTCCTGCGGTCCTGACGTGTTTGTTTCCTTACGGAAATCCTTTACAGACAGGTTTATGA

ATGCCGCCAGCCTCTCCCATGACTTCTATAACCTTTCCACAATAATGTTCAATGAGTTTGATGAAAAATATGC

CCAGGGCAAACTATACTATATCAATGTCACCAAGAGCTGCCACACCAATTCCTTCCATGCTCCCGAAGAAAG

AGATATAGTCCAGCAGACGAACATTGAAGACCTTAGTAAGTGGACACTCGTGTTGCTGTACTCCTGGAATAA

TCCTCTGCATCATCTAGTCACGGAGCTGCAGCATATGAAAGAACTGTCAAACGCCTTCCTATCAAGCGCCACAA

SEQ. ID. NO:83      AW465056
       GGGACCAACGGGATCCCCTCTACCCCACCAACCCGGGAGGACGAGTTGGGGTCGGAGTTGGGTGGA

CTAGCTTTCCTGGTCCTCTCCCCACAGAGCTGACGTGTCCTGGGTTCCAGGCGATGGGCATTTCCACGGGGCG

GGAGGGTTCGGGTGGTGGGTACAGGCACGTCGCTGGCGCTTTCCTCCCTCCTGTCCCTGCTGCTCTTCGCTGG

GATGCAGATGTATAGTCGCCAGCTGGCGTCCACCGAGTGGCTCACCATCCAGGGCGGCCTGCTTGGTTCCGGC

CTTTCGTCTTCTCTCTCACTGCCTTCAATAATCTGGAGAATCTTGTCTTTGGCAAAGGATTCCAAGCAAAGAT

CTTCCCTGAGATTCTCCTCTGCCTCCTGTTGGCTCTGTTTGCATCAGGCCTCATCCACAGAGTCTGTGTCACCA

CTTGCTTCATCTTCTCCATGGTTGGTCTGTACTACATCAACAAGATCTCT

SEQ. ID. NO:84      BF046404
       ATTTTTTCTTTTTTTAAATTTTCAAACACTACTGGGGAAATTATTCTTGTCCAATAATTATTAAAAGTC

TTTTCGACTTGAGCACATGGACAAATGAACTTGATTTGAAACTAGAGGCATAGGCCATGCATGTTAGTACTTT

ATTATTTGGCTTCCTGCCATGTTAGGAAAACAAAATATGAAAAAGGTCATTTTCTTTAAACCATGGAATTTTT

CTTCAACTAAGATGAATCAAATTTCCTTATGTATGTAAATTCATACATTAACACAAAGTTTTATATCATGCCA

GTTCACATAGCATAGTGGAGTCACCATTCTCTAGAATGTGTGTTTCTGCGAAACTTAACTTGCTTTAGAATTTT

AAATTTTAACCTTGCGCAGANNCCAGCTCCCGAAAGCTATGAAAAATTCCCAGTGGCTGATGTGGAAACCTC

TTTCCACTGCTGCCCAGCCCTCAGGATGTGCAACTTAGTGAAAGGAGAGAATCTTTTTCTAGGAAAAATGAGCC

SEQ. ID. NO:85      BM366368
       GCACGAGCAGCAGCCGGACTTCCAGACCCAGATGCCAAGCAGTCTTGTGCTGGACTGCTCCATCGCT

GACTGCCTGAGGTTCCGCTGTGACATCCCCTCCTTCGGCGTTCCAGGAGGAACTTGACTTCATCTTGAAGGGCA
```

-continued

ACCTCAGCTTCGGCTGGGCCAGCCAGTTGCTGCAGAAGAAGACATTGGTCGTGAGTATGGCTGAAGTCACAT
TCAACAGATCTGTGTACACCCAGATTTCAGGACAGGAGGCATTTTTGAGAGCCCAGGTAGAGATGGTGCTAG
AAGAGTATGAGGTCTACAGCCCCATGCCCCTCCTTGTGAGCAGCTCCATGGGAGGACTGCTGCTCCTGGCCCT
CATCACAGCCTTACTGTACAAGTGTGGCTTCTTCAAACGTCAATACAAAGAAATGATGGATAACAAGCCTGA
AAACACTGCACTCAATGGGGAAGATATCCACCATGAGACCCCAGATCTACCTTTGTCCGAATAATCCACTTTC
TCATTTATGTCTATTCCCATTGGCTGACCTTGGCTTCACCTAC

SEQ. ID. NO:86    AW462010
ACAAGAAAATGTTATCAACCACACGGACGAAGAAGGATTTACCCCTCTGATGTGGGCTGCAGCACAC
GGGCAAATAGCTGTGGTAGAGTTTCTACTTCAGAATGGCGCTGATCCTCAGCTTTTAGGAAAAGGTCGAGAA
AGTGCTCTGTCATTGGCCTGTAGCAAGGGCTACACAGATATTGTCAAAATGCTGCTGGATTGTGGAGTTGATG
TAAATGAATATGATTGGAATGGAGGGA

SEQ. ID. NO:87    AW465551
TTCTAGCAGTGGGACCAGGCAGCAGGACGAGGAGATGCTTGAACTCCCAGCTCCTGCTGCAGTGGCT
GCGAAGAGTCAGGCCTTAGAGGACGATGCAACAATGAGGGCTGCAGACCTGGCCGAGAAGAGAGGGCCCTC
TTCCAGCCCCGAGAACCCCAGAAAGAGACCTCGGGAAGACTCTGATGTGGAAATGGTGGAGGATGCATCCCG
AAAGGAGATGACAGCCGCTTGTACCCCCCGGAGAAGGATCATCAACCTTACCAGTGTTCTGAGTCTCCAGGA
GGAGATCAACGAGCGGGCCATGAGAGTACCTCTCCGGGAGATGCTGCATAACCACTCCTTTGTGGGCTGCG
TGAATCCTCAGTGGGCCTTGGCACAGCATCAGACCAAGTTATACCTTCTCAACACCACCAGACTTAGTGAAG

SEQ. ID. NO:88    AW465274
TGCCCAATTCCAAATGTACAGAACTCTCCCATTCCTACAAAGCTCCCTGAACCAGTGAAAGCCAGTG
AGGCAGCTGCAAAGAAGACCCAGCCAAAGGCCAGACTGACAGATCCCATTCCCACTACAGAGACGTCAATT
GCACCCCGCCAGAGGCCTAAAGCTGGGCAGACTCAGCCCAACCCAGGAATCCTCCCCATCCAACCAGCCCTG
ACCCCTCGGAAGAGGGCCACAGTTCAGCCCCCGCCTCAGGCCGCAGGATCCAGCAATCAGCCTGGTCTTTTA
GCCAGTGTTCCTCAACCAAAAAACCCAGCCCCCACCCAGTCAACCCCTACCACAGTCTCAGCCCAAGCAGCC
TCAGGCTCCGCCCACCTCACAGCAGCCGCCTTCCGCGCCGGCCCAGGCTCTGCCCACCCAGGCCCAGGCCAC
GCCCCAGCACCAGCAGCAACTCTTCCTCAAGCAGCAGCAGCAGCAGCAGACAGCGCCGCCCGCACAGCAGC
CAGCGGGCACGTTCTACCAG

SEQ. ID. NO:89    AW462049
GGTATCCGCCCCCAGATCATGAACGGCCCCCTGCACCCCCGCCCCCTGGTGGCGCTGCTCGACGGCA
GAGACTGCACCGTAGAGATGCCCATCCTGAAGGACCTGGCCACCGTGGCCTTCTGCGACGCACAGTCCACCC
AGGAGATCCACGAGAAGGTTTTAAACGAGGCAGTCGGTGCCATGATGTATCACACCATCACGCTCACCAGGG
AGGACCTGGAGAAGTTCAAGGCCCTGAGAGTGATCGTGCGGATAGGCAGCGGCTATGACAACG

SEQ. ID. NO:90    AW463986
GTCTGGCTGAGCCTGACACCCCCAGGGGAAAGCAGTGCAGAAACCACTGGTTTCCCAGCCGCGGAG
GGATCTGCACTTTTGTTTGTTTTTGACCAAAAAAAAAAGGTTAGCAGTGAGGGGCTAAGGAGACATCCAGCC
TCTGATACCTAAGAGGAGAAGTCCCTGGACTTGGACCCTCCTATTGTGTGACCTCAGCCCAGGGTGGGAACT
GCTACCGTGAGTACCTGGGGAGGAGGGGATGGGAGTT

SEQ. ID. NO:91    AW462385
TGGAGAGTGGGAACCCGCCATCTTTGCCTCCGGGATCATCATGGACTCCAGCATCTCGAAGCAGGC
CCTGAGTGAGATTGAGACACGCCAGAGCGAGATCATCAAGCTGGAGAACAGCATCCGGGAGCTGCACGACA
TGTTCATGGACATGGCCATGCTCGTGGAGAGCCAGGCGCTGTCTTCCCAAAATCCCTCCTCGGGCCCCCTCGC
CGCCTGGAGGGGGCCCCTCTGGAGCTGGGGTGCCCCTGGCCCTGCAGGGGGAGATGATTGACAGGATTGAGT
ACAACGTGGAACATTCGGTGGACTACGTGGAGAGGGCCGTGTCTGACACCAAGAAGGCCGTCAAGTACCAG

-continued

AGCAAGGCTCGCCGGAAGAAGATCATGATCGTCATCTGCTGTGTGGTTCTGGGCATCGTGATCGCCTCCACCT

TCGGGGGCATCTTCGGATAGAAACCACCCCGCCTGCCACTCTGCTCTGGAC

SEQ. ID. NO:92    AW462546
    TTTTTTTTTTTTTTTTTTTTGGCAGGAGACAAAAGCAGGTTTATTTGGGCTCTGGGGCCAGGGATGCC

TAAGGTGTGAGTTAAGGCAACTCAGCTGGTTGTCAATGCCCAAAGGGCAGGCCAGGGGAGGGAGAAGGGGT

GACTCNNNATTGAAGCCAAATCTCTGCATTTCAAGTCCCTGGCCGGAGACCTCGGGAGTCAGTTCTGGGAGG

GCATGGGTTTCTAGTGTTCCCTGGGGTCTCTGTGCTTTTGCTAGGATTGGGGGAATGGTCTGGGGGCAGGAGC

CTTGAATGCACAGCCTTCATTTCAGTAACGACCATTTAATTTGTTCCTTGGCAGACTGANNNACCTGGGCCAC

ACTGTGTTCCGTCAAGCCGCTGTCATCCGCCCTAAAATTCACTTTCTGGATCACTTGCTGGGGGTCACTTTC

SEQ. ID. NO:93    AW463148
    ACTGCGCCCTCAAGCCTACATCATCAAGATTCAAAACAGCTGCCGCAGCGTCTTTCAAGGAGGCACA

GAAAATAGCTCTCTAAACACCTGGATCCTTGGTGATATCTTCCTGAGGCAGTACTTCTCGGTTTTTGATCGTA

AAAATAGAAGGATTGGCCTGGCTCCGGCAGTGTAAATGCTTGGACTATCAGCAAGCATTTGACTAAATCAGTC

SEQ. ID. NO:94    AW464583
    TGCCGCGCCGGTCGCCAGGCGCCTCGCCTCCCCACGCCTTCCGGGCGTCGGGGCTTTCTCCCGCCCCG

TCCCCCACCCCCACGCCTCCCGCGGCCGTCTGTCCGGTTCTCCCGCCCTGTTCTCGCCTCTCCCGTACCTCTG

ACGCGTGTCCCCTGCCCGCTTGGCGCCCAGCTCCCCGTCGGAGCCCCTTCCCTCCGCCCTCGGTGGTGGTGTG

TGGGGGGGGG

SEQ. ID. NO:95    AW465767
    CCGGCCTCGGGCGGGAGGGAAGAGAGCATAGGAGGCGAGGCTGAAGGCGCAGCTGTTGCCTGGACG

ATGGCGGGGACGGCACTCAAGAGGCTGATGGCCGAGTACAAACAACTAACGCTGAATCCTCCAGAAGGAAT

TGTGGCAGGCCCCATGAATGAAGAGAATTTTTTTGAATGGGAGGCATTGATCATGGGCCCAGAAGACACCTG

TTTTGAGTTTGGGGTGTTTCCTGCCATCCTGAGTTTCCCACTTGATTACCCGTTAAGTCCCCCAAAGATGAGAT

TTACCTGCGAGATGTTTCACCCCAACATCTACCCAGATGGCAGAGTCTGCATCTCCATCCTGCACGCTCCTGG

CGACGACCCCATGGGCTACGAGAGCAGCGCCGAGCGCTGGAGCCCCGTGCAGAGCGTGGAGA

SEQ. ID. NO:96    AW466125
    CTCGCGCAGTCGTCTGGGCGAGCGAAGATGGCGGCCGAGAGGGGAGCCTCCTCCGCTAGGGGACGGG

AAGCCCACCGACTTTGAAGAGCTGGAGGACGGAGAGGACCTGTTCACCAGCACTGTCTCCACCCTGGAGTCA

AGTCCATCATCTCCGGATCCAGCTAGCTTTCTTGCAGAAGATATTAGTACAAACTCCAATGGTCCAAAACCTG

CAGAAGTTGCGCTAGATGATGACAGAGAAGATCTTTTTGCAGAAGCTACAGAGGAAGTTTCTCTGGACAGTC

CAGAAAGGGAACCTATACTCTCCTCCGAACCTTCTCCTGCAGTCACACCTGTGACCCCCACAACACTCATTGC

TCCCAGAATTGAATCAAAGAGTATGTCTGCTCCTGTGATCTTTGATAGATCCAGGGATGAGATTGAAGAAGA

AGCAAATGGAGATGTTTTTGATATAGAAATTG

SEQ. ID. NO:97    AW466146
    GCGTCCCTGCGACCCTCTTTCCGGAAGCGTGGATAGTGCCCGTGGGATTTGTGGCCGTAGTTTAGGA

ACTCACATCCGGGACAATGGTGTGCATTCCCTGCATCGTCATTCCAGTTCTGCTCTGGGTCTACAAAAGTTC

CTGGAGCCATATATATACCCTCTGATCTCCCCCTTTGTTAGCCGTATGTGGCCTCGGAAAGCTATACGAGAAA

CCAATGATAAAAACAAAGGCAAAGTAGACTATAAGGGTGCAGACATAAATGGATTACCAACAAGAGGACCA

ACAGAAATGTGTGATAAAAAGAAAGACTAAACTGATTGTCCCGAAGGATCTCATTGTTATAAAAATGGACCT

GATACTATGAAGCACCTTCTTGTAATTGTCTCTGATCTTTTTCCAAGACCAGAATTTGGGTTAGATATTAACA

GTTTAGACATTTACCTATGCTAATCAGGGAATACCT

SEQ. ID. NO:98    BF042961
    GTGGTCTCAAGGCAGGGGGGCAGGCAGGGGTGGCCTGTTCAGCCCTTCACAGATCAGTGGTCTTGGC

AGGTCTGAGAGCTGCCCCACTGGCCAGACTCCTCTCCAGCAGCAGAGCCAGGCTGGGGCTTGCATGTCCAGC

-continued

CTGAGCAAGCTTAACAGGATGAAGCTGAGGCTTTCTCCCCACTGTGACTGGAGTGCATGTTTACACCAGCACC

TTTTCTGCACATGTATCTTCAATCCCACCACAGGGAGCTCGTCACCCCTGCACAATGACATTCCAACCACCAC

CAGCCAGAAGTTACAGCCAACCTTGCTGACTGTCACAAGCAGGACCTTGGGTCCATTGGCACGGTCAGTGAT

GTAAGC

SEQ. ID. NO:99  BF043647
  GAACTTGAGGGCCCAAGCCTTATCTGAGCCTTTCCTCAATACGGGGTTCGGTTGGACTGGGGCTCCTC

CATGCCTAGTGAGAATTCCATGTGGGCTCAGAAGACTTGGGCATGCAGGTGCCGCTGCTGATGTGCTGCCTGT

GTGTCGGACACACAGTGGAAGCTGGAATTGATGGTCCATGAAGGCTTACCCCACACACACCTGCAGCCTCCC

CAGATCAAGTAGGTGTATTCCCCTGGCAGTCTGGGCAACGGAGACCAACAAGAAACATTTTTAGGTTGTTTTA

AATTCCTTTTTTTAAACTTGCAGTTTATTGCGTACTGAGAGTTGATCACAACCTCCATGCTTCATAAGCGGACG

CCATGTTAGGGTCAAACGTGGGCACCATGAGTCCTCCGTGGCTCCTGGACAGAGACCCACCTCAAGATCAGA

AGCCCTTTGGATGGCGTTGCAGATCTCATTGCTCAATTAGCCTCGAAGNNTCTAATTCTCATCCCAGTCTCAGT

TGGATTTTCTGGCACTCTTCCTGCATCGAGTCTTCTGGGACTGAACCAAGCTCTGTGGTT

SEQ. ID. NO:100  AW462175
  GTACTCGGGCGGCCATGGGGGGGTTGGCAGGCAGGTTTGCCAGGCGCTGGTTCTGTGGGCTTCTCGG

CAGCCCCCTGCAGGTCCCAGCCCTTGGGTTACACGTGCGCGGCGCCGCCATGCTAGCCAGCCAGAAGGACTT

TAACAACGCGGTGAGCCAGGTGAAGCTCCTGAAGGAGGATCCGGGCAATGAGGTGAAGCTGAAACTCTACG

CGCTCTACAAGCAGGCCACTGAAGGACCTTGTAACGTGCCCAAACCAGGTATGCTGGACTTTATCAATAAGA

CCAAATGGGATGCATGGAACGCTCTTGGCAGTCTGTCCAAGGAAGCTGCCCGACAGAACTACGTGGACTTGG

TGTCCAGGCTGAGTGCTTCCTCTGAGTCCCCCAGCCC

SEQ. ID. NO:101  AW464554
  ACGCCTTTCCTTTCCTACCCAGAAGTAGAAGCCCAGTGGCAGGGCAGCAGCCTGCATAGACTCAAGT

CTGCCCACTGGTCACTGGGCGCTTGGTGGCTCCTGGGTTCGATGCTACCTCTTTTCCCCAAGTTTAATTTTAGA

TAAATTACACTGCCTGAAGTNGGGGCACCCCTTTCTTTCCCTGAGGAGCCCCAAGACCAGAGACAAGGCCAG

GACAGCTTGGGGACACACTCCTGGGAGAGGTGCAGTCCCTTCCCTGTTGGGGGGAAGCCCAGACCCATGCGA

ATCAGCTCGCAGCCAGGCTTTGACAATCTCGCAGCCCTCACGATTTGGTCCCACTGGCCACTTGGGTTCTCTC

CTGGGCAGGC

SEQ. ID. NO:102  AW464010
  CACCACGCTGTGGCGCCGGAACGCCAACGGGGACCCCGTGTGCAACGCCTGCGGCCTCTACTACAAG

CTTCACAACGTGAACAGGCCGCTGACCATGAAGAAGGAAGGCATCCAGACCCGGAACCGGAAGATGTCCAG

CAAGTCCAAGAAGAGCAAGAAGGGGTCCGAGTGCTTCGAGGAGCTGTCCAGGTGTGTGCAGGACAAGGCCT

CCCCATTCAGCGCCGCCGCCCTGGCGGGGCACATGGCGCCTGTGGGCCACCTGCCGCCCTTCAGCCACTCCG

GTCACATCCTGCCCACCCCGACGCCCATCC

SEQ. ID. NO:103  BF045005
  GATGCGAATACCTGCCCTCAACGCCTACATGAAGCACCTCCTCAGCCTGCCCATCTGGGTGCTGATG

GACGAGGACGTTCGCATCTTCTTCTACCAGTCGTCCTACGACGCCGAGCAGGTGCCTCAAGCGCTCCGGCGGC

TCCGCCCGCGCACCCGGCGAGTAAAAAGCGAGTCCCCACAAGCTGCTGGCATTGACCGCATGGCAGCTCCAC

GAGCAGAGGCCCTGTTTGATTTCACTGGGAACAGCAAACATGAGCTGAATTTCAAAGTTGGAGATGTGATCT

TCCTTCTCAGTCGGATCAATAAAGACTGGCTGGAGGGCACTGTCCGGGGAACCACAGGCATCTTCCCAGTGT

CCTTTGTGAAGATCCTCAAGGACTTCCCAGAGGAGGAAGACCCCACCAACTGGCTACGCTGCTATTACTATG

AGGACACCATCAGCACCATCAAGGACATTTCAGTGGAGGAGGACCTCAGCAGCACCCCACTCTTCAAGGACT

-continued

TGCTGGAGCTCATGAGGCCTAAAGGCTGCTGGACCTTTCCCGAACTCTGATCTCTCCCACCCAGGCGGGAGTT

CCAGAGAGAGGACATCGCCCTCAACTACCGACGCTG

SEQ. ID. NO:104    BF045561
    GGATCCCGGGAAGTGGAGACCCGGGGTCCCGGCAGCGGGGCGGCCCGCGGGCCACGCCGGGGATGC

ACCGTCGTGGGGTGGGAGCTGGCGCCATCGCCAAGAAGAAGCTTGCCGAGGCCAAGTACAAGGAGCGAGGG

ACTGTCTTGGCTGAGGACCAGCTGGCCCAGATGTCAAAGCAGTTGGACATGTTCAAGACCAACCTGGAAGAA

TTTGCCAGCAAACACAAGCAGGAGATCCGGAAGAATCCTGAGTTCCGGGTGCAGTTTCAAGACATGTGTGCC

ACCATTGGCGTGGAT

SEQ. ID. NO:105    BF046270
    AGCCCTTTAGATTTCCTGGAGTGGACCGGCACCACTTCTGACTTCCCTGAGAGACCTGGAATCTGAGC

TCTTACAGCCAAGGATCTTGGTGGGCTCAAGCCTGGGGAGGGACCAGGGATGGGAAGATAGAAACTGGTATC

AGTGGGACATTTCTGGAATCTGCCGAAGAGGGACCACAGAGAACATCTTCAGTCTCTCCTTGTGTCTCTCTTA

CCCTTTCCCAGAGATAGTTCCACCCCGAGTTTCTTAACCCTCTCTTCAGAGGCATCCAGAAGCTGATAGCCTA

GGCTGGATGTGCCCTAAGGAAGTGGGATTCCAAGTCTATACTTGATTCTGACTGTGTGTAATCCCTGCCCCTT

CCATAACCTGTGGAGGTTCTCTTCCCCTTCATAGAGGAGGAAGTGATCAGGTCTGAAGGTGGAAAAAATGAC

CATACAGCCAAGCAAAACCCAGGATCTTACAGAGGCAATGGCACTGGTTGAGGCCTCCATACCTCCTCATTT

CAAATTCCCTCCTATTTGGATC

SEQ. ID. NO:106    BF043456
    GAATTCACCTTATGCCATCCATGAATCCTGATGGGTATGAAAAGGCCCAGGAAGGAGATCTAGTAAGG

TGTAATCGGCAGAAACAACAGCAACAACTTTGACCTGAACCGGAATTTCCCGGACCAGTTCGTTCAGATCAC

AGAGCCCACCCAACCAGAAACTATTGCTGTGATGAGCTGGATGAAGACCTATCCATTTGTGCTGTCAGCAAA

CCTGCATGGAGGTACTTTGGTGGTTAACTACCCTTTTGATGATGATGAACAAGGCATTGCCACATATAGTAAA

TCACCAGATGATGCTGTGTTTCAACAAATAGCACTTTCTTATTCCAAGGAAAACTCACAGATGTTTCAAGGTA

GACCTTGTAAGAACATGTACCCTAATGAGTATTTTCCTCATGGAATAACAAATGGAGCCAGTTGGTACAATGT

CCCAGGTGGTATGCAGGACTGGAACTATTTGCAAAGAAATTGCTTTGAAGTGACTATTGAACTANNTTGTGTG

AAATACCCATTTGAGAAAGACCTGCCAAAATTTTGGGCACAGAATCGAAGATCCCTAATCCAGTTTATGAAA

CAGGTGACTA

SEQ. ID. NO:107    BF040324
    GGAGTGAGTCCGGCCCGGCTCCCTCGCCCGCCGAGTCAACCCAGGCCTCAGTGACACTTGCGCAGCT

CCTGCAGCTGGTCCAGCAGGGCCAGGAGCTCCCCGGCCTGGAGAGGCGCCAGGTCGCTGCGACCCTTGACGA

ACCCACGGCGTCCCGACTCCCGCGGATACCCAAGCCCTGGGAGGCCGCGCGCTCCGCGGAGCACCCAGCGCC

ACAGTTCCAGACTGGGGACCGCGGGCTCGCCGACCCTCCGAGTGGGCAGAGGAACCGCCTGGAGGAGCCTG

GCTCGGCCGTTTCTGAGGCTCCAGGTCCTTTGCAGCTGTGAATGAAAATTTTGCTGCCCTGTCGGCAAAGGA

CACTGCAGCCCCAAGGGACACCCCCAGAATGGAGGAAGGCCTGACTACTACTGAACCCTCAGCCACTGCGGA

CACTCCCAACCGTGCACCCTGAGGTGCCTCCGGATGGGATAGAATAAGATACTGGCCTTGGACAGCTANGGT

TCATAGCAAAGGAATGATATTAGTGAGCCCGGACTCTTATGACTTCCTATGCATGAGAAAAGCTAAATTCTTT

GATGTG

SEQ. ID. NO:108    AW462307
    GGTCCTTATCATCTGTTCCATCAACATGTACTTTGTCGTGGTTTATGTCCAGGATGTAGGGCATATGG

TATTGTATGTGGTGGCTGCAGTGGTCAGCGTAGCTTATCTGAGCTTTGTGTTTTACTTGGGYYGGCAGTGTTTC

ATTGCACTGGGCATGTCCTTCCTGGACTCTGGACACACACGCTTATGAACCTATCTCTCTGATGGATGGAGGT

GTCAGTGCCATTGAAGGATACGAGAAGAGATTGTTCCACGTTGCTCTCTTTCCGTACTCCAACATGACTACAA

-continued

TTTTGATTATTGTAAAGAGTTTGTTTCAGGATTCCTCAAAATCTACGACTCTTGGTTTCAAAGCCATTGTGCAA

GTTTAGTGTTGAAATCTACT

SEQ. ID. NO:109    BF043382
GGGTTCTTGGAAGACCTGGCACCTCTGGAGCGCAGTGGCCTAATCCAGGACTGGGAAACATCTGGGC

TTGTTTACCTGGACTACATTAGGGTCATTGAAATGCTCCGTCATATACAGCAGGTGGATTGCTCAGGTTATGA

ACTCGAGCAGTTGCACACCAAAGTGACCTCACTGTGCAACAGGATAGAGCAAATCCAGTGTTACAATGCCAA

GGACCGCCTGGCTCAGTCAGACATGGCCAAACGTGTAGCCAACCTGCTGCGGGTGGTACTGAGCCTTCAGCA

TGCCTCTGATACAACCTCCGACTCAACGCCAGACCCTCAGCGAGTCCCTTTGCGCCTGTTGGCTCCCCACATT

GGCCGGCCCCCCATGCCTGAGGACTATGCCTTGGAGGAACTGCGCAGCCTCACACAGTCCTACCTGCGGGAA

CTGACTGTCGGGAGCCAGTGAGCCCTNNNCTCCTCCCACCACACTCACATGCTTGTTCACACTCACCACACAG

AGGGCTCCTGCATCAAGTTGATTGCCCTGTTTGCCGTTCTCTGGCTTGGCCATGGAATCTCCCCTCCC

SEQ. ID. NO:110    BF043624
TTTCTTTCCCCCTCACAAGGCTCCCAGAAGCCCTAGTTGGCCTTGACCTGACACTTCCTTTTTATTAGG

CGTCCTGTTGGGGTGGCTGAGAATCATGAAAAACAGATCCTCTGCTAGCCTCCATGATGAAGTTGTTAGACAC

CAGCTTTCTGGGAACTCGTGTTTGATTTTTAAATGGCATGTGACCCTTCTGTGTTCTGGGGACTCAATCAGAA

AGGTAAAAGCCATTAACAAAAGTTAGTAAGAGTTTTATTCATCTCATATCTTCCTGCCTGGGTTCACGGCCTT

ACTGACTGAAATAAAATCATTTCTGATTGGACGCAGACCTGCGTTTCTTTGGACTTCTGAATCCATGTTCATAT

TTTCTCTGGCCACTGAACACCTTGGAGATTCCGTTTAGGGAGT

SEQ. ID. NO:111    BF440494
AGTTTCTTGGAAATCTTGACAGCTTCAAATATTTAGACCCATTTAGTTCTAATACAAGTTCATCTTTAT

TGTCAAAGTAAAAGCAATATTCTTGTAATACTTAACTATGTAAATGCAAATGAGAACCTTCTTCTCAGAGTAC

TTCTCACGCTCTAGGATTTACTAATTCTTCCTCCTTTCCTCTTAAATAGGGTTAATTGTTCAAGGCAACAAAG

AGCAGTTCTTTTGGATTTTGATAAAGAGAAAATTTGGGGATACATTAGCAAGTGTGCCTGATGTAAGCAGCTA

AACACAATAGCCAGCATAGTCATTAACACTGCCTGACATATTCAAGAAAGAACTGGCATAGCTAAATGTGAT

TGATGTGTGTTTATTGTCAGAATCAAAACTTCTTAGAGTCCACGGTTGTGTGTGAACACACTGGATGTTTTCAT

CATCAGCTCAATTAAATGGGTTCACTGTAGAAAGGGAAAAAAGCCAATGAAAGGTATCTACAGGCAGACCTC

ATTTTACT

SEQ. ID. NO:112    AW461523
GAAAAAATGGCGCCGACGTGAGCGCGAGCCCGCGGCCACCGAAGGAGTCGCCGCAGCCTTAGTTGG

AGCCGCTGAAGCCGCGGGAACAAGAGGCTGAACCAAGCTGAGGATGGATGAGGAACCCTCGGGGCCCAGCC

TGGACATGCCGGCTACTGCAGAGCCCAGCTCCAGTGAGACCGACAAGGGGGTGTCCCCAGTTCTGGCTGCTA

TAGACAAATCCTCTTCTATGGAGGAGGAGCCGGGCCCTGACCGGGCAAGCACACCCCAGTGTGGGAACGTG

GAGGGCCCACCGGAGGGACCCAGCAGGGTGCCTCCCCAGCCCCAGACAGTGGCCATTCCGGACCTGGACAC

ACCCTTGGCCCAACCAGCACTGTCTCCGGGACCAGTGAGGACCTGCGGCGTCCCAGACGACGCCCACCACCA

GGGAAGCA

SEQ. ID. NO:113    AW461688
TTTTTTTTAGAAAGACAAACTGCTTTATTTTAAAACACTGGAAAAAACATTAAAAGGCAAATGTCCA

TTATATAACCAAGAATGTTAAGCATTTGGAAAATGTTAATCTTCTAAATTGTGGTAGGCACTTCCAGAGAGCT

AAATATTGCAAATTATCCTACCAGATGTCTTCTGTAATACCAAAAATACTTGATATGATGAAACACACAACTA

ATTACCCAAAGTCACCATGTTAGGTTTCAATTTAATTACAAGTAAAAGTTTTGTCCAAGATGTTCCTGACACA

TGAAGCGTCCAGTTGAATTTCAGAAATGTTAACAAAAGTATCTTCCTTTTTTGCCTGTGAATGTTTGGGTATTG

CTGTATTGTTGGCTTATATCCACTACAGATACTGGTTCTAGGCCAGCCCAAGGGTCTTCAAGCATTGAAGGCT

```
TGAAATAACTCTCCAACTCATTAGACATTCTCTTTTCTCTACCACGCCCTGATCCAAATGGTGTAGATGTCCTT

GGAGAACCCTGGGGGTGGGTCTGCTGCTG
```

SEQ. ID. NO:114    BM362465
```
GCACGAGGCCAGGGTCACCCTGAGCAGGGAAAGCACCGCGATGCTGACCAGGTTCCTGGGCCCGCG

CTATCGCCAGCTGGCCAGAAACTGGGTCCCCACGGCGAGCCTGTGGGGCGCTGTGGGTGCCGTGGGGCTGGT

ATGGGCCACTGACTGGCGGCTGATTCTGGACTGGGTGCCCTACATCAACGGCAAGTTCAAGAAGGATGACTA

GACTCACAACCTCAGGCCCCTCTGATGTCTGCTGTGCTGCCTCCTGCCATCTGCATCTGGAACTGCCCAGGCT

CTCTGGATGGACTCTAGGAAGTCCCTGGCACGAGTTCATTTCCTCTTTTGGTGGAAATAACTTTTGTGTGTGG

ACACACAGCATTAAACCTCACTCTGAAACCTGAAAAAAAAAAAAAAAAAA
```

SEQ. ID. NO:115    BF440206
```
ACATTTTAATACATATTTACGTGCAACGTTGTTAGAAGCCTAAGTTGGTGAAAAACTTTTCATTTCAG

TGGGCTGTTAGTACATTAAAAGTCTCAGAGTTTAAAGGTATACTTTGTTTATCCGATTCAGTAATCTTCAAGA

ACTCATAGGGAAGTCAGTATCAGCAGGAAAGTGGTTAGCTTGGCTGAAACATACCCACAAAACCCCCAGAGG

TGAGGGAAGGCATTTTAATGCTTA
```

SEQ. ID. NO:116    AW464711
```
ATTTTTTTCAGGCCTTCTTCCAGGAGCATGTGTTCCCAGTGTACCGCAAAGTACTAACAGTATATAAC

TGACATCGTGTCATAGTTTGCAAGGCACTCCGGATGGGCAAACTGTCTTATTCATATACCTAATGTCCAGTAT

GGTGCCTGGCACATTATGGCACCTCAAAATATGTTCATGGTTAAAAATGGTAGGCTGTATGTTTGTCAGCTAG

GAAAACAGTACATCAGCACTTTATACTTGGGTCCCTTTCTGGTCAGTGGCACATATCTCGTGTTAGACTTGTA

CCTAAATGGATAAGCACTCCCCAGTGGTTCACGAACACTGCGAAAACAGAAGTATGGGGAGGTGCAACCCTG

GCAGGCAAATGCTGCCTGACAAATACCCTTGGTAGCAAAGGCCTGCACTTGGATGATCCTGATCCCTCTGGTT

TGTCACGAAGAATAGGATGGGATAAATAGAGCATACATTGACATTAACCT
```

SEQ. ID. NO:117    AW465606
```
ACCATTTGTGTTTTTTGTTGTTTTTTAATTTAGACAAAACCGCTTTGGAAAGGGGAAGTCTCATGCAG

GTTATAGGTCTTTCTCTGTCTAGGTTTCAGGTGCTTGCAACTGGACTGCAGACTCTTACCAATCACGGGCATTT

TACCTTTTCTGAACACTGCAGTTTGTTAGGCTAGAGCTGAAGTTGGAGGAGCCTGTAGTGCTTTCAACAGTGA

TGCATGTTTTAATGGATAAAAATAGCTGGTTTCTATTAACTGTATAGACAGTAAACAAAAAATCCTTAATACT

TAACTAGCTTCTTTTCAGAATGCGTTTTATTTTTGTCAGTTACAGTCCTAGATATACTTACTGCTGGTACAGTT

GTACTCTAAGATTTGTATTTGATATCCACGTTACTCCCT
```

SEQ. ID. NO:118    BF042255
```
AATATATTACAATCTTTCAAAGTCGTACACTCCTCAGTTTCTATTGTGTGATCAGTTTGTGTTTTATTT

TGTATTTGTCTCCCCCATCTTGCCCTTCTTCTAAGAAACCCTATCTTCTCTTTTGCCATCTCAAATTGAGAATCT

CAACTCTGGTTGCTGAACTGCCTGGCCAGCTCCCACAAGCAATACCTCCCTTGTTCCAGCAGGACCAAGGGA

GCCGGCCTTCACTGAGTGAGTAACTTGTGCAACTGCCTCTCCCTCAAGGGTCGGGGACCTTGGCTGGAGTCCT

GACCCTGGGCTCCCAGACAGAGATCTTCGCCTTCCTTGCTGTGAGGCAATCTTTTGGCACACCTGGGATTTC

CCCATGACCCAGGTCATTTTTTTTTGTTCAACGGACTCTGGACTCTCAAAAGGATCTGATCCTTTTGAATTTT

GCACAGCCCT
```

SEQ. ID. NO:119    BF042909
```
GCACGCCTTAACAGTGCTGTTGCTCAGACTATTCTCTAGGACTTGAATTTGGAGCAGAAACAAAACA

GCACCTGGTCCTCAGTTACAGAGTGGGGCCTTGGTTAGGATAAATCAAATTATTGAGTTTACTGAGGGGAAC

AAGCATCTGGCTTCTTTCATCTTAGCATCTTTAAATCTGAGAATGCTAGCTGAGGGTGAAAAGCCTGGGATA

GGCCTGCCTGAACACTCCTCTGCTGCTTATTACAATCTTAGCTGAGCACCTTCAAACCCTGGTTCCTGTATATG

CAAATAGTTCCCAATAATAGCATTATCTTATAAGACTTGACAGGAAGCTAAATTATGAAGCATCTCGCCCAG
```

```
GTCCTGACACCTGGGAGGTGCTGAATACTGGTCAGCTTCTTCCGTAGGTACCCGCCAGAAAAGGTGGCAGGG

GACTGAACCATATATCTGACCTCTGCGAGCCTTTCCAGTTCTTAGATTATGGGGGTCAGTGGTATAATTTAGG

TTTGTTAACAGCAGTAGCCAGTATTGGAGTTATTTACCACATAATCGAG

SEQ. ID. NO:120      BF042997
         TTTTGTTGAATTGATTTAAATATTTTATTTAAGGAAATATTCTGAAGACTATAGTTCATTATTTATAGG

AAAAATATAAAGCATACATGTTTAAAGATCATTTTGTAGTGACATTATAGGAAATAGATTTCTCCAAATAACA

TAATTAGTTTTGTAGTGCTACCAGTGGAATGCATTCTGCAGAAACATGGTTTTACCTTCAGATCTGAGCACAC

TGCCCTTACATCAAAAAAGAAAAAGGTAATAAAAAAAAAAAACACAACTTTGATTAGTTTAAATTTTA

GTAGACGACATCTGATTTGTTGAAGAGCAAGTTCTTTTATTTACCTCTTCAAGGAAGTGCTTATTTTTTCACC

TCTTTCTGAGCATCTTTATCCTCTTTGGTAATACAAGGAAGCAACACCGCCAAATTACAGAACTTCATAGCAC

TGTCGATTTGATTAAGATCGGCATAACACTTGGCCATGAACATGTAATTGGACTTAGAAAACCCAGGCTGTA

GTTCTTCAACCTTAAGGAAATTTTGCAAAGCTTCTTGTAC

SEQ. ID. NO:121      AW461908
         GGCTTCTTGGGGCTGCGGCCCACGTCAGTGGATCCAGCGCTGAGGAGGCGGCGACGAGGCCCAAGA

AATAAGAAGCGAGGCTGGAGGCGGCTCGCTCAAGAGCGTCTGGGACTGGAAGTCGATCAGTTCTTGGAGGAC

GTGCGGCTGCAGGAGCGCACGAGTGGCCCCCTCCGATCTATGGCTGACATTCTGCATTTCCATCTCCCAGTGG

CTTGATATCAGAGGCCCCCGATGAGAAACTTTTCTTCGTGGACACTGGCTTCAAGGATAAAGAACTGAACAA

GAAGAGGACCAAAGGCCAGAAGAGGTCACTGCTTCTCAAGAAGCCCCTCCGGAGCGACCTCATCCTAGAGA

ACACCTCCAAGGTCCCTGTTCCCAAAGACGTCCTCGCCCA

SEQ. ID. NO:122      AW462811
         TGGACGGCCGAGTGCAGCTGATCAAGGCCCTCCTGGCCCTGCCCATTCGGGCTCAGACACGTCGGTG

GAGGAACCCGATCCCCTTCCCCGAGACGTTTGACGGCGACACCGACCGGCTCCCGGAGTTTATCGTGCAGAC

GGGCGCCTACATGCTAGTGGACGAGAACCTGTTCACCAACGATGCCCTGAAGGTGACGTTCCTCATCACCCG

CATGACCGGGCCAGCTCTGCAGTGGGTGATCCCCTACATCAGGAAGCAGAGCCCCCTCCTCAACGATTACCG

GGGCTTCCTGGCCGAGATGAAGCGGGTGTTTGGATGGGTGGAAGACGAGGACTTCTAGGCCGGGAGCGCCTC

GGGTCTGGGGGCGGGTGCTCGGGGGAGGGTCCGCCGC

SEQ. ID. NO:123      AW461534
         CATTTTTTCAGCGGATCAATTTTCAGATCCTCAACTTCCTGTTGCAGTCTATCCAAAGATTCATCAGTG

TGAGAAAATGCCCTTTTCTCCCCTTACAGAAGGAAGTAGGTCTTCTCCCCACATTCAGTCTTACTCTAGAGCA

GGACTCAAGATACAATTGAGTATAGTGTCTGGAAAGTGCAAGCCTCTTAACAGGATACGGGTCCTCCTCCAG

TGCTGGTGGTTTCCAGTTCCTTGCTTTCAACAAAACTGAAGGAATACCCAGATTTCTGAGTATCCTGAGATTA

CCCTGCTACCACTAACTCCTTCTGTTCTCATTTGTCTGTGTGAAAAAAGGATCATTCGCATTTCCATTTGTAAA

ACTGAAAATGGAGAACAGAATCGACACTGTATCGCTGCCGTTCTGCC

SEQ. ID. NO:124      AW461574
         TTTTTTTTTTTTTCCTGATAACGTGCTTTTAATTACGTCCATTCCAAAGATACCTCCTTTCCCAGTTAA

AGACGACGCGTGGTGAGGCCTGGCTGTGTGTCTGCAGAGGGGCGGCGAGCTCCACACGGGGGCCAGCTCCT

CCCAGGCCTCACTGGCCGTCACGCCACAGCGGCTGGCCTGGGGCGCTGCTCCCTGCTGGCAGCCCCAGGCCC

TCTGGGCCCCGACCCCCTTGGGGGG

SEQ. ID. NO:125      AW465706
         GAAAGAACAAATGCTCGGAAGAAAAACAATCACAGTGAAAGGAAGTACTACTACTATGAAAGGCAT

AGATCAAGGAGCCTATCTAGTAATAGATCAAAGACTGCATCTACAGGGCCTGACCGGGTGAGAAATGAAAA
```

-continued

GCCTGGTGGGAAACGAAAATACAAAACACGGCATTTGGAGGGTACTAATGATGTTGCTCAACCATGTCATGA

ATTTGCTTCTAAAGTAAA

SEQ. ID. NO:126    BF041813
TACAGATGAGGAAATTAAGGCGAGAGAAACTAGGGAATTTGCCTGAGGTCAGGTAGGTCTCGTGTC

AAAACCAGTTTATATTAATAAAACCTTATTTTCATTTAATGATGATATAGGGGGAAAAAAAAAACAGTCCTA

GTAACATCATTAGCTCAGAGAGGAGTGGGCAGTGTCCTTCTGAAATGGATTTTCACATAATGGCATTTTAGAA

GGTATTTAAATCATACAGATCTGACCCGTTCTGGGTATGGTTTTATGCAAAGAAATCTTAATGAAGTTTTCAA

CATGGCTCCTAATTTGGGGGCATTTCATGGTTCAAATTTTTGGTCCCTTCTGGAACTTCAAGGTGCTTCCAATT

AACAATAACTTTGAACACTGACTCCTGCAGTATGGTATGCCTCCCCTGCCAGGTGGGCTTTCTGTGGATACTC

ATGGCACTCTACGTGCCCGCAACCAAGACAAGCAGAGGTTCACCACTGTATTCCCCAGNNGAGGTATGGCAT

TGATTTAAAACTTCAACATTATTTTCCAGGTTGAGAAACTGGAAACATCGGAGCAAGTAAGCCTAAAAATAG

CCTTGTGTTTTCTGGTTACTATATCTTTCATATAGAACTCAAAATTGTGAAAAG

SEQ. ID. NO:127    BF041863
TTTTTTTTTTTTTGAGCAGCGCTTGATTTATTAGCATTAAAAAACCCAGTTCATATATACAAAA

CAAGCTGATTTTGTTGTCAAGTGTTAAAAGCACTCCTTTAAAATTAATACAATTTAAAGCATGGATTAATG

AGTTGATTTCCTGGGAAGCACTTCAGTGAATGAATATTTGGCAATGGAAACATCAGATGCACACCACGCGGG

CACCAGGGGGNNNNGGGATCCACAGGGCTGCTCATCACAGCGTCTGACCCCAGACACTGTAGGTGCCACACA

CGTCCCCGGTGGGTATTGCCGCTAAGACCCAGGGCGGGGGCACGACCTGTGAAAATTCACTTGCACGTTAGA

ATAACGAGCAACTTCAGCTGCAACTTAAACCTCGCCCCAGGCCCACCGCAGCTGCAGCGATGAGCCGTGACA

CTCGGGGCGNNCAGTGAAAGTTCGCTGGACAATGTTGTGTGAACGTCCATGCTCGGCTGTGGGCCCCG

SEQ. ID. NO:128    BF044557
ATTCATATGAAGCTACAGAGGGTTCTGGACTGTTAGTGGGTTTAGGAACCAGCCCATCAACGTCAGT

CAGCCCTCTGAGGATGGGCGTATGGCCGGAAGTGTCCATTCTTCACTGTGGCTGGTCTGTGGTGAAGTGGCTG

GTCTACGGTGAACGTGCTGTAAGGCATCTGCTGAGGAGGAAAGGGCTCTGATCAGTATCACATTAATTAAGA

TAATTAGAAAAATGGAGTAACTGGCAGAGAAAGAGGAAAGCGGTAATTTACTACTATATATGGGATCTAAA

AACAGACCCAACAGAAGTTCATTATTTGCCAGGAGCCAGTGTGAGGAGCTCCGCCCGTGGCAAAGGTCATGA

GGAAGGAGGCTCGGCAGACGCAAAGGCGGGATCAAGCCTCAGGAGTCCCCCTGGAAATTCTCGAGCTTCTAC

CCCCAAACCAGAGTCTGCCTACTTTCTGCTTTGTGCTCTCACCTACACCTCTGACTTTACGGGGGGCTGTCCCC

TACCACCTCTCTCTGAAAAGAGTTAAATTACAG

SEQ. ID. NO:129    BF046723
TATTTTGCCAGGTTCCCGGTCTCAAATGCACAGGCTTGGATTGCTTTACATCATGGTATCTTCCCATCC

TGGGTGGACAAACGGGCAATGAGTTAAGATTACAGCCCCTTAATCCTACCCAGCACTAGTCACACTGGAGAC

CTTGGGGTCACCCAACTTCAATCTGGGGATCCCAGAAGGTTGACCTGCCTCAACCTGCCTAGGGATCTGGTCC

CCTGGAGGTTGTGACGCCTCAGCCTGCTCGGAGATCTGCCAGTCCAGGGGTCCCAGGAGGTTGACGTGCCTC

GACCTGCCTGAGGATCTGCACCCTGACCCAGGGAAGCCCAGCTCTCAGGTTGCAACAGTACTGGGTAGGATA

AGCTTCAGAAAGACTCACCCCTAAGTAAGTCCACCCATGGAAATAGAAGGAAGCCTATTAGTTGTGGGACTG

TGCCCAGTTTCAACAATAACTCANGAGTCCAACAAGAACCCCATTGCCCTTCTGGAAGTCTAAAAGAGGCC

CTCCCAAAGTTTGCCAATCTGGACTTAGACTCTTACGAGGGACAGGTGATTTTAAAGGAC

SEQ. ID. NO:130    BF440382
TTTTTTTTTTTTTTAAATATGAAGGAGAAACATAAGGTTTGGGGAGGGATAGCAGGAAAGAAATG

ACATCAATTTTATCTTTACATATTCCCCTCCTCTAGGCAGTTCTCCAGACATCAGATCTCTTAACTTGGGGTGT

GGATCAGCTTTCATACTCATAAAGGGGACCAGTTCTTTAAACATGCATAAGCCTGGAGACTCCAGGATGGTTC

-continued

TCCTCCCTCTCTTTAAATGCTGTGGACTAGAAAGGCGCCCACTTTGCTAAAAACTCTACATCAGTGTCCCTGG

AGCCCCGAGGCTCCTCAGGTTCCTCCTGAAGACTTAAAGGATAGCACAGAAAAACTTCTTCTCCCTAAATGG

GTTTTCTGAAGCCGGAACAGGTGTCAGGAGGGGATCTTCCTTGGCATGCGCTTCACAGTAGGCCATCAAATCT

GCAGCTGCCTTGGACACCTTTATCCTATCGATGTTGGCTTCCATCTTCAGCTGTTCTACCAGTTTCCTGGCTTG

TGCTATGCTGGCGGTGTTGTTGCTGGCCATTGGAATGCTGGGTAGGTTTC

```
    SEQ. ID. NO:131    AW463169
    AAGAGTACCAGACTCGGGAGCAGCTTCGAGCCCGCTCCCTGCAGGGCTGGGTCTGCTACGTCACCTT
```

TATCTGCAACATCTTTGACTACCTGAGGGTGAACAACATGCCTATGATGGCCCTGGTGAACCCTGTCTACGAC

TGCCTCTTCCGGCTGGCCCAGCCCGACAGCCTGAGCAAGGAGGAGGAGGTGGACTGCCTGGGGCTGCAGCTG

CATCGGGTCGGGGAGCAGCTGGAGAAGATGAATGGG

```
    SEQ. ID. NO:132    AW463234
    GGCACCAAACCCAAAACCGCAGTGCCCAAGTCACAAGCCACGGAGGAGTCTATGAAGCNNNATGTA
```

AAGGAGAAACAATCGCAGAAGATATCTAGATCAAACAATAGACAAAGAAAGCCAAAAGCCACTTGAAGT

TAAAAAAGTCTTGTCTGACCGTACACCGTGGGGATTGTCCACACATCCTGCTGGCGGTCTGGCGCCCACCCCA

TCAACAGGAACCAGAGCCGGGGGGCAGCCTCCAGCCCCTCCTCCTGAGGCCAGAGGGAGCCTTTTGGAGAAA

CAAGTACCAGAAGCAGATGGGGAGCTGGCTCTTCCCCTGTTCAAAACAGAAAAATTGGAAAAGCAGGCAGC

AGNNGGAATCTTAAAGGCTGAGGAAGAGATTTTGGAAGATCAGCTGCCCATGCAAAATTTGAAGCCAGCCCCT

```
    SEQ. ID. NO:133    BF039617
    TGAATTGCTACACCCTCCTTCAGGTGATCTTCCGAACCCAGGGATCAAACCCACGGCTCCTGCAGCTC
```

CTGCACTGCAGGCAGATTCTTTACTGCTGAGCCACCAGGGAAGCCCTAGAGTACATAGGCTGAGTATAAATG

TCATAGATCAGAAGGGGCCTGCTTCTTTGACATTCCCTAGATCCTGCCTTGAACTGCCATTTGGTCATTAATTC

CACATTCTAGTCATCTACACAAATCTTAAAGGTATCACATCTTCTGTGTTTGTTTTAAAGCGACCAGTGAAGA

CTATAAGCTCCTGGAAAATATGAATAAACTAACCAGCCTGAAGTATCTTGAAATGAAAGATATTGCTATAAA

CATTAGTAGAAACTTAAAGGACTTAAACCAGAAGTGTAAGTAATAATTTTACAATTAAACATATTTGTTTGTA

TTTAATGTTCATTTGTGCTTG

```
    SEQ. ID. NO:134    BF039493
    GGAAAATGGCGGATTCCTCGGGGCGGGGCGCTGGGAAGCCTCCTGCAGTGGGCCCCAGTACTGCTA
```

GGGGTGCTAGGAGCAAAGGAAGAACACAAGGTGGAAGAATAGTGGAGTCGCGGTACTTGCAGTATGAAAAG

AAAGCCCCCAGAAAGGCTCCTGCAGCAGATGCATTAAAGGCCGGTGGGACGATGCCTGCAGGTGGAACAAA

ATCCAGCCAGCTCCAAAAGAGCAAAGATGGCAGTGGGCTTGACAAAGGCAACCTGCAGTCTACCTTGCTGGA

GGGGCATGACACTGCCTTGTCTGACCTGGATCTCTCAGGCATTCATGATAAAAGTGTGGTCCGAAAGACTCCA

CAACTAAAAAAAAAGTCAAAGAAAGCCGAGTTGTCATCCTCTTCTGCTGTGAGTGAAAAGAGCCCAGATCTG

TTACAAGCAATGGAAATGATGGAGTCCCAGACTCTCCTTCTGACCCTGCTGACCGTGAAGATGGAGAATGGC

CTGTCTGCATTCGAAGAACAGGCAGAAAAGAACCTAGAAATATTGTGTAAAGAGA

```
    SEQ. ID. NO:135    AW461726
    TTTATTGAGTCAGCTCATGATCAGAAGTCTACTCATACCTTGATCATTGCAAAGGAAGTAGACCCCTG
```

TCCTTTATCTCTTCCCTTTTCTGTAAGCTCCAGGCCCTGGCCATGCAATTGTCTTCATCCTCTCCTAGTCCAGTT

AGTGAAGCACTTCTCCACATAACCATAGCCTCCGCTCTGCTGGCTTTTTTTGTTCCTTGCCATGGGAGTATGTG

CAAGGCCAGTGCATGGATGTGAAAACCTGTCACTTGCCAGGTCACAAAAAGGAGTCATCACTACCCTTACTG

-continued

TCCGAAGCCCTGAGCTGTATTCTGGCCTCACTCTAAAATGGTCCTGTCCTAGAGCTGATGGCCAAGCAGTAAG

CTGCAGGTGTGGGTGCCACAGGTAATTCTGGAAGGAGCACAGGGGGATGGTCGAGCCAGCTTGGACCACCAT

CTA

```
    SEQ. ID. NO:136      AW463524
        ATGTTCCTCACCATGTTTGGGGAGAAGCTGAACGGCACAGACCCTGAGGACGTGATCCGTAACGCCT
```

TCGCCTGCTTCGACGAGGAGGCCTCAGGTTTCATCCATGAGGACCACCTTCGGGAGCTGCTCACCACCATGGG

TGACGGCTTCACAGACGAGGAGGTGGACGAGATGTACCGAGAGGCGCCCATTGATAAGAAAGGCAACTTCA

ACTATGTGGAGTTCACCCGCATCCTCAAACACGGCGCCAAGGACAAGGATGACTAGGCCATCCCAGCGGCCC

CTGCCCGNNNCCTGTCCCAGCCACCTGCTCCCACATATACCGTATGCACCAGCTCCATGCCCATGAGCCCAGA

GCCCCCTCTCAGAGGACTCTCCCCCTGAGGGGCCGGGGCCCAGCTCCGAGTGAAGGAAACGGGCTGAGAA

AGCACAGCACCAGGCCAGGGGCAGAGCCAGCGGGAGGCCGGTGACCCTCCAAGGAAACCCCATCTTCTCGG

GAGCTGGGCCAGGGGGCTGGACCGGG

```
    SEQ. ID. NO:137      AW465396
        AAGCCCATCACCTTTCCTGATGGACGCTCCTTACCTGCAGGAATCTTAGTCTCCCTCTCCTTTTATGGA
```

CTTCATCACAACCCAAACGTGTGGCCGAATCCAGAGGTGTTTGACCCAACCCGGTTCTCACCAGGTTCTACTC

AACACAGCTATGCCTTCCTGCCCTTCTCAGGAGGATCCAGGAACTGCATCGGGAAGCAGTTTGCCATGAATG

AGTTGAAGGTGGCCGTGGCCCTGACCTTGCTTCGCTTTGAGCTGTCACCAGATCCCTCCAGGGTCCCTGTGCC

CACTCCAATCATGGTGCTGAGATCCAAAAATGGGATCCACTTGCAGCTCAGGAAACTGTCTGATCCAGGACT

TTTGTGATTAGATGAACAACTCATATAAGACAGACTTGTTCTCCTGTCTGGTGATTAGGATGAGGACACCTGG

GCAGCCATTGCTGGACATGTTAAGTCTTGTGTGACCACCATCAGCCTGTCTCCGGCTCTCTCCAGTGCCTACC

CATGTGTCAGTCATGTGGCTTCCCCTCTCTTGCTCTCCCTTAATAAAGTTTGCATG

```
    SEQ. ID. NO:138      AW465666
        GCTCACAATATATGCCGCATTGCCCTTTGTCAGGCAGGCTGGCCTGTACTCCATCAGTTTACCTAACA
```

AATACAATTTCTCCTTTGATTATTATGCATTCCTAATTCTGATAATGATCTCTTACATTCCACTTTTTCCCCAGT

TATACTTCCACATGATACACCAGAGAAGAAAGATCCTTTCTCATACTGAAGAACACAAGAAATTTGAATAGT

TCCTTCTTCCTGCACANNNCCAGAAACAAACTTTCCAATGACAAAAAATGCTGCAGACTTTTTCAGTTCCCAA

TACGTTTCATAGAAAATAAGTAAGAACTATTTTTAAATACTAAAAAATAAATAAATAAACCAAAATCCAGT

GTCATGTGGGCCTGGGGTTTTCTAAAAAACAAAACAAAAAAACGAAAGCTGTTACATAAAACATCCTNNCCG

GTCCATTTCAGCATGCTCTTTCAACCAGAAGTTCCCAATATTTATGATGGCGCTGGAAAGGGATTTGGCATTT

TATATCCTCC

```
    SEQ. ID. NO:139      BF040830
        GTTATCTGTACCTGGACTTGCTGCTATGGGAACCAGCTGTTGTTTGTACAAACACCTTGAAAACTTTG
```

AAACCTGACCCTTTGAAACCTTACCCTTTATCACCTTTTACCGCGTGCCAGGCCCTTTCTGACTTTCACTGGTT

GACTCTGCCCCTTTCCTTCCCAGAGCTGGCTGGACCATCGCTCTCTGGTGACCCGTGGAAGTTAGGCGCACAG

CAGCTTCCAGCTGCCATGCAGAGACCTCCAGCTCAGAACAGGCTCGTCTCCGCCACGCCCAGACCCCCTCCTG

TTCCTCAACCAGTTTCTCTCTGCGACTCGGAAGCGATGCAACCAGGGAAGAAACCTTTTATCAACATGGGCCC

TTGTCCACATGTCTGGTCTTAAGACTTCAAAGGGGCCTTGAAAGCCACATTTTGATGAGTTTGGTGTAAAATG

AGTTGGGCACACAGGGATTTAATTTTCCTTGAAAACTGCACAGCCTTAGAAATTAGCAGAGTAAAAATTAAT

GGTGAAATGGGTGCTTAATCCTCGTCAACCCCCTAAGTTTTTTATTGAAAATGGGCAAGATTGTTAATTCAAG

TGCTCTTTGGCTTTGGTGCTTGAGCAAAAGGATGGACTCTCTCCAAGTCTCCATTAACTGGTGGGAAGATGGG

GCTTTG

SEQ. ID. NO:140    BF040980
TTTTTTTTTTTTTTTGCAGCAATGACATTTAATACTTCTGGAATGATTGGGTATCTGAGAACACGCTGT

GGGCGGCTATGCTGGGCTCCCGGATGTGGGAGCTGGGCCCCGCCTCCCGAAGGGGTCCCTGCCCGGGTGGGA

GGAGCGGGCGGCGCGGCGGGCCCTGACCGGCAGGCGGGCAGCCCGGGCGGCNGCGGAGCTTCCAGAATGGC

ACAGCANNNGGCCCATGGAGAGGCTTCAAGGACCGGAGGGTCGACACGCTCGGCCGGGGCCAAACTCCATG

CCCTCGACGTCCACTTCTTGCTCCGAGTCGTCGGTGGAGACGGCNGAGCCCGTGCTGTCGGTGCGCACGCGCT

CCAGGCTCTGCGCCGACA

SEQ. ID. NO:141    BM364711
GCACGAGCCCAGTTGAGCGTGGGGAAGGGGATGAACAGCGGTTACAGGAGGTTACTCAGGAACAAG

GAACCCTCTGAGATCTTCAGAACCTGCACTGTGAGAAGACAGACAGACAAACAAACCTAAGGATTAAAGGC

ACACTGCTTATCATCAGGCTTTACAACTCACACAGGCAATGCCAAGACTTTGGTATGGATCAGCTGCCATGTT

TGCCCATGCAGGAAGAGAGGGGTTTGGTTACACCAATGTACGCATTTCTCAACAGGCCAAACCATCTGCTTG

GGATGTGTTTCTCACTGTATGCAAATGTCCTCAGAAGAAACAGGAGCTACAAACACACACTGTACTCTAGTTA

AGGACTGGCCAGCTGGAGGGTCTACTGGTGACGTGAACTGGAACTTTCTCTGCAATGCATCTCCCAAAATAA

GATGGGCTGGTGGACGGACAGAGGCAGAGACAGCTGTGTGATGTCGGTGACAAAAGCCACGGGTAGGTGTT

CAGGCGTTCATGGCTCTTTCGACTTCTGTGCAT

SEQ. ID. NO:142    BF039094
GCTGATGGACCTGGTGGAGCGCCAGCTCGGGCCTGGCCTCACGGAGCCTCGAGCCTTGCAGCTCTGC

GGTGGACGCGCTGCAGGCCGTGCTTGTCCGCGGTGGCAATGAGGATGTGGTCCAGTGCATGGAGCTGGACGG

GGGCTGGCAGTTGCTCAGGACCTCGGCTGGGCACGAGGAAGGTGTCACCCGGCTGGCCAGTGCCATGGCAAA

GTTCGCAGGCCCCCGGCTGCCCCTGGTGATGAAGCTGCTCTTCACCACACAGAGTAGCATGTATGAGGTCCA

GAGGGTCACCTCCACAGCCTTCCTGGCTGAGCTGCTCAGCAGCAATGTGGTGAACGACCTGATGCTCCTCCA

GTCACTGCTGTACAACCTGATGGCACGGCAGAAGGACACGAGCGCCCGCGTGCGGAGGCTGGTGCTCCACGG

CCTGGGCAACATCACCTTGGGCTCCCCAGATAAGGTACAGACCCACAGCCCCCAACTCCTGACAGCCATGAT

CGGTGGGCTGGACGACGGGGACGACCCACACAGCCTGGTGGCGCT

SEQ. ID. NO:143    BM366975
GCACGAGCCGACCCCTGCCTTTCTCCTTTGGGGTGGTCGGACCTAGCATGATGGGGACTGAGGCCGA

GGGGAGACAGGCCCCCGTCCCAAGCTGCTGCTTCCTCTTGGCTGTTTGCGGGGAGTTGGAAGCCTGGACACC

GTTCTTAGGGTCTCCGGCTTCTCCCCTCCCTGCCCCCTCTCTCTTGCTTGTGATCGCCCAGGCTCTGTCACAGC

CCAGCCTTCTCCAAGCAGCAGGAGGCCTCCACTGCTCTAGGCAGCTTCGTTTGCTGCTGCAGCCTGGAAACGA

GTTGTCCACGCCAGTGGCAGAGACCAAAACCCCGGTTTTAGGCCGGGTGTTGGGAGGACAGACTGGCCAAAG

CGGGGGATAGACGAGGGGGCCCGGTGTCCTTCAGGATAGCGGGCATGTGCAGGACCCGGGGTCTGGGGCAC

AGGGAATGCAACCCCGCTGGCCAGCCCTGGGGCAC

SEQ. ID. NO:144    BF044410
ACCTGAGGTTCTCCGAGATGAGCCCTACAATGAAAAGGCGGACGTGTTCTCTTATGGTATCATCCTCT

GTGAGATCATCGCCCGCATCCAGGCTGATCCAGACTATCTTCCCCGAACAGAGAATTTCGGGCTAGACTATG

ATGCTTTCCAGCACATGGTGGGAGACTGTCCCCCAGACTTTCTGCAGCTCACCTTCAACTGCTGTAATATGGA

CCCCAAACTACGCCCATCCTTTGTGGAGATTGGGAAGACCTTGGAGGAAATTCTGAGCCGGCTACAGGAGGA

AGAGCTGGAGAGAGACAGGAAGCTGCAGCCCACAGCCAAGGGACTCTTGGAGAAAGGACCTGGGGTGAAGC

GACTGAGCTTACTGGATGACAAGATACCGCCCAAGTCCCCACGCCCAAGACGTACCATCTGGCTGTCTCGAA

```
                                    -continued
GCCAGTCAGACATTTTCTCCAATAAGCCCCCACGTACAGTGAACGTCTTTCTGATTAACTCCCTGAGTAAACT

GTTATAATAATGAAAAATGTGCTACTCATGGCAGTAGTAGGTCACAGAGATGCCTTTTCTGTGATGTTACTGG

CTCTGATTCTTCATTCAGTATTTTT

SEQ. ID. NO:145      AW465824
        GGAGGGGGCCTCAGGGTGGAAGAGCAAGAGCGGGACCACACCTGCCTCCTCACTCACTGCCCCTCTC

CCTGTCCCATGCAGGGCGACTCCCACAAGCTTGACTTTCGGAACGACGTCCTGCCCTGCCTTCCGGGGCCCTA

TGGGGCCCTGCCCCCTGGGCAGGAGCTCTCCCACCCGGCCGCCTCCCTCTTCACTGCGACTGGTGCCGTCCAT

GCTGCAGCCAACCCTTTCACGGCAGCTCCCGGGGCCCATGGACCCTTTCTGAGTCCCAGCACCCACATTGATC

CCTTTGGGCGTCCCACAAGCTTCGCCTCCTTGGCTGCCCTCTCCAACGGGGCCTTTGGAGGCCTGGGCAGCCC

CACATTCAACTCCGGCGCCGTCTTTGCCCAGAAAGAAAGTCCAGGGGCCCCACCAGCCTTCGCCTCCCCCCCA

GACCCATGGGGCCGCCTGCACCGCAGTCCTCTGGCCTTTCCTGCCTGGGTCCGGCCCCCT

SEQ. ID. NO:146      BF045830
        CGGGGTGGTGTACGCCCTCTGGGACTACAGTGCGGAGTTTGGGGACGAGCTGTCCTTCCGAGAGGGC

GATTCGGTCACCGTGCTGCGGAGGGACGGACTAGAGGAGACGGACTGGTGGTGGGCGACGCTGCATGGCCA

GGAGGGTTACGTGCCCCGTAACTACTTCGGGCTCTTCCCCAGGGTGAAGCCTCAGAGGAGTAAGGTGTAGCT

GGAGAGAAGGACGTTTCCAAGGGAGACAGGATGAAGCAGCAGCTGCCTTCGCTCCAGACCTCCTCCTCCTCT

TCCGCTGCATATCTCTGTACCCCCAAGCCCTTGCAGCGGTGGGGTCCTTGCCAACAGCTCTCCGGAAACCCTG

GGGAGAACGAGAACCCGAGCCTTAAACTTAGAAGCCTGCCTT

SEQ. ID. NO:147      BF046712
        GCTTCCTGAATGGAGGCGAGATGAAGGTAGAACAGCTATTTCAAGACTTCAGCAACAGAAGAGCTG

ACAACCTTCAGTCGGATGGTGTCAACGAGTCTGAAAAATGCTCTCCCACCGCTTCTCAGGAGCTCCGGAGATC

ATCCTGGGAAGCCGCTACAGCACACCCATCGACATATGGAGTTTTGGCTGCATCCTTGCAGAACTTTTAACAG

GACAGCCGCTCTTCCCTGGAGAGGATGAAGGAGACCAGCTGGCCTGTATGATGGAACTTCTGGGGATGCCAC

CAGCAAAACTTCTGGAACAATCCAAACGTGCCAAGTACTTTATTAACTCCAAGGGCCTGCCTCGCTACTGTTC

TGTGACCACGCAGGCCGATGGGAGGGCTGTGCTTGTGGGAGGTCGTTCGCGGAGGGGTAAGAAGCGGGGTC

CCCCAGGCAGCAAAGATTGGGTGACGGCANTGAAAGGGTGTGAGGACTACTTATTTAT

SEQ. ID. NO:148      BF039623
        ATTTCTGTTTTATCTTTAAGGTCTTTTTGGTTCATCACGGGTACAGTATGTTGTAGATCATGCAATGAA

AATTGTCTTTCTCCACACCGATCCCTCCATTGTCATGACCTACGACACTGTTCAAGGTCTGCACTCTGTGTGGG

CTCTCCGGAGAGTCAAAACAGAGGTAAGGGTGAAGGCAAGTCACTTCTTAACAGAAGAAGATAGTTAATACT

GAAAACTTGCATATTTTTTTTTTTTTGCTACTCATTAAAAATTATTTTTAAAATTTGTTTATTTTTAATTGNNN

GATAATTGCTTTACAGTATTCTCTTGGTTTCTGCCATACATCAATATGAATCAGCCATAGGTATACATATGTCC

CCTCCCCCTTGAAGCT

SEQ. ID. NO:149      AW465584
        ACAGCCAGGTGCCGCTGAGAGAGGTGAAGAACCNNAGACAGCAGGAGAGACACAGTGGGGATCTC

GGAGCAGGAGTGTGGGTGGCCAGGAGCCTGGGGCCGCCCGAGGGACGTGCTTACATGGGATACTGTCTGTGA

GGCGCTTGGAACCGTACCTGATGGTGGGAAGCAATCAGTAAAGACCGTTACTGCCACCTGCTGAAGTCTTGC

CTTTTCCAGTCCCCACTGCTCAGGGTCTCCCGCCCCGGCACCGTTCAGGCTGGACGATCGCTCTCCTGCTCCCG

TCTCACCCCTACATCTCCTCTCCACGTGCTGCCCGATGGAGCCTT

SEQ. ID. NO:150      AW462929
        AGATTAAACATTTTATATAAATGACTCTTAAAGCTTTACACCTTGGGGCCANNGTACTCCTTGGGCAG

AATACATTTAGATATAAAAGACGTTATTAATACATTGCACAGTTGTCAAACTTTAAACACGAAACCGAACGC
```

-continued

TGCTCGCGGCAGCTGCCGCGGGTTGCTGCTACATGGACGNNNCCAGCCGAGGCCGAGCGCTCCTCTCCTGTCC

ACTGCCCAACGGGCTCCGTCAGGGCTCTTTGAGCACGAGGCT

SEQ. ID. NO:151    BM366972
GCACGAGGTAAAAAGCAACAATCAACTAGCCGAAAACGAGCCTCTAAATTCCGTCTCACTCCAGTGC

CGTCTTCTCTAAAGTTTGCTCCACGGTCCAGTCACAGTTCTCAGGGGTCCTGGCGGTCTCCCAACGCTGTGTTC

CACAGGAAAACAGGGTCCACAGGAAGGGAGGTCATGCGGGACGCCCTGGGTAAGCACCTGTACAGCGGCGA

TACCGCGGGGTCTCAGTTCTCCTCCGGCTTGTCGGCTGGTGGGCCGCAAGGCTGCAGCATCTTCTCCATCAAG

TTGAAGCGGACTCGCGCTTTGCTCTCATTCTCGGCAATGGCGAAGTAGTTGAGAAGATCGAAGTGGCCCATGT

AGGAGCAGTAGGAGTCGCGGTGCTGGTTCACCAGCCATTCCCACTTCGTGGTGTCCGCGTGGCCGGTGCGGA

TGTACTTGGACTGCAGATGCTCTAGCTGGCTGTGAATGGTGTAGCGGTCCGTCATCTCACCGCTTTTCCCTTTG

CTCCCAGGTGAAAGGCAGCCGACTACAGGCACTCGCTCTGGAACTTCA

SEQ. ID. NO:152    BF041965
TTGATGAGGGCCAGAACCAGGCCTGGCGTCACCCCTGGGCCCCACCTGCTTCTCGCCCACCCCAGGG

CTGGAGCGACCCATAGAGGTGCCACCTCCCCTTCTGATGGCAGCCCCAGCCACGCTCCCCCAGCCAAGTGCT

CTCCCTCAGACAGCCAGAGACACCTGGAAGCCTCCCTGCTCCCACCATTCCTGCTGGGAACCCTGAAGGTCTC

TCAGAGGCTTGCACCCTGTGGCCTTGCTCCCTCCGGTCCTGGGACCCCCAGTGCTGTCCCTGACGTCTGTCTG

GGGCTCACCTGCGAGGAGCCGTTTCCTGAGCTGCCCCATTACCCCTCCCCCCAACTACCCCAGGTGGTGGTCC

TCCTGCTTCAAGCCTTGCAGGGCCTGGGCACAGGTAGGCAGGCAGATCCTGCTGCTCTGCCAACCGCCCCGCT

GGCACCTAGTGGTGTTTAGCTGTGCTGGTTGAATGTCAGCACCCTCTGCAGGCACTTTTAAAGGAGTGTTTAT

GTTGCTG

SEQ. ID. NO:153    BM365835
GCACGAGGAAGAAGATCCTTTGCGAGAGGCATGTTCTGGTGAGGATCTTCTTCATCCCTCTCCAGAA

GAGGAGAAGAGGAAACACAAGAAGAAGCGCCTGGTGCAGAGCCCCAATNNNTATTTCATGGATGTAAAATG

CCCAGGATGCTATAAAATCACCACCGTCTTTAGCCATGCACAAACAGTAGTCTTGTGTGTTGGCTGCTCTACT

GTCCTCTGCCAGCCTACAGGAGGAAAAGCGAGGCTTACAGAAGGATGCTCTTTCAGACGGAAGCAGCACTAA

AAGTACCCTGTATCAAGATGAAGGGGAAACCATCCCAATAAACACGTTTTGGATAAAAAAAAAAAAAAAAAA

SEQ. ID. NO:154    BF045124
TGTAAAAGTGCCAAAGACAGGACGTCGATGTCCGTGACGCTTGAACAGTGCTCAATCCTGAGAGATG

AGCATCAGTTACACAAGGACTTCTTTATCCGAGCACTGGATTGTATGAGAAGAGAAGGATGCCGCATAGAAA

ATGTACTGAAGAATATCAAATGCAGGAAGTATGCTTTCAACATGCTACAGCTGATGGCTTTCCCCAAGTACTA

CAGACCTCCAGAGGGGACTTATGGAAAAGGTGACACCTAAGTTTACCAACATGTAAATAAACAGGAACACA

AATACGCTTCCGTTGGAAAATCTCCACCGTTTTTTGTTTTCATTGTCATGAATT

SEQ. ID. NO:155    BF040256
GATGAATCATCTGACCGAAGATGGCTTGCTACCTGACATTCTTTGTTGAACCAGGAAGCACACAGAA

TTGACTCAAGTTATAGCAACACCAGCAAGCACAGTGCAGACATCCTGGTGTTGGAGGAGCCTGACCACAATT

GAACCCCGATCCTTACTCATCACGCGTGTTACCTTGGGCAGGCACAGAAGCCCGCACTTCTATGTAAGGACTC

ATTGGAAAAGTCCCTGATGCTGGGAAAGATTGACGGCAGGAGGAGAAGAGGGCGTCAGAGGACAAGATGGC

TGGATAGCATCATTGGTGCAATGGATATGAACTTGGGCAAACTTCGGGAGATGGTGAGGGACAGAGAGGCCT

GGCGTGCTGAAGTCCATGGGGTCATCACAGAGCATCAAGCCGAGTCCCCTGTGTTATATAGCAGCTTCCCAGT

```
SEQ. ID. NO:156      BM364415
GGCTATCTATTTACACAAGAAGCCGAAGCCTGCTCTCCTCCACCCTGCAGTAGAGGCTCTTGGAAGACGGGT

AAGCAGATTGTTCCAGCTGTTTAAACTACGCTCCTGATCCCGTGA
    SEQ. ID. NO:156      BM364415
    GCACGAGCGGGGATGGGGGGGCTGGGCAGCCTCTTGACAAGGCTCGGGGTCGCAGGAGAGCCTGG

CACCAGCGGGCTTCTCCCCACAGCCTCCAGCAGTGGAAGCAGCTCAGGGCCAGCATCTCAGCTCCAGGCAGA

CCCATGGGTACCCTCCATGGCCCATCGAGCAGCTGGCCCAGGTTTTCAACCCCTTCCTCAGCAGTGCCTTGCT

GGCAGGGAGTGGCTCTCTCCTGAGGGAACACGGGTGCCCCTCTTGGCCTACCAGTTAATGCCCGGGCACCCC

AGGAACCCGGAATAGAGGCGAGGGCTGTGGGCCAAGTAGATCAGAAGGANAAGACAGGGGGGAGCGTGGG

GGTCCTGGGTCCAGGGCACTTTCCTCATGACCACCCTGCTCCCATGAAGGCCCCCTGGATGTCACTGCAGCAG

GGAGAGCCAAGGGGCCGTGTTGGTGGGTCTGGCTTCCTCCCACAGAAGGAGACTAGGGGATAACAACCAGA

CAGGCCTGATAAGAGGCACTCAAC
    SEQ. ID. NO:157      BM365799
    GCACGAGGGTTACTCCGTGGAGTTGGAGCTTTGGCCTCCCAGGCCCTGAGGGCCCGGGGTCCAAATG

GAGTCTCCGTGGTGCGCTCTATGGCGTCTGGAGGTACTCGCCGGCAACGTGCGCCGTTGCCCTCCCGCGGTGG

TGTTCCTACTGATGAAGAGCAGGCGACTGGGCTAGAGAGGGAGGTCATGCTGGCTGCTCGCAAGGGACAGG

ACCCATACAATATACTTGCCCCAAAGGCAACCTCAGGTACCAAGGAGGACCCTAATTTAGTCCCCTCCATCAC

CAACAAGCGGATAGTGGGCTGCATCTGTGAAGNAGNCAACAGTACTGTCATCTGGTTCTGGCTGCACAAAGG

CGAGGCCCAGCGATGCCCCAGCTGTGGAACCCATTACAAGCTGGTGCCACACCA
    SEQ. ID. NO:158      AW462329
    GTGACCGGCCGATGCGTGTCGGCCCTGGGCCGCCGCTTCCACCCGGACCACTTCACCTGCACCTTCTG

CCTGCGCCCGCTCACCAAGGGCTCCTTCCAGGAGCGCGCGGGCAAGCCCTACTGCCAGCCCTGCTTCCTCAA

GCTCTTCGGCTGACCGCCTGCCGGGCTCGCCCCTCCGGGAAAGCGGAGCCACAAAGACCTCGCCTTTCCCCCC

ACCCCCTCAAAAGATCGGGCTCTCTAGACCCCAAGGCCTTGCTGTTGGAGCTTCGGGCTCCACGAGCCCGGCT

TCTTGAGGCCTCACCCCACTGCAGGGACTGGCCCTGAAGATACTGTACGTTCTCCGTGGGCGAGTTCAGAAA

AGGCTCCGTGAACCCTTAAGGCCACACGCCTCCCGAAGTGGGTCCGTACACTGACCGATCCCACGTGAGCCC

TTCACTTTGTTCC
    SEQ. ID. NO:159      AW462136
    AGGCTGAGAGGAAGGACGGTAGCCACCCCGTCCACGTGGACAACTGCATCCTGAATGCCGAGGCCC

TCGTGTGCATCAAGGAGCCCCCTGCCTACACTTTCCGGGACTTCAGCGCCATTCTTTATCTGAACGAAGACTT

TGATGGAGGAAACTTTTATTTCACTGAACTAGATGCCAAGACCGTGATGGCAGAGGTGCAGCCCCAGTGCGG

AAGGGCTGTGGGATTCTCTTCCGGCACGGAAAACCCGCATGGAGTAAAGGCCGTCACCAGAGGGCAGCGCTG

TGCCATCGCCCTCTGGTTCACTTTGGATGCTCGACACAGCGAGAGGGAGCGAGTGCAGGCGGACGACCTGGT

AAAGATGCTCTTTAGCCCAGA
    SEQ. ID. NO:160      BF041338
    TGAATAAGGAAACTGTTGGAAAGTTTTTCCAAACAGACATTGCAGAAAATGCTTTGAAAAATGCCTT

AGAAACAGAAATTCCTACTGTCAGTGTTTTAGCTGACGAAGAATTTCTTCCCTTCAGAGAAAATACGTTTGAC

CTGGTGGTTAGCAGTTTAAGTTTGCACTGGGTGAATGACCTTCCTAGAGCACTTGAACAGATTCATTATGTTT

TAAAACCAGATGGCGTGTTCATTGGTGCAATGTTTGGAGGTGACACGCTCTTTGAACTCCGGTGTTCCTTACA

GTTAGCGGAAACAGAGAGGGAAGGGGGCTTTTCTCCGCACGTCTCCCCTTTCACTGCTGTCAATGACTTAGGA

CATCTGCTTGGGAGAGCTGGCTTTAATACTCTGACTGTGGACACTGATGAAATTCAAGTTAACTATCCTGGGA
```

TGTTTGAATTGATGGAAGATTTACAAGAAGAAAGTCCAGAACATTGACCTAATTTTGCAAAACGCGTATCAG

CTGAGGAACACATGAGAAGTTTTGGAGGCTTTCACAGTAGTTTTAAGGGATGGGTGAGAG

SEQ. ID. NO:161    BF041765
GCCCCGAGGGAGGCAGAGGCTCCCACCTCGGCCAACGGCTCGGCGGGAGGCTGCCAGCCGCGGCGG

GACATCGTGTTCATGAAGACGCACAAGACGGCCAGCAGCACGCTGCTCAACATCCTGTTCCGCTTCGGCCAG

AAGCACGGGCTCAAGTTCGCCTTCCCCAACGGCCGCAACGACTTCGACTATCCCGCCTTCTTCGCGCGCAGCC

TGGTGCAGGACTACCGGCCCGGGGCCTGCTTCAACATCATCTGCAACCACATGCGCTTCCACTACGACGAGG

TNCGGGCCCTGGTGGCGCCCAACGCCACCTTCATCACCGTGCTGCGCGACCCCGCCCGCCTCTTCGAGTCCT

CCTTCCACTACTTCGNCTCCGTGGTCCCTTCACGTGGAAGCTCTCGGGCCGCGACAAGCTGGCCGAGTTCCT

GCAGGACCCCGACCGCTACTACGACCCCCGCGGCTACAACGCCCACTACCTCCGGAACCTGCTCTTCTTCGAC

CTGGGCTACGACAGCGACCTGGACCCCAGCAGCCC

SEQ. ID. NO:162    BF045167
GGTGAGAAGTGACGATTCGGAACACAAGTACAGCTCCACGCCGCTGGACTGGGTCATGCTGGACAC

CAACATCGCTTACTGGCTGGACCCCAGGACCAGTGCGCAGATCCACCTGCTTGGGAACGTCGTGATCTGGGC

CTCCGCCAGCCTTGCCACCCTGGTGTACGCCCTGCTGTTCATCTGGTACCTGCTCAGACGCAGAAGGAGAGTC

TGCGACCTCCCTGAAGACCGCTGGCTGCGCTGGGTGCTGGCCGGGGGTCTGTGCGCCGGGGGCTGGGCTGTG

AACTACCTGCCTTTCTTCCTGATGGAGAAGACGCTCTTCCTCTACCACTACCTGCCGGCGCTCACCTTCCAGAT

CCTGCTGCTGCCCGTGGTCCTGGAGCACATCAGCGACCACCTGTGCAGGTCCCAGCTCCAAAGGAGCCTCTTC

ACGGCCCTGGTCGTCGCATGGTTCACCTCTGCCTGTCACGTGTCGAACATGCTGCGCCCGCTGACCTATGGGT

ACAGGTCGCTGTCACCCAGTGAGCTC

SEQ. ID. NO:163    BM362349
GCACGAGGTACTAGCCGAGATGGCGGCGGCTGCAGCGATTGGTGGGGTCCGAGGCAAATTGGGTCTT

CGTGAAATTCGTATCCATTTGTGCCAGCGCTCGCCCGGCAGCGAGGGCGTCAGGGACTTCATTGAGAAACGC

TATGTGGAGCTGAAGAAAGCGAATCCCGACCTGCCCATCCTAATCCGCGAGTGCTCGGATGTGCAGCCCAAG

CTCTGGGCCCGCTACGCATTTGGCCAAGAGAAGAATGTCTCTCTGAACAATTTCAGTGCTGATCAGGTAACTA

GAGCCCTGGAGAACGTGCTAAGTAGCAAAGCCTGAAGTCTCCACTGAGGATTAAAAACAACAGCCCGAGAG

TCTGGGCTCTGCTGGACTGAGAACAATGTGGAGAAATGTATTTTGTTCTGTATAAAGATTGTGCTGAAAATGC

TGTCTAAAAATGATCTGATTCGGATCCCACCAACTACCCATTATTGTGCAACCATCTGAGGGAAAGCAGTTGA

ATATAAAAATAAAACTTATTTTATTCTGT

SEQ. ID. NO:164    AW462081
CTCTTTGTTAAGCAGAGATTTAACTCTGTGGTATTTGTGACAAAATGGGAAGAAGAGACATAGTGAT

TAAGGCCAAGTTGGTGGCTTAGCTAAACTGAGAAAGAAATTTTCACAGTGGAAGGCCTGGGGCGTGGTCACA

ACTCAGACCAGGCCTCACACAGCTGTCCCTTGTGGAGACCTCTTGCCGTGGACTTTGCTTGGTCTCTCGCTTA

AAGCCAAGGCAGCACTGTGGAATTTCTGTAAAGCCACAAAGAAGCAATTCAGTGGTGGGAGCACCACACAA

ATTATGGGAAAAGGGGGCAGTCCTACAGCAGGATTATATCAGGGTTATGTTATTAGGAACCTCTCTCTGTGCA

ATCATGTTGTATAAGATGTGAGAGAGATGGACATAGATCCTTGCAACTCAATCTGTTACTCTTCCCCTAAATT

ATACCCTTTTGAGGAAGTTTTATCTAATTA

SEQ. ID. NO:165    BF042546
CAACCCCCTCAACGCCATGCAGATCCTGTGGATCAACATCATCATGGACGGGCCGCCGGCGCAGAGC

CTGGGTGTGGAGCCGGTGGAGAAGGACACACTCCGGCAGCCGCCGCGGAACGTCAAGGACCAGATCCTGAG

CCGAGCCCTTGTCCTGCGGATCCTCCTCTCGGCCACCACCATCATCAGCGGGACCCTCTTCATCTTCTGGAAG

GAGATGCCCGAGGACAGGGCAAGCACCCCTCGCACCACAACCATGGCCTTCACCTGCTTCGTGTTCTTCGACC

```
                                      -continued
TCTTCAACGCCTTGACCTGCCGCTCCCAGACCAAGCTGATCTTCGAGATCGGCTTCCTCCGGAACCGCACGTT

CCTCTACTCTGTGCTCGGCTCCATCCTGGGACAGCTGGCTGTCATTTACACGCCGCCCCTGCAGAGGGTCTTC

CAGACAGAGAGCCTGGGGGCGCTGGATTTATTGCTTTTAACCGGATTGGCCTCGTCTGTGTTCATCTTGTCAG

AGCTCTTCAAGCTGTGTGAAAAGTTCTGCTGCAGAGCCCAGAAAGCCC

SEQ. ID. NO:166      BF043129
                GCTCTCTCAACCTAAAGAAGACTGGGCGCCCACGACCTTCCTGGGTCCCTTCCCGCCCCTATTAGGTC

GCTGCAGATCTGTGAACGGTGCGGGCGCAAAAGTCAGACTCTTTCCAGGGAGTTTCCCGGCCAGTTGAGGAT

GCACCGGGGAGGGCTGTCCCGGCCTGGAACCAGAGATTTGAAAGCAGCAGGAAAACCGGAACGACCTGACC

GCAGAAGGAATGCAGAGTAGGGGCAGTAAATAGAGTGTGTTT

SEQ. ID. NO:167      BF043441
                ATTTGTTCTGTCTTCACCTGCCTTCATTAAAAGCCCTGACTCAATTTTGGTGTTGAGAAGGAACAAAA

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAAGCGTTTCACTGAGCTCCTGT

GGTAGCTCAGATGGTAAAGAATCTGCCTGCAGTGCAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

SEQ. ID. NO:167      BF043441
                ATTTGTTCTGTCTTCACCTGCCTTCATTAAAAGCCCTGACTCAATTTTGGTGTTGAGAAGGAAGAAAA

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT

GGTAGCTCAGATGGTAAAGAATCTGCCTGCAGTGCAAGAGACGANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

SEQ. ID. NO:167      BF043441
                ATTTGTTCTGTCTTGACCTGCCTTCATTAAAAGCCCTGACTCAATTTTGGTGTTGAGAAGGAACAAAA

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT
```

GGTAGCTCAGATGGTAAAGAATCTGCCTGCAGTGGAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

```
        SEQ. ID. NO:168      BF043441
        ATTTGTTCTGTCTTCACCTGCCTTCATTAAAAGCCCTGACTCAATTTTGGTGTTGAGAAGGAACAAAA
```

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT

GGTAGCTCAGATGGTAAAGAATCTGCCTGCAGTGCAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

```
        SEQ. ID. NO:168      BF043441
        ATTTGTTCTGTCTTCACCTGCCTTCATTAAAAGCCCTGACTCAATTTTGGTGTTGAGAAGGAACAAAA
```

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT

GGTAGCTCAGATGGTAAAGAATCTGCCTGCAGTGCAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

```
        SEQ. ID. NO:168      BF043441
        ATTTGTTCTGTCTTCACCTGCCTTCATTAAAAGCCCTGACTCAATTTTGGTGTTGAGAAGGAACAAAA
```

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGNAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT

GGTAGCTCAGATGGTAAAGAATCTGCCTGCAGTGCAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

```
        SEQ. ID. NO:169      BF043441
        ATTTGTTCTGTCTTCACCTGCCTTCATTAAAAGCCCTGACTCAATTTTGGTGTTGAGAAGGAACAAAA
```

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGGAAGCTGGTTTTGTGATTGAGGCGGTGGA

TTAATTCTGAGTTGAGTCCAGAGGGTCGGAACTGGATACAACTGAGCGACTAACCGTTTCACTGAGCTCCTGT

GGTAGCTCAGATGGTAAAGAATCTGCCTGCAGTGCAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

SEQ. ID. NO:169    BF043441
ATTTGTTCTGTCTTCACCTGCCTTCATTAAAAGCCCTGACTCAATTTTGGTGTTGAGAAGGAACAAAA

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTGAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT

GGTAGCTCAGATGGTAAAGAATCTGCCTGCAGTGCAAGAGACCANGGTTCAATCCCTGAGTTGGGAGGATCC

CGTGGAGAAGATAATGGCAACCTATCCAGTATTCTTGCCTGGGAAATNCCATGGAGCTGTAGTCTGATGGGC

TACA

SEQ. ID. NO:169    BF043441
ATTTGTTCTGTCTTCACCTGCCTTCATTAAAAGCCCTGACTCAATTTTGGTGTTGAGAAGGAACAAAA

CCCAGGCCCATCCCAGTGCTTCTGCCCCTCAGCACCAGGGCCCAGCATGGACCTGGTAAGGAGGGCACAGTG

GATATCCACCCAAGACAGGGAAATGAGGATTATGAGGAACTATGAATGTAGTGGATAAACTAGACCCCTCTG

ATGCCTCAGCTCCCAGCATGTCCTCAAAAGCAGTTCAATGTCTGGGGAGGAACAGGGCTGTCATAGCTCAAA

ACCACCAACCTCTACCCTATTTATTCCTGGTTCCTCCAGAAGCAGTGCTGGGGAGAAACATGAATATTCATTG

GTTTGAGATTACCAAAAAAATGCAAGGCAAGTGTTTTGTGGGGAAGCTGGTTTTGTGATTGAGGCGGTGGA

TTAATTCTGAGTTGAGTCCACAGGGTCGGAACTGGATACAACTGAGCGACTAACCGTTTCACTGAGCTCCTGT

GGTAGCTCAGATGGTAAAGAATCTGCCTGCAGTGCAAGAGACCANGGTTCAATCCCTGAGTTGGGAGGATCC

CCTGGAGAAGATAATGGCAACCTATCCAGTATTCTTGCCTGGGAAATNCCATGGAGCTGTAGTCTGATGGGC

TACA

SEQ. ID. NO:170    BM361957
GCACGAGGAGGCCTTCAGGATGGTGCAGCGTCTGACGTACCGTCGTAGGCTGTCCTACAATAGAGCC

TCTAACAAAACCAGGCTGTCCCGGACCCCTGGTAACAGAATTGTTTACCTTTATACCAAGAAGGTTGGGAAA

GCACCAAAATCTGCATGTGGTGTGTGCCCAGGCCGACTGAGAGGCGTTCGTGCTGTGAGACCAAAAGTTCTC

ATGAGGTTGTCTAAAACGAAGAAACACGTCAGCCGAGCCTATGGTGGTTCCATGTGTGCTAAATGTGTCCGC

GACAGGATCAAGCGCGCTTTCCTTATTGAAGAGCAGAAGATCGTTGTGAAAGTATTGAAAGCACAAGCACAG

AGTCAGAAAGCTAAATAAAAAATGAACCGTTTTTGAGTAATAAATCAAAAAAAAAAAAAAAAAACTCGAGG

GGGGGC

SEQ. ID. NO:171    BM362618
GCACGAGCCTGGGCTGGGGGCGGGGAGCAGGTGGGCTGGAGGGGACCCTGCCCTGGGTGTTGGGCG

CCAGGGCCGCACTCCCGCTGGGATCTTCCTGTGAAAAACCTCGGGTGGCAGCGTGCTCGGTTGGCCTCCAGCC

TCTGACAGTGTTTACAGACAAGGCCGTCACCCTGGGAAGGGGTCGCCTCCCTCCAGCGTCCCCTGGGCTCTTG

AACCGCTACTTGAATTAACCGTAGGCGCTGCTTGTAGAGTCCACTTGTTATTTGAAACAAGGCATGTTTCAAT

CCAAAGTGTTATCGTCAAAGGTACTAACTTTGAGTAGAAGAATTCACAGATGACTTCTCTTTAATAAATAAATT

CTCCTTTTCCAAAAAAAAAAAAAAAAAAAAAAA

SEQ. ID. NO:172     AW461418
AGTATATGGTGATGTACATCGAGTGAAGATAATGTTTAATAAGAAAGAAAATGCATTGTTTCAGATG

GCAGATGCAAATCAAGCTCAACTAGCAATGAATCATCTGAGCGGTCAAAGACTTTATGGGAAAGTGCTTCGT

GCTACACTGTCCAAGCATCAAGCGGTTCAGCTTCCTCGAGAGGGACAAGAAGACCAAGGTCTGACTAAGGAT

TTTAGCAATAGTCCTTTGCATCGCTTTAAAAAACCTGGCTCTAAAAACTTCCAGAATATTTTTCCCCCGTCAGC

TACTCTGCATCTTTCCAACATCCCCCCCTCTGTTACAGTAGATGACCTGAAGAATCTTTTCACANNAGCTGGA

TGTTCAGTGAAGGCTTTTAAATTCTTCCAGAAAGATCGCAAAATGGCACTCATTCA

SEQ. ID. NO:173     AW461640
GGAGATGATGAATTTTTTGACCTTGATGACTACTAGGTAGTCGACATGGGTCCGGCAAAACGTGCCT

CACCCTCCAGCATCCAACCCAAGGAGCATACCCGTGGTGGAATCCAAACAGATCCCTGCCTTACAATTGGAA

CATTTCCGGAACTTAATCCATGAGCATTGGATATTGAAAAGAAAACCGAAACAAAACCAGACCCAACCCTAC

ACTTTGGTTTGTCATGGTGTCAGCGCAGCAGCCTACAACTAGTTCCTAAATGCCACTTTGGACTAATTTAAAA

AAGAATCCCAGTTTTTACTTTTACTCGATGGTGAAATTGGTTGCTCTTGTATTTTATGGGGAAAAAACAAAAA

GATTTTTTTAACCTTCATACATAGAAGCAAAAATACTTTAACTGCTGTAAACCTTCAAA

SEQ. ID. NO:174     AW461984
GGAAGGGTGTGGTCCAGGAGCTCCTGGGCGGTGGCTCTCTCCTGGGGGTCCCGCACCAGCATCCGGT

CCAGGAAGTCTCGCAGCACCGGGGAGACCTTGTAGGAGTTCTTCAGCTTGGGTGGGGGGCTGTCCCGAAGCC

TCTTCATGGCTTGCACAGGGGAGTCACTGAAGTAAGGTGGTTCTCCATCCACCATCTCAATCACCATGATGCC

CAGAGACCAGATATCTACCTCAGTTGCATACAGAGACCTGGAGATCACTTCTGGAGCCATCCAGTATGGGGT

TCCCACC

SEQ. ID. NO:175     BF041453
GAGTTGGACACGACTGAGTGACTGTCTGAACTGAACTGAACTGAATGCAGTGGATACTGTTTTGGGG

ATCTGATTGGACACTTTCCATGGGAATCTTTATAACTGAGGGAGGAGGGAACTGGGGCTGGAGAGCAACAGT

GGGAAGAGCTGATAAACACCACCAGTACAACAGTGTTGGCTTTCTTGCCAGGATGGAAAACACATGCATCCG

CAGTGTGCAAATCACCATCCTCTTCACACCCAGACAGGTGGTGGGTACTGCAAATACCCTGGGGCCCACTGA

GGACACTGGAGAGGACACTACTCTTGCAGGAATGTTACTCATTAGAACTGTTTCAACTGTCATGATAACAGTC

ATTTGGGAGTGAACCTCACACCAATTGTGAAGATGTGTGTAAAATGAATTTATGTAAATTGGATCCCAGTTTT

CCTTTGCATATATAAAGGAAGCTTTTTTCCCTCCCCTGAAATAGTTCCTGGCATGTGGTAGGCACTCAAATATT

TATTGAATGAATCAATGAAAGAATATTTGTCTTTAAAAAAAAAAAAAAAAAAAAAAAAAAAAAAA

SEQ. ID. NO:176     BF042148
GAATGACAGCAGTGCTCTTCTGTTTTTTTTTTTTTAAATTTTAACAGACCAGCCTTAACTGTGGGTTT

GAATCCTAAAAGGACATTTGCCACAGTGTGACTCAAGGAAGTATTTGGTTGGCAGGTGAGCACCAGTGACAG

CCAAATGGAGGGACATACTTGCATGGTCAGTTTATTCTCTAATTCCAGGAAGTTCTTTGCTTTCAGAATGAAG

AAAACATTTTCTCCCCCTTTCCCCCACCCACCCGTTGTTTTTTTTTTTTA

SEQ. ID. NO:177     BF042689
ATCAGGAGAAGGAACTTGTGGTCATCAATAAGCCCTACGGTCTCCCTGTGCACGGTGGCCCTGGGGT

CAAGCTCTGCATCAGTGATGTACTGCCTGTCCTGGCAAAGATACTCCATGGCCCCAAGGCAAAGCCGCTGCA

CCTGTGCCATCGGCTGGACAAGGAAACCACAGGTGTAATGGTGTTGGCTTGGGAAAAAGAAGTGGCGCATCA

AGTCCAAGAGCTGTTTAGAACCCGTCAGGTGACAAAGAAGTACTGGGCCATCACCGTGCGCGTCCCGGTGCC

TGAAGCGGGAGTCGTGGACATCCCCATCGTCGAGNNGAGGCGCAGGGCCAGCAGCATCACCACAAGATGA

CGCTGTCCCCGAGCTACCGCATGGACGACGGGAAGATGGTGAGGGTGCGGAGCAGCCGGAACGCACAGCTG

-continued

GCAGTGACTCAGTACCGGGTGCTGAGCAGCAGCCTGTCCGCCGCCCTCTTGGAGCTCCAGCCTATCACGGGA
ATAAAACATCAG

SEQ. ID. NO:178    BF045165
AAGATTTAAAAATTTTCTACATTTAAAACAAAACTCGAAAGAATTTTTTTGGAATGTTGAGGAGGAC
TTCAAACCTGTTCCAGAGTGCTGGATACCAGCGAAGGAAATAGAACAGATAAATGGGAATCCGATACCTGAT
GAAAATGGACACATTCCTGGTTGGGTCCCAGTGGAGAAAAACAGCAAACAGCACTGCTGGCATTCGTCCGTA
GTCGATTACGAGTCTGAGATCGCCCTGGTCCTGAGGCATCATCCTGACGACCCTGGGGTTTTGGAAATCAGTG
CAGTGCCGCTCTCAGATCTTCTAGAACAAACACTGGAGCTTATAGGAAGCAATATTAATGGAAATCCTTATGG
GTTAGGAAGCAAAAAGCATCCATTACATCTTCTTATACCACATGGAGCGTTTCAAATAAGAAATCTACCTACC
TTGAAGCACAGTGATCTGTTGTCCTGGTTTGATGGTTGCAGAGAGGGTAAAATTGAAGGAATAGTATGGGAT
TGCAATGATGGTTGTTTAATCAAGGTCCATCGGCACCATCTTGGTTTATGTTGGCCGATCCCAGATACTTATAT
GAATTCAAAACCAGTTATTATCAACATGAATCTGAACAAATATGAGTA

SEQ. ID. NO:179    AW461802
GACAGACATTATGGCCACCTTCCCAAGAGCAGCCAGCCCGTCCAGGCAGCCCCCAGGCCCAGAGGA
TGAAGATGCCGTCCTAGACGAGTACGACCTCTACAGCCTGGCTCATTCTTACCCGGGAGTGGGAGGCCGGAA
AGGTCGGAGCAAGAGAGAAGCCGCCATCAACACCAACCGCCACAGCCCTGGTGGGCATGAGAGGAAGCTGG
TGACCAAGCTTCAGAACACGGAGCGGAAAAAGCGAGGGGCACGGCCCTGAGACAGGACTGGAGATGAGGCC
AGAGGACGGACACCCACAGCAATGGAAATAGGACTGAGGAAGAGCCAGCCCCTGGGGCGGGATCCAGGCC
TGCTTGCCCCACCCCAACCCCAGGACTTATCCCCACCTGACTGAGACTCTGGGGGCACCACGGAGGAAGCAC
CCCCGGCCCCAGAGAAAGGACAAGATGAGAAGCA

SEQ. ID. NO:180    AW464520
ATGAAAGTATCTGCTGAATTGGTTGGTGATCATTACATTCAATGATCCAGTGAAGAAAGGAATTGAC
TTGGGGCCTTTAGCAATATCAGAAGAGGCACCATCCTAAGACCCTATAGCATTATCAAGGAAGGGAATCCAG
GCCCCATTCTTGGGTCTGTTTTCACACATCAGCACTTAGTGTTCAATTTGACCTGATGAATAGCATATCCATAG
AGATGCAGATGATACAGAAGGTTGAAAAAACTAATTCAGTTCCACCCTTCTGCCTGTTGGCATTGTCCAACCA
GAACTCTGTTTGCTATTATCTCCCTAGCTACCAAGTGAACATGTTTATGTTAATGTCTGAGAAAAAGCTCGTG
TCCTTAAGTCTAAGTATCCTGCAAAGAGTTGGTAATCTACTCACATGAACTTGCATTTGATGGACCATAGGGT
GATCAACACGCTTTCCTGGCATCTC

SEQ. ID. NO:181    AW465157
GGCAGCCCGCGGCTCACCGAGGTGTCCCCGGAGCTGAAGGATCGCAAAGAGGATGCAAAGGGGATG
GAGGACGAAGGCCAGACCAAAATCAAGCAGAGGCGAAGTCGGACCAATTTCACCCTGGAACAACTCAACGA
GCTGGAAAGGCTTTTTGATGAGACTCACTACCCGGACGCCTTTATGCGTGAAGAACTGAGCCAACGGCTGGG
GCTGTCCGAGGGCGGAGTGCAGGTTTGGTTTCAAAATCGAAGAGCTAAATGTAGAAAGCAAGAAAATCAACT
TCATAAAGGCGTCCTCATAGGAGCTGCCAGCCAATTTGAAGCTTGTAGAGTAGCACCCTATGTCAATGTAGGT
GCTTTAAGGATGCCATTTCAGCAGGTTCAGGCGCAGCTGCAGGTGGACAGCGCCGTGGCGCAGGCGCACCAC
CACCTGCACCCGCACCTGGCCGCGCACGCGCCCTACATGATGTT

SEQ. ID. NO:182    BF039056
ATGGCTGGAGGCAGTCTTCCAAGCCCCCAACAAATCCACTCCAGCCTGTCGTGAGGTCCACTCAGAC
AGACAGATTTCCTGTGGCTAAAAACCAGCCAGGATATAGAAAGCCCAGTCCATCCCCAGCATCCTGAGGAGCC
CTCCTGAAGGCCACGAAGATGAGCGGGCTCTGGCTCTCTGCAGCCCTTCTCCTTCTCCTGGGC

SEQ. ID. NO:183    BF040869
GTCATTGGCATGAGATCTTTCATTAAAGCTGAAAACACGACTCACGCTACGTCCATCAAAATCCTTTG
CTGTGCGGACTGCCTGATGGGTGTGTATCTGTTCTTCATTGGCCTTTGCGATCTAAAGTACCGAGGGCAGTAT

-continued

CAGAAGTACGCGCTGCTGTGGATGGAGAGCTTGCAGTGCCGCCTCCTGGGCTTCCTGGCCATGCTGTCCACTG

AGGTCTCTGTCCTCTTGCTCACATACTTGACCCTGGAGAAGTTCCTGGCCGTTGTCTTTCCCTTC

SEQ. ID. NO:184    BF043917
    TGTGTGGTGTCAGATGCCCCAGCCTCCAGGAAGCCAGTCAAAGAGGGATGTGGCCACAGAAAAAGA

AACACCGAAAACACAAGCACAAAGGCAAGCAAAAGAATAAAAAATCAGAGAAAAGTAGTAGTTCTGAGAG

TACAGACAGCAGCGACAGCCAGAGTGAAGAAGGGCCCACAGACCTGTCACCCCAGGAGTTGCTGAGACGGC

TGAAGCGTCTTCCAGTAAGGAGGCAGTAATTGAATTCTGCCCCTGCCCGTCCCAATACCAGACCTCCTCCAGG

ATGGAAGTTCATTGATCACTCAGTTATACATTGTATAGATTGTATTTATATGTAATTCATGCTGTGAAATA

ATTTTTTTTTAAAACCTTGACATTTCAAAGCCTGCCTTGGAAGTTTGCTGAAATTGATTTCTATTTTTAACTTCT

GTTAGTGTCAGAGAAAGAAATTCAGACTGTACAGTTTAATTAAAATGGCATTTTTGTAAA

SEQ. ID. NO:185    BF045154
    TGTAAAGCTATAGTTTCATAAGAACAGGGGTCTTATTTGCCTGAATCCTTCCCTCCCTGAGTTCATAA

TTGGTGCTGGGCACATAGTAGGTAGCTTGGGAGAAATTTGTAAGTAAGAAAAGAAGGTCAGTGCTAGGCCAA

GGTTTCCATCAGNATGCACTCCGCCTGCTGTGTTTCAACAACCCCAAAGGGCCTATAAGCTGTATTCTGTTCC

CTTGCCCCCCAGAGGTTCCAATGCTGAATAATCAGCACCTTCCCAAGGCCTGACCCTCACCCATTGGTCGTTT

TAGAACCCCTGCTCCTTCTCTAAAGGAATAGCCCATTGCTATAGGACTGTTCCATGCTCCTCCAACACTTGCT

AATTTAGTAACCATAAATTCCTATAACAAGTCATGGGCACTAAATAGCCTCCTTACAGAGAAATGAAATGTTT

GAACCCTGAAGCACTTAACCAAAGGATCAATCTACTGTGGAGTT

SEQ. ID. NO:186    AW461470
    GGGCTTCGCACTTGTTCATCCCAACACATCACTTCCCTTAAGACCTGTGGAAGCACTGCCTGGACACA

TCCGCCCATGGTCTCTACCACACCTGCCGCCCGCATCCCGGCTGTTCTCGGTGGTTCTCTCAATTGCCTTGCCC

TGTCCTGTCATTGCACTAAAGCCCAGAGGAACGAGATACTACGAGCCCCACCCTAGCTGAAACTCGCCTCATC

GCTTTTACCCTCAGTAAGAAATAATCAACTGCCTGCTGTAAACACTGAGGATCCNNCACTGAAAAAATGGAC

AGAAGCCCCAGCCTTCAGGGAGTTATTCTAGGACAGGAGAACAAACCGCTGACAGAATAAGTAAGCAGAAT

ATCTAGTACATGGAAGCACTATG

SEQ. ID. NO:187    AW464274
    GCTATTTCTGACCTTGTGGGGCGTGTGGCTTCTGGGTGGCTAGGCGATGCTGTCCCAGGGCCTGTGGC

AAGACTCCTGATGCTCTGGACCACCCTGACTGGGGTGATACTGGCCCTGTACCCTGTGGCTGAGGCGCCCACT

GGCTTGGTGGCCCTGACTATGGCCTACGGCTTCACATCAGGGGCCCTGACCCCAGTGGCCTTCTCCGTGCTGC

CTGAACTGGTGGGGACTGGAAAGATATACTGTGGCCTGGACTGGTACAGATGGTAGAAAGCATCGGGGGG

CTGCTGGGGGCTCCTCTGTCAGGTTACCTCCGGGATGTGACAGGCAACTACACAGCTTCTTTTGTGGTAGCTG

GGGCCTTCCTTCTGGCAGGAAGTGGAGTTCTCATCACTTTGCCCCACTTCTTCTGCTTCTCAGCTCCTACCTCC

AAGCCCCAGGATCTTGTAACA

SEQ. ID. NO:188    BF044013
    GTGGCCATGGCTTTTACGTTGTACTCGCTGCTGCAGGCGGCCCTTCTCTGCGTCAATGCCATCGCCGT

GCTTCACGAGGAGCGTTTCCTCAAGAACATTGGCTGGGGAACAGACCAGGGAATTGGAGGATTCGGAGAAG

AGCCAGGAATTAAATCTCAGCTAATGAACCTTATTCGATCTGTAAGAACCGTGATGAGAGTGCCATTGATAA

TAGTAAACTCAATTGCAATTGTATTACTTTTACTGTTTGGGTGAAGATCAGTGGGGGAAACGGAGACTCCAAA

GAAGAGCTGCCAGCAGAAGTTATTACTTCAGTCTTTATTGAAGTATACATATCTTAGCTGGCTCTCCTTGGAC

TTGACAAAAATGTAAACCTGACAATAAAACCAGAGTCCCTATTTATCTGATTTTTAAAAAATGTTGTACTTAC

AGTTTTATTGTAAAAAGATCGTATCATCAGAGGCCATAACTGTCGAGGATTGGAATACATTGGATTGCTGACT

GCTGATAAAAGTTCATGCTATGGAAAAGATTGTTAAAAGG

SEQ. ID. NO:189    AW461516
    GGCCCTGCTGTCTCCACACAGTGGAGGTACCATGACCTCAACGGTCAGGACACCAGACGTCGCCAGA

AGCCCTGCAGCACTGGCTGGGACAACTCCCTGACACTCGGAGGGGAGCCCAGGCTGGGCAAGCCACATCTGT

CACCTACAGTCATTTCCCAGGAAAGGCGGGTTGCTAGCTGCTAGCCTGGTGCGGACGTCAAGTTTATGGGCTG

GAAGTCCTACCCGGAGGCTGCTCACTGAAGTGTAACCAGCCACAAGGCGGATGGAAGGCATGCCTGCTGCTG

CTCCAGGTCTCCCCCGTCCCCAGGCCCAAGATGACATCCAACAGCACCAGGGAGGTGCCCAGCCCCGTTCCT

GCAGGGGCCCTGGGGCTCTCCGTGGCCCTGGCAAGCCTCATCGTCGCTGCCAACCTGCTCCTGGCCGTGGGTA

TCGCCGGGGACCGCCGCCTGCGCAGGCCGCCCGCT

SEQ. ID. NO:190    AW462075
    TGAAACAGTTCAGTCTCCTTGCATTTCTTCTCTCCCCTACCTTCCTCAGCAGAGCCTGCCTATTTCCTT

TCCTCTATGATGCTGAGAGACTTCCCTGGTGGCACAGATGGTAAAAGCGTCTGACTACAATGTGGGAGACCC

GGGTTCAATCCCTGGGTCAGGAAGATCTCCTGGAGAAGGAAATAGCAACCCACTCCAGTGTTCTTGCCTGGA

AAATCCCATGGACAGAGGAGCCTGGTAGGCTACAGTCCATGGGGTCGCAAAGAGTAGGAGACTACTGAGCA

ACTTCACTTCACTTTATGATGCTGGGGAAGATTGAGAGCAGGAGGAGAAGGGGACAGCAGAAGATGAGATG

GTTGGGTGGCATCACCAACTTAATNNNCATGAGTTTGAGCAAGCTCTGAAACACAGTAAAGACAGGGAAGTC

TGGCATGCTGAAGCCCATTT

SEQ. ID. NO:191    AW462448
    TGCAGGCCTGCAAAAATCAGGCAGCAAGCCAGACCGGGCCACAGACGAAGTTTGCCAACCCCTTGTC

TAGATGACCGCAAAGGGCCTAACCCTCAAGAGAAATGCTAGCCAATCACCAGGCTCCTTTGTGTTTCGGCGC

TGATCACGTGACCAGGCCTGGGCACACAGATCCAAAGGATGGGGTCTGTCCCAGGCGAGAGGCTGCTCGGGC

GTAAACCACTGACCCGAGTCCTGTCCTCCTAGACCTCTGAAAAGTCAGTGGCCGAGCAGGTCTGTTAGGTGG

GGCTGAGCTGAGAGGTCAGACCGGTGTTGTGGCCAGAGTTCACGCAGGTGAGGATAGTCAGGTGTCAGAGTG

AACAGCCCGTGAGTGAAGCCCGAGACGGGAGCCGCTGCCGTCAGTCAGTCGTCTGTCCCGGAGCAGCCCGGG

GTGCTGGTGACAGGCATCGCCGTGGGGGTCGTGCAGCCGCTGACTTGAGTCCA

SEQ. ID. NO:192    AW462519
    ACAGCTTGAAGGATGAGATGGGCAACCTCAGGTGGGGGCAGACAGGACAAGGTAGGGGCAGGGGT

CCGGAGGGGGCCGGACAGAGCACAGGAAGTGTGGGGTGTGGGCACCTAGTGGGGTCCTCCCCAGGATTTG

CTGAGGGCTGGAATCAAGGTCTAGCCCACGAGGATCCTTCTGACCCTCCTTTGTCACTCTGGCTCAGGACCCA

TGCCCCTGTTCCCCTACAGGAAGCTGCTAGACACTACCCCATCACCAGTGGTCTTTTGCCACAATGATATCCA

AGAAGGGAACATCTTACTGCTCTCAGAGCCTAAAAACACCGACAGCCTCATGCTGGTGGACTTCGAGTACAG

CAGTTATAACTACAGGGGCTTTGACATCGGGAACCATTTTTGTGAGTGGGTTTACGATTATACTCACGAGGAG

TGGCCTTTCTACAAAGCGCAGCCTGCAAACTACCCCACTGAGGGACAGCAGCTCCATTTTCTTCGCCACTACCT

SEQ. ID. NO:193    AW464128
    GCATAACAACTGACCAGCTGAGACCGTATTGCCTGTTGCATCAATAGTGGAAGGCAGAAGTGTTGAC

ACAATTTCTCCTTGTCCTTTCTGATTTTTATATAAGAAACACTGGAACAGTAGAGAACAGCACAGCGTAATA

CAAATGGCTGCCTTTCATTAACCATGGACATAAGAAGTACTACGATGGCTGGTCTTGGTGGGTTTGAAGGTGC

ATTTACAGAAGCAAAGTAGTCTTGGTTTACTTGGCAGCCTCGAATAACTTCTGATACAGTATTAATGGTCTCA

GTCAGGATATCAGCAGGAACTCCAGTAGTCTCTCAAAAGCATTTTCAAAAGCAACAATTTTCTGGATTGCTCC

-continued

ATTGCTTCTTGTTAGTGCCTGCAGTAGTAAGACGCCATCATTCGTATAACTTCCCTGGAATCTGCTAATAAG

TCCATCAATCTTGAAACACCCATGGGACTGACTAAAATAATTTGCTGAACCT

SEQ. ID. NO:194 AW465040
GAGGGGGTTTGGCTGTCAGGGCCCCAGGAGCCGTTCTTGAAGGGGTCCTGGTGAGGGTCCCAGGTCC

AGGATCGGGTGAGGTTATAGCCTCCTCCGTCTTCGGAGGGTCTGCCCCTGGGGCCTGAGGCACGGACATCTC

GGCTCCAGCCACAGCCTCGGGCACCAAGGGCTCCGGGCCGGAGACCTGCGCCCTGGGGGCATCGGGTGAGG

CCTCCAGAGTCAGTCCCACCTCCGTGCTGGCTGTGACCGTCGGGCCGGGGACCGAGTCTGAGGTCTGGGTCA

GACCCGGTACCCATGCGGGCCGCGCCTCCCCGGGGGCCACCAGGGTGACCGGGGCCGAAGTGGCCGTAGTCA

CTGGCGGCCCCGGAGCCACCACCAGGACGGGCCCGGCCCGAGAGCCGCGGGGCGGCGGCGANNNGGCCGCG

GGGGCGCCATGACGGCGCGGCGGGGCCACCAGGGGCGCCGGGCCCGTCTCCATGTCCGCGGGCCGCCCCTCA

CATCCCCCCGCAGCG

SEQ. ID. NO:195 AW465639
AAACCCTCAGNGAACAGCAGACAGAGATGTCAGAGGTATCAATTCTTCTCCAGTGACCCTTCAGTTG

AGTTGGGTCAGTAGGAAAGGATGACTGGACAGTATCTCATGCTCTGTCCTCAAGGAATCCTTCCCTAGTCGTG

CCAGCTTGCTGCTCATTAGAATGAACAACTCTTCATCAGCATCTAATTGCCATTCTCTGATAACATAGCCAAG

AACTGCAGACTTCATCTGTGTTTTGGAATGTCGATTGTCAATGGTGAATACACTAACGTGGTTTTTCAGGATA

ATAAGTGGTCTTTAATTGCTAATTTAGAGAAGATTGGTTGGTGTGTATCTCTGTAAAGAGATGATAGCCTGAA

ACTATCATTAGGATAATTCCCATTAAACATTATGCAGACATTATCAGACTGATAAGCTCCCAAGCTGGGCTG

SEQ. ID. NO:196 AW465776
GAAATTGACAGCTGAGAGCTCCTCAGTAATTAAACGTTTTAACTCGGCAGTTGATTAGCTGTGGGAG

AGAGGTCGATCCTGAGCGATGCTAGTTTAGCCACCTGAAATCTCTGGTGGTTCTGTTTATATGGTGAGAAAAA

CCAGAAGGGGAGGAACAACCTGTGCTCGAAGGAAGATGGAGGTGGTCTCTGAAGATGGCTGTTTGGGTTGG

AAGCATGCTTTTGTTATTTTCTGTCAGGCTGGTCAGTAAATATTTACTGAGTATATAGTATGCTTTACAACCTT

AGGCAAAGACAAGCCATCTAAGCCTCAGTGTCTCCTTTGTTTGAAAGTTTATCTTGGTACGGAAGAGCATTTA

GAGAGTAAAATTAGTTTGCAAAGTGCTTAACCATTGTAAGCATGCTGGTGGTAGCTGCTCATCTCCACATGGG

CTAAAATGAGACTGGTCAGTAGTCGGAGGTC

SEQ. ID. NO:197 AW466079
TCAAGGACTCAAACCTTATTAAAACGCAGGATGTGTTTACAGTCATTCAGTACATCTCATACAACAG

CTATGGGAAGACTATGCCTGGAATTGGATACAACTCAACTGGGAATATCTAGTCAACAGGTATACACTCAA

TAACAGAAACCTTGGCCGGATTGTCACTATAGCAGAGCCATTCAACACTGAACTACAACTCTGGCAGATCAA

GAGCTTTTTCGAAAGATATCCTGAAGCTGGAGCGGGACAGAAACCTAGGGAGCAAGTACTGGAAACAGTGA

AAAACAATATCGAGTGGCTAAAACAAAACAGGGACACCATAAGAAACTGGTTTCTTGATTTGAAT

SEQ. ID. NO:198 BF039189
CAGCCGGCCAGGAAGCGCAGGCCCTCAGGCTCCGAACAGTCGGACAACGAATCCCTGCAGTCTGGG

CGGAGCCGCTCCGCAGGCTCTGAGATGGACTCCCGGCCCGCGTCCCAAGTGCTGAGTCGGACCACGACTCC

GAAAGAGCATCTGACAATGAGGGCTCCGGCCCAGGTTCCGGAAATGAATCTGAACCCGAGGGATCCAACAA

CGAGGCCTCGGATAGGGGCTCAGAACGTGGTTCAGATGATAGCGACTAGGCTTTATTTCATGAATATGCTTCA

TCTCTGCAGGAAACTTTTTTTTTACATATGAAAGCTGTGATAAAAACATTCAGGTGTTTGGTCAGTGGTGAA

ATTTTTGCTAAGGCAATTTTTTTCCCTATCCATTCGTACATTACTATGACCGCAAGAGATATTTCCCGTGTTAG

-continued

AGTCTAATATTTGAGTCTCTTGAGCAAAAGGTGACTATTCTTCATTATGGTACAATTCCACCTATTACATGTGA
AAACC

SEQ. ID. NO:199  BF042267
GGAATAAACAACAGAACCGTGGCTCCTAAAGAGCAGGAAGACTTCTCTTCCTGCAACCATGGTCACC
ATAAAATTTATCGTCCCAACCGGGGCATTTCTGGGCGTGAAAAGGAATGGTATTGACAAACACCCCGAGACA
AAAGGCATCACTGGACGTCTTCGGTGAACCAGGAGCACGCTCACCCTAAACAGGACCCGACATCTCTGACTG
TGCTTGCACTAAAGGGGTGAGGCGCACGGTAGGACGCCCACCGCAGCGCAGGAGAGGCCGTGGGCTGCGGC
TCNNNACCCCGCCACCTCTTCTTCCAAATCCCTCACTGGTGTCCGGCCGCGCCGTGCGGTGATGGGATCACAG
CCCCCGGCCAGGGCTGAAGCTGGGCCCCGCAGGGACAGCGCAGCCTACTACCTGCTGGGCTGCCAGGGAACC
CGTCGGGCTCTCCTGAGTCACGGAGATGCCAAGCAAAGTGCTGAACACCCCACAGCCTCAGTGCAAGAAGGA
CTGGTATTTATCTCACAGGGCTGTGCTGAGGACTGAACAGTTTCATATATGTGAAACAGCTAACACAGTGCCA
GGCATAAACAATAATAAA

SEQ. ID. NO:200  BF043458
GGTTCTTTTGCTGGAGATATCTGGGGAGAAATTGATACAAGATTCTCTTTTTGTGCAGTGGCAACTT
GGCACTATTGGGAAGTTGGATGCTATTAATGTGGAAAAGGCAATCGAATTTGTTTTATCATGTATGAACTTT
GATGGTGGATTTGGTTGCAGACCAGGTTCTGAATCCCATGCTGGGCAGATCTATTGTTGCACAGGATTCTTGG
CTATTACTAGTCAGTTGCACCAAGTAAATTCTGATTTTACTCGGTTGGTGGCTTTGTGAACGACAGCTTCCATC
AGGTGGACTCAATGGAAGGCCAGAGAAGTTACCAGATGTATGCTATTCATGGTGGGTGTTGGCTTCCCTAAA
GATAATTGGAAGGCTTCATTGGATTGATAGAGAAAAACTCCGCAGTTTCATCCTAGCATGTCAAGATGAATA
AACAGGAGGATTTGCAGATAGGCCAGGAGATATGGTAGATCCTTTTCATACTCTGTTTGGAATTGCTGGATTG
TCACTTTTGGGAGAAGAACAGATTAAACCTGTTAGCCCTGTTTTTTGCATGCCTGAAGAAGTACTTCGGAGAG
TGAATGTTCAGCCTGAA

SEQ. ID. NO:201  BF043688
TCATTCATGCCCGGGGTCCAGCGACCCATCCCAGGGAGCCCAAGAGGTGGCAGCTGTAGCACCAGG
GACTTAGGTCGGAAGTCAGCGGGACTTCCTCAGACTTCCCTCTCTCCGTGAAGGGGAGGGGCCCAGTGCCCA
GAGGCCGGGGATGCACCCGAAGAAGCCCACCCCTTGTCACTGATCAGAAGCAATAAGGCCCTCCATGTGCCT
GAAAGCCCAGAGGGAGCGCGGGCAGGGTCCCCAGCGGCGGGACGGCATCTCCCCGGAACGGCCCCTCTCG
CCTCCGCAGGGACAGCGCTGGCCCCCGTGGGCGCCCCGGCCCTCCGCACCCGCCGCAGCCGGAGCCCTGCGC
CGCCGCCACCGCCGCCAACACCAATGCCTCGGCCCCCGACGCCCCCCGCGGGCTGCTGGCAGTGGGATGGGC
CGTGG

SEQ. ID. NO:202  BF044377
AGAAGGAGAAGATGATTTTTCTCCTCCTTAGGATAAATGAAACCTTGTTTTTATGTAAGAATCAGATG
ACCAAATTTGACCTCGGTCTGAATGGCCCCACAGGTTGTGCTATGATGTAGAGCCCTCAAGTAAAGCCTACCC
AGGAAGAGAGTGAGAAAGAGAACCACTTCTTTGTCTTTGCTTTTGCAGTTCATCTTTAACCTTCTTGGGAAGA
AAAAGGACTCTCCCTTTTAGAGATGAGGGGAAAAGAAGGTTTACATTTTAAGACAGGGAAAAAGTGGAATC
AAATCCTAAAAGTGTGACTGGGGAGAAGTCAGTCATTTCTGTGTCTTTTGACCCTTGTGATAATTAACCCCGC
GCAATACCATGTTAAGATGCATTTAGAATAACAAAATTAAAAACTTGACATAAGATCTCATTTTCAGAAAG
CAGATTACAGACCACCAGAGGGAAATCATGGGGGCCGTATTGCACAGGCAACTCTGAGAAAGTTGTGCTGAA

-continued

AATGTAATTCCTTCTAACCAGGTTTCCTTTTCTCCTTTGAAAGAAGAACATTCCACTTTGTTTAGAATTCTGA

GTTTTTGTTAAATCATCCCACTTAAAAGCTCTCTTCCAACCCAACTTATACAGTTTGAAAT

```
SEQ. ID. NO:203       BM362629
    GCACGAGGTCGCTCAGCTGCGGTACCGCTGTCTGCGTTGTCTGTTTGGAGAAACCCAAATACCGCTG
```

CCCCGCCTGCCGCGTGCCCTACTGCTCCTTGCCCTGCTTCCGGAAGCACAAAGAGCAGTGCAGGCCTGCAGCT

GGTCCTGTCGAGAAAAAAATAAGATCAGCTCTGACTGCAAAAACTAAAAAGCCTGTGGAAAAGGAAGGTTC

CTTAGATGATGATGACTCTGTGGCTGATTTTCTCAATAGTGATGAGGAAGAGGACAGAGTGTCTTTGCAGAAT

TTAAAGAATTTAGGGGAGTCTGCAGCACTGAGGAGCTTACTGCTCAATCCACACCTCAGACAGCTGATGGTC

GACCTCGATCAGGCGGACGACAAGGCCAAGCTTGCGAGCCTGCATGCAGGAGCCCTTGTTTGTGGAGTTT

GCTGACTGCTGCTTGAGTATCGTGGAGCCGTCTCAGAACGAGGATCCTT

```
SEQ. ID. NO:204       BM366480
    GCACGAGGATGATGCAAACAGAAATTCCACCGGCCTCCAGATACTATCATGTGTCATGTTTCACCAG
```

GCTCCACAAGCTTGAGCTTCAGACTGTCTCGGTCACTTGCAGGTGAGCAGGCTCAAGACTCTGCTCCCCAGCC

AGGAGAAGATGACTGACACTGAGTTTGGCTACGTTCACGGGCTGGCTGAGGACTATCTGAAATATGTGTTGC

AGATACAGCAACCTGGATCCAAGCCAAGCAGAAAATTGCCAAGAGGTCAAAGATCAAGTCTTTTGTGAAAGT

TTATAATTATAATCACCTCATGCCCACAAGGTACTCTGTGGATATCCCCTTGGACAAAACTGTTGTCAACAAG

GATGTCTTCAGAGACCCTGCTCTCAAACGCAAGGCCCGACGAGAGGCAAAGGTCAAGTTTGAGGAGAGATAC

AAGACGGGCAAGAACAAATGGTTCTTCCAGAAGCTGCGGTTTTAGGTCTGTCTCA

```
SEQ. ID. NO:205       AW465210
    TACAGTGTGCCTTTCGGAGTGCTATGGTCGGTAGGTTGCTGTTCGCAGCAGAGGCCCGTACCACGAG
```

CCAGCGCAGGGAAACTACACCACTACACTAAAATTTACCATATTTTATATGGTCAGAAATCTGTTCAAAGCA

AAAGATAATTTGAGAGGGACTTGGATCAAGAATGGATTCTCTTAACTATACAACAGCATGTGATTCAGCTGT

GGAAACTGAGAATCAAAGTGACAAGTCTTCCTCTGGTAGCAGCTTATTTAAAACTCAGTGTGTTCCTGTCCCA

CCTAAACGGAGGCAAAGAAACACTATTAGAAAATTCGTTCACATACCCAAAAATACTCAAGCAACAGAGTCA

TCTAGTGACTCATCTATAGAGCCAAGACCACTGACTTTAAAGGCTATTTTTGAAAGATTCAAAAATAAGAAA

CGTAAACGTAAAAGAAGAAATACAAGCCAACGGGAAGATCAGTGGGAAGACC

```
SEQ. ID. NO:206       BF043768
    GATTGGATACACGGCTGCCACGGGGCTGGTGGGGCCTCTCCTGGTGTGGATCATGGGTATTCCCAGC
```

GTTACCAGCTCTCAAAGGATGGGAACTGAGCAACCCTCGGCCCTGTGTTTGTTCACAGACCCTGTGGGCTCGT

GTGTACAGTGTTAGAGATCCTCTTTCATCACAAAAGGACTGTGGGTGGAGGAGTAAGGTCATAGCTCAAAGG

GCTTTGCAAAATTTTAATATATTAAAACAAGAGGCATCTGCTAGAAAACCTTCTATTGTATAAAACCCGAGCT

TTTAAAAAAAAAAAAAAAAAAAAAAAAAAAAAAAAAAAAAAAAAAAAACCAA

```
SEQ. ID. NO:207       BF045850
    CCAGACTCACTTCCGCTGCCCGGGATGTGGGCGGGGCTTCCGCCGGAAACCGCACTTGCTTAGCCCC
```

CTGGCGGTCCGGGCTGAGGAGAGCCGCCCGCTGGGCCTCGAAAGTGAAGAAACGTGTGGCCACCGTGTGAC

ACCGCCAAGNNNCNNNTCCATACTCCGGTTGCGACGAGGGTGCCTCCCGGGGCCCCCGGGCATGGAGAGGC

CAGTCTCCCCGAGAGAGGGCGCCGGGGCGGCCTCTGAGCAGGACGAGCTCCCTCCGAGCTCGAACCTANNTG

GTCAGAAGTGTGGCCGCTGGGCTGGGGGGCCGGAGGCCCTCAAGCCTGGCCCCGAGGGGAGAGACC

```
SEQ. ID. NO:208       BM365541
    GCACGAGAAGGAAAAGACTGTGAAATAAGAGCTGTGGTGAACAGGACTGCCTAGACCTATGGGCCA
```

GTAGTGGACTTTGACCCCTGCCAGCACGGTATGATGTGAAGCTCTCAGTCAATAGAATCCACAGCCTTCTTCA

GAGTCCTGGTAACCAGGTCTTGCTTCAAGTTGGTGTCTTGAGTTTGGGATTTCTGAAATCAGCTTTCTCAAGA

CTTTGGAAGGCTCAGACCTCTGTGCTCACAGAGCTGGGCACATAGCTGCCTTTTATGCAGAGGTGACACAGG

GCAAGAAACAGTAGTAGAGGTGGTGTAGAGCCCCAGAAGTTTCTGGAACTGCCCTCTCCCAAGAAGCACTAT

TACAAAATCCTCTACAGAGAAACAAGTTGTCGCCCAAATGTTGTTTCTTCACATATAAACAGAGGTCTGTGGA

CATGTGAGGATAAGAATAAAGACAAAAATCTTGCTCTTTACATGTGTATCTCTGGCTTCCACTGTGGAGAGAT

AACCAGCAAAACAAGGCAAGAGATGTGAGAATAAACT

SEQ. ID. NO:209    BP230001A20G6
    AGGACTTGGGGAGTCNTTATCTGCTCCATCTCAGCCACTCGCCACANTCAGAGGATATGCCANGGAG

GTCAGGNGGACTGCTTCCAGATCCTCCTAGAAGCANTTACTTGGAAGGTCCAAGAGGCCCAAGATTNGATGG

TCCTCGAAGATTTGAGGATTTAGGGTCAAGGTGTGAAGGACCGAGACCCAAAGGGCCTTGTTTTGAAGGAAA

TCGCCCCGATGGGCCAAGNACCCANATTTGAAGGTCACCCACNAGCAGGGCACTAAAAGCAANATGGGGNA

ATGTATTCCCCGGGGGCCAAGCATCTTAAAGTTTNCTATATTACCCCCANTACATCCCTTCANCCCTCNGACA

GANTTGGACCACAGGTGGAAAGGCCCCAAACCCAACTTTTTGGACAAGCAACATCANNCAANCAACCTAAA

GTTCACAAGCCAGTAACCAAGGAAANAAAA

SEQ. ID. NO:210    AW462359
    GTCATCGACGATCACTTTCAAAAGCAGTGTACGTCACAGGAATGTCAGTCCCCAGATCAGAAGAGTG

TTTATTTTGAAAAGCTGAGGGAAGGTTGGAGTGTAAGTGGATGGATTGGAGGATGTATACAAGGGGGGCTTC

AACTTAAAATATTTTCTTTCTTTTAAAGAAAAGAGAAAAATTCAAAACGTGGAAAACTGTTAAGAGTAGATA

AGCTATGAGGTGATGGGGATATTCATCATATTGTTTTTTCTACTTTTCTGTAGGCTTCAGATATTTTTTAAAAA

ACCATTGAGTGACTTTGTTGTGGTGATGCAAACAGTGCTACGTATCAGACATTTTGGAAACAGTTAATTGACC

TGGGAAACTACACGTGTACATAGGCTTGTGTAAGAGGAAGAGAGCGCCTTCTAGATCTGATCGCCACGTTTC

TAGTGCTGCAGTTCCTTCGCACCAAGTTGAAACA

SEQ. ID. NO:211    BF440272
    TTTTTTTTTTTTTTTTATAGATACATATTTAATATAATAAATGTGATTGTGGTTACAGATACATATTTG

GTGCTTTATCAAGTAGTATGAATTCCAGAGTACACAACACGTGGGATACAAAATTTGAAGATAAACACAATT

GTTCCTAAATGAAAAACATGGGATACATGCTGATGAATGGATTCCAAACTTTCATTTCCACTCTTTTCTCCA

GGCTGGTCTCCTGAAGATGAGTTGCAAGTTGTAGCAGTCTTAAAAAAAAACTCAGTCCCCCAAATTCTAATA

ACATGTAATATGAAAAGAACTTTTGGC

SEQ. ID. NO:212    AW461819
    ATTTTCGAAGATTGTGGCAACGTGCCCAGCGAACTCAAAGATCGAGGAGAATTGAACAACGAACAA

GGAGAGCGAAAAGTCTGCAGGTTCAAGCTTGAATGGCTGGGAAATTGCTCTGGAATAAATGATGAAACTTAC

GGCTACAAAGATGGCAAACCATGTGTCATTATAAAGCTCAACCGAGTTCTGGGCTTCAAACCTAAGCCTCCC

AAGAATGAGTCCTTGGAGAGTTACCCAGTGATGAAGTATAATCCGTATGTCCTGCCTGTTCAGTGCACTGGCA

AGCGAGACGAAGATAAGGAGAAAGTTGGAAGCATAGAGTACTTTGGACTGGGCGGCTACCCTGGTTTCCCTC

TGCAGTATTATCCCTACTACGGCAAGCTTCTGCAGCCCAAGTACCTGCAGCCTC

SEQ. ID. NO:213    AW463150
    GCAACAATGCTTTCTGATCCAGTGAAGGCTTTAAAAAAAAAAAAAATCCAAGAACAGAATTCATTT

TCATCATCTCTGGTTTTCAGAGGATTTAAAAAAAAAGTGTGTTTCCTGGGACGCCCGTTAAAATCCTTTTCTTT

GTCGAAGGCTGCCATGAGCTGCACTTTTTGGGGTGGGAAGGGTGAATGCCGCGTGGGATAGGGGGGACAG

GGGCAGGGGCCTGTCGTGGATGAGGGCCTGTGGCTGCGGGGGAGGAGTCCTGTCTCGCAAACCTCACCCCA

CCAGCCAGGGGGACTTATTCTAAGACCCGTGCATGAGGAATGGTGGCCAGTGTTGTTCTAGATCGACAAGGT

-continued

GTTGGTTTCTCTGTAGGCTGTAACTTTTAAAAATAAAGAGTTATTTAAGGGTTATGCTGCACTAGTATTTCTTA

AGNGGAAACTGTTCCTTACAGCTAGGAAAGGGAGTGGGCA

SEQ. ID. NO:214       BF039065
    ATCACACACGATATTGAGGAGAAGGGCGTCGGCATGAAGCTGACAGTCATCGACACGCCGGGCTTC

GGGGATCACATCAACAATGAGAACTGCTGGCAGCCCATCATGCAGTTCATCAACGACCAGTACGAGAAGTAC

CTGCAAGAGGAGGTCAACATCAACCGGAAGAAGCGCATCCCGGACACCCGCGTTCACTGCTGCCTGTACTTC

ATCCCCGCCACCGGCCACTCCCTCAGGCCCCTGGACATCGAGTTCATGAAGCGCCTGAGCAAAGTGGTCAAC

ATCGTCCCAGTCATCGCCAAGGCTGACACGCTGACCCTGGAGGAGAGGGTCTACTTCAAACAGCGGATCACT

GCGGACCTGCTGTCCAATGGCATTGACGTGTACCCCCAGAAGGAGTTTGACGAGGACTCTGAGGACCGGCTG

GTGAATGAG

SEQ. ID. NO:215       BM365510
    GCACGAGGTTGTCTTGCACTGTTTGGAAATCTGCCCCCGCTCCTCCCTGCCCTCACTTCCTGAATGAA

ATGCTTCTGAGGTTGTTTATGAAAGGAGTGATCCTTGGGCAGGCAGGAGGCAGTGGGCTTTATGGCTCCTTGG

AGTTACTGTTGATCTTGACCTTCTCTTTGGCTACCTTGAGACAAAGAATATGCCAATACTTGGGGCTCTGAGTT

TTATAGTCAATATTTATTTGTATCATCTCTTTGTCTAGGAATGTAAAAGTGACTCTAAACTAAGATGTGTAATA

AAAATCAGATTTATTGTACCTCCAAAAAAAAAAAAAAAAA

SEQ. ID. NO:216       BM365938
    GCACGAGGACCTTCGCACCCCCATCCCAGTTTCTGTCCCTTCTCGGTTGCTTTTAGGTGGATCCCTTG

GAGGCAGAAGCAGCCAAGGACTGATCCCAGGTACTCTGTGTAGCAAACAAACTGTGAATTCTGACTCCCCTT

GCCCTTCTTCCAGCTGTAGGTGCCTCCCCTCTGATCGCCTGGGAGGGGACTGAAGAAAGGCAAGGGCCAAGA

TGCTGCTACTTCTGACCCTCCTCTCTGGGGCAGGGCAGGAGAGGAGCCTGGTTCATTGTGCCACATTTCATAC

CCGTGCAGGCATGGGCGAGCGACTGGCACCCCTTTCCGGCCTCAAAGCCCTCCCTGCAGTGAAGCAGGGCAG

GAGGGAAGAGGCCCCAGCATTGGGGTTTGGATTCTAGAGGGGACATGATGACCGTCAGGGTCAAGTGCAGA

AATCTTTGCCTTTGCTACCATTTCTGTATGATGAGAAATAAAAGTTCACCAAGGTTTTGTTTTGTAAAAAAAA

AAAAAAAAAAAAAA

SEQ. ID. NO:217       BF039954
    AGCTCAGCTCGCTCGTGTGAATTTTGTCACGCCCCTTTGCCTCTCTGAGTCTGCTTCCTCATCCATAAT

CAAGGGGAATCTTTGACATCTCATAAAGCGTGGATGAGCCTTCACGTTTCTGAAAGAATAGTGCTCGGCGCA

TAGAAAGTGCTGGTAGATGTCATCTGTTAAAGATCTTTTCTTCATGTGGTGTAGGCTGCGAGGGACAGGAAA

ATATCTGAAGCCATAAAATAGTTTCATCAGCTATTCCTAAAGGCGAATGGTTTTCTTTTCTGTTTTTCCTGAAA

TGGCAAAGGTACGGGATGGGGAGAGATGACAGGAGGAGATGAAGAGATAGGACAAGACTGGTTTCTACGCT

TCATTTGTATCATGTTATCGTTCGGGTGCATTTTTTTTAGCCACCGTCCCATTTTAAAGCAGAAGGTCAGTCAT

AACAGGGAACTCTGTTCAATGTTATGGGCAGCCTGGAAGGGAAGGGAGTTTGGGGGAGAATGGATACATGT

ATGTATA

SEQ. ID. NO:218       BF040540
    GTGGGGAGCCAGGACGACAGAGACCTTAGCACATACGGGACAGCCTGTCTGGCTGGTGGCTTCTGT

GGAAGGGGCTGAATCCCTGGGCAGACAAGATCAAGGTTCCAGATATGGCAGAGATCCAGTCTCGCCTGGCCT

ACGTGTCCTGCGTGCGACAGCTGGAGGTTGTGAAGTCCAGCTCCTACTGTGAGTACCTGCGCCCACCCATCGA

CTGCTTCAAGACCATGGACTTCGGGAAGTTCGACCAGATCTATGATGTGGGCTACCAGTATGGATCGACCGTC

TTTGGGGGCTGGAGCCGGGGCGACATCATTGAAAAGATTCTCACAGACCGGTGGTCTGCCGACCTGAACGAG

AGCCGCCGTGCAGACGTGCTCGCCTTCCCCAGCTCTGGCTTCACCGACTTGGCGGAGATAGTGTCCCGGATCG

```
                                 -continued
AGCCGCCCACCACGAGCTACGTTTCGGTTTCCGACGGTTGTGCTGATGGGGAGGAGTCGGACTGTCTGACGG

AGTATGAGGAGGACGCGGGCCCTGAGTGCTCACGGGACG

SEQ. ID. NO:219        BM366584
    GCACGAGGGACGAAGCCAGAGATGGTATATCCAGCATGAAGGTGTCAGACCATGAGGTCCTCGCAG

GTTCCGTAGATGGCCGGGTGAGGCGCTATGACCTGAGGATGGGGCAGCTCTTCTCAGACTACGTGGGCAGCC

CCATCACCTGCATCTGCTTCAGCCGGGATGGCCAGTGCACCCTGGTGTCCAGCCTAGACTCTACCTTGCGGCT

TCTGGACAAGGACACAGGGGAGCTGCTGGGCGAGTACAGGGGCCATAAGAACAAGGAGTATAAGCTGGACT

GCTGCCTGAGCGAGCGCGATACACATGTGGTCAGCTGTTCTGAGGACGGGAAGGTTCTTCTGGGACCTGG

TGGAAGGTGCCCTGGCGCTGGCCCTGCCTGTAGGTCCTGGTGTGGTGCAATCGCTGACCTACCACCCCACAGA

GCCCTGCCTGCTGACTGCCATGGGGGGCAGCATCCAGTGCTGGCGGGAGGAGACCTACGAGGCTGAAG

SEQ. ID. NO:220        BF043047
    GGTTCACTGCCCTGGTCATTCTCCTGCATCTTCTGTCGCTCTGGTGGCTGTCTCTGGGAGGGACTCAG

ACAGTCCCAGGAGACCTGGAAATGGACTCATTGGCCTTTGAGGATGTGGCTGTAAACTTCACCCTGGATGAG

TGGGTTTTACTGGATTCCTCACAGAGGAAACTCTACAGAGATGTGATGCGGGAAAACTTCAGGAATGTAGTC

TCAGTAGAAGCAAAACAGGAAGATCAGGACATTGACGATCAGGAGAAAAACCAGGAGAGAAAATTACGAA

ATCCCAAGGCAGAGAGACACTCCGAAAAGAAAGATATTAATTCCTCTGAAGAAAGCTTCAACCTTATTCCAA

CTCCCAATGTGAAGAGAACTCGTGATATAAAACCATGGGAATGCAGAGCATGTGGGAAAGTCTTCATGTATC

ATTCATCCCTTACTAGACACATGAAATGTCACATTGAAAACAGATCAGATCGCCGAAAGTACC

SEQ. ID. NO:221        AW461654
    AGCCAGCTACCTCGGTAACTCCAATTCAGGTTAACTTCCCTAGGGAACAGTGCAGGTGTCCACGGAC

ACCGCCTCCTCGGTGGGGTGGGGGCTGCCACTTCGGAGGGGTGGCACGGACCTGCCTGGCCTCTGCATTTGG

GGTGGTTCCTCCCCCATCTTCTTGCTCTTGGGTTTTCCGACGGGTACAAGGCCTGCCCGGCTCCCCCCTCCCCC

GGGAGCCTCACTCTGGTCTTCCAACAGGACTGGGCGTCAGCTCCCCGCCCGGCTCCACCCGCCCCCCAGTGGC

TCCC

SEQ. ID. NO:222        AW462133
    AGAAGCTTTAAATATTAGTGTTTCATCAAATTGGGCTTAATTTAAGAGAATCCATTGACACGAAAAT

GAAAGAGAATGATCTTAGGGTTTCAAGCTTCTTAAACGAACACCCCAGTCAGTCCTTCAGACGCAGCTGTTCA

GAGCTCTAAAGCCGACGAGGTTCAGTCACTGGTTGGGCTTCCATGATGTAACTCGGCCTTTTCTGGTTTTAAT

ATTTACAGGGTATTGCACATAGGAGACAGATGACCAGAACCCGAAAGGCTCTATTGCACACACAGATAATCA

CACGTGAAAATAAAAATCCACAGGACCAATAGCGCATCTTAAACTTCTTCATACTTAGAAAAATATATTTTTA

AATAGCAGTCTGCATAATTTCCAGTCCTCAGGAAACTAGAGAGAAGCTAAATAGGAAGTTCCTGAATGGCAA

GTACTGATCTTTGGCAGCATTTAAAGGGAACAGGAGTAAAGACCT

SEQ. ID. NO:223        AW462711
    GATACTACATTCTGGGTTTTGCTTGACCACCAGTGTCATTCTGACTGGCAGTCAGGGTCCTGACGGAC

GCTGCAGTGTGCACGCTCTTTAAATACGATGGATTGTTTTAGTGCTGTCAGTGATAATGCTAGCCTACTTCTAT

TTTGACTTTAGTACAGAGTTTATAATTGTGTAACTCCTAGAACATTACATGGAGCCCTGGTCCCTTTTCCCTAC

TTGATGATTTGACTTTATTCTTTTTCTCGATCGCTCACTTTCCTGATTCTCCAAGGACCAAATTCTCCAGTGAG

CACTGGAGCGTGTCTCCAGGGTAAGCCAAAGGCTGCGCTCCTCAGCCTCTAATTGTTCTGCAGCTGCCTCTGG

CAGGCACAAGTAGCCCCACTGTGTGCAGGAACACATGCCAAGGAA

SEQ. ID. NO:224        AW466082
    ACCTGCCCTCTTGCTGGCTCGGGCCCAGCCGTGGTCCCTGGAACCCTCAAGTTGGGGGCTGCGGCCTT

GGGATGGGGGGTCGCAGGGGGGCTGCTGCTTCCCAGGCGTTGCCCACCGGTGCCTGGTCCAGCTGCGGGTCA

GAGCCCCGAGCAGGGTGCCGCACACCGGCCCTGAGGATGCCGCCCCCGCGGGTCCCCGTGCTGGTTCCTGCT
```

-continued

```
GAGGCCCCGCTTCGCCCCGCACCTGGTCGGTCATCACAGAAGTCTCCAGAATCCTGCTCGCAGCGTTTCTCCT
GCAGACTTAACAACTCTGGACGCATTGGCAGTTGGGACCCAGGGGCGGGCTTGGTGTTCTGTTCCGGGGGA
CGGTTTCCAGAGGCANCTGGTCCCCTCTCACTCTGCCTTGCCCTGCCCCGGGCATCACTGGTCACTTGCCTCTG
CCAGGGAC
```

SEQ. ID. NO:225    BF045301
```
GCGCTCTCTCGGGCAACATGGCGGGTGTGGAGGAGGCAGCGTCCTGCGGGAGCCACCTGAATGGCG
ACCTGGATCCAGACGAAAGAGAGGAGGGAGCTGCCTCTACGGCTGAGGAAGCGGCCAAGAAAAAAAACG
GAAGAAGAAGAGTAAAGGGGCTGCCACAGGGCAACAGGAACCTGATAAAGAAGCAGGAGCCTCAGTT
GATGAGGTGACAAGACAATTGGAAAGACAAGCATTGGAAGAGAAAGAAAAAGATGATGATGATGAAGGTA
GGATTATCGATTGTGCTTTTACTGTCACTTTTAATCCCAAATATGATACATTATTAAAAGCTGTCAAAGATGCC
ACTAACACTGGAATAAAGTGTGCCGGAATTGATGTTCGTCTCTGTGATGTTGGTGAGGCTATCCAAGAAGTTA
TGGAATCCTATGAAGTTGAAATAGATGGGAAGACATATCAAGGCTTCCAAGAACAAAACACTTGTTAAATGT
CATCAATGAAAACTTTGGCACTCTTGCCTTCTGCCGCAGATGGCTGGATCGTTTGGGAGAAAGTAAATACTTG
ATGGCTCTGAAGAATCTGTGTGACTTGGGCATTGTAGNGCCATATCCACCATTATGTGACATTAAAGGATCAT
ATACAGCACAGTTTGAACACACCATACTT
```

SEQ. ID. NO:226    AW461425
```
TTTGTTTTTTTTTTTTTTTTGCTTTTTTGTTGCAGCCTTTAGTCCTTGCCATGGCAGGCTGGTTCTATT
AAAATACATCAAAACATATCCTAATGATTCCATGTCATCTCGGCGACTTTGTTCAATACCAAGATGTGCATTG
ATGCTAGCATACCGAGCAGTGCCANTGAGATTTTTATCTTCTCTGTATGGGATGTGTTGCCTTGTCCTGTTGTC
TCTGTACTTTTTGGCCAAACCAAAATCAATAAGGAATAACTTATTACAGTGACGCCCAATACCCATTAGGAAG
TTATCTGGTTTAATGTCTCTGTGTATAAAATTCTTTGTATGCACATATTCGATTCTACTGATCATCTGGTGAGC
TAACATAAGTACAGTTTTCATTGTGAACCTTCTTGAACAGAAATTGAAGNGNNCTTCAAGGCTGGGTCCAAG
AAGATCCATAACTAGCACGTTATAGTCTTTTTCCTGACCATACCACC
```

SEQ. ID. NO:227    AW465281
```
AGAGAGAGAGAAAAATCCATGATGCTTACCTGTAACCCCCTAGAACCCAAGTGCCAGAATTAATTCC
TAGATGCTGCTTCTGTTTGAATAAAAAGTCACTGCTTTTACACTTGAAAAACACTCAAAAAATGTTCAACTCC
ATGAAAACTGTTTTTGGCTTTAAGAAACTGTTTGATGTTTAACTGTTTCCTTTGATTGCCATTCCACCAGTAAA
TTGTTGGTTGATTTGCACTGCACACTGGGGTTGGGGGA
```

SEQ. ID. NO:228    BF045176
```
GAGGACAACATGGCTTCTTCTTTGGCATGTTTAATTGTGATGTTTAACGGACATCCTTGCAGTTTAAG
ATGACACTTTTAAAATAAAATTCTCTCCTAATGATGACTTGAGCCCTGCCACTCGATGGGAGAATCAGCAGAA
CCTGTAGGATCTTATTTGCAATTGACATTCTCTATTGTAATTTTGTTCCTTTATTTTTAAATTTTTCTTTTTGT
TTCACTGGAAAGGAAAGATGATGCTCAGTTTTAAACGTTAAAAGTGTACAAGTTGCTTTGTTACAATAAAACT
AAATGTGTACACAAAGGATTTGATGCTTTTCTCTCAGATAAACTTAATATGACTTTCCAAGTTTGACTTGTGTA
ATGTTATTGTCAAACTTTTTGTCACCCTATCTTCGTATTTTTTGATACGCACTTTGCAGGATGACCTCAGGGCT
ATATTGATTGAGTAAAGGGATTTGAATCAATGTATTAATGTCTCCATAGCTGGGAACCCATCATGGGTATAAT
TTGCCATTAGTTTCTGAAATCTTTCACATCATTGAGGATACCAGATTGCTGAAAACTCGGTTCTGAATGTGTTG
TACTTTTGATTTGTATCTCAAATCATT
```

SEQ. ID. NO:229    BF045836
```
AACTGCTGGGGTCTGCTCTCGCCGCCCGCCCGGCAGTCAGTCAGCCTCGCTGCCGCTGTCGCCGCCTC
AGCGGTTCCGGTAGTCTTAAGCCCGCCCCACCACCTTTTCCCCGCGCCTCCCGGAGCCTCCGGGTGTTTCCTGT
CCGCCCNCACAGGCCGGCCGCGACCGTCTGCGTCTTCTCGGCGCCCCTCGCCGCTCCGGCCGACATGAGTGG
```

-continued

GGACCATCTCCACAACGATTCCCAGATCGAGGCGGATTTCCGACTGAATGATTCTCATAAACACAAAGATAA

GCATAAAGATCGAGAACACCGGCACAAAGAGCACAAGAAGGACAAGGAGAAAGACCGNNAAAAGTCCAAG

CACAGCAACAGTGAACATAAAGATTCTGAAAAGAAACACAAAGAGAAGGAGANGACCAAACACAAAGATG

GAAGTTCAGAGAAGCATAAAGACAAACACAAAGACAGAGACAAGNAAAAACGAAAGGAAGAGAAGATTAA

AGCTTCTGGGGATGCAAAAATAAAAAAG

SEQ. ID. NO:230    BM364051
    GCACGAGAAAAGATCAGTGAGGATGAGATCCCGCCTCCAGTGGCCTTGGGCAGGAGGCCCCTGGTC

CCCCAGGAAACAACTAACAGGAGCCCTGAAGCAGAACCCCCAGCTGCCCCCTCCGTGGAGCCAGATAACCCC

TCCCAGCCTGAGACAAGCCTCTTGGGCAGCCCTGGTATTTCTGCCCCACCCGACTCAGACCCGGACCCACGGG

CCCTGCTGTTGGCCCGGCAGAGAGAGTACAAAGTGGCTGCTCTGAATGCCAAGCGGGCTGGAGACCTAGACC

GTGCCCGAGAGCTCATGAGGGTTGGGAAGAGATTTGCTGCTGTCCTGGAGGCCCTGGAGAAGGGGCAGCCTG

TGGACCTGAGTGCCATGCCCCCATCACCAGAGGACCTGAAGCCCCTTCCACAGGCTTCCCAAGCCCCGACAG

CGCCCTCCGATGCACCCCCGGCAGTGGAGCGAATGCACCCAGTGATGGCCTCTGACATCCCAGCA

SEQ. ID. NO:231    AW464893
    AGAATTTAGTGTTCTGCAGTTATGAGTAATATAAACTGCTAGCTGTTAAAGACAGATTGTTCATGTTA

AAATTCTCTTCATTTTGTTGTTCACTGAGGTTGGATATATTTGACACTGTAGATTTCTATATGTAAAAATATCT

CCCAGTAAAAAAATGCCTTTCTTTTCTCTCCTCCTTTCTTTTTCCTTCCTAACTGAAGAACATTTTATCATCACT

CAGGTTGAATTAAATTAACATCTCAAGCTAAAAGCTCTGTAATTGAGGTTGCCTCTGGAGAAGATAGGAAAC

ATTGCACAATGCAAACTCCTAATGTCTGTTGAGCTTTTACGTATGAGTAATTCCCTTTGATGTAGNTAAAAGC

TTTACCTGTTTACTTTTAAGGACACACTNNNATCATTTGAATCAGTTCTTAAAATCCANTTTATACTATGGATA

TCACAACCCTATGCATAAATTAAC

SEQ. ID. NO:232    AW465985
    AAAAATGTCTGGAGGGATGGGACCTTGAGGATTTATTCATATTTAAGATGTAGCTTTTTGTTGTTTCC

GGCATTATGTATAAAGCGACGATTATTTTATGGACCAAGTTTTAATGTAACTGTTGCAGTGAAAGTGCAATAT

CTAACCCCCTGCTCCCAGCGGGAAACGCTCGGCCCGACAATCACAGCCCCAGCCAGGGGCCCCGTGGGCAGT

GCCTCCTCCTGTCGGTCCCACCTCACCCCATCTCGCCTGTCGCCTCGGTGAGCAGCCATCCGGATGGAGGAGC

ACCTACAAGAGTCTCGGCCCGCCTGCAATAAAGGCCTGGAGGCTGCC

SEQ. ID. NO:233    BF042374
    GCCAGGGCCAGACCCCAGCCCGCGGGCCCGAGTCCAGCCACTGCCCCTGCCCCAACCCTTTCTCCTG

TCTCTTGAAATCTGAGGCACAGCCCAGGGCCCGCTCCCTCCCCGGGGGGAAGGGCTGGAGGTGGGAGGAAGC

GTCTTGCTTGTTTAAATTCGTGGTAGTTCCAGGACGTGTTTGCAAACTTTTCTTCTTGTAATGTTTTAAGTCATT

TTGATTCTAAACTTTTATTTAGAGGGTGACTTGTTTTGTTTTGCTTCAGTGTCTGTGTTTTTGGTGTAACCTTG

TTAGGTTTGTAAAGCGAATTGGAAAACTTCCTACCCTGATCTGGAACTGCCAAGGAAATATAAGCGAACTGG

CCCTTGTCCGGGCTTTGAACTGCCCCACTCTGTAAAGGAAAAGTCTTTATAAATTGAAAACGAAAATGTAATT

GCCTATATTCCCTTTTACTTTAACGCAACTATTTAAAAAATCTGTTTTCTATGCATATAAGCATTTTGAGTCAT

TCTAAGTAATGTGCGTATTGTAGTTTTTCCAAATAATTTTTTACATTGATAATTACTATGCTGTGTGGCTGACC

ATTTTGTTCAATTTTTTTTGCTACTATAG

SEQ. ID. NO:234    BF043142
    TGCACCCTGAGTGCCCCAGCCCCATCTGCAGTCCTGCACCATCTCCCTGAGCAGTAGGCTTCCCACTG

ACGGGGAGGCTGTGGGACCAAAGTCCACTTTGACCCTTTGGTTGGGTGGAACACTTGCTGGGGGGCCTGGAA

CAGACAAGGGAGCCTCGACAGGTCTTCCCACATATTATTTATTCACTTCTTTCCTCAACCCGTGAGACCTGGA

ACCCCAAGTGCGCTGTTGGCAATGACCAGAAAATGCCTCGCACCAAGTATACTGGTCAGCTTAACAGACCTT

CCCAGTGACAGAAGTGATTCCTACAAGTCTGGAGAGAAGGTGGTGACACCTATGGGTTCTCAGCCATAAGGA

-continued

AGACACCAGACCTTCGTGCCCTGTTCAGGGAAACCCCTTAGTTTTCTCCAGGAGCAGCTTGCTCTTCGCGTCC

ACATGGGGCTTGCAGTGCGGTTTTCCTGGGGCCTGAGTGCTGCCTGAGCCCACCCACTGCCCGAACCTAGTG

TTTGTGTGTGAAGTCCATGGAGCAGGTACACACAC

SEQ. ID. NO:235    BF043207
CATCCGGGATGATGCCAACCCCAGCTCCCGCCAGCGAGGACTCAAGCGCTTCCAGGCCAACCCTGAG

GCCAACTGGGNNNCCCGGCCCCGTGCCCGGCCAGGAGGCAAGGCNGCAGGAGAAACTGTGGAAGAGAGACG

TAGNCTGCTCCAAAATAAGCGAAAAGAGCCGGTGGAGGACCCAGCTGAGCGGGCTGCCTGGCTCAAAACAT

TTCCCTGCAAGAGNNNCAAGTAGGTGAACCAAACCACCCCCCAACCGAAGTACCCATGGGTTCTCCCAGCTA

CAGGACTGGGCCAATGGGCC

SEQ. ID. NO:236    BF043909
TGCCTGCAGTCCCGGGCCCGGCGGCGACTGCGTGCTCTGCCCCAACAAGGGTGGCGCCTTCAAGAAG

ACGGACGACGACCGCTGGGGCCACGTGGTGTGCGCCCTGTGGATCCCCGAGGTGGGCTTCGCCAACACCGTG

TTCATCGAGCCCATCGACGGCGTGCGGAACATCCCGCCCGCGCGCTGGAAGCTGACCTGCTACCTCTGCAAG

CAGAAGGGCGTGGGCGCCTGCATCCAGTGCCACAAGGCCAACTGCTACACCGCCTTCCACGTGACGTGCGCC

CAGCGCGCCGGCCTCTACATGAAGATGGAGCCCGTGCGCGAGCTGGCCGGCGGCGCCGCCACCTTCTCCGTC

AGGAAGACCGCTTACTGTGACGTCCACACGCCCCCCGGCTGCACCCGCAGGCCTCTGAACATTTACGGGAC

GTGGAGATGAAAAACGGCGTCTGTCGGAAGGAGAGTTCGGTCAAAGCGGT

SEQ. ID. NO:237    BM365156
GCACGAGGTTTTCTGTAATCCTGTTTGGCAAGATTTTCTTTATTTGATGGTAACAACAAAGGTTACAG

TTTAGTACTTAAACCAGCAGTTAATAGTGATTTTCTCCCCAGGCAGAGTAACTAAAAGCACCTGTGAAAACTG

CAAAGAAAACTAGGGACAGGACAAGAGGCAGCGGAAGCCTGGCTGCTGTAAACTGGTGTGCACCCCTGCAT

TCCAGCAAGGGCAGGGGAGCCAGAATCACCGACTGCTTTCCTCAGGGACTTGAATTGACAGTTTTTTCCCAAC

TATCTTNNTACTGNNNGCATTCCACTGTACCCAGTTAAATATAAAGAATTAGTCTTCTTAATAAAATCACCTT

TTCAGNNGAACTATACACATTAAAAAAAAAAATCACTGATTGTGTTTCCTTCGTCTTTTTTTCTTTGAACTTGCA

GGTGATTGAGTCTCCTGTGTTTCTTCTTTTACACC

SEQ. ID. NO:238    BF039394
CAGTGCAGGTGGACGGAGAAGCATGGGTTCAGCCTCCAGGGATTATCAAGATCGTGCACAAGAACA

GAGCTCAGATGCTCACCAGGGACAGGGCCTTTGAAAGCACCCTGAAGTCTTGGGAAGATAAGCAGAAATGTG

ATTCGGGTAAGCCAGTTCTCCGAACGCACTTGTACATCCAGCACGCGGCGGACCTGGCCACGGAGGAAGTGT

CTCAGATGCAGCTGTGCTCGCAGGCGGCCGAGGAGCTCATCACCAGGATCTGCGATGCGGCCACCATCCACT

GTCTATTGGAGCAGGAGCTGGCCCACGCGGTGAACGCCTGCTCCCACGCCCTGAACAAAGCCAACCCACGCT

TCCCAGAGAGTCTTACAAGAGACACTGCCACTGAAATAGCCATCAATGTGAAGGCCCTATATAACGAAACAG

AATCTTTACTAGTGGGCAGGGTTCCTTTGCAATTGGAATCTCCACATGAAGAGCGAGTATCCAATGCCTTACA

TTCCNNGGAAGTGGAGCTACAGAAGTTAACAGAGATTCCATGGCTTTATTATATCTTACACCCGAATGAGGA

TGAGGAGCCCCCCATGGATT

SEQ. ID. NO:239    BF039014
GGCCAGGTGGTGGCCTGGGACTCCCAACACAGTGTGCATCTGTTTCCCTGTGCAGTGAATGTCAGTC

CGACCAGTACATCTGCTCGCTAAGAGGATGGTCCAATTTGACAATGTTACTCCCATTCGGATTCTGTACTGCC

TTTTGGTAGATGAAAACTACCAGGAAAAGAAGGGAAGGGAAGTTCCCAGTTAAAGTTCCCAAAAGATCGAG

-continued

GCTGTGAGACGCATAGAGGTATACAGAAAGCTGAGGCCAGAACGCTCTGGTGGTGGGGCGTGCAGATGGAG
GCAGC

SEQ. ID. NO:240  AW465409
GTTTTTAATAATTCCTGAGAGATGTCTCTGGAAGGAAAAGTGTTTTGAAAACTAATGACTATTTTTGA
GGACAAAAATGACAACTTAAGCTAATTTCTTAAATACAGTAGGATAACTTTCAGGACAATATTGCCTCACAA
CCCTGCTCACATTGAGAAGTCTTTTTTTCGTTTCCCCTTAGCTGTTCTGACTGGATTTTTCTACAGAAGCTATG
GAAGATTATCTTGTTTCTCGTTTGCTGCTATTTCCTGTCCTACTTTAAGAAATATAAATACATAGAAATGGTGC
ATCTTTAACATTTGTTTGTACATGTATAAATGTCTTGTATTTTAATTCGTTTTTAGCATGTAGCAACACGAATT
GTTCAAGGGTAAGCCACAACATCTAAAAATCACTCCTAGATACGAACAATAAAGGAAAAAAAATGGTACCG
ATTTAGGAGGAAACAAAGCCGCTGTCGCTGGGTTTTCTGTGCAGCCTGCAGTGACTTCCGACACACGNNGAG
AAGCTGTCACTGTAAACCAAGTCATCCTTGTTGGGAGAGCGCCACAGCCTGCTGCTT

SEQ. ID. NO:241  BM366532
GCACGAGCCAACTACAAAAAGCCTCGCACCCCGACCCTTCTCCACCTCTGTGCATCTTCTCCCGACTC
GACGTCGTCGTTACAGGGAAGAAGAAGCGGGTGAGAAAAACTTCTGTTTCCACCGTTTTGCCCATTTCTGCAG
ATTTGTTCCGAGGCCGAGGAGCCTTTGTTGGAAGAGATGGTCATGGTCCTGAGCCCCCTGTTTTTGGTCTTCA
TACTGGGTCTGGGTCTGACCCCAGTGGCCCCGGCTCAAGATGACTACAGATACATACACTTCCTGACCCAGCA
CTACGATGCCAAACCAAAGGGCCGGAATGACGAATATTGTTTTAACATGATGAAAAATCGACGCCTGACCAG
ACCTTGCAAAGACCGCAACACCTTTATTCATGGCAACAAGAATGACATTAAGGCCATCTGTGAGGACAGAAA
TGGACAGCCTTACAGAGGCGATCTCAGAATAAGCAAGTCTGAATTCCAGATCACCATCTGCAAGCATAAAGG
AGGTTCCTCCCGGCCTCCATGCCGGTACGGAGCCACAGAAGACTCCAGAGTCATT

SEQ. ID. NO:242  AW462090
TTGACCGCCGTGGCCCAGAGCGAAGAGGTGGGAAGCGTGGCCGAGGGCAAGCAGGTGCATCCCAGC
CCCGCACCCCTGGCACCCCGCAGGCCGCGTGCTCTCAGAGCTCAAGACCAAGCAGCAGATCCTGAAGCAGC
GGCGCCGAGCCCAGAAGATGCGCTTCCTGCAGCGTGGGGCCTGAAGCAGCTCTCTGCCCGCAACCGGCGCC
GAGCCCAGGAGCTGCAGCAGGGCGCCTTTGGCCGGGGTGCCCCTTCCAAGAAGGGCAAGATGAGGAAGAGG
ATGTAAGAAGGTGACACAGCCCCGCGATTCCTCCGTTGGTCCAGGCGTGGGCATCAGCAGCGTTCCCCATGT
ACCGCTGTGTCCCTGGCCCTGAGTTGGGTGCTGGGGG

SEQ. ID. NO:243  AW462739
TTTTTTTTTTTTTTTTTTCTTCCAAGGNNNGGTTTATTTCAAAATTATGAAGATTTATATATTATTTT
TTATTACATACAATAAAGGGGTTTAGCTTAAAGTAAAAGCTTTCACATTTAAAGTTTTTATTTTAAAAAGATA
TTTTAAAAATGTAGACCCTTAAAAACCACCAAAAAAGCTGAATATATCTTGCAGCGTAGGTTTATCCTTAAAT
ATTCACATCTCAAATGCTGTTTAGAAAAAAGATTTAAAAACTGGCTAAAAATCATTTACACTTGGCAATGATT
AAAATCTCATCTCTGACAGAGCATATTAATGGCACATAATGAATTTACTGTCACAAGCATTTAACAGTTTAAT
GGGTACGTAGTTTTATCAGTATACAAA

SEQ. ID. NO:244  BF039410
AGGACCTGACCAGCTGAGCTTCCAGCGAGGGGAAGTGCTGCGTGTCATCGCCACTGTGGATGAGGAC
TGGCTCCGCTGTGGGAGGGATGGAGCGGAGGGGCTGGTACCCGTGGGGTATACCTCCCTTGTTCTCTAGGCCT
AGCACCTGTTCCTTTCCTGCACCTCTCTCTCCCTTCTGTCACCTGGGAATGGAATGGCCTGTGAATACTCACCC
ATGTATACTGACTGTCCCCAAAGTATCTTCCCTGTCTGCAAAATGACACTTTCCTCCCATAGCCATTTCTGCTA
ATACCTAAAATAAACTTTTTTCCTTCCTTCCTATACCCATCTATAAGGTGAAATCTGCTCTTCGAAAATATATA
AAAACGAATTTCCCTCCATGCCATCTCTTTCCTCTTTCCAATCTGTATTCTGCAAAATGGAAATCTAGCCCCCT
GTATCTTCTTCCTCCATAAGTGGACTGCACCTCTATATACGCCTCAGTTCCCAAGACTTGAAGGGCCTCTATA

-continued

GTCTTCTTCCTGTGTATGGAACCTTCCCCCACCTCACCCATCCCGCATTGCCTGTATTTATGATGTACTCATGC

TGGACTANGTGCTGAAGTCTGGACACCCCTGGTGGGTGGGCCTGTGGGGTCAGTCTGT

```
SEQ. ID. NO:245      BF045989
TTTAAGGTGGAACAGGTCATTTTTTTGTTTCTCTGCTTTTAAATCTAATGCTTATAAAAGAGGTGTGTT
```

TATCCCTAGACCACAGTGCCTTGCACCCCACCACCACCATTTGGTAAATGGGCATTAGATGCTGCACAAGCCT

TTAGGGCACTATTTTGGTAGCTATAAAAGTTTATCCAGAAACTGTACCTGGTGTCTCAGTTTATTGTCATTCAA

CTTGTTCATGAATATTAACTATTTCCAGGGTTTGTTTAGAAGGAAGAATTGATCTGTTCTTTAGTTTACTATAT

TTTTTTTTCTGGTGTAAAAATGAGCCAGAAATAAGCCTTATTGCTAAGTAATTATATAAACCCACATAATCC

CTGCATAAGATTCCCTCCACACACTTCACTATATGTATGTGGATTTGGATAGAAAATGATGTTGCCAGCATTA

CCAGTTTTAAATACTTGACTATACAGATTGATGGAATAAAATTATTAAAGTGTTTTCAGGGAACTTAATCCAT

ATGTCACCACCAAAGATTTCTACAGTGTTATAAGGTATGTAAATATTCCAAATTTCTGTAAACATTGGTTAGA

TAAAGAGTTTTTCTCTTTTTTTGGAATAACACAGTTTGTACTCT

```
SEQ. ID. NO:246      BF440222
TTTTTTTTCTTTTATCTTTTAAAATGGAAGCAAGTGTTTCGACAGAATACGATGGCTGCTCTATAAGA
```

GCCGATCTAGGAGTAATTCACTGGGTCTTCTCTCGGATAGCTCGGATTTAAAAAAAGAAAAAAGACAAAACA

AGAAAAATAACCCACAGAGCGTCAAACACCAACTCTGAGCCTGGTGGGGAATCCGTTCATTAAATAAGCCAT

AAGCTACACATTCAGGTCAGAATAACTGGCTCCTGCCTCCTTATGTCTCCAAGCCATATTCCCTATGGTGTTTC

ACCACCAACAACAATTTTGCTCACTTAATTAATTGGGTATCAGAACCTTAGAACATTTCTGAATCTTAATAAT

GAAGGTCTTCAGCAGATTGTGTTGATAAAGAAACACATACAGGCTTGAATATAAACCACTGTAATTATTGGTT

TCTTTATATCTCATTATCCACTTGAGTATTTAAAGCACACGTACACACAAAACCACACCAAACATTCAAAT

ACCCTGAAACT

```
SEQ. ID. NO:247      AW464311
AGGCTTATAAGGAACAAATAAAAAGAGAGAGTGTCTTGACTGCTACAAGCATTTTAAATAATCCAAT
```

AGTGAAGGCACGATACGAACGTTTTATTAAGGGTGAGAATCCCTTTGAAATTCAAGATCATTCTCAAGATCA

ACAAATAGAAGGAGATGAGGAGGGAGAGGAAAAGATTGACGAACCTGTGGAAGAAGAGGAGGAAGAGGAG

GAAGAAGAGGAGGAAGTGGGGGAAGGGGA

```
SEQ. ID. NO:248      BF040466
ACGGCAGCTCAAAGGAAGGCACTTCTGTCTGAGTCTCCTGCAGAAAATGAAATTACTGTTCAACTTA
```

CCAAAATGCCTTACACATTCCTTACAAATAAACCAACCGACACAGCGTTATCCGGGCCCAACTTCGGTAGCTC

TGAGAAGCCATAAAGACAAGAGTTTCTTAGCACCAGAAGTAGATCTTCCAGACCCAGTTTGTACAAGAAGAA

CCTTTGTCACATTCGAGAAACACTATCGCCCTGGCCCGGCCCTGGACCACCAGCCAGCAGACGCCAAAGCCC

TCGTCAGCCGTGCGACAGACCCAGGGCTTGTTCTGGGAGGCGGGCCCGGGGTCTGTATGTCAGTCAGTGCAA

TTGTGTCTTTCGCGGGGTTGGGGGTCGGGTGGTTCTAGTGCTGAGTCCCTAAGGCTGCAGAGCAGACTGGAA

GGTCACAGCCAGCGAGGCAGCAGCCCCAGTCCCCGGAAGATGCTGCCCCAGAACCGACGCGTGACTCCTGG

GTGTTAATGCCATTAAAACCCGCGTGTCGCCCGGCAAAAAAAAAAAAAAAAACAAAT

```
SEQ. ID. NO:249      AW465742
TTGAAAAAGCTGTAATTTGGCCTCAGTATGTGAAGGATAGAATTCATTCCACTTACATGTACTTAGCA
```

GGAAGTATTGGCTTAACAGCTTTGTCTGCTGTGGCAGTGAGCAGAACTCCTGCTCTCATGAACTTCATGATGA

GAGGCTCTTGGATAACCATTGGTGCAACCTTTGCAGCCATGATTGGAGCTGGAATGCTGGTACAGTCAATATC

ATACGAGCAGAGTCCAGGCCCAAAGCACCTTGCTTGGTTACTACATTCTGGTGTAATGGGTGCTGTGGTGGCT

CCTCTGACGATCCTAGGGGGGCCTCTTCTCCTCAGAGCTGCGTGGTACACGGCTGGCATCGTGGGAGGTCTCT

```
                    -continued
CCACCGTGGCCATGTGTGCGCCCAGTGAGAAGTTTCTGAACATGGGGGCCCCCCTGGGTGTGGGCCTCGGTG

TCGTCTTTGTGTCCTCACTAGGATCGATGTTTCTTCCACCTACCAC

SEQ. ID. NO:250    AW463923
    TCCTCTAAAACTATTTCCTTGTGGTCCGAGGGCAAGTTGCTACTCATCTTGAGTAATCTTTGCCTCTCT

TTCCATGGCATTTTGACCTTAAGTCCATTGAAGCATTCTGATCTTCCACCTTCCTAATGGGGATATGGGAAGA

CATCTACCTTCCTTATGGAGATATGATTCTCCTAGTTGAGAGAATATGCGAATGGAGCTCTCCCCCATATTAA

ACCAGCTCTAATGGATTTATTCTGACCTCGAGTCACTGTTGCCATGATTTCCCAGGTGTTTGCTTCATGTTCTC

GCTTTGAGAACCATTTCCCTTTGTTTTCTTTCCTCCACCACCTCCGTATGAGGTAATGGCACCTTGCCATTGGA

TGGTTGGACTCTGCCCTTTCCTCCGTGCAG

SEQ. ID. NO:251    AW466175
    TAAAGATCTAACTCAAGACTGACTCTGCTAGTGTAGCATTTCCCTGGGGGATTTTGGTTTTAATTAGA

CGGTTCACTGCTACTGTGTAGTGCCGGGATGGCCGGACATGGTTAGGGGGTAACCCAGCGACACCAGCACTG

ATTGGACGGCCCTTCACCAATCAGAAGCTCAGTGCCCAGTGGGCCGCTGTGTGACTTGGAATCATGTTGTGCA

CTATAGTCACATGTACTGTAAAGTGAAAAGGGATGTGCAAAAACAGAAAGCGAGACCTGCTACTAGAAAAG

TGGGAAGGGGAATGAGTAAACTTCTTTTCTTGCGGACAGATGTGCACATAGCCGCTAGTAAAACCAGCCTCA

AACAGAATGCTCATAGCTTAATAATAAAAGCTGTGCA

SEQ. ID. NO:252    BF044437
    TTTATCCTCTCTCTTTCAGGGTAGATTTCTGGATAGCTAGTAGTGATGGCATCTGAAATAGCCATTGA

GGGGTGGGTGGTATTCATTTAGTAACCCGAGCTTTTGCCTGAAGAGCTTCTGCTTAACTCTTCTTTGCTGTTTC

AATAGGTCTTTATTTGGTTTTCTTCCTGCTAGGTTGATGCATATTAGCTTAAGAACTTTTAAATTGTGGGGCA

GTAAGAAAACTTTGAATGCCTGGGGCCCTGCACTTCTCTCTTAGAAGCAGCCAGAGGGTTTAGTGTGTATCTG

TTAGCAGGAGAGTCTTCTAGAAGGTCCATTTGGTACCTCTCACACCCACAGCTTTGTGCTATGGTTTGGCCCT

CCTCCTCTCCTGATGAATCCATGCCATGACCCAGTGTAGCTGAATCTCATGTGCTCTGAAAGCCATTGGAAAG

GCACGTGTTGC

SEQ. ID. NO:253    BF039323
    GCAGAATGGATTTGTTGATTTAATCCAGAGGCACTTTATATAATGTGTTCTCTGTTTTAGTTTATCAAA

GACTCCTCAGAGATAAGAACCCTTTTAACAGTGAGCAAGGCTCGGGGAGTGAAATGGAGTCAGAGGTGGAG

CGTCAAGGCCAGGGTGTGGCCCCAGGTCTGCCTGTCCCTCCCAGCCTCAGTTTCCTCAGATGTAGAGGGAAG

ACCACCACTCCCCGCCCGCCACATGTTTTTCTAGGAGGAAAACTCTGTGTCCCCATTTTTGCACATTAGTTCTT

TTTTCGGTCCTGACTTTTACATATATATATACTTTTTTTTTTCTTTTGTCTGTGCTNTGCGGGATTTTATTCCCC

AACTAGGGATCGAATCTGTGCCCCCTGCATTTGAAGCACGCACTTAACCACTGGACCGCTAGAAAAGTCCCC

TTTATCTGTTTTATTATTTTGTTACATTTACTTTGTGGGATG

SEQ. ID. NO:254    AW462705
    TTTGAAAATTAATTTTGTATTATGCATTCTTGATTTGGTTCATCAGTAGGTGCTATTATTCATCCTGTG

ATTCCAGTAGATTAGGGGAATTGATACCTTTTTGCAGTTTTGAATAAAAGTGTTGATAATTTCTAAATTATCAT

TTATAAAATTCTTAGAGCTTCAACATTTTGCGTCATCACAGGCTGATTTAGTATTGTTTTGTATTAAAATAGTC

CTTTCCCTTTCGTGCTGCCATTCATTCCGTGCCATTAGTCCTTAAAATGCGTTTAAAGAAGAAATAGCCAAGT

TGACTGTTACACCTCATCCAAACAGACACATCACAAACATACGAGGGCGACAGTGCCTGGGATGGACGTGGT

ACTTCTCAGTCTGCCTGTTCTGAGAGAAGAGCAATTAGCATGGCCACGTCACCTTGTGCTTGAAGTGGAAAAC

TTTAAGATCGGAAAAATTTAAAGTCAGATCAGGGATTTACAGCTATCTACTTTGGTAGT

SEQ. ID. NO:255    BF040988
    GGTAAGATCATAGTGGATGTGGGGTCACAAATATGTAGATGGCCACATGAAGATAGGCAGAGACTG

GAGTTATGATGCTGAAAGTCAAGGAATATGTGGGGCCATCAGAAGCAAGAAGAGTCAAGGAAGGTTGGAAG
```

-continued

```
GATTCTTCCTTGGAGTGCAGAGGGTACATGGCCCTGCTGACACCTTAATTTTGGGTTTCTAAGCACCAGAATG
GTGAGAAAATCAATTTCTGTAGTTTTAAGCCACACAGTTAGTGGTAATTTATTACAGCAATTCTAGGAAACTA
ACACAGTCACCAAACTGATTATCTTTGCTAATTTATGATAAATTTATGTTTTTATCATGTTACATAAGCAGATG
AAATGAGTGTGAAGAGTTGTAGTTTCTGTGAAAACCAAGTTGAATACTTTGGAAAAGCTAGATGAAAGTGTG
TTGCTTTCCCCATGCCCAATTTAAATGTATTGGTTAATTATTGGTAAAACAGTTGTAAAAGACTGGCCAGCAA
TGTACTAAAAATCCACAGGTATTCATTACCAGTGTACAACTATATAACGTAACACATATGATTT

SEQ. ID. NO:256    BF044083
    GCAACTAGAGAGTAACCCCTGCTCTCCACAACTAGAGAAAAGCCCATGCAGCAACGAAGACCCAGC
ACAGCCAAAAATAAATTAATAAATAAATAAAATTTTTTTAAAAGAAGGTCCCTGTAGGAGAAAGCCCTTCA
AAATACCTCCTGAATCCAGACTATAACCTGCCCCAGTGAAAGAAGAGTAGCTTATTCATTTCTGTGTCTGCTG
TGTGGATCGCAAGGCCAGGCATGGAGCAGGACTCCCAGTGATGCTGGCTGAATGGACAAGTGGAGAATTTTG
AGAGGAGTGCTCCGGATCAGGGTATCAGAGGAGCTGGAGCTTGCCTTGTAAATATCATCTATTGGTATTTTGC
GGCAAGTCACTTAACCTCTAGCCTCAGCCTATTTGGCTGTCAGATGGAGCTGAGAAGACTTGCTTCAAGGATT
GTTTTCGAGCAGCCTGAAGAAGCTGATGAAAGGCAGATCCTCAGGAGCCTATAAAACAACTACACGGATTGG
TGCAACCGCATGTCAGTCACCGCGT

SEQ. ID. NO:257    BF045148
    GCATTTGTTTTTTTTTTTTTTTTTTTTAAATGACTCTGAAACTTTAATTACAGATACTTATCAACATCT
GAAAGTGTGGATTCGTTCTCTTTCTGCGGAAAGGCTGGCACGGTTGTTCCCTTACACCCATGTCTTTTCCTGCT
CCCTGTCTCTTCTTTATGTAAAAAAAAAAATGTCTGGATCACAGTCCCAACCAACTCTGCTCTGCATCCCTTGC
TGGGAAC

SEQ. ID. NO:258    BM363855
    GCACGAGGACATACTGGACCTGAACGAGATGGTCAGACAAGTGACGGGGAAGATCCCCATCTTCTTC
TATTCACACTATGGCTGTTACTGCAGAAAAGGTGGCCAAGGCCAACCCAGAGATGCCACAGACAGGTGCTGC
CGTGAACATGACTGCTGCTACCGTCACCTGAAATCTGACAACTGTGACATCAGCTTCGACCACTATGACTACA
CCTTTTTCCAGGGGAAAGTCCAGTGTTCCACCAAGGGGAGCTGGTGTGAGCAGCAGCTGTGCGCCTGTGACA
AGACGTTGGCCTTCTGCCTGCAGCGGAACCTGAACACCTACAAGAATCACCTGCGACGTCTGTCCAGATGCG
AGGGCGAGACTCTAGCCTGTCCCCCTGCATCTTGAGCTCTGGGGAAGGCCCCCCAGGACCACTGGCCACAGC
CCCGACCTCTGCCTGGAGCCTTTAAAGCACTCCTGGAAGAGGAAGGGGCTTGGCCTCGCCCCTAGCTACCACT
TGCCTCTTGGACCTTCTGAATCTCCCAGGCTGTCTGTTCCGAGGGTGGATTGAGATC

SEQ. ID. NO:259    BF044419
    AGATGTTTCACTTATAACAAATGCAAAAACTTAAGACAAAAGTGATATGTGAAGAAGTCTTTTACAG
TAAAATATATCCTGAATCCATATAGGTTCGTTCATAATTGAGTCTCTTCTTGAGCTACCTTTTCTAACACGTAG
ACAATGTGAAGACAGTGACAGCGTCCTTTTCTAGAGGTGTTTAACCTGTTCTTACAAACTGTGAAAACAAAG
AATTTTCTACTTTACTAATGTTTGTGGTTTTAAACAGTTATTTTCATTCTAATCAGTTCTCTACCCTCTAATTTC
TACTAAAACTGTAAATACATTTAGAAATGATATTTGTAAATACAGTATATGAAGTCAAGTTAATTTTGGGGAC
AGTGGAGAACCTCCCAATTGGCTCTGCCTTGGCAGTTTTGTTTTTTGTTGTTGCTGGTTTTTTTTTTTTTAAAC
AGC

SEQ. ID. NO:260    AW465703
    TCATTTCCTATTGCAGCTGGGGGGACCGCCACAAACGCAGCGACGTAAACCCGCAGGAGCGTGTGCT
GACAGTCCAGGGGTGTTTCCTCGGCAGAGCCCAGGGAGGGTCAGCGTCCTGTCTCCCGGGGTGTCAGCAGAG
CTCAGCCCCTGCGGTAGGGCGAGGTCCTGCTCCTCGCCGCTGTGAGCTGAAGCCCTTATTGGCTTCTGGAAGC
CTCTGGGCTGGCCGCTCGGGCCCCTTCCTCTTCCAAGCTGGCAGCTCCTCTCCCATGTTGGGCCTTCACACGTC
```

```
                                         -continued
CCCTGCTGCTTCCAAGGGCTGTGCAATTAGGGGTCCCACGAAGATCCAGGGTCGCCCGTCCGCCTGTGTCCGT

GTCCCTGCGCTTACCGGCCCGCAGNGGCCGGCTCGGGCCCCGGCGGGCAGGCCTCCTTGCGGCAGGAGGGGC

AGAGCTGGCTCTGCGCGGCTCGGCGCAGCTGTGCACGTTGCCGCCCTGAC

SEQ. ID. NO:261       BF039660
              GTGTAACTCAGTCTTGTCTTCCTTCTGGGAGCTCTAGGTTTGGTCCCAGCTCAGACCATGGTTGCCTCT

AGCCACTACTATGGGGCTGCCTCCTGTACTTCTCTTCCTCCTCTGGTTCTGCCATCTCTGACTCTCTTGAGGAT

TCTTCCCCTATTGCTCATGCCTTCAGGGTCCCTGTATTCCATCATTGGTCCACTTCTCTTTCCTCTCTATTTACT

CCCAAAATAGAATCATCCATCCTGATGTCAACTGCCATTGATATGCTGGTGATTCCCAAATATATATCTCAAG

CCCTAACTGCCCTTTATCTTTAGATCTGTATTTTTATCACCTGCTGGATATCTCCTTGGACATGTCCAGATGGA

CTCAACTCTTTCTGTCCCTACTGCCAAGTATGTTCCTCCTGAATTCCAATCCTGGTTACATTCATCACTCTTCAT

AGGCTCACCAGCTAGAAACATTTTATGGGCTTAAATTCCTTCCCATATTTTACTAGTCAGTATATCATATCCAT

TCCACTCCAAGTTTTCTTGTTTTTGGCCCTTCTTCTCCCCTCTGCCTCTACTCTAGTTCACAGGAGCTTGGGATT

TGGAGTCA

SEQ. ID. NO:262       BF039699
              GGAAAGAGAACAGCCACCACGTTTTGCTCAGCCTGGGACATTTGAATTTGAGTATGCATCTCGATGG

AAGGCTCTGGATGAAATGGAGAAGCAGCAGCGCGAGCAGGTTGACAGAAACATCCGAGAAGCCAAAGAGA

AACTGGAGGCGGAGATGGAAGCGGCCCGGCACGAGCACCAGCTGATGCTCATGCGGCAAGATTTAATGAGG

CGTCAAGAGGAACTCAGACGTTTGGAAGAACTCAGAAATCAAGAGCTACAAAAACGAAAGCAAATACAGCT

GAGGCATGAGGAAGAGCACCGTCGTCGTGAAGAGGAAATGATCCGACACAGAGAAGAGGAGGAGCTGAGG

CGACAGCAGGAGGGCTTTAAGCCAAACTATATGGAAAATGAGAAAAGGAAACATGGATGAAGCTACCTGAA

ATTTGGCTTCCTGTGTGAGCCCAAAGTTGAGAGCTGAGGAAAACCTGCCAGAGTTTCCTTTCAGTGGTCTTGG

GGAGCAGGAACCTCAGCCTTTCTTGATTATCGCTTGTGAGATGAGACTGATGACATCAGAGCACTGGCTT

SEQ. ID. NO:263       BF044525
              CGCAACTTTTTAAAAGATTCAGTTACAGCTCTTTTGAAGAGGTTTTCNNNTTTTATTTAAACTACTAAT

GGATCAAAGAACAATTGTTTATTTTTTCTCTTTGGTTTTAGATATTAATGATAACCTTGTTGGAATTTTTTTCC

AAAGAAAATATTTTTATAATTCCGTAATTTAATGTGTTCCTTTTCATCATCCACTCTTGGCAGTGTTAGGCTAT

GTTTACCTTAAAATAAATCTGACTCAAGATTTTTTATGTATGTATAAAGAAGTATTTTGTGTGCTACAAAAGC

CTTTTCAAATTATCAGTAATTTTTTTTTTTAAAGAATGAGCCAGTATTTGCTCAGTGCTCTGTAAGGGAACAT

GCAGATGGAAGCTCAGNTCTTANGNAAGGGCTGGGGAGATGGGTTTATTTTTCCCACCTGTGAATATGTAAA

ACATAAAACCATTATCTCTGAGGGACTTCTCAC

SEQ. ID. NO:264       BF041013
              CTCTTACCTTTTCCTCTTGTTCCACCAAATGGTTGCTCTTTTCCAGAGCAGAAACTGGCGGATATGCA

ATGATAGCCAGAACCCCTGTTCCTCACCCACCTGGGTCTGTAGCTGAATGTGGGCTGGCAGAACAGGGACAC

CAAGAGATGGAGAAGGGGGCTTCCCAGCCTCCCAGCAACTTCCTAGCCCATAAGCAAGCACAAAGATGAGG

CAGAGATCTGTCAGAGCTGAAAGTTCATTTGGTTGCTCACAACTCAGGTATGCACACCGTGTGGCANNNGGG

CAGCAGAGCCCTACTTGACCGCAAGTCCCGTGCACCCAGACCTGTGGCCAGATCGTGGACTCTGGCTGCCTC

AGGCGCCGCCTCTTTGCATAGGGTTCTCCTCCATTAGTAACTACAGCCGACTCAGACATCCTCCACATTGTGC

ACACTGGTTCTGCCTTTGTCCTCGCAAGTTGATACTTGGCATTAGCATGAAACTTGTGGGTGTGGGAGGGTTT

AGAGAGAATTCTAACACAAAACATCCTATTAAATTGTACTTGAGAGATGAAAAAACTCCTGTTGTATTTTGAC

AGAATTATTTTTATTAAAATATACATCCATGAGCAAAAAAAAAAAAAAAAAACA

SEQ. ID. NO:265       AW464094
              GCAAATCGAACTCCTGCTTCAGCTCCGGCTGCAGCTCTAGCTCCAGCCCCGGCTCCGGCAGGCTCTG

GGACCACTGTACCAGCTCCATCACAGACTCCCGGTTCAGCTCCCCTGCCTCAGGCCCAGGGACCCCCGTACCC
```

-continued

CACCTATCCAGGGTATCCCGGGTATTGCCAAATGCCCATGCCCATGGGCTACAATCCTTATGCGTATGGCCAG

TATAATATGCCGTATCCACCAGTGTATCACCAGAGCCCTGGGCAGGCTCCATACCCGGGACCCCAGCAGCCTT

CATACCCCTTCCCTCAGCCCCCACAGCAGTCTTACTATCCAGAGCAGTAATATGTCAGCTCAGAAGCTCAGCT

GGTTCAGTTCAAAGGGAAAGAAATACCAACCCTGCAATAAGTGTACTAAACTCTACGCTC

SEQ. ID. NO:266    AW464164
    GTGGCCGTGGCTACCATCTCAACGAGGAGGGAACCCGCTGCGTTGATGTGGACGAGTGCTCTCCCCC

CTCTGAGCCCTGTGGGGCGGGGCACCTGTGTGTGAACTCCCCTGGAAGTTTCCGCTGTGAGTGCAAAGCCGG

GTACTACTTCGACGGCATCAGCAGGACATGTGTGGACATCAACGAGTGCCGGCGGTACCCAGGGCGCCTGTGC

SEQ. ID. NO:267    BF045865
    CCCCGACACCACCACCCCATGGAGAGTACCTGCCAGATATGGGCTGGGAATCGAGGGAGCGAAAC

CCCCGCACGCCTACGNTGCTAAGAAAGGCAAGAATGGAGGAGGGCCGGCCTACGAGATGCCCGCGTTCACC

GCTGAGCTGACGGCGCCTTTCCCGCCCGTGGGGGCCCCGGTGAAGTTCGACAAACTGCTCTATAACGGCAGA

CAGAACTACAACCCGCNGACGGGCATCTTCACCTGCGAGNNNCCTGGGGTCTACTACTTTGTATACCACGTTC

ACTGCAAGGGGGGCAACGTGTGGGTTGCTCTGTTTAAGAACAACGAGCCCGTAATGTACACGTACGACGA

SEQ. ID. NO:268    AW462758
    AAGGGAAAGCAGTTTGATTTGTTTTAAAAACACTTTTTATCAGCTTTGGAGAAAACCGAAATGCAAA

CGAGAACAGCTGCTCTGAAGCCCCTTCCTTGTGCAGGGAGAAGAAAAAAAAAAAACAAAACCAAAACTCA

GAAAGCCGTTCAGCAGCGTGAAATGCCTTTTCAGAAGCTAACCCGGGGATTTTGAAAGCCTGGCTCCGTGTCT

CAGTTTGAAAAAAAGATTCCAGGCTGTAAAAGGCTTTCAT

SEQ. ID. NO:269    AW462782
    ACAAAGTAGCGTTTTAATAAAAAAAAAAACACTCACAGACATAAAGATCCCGTCACTACCCCCAAA

GCTGAATAAGTTAAGTTTGTGTCCCTGCTGCCCTGTGACGGAGGCGGGCCCGTGCGCTCAGGGCTCGCCCCTTC

TCCAGATGGCGACAATGTTGGAGTCAGTCAGCGCAGTGAGGTAGGTAAAGGCGGGGTTGGCCACCAGCGTGT

TCACCATCGTCTTGGTCACCGTCTGGCCCATTGCCTGGGGCTGGGGCCACTTAAGGATCGCGTGGGGGCCTG

CGGGGCGGTCTGTGGTGGGGAGCGCTGCGCCAGGAGGGGCCTGACGTCATAGATCCACACGCTGCCCTGCTC

ATCCCCGCAGAGCACAAGCCCCTTGTCAGGACAGGTGCTGAGGGAGAAGTAGGCCAGGATGGTGGGCGACC

ACTGCAGCCAAGCCAGGACTACCACAGCCACTGTGGGCTGGCTGCCCCGACCCTGCCACGTC

SEQ. ID. NO:270    AW463320
    TGTTTAAGTCCTTTGGGTGTGGTGTGTGTGCTTAACCATGTCTGACTCTTCGATCCCCCTGGACTGT

AGCCCATCAGGCTTCTCTCTCCATGGGATTCTTCCAGCAAGAATATTGGAGTGGAGTGCTATTTCCTCTCCAG

ATCAGGGATTGAACCTACATCTCATATGCCTCCTGCATTGGAGAGATCCAGTGAGCCTGGGTCTGTCTGGAAA

ATTCTTGGATCCTGTGGGGACACACCCTGAGTGTGAACCTGGATACCGGACCTTGGTGGCAAAATTCATCTTT

CTCTCACTGGGGTGTAATTTTTAAAACACAGCAACATCATCTCATTGATCTCTCCATTTGTCTTTGGTCTCAGC

TCAGTAAACTGAATGAATGAAGCTTAAATGCAATCATTTTCTAAACATTTTACATCTGTCAGTATAAACAACT

GCCTTGAGCCTCACATATCTTTCGCTACCATGAANNACCCATGTCAGCTGAAGTGTACAGCGGCATGCTTTCT

CCAAACTTATCAAGTTTACTGCACCCTCTCTCCTCTGGCCTGCTACTCAT

SEQ. ID. NO:271    AW465653
    GCGGCTTGCTGCCCCGGCGTCGGCTGCGGCGGAGCTGCGGCTCAGCTCTTCGGCCCGCCGCACCCCT

AAGGTGCCCTTGGCCCGTGCTCCCATTCACACGCTCGGGTGAGGTGGCTTTGACCCCGGCTTGGCTGGCTAGC

ACGACCGAGGAGGTGGCTGGACGGCTGGAGAATGAACGGAGAAGCCGACTGCCCCACAGACCTGGAAATGG

CCGCCCCTAAAGGCCAAGACCGCTGGTCCCAGGAAGACATGTTGACTTTGTTGGAATGCATGAAGAACAACA

TTCCATCCAATGACAGCTCCAAGTTCAAAACCACCGAGTCACATATGGACTGGGAAAAAGTAGCATTTAAAG

```
ACTTTTCTGGAGACATGTGCAAGCTGAAATGGGTGGAGATTTCTAACGAGGTGAGAAAGTTCCGTACATTGA

CAGAATTGATCCTCGATGCT

SEQ. ID. NO:272       W465738
           GTCATCACCTCCATCTTGGAGAAAATGGATATATTCTTGTTGCCGGTGGCCAATCCTGATGGATATGT

GTACACTCATACTCACAACCGATTATGGAGGAAGACACGGTCTGTAAATCCTAGAAGCACCTGCATTGGTGC

TGATCCAAATAGAAATTGGGATTCTCATTTTGGAGGAGTGGGAACCAGTAACGACCCTTGCTCTGATACGTAT

CATGGACTCCATGCCCATTCAGAAGTGGAGGTGAAATCGGTGGCAGATTTCATTACAAATCATGGGGACTTC

AAATGCCTCATCGACCTGCACAGCTACTGGCAGCTGGTGATGTATCCATATGGCTACACAACTAGCAGAGTCC

CGGATGCTGATGAACTGGATATGGTGGCACGGAATGCATCCAAAGCTATGGCTTCCTTGTCGGGCACTCAGT

ACCAAGTGGGTTCTGTCGGCTCCACTGTCTATACAGCTAGTGGGAACACTATTGACTGGGCATATGATAATGG

CATCAAGTATGCGTTCTCTTTTGAGTTGAG

SEQ. ID. NO:273       BF039874
           AGAGCTGCTAAAGGCGACCCTCTACCCCGGCCGAGGGACAACACAGACCAGTGCTGAAGGCTAATG

TGTGGCTTTTACTACCCTCCCCACCCCCTATTTTCCAGGGGGTTTAGGCTACATTTAAAATCTAAACCTGCAGT

CCGTGACTTCCTATCAAGCCCAAATGCATTTTGGTTTTGGTTTTCTGCTTCTCTGCCCCTTTCCACTTCTTTCGT

ATTTGCTTTATGTGCGAGTGCTGAAATGGCCCTGGAATTGAGAATTTGGCTCTCCACCAAGCACCTTATCTTG

CCACCTTAGCCTTAAGAATGAGTATGAAGAAAATGCACAGCCCCTTCTGTCCAGGGCAGTGAGAAGCCCTG

CAAGGAAGAGGTCGGAGACAAGGAAAGGAACAGACAGTCACTCCCACAGTTCCGAGGCTACCATGCCTCAG

GGGGCCCCAGGGATTGCAGAAGGGGGATATCCTGGAAGTTCGATTTCTGCAGTTTGTGCC

SEQ. ID. NO:274       BF042207
           GCTTGGGGCTATTTTTGTGTATATTGATGATGAAGACATGTGCAATGTAGAATTACAGTGAAACTCTG

GTGACTGTGGGTAGTCATTCTTACTGAAAACTGCACTGNNNTTCCCACACCATGAACTGGCTGGTCGCCTCTA

TTTTCGGGATTCTTTGACACTTGGTGGTACTTCATTCTTGCCAGGCATACCTTCTAACTGAGTAGGAAGGAGC

CTTGTAAGATCCTTCACAGGCAGTGCATGTGAAGCATGCTTTGCTGCTATAAAAATGAGCATGAGAAAGTGT

GTATCATGTTATTTTATTATGTTCTTGCTTTTGGTGTAGAATTCAGCAAATTTTCATCAAAATCTAGCCAGAGC

CCTTCACTGCCATGATAGCTGGGGCTTCACCAGTCTGTCTACTGTGATGATTTGTAGACTTCTGGTTGTATTTC

TGTATTTATTTTTAAATCTACCGTGTGGATATTTAGTGCTATGTCTCTTTAAGTTTGGATTAGTGTTTCTAAAAT

GGTGGAGTTGCTCTGAATGTTACAAATGGATCAAGGCATTAAAATGAATGAGATCTACCTTTCACCAAGTACT

GATGCTATT

SEQ. ID. NO:275       BF042293
           GCCTGACCCAAGGGCCTTTCCTGGGGCTTCTGGGGCCCATCCTGAACCCAGATCCACATGGACCTTC

GTGTTGAGCCAGGGTGAGGGGAGCAACCCCCACCCCGACCCACTCAAGCCCCTGGCCAGCTTCACAGGGCAG

GGGGAGGCTGGCTCTTACTCACTGGAGCTGCTAGAACCTTCCCTACAGTCTGGACCCAGCTAACCTGAGGGG

AGCCATTGCCACCTTTCCAGCACCACCCATGTGCCCCCACCCAC

SEQ. ID. NO:276       BF044365
           TGTTACCATTCTGATGTTGGAGTGGCCGCATTTGTTTTTTTTTTTTTTAATGATGAAAGTAGTTAA

TATTTGGTCAATATGTCCATTGTAACCATAAGGTNGAAAATGAAACACAGGTCTGTTTTCTTTCCTGTAAACT

GGAGATCCTCTGCACTGGCCACCTTGTTAGAGGAGAGCATTAGTGCCTCCCTGCAACCCTATCATCCCCCTCA

GAGCAAAACTCGATAGAAGGTGAGTGCCAGGTATGGGAAGAACTGGTCTTGGGAGTCAATTTCTTAAAGAAT
```

-continued

TTATTTCCAGTACTGCTTTAGCTAAACAGATGGCTACTTATATCTCTTGAATGATTTAATTACCCCAGATCCTA

TAGCCAGTCAGAAACGAGCTTATTCACAGAAGTACAGCATAACCC

SEQ. ID. NO:277    BF045161
GCTTCCGGGTAGGAATTAGGTGACCCCGGCTGCCGCTGGAACCTGCGGTGACAGCAGCCATGGGGGC

TCACCTGGCCCGGAGATACCTGGGCGATGCATCGGTGGAGCCCGATCCCCTGCGGATGCCCACTTTCCCGCCC

GACTACGGCTTCCCCGAGCGCAAGGAACGCGAGATGGTGGCCACTCAGCAGGAGATGAACGACGCCCAGCT

GGTGCTCCAGCAACGCGACTACTGCGCCCACTACCTCATCCGGTTTCTCAAGTGCAAGCGCGACAGCTTCCCC

AACTTCCTGGCCTGCAAGCACGAGCGGCACGACTGGGACTACTGCGAGCACCTCGACTATGTGAAGCGCATG

AAGGAGTTTGAGCGCGAGCGGCGGCTGCTCCAGCGGAAGAAGAGACGGGAGCAGAGGGAGGCGGACATGG

CCAAAGGCCTGGGGCCC

SEQ. ID. NO:278    BM361926
GCACGAGGTATCCCGGGCATCCTGGCGCCGGCGGCGGCTACTAGGCAGGCGGGTACGGAGGGGCTC

CCGGAGGGCCTGCGTTTCCCGGGCAAACTCAGGATCCGCTGTATGGTTACTTTGCTGCTGTAGCTGGACAGGA

TGGACAAATAGATGCTGATGAACTGCAAAGATGCCTGACACAGTCGGGCATTGCTGGAGGATACAAACCTTT

TAACCTGGAGACTTGCCGGCTTATGGTTTCAATGCTGGATAGAGACATGTCAGGCACAATGGGTTTCAATGA

ATTTAAAGAACTCTGGGCTGTACTGAATGGCTGGAGACAACACTTTATCAGTTTCGACAGTGATAGGAGTGG

AACAGTGGATCCCCAAGAATTGCAGAAGGCCCTGACAACAATGGGATTTANNNNNGAGTCCCCAGGCTGTG

AATTCAATTGCAAAACGATACAGTACCAATGGAAAGATCACCTTCGATGATTACATCGCCTGTTGCGTCAAG

CTGCGAGCTCTAACAGACAGCTTTCGAAGACGAGATACTGCTCAGCAAGGTGTAGTAAATTTCCCATATGAT

GAT

SEQ. ID. NO:279    BM364516
GCACGAGGAAGGTTGTAGCTGCCCGTGTGAAGTCCAGAGAGCGTAAGCCCTGTCACTGGACCCAGTC

TGACCTCCTTTTCTGACGGCTGCCTGGTGTAATCACTAGGAGATCTCTCACTGGGAGTTACCACCTTCCCCCG

GTGGTACCCCCTTTTGTAGCTGGATGAGAACTGTGGGGTCCTGATCCCTCTGCATCTTCGCTGGGAAATTTCC

CATCCCTTGGAAATATCCCTTAGAAAAACCTTCATGTCCCCTAAGGAGACCACTGACATTGCCAAGTTGAAAA

ATCCCATAGATTGTAATCCTGCAACCTCGCTGGACTCTCAGCCTCTGAGCAGTGATGGGTTCAGTGTTAAATG

TGATAAATACTGTATTTTGTATTGTTTAAATGGCATCTCCCACAAAATGTGAAAATGGTCCCGGAGAAGGCAG

CTTCCTGTATGCAGTGTGCTTTTTAAAAAAAAAAAAAAAAAACAAGTAACAACTCCTTTTGAGAAACAATTTC

TACTTTGAAATCATATCAATGAAAAGATGTATATGCACTTATAATTTTCCTAATAA

SEQ. ID. NO:280    AW462100
GAGATCAGCTCCCTCAAGGACGAGTTACAGACAGCTTTACGGGATAAGAAGTACGCCAGTGACAAG

TACAAAGACATCTACACAGAGCTCAGCATCGTGAGGGCGAAGGCCGACTGCGACGTCAGCAGGTTGAAGGA

GCAGCTGAAAGCCGCCACGGAAGCACTGGGTGAGAAGTCCCCGGAGAACCCACCTGTGTCCGGATATGACAT

CATGAAGTCCAAGAGCAACCCCGATTTCCTGAAGACAGACAGGTCATGTGTCGGCCGGCAGCTCAGAGGCCT

CAGGTCCAAGAGTCTGAAGGAAGGCCTGACGGTGCAAGATCGCCTGAAGCTCTTTGAGTCCCG

SEQ. ID. NO:281    BF039681
GGCCCAGAAGCTGCTGAACTCCGACCTGGGGGAGCTCATCAACAAGATGAAACTGGCCCAGCAGTA

CGTCATGACCAGCCTGCAGCAGGAGTACAAGAAGCAGATGCTGACAGCCGCGCACGCGCTGGCCGTGGACG

CCAAGAACCTGCTCGACGTCATCGACCAGGCCAGACTGAAGGCCCTGGGGCAGCCGAGGCCGCANNNNGCA

CGACCCGCCCTTGCCCCACCCGCCACGAGGCCACCCGGCGCAGGCACACCCAGCGCCAACGTTTTGACTGAC

GGCTGCTTGGAAATCTCACATAAGTTTAACTGCGTTTTGATTTGGGTTGTTGTTGTTTCAGCTCTTTAATCATG

-continued

GTGTTCAGAAAAGTCCGGGATCCACAGTGCAGCATTTTTCTGAGAGTAAAAGTTGTATGTGAGAAGCTCTTA

AAGAACGATGAAGGATAGGCTGTGCTCACGTCAGGATACGCTTTCGTGGAAAT

SEQ. ID. NO:282  BM364428
GCACGAGCCTAGTCCATTGGCCAGAGAAGAAGGCCTTTCCCTCCCTGTGTCCAGCCCTCCCCCAGAT

GGGGACAGGCAGGTCATGGATTCAAGTATAGATGGCCCAGTTGTGAATCTGNNGGCTACAGAGGTGACAGCA

GGCGCCCTGGGCACACACTTGTCACAGCCGGAGTTGGAAGAGACTCCTGAGGACCGAGAACCCACCCAGGA

AGACGCAGAGCCCAGGTCTGCCGCAGGCTCCTGAAGGAGCTCAGAAATTTGCTGACGGTGACCGCCGAAGT

AACAGGGGAGTCCGCTGTGCTTGAGGTTGAGAAAGATACACATGAGGAGGCCCTTGTTCCCAAGATATTGA

AAAAGAAGAGGAAGCAACCCAAATCGACACAGAGGCCAGTCAAGCATCTGCTTCGGGTCAGGACAACTGTG

AAGAAAGTGAAGTCGGTGAGGGGGAGGCCCATGGTCCAACTCCCAAGGCCGAGGCCAGCGGGGTGGAGCTG

GGAGAATTTCCAGATGCTCAGCCAACCT

SEQ. ID. NO:283  AW462966
GAATTGGAACGTTCTGCTTTGGTGTGATCATGTTTCTCCAGTATTACCTCAACGAGCAAGGAGAGCG

GGTCTACACGCTGAAGAAGCTTGATCCTTTGGGACAACAGACGTGCTCGGCCCACCCTGCTCGATTCTCCCCA

GACGACAAATACTCTCGACACCGAATCACCATCAAGAAACGCTTCAAGGTGCTCATGACCCAGCAGCCGCGC

CCCGTCCTCTGAGGATGTCTTAACATTTCGTGTGTCTTCTGCTGCCTGCCAGCCCCAAGAGACTTTGTGCAGC

CAGGCTCTTCAGTCTGTGAGCCTGGAAGCTTGCTCCGACCCTTACTCCTCGAATCCGGTCTCATCTTTGCCTTT

GATTATGCTTGTTGTGAAGCAGTCATGGTAGCATCCCCGTCCAAGGGGAGATATTTGAATCTTTTCGTACCTT

GAATCACTGCCAGGTTATTAAAATGATTT

SEQ. ID. NO:284  AW461868
TTTCTCTACCTTGCCCCTAGGAGCGAATCCGTTTAGCTCGACAGATTGAAAAAGCGGAGTATCGGAA

CTTCCAGGCTTGTCTGCACAACTCTTGGATCGAGCAGGCCGCGGCTGCCCTGGAGATTGAGCTGGAAGAAGA

AATGTATAGGGGAGGAAAAGTTGATGAGCAGGAAGAGCGTCGGAGACAAAAGCAGATGAAGATCCTGAAG

AAGGAGCTGCGCCATTTACTTTCGCAGCCGCTGTTTAAAGATGACCTGAAAACCAAGTATCCCACTCAGTCAG

GCAAGCTGCCCCTGCTCACGTGTGCCCCAAGAAAGGGTGAGTCCGCGCTGAGCTGCCTTTCCAAACAGAAGA

AGAAGAAGAAGAAAAAGCAGCAGCCGCAGGAGCAGCCGCAGCCGAGCACAAGTGCA

SEQ. ID. NO:285  AW462382
CCCTCGCCCGGCCTGCCGGCGCCGCTCTCCGCCGCAGCTTCAGCACCTCGGCCCAGAACAATGCTAA

AGTAGCCGTGCTGGGGGCCTCTGGAGGAATTGGGCAGCCTCTTTCGCTTCTTCTGAAGAACAGCCCGTTGGTG

AGCCGCCTGACCCTCTACGATATCGCTCACACGCCCGGAGTGGCCGCCGACCTGAGCCACATCGAGACCAGA

GCGACCGTGAAAGGCTATCTCGGACCTGAGCAGCTGCCAGATTGCCTGAAGGGCTGTGATGTGGTGGTCATT

CCGGCAGGAGTCCCAAGAAAACCAGGTATGACCCGAGATGACTTGTTCAATACCAATGCCACGATCGTGGCC

ACCCTGACCGCTGCCTGTGCCCAGCACTGCCCGGAAGCCATGATCTGCATCATCTCAAATCCAGTTAACTCCA

CCATCCCAATCACAGC

SEQ. ID. NO:286  AW464067
TTTTTTTTCACCGTCCAAATCTTGACTTTATTTTTTTTATATAAAAAATGCAATTTTGGAAACCCACCC

TACCTTTTCCCCTAACATAATGCTTTTACCTCTTAAAAATAAAAATAAAGTACTAATCCTATGTACATCACATG

TACCATAAAAAATGTATCCAAAGTTTCTATTGCTACCAAAGTGTTCTAAATCAAAACGAGTTACAGAAAGCC

CCTCATTGTAAACAAAAGATTACAAGTTACAAAATCAAAGCACACACAGCCAGAGTCATTTATACAACAACC

-continued

AACATCCTGCTCCCAAAGCAAGTTGAATTTTTATGTGCCTGTATAAAAATGCATATCAATATACTTCTGCAAA

TTTATTTTTCATTATAAAGCAAATGAATACACTTTCTACAATAA

SEQ. ID. NO:287    BF042174
GCTCCTTAGGTATAAAGGTAAATCTTTCTGATTAAGTGGTTATTGAAGTGTTTTGAGTTTGTACATTTT

TGCCACACGTGTTCTGCAGATGGTTGATTATAAACATACTTTACCTCTCATACTAGTAAGTGTTTAGTTTCAGA

ATCATAAGTATATTTTTAGGTAAGAGCCCCCTGATTCAAAGAATGCTCTTGTTGCTGCAGTTTTTAAAACATG

GGTTTTTCTGTGTACACACTTAAATCTCTTTATTCATCTTTTTAGGTCCTACAGCTCTGCTGGCTCATGAAATA

GGTTTTGGAAGCAAAGTTACAACACACCCACTTGCTAAAGACAAAATGATGAACGGAAGTCATTACAGCTAC

TCCGAGAACCGTGTGGAAAAGGATGGCCTGATCCTTACCAGCCGAGGGCCAGGAACCAGCTTTGAGTTTGCT

CTGAAGATCGTCGAGGTGCTGGTTGGCAAGGAGG

SEQ. ID. NO:288    BF043744
GCTTGAGAGAGATTTTTATCTGGTGCAATCTCCCTGCAGTGTGTGTGACAACTTAACCTGGCTACTGA

AAAAGAGTGCCATGCCCAACACCACTGCCAGGACCTTTCCTTCACCTAATAGCAGGAGTTTCTCTCATCAATT

GGAATCTCCAGGCCCCACAAAATGGTATTGTTTTTGGAACAATAGGACTGTAGAATCTTTCATCATTTAACTT

GGTGGAGGCAGGGCTGGAGGGGGAATATAAATCAGCAAGCCTTTGAGTTAGGGGCCAGGAAATACAGCTTT

AGATCCATTTTTAATGATTCATTTCCTTTTTGGTCATATAACTGCACAACGGGAGATGAAAGGGGAAAATAGA

AAATTTGACTTTTAGGTGCCAATAGTACATTGCACTACACTGATCGAAGAAGTTATCCAAAGTACTGTATAAC

ATCTTGTTTATTATTTAATGTTTTAAAAGTGAAA

SEQ. ID. NO:289    BM365103
GCACGAGGGCCAACGAAGGCTTGATCACCAAGCTTGAGGCTTGCTGCCGGGGGTACTTAGTCCGACA

GGAGTTCCGATCCAGGATGAATTTCCTGAAGAAACAGATCCCGGCCATCACCTGCATTCAGTCTCAGTGGAG

AGGATACAAGCAGAAGAAGGCGTACCAAGACCGCTTGGCTTACCTGCGCTCCCACAAAGATGAAGTTATAAA

GATCCAGTCTCTGGCAAGGATGCACCAAGCTAGAAAGCGCTATAGAGAACGCCTGCAGTATTTCCGAGATCA

TATAAATGACATTATCAAAATCCAGGCTTTTATCCGGGCAAACAAAGCTCGTGATGACTACAAGACTCTCATC

AACGCCGAGGATCCGCCTATGATTGTGGTCCGGAAATTTGTCCACCTGCTCGACCAAAGTGACCAGGATTTTC

AGGAGGAGCTCGATCTTATGAAAATGCGGGAAGAGGTTATTACCCTTATCCGTTCTAACCAGCAGCTGGAGA

ACGACCTCAATCTCATGGATATCAAAATCGGACT

SEQ. ID. NO:290    AW464273
ATCACTCCCATCTGACTGCTAATACACATGCAGGCTGCAGGCTGGGTTTAGCCCACAGTCAGAGTTG

CCAGCCCATGAACTACAGCATAAGAAACAGTAATAATGCAATTACAGAATTTTGAAGTTAAAGGAGACTTTA

GAGATAATTTAACCGAATTCCTTTATTTCAGGGATACAAAGATATTCAACAATTTGTTCAAGTTTTAAACCTA

ACCTTATCACTGATCCACTCTCCACAGACCTGGAAATTTCACACCAGAAAAACCAAAAACACATAGCCACAT

AAAAACTCATACACGACTATTTAGAGCAGCATTAGTCAAGGAAATGGCAACCCACTCCAGTGTTCTTGCCTG

GAGAATCCCAGGGACGGGGGAGCCTGGTGGGCTGCCGTCTATGGGGTCCCACAGAGAAGGACACGACTGAA

TCGAGTTAGCAGTAGCAGTCACAACAGTCAGAAAGTGGAAAAGTCCACACGTCCATCCACTAATGGGATAAA

CAAGTTGTGGTCCATCCATATAATGGAGCGTTATTTAGC

SEQ. ID. NO:291    BM366541
GCACGAGATCAAAGAGGGCTCACAACTGAAGCAGCAGATCCAGTCCATCCAGGAGTCCATTGAAAG

GCTCTTAGTCTAAACTGGTGGCCTCAGCCACACTCCCAGCTGACTCCTCTCCACCCCCCCGCCCCGCAGAGT

TATGTATCATATTGTCTGTTAGCATGTAGTGTTTCCAGCTACCTTCTATTGTTATAAAATATTTTAATGCTCAA

TCTGATTTTTGCATTTTTGTACTGTTGTCTTGTTTTATAGGTTGTCAGCCCCTCCCCTAATCTCCCCTTCCTCTCT

GCCATCTTATCCTCCCTTTTAGAAAAATGAACTAACGCCAAGAACAGGTGGAACAGGCTGGATGACACCACT

-continued

TAAAGGCAGGGAAGAGCCGAGAGAGTAGAGAATTGGTTCCAGCTTTCAGGGGCCTGCTTCCTACTGTGCAGG
GCATGATGGCATAACTGTCTGCTTGTACCCCTCATTCCCATGTACAGGATCGTTGCACGTGTGTCTGAATCAT
CGAGGGGTTTCCTTTGCTCTGCAGGGCATAATGTATCATTTGGGGAGGAAGCATGT

SEQ. ID. NO:292    AW462227
GCGTCAACGTTTTAAGTCCCATCTTTTACCTCCACAAGCTAGAGAAAAATCAGGACATGTTTTCCCTA
CCCGTGAAATTGCCACACCTTGTACTAATGAGAAAATGTTCTTTTTAAAAAAATCCCCCCCTCCACCTATGTT
ACTGTTCCCCATTTCCTAAAAGGGCACAGATCTCCCTTCCAGGCTCTTTATGTTCAGTTTTTCATCACGCTCGG
TTTCTGTCTTCCGCTTGCCATGCATCACTGGTGGGTCTCAGGCTCCAGGGGACTTGAGCACGTTTTGGCCAC
GTGGACAGTATTGAAGCAGCATTGCGCTGCCACAGTCAGGACTGTCCAGGCACTCGGAACGTGCATCTTGCT
TGGCCAGCACAGTGTTTAACAAAATTGAGCCACTTTTTAAATATCTGGAGATTTTGCAAACAAATTTTGGATC
CCCGAGTGAGACTAGATAGCTGATGGCTTACAGTTCTCGCTGTGCCACGTCATTCACAGATGATGGTGTAGAC
ACACTTAGAAAGCTGCTCTCTTCCCCTGTGAACATTCGTGTTT

SEQ. ID. NO:293    AW466159
AAGAGTTCCATGCTGATAGCCCAGCAGACTGACACGTCTGACCCGGAGAAGGTGGTCTCCGCCTTCC
TGAAGGTGTCCTCCGTGTTCAAGGATGAAGCCTCGGTGCGGACAGCTGTGCAGGACGCTGTAGATGCTTTGA
TGAAGAAGGCCTTCAGCTCGTCCGCCTTCAACTCCAACGCCTTCCTCACCCGGCTGCTCATCCACATGGGGCT
GCTCAAGAGTGAAGACAAGATCAAGGCCGTTGCCAACCTGTACGGCCCCCTGATGGCGCTGACCCACGTGGT
GCAGCAGGACTACTTCCCCAAGGCCCTTGCCCCCCTGCTGCTAGCGTTCATGACCAAGCCCAACGGCGCCCTG
GAATCCTGCTCCTTTGCCCGCCACAATCTACTGCAGACGCTGTACAAGGTCTAGATGCCAAGCTGGCCTCTGC
CCATCCCTCGCCT

SEQ. ID. NO:294    BF045523
TTTATTTTAAGATTGAAAAGGGAGCGCATGTTCCTTGGAAGGGAGAGCATTGCTCGCCGAGACGAAG
CTTCGTGGCATACAAAGGGGGCGGTTCGTGAGTTCTCCCATGCACCCTGCTCCAGCTTCACCCAGTGGGGCTG
CTTTTGCTTGATCCATCCAGCCTTTTACAGCCTTGTCATAGATGTCCTAGATATTGGATGCTTTTCTTCTTTTTT
GGTAGTAAATGCTTAAGTATTAACTTTTTGTTGTCCCTCTATGTTATAGAGGGGTTTCGGGTTTGTTTGTTTGT
TTGTTTCTGTATTCTTAATCATGTTTTTCCACTCCCACTTGGGAATTTTGGACGCTGGTCAGCTTGTGGGTTTTC
TAGGATGTTGGGAAACCTAGATGACCTTACTGGGTGCAATACTAGCTACGTTAAAGCTAGAAACCTACACTG
TCACTTTACTGAGATTTCTGAGTATACTTTCCATATTGCCTTAATGTAGCAGTAATGTGTTTATGCATTTGTTTC
TTTGCACAGACATTTTGTCAAATATTAAAACTCTACTTTTTTATGGCACATATTAGCATATAAGCCTTTATTCC

SEQ. ID. NO:295    BF044848
TCTCCACAGGTGTTAAAGTTCCTCGTAATTTTCGTTTGTTGGAAGAACTTGAAGAAGGACAGAAAGG
AGTGGGCGACGGTACGGTCAGCTGGGGCCTGGAAGATGATGAAGACATGACACTCACAAGGTGGACAGGCA
TGATCATTGGGCCACCACGGACAAATTACGAAAACAGAATATATAGCCTGAAAGTAGAATGTGGACCTAAAT
ACCCAGAAGCTCCTCCATCAGTTAGATTTGTAACCAAAATTAATATGAATGGAATAAATAATTCCAGTGGAA
TGGTGGATGCACGAAGCATACCAGTGTTAGCAAAATGGCAAAATTCATATAGCATTAAAGTTGTACTTCAAG
AGCTAAGACGTCTAATGATGTCCAAAGAAAATATGAAGCTTCCACAGCCACCAGAAGGACAAACATACAAC
AATTAATTTTAGTGGATCTCAAACTTGTCTTAAATCAGCAACCTTCTACTCATGTTAATGTCTTGATTAAATAT
CACAATGCAAAATACCCACACATTAAAGTAAGATAATTCCAGCTGGTAAACATGACCTGGACGTTTGTAAGA
ATATATTTAATATATGTACACCCATTATGTTT

SEQ. ID. NO:296    BF040663
TGAGTGGTGGGCAGTGTGCAAGCTTGCAGACCTCACTTAGTGGCAGCGATGTGGTCTTGATTTGTGCT
TCTTCATTTTAACATGGCTGTTAGAGAGTGTACTGAGTGGTGGGCAGTGTGCAAGCTTGCAGACCTCACTTAG
TGGCAGCGATGTGGTCTTGATTTGTGCTTCTTCATTTTAACATGGCTGTTAGAGAGTGTACTGAGTGGTGGGC

-continued

AGTGTGCAAGCTTGCAGACCTCACTTGGTGGCAGCGATGTGGTCTTCCCCAGACAAAGCCTTTCTTACAAGAG
AATTCCCTTGTTGGTGTTGGTTGAGCACTCTCACAGATAGACCTTTTGGTTTTTAATATTTATTTATTTGGCTGC
ATCGGATCCTAGTTGTGGCACGTGGGATCTAGTTCCCTGAC

SEQ. ID. NO:297    BF042477
GCGGTACCTTCTTCATGGTTTGGAGTGTGTGGTAGCAATGCATCAAGCTCAGCTCATTTCCAAGATTC
CACATATCTTGAAGGAGATGTATGACGCAGACCTTTTGGAGGAAGAGGTCATCATTAGCTGGTCGGAAAAGA
CCTCTAAGAAATATGTCTCAAAAGAGCTTGCCAAAGAGATTCGTGTCAAAGCGGAACCTTTTATAAAATGGT
TGAAGGAAGCAGAGGAAGAATCTTCGGGTGGTGAAGATGATGATGAAGATGAGAATATTGAG

SEQ. ID. NO:298    BF042245
GGAAGCAGCACGAGCTGTTCTGCTGCAAGCTGTGCCTCAGGCACCTGCAGATCTTCACACACGAGCG
GAAGTGGTACTCACGCAAGGACCTGGCTCGGCACCGCATGCAGGGTGACCCCGACGACACTTCACACCGCGG
ACACCCCCTCTGCAAGTTCTGTGACGAGCGCTACCTGGACAACGACGAGCTGCTCAAGCACCTGCGTCGTGA
CCACTACTTCTGCCACTTCTGCGACGCGGATGGGGCCCAGGACTACTACAGTGACTATGCGTATGTGCGTGAG
CACTTCCGCGAGAAGCACTTCCTGTGTGAGGAGGGCCGCTGCAGCACCGAGCAGTTCACGCACGCCTTCCGC
ACGGAAATCGACCTGAAGGCCCACAGGACGGCCTGCCACAGCCGCAGCCGCGCCGAGGCCCGCCAGAACCG
CCAGATCGACCTGCAGTTCA

SEQ. ID. NO:299    AW463964
GCCTTGGCACCAGCGACGGGAACCTGTCCCATCACACCCACCCCTTGAGGGTGCACGGGGACCCCAG
CCCCCCTGCCCCGTGCCCCTCCCCAGATGGGCCGTGGCCAAGCCTGTGCCACCAGCCAGGCCCTACGCGGCTG
CCCATGTGCGCTCACACGTGTGCGTGTCCGTGTGTGTGCGTGTCTGTGTCCGTTGCTGTGTCGTGAAGCTGTGC
CCGTCCCCCAGTCCAAAGAAGTGAATGGCCGCCGAGGCCACAGTTATGCAACTTTCCGTGTGTGTTGTGACAG
CGTCACTGCTTTTTAAACTTGATAATTCTTTATTTTAGTAAGATGCCCCAAGAGTCCACACAACTTGTGTTGGA
CTTGCAGAGGTTTTATTTTTTTGGCCTTAGAATCTGCAGGAATTAGGAGGTACCGACCCCCGTGCAGCAGCCT
CGGCCCTGGATTGCGTTTGCCT

SEQ. ID. NO:300    BF041775
CCTGCGTCCAAGTCCAGGTGTCTGTGGCCGCCGATCTGGACGTCAGGGGCTCAGCTTCCCTTCTTCGG
ACCAGCCAGCCCCCTGTTTTGCCTTTGCCAATTGGTGCCCATATTTAGGTCGGCTTTGGCGAGGCTGAGAAGG
CCGCCGGCAAGATGTTCAAAAACACGTTCCAGAGCGGCTTCCTCTCCATCCTCTACAGCATCGGCAGCAAAC
CCCTGCAGATCTGGGACAAAAAGGTACGAAATGGCCACATCAAAAGAATCACTGATAATGACATCCAGTCCC
TGGTGCTNGAGATTGAAGGAACAAATGTCAGCACCACGTATATCACATG

SEQ. ID. NO:301    BF440363
TTTTTTTTTTTTTTTTATAAGACAAAATTTAATGAAAATTGGTAAGTAATAATCCAAGGGGCTAAA
TAGTTACATGGGACTGTATTAGAAATTTAATATACAAATGTTACATGTTATCATCATCTGATTCATCTTCTTCC
TTCAAAGATTCCTTGGCATATTTCTCTGCCTCTTCCCTTACATCTTTAGGAACTATTTCATGTCTTCCATTAGTT
ATTTCACCAACCCAGCTGAGCTCTAGTTCAAAAGCTTTATCCTTAACTTCATCGTGTACTATGTAAATTATCTT
TGCAACTTCTTTAACAACATCACGGCAGGTCATTTCTTTCATCTGAAGCTTTTCAATTTCTGTCTTTGCAGCCT
GCCTTGCTTTGCCAATGGCACAGCCCGAATAACCATATGAAACACCCGATGGGTCAATCATGTAGAGCTGTG
CACCGTCATTCACACTGTAAGACCCTAACATGAAACTGCAGCCAAAAGGTCTAACAGCACTGTAGAGTGTAT
ACGCGTGTACATACATGGCCACTCTATCTGCAAGATGTTTAGTGGAATGTTATATCCAAAGTTAGATCTAAA
GTTGGAAGCC

SEQ. ID. NO:302    BF040230
TGGAGATGTGTGTTGTGGGTTTCTTTTTTTTTTTTTCCCTCCCCTATTTTAGTTGCATATGAATAAAC
AAATACAACACAAGNNNGGCCTTGTGTTGCCTGGTTCCTCTTCAGTATTTCCTGGGGATTATTTGCTTTCTAAG

-continued

TAAAACCCTTCTGACCAACAGCCCAGTATGTCTTAAGACCGGAGGTCATGTCACCTACTTTGGAAGCTCTCAC

AGCAGGCTGCTCCGCTCGGATCTG

SEQ. ID. NO:303       AW462792
    GCAGCTGCAGGGGAAACTTCTGCAGAGCCGACCAGGTTTTTCCAGTCCTCCATGGGGACCAGCGTTA

GCGGTCCAAGGTCCAGCTATATTTTCAGAACCAACAAATGATACCAGTGGAAGTACGGAGACGTCCAGCCTT

TTGGATAGTATATTTTGGATGGCAGCTCCTAAAAACAGGCGCAGCATTGAAGTGAACCGGTGTAGGAGAAGA

AACCCTCATAAGCTTATTAAAGTTAAGAACAATATAGACTTTTGTCCTGAGTGTGGTCACCTGAAACAGAAAC

ATGTCCTCTGTGGCTATTGCTATGAGAAGGTGCGCAAGGAAACGGCAGAAATCAGAAGACAGATAGGGAAG

CAAGAGGGGGGCCCTTTCAAGGCTCCTACTGTGGAGACTGTGGTGCTGTACTCGGGGGAGACACCCTCTGAG

CACGATCAAGGCAAGAGGATCATTGAGCGAG

SEQ. ID. NO:304       BF046632
    TGCTTTTGGAAAGAGGGTGCGGGCTGGGACCTTGCTTTTTCTCCCCTCGGTTCCAGACACGCATTCA

GTTCCTGTTGTTGAAGGGCCACTTGTATTTCCACGCATGCCCACACCCAGGCGTCCAAGGCCCCGTGTCTTGG

AGCAGAGGCCTGGCTGAGGGGAGTGGGCTGAGCCAGGCGTGTGGCATGAGGGTGTCCGCGCTGCGTCCGGG

GAAGGTGACGGCCGCGCGAGGGGACCCAGAGGCCATGGTCTGCCAGGGCGTTGCTTGAAAAGAATACGTTCT

GTGGGTTTTTCTGGTTGGAGGAACAAAAGAGCCTTTCTTTCTGAGATGCTCGCACATCTGTCTGTGAAAGTAG

TGTTTCCACAGGGAGTGGCCTTTGGGAGGGTGAG

SEQ. ID. NO:305       BF045608
    AGCCGCCCTGCGGTAGTTCTCGCGGTATTTGCTGCCGCCAGTCTGGTGGAGAGGTTGCTGTTTCCTGG

CGGTCCTTTCTAGCTCATCTGGTCGCCGCGGCTGTTGTGTTTCCAGTTGCCAGGTCGCGTATCATGACGTCCGC

CTTGGAGAACTACATCAACCGAACTGTTGCTGTCATTACTTCTGATGGGAGAATGATTGTGGGAACATTGAAA

GGTTTTGACCAGACCATTAATTTGATACTGGATGAAAGCCATGAACGAGTGTTCAGCTCTTCACAGGGAGTA

GAACAAGTGGTACTAGGGTTATACATCGTAAGAGGCGAGAATGTTTCTGGAGGTCCGAAGTCCAGATGGATT

TCACGAGGCTAAAAGCAAGGACTGATGCTAAAGCTAAAGTTCCAACACTTTGGCCAGGTGATGCAAAGAGCC

AACTCACTGGAAAAGACCTTGATGCTGGGAAAGACTGAAAGCAAAAGGAGAAGGCGGCAGGAGAGGATGA

GATGGTTAATAGCATAATCAACACGATGGACATGAATCTGAGCAAACACCAGGAGATAGTGAAGGACAGGG

GAGCCTGGTGTGCTGCAGTCCATGGGTTCAC

SEQ. ID. NO:306       BF040483
    AGAAGAACCAAGCATTAATACAGCACTTTTTTTTTATAATAAAGTATATCTTTGTTTTTCCCTAGTTG

GCCAAAACTTTTTTAGTTTTAGGTGTTAATCTTCCCATAGCTATTTTAGTTTATCTCCTTATATTATAGTACTTA

ACATGAACTCTGATGAGAAGTGAGCTGCTGCAGCAGCTTAAACATACAATGGCTCTGCCACAGTAAGGAAAA

CCAATATCCTGAGATTAGGTTAATTTATTGAACTGTTAATACTTAGGGCTCCCTGTTTTGGAGGGTTAAACTTG

AGAAATAGCTTATAATTGGCTGACTTGTACAAAATTAATACTGAGCATTAGCTGATCAGGCAGAATTAGTAA

CTAGTTTCTTATGTGACATAACTTCATGCAACATGTCAACGGTACAAAATTTCCAAAATCACCTATTTTTAG

AAGTTACTGTAACGGTATCCCTCATGCAACTTTAAATCTTGCTGTTCTCTTTTGTGTTTGATGTCAGATGACCT

TCAGTAATTACTAATTGTGAAAAGAAGCATACAATGAAATTTCAAAGCCAAGACTTGCTTTTAAACCAGTC

TTTGGGAAATTTAGTTACATATTCAGGTTTTTGCATAAGTTCAATTTGCTTTG

SEQ. ID. NO:307       AW462063
    TATTTCACCATTAATAGTGAGGGAAACATGCTCTCTTATGCAAAGACGACAAACTCGAGTGTTGAAT

GAGTAACTGGTACCCACAAAAGAACATCAGGACTCTTATTCTCTTAATTCACCCTATTTTGGGTTTGTCTTAA

GAACTCCAATATAACCTCAGATTGTCGGGCCTCTTTCAGCAGTGTGAGCCCCCGGAGATGCTGACC

-continued

SEQ. ID. NO:308    AW461912
GCGCTGTGAGAAAACACATTTTATTTGTTTTAATGATACGCATGCTTTTCTTCTGTAAATAGACAATA

AATTTTTGTAGATAGTCTTGGTGTGTTATCTTAATTTCGTATTTCACTGTGTAAAATCAGTGAATATAGCTCAA

GTGTTAGTGGACTGGATGAAAAGAAACTGGTTACTAGGCAAGAACAGGAGGCTGTAGTTACCCATGACTACT

TTTAGCTATGCAGACTAATACATTCTGCAGGTTTACAGCTCAGCACCTTCACCTTTTTTCACTGGTATTTCATG

TAAGGCATCAACCACTGTAATTTTTGCTGATGCTGAAGCCTGTCCTTGGGAATTGGATGCATGGCACTCATAT

TCTCCGGCATCTTCCTTACTA

SEQ. ID. NO:309    AW464194
ATTATTAGCTCATGTATTTGAGGAAGAGCAGCTGTCTTTTTATATGTTTTTTGACAAATCATATTGTAA

TTCTTTTGTACAAAAAAGAACTACTTGTATTCTAGAAGAAATATGAAATGCTTAATTTATAAGCGGGCTGGAG

ATTTTTTCCAATATTGTTTTCTTTGAAAATGAAAGGGGATCATCTATTTTAGTTTCGGGGTCTGGGAACTTTTT

GAAAATTTAATTTGTGGACCAATGTTATGTGAAAGCTAAGGAAGGGCAGGGGTAAAATAGGGCTTGATTTTC

TCATTCTGTACAGACCAGCAAACTTCCCTCTGCAAGGCAGGCTCAAATCACACACCCAAGAGTGTTGGCGTC

ATAAAACGCTAGTTTGCTTCAGCCCCTAGTAACCTCAGGACTTGGTTTGAATATAAAAGGTAGACAACTGATA

TGTTTTCACGAGTAAAATATTGTCAGCCAGAAACAGCTGGTGTCAGGTAAACTTTTTTTTTTTTAAGCTTT

SEQ. ID. NO:310    BF040204
TTGAATCTGAAGCCTGGGGAGGGGGCCCCGAACCTGCCCTTCTCCAGGGCTCAGCTGCAGGTCCTAG

CCAGCCAGCCCTTCCTGCTCGCCCGGCCTCCCCGCCAATCCTGTAGCTGAATGTGCATGGTCGTCATGGGCCC

CCAGCCCTAGAGTTCAGGACTGAGGAGGGGGCCGGGGCAGCCGTGGCATGTGTCCCCTTGGGCTCTGGCCGC

ACCAGGTCTCTCTCTTGAGTTGGGGGTCCGCGGGCTGGACCCCTCCCTCCAGGATGCCCTCCTCCTCCTGGGA

CTACATCCAGCTCCCCCGCCCCACCTTTGCGGGCGGGGCCTGCCCACCGCCAAGGGCCCCTGGCTGGGAAC

CTCCAGGGGACCTGCAGGCCTCACCTTTCCCAGCTCCACCTCGCTCCTCCTCTATCTGGCAGCTCNTCTCTGGC

TTCCCCCCGCCCCCCCGGCTCTGCTTGCCAGATCCGACCTGT

SEQ. ID. NO:311    BF041103
GCTCCCTAAGCATGTGATGTTTCAGGGACTGGTAGAGCTTCTTTCTGGCAACTCTTGCTAGAGCCAGA

AGTACATCCCCAAATGGTGGCAGGGTCCTCCATTTACTCCTCTAGGACCTCTTGGGTGGGCACTTCTGACTTC

ACAGGGCTTCCCCAAGAGGCCAGGCCCCAAAGTGCAAGGAGGACTGGGTTCCCTTACCTGCAGGCTGCCTCA

GTGCTGGGCCATCCAGGTGCTCCCGTGAGTGAGAACCAGGTAACTGCAAGTCAGGGATGACTAGACTTCTGG

TCAACGTTGCAACCTTCTCTGCCTTGGGCCAGGCATGACCTTCATTTTCCCTGCTCCCCCAGACTGTCCAGTGG

AGGCTGCAAGGCCACTCTGCTGAGCTGAGTTGTTGGGAACAGGAAGGGCAGCGGTCTCCACTCCACTTGTAT

NNNTGGCTGGGGGCTGCCCAGGTCCCCAGGGTTACAAAATGCTACACCCCTGCGTAGGCCACCCTACGGATA

GTAGGCAGCAGGCTGGAAGTTCTCTGCCTTGTCTGGATACACAACTGTGCCCAGACTGCCATGAGTCCA

SEQ. ID. NO:312    BF044164
TATAGTTCATTTCACTCAGCATATCCAAAATATTATCATTTCAACATGTAATTTATATAAATCTTTTAA

GATAGCTTGCATTCTTTTGTACTAATTTTTTTTATTTCTGGTGTATATTTTACTAATTTGGGCTAGCCACATTTC

AAGTTAATTTTAATAACTTAATAATACACAGTTCTGTATTAATCTACATATTAATTTGTTGTTCTATAAGATGT

TGTAGGGAATTTCCTAGAATCACTCTCTTAAGTACAAAATCTTTTCTGGTCTCTGAAGCCTTCAGTGCTTGCTT

TTAGTGTGCCCTAAGAAGTGTGAACTTCTTAACATTAGAAATAAATCAGTTAGAAATAAATATCAATTGTCAA

TAAAATAAAAATGATAGCCCAAAATATTTCCCTTTAAAGATAACAAACTTTTCATAGGACTGTTGATGGAATG

AAAGAATATAATCTGCCTTGTGGCAATATGATTGATTATTTTCTCTGGCTTATAGCTAGTTTGTATTAGAAACA

CATGTATGTAGGAGATATTTGGCATAGTACTGTTTTCAGTACATACCTATTTTTTTT

SEQ. ID. NO:313    BM362196
GCACGAGGCTGAGACTTGTCCCACCGCGCGTGGGAGGAATTCATACAAGTGTCCAGTTCAAGCTGCA
GTATGGCCCGTTGGCGTACATACTTGGTGAAAAAGCAACCAAAAAGATGACAGAAAAGAGCAAACTGATAA
CTGTAGATGGCAATATATGTTCTGGAAAAAGCAAGCTTGCGAAAGAAATAGCAGAGAAACTAGGCCTGAAG
CACTTTCCCGAGGCGGGAATCCACTATGTGGACAGCACCACAGGGGACGGGAAGCCCCTGCCTGTGCAGTTC
AGTGGCAACTGCAGTTTGGAGAAGTTTTACGACGACCCGAAAAGCAACGATGGCAACAGCTACCGCCTGCAG
TCCTGGCTGTACGCCAGCCGCCTGCTGCAGTACGCGGATGCCCTGGAGCACCTGCTGAGCACAGGACAGGGTG

SEQ. ID. NO:314    BM362608
GCACGAGATATCTGAACACCTCTAACAGAGAAGTGAAGGTACGCATTTGTAAATCTGGACAAGTGAC
CGCCATTCCATTTTGGTATCATATGTACCTCGACGATGAGATTAGGTTAGATACTTCGAGTGAAGCCTCTCAC
TGGAAGCAGGCCGCAGTTGTTTTAGATAATCCCATCCAAGTGGAAATGGGAGACGAACTTGTACTCAGCATC
CAGCACCACAAAAGCAACGTCAGCATCACCATAAAGCAATGAAGAGCAGATTTCTAATGAAAAAGTGTGGA
AGTAGAGCAGTGGGTTTCCAGTTCTAGTCTGAATTAGTAGTGGGATTGTAACCATAAAATGCAGGTGTATTA
AGTCCTTGAAATGGTGAAATGTTTTTAAAACATTGACATTAATAAAGTGTATTTAAACACCCTAACTAAAGAG
TAGCATTATTACAAAAATCTTACTGCAGACTTCCTTTCTGGCAAAGGCTGTCATTAATTTTTCAAATTAAGAA
CTTTTTATT

SEQ. ID. NO:315    AW465430
GGAGAGGGCTGGACCACTCAGGGAGGGGAAAGGATCAGGGGAATGGACAGGCGTCTTGCCGCTCC
AGAATCTGAGGCCTTCACCTTGAGCGATTCCTCCCTCCAACTCACGAAAGCCCGCTCAAACTTCCAGCTGGAC
TCGACCAAAGGAATAAGGTTACCAGAAACTACAGAAGAAGCCAACCCTCTTACCATCGGTTCTGAGGGGAA
ATGCGGAAGGGCCGCCTCGAGAGCCGACGTGCGCCCACCGCTGTACCTCCAGGCGCGCGCGTCCAGCAGGGA
GTTCGCGGAGCAGTGGGTTCAGAAGGCCCGAGGAGGGCAGCAAGCCCAGAGGCCAAGAGCCTAGAGGTGCC
CTGGAGGCCGGAGGATCGCGGCTGCGCTCGGAACGGCCCCGCCGCGCGCGGCCCGGGTCCCTGCCGGCCCTG
GGCGACAGGTGCAGCCGCAGCCTCCGCCGCCCGCTGGGCCGGG

SEQ. ID. NO:316    BF045069
AAACTTGGACTCCAGATAAATGCATTTAACTTGGTTACAGGACCTCAAGATGTGTATGTCAGCCTCAT
TTTTTACAGATTGATGGTCCTGAACCATGATAGTTTGTTGATCCATGAACACAGCTTTACCCAGTCATAGGAG
TTTTCACTGAACTTAAAGAAACAAAGTTTCCATTCAGGAGGTTGATATTTTCTTTTAACACCAGTTTTCTCAA
ATACCACAAATTTCTCTTGGATACTACACTCTGTTTAAGAATATTGTACATCTGTACAGAAACTCATGATAGA
TTTTTGAAATGGTAGTTCCAAGTATTTGTCCAGTCTTAGACTGATAGGGCATTTTGGACAGTTTTAGCCCCTTC
CTAGCCTACCTTCAAAGGTGCTCAGAAGGTATTTAAGGAAATTATTCCCGTGGACTAATTGGTGTAAATGTGT
TTGCTTTTATTAAGATCCCGGTCCAGGTCGAGATCAAGATCCAGGTCTCTTTCACGGCCTAGAAGCAGCCGAT
CAAAGTCCAGATCTCCATCTCCAAAAAGAAGGTAAGCTAAATAATTTGTTGCCATATCTTAACTGTCAAGTGT
GGCCTCTGCAGAATTTTGCTTACTNNCTACTTCCCTGAGCTCTTTGGAGAATTGGTGCTATATGTTAAAATACT
AAATAGAGTTTC

SEQ. ID. NO:317    AW461462
AAGTGATGTGCGCAAGACACCGCGGCAGCACCGGAGCGCGCGGCGAGCGCTGCCGTGCCGTTCGGC
CTGGCTGCACACCGCAGGAGAAGCTGTCACGTGTGGGTCAAAGCCCTCTGCCCTCCTCCGCTGTCTCCCGTGG
CGCTGAGAGAGTGTGCGAGTGAGCGAGGCGTCAGATGGGAAGCGGGCGGGCCCGTGCTCACCGCTCTGCTGT
TGCTTTGCAGCCGCATCTGGGACACCGCCTCGGGCCAGTGCCTGAAGACGCTCATCGATGACGACAACCCCC
CCGTGTCCTTGGTGAAGTTCTCTCCGAACGGCAAGTACATCCTGGCCGCCACCTTGGACAACACGCTGAAGCT
CTGGGACTACAGCAA

-continued

SEQ. ID. NO:318    AW461475
TTTTTTTTTTTTTTTTCAGCATTTACACTTTATTTGTGACATAAAGAAGCCGTATTTACACAATACATT
CATATTTTTAAATATGTTACACAGCTCTCCTAGAAAACCACTCCATCACAGAACAGCAGCATGTAGCTTGGGT
TCCGTCTTTAAAATATTAAATCAAGTAGAAATACTCTTTAATTTCATAGCCCATCACAGAGGGAGACTCTGAG
GGAG

SEQ. ID. NO:319    AW461535
CCTGGACCTGGGCAGCAACCGGCTGGGCGACGCGGGCCTTGCGGAGCTGTGCCCCGGGCTGCTGAGC
CCCAGCTCCCAGCTCNNGACCCTGTGGCTCTGGGAGTGTGACCTCACCGTCAGCGGCTGCAGAGAGCTCTGC
CGCGTCCTCCAGGCCAAGGAGGGCCTGAAGGAGCTGAGTCTGGCGGGCAACAGCCTGGGGGACGAGGGCGC
CCAGCTGCTGTGCGAGAGCCTGCTGCAGCCCGGCTGCCAGCTGGAGTCCCTGTGGGTGAAGTCCTGCGGGTTT
ACGNNNGCCTGCTGCCAGCACTTCAGCTCTATGCTGACCCAGAACAAGCATCTCTTGGAGCTGCAGCTGAGC
AGCAACCCGCTGGGCGACGCGGGCGTCCACGTGCTGTGCCAGGCCCTGGGCCAGCCGGGCACTGTGCTGCGG
GTGCTCTGGGTGGGCGACTGTGAGCTGA

SEQ. ID. NO:320    AW461605
GCCGTGGGCCTGCGGTTGGGAAGTGCTGGTGTCAGGCGGGGGTTCGGAGACCCCCACATACCGCCGG
CGGCAGAACAGGCCCGAGGCAGCCCGGGGTTTGCTTTAGGAAGAGCGGCTTTAAAACCTGCGCGCCCGGCTC
CTCTGGCAGATACCATTGTGTAGTTTGAATCAGGAATGAAATTTTCTGAAAGCTAAGAGTAGAAGTCTTGGTC
AGCATGGAGGACAAAAGACGGCGAGCCCGAGTGCAGGGAGCCTGGGCTGGTCCTGCTAAGAGCCAGGCCAC
TGCTCAGCCAGCTCCCACTGCTGAGAACAATCTCCAACAGAGACCTGGTAAAGCCTGGATGAACAAGGAGCA
GCATCTGTCTGACAGACAGTTTGTGTTCAAAGAACCCC

SEQ. ID. NO:321    AW461982
GGTGAACCTGGCATCTTTCCACTTTCCAGTAGTCAGTGAAACGCAGTTTGATTTTTCTCGTTGCTTCCT
ATAAAAATACTTGTAAGCTCAAGCACGGTGCAGCCGTAAGCTCATGCTGCCCTGGGACCCTCCCCACCCATTC
ACCGCAGCCAACCCTCCACTTCATGCCTTAGCAACGCGTGTGGCTCATGTAGACGCGCTTCGTCTGCACTTGT
AAGACGAGACAAGGCCTCATCAAGAAGAGGAACGCCCTGTCCTTTAATGCCTGCACATCCCGACACACCCAC
CCGGGGCTACCGGGGCCAGGGTCCCTGGACCAAGGAGATATTTTGTATCTTCAAGGGGCCTGCACTGCTTGG
AAACAAGTGGAGAGAATCAAGTGGAATCTTGTTTGGAAAAAAAAAAAAATGA

SEQ. ID. NO:322    AW462169
GCCTACATCGGCCTTTGTTTGCCAAAGCTGCTCAACCCCCTCATAAGGCTGCAGCTTCTCACCTGGAC
TCCGCTTGAGGCAAAATGTCGTGACTTTGAGAACATGCTGTGGTTTGAATCTTTGCTGTTTTATGGTTGTGAA
GAGCGAGAGCAAGAAAGGACGATGTCGATGTCGCACTGTTGCCTACCATTGTTGAAAAGGTGATTCTTCCT
AAACTAACAGTGATTGCTGAAAATATGTGGGACCCCTTTTCTACAACACAGACTTCAAGAATGGTTGGAATT
ACTCTAAAATTAATAAATGGATATCCTTCAGTGGTGAATGCAGAAAATAAAAATACACAGGTATACCTAAAA
GCACTTCTATTGAGAATGAGGAGAACTTTAGATGATGATGTATTCATGCCCTTGTATCCCAAAAATGTCTTGG
AAAATAAAAATTCTGGGCCTTACTTGTTTTTTCAACGACAGTTTTGGTCTTCAGTTAAGCTCT

SEQ. ID. NO:323    AW462456
TTTTTTTTTTTTTTTCCCATCTCGAAACATTTTTATTCAACAACAGGTTGATTCCTCTCTTTGCTCTTTT
CCTCACTGGGTTTCAGGACACAGTTCACGTAATCCTTGATACTTCATCAGTCTAACAAGTTGTGGCTTGCTTTC
TTGATCAGTTCATGCTGTGTGACGTCTTGAGAACTTATATCCACTTCAAGTGAATGAGCACTCCAGTTCTCAG
CCAACATCAATCATTCTTACCATGTCGCTTCCCATCATGGAACCACTCATTGTTGCCGGTGGAACGCCAGGAT
TAGCTTCATAACCTATGCCAGCACCACCACCTNNNGNTGGAAATTTCTGGCCTCCTGAGCCATAGGGATCTCC
CATGTTCATTGCTCCTCCACCACCCATTCTCATGTCTCTTTCTCTTGGATCCATATAGCCCATCCGACTATAAC
TTTCCTCTCTTTGGCGTCTCATCTGTTCTTCCATCTCACGTTGACGAATCATCATCTCTTCTT

-continued

SEQ. ID. NO:324    AW462702
ACTGTCCATCCTGAGCAATATGCTAAGCGATTCCTGGATTTTATTACCAACATCTTTGCCTAAGAGAC
TGCCTGAGTTCATGAGGAGGAGCTGGGGGAAGGGGGTTGTTGGCCATCTTCAAGACCTGACTGGACAGATCG
CTTCAGTGGGGGTGTGGTCAGTTCTGGAGGCTGGACGGATGAGCCAAGGGAGTAAGGTTCACTCCCTGTGTT
GAATTTCCTTTCTTCATGTCTAGCCATCCCGGAGGTTTTAGTCCCAGCAGAAGGGAATACCTCTACTTGGGTT
AACCCTGGTCATCTCAAGAGAATGGAAGTCTCACATGGGGAGCGTCCTCCACTCCCTGAAAGTATGCCCCTT
CCTCCCCTGCCCCTTCTCAAACCCTTTTCCCAGTTGGATTTGTTATTCTGTTCTTTTCTGTCCATCTTAACTGCT
ACTGTGTCTCCCANNGGACAGATGGCCCTCTTTGTCATCTTCACTCTCCACCCCCAG

SEQ. ID. NO:325    AW462838
GGATCTTCTGCGAGCACTTGGAGCCGGGAAAGAAGCATGAAGTGGCTTGTGCTCCTTGGGCTGGTGG
CCCTCTCAGAGTGCATAGTCATATGGCCTATGTGGGCAACATCACCATTGGAACACCCCCTAAGGAGTTCCGG
GTTGTCTTTGACACAGGCTCATCTGACTTGTGGGTGCCCTCCATCAAGTGCATCAGTCCTGCCTGTCATACAC
ATATTACCTTCGACCATCACAAATCTTCCACCTTCCGGCTTACGCGCAGGCCCTTCCACATCGTCTACGGATCT
GGGATGATGAACGGAGTTCTTGCCTATGACACTGTTCGGGTAACATGGAAACAGAAGCTGAATCAGATCTGC
ACTAACCAACCCCCTCGTGGTCCCCATAGATGGCCTATGTTAGATCGGGAAACTTGTCAGCACTGACCAGCCG
TTTGGCCTAAGCCTGCAGCAATTCGGGTTTGATAACGCACCCTTTGAT

SEQ. ID. NO:326    AW463978
AGATTTCCTCCATTCAGTCCTGTTGGGCCATCTCCCCATCAGCAGCAGTCCTCATCCTGGGATTTCTCT
CCAATCCTCATGGCTCCAGCATCTAGCCATCGTGGGCACCAGTGGATTTGTGACCTTGTTCGAGGGTCCTGCC
TGCTCCTGCTGCTGGTGGTGTCAAATGTACTCTTGTGCCAGGGTGCGGAGGATTATGCACCATACTGTAAAAA
CCAACCTGGCAACTGCCGGATTCCCCTTCAAAGCCTGTTTGAGAGAGCAACATTGGTGGCTAGCAACAACTA
TAGGCTCGCCAGGGAAATGTTCAATGAATTTGACGAAGCCCTGTTGAGGTTGGTTATCAGTTTGCTCCACTCG
TGGGATGAACCTCTGCATCAGGCAGTCACAGAGTTGTTGCACAGGAATGGAGCCTCACCTGATATCTTGGCA
AGGGCTAAAGAGATTGAGGACAAG

SEQ. ID. NO:327    AW464129
AGAGCCAGGCTGTGAAGTTTGCATTGGACATGGCAAGGGGCATGGCCTTCCTACACACACTAGAGCC
CCTCATCCCACGACATGCACTCAACAGCCGTAGTGTAATGATTGATGAGGACATGACTGCTCGAATCAGTAT
GGCCGACGTCAAGTTCTCCTTCCAGTGCCCCGGGCGCATGTATGCACCTGCCTGGGTGGCTCCTGAAGCTCTG
CAAAAGAAGCCTGAAGACACAAACAGACGCTCAGCAGATATGTGGAGTTTTGCAGTGCTTCTATGGGAACTG
GCGAGACGGGAGGTACCCTTTGCTGACCTCTCCAACATGGAAATTGGAATGA

SEQ. ID. NO:328    AW464130
TTGCGGCGTCGAAGGGGAATGGGGGCGGCGGGGCCGTGCCGGGGCCGGCGAAGCCAGCAGCTCGC
GGAGGAAGAAGGGCCCAGGGCCTCTGGCCACGGCATACCTGGTCATCTACAATGTGGTGATGACCGCGGGT
GGCGTTATAGCAGTTGGTCTGGTCAGAGCATACCTGGCTAAGGGTAGCTATCATAGCCTTTATTATTCCATTG
AAAAGCCTTTGAAATTCTTCCAAACTGGAGCCTTATTGGAGATTTTACACTGTGCAATAGGAATTGTTCCGTC
TTCTGTTGTCCTGACTTCTTTCCAGGTGATGTCAAGAGTTTTTGTAATATGGG

SEQ. ID. NO:329    AW464611
GTCACAGTGAAGAAAGAGGAAGAAAAGAAGCCCCACGTGAAGAAGCCTCTTAATGCCTTCATGTTA
TATATGAAGGAGATGAGGGCCAAGGTGGTGGCTGAGTGCACCCTGAAGGAGAGTGCAGCCATCAACCAGAT
CCTGGGGAGGAAGTGGCACAACCTGTCCCGAGAAGAACAGGCCAAGTACTACGAATTGGCCCGGAAGGAGC
GGCAGCTTCACTCACAGCTCTACCCGACCTGGTCAGCCCGGGACAACTACGTACGTGCCCACTCAGGCACCG
GGGGCCGCCTCCAAGGTAAGAAAAAGAAGAGGAAGCGAGAAAAGCAGCTGTCCCAGACGCAGTCCCAGCAG

-continued

CAGCAAGTCCAAGAGACAGACGGTGCTCTGGCCTCCAAAAGCAAGAAGCCATGTGTCCAGTACCTGCCCCCC

GAGAAGCCCTGTGACAGCCCTGCTTCCTCGCATGGCAGCATGCTGGACTCCCCAGCTACCCCCTCCG

SEQ. ID. NO:330  AW464647
  ATTGAAGATAGTGCGGCGGTCGGGGTGGCAGTGGCAGCGTTCGTGTGCTCGGGTGTGAATCGCCGGG

GGAGGAGGCGGTGGAGGAAGAGGTGGCGGCGGTGGCGGTGGTCGTAGCGGTGGCGGAGGAGGCGGGTANN

NATCAGNTGCGGGCGGAGACATGGCCAACATTGCGGTGCAGCGAATCAAGCGGGAGCTCAAGGAGGTGCTG

AAGAGCGAGGAGACGAGCAAAAATCAAATTAAAGTAGATCTTGNAGATGAGAATTTT

SEQ. ID. NO:331  AW464892
  GTGAATTCAGTTTTACTTTTAAGAAAGTAGAATTTATCCTGAAAAATATGAATTAAAGTGCTAACTTG

ATTTTGTTATGTGTGAATATATTATACAGTAACTTTTGTAAAATGTTACTCTACATGAAGGTTTCACTTTGGGC

AATCACTGGGATATGTTACTACTAACTGGGTATTATTTATGGAACTAAGAGCCTCTCGTTGAATGACTAATGA

CTATTCAGATTTTGAGACAGATTTCTTGAATTGTTTACGTAATCTTTGCCTGAAGGATGTAGATTCTGCTTTCT

AATAGTGAAACTAATTTATATGGTGGCCAGAGTGTAATATATGCTAATACTTTGGCATGGGAGATATTTATCA

TGAGTTTTTACTATTAAAAAATGTTATACATTTGCCTACTAGTTTTATAAATGATGTTGCCTT

SEQ. ID. NO:332  BF039385
  ATTATCTCTTCCCTTATCAGGGTGAGCACGGCCGTCTTATCTGATTCGCTGAGGCAGATGCCATCCAG

GGGGCTCTCCACCCCGCAGGCCACGGACACGGGGGTCTTCTCCACCGGGGACTCCAGCAGTGCGGGCACAGT

GGATCCATCCTTCTCCATCTTCTGACATGGATCCTTCTCGGAGCCTTTCCCCTCGGCCCCAGTGGGTTTCTGAA

CCGATGATGTGGACGCCAGCTTCTCCTCATCAGTAGCATGACCGTCCCTGTTAAAAATGTCTGNNNTCTGGGA

GATCACTGCTCCTTCATCCTGAGNACACCCATCCAAAGCAAGAGACTGGGCTTCATATTTCTTCACCTTACAG

CCACTCCTGAAACTCAAGGATTTGGTCTCGGCTTG

SEQ. ID. NO:333  BF039551
  GGATCAGCCAGGGGCCAGNATGAGCCGGAGGGAGGGCAGTCTGGTTGGAATGGGACAGAGCCTGCC

TGGCTTAAAAATTGGAGAATTCAGAGTGGAGCCTCTGGGTTCAGGAAGAGCGAGCCTGGAAGAAGTGGTCA

AGAAGCAAGGGGTTGGGGTGCTCTCATTCCTCCCCTGCTTTTCCCACCAGAGGACCCCCAGGCTGACTCCTCA

GCCTCACCCCTTCCCCACTTGGAGGCCAAGATCCAACAGACACACAGCCTTGCCCGCCTCCTCACCAAATATG

CTGAGCAGCTTCTCCAGGAATATGTGCAGCACCAGGGAGACCCCTTCGGGCTGCCCGGCTTCTCGCCCCCGCG

GCTGCCGGTGGCCGATCTGAGCGACCCGGCCCCGGGCCACGCTGGCCTGCCAGTGCCCGAGCGCCTGCGGCT

GGACGCCGCGGCGCTGGCCGCGCTT

SEQ. ID. NO:334  BF039606
  GGGAACTGCTCCGGAAGCCCCTGGCGTCGCTGTCTGCTGGGTGGAAACGTGTACCGTCATCCGTGGG

CCTGGCCATGGCGCTGCAGCTCTCCCGGGAGCAAGGCATCACCTTGCGCGGGAGCGCCGAGATCGTGGCCGA

GTTCTTCTCATTTGGCATCAACAGTATTTTATATCAGCGTGGCTTATATCCATCGGAAACCTTTACTCGGGTGC

AGAAATATGGACTCACCTTGCTTGTAACTACTGATCCTGAGCTCATAAAATACCTAAATAATGTGGATCAACT

AAAAGAATAGTTATACAAGTGTTCAGTTCAGAAACTGGTGGTAGTCATCTCAAACATTGAAAGTGGAGAGGT

CCTTGAAAGATGGCAGTTTGATATTGAGTTCATAAGATGTAAAAGATGATAGTGCACCCAGAGAAAAGTTTC

AGAAAGCTATCCAAGATGAAATCTGTTCAGTGGTCAGACAGATCACAGCTACAGTAACATTTCTGCCACTGTT

GGAAGTTTCTTGTTCATTTGATCTCCTTATTTGTACAGACAAAGATCTGGTTGTACCTGAAAAATGGGAAGAG

TCGGGACCACAGTTCATTACCAATTCTG

SEQ. ID. NO:335  BF039758
  GTCTCTGCTCCACTTCTTTATCTCGTGGACTTTCTATGCCATCAAGGGAAGTATCTAAAGTTTTAGATG

AAATTATTTCTTTGCTGGTGGTAGAAAGTAAAACATCAGACTGTCCTTTCACAGGAGAAGAAAGTTCAGCAG

TGATGTCTTTATCGTTACTATTTTTAATGGACTTAAAGCTTGTAAGGCTATCTACATTTTCTGAGAAATCATGA

-continued

ATTGGCATAAAATGGTTTGAAGGTACAAACTCTTCCTTGGGACGAGTGTAATCTGGTGTATCAAAATCAACA
AACCCTACACCAGAAGGGCTAACTTCAGAAAACCCACCAAATTCCCCAAATTCATGGTCATCATCATCCTCAG
CTCCGTTGTCTAGTGGTGGTGGGGACGAAGAGTACATTCGAATGATGTCTGGCTCCATTGTTCAATTGCTTTC
AATACTTAATTTATACCTGGTTCGTCCGGG

SEQ. ID. NO:336  BF041379
  GCTCAACAACCTGCTTCTGCGGAAGGACGTCTGCTCCTGGAGCACAGGCATGCAGCTCAGGTACAAC
ATTAGTCAGCTGGAGGAATGGCTTCGGGGAAGAAACCTGCACCAGAGCGGAGCTGTTGAGACCATGGAACC
CCTGATTCAGGCTGCCCAGCTCCTGCAGTTAAAGAAGAAAAGCCCCGAGGATGCTGAGGCCATCTGCTCCCT
GTGCACCGCCCTCAGCACCCAGCAGATTGTCAAAATTTTGAACCTTTATACCCCTCTGAATGAATTTGAAGAA
CGGGTGACAGTGGCTTTTATACGAACAATCCAGGCACAACTGCAAGATCGGAATGACCCTCAGCAGCTGCTA
TTAGACTTCAAGCACATGTTTCCTGTTTTGTTCCCGTTTAATCCATCTTCTCTGACCATGGACTCAATCCACAT
CCCAGCATGTCTCAATCTGGAGTTCCTCAACGAAGTCTGAAAATGCACATGCCAGAGCTTGATTGCCAGTGA
GAGCACGAAGGAAGTACATAGGACAGTGAAGTGAATTTAAGAATCTGTTAAAATCTGTAAAAGGAGATCAG
ATCAAAGTTTGAGAGCCTGTGCAGAGTGAACTATACAGAATAAGACACATCTGTCATTAT

SEQ. ID. NO:337  BF041571
  GTGGCCCACATGGGCCCGGGCGACGGCACTGCAGGTGCTCATGGACCTGCCTCTGAGCGCCGTGCCC
CCCGCCCAGGAGGAGAGGCCGGGCCCTGCCCCCGCCAGCCTGTCCCGCCCACCTCCGCCCAGGAACAAGCCC
TACGTCTCGTGGCCCTCGTCAGGGGGATCTGAACCCGGAGTGTCTGTGCCNNNAAGGAGTATGTCTGACCCT
GACCAGGACTTTGACAAAGAGGTGAGGTTCGCCTGGCGAAGGCGGAGGCCTGGGGTCTGAGGCTCTGTCTGC
CCTGGAGTGGCCACCTCGGGCCTCCGTGGTCCCCAGCCCCCCAGAACCGCCTTCTCTGGACTGCTC

SEQ. ID. NO:338  BF041789
  GTGATTGCCCTGAAGAAGAATACAAGGCGTACTTGTATCTAGATGAAGCTCACAGCATCGGGGCTCT
GGGCCCTACAGGACGAGGCGTGGTGGACTACTTTGGCCTGGATCCTGAGGATGTGGACATCATGATGGGAAC
ATTCACAAAAAGCTTTGGTGCTTCTGGAGGATACATCGGAGGCAAGAAGGCGCTGATCGACTACCTGCGGAC
GCATTCNNNNGCGCGGTGTACGCTNNNTCGCTGTCCCCGCCTGTGGCAGAGCAGATCATCACTGCCATGAAG
TGCATCATGGGGCAGGATGGCACCACCCTTGGCAAAGAGTGTATTCAGCAGTTAGCCGAAAACGTCAGGTAT
TTCAGGAGACGTCTGAAAAGCATGGGCTTCATCATCTATGGAAATGAAGATTCTCCAGTGGTGCCTCTGATGC
TCTACATGCCAGCCAAAATTGGCGCCTTTGGACGGGAGATGCTGAAGC

SEQ. ID. NO:339  BF041797
  GAGGAAACTGAGGTCCGGAGACAGGAAATGACGCACTCCCGGGGATGCCCTGAGTCATCTGGTTTCT
ACGCCATCCTCAAAGTGCTCCCACAGGTTCAGTTCTGGGCTGTTCATCTTCCCTTTCAACTTTCTGAAAGATGC
TGGAGATTCCGGTCAACTGCAAAATGAATGCGCTCTCAGTCTCATACACCTTATGCCAGTCTGGAGAGTGACT
GGAGTGTCCACCTTCTCTGGCACAAAGAGGGACTTGGCAAAGTGGTTGGTGGGCAGTTTAGCCAGAGGGTAG
CCAGCCGCCACGGGTTGGGGTTGAGAGGAGA

SEQ. ID. NO:340  BF041818
  GAAACGCTTAACAGCCAGTTTGTGGAAAATTGCAAGGGGGTGATTCAGCGGCTGACGCTTGAGGAGC
ACAAGATGGTTTGGAACCGGACAACCCACCTCTGGAACGACTGTTCCAAGATCATTCACCAGAGGACGAACA
CGGTGCCCTTTGACCTGGTGCCCCACGAGGACGGCGCGGGCGTGGCCGTGCGCGTGGTGAAGCCCCTGGACG
CGGTGGACCTGGGCCTGGAGACTGTGTACGAGAGGTTCCACCCCTCCACGCCGTCCTTCACCGACGTCGTCGG
CCACTACCTCAGCGGGGAGCGGCCCAAGGGCGTCCAGGAGACGGAGGAGATGCTGAAGGTGGGGGCGCCAC
TCACGGGGGTGGGCGAGCTGGTGCTGGACCACAGCTGCGTGCGCCTGCAGCCCCCCAAGGGGCCGGGCATGC

```
AGTACTACCTGAGCAGCCAGGACTTCGACAGCCTGCTGCAGCGGCAGGAGTCCAGCGTCCGGCTCTGGAAGG

TCCTGGCGCTGGTCTTCGGCT

SEQ. ID. NO:341    BF041917
    TGTTTCACCAAGTATATTTTGAGTTGGTTTCCACACATTTCCAGAGTGCAGCAGTACAGTTCTCTGTTC

ATTGCACGCTGGCAAACTTCTGTAGCTATGTGGGATGGTATGTCAATGAAAAATTAGATAAATTCTTTTTTCT

TATAATTAATATAACACTTCTGGACTTGAACTTGACAGGAGATGCCAAAAGGCAGTGGTACCGTGTTATTTG

TTTATATGAATTACTTTTTAACAAGGAATGATTCATATTCATTAAATGAATTCAATATTTTCCCTGTAAAAACA

ATAGAATTTCAGTACATGAACTATAGAAAAAATATATATATAAT

SEQ. ID. NO:342    BF041933
    CCCACCGGGCCCCACTGCGCCGTCGTCTGCAACTCTACCTCTCTGACGCCTGGAACCAGTGCGACCTG

GTGGCCCTCGCCTGCTTCGTTCTGGGCGTGGGCTGCAGGCTGACCCCGGGCCTGTATGACCTGGGCCGCACTG

TCCTCTGCCTTGACTTCATGATCTTCACGCTGAGGCTGCTGCACATCTTCACAGTCAACAAACAGCTGGGGCC

CAAGATCGTCATCGTGAGCAAGATGGTGAAGGATGTGTTCTTCTTCCTCTTCTTCCTCGGCGTGTGGCTGGTT

GCCTACGGGGTGGCCACTGAGGGGCTCCTTTNGGCCCCAGGACCGTAGCCTCCCGAATATCCTGCGCCGTGTCT

TCTACCGGCCCTACCTGCAGATCTTTGGGCAGATCCCTCAGGGGGAGATGGACGTGGCCCTCATGGAGCACG

SEQ. ID. NO:343    BF042179
    GCCATTCAGCCCAGCAGTGGTTGACCATCGAGAAGTATATGACGGGGGAGTTCCGGAAGTACAACA

ACAACAACGGTGATGAAATTGCCCCCAGCAACACCTTGGAGGAGCTGATGTTGGCTTTCTCTCACTGGACCTA

TGAGTATACTCGGGAGAGCTGCTGGTTTTAGATTTGCAAGGTGTTGGAGAAAATTTGACGGATCCATCTGTA

ATAAAACCTGAATACAAACAATCAAGAGGAATGGTGTTTGGACCAGCCAATTTAGGGGAAGATGCAATTAG

AAACTTCATTGCAAAACATCGTTGCAACTCCTGCTGCCGGAAGCTCAAACTCCCGGACTTAAAAAGAAATGA

CTACTCTCCTGGAAGGATAAATTCTGCCTTTGGACTTGAAATCAAAATAGAACCAGCTGAGGAGATTCCAGC

GGGGGAAGAGGGTAGTAATTCTCCAGAAGATCTCACACGATTGTAAAAAAAAAAAAAACAAAT

SEQ. ID. NO:344    BF042480
    GCTAAACATAGCTGGGGATTTGGGTCAGAGTTGAAAGAAATGGCTATATTAAAAACGCGTTGTATCA

AGCTGAGCTTAACATTGTCAAGCTTAGCTTAACAATATCGTGTTAAGTGATATTGGGTGAGAACTCTATTAGC

TTTCTTATTAAAACATGTTTCCCACTCTAAGAGTAGTAGAGAGAGAGTGATTGGGAGTTTAAATATTGGTATA

TGACGTTCATGAAGTTTCAGTTTATTTTACAGGTTGTTTTGCAAAAACACTCATAGAACGTGTTGGTGTGAAG

AACCTGAAGTCCTGGGCTAGTGTCAATCGAGGAGCCATTATTCTCT

SEQ. ID. NO:345    BF043417
    TGTGTTGCCATAGCAAAGGCCTTTGCCTGGGAAAACCAAAAACAAAAAATTTAAAAACACACCCTCA

GTTGTTTATTTTTGTATAGTAATTTATTTAAAAGTGAACAAAATGGTCATTCAAATCCAAAGAGAATCTTAAA

ACAGTCCTATTCTTTGAAAGTATTACGTGTGCTCAAATTTTCATTCAAGTTTGAGAATGCTTTGAGACCATTTA

GATTGTTTTAAAACTGCTTGGTCCTTACATGAAAAGTGTTATGGTTTGTGTCATTATTTGAGGTGTCAAGTA

TTGATGTTGAAGGTTTATTCAGTCTATAGTCAGGTGATACTAAATTTTATTTTGGGCTGGCAAGGCCATCGGC

GTGCTGACCAGTGGCGGTGATGCGCAAGGCATGAATGCCGCTGTCAGAGCCGTGACTCGTATGGGCATTTAC

GTGGGGGCCAAGGTCTTCCTCATCTACGAGGGCTATGA

SEQ. ID. NO:346    BF043962
    TGCTTCCTCACCCCAAGGGGTTCAGCAAGATACAGTTTCACAATCTCTGGATCAAGAAGTTTTATTAA

AAGTTAAAACTGAAATTGAAGAAGAGCTCAAATCCCTGGACAAAGAAATTTCTGAAGCCTTCGCCAGCACAG

GCTTCGACCGCCACACCTGCCAGGACTCGGGACCCAGGAGAAAGAAGGAGGGTTTTAGTTGTCTCGACTGAA

TCCGAATGGGCAGCAGCTGGTTGGACATCCGCAGGACGCTCTGGGGTGAGGAGCTGGGTCAGCAGGGCAGG

GGCGGCCCACCTGCCGGGGCTTGAGGTAGAGGCTGTGCACGCGGTCTGCTGGGCGGTCCCTGGCCTGGGTTC
```

-continued

CTCTGAGATTCAGGGTCTAGGGTGTCAAGTGCTTCCTCAGTCTTGTCTGTGGCATCTGGGCAACCCCGGCTGT

GAGCACCTGTGCCCCCGAGGGTNNNTAGCCTCCCCCATCAGCCCCCGTAGCACCTTCCCCTTTGGTGACAGCA

CCCCCCGATGTGCCAAACGTCCCCGGGGTAATGGGTCCCGTGAGAGCCTCAG

SEQ. ID. NO:347  BF043971
  GATGTTCCCATTCGAAGACGCCGCTGCTCTCGCCTGTTTTAGCAAGCCTCTGCTGATGGAAGCCCTGG

GATGAATCTAGGCTTTTAAATGGATGTCTCGATAATGTCAATAACTAAACTGTTCTCAGCTTATATTAATAGG

AGGAAGACTAGCATGAAATACTGTGCCAGGCCCTGGGTTCTGTGCGATGCTCCTTTAGGAATTGGATTGTTTG

GGTTTGTTTTGTGGTTTTGAGGNNNNNNNNNGAAACGGGAATCTTTTTTTCTCTTCTAGGAGTTAATGGGAGAA

TAGTTATCTAGCTAAGGAACAGACATTACTTTATTTAAAAATATTTTATACTTATAAAAATATGGAACGGAA

GGGAATTGGTTTGAAAGAAGATTTAAAATGAATCAGAAATACCTACACAAGGATAGAGAGGAACTATGTGA

CTGAATGGTTCTGTGAAAAGACGTATAAGTTATTTAGAAATGAACAGAATTTGTAATTAGGCTAATCCA

SEQ. ID. NO:348  BF044310
  GCAGGGGGCGGTCTTGAAGACGCGTCGTTTGGTTTGACCTCAGTGACGGAGTTCTCCGTCTTCAAC

CGCTGGGCGGAAGGCGTTTGTTAGGGGCCCGGCCAAGAAAGAGGCCCTCGAGGTTCCTGATGGTGTCCATGA

CTTTCAAGCGGAGCCGCAGCGACCGGTTCTACAGCACCCGGTGCTGCGGCTGTTGCCATGTTCGCACCGGGA

CGATCATCCTGGGGACCTGGTACATGGTGGTCAACCTGTTGATGGCAATTCTGCTGACTGTGGAGGTAACACA

CCCAAACTCAATGCCAGCTGTCAACATTCAGTATGAAGTCATTGGCAATTACTATTCGTCTGAGAGAATGGCT

GATAATGCCTGTGTTCTTTTTGCCGTCTCTGTTCTTATGTTTATAATCAGTTCAATGCTGGTATACGGAGCAAT

TTCTTATCAAGTGGGTTGGCTGATTCCGTTCTTCTGTTACCGGCTTTTTGACTTTGTTCTCAGCTGCCTGGTNGC

TATCAGTTCTCTGACTTACTTGCCAAGAATCAAAGAATATCTGGATCAGTTACCTGATTTTCCC

SEQ. ID. NO:349  BF045055
  TGAGGTGCACTGGGTGGGATAAAAATGGAAGCAGGAAAAAAAGGAAGTAGAAGGTCCAATCATG

AGGTGGGGTGGACCTAGCCCCATTCTTCTCCTTCTCCAGGTCCAATGAAGCGCCAAGTGGCAGTAAAATCCAC

CCGGGGTTTTGCTTTGAAATCAACCCATGGCATTGCCATTAAATCAACCAACATGGCATCTGTGGAAAAGGG

GGAGAGTGCACCCATTCGTAAGAACACACGCCAGTTCTATGATGGGGAGGAGTCTTGCTACATCATCGATGC

CAAGCTTGAAGGCAACCTGGGCCGCTACCTCAATGTGAGACCCCTTTCGCTCACCTGTATGTGCTGGTTATCC

CCTAGTCCTCACATTTCTAGTTCTTTTAAATACAACTCCATAAACC

SEQ. ID. NO:350  BF045103
  GATAAAGTGACTAGTCCAGAGAAAGCTGAAGAAGCAAAATTAAAAGCAAGGTATCCTCATCTGGGA

CAAAAGCCTGGAGGTTCCGATTTTTTAAGGAAACGATTGCAGAAAGGGCAAAAATATTTTGATTCTGGGGAT

TACAACATGGCTAAAGCAAAAATGAAGAACAAGCAACTTCCTACTGCAACCCCGGATAAGACAGAGGTCAC

TGGTGACCACATTCCCACTCCACAGGACCTTCCTCAACGGAAACCATCTCTTGTTGCTAGCAAACTGGCTGGC

TGATTAAAAAGAGCTGAACTGCATGAATCTTCTAATGCCCATTATTTCTCCTTAATATGTTACTCCTCTGCTTT

TTATTTCCTTTTACTCCCTGTGTCATTTGAGAGTGATGGCTTTGCAGGTAGCGGTAGTGTGTGCTGCTATTTTA

AGGGAATATACATGTGTAGAGTTTTTGATTAGTTTAACAGTGCACTGATGAAAAGAACATGTTAGAGCAACA

TAAAGTAATCTACTTGAAAATAATTGTATATATTACCTAACTCCTAGTGTAGGGCTGGATCCAACAAGTAACT

AACAAGTTTTGCAGTTTAAATGTTG

SEQ. ID. NO:351  BF045200
  TTTTTTTTTTTTTTTTTTTTAAACTTGCAGAAGCCTCTTTATTTTCATCCATCAGAGGGCAGACAGAAT

GAAAACCACAATTACAGAAAACTAACCAAAATGATCACATGGATCACAGCCTTGTGTAACTCAGTGAAACTA

TGAGCCATGCCGTGTAAGGCCAGCCGAGACAGACAGGTCATGGTGGCGGGTTCTGACAAACCGTGGTCCATT

GGAGAAGGAAATGGCAAACCACTTCAGCATTCTTGCCGTGAGAACCCCATGAATGTATGAAAAGTGTGAGAA

-continued

GCAGAGAGCAAAAGCTAGTGACTGGNNGGCCNNNTCTGCCCCACAGATAAACTTCAATTTACATGTCATTAT

TTACAACTTTAGGGGCGGTTTAAACAAAACAGTTGGGGAGAAAAAATGGCATTTCTGACTTGCGTTAAAAAA

TCGTCAA

SEQ. ID. NO:352    BF045261
    AGACAGGACTCTAAAGTTAGACTCTCCTGATTTTTCACAAGATGCTGGACTGGAGATTAGCAAGTGC

ACATTTTATCCTGGCTATGACACTGATGCTCTGGAGCTCAGGAAAAGTGTTCTCAGTGGGTGTCACAACAGAG

GCCTTTGATTCTGGAGTCTTAGGTGTTCAGTCATCACCCACAGTCAGAGAAGCGAAGTCGGCCACTGACCTGG

CAGCAAAACTCTTACTTCTTGATGAACTTGTGTCTCTGGAGAATGACGTGATTGAAACAAAGAAGAAAAGAA

GCTTCTCTGGGTTTGGTTCTCCCCTGGACAGACTCTCAGCTGGCTCTGTAAGTCATAAAGGTAAACAGAGGAA

AGTAGTAGATCATCCAAAAGGCGATTTGGTATCCCTATGGATCGGATTGGAAGAAACCGGCTTTCAAATTC

CAGAGGCTAATGGATTCCAATCACACAACTTCCTTGGGTGAAATGTCACAGAAACATGGAAGATATTTTGGT

GAAGTTCTTCACACTTCTTAATGA

SEQ. ID. NO:353    BM364511
    GCACGAGCCCATCTCTAGGGTGGTGAACTACCCTGAAATCTCTGGGACTGGAATTTGTTCCCCAAAG

TCTTGAGTGGCTCTGGCTTATTTGTGTCTCCACCCTGGTTCTGTGAACCACCCCACTCCAGATGCCAGAGCCAC

TGGGGTTGGGGCCTGGGACAGGGATAGGCCTGTCAGAAGGAGCTGGAGCCAGTATGCGAAGCAGCTGTAAT

GGTCTGAGTGGATTTATTGACAGTGAATAAAGGGCACAAAGCCCGAGCCAGGCAGACTCACCTCACACACCC

CCTGCTCCCCGTGGTGGGGACACCTGAGAGAGGAGGGGTGGACAATGAGAGAACAGGAGATGGGTCATA

CCAGTGGCCTCGCAGAGCAGGGGCAATAAGAGCTCAGCCCATTGCAGTGCTGGCCATGTCTTCATACCTGGT

GATCTGAGGTGTCCTGTTTGCTTGGCTGTCCGTTTGCTTCTTTTCTGGCT

SEQ. ID. NO:354    BM364839
    GCACGAGGCTGGCGGGGGAACATGTCGGAGTCAGAGCTCGGCCGGAAGTGGGACCGGTGCTTGGCG

GACGCCGTCGTGAAGATAGGTACTGGCTTTGGATTAGGACTTGTTTTCTCACTTACCCTCTTTAAAAGAAGAA

TGTGGCCATTAGCCTTTGGCTCTGGAATGGGATTTGGAATGGCCTACTCCAATTGTCAGCATGATTTCCAGGC

TCCGTACCTTCTACACGGAAAATACGTCAAAGAGCAGGAGCAGTGACTCACGCCTGAGAGCACCCCAGGGGG

AGGGCAGGAGAAACCACGTTCATTCCTCAGGAACGCTGAAGCGCCCGAGTGAGCCGCACTCTCCGTGAGCGT

CGCCAGTAATGCTCAACTCCAGCACACTGTGCACGTGTTTGAAACCAAGTCCGTTTCTTGTTTTGTATTTTCTC

TCTGGAAATTGCAGGGCGGTGGTCTTAAAATAAATAAACTAAACTCGGCAGCCCAGAAAAAAAAAAAAAAA

AAA

SEQ. ID. NO:355    BM365207
    GCACGAGCTGGCCTCAGTCAGTGATGAAAACAAGGGAAGGGACAGGGAGGGGCAGTCTCCTAGGTC

AACCCTCGGGGAGGGCCCTGGGCCAGGATTCACCCTTCCTAGTGCCTCTGAGTCAGGATCCGCGGGACCCCC

AGCCTTGACCCCACCTGTATTCTGTAGTCCCTTCTCCTGCCCACTCAGGACTTAGAGGCACTCATCCATTGCAC

ATGTTTATAAGCACCTGTTACCAGCCAATACTGAAAAGGACAGACTCATGGATTTAGAGTCTAGTGGGGAA

TTCAGACCCTGGTGATGAATGTTGGGAAAGAGGAAGCTATGAGGTGACTGCATTGCAATCCTGGGGGCCTAA

CTGGGCCCAAGACTGGGCAAGAGTCCTGCAGAAGACTTTGAAAAACCTCAAGTGGGAAGGTCTGGGGCTGT

TGGAGGCTGGAGCCAGTATGAGCTCCCCATGGCTCCTCTGACCCGTAATCAAGGACCCAAGGAGCTGACTTG

ACGACAGTTTTTGAGGAAGTGGAGCAGGT

SEQ. ID. NO:356    BM366035
    GCACGAGGTCACGGACAGTATGGTTCCGCCGGTGCAGGTCTCTCCGCTCATCAAGCTCGGCCGTTAC

TCCGCCCTGTTCCTCGGCATGGCCTACGGCGCCAAGCGCTACAATTACCTGAAACCTCGGGCAGAAGAGGAG

AGGAGGCTTGCAGCCGAGGAGAAGAAGAAGCGGGATGAGCAGAAGCGCATCGAGCGGGAGCTGGCGGAAG

GTGGTCATGCGTTTGGCTCTCCTAGATTTTCCCCCGCCCCGCGGGGTTTTCAGAAACAGCTGCTGCTTCATACG

-continued

```
GAGCAGCAAGTGGAGAGGAAAGGCTGCCTTCTCCATTTCCACTGGCCCCTGGGCCATCCTCTGCTGAGTGGG

GTAGGG

SEQ. ID. NO:357      BM366605
            CCACAGTCTGTCTCACCATCCACAAAAGCTCACAGGATCGCCTAGGTGACATCCGAAGCTCTGTCAC

ATACGATCTGGCGTTGGATCCAGGTCGGCTGATTTCTCGTGCTGTTTTTGGTGAGACCAGGAACTGGACTTTG

ACTCGAAGAAAAACCCTGGAGCTGGGAGAGCACTGTGACTCCATGAAGCTGCTTATACCAGACTGTGTGGAG

GACATGGTGAACCCCATTATCCTGCGACTCAACTTCTCCCTGGTTGGGGAGCCCATTGCCTCATCTCAGAACC

TCCGCCCCGTGCTGGCTGTGGGCTCCCAGGACCTCTTCACGGCCTCTCTCCCCTTTGAGAAGAACTGTGGGCA

AGATCACCTTTGTGAAGGGGACCTCAGTGTCAACCTGAGCTTCTTAGGGCTGGAGACCCTGGTGGTGGGGAG

CTCCCTGGAGCTCAATGTTGCAGTGATGGTGTCCAATGAGGGCGAGGATTCCTATGGAACGGTGATCAGCTTC

TACTATCCAGCAGGGCTGTCCTATCGACGCACGTTAGCAATCCAGCAACCTGGTCAGCGTCCCCTGCGC

SEQ. ID. NO:358      AW464111
            ATAATCCTGGCGTAGGGCGGCTCGGGCTGCGCCCCAGCTACTCAGAAGAGGCCCCAGACTGTGGCAG

CACTTCCCCAGGGGTCTTGCTGGGAACTTGACATCTCGGGCCCCACCCGGACCTGCTGATTCAGGGCCCACCT

TTCACATGATCCCCTGGGAATTCTGAACATTTCCAAGGCAGCCTTCCTTGCACAGCCCTTGGCTCTGGCCACA

CCCCAGGATTCCTGGGGAGGCAGAGAAAACCCTGATGCTGGCCCCACTCCAGAGGCTCTGACTTAATGGGGG

TAGGCCGGGTGTGGGGTC

SEQ. ID. NO:359      AW464166
            TTTTTAAAAAAAAAAATAATTACCTTTATTACAAAACTCATGGTAAACCTAGGGATTTATGTCCGGTT

AAGCTCTTTCACCTGAAATTAGTGGGTGGCTCTGAAAAGAGCCTTTGAGGTTTTCAAAGCAGGAGGTGCCGCT

GAAGATTTACTTCTTCTTGGAGACCGCCTTCTTGGCCTTTGTAGCCTTGGGTTTGGCAGCTTTAGGTTTGGCTG

CCTTGGGCTTGGGGGCTTTGGCCTTGGCCGGACTCTTAGTCGGCTTCTTCGGCTTGGCTGCCTTCGCCTTCTTC

GGACTCTTGGCTACTTTCTTGGTCCCAGCAGCCGCAGCCGGCTTCTTAACTTTCTTAGGGGTCTTCTTGGCAGC

CTTCTTCGGAGTGGCCGCACCCGTGGATTTCTTGGGTTTCTTAGCCGCCCCAGCAGCCTTCTTGGGCTTGGCCG

CGCCCGCCTTCTTCCCC

SEQ. ID. NO:360      BF045977
            TGGAAGCTGAAGATTTCCCAGAACAAGAACCCAAGATAAGCTGGAGTTAATGGAAGCTTTTCTTTGG

CTTTTTCGGTTGTGACCTACCTTCCAACCAGTGCTGCAGTATATAACCACCTAGACCAGCAACGTTCCTCTGG

AGCCAGCATAGGGCCCTTCTTGAGCAAATACCACCAGACTCACAAACAGCTCTGTTACTAAGGTTTTATTTAA

TTTCAGAGTGCAAATATTTTTCAAATGCTCACTAGGTTTTATATACTAAGAAGCTATATTTTTGCCCTTAAACA

CTCCTTGTGGATTATGATTTATATTCACATATACTGGCCTCAAATGAGATAAAAACCAAACTGTCTGTTATGTT

TACTTTGATATATTAATTTCTTTAGAGCAGCGTTTTAGCTACTAAAGTTAACATGTTTATTCTTTCCTTCTCACA

TGCTTGATTAAAGGTGAGCTAATTCTTTCAAGAGTTTTGATTAATTAACAGAAAATCCTAAATTCAAACTGC

TAAAGAACAGTTTGATTTTATGGCTCTCCTTAAGTATGAGACACATCTTATTTTATTGAATTTCTTTCAATAC

CCT

SEQ. ID. NO:361      BF040267
            GACTAATCCTCTCCTGCTTCAGCTGTTCAAATTTTCGCTTTAACTCGGCCTGCCGCTCCACTTTCTTTT

GTGCACGGCCAACGAAAATGACCTTCCCAGTGATTTCTTTTCCATTCATCTCTTCCACAGCCAAACTGGCTAA

ATAGCTCTTTCAGATTCTCATCATCAACCTCTTCCCCAAAGTTTTTGATGTAAACATTGGTGAATTCCTTGGCT

TTGGCTCCAAGTTCGGCTTCCCGCTCTTTTCGAGACTTGAATCTGCCCACAAACCAGCCCTGGAGTGGAGAGG

TAGGAGCAGGCCACACTTGGGCCGAGAGAACCAGTAGCCGCCTTGTGTGTGCCAGTTTATACCGAGGTGGGG

CCACGGCTGG
```

-continued

SEQ. ID. NO:362    BP230002B10G5
AACCCTNTTAAAACCCCCANACTTTTACTATAGGGAANTTGGCCCTCGAGGCCAAGAATTCGGCAC
GAGGCGCAAAGATGTCAGTNTTTTNGGGGGGTGGNGTACAATACCTGCAGTGAGGCCAGGGCGGGCCCTGC
AGCGAAAGGGCACCTCTCACAGGTGCTCTAGCTACTGCCCCTTTGGGAAGCCAAATCCTCCAGCCGGGACCC
TTGGGTATGTGTTCTGGAACATCCTGACCTCTGATACCCTGCCTGTGACCCTGACTTGCTGNGCAAGGCATCC
TTCCCCCTANAGCTTNTTGCAAATTACTGGCTTCCTTGAGCCCTGCCTTGGAGCCACCCAATCCAGCTGTAAA
ATGAACACNCAGGAAACCACACATCTTGACTCAACTTATCCAGGTGATTCCTGGAGTGGGCCTGGGGCTATA
AATAGGCATCATGAGTTGATCACAANAAGGGCTTGAGAAAAGCTGAAAGGAGAGTAGGGGAGGAAGCCANT
GTTAGACCCANAACTATAGGCACACACACCTTCAGGCCAGCTTNTGAGCTGTGGGAACCGTGTTCTCTANTTA
AGGCACNTGATGGTGTTTGGAAGAGGGGACGGGGTTTCTTCCTTGTCTGCNTGATGGGACNACTCATCCATAC
TTGATGGCGGTCTTTTGCAAGCGGGTNCCCTTCCACCCCCCAGGGCCAANAAACATGTCCCCCTTCACTTCCC
ATGGAATTTTTTCTTTTATTATCCCCCCCACCCTTTGCAGGGAAACCCCTTTGCAAAGAAAAAAGGNCCTTGA
NACNAGNGA

SEQ. ID. NO:363    BF044279
TTAAGATGGCTGCCGGGCGGCACCGTCCGGACTGAAAAGATGTGGAGTGGGCTGTTACCTCCTGGCC
TAAATGAAAGTGATGTTGAATTGAATTCTGACGATGATACCACATTAGAGAGCTCTGAATTAACTTACAAG
AGGGTAAAGAAGATGGGACCTTTGAAAAGACAGAGATGGTAGATATTCCTACAGATGGACCAAGCACTGAA
GCAGAGGCAAATATAAATGCATATGAAGAGTGTCCCTCTGGAATTCCCTTAAATATGTGGAATAAATTTCAA
GAATTGCATAAAAAGCATTCTGAACAGAAAACTTCAGCTTCTAGATCCGAAAAGAAAAAAAGAAAACGCTC
CAGAAAAGGTAAATTGAAGAATGAAGAAGAATCTCATAGTGAACAATCTTCAAGTGAAACCCAGTGGAAGG
AGCTTACCCAGTATTTTGGAGTCAATGAGAGGTTTGACCCCCCTGTTAAAAGGAAAAAAGTTGAAAAGTCGG
GACTTGAAAAGAGGATAGACCAAGCTGTGGAAGAGTGGAACATTGAGAAGGC

SEQ. ID. NO:364    AW466058
TTTTAATAAGGATGGGGTAGAAGGCTGGTTGGTTGAGATGTCCTGGCGAGGGTCTCCCGGAGCCAGG
GCAATCTGAGCCAATTCATTCCTCTTCCCTCTCTTCCCCTGGCCTTACGCGAAGCCTCGGGCTCCTTGAAGCAG
CGCCAGGGCTCCTGACACCCCCATGGTCAAGGCAGAACGCGCACAGGCTGGGACCACGCCGGAGATCATCG
GGTCATTTTG

SEQ. ID. NO:365    BF042062
GAATTCTCTTCCAAGTTTGAAAATTCAAGTTGGATAACCAGTATTATCCTCGTTGGTCCTGTTGCTGTT
AAGGCATTGACATATATGTGGAGGAATGAAATACTTAACTAGAATTCTTTAATAGGGTTTATGGTTTAACTTT
AGAGAGCACCTTTGTATTTTTCTTATCAGCTAGGACAAAATATTGTATTAAGCATATGTAGCACTTCATAAAA
TGGCTATTGTGTAAGCTACAGGTAAAAGCAAAGCTATAGGGTAGATTTATAATACAGTGAAGGCACGAGGAC
TTCAAACGTGCCGGCAGTTTGGCCATAGAAACTGGAAGTTAAAAGTCACATGAAGGTCAAGATCCAGACTTA
ACTCATGCCACTGTCCTTCAGGATCTCTGTCTTGGAGCATGAGGGAGTTGGCAAGTTAAATGTAGAAAGCAG
GCCCAAACTTGGAAAGGTTTTGTTTTTGTAAATCATTTGACTTACTTTTAACATGCTCAGTAGAACGTTTTTAC
TTTTACTGTTTTGTACCCAGGAGTTATTTTTACCTAGCCGTAGAGCAAAACTGTTCATAAATGTATCCCTTTCA
AATGTCTTTGAGAAAAATGGAGGGAAAAAC

SEQ. ID. NO:366    AW464065
GAATGAAAGATATACCTAGAACACCATCCAGGGGAGAAGTGAATGTGATTCCTCTCCAGAACCAA
AAGCTTTGCCTCAGACTCCTAGGCCAAGGAGTCGTTCTCCATCTTCCCCGGAGCTCAACAATAAGTGTCTTAC
CCCTCAGAGAGAGAGAAGTGGGTCAGAGTCATCAGTTGAACAGAAGACTGTGGCTAGGACACCTCTTGGGCA
GAGACGTCGGTCTGATCTTCTCAGGAACTCGATGGGAAACCCAGTGCATCCCCTCAGGAGAGAAGTGAGTC
AGACTCTTCTCCAGATTCTAAAGCTAAGATACGAATGCCACTCAGGCAGAGGAGTCACTCTGGATCCTCTCCG

-continued

GAGGTGGACAGCAAATCCCGGCCTTCTCCTCGGCGTAGCAGGTCTGGCTCATCCCCTGAGGTTAAAGAGAAG

CCAAGAGCAGCACCCAGGGCACAGA

SEQ. ID. NO:367    AW464444
GCGGTGCCGCCCGCCCTGCGCTCTCGGAGCCCGGAGCCGCCGCCCAGGGGATGCGGGAGCCCCCG

GTTTGGGGGAACAGAGAGGCAGGCGGGGAGCCGAGGACGGCATGTCCCAGGCCCCAGGAGCTCAGCCAAGC

CCGCCCTCCGTGTACCACGAACGGCAACGCCTGGAGCTCTGTGCCGTGCACGCCCTCAACAACGTCTTGCAGC

AGCAGCTCTTCAGCCAGGAGGCTGCCGATGAGATCTGCAAGAGGTTGGCCCCAGACTCCCGGCTGAACCCCC

ATCGCAGCCTCCTGGGCACCGGCAACTACGACGTCAACGTGATCATGGCTGCCCTGCAGGGGCAGGGCCTGG

CTGCCGTGTGGTGGGACCGAAGGAGGCCCCTGTCCCAGCTGGCGCTGCCCCGGGTACTGGGGCTGATCCTGA

ACCTGCCGTCGCGCGTCTCGC

SEQ. ID. NO:368    AW461405
TGCAGGGGTTACGTTTGCAGTCAGTCCGGTGTTTGCAAATATTGTGCGGGCTCGCGAGCGCGTCTCCG

GGCTCCGGCCAGGACCCGAACCGGGGGCGCCTAATCGCTGCGCACTTGAGTTTGCATGAACTTCCCCGGCGCT

GCAGGCACGNNCGCCGCGCTCCCGACTGCAGACCGCAAGCCTCCCTGTTTTTACAGCAGCGGGGACGNNNTC

TTCCAACCCGACATGGATGTGCTCCCAATGTGCAGCATCTTCCAGGAACTCCAGATTGTGCACGAGACTGNN

NACTTCTCGGCGCTGCCCTCCCTGGAGGAATACTGGCAACAGACCTGCCTGGAGTTGGAACGTTACCTGCAG

AGCGAGCCCTGCTACGTGTCAGCCTCCGAGATCAAATTCGACAGCCAGGAAGATCTGTGGACCAAAATCATC

TTGGCTCGGGAGAAAA

SEQ. ID. NO:369    AW461482
GAGTACAGCATCTTCGCTCCCCTCTCCCGGATGGAGGCCGAGATTGTGCAGCAGCAGGCGCCTCCCT

CCTACGGGCAGCTCATTGCCCAGGGCGCCATCCCTCCTGTAGAGGACTTCCCTACAGAGAACCCTAATGATA

ACTCTGTTCTGGGCAATCTGCGTTCTCTGCTACAGATCCTGCGCCAGGACATGACTCCAGGGAGCACCTCTGG

TGCCCGCCGCCGCCAGCGGGGCCGCTGTATGCGCCGCCTGGTGCGCCGTCTTCGCCGCTGGGCTTGCTTCCC

CGAACCAACCCCCCAGCCCGGACCCCTGAAACCAGATCCCAGGCCACACCATCCACTGCTCCTCCTGAGACC

TTAGATGGCAGCACAGGTCCAGCCCAT

SEQ. ID. NO:370    AW461511
GGAGGCTGATGAAGGAGCTTGAAGAAATCCGCAAGTGTGGGATGAAAAACTTCCGTAACATCCAGG

TCGATGAAGCTAATTTGCTGACTTGGCAAGGGCTCATTGTTCCCGACAACCCTCCCTATGATAAGGGGGCCTT

CAGAATCGAAATCAACTTTCCAGCAGAGTACCCCTTCAAACCACCGAAGATCACGTTCAAAACGAAGATCTA

CCACCCGAACATCGACGAGAAGGGGCAGGTGTGTCTGCCTGTAATTAGTGCTGAAAACTGGAAGCCAGCAAC

CAAAACCGACCAAGTCATCCAGTCCCTCATAGCACTGGTGAACGACCCCCAGCCGGAGCACCCGCTCCGGGC

TGACCTAGCCGAAGAATACTCTAAGGACCGTAAAAAATTCTGTAAGAATGCTGAAGAATTTACAAAGAAATA

TGGGGAAAAGCGACCTGTGGACTAAAATCTGCCGCAATGGATTCCAGCGAGTGTGAGC

SEQ. ID. NO:371    AW461572
TTTTTTTTTAAAACAAACAAAAGTTTATTAAAAGTGTTCTTAATGCTCGAAACGGAAAAGATTCCCA

AATATACAGATGCCTCTTTTCTCATAGAAATAGATTATTTTTTATGATACAAAAAAAAGGCCAAAAAAAAAA

AAAAAAACCAACAAAAACAAAAAACAACATCAACAGCAACAACCCCGTAGGAACATCTTAAGCGATTACT

CAGGGCCCGGCTGACAGTTACACGTGGGTTGCGTCAGTCCCGTGTACACACGCGTTCAGCCATGTTTAAACCG

ATTGCATCAACTTCGAAACCGGCCCGCCCGCCGGCGCCCGGAGAGGGGGTGGGCAGGAGGAGAGGCAAGA

GTTTATCATTCATCTGTACACATAGACATCTCTTCTTTAAATAACACCGCGGGCGGGCGCCCCGTCTGCACGT

GCG

-continued

SEQ. ID. NO:372    AW461591
AGCAAGGACAGCGAGCAGGGCTGAGCTGGGGGTGCGTGGGCTGCTACGGCCCGCCACCTCCATCAC
ATGCACCTCTGCACCCCCTGCTGCCTGACTCAGGAGTGGGGGGGGGGTCCTGTGCTTCCTTCACTCCAGACC
CACGGTGCTGACCCAGTGCACCCACCTGGTCCTCTAGTGCGGACCTGGCCACAGGGCTCCTGTGGGCCCACG
CTGATCCCGCCCTGGTCCCTTCATAAAGAACTCTTGAGCACATGCAGCCCAGGGGAGCCAGGAGGCTCCAGT
GTGCTGTGTCCATCTGCCTCCCTCCAGCCCCTTCCGAGACACTGCGCATCATGCCCCCCTCCACCCCCACCCA
CACTGGCAGGAGGAACAGACAGGGAGACCACACACAGAGCTCGTTGTTTATAAATCTCTGCCTGGCTCATCG
GTCTGTTTGTCCATGTATATATCTGTATATCTCTATG

SEQ. ID. NO:373    AW461600
CTTTGATTTGAGCATGCCCCTCAAGTAGACAGCATGCTCTCTGGTCCCTTGGGGGCAACACCTGATCC
AGATGGTGAGGCTGTCTGCCTAGACCCCAGNNNGTGGTGAGAACGGGGAGCAGAACGCCTGTCAGTCAGAG
GNNGCCTCCTGGCAGCCTCAGCTGAGCAAAGGCCAAAGAAAGTAGCCAGCGGAAGCAGCCCAAGAGCCGCC
GGGAGGCCCCACGTGGGAGAAGCAAGGGGGTCAGACCTGACCAGGGGCGCTCACGTGCCCCCCTCCCCTGC
ATCCACTCCAAGGTTGACTGCTGGCTCCGGCCAGCACTGTCCGTGGCCCCAGCATGCTGAGGGTCCTTCTGGT
GACCCATGTTTGAAA

SEQ. ID. NO:374    AW461650
TCCTGAGAGCCCCGAGGAACCCCTCTCCCCGCCAACATGGCCAACAAGGGTCCTTCCTATGGCATGA
GCCGGGAAGTGCAGTCGAAAATCGAGAAGAAGTATGACGAGGAGCTGGAGGAGCGGCTGGTGGAGTGGATC
GTAATGCAGTGCGGCCCCGATGTGGGGCGCCCCGACCGCGGGCGCCTGGGCTTCCAGGTCTGGCTGAAGAAT
GGCGTGATTCTGAGCAAGCTGGTCAATAGCCTGTATCCTGATGGCTCCAAGCCAGTGAAGGTGCCCGAGAAC
CCGCCCTCCATGGTCTTCAAGCAGATGGAGCAGGTGGCTCAGTTCCTGAAGGCAGCTGAGGATTATGGCGTC
ACCAAGACTGACATGTTC

SEQ. ID. NO:375    AW461778
CGGGCCCCCGCGCGCAGCGGCTGGCCCCTCAGCCCCGCGCCCTGCCCGCACCCGCCGGCCCTAAAGC
TGTCACGATGCAGCCGCCCGCGCCCTCCCGCCTGGGGCTGCTCCTGCTGCTGCTCCTGAGTCCGGCGCACGTC
GGCGGACTGTGGTGACATCCGGGAGACGGCCTTCGTGTTCGCTATAACGGCGGCAGGCGCCAGCCATGCGGT
CACGCAGGCCTGCTCCATGGGCGAGCTGCTGCAGTGCGGCTGCCAGGCGCCCCGAGGCCGGGCCCCACCCCG
ACCCCCCGGCCTGCCAGGCACCCCTGGGCCCCCCGGCCCCGCGGGATCCCCCGACGGCAGCGCTGCCTGGGA
GTGGGGAGGCTGCGGCGACGACGTGGACTTCGGGGACGAGAAGTCGAGGCTCT

SEQ. ID. NO:376    AW462000
TACAACCTACGCGGAAGTCTACCTTTGATGCAGCGAGTTTCATTGGAGGAATTGTCCTTGTCTTGGGT
GTGCAGGCTGTAATTTTCTTTCTCTATAAATTCTGCAAATCTAAAGAACGAAACTACCACACTCTGTAAAGAG
ACCCACTAAATTAACAAGGACTGGCGTGTAACTCACTGAAACCAAAATATTATCTTTCAAGATGTCCCACATG
GAAGACGCTATTCTAGGATCTTTAATTTTTCAAAGGATGCATATAGGAGCATCACCCTTGAAGAAGAATCAGT
TCAGTCACTTTGCTCAACGGGCCTATTTAAAGTACGCTGCATGAGTCCTTGTGGCTGTCTTTCATTTTACATGG
CTGCTGCTGTGGGATTGTGTTCTCTCTGCTTGACATGCCAAATGTAACTTTAAGTGATGGAAAACATTGTCCT
GCG

SEQ. ID. NO:377    AW462221
ATTACTTCTGTTTATATGGCAGCAGTTCATTGACTGAACAAGTACACACTGCTCAATATGTTGATGC
TATGTCCAAAAATGTTTCTTTAGCATTGGCAACAGAGGAAGCTATATTCAGGAAGCTGGAGATGAGGATAGA
TGCCCTAGAGGAAGCAATATTGCATATTGGAAATGAATTGCAGGCTTTAAAAGTGAGATTGGGACTGTCCTG
TCATGCCGACTATCGGTGGATTTGTGTAACACCCCTGAAAGTAAATGAGACAGATTATGACTG

SEQ. ID. NO:378      AW462277
GGAAAACCCACTGCACCTCCTCCACCCATCCCTCAGCATGTGGATCTGCATTTCTGCACTCCCGGAAA

GCCAGAGCTTGTCTGCCAGGCCCAAGGAGCTGCTGCTCCCCACCTCCACAGAATTACATTGATTGATCTGTCC

ATTATTTAGATTTTCCAGAGTTTTAGTAACTTTCGGTAGAAGTGCAGGATAAGATTCTTTAAGATTTGTTGATA

ATGTAATGGATTCATGGTTTTTTTTTCCTTTCTGTTTACTTCTGAATTTAATACTTAAAAAAGAGAGAGAAA

AGGGTGTAGTGTCCACATTCTTGTCTCCTTTTCTTACCTCCATGGTTCCTCTAGTGTTCACAGTGGTGCTGATA

CTCTGGGGAGGGGGCGCGTGCCTCCTGCGCGTGATAAAGGCATGTTGGGCACCGTGGGAACCTGTGGCGA

CGGTGCTCCTCTTTCCCACAAACGTTTGAAGTTAAGAATAGAAGCTAAGCTTCCCGGGATTGCC

SEQ. ID. NO:379      AW463060
TCCTTAGATTTATTATGCCTGTAATAAGAAAATAACCTAGCAAATGGTTCACTGGATTTTCTTCTTTG

AATTTTTCAAGGTATCTGCATATAAAATCTTCAGCGGGTAGATGGTGACTTCTGAAGAAGAAAAGGCTTTGAT

AACAGAAACAATTTCTGGGTGGCTTGGAGACAGTGGTATTTGCTGAGTCTTTTGACCTCCTAAACATTGTCTG

TTATTCTTTTCCTGAAAAGAAACTGAATTTGTCTGGTTCACCTGTGTTATTCTACTGAGTATTGATAAACTTTA

AATTTTTAAAAATTGCCTTCAGTTGGGAGAGAAAGGAACTTTATATTTTCTAAGAGATACATTTGATAGTTTCT

TAAAGCAGCACACAAAAAAGGAAAAACCTTTGCAAACTTTTGCACATTCTCCCCACAGTGCCTGTAAATCTC

ATTAGTATTTTCGATTTGCACTTATTTTTGTTGTTAGCATTTGGAAAACGA

SEQ. ID. NO:380      AW463121
AGCTGCTGCAAGACTGTGGTGCCCGGCTGTGGGCGGCGGGACCACGCCTCCAACATCTACAAAGTGG

AGGGCGGCTGCATCACCAAGCTGGAGACCTTCATCCAGGAGCACCTGAGGATCATCGGGGCCGTGGGCCTGG

GCATTGCCTGTGTACAGGTGTTCGGGATGCTCTTCACCTGCTGCCTGTACAAGAGCCTGAAGCTGGAGCACTA

CTG

SEQ. ID. NO:381      AW463263
TGCTGAAGCGGCTCAAGGAGCGCTCGCTGGACACGCTGCTGGAGGCGGTGGAGTCCCGCGGCGGCG

TGCCGGGCGGCTGCGTGCTGGTGCCGCGCGCCGACCTCCGCCTGGGCGNNCAGCCCGCGCCGCCGTAGCTGC

TGCTCGGACGCCTCTTCCGCTGGCCCGACCTGCAGCACGCCGTGGAGCTCAAGCCCCTGTGCGNNTGCCACA

GCTTCGCCGCCGCCGCCGACGGCCCCACAGTGTGCTGCAACCCCTACCACTTCAGCCGGCTCTGCGGGCCAG

AATCACCGCCACCGCCCTACTCTCGGCTGTCTCCTCGCGACGAGTACAAGCCACTGGATCTATCTGATTCCAC

ATTGTCTTACACTGAAACAGAGGCCGCCAACTCCCTCATCACAGCTCCGGGTGAATTCTCAGACGCCAGCATG

TCTCCGGACGCCACCA

SEQ. ID. NO:382      AW463937
TGAGAGACTTCACTTTCATTTTTCACTTTCACTTTTCACTTTCATGTATTGGAGAAGGAAATGGCAAC

CCACTCCAGTATTCTTGCCTGGAGAATCCCAGGGACCCTGGAGCCTGGTGAGCTGCCGTCTATGGGTCACAC

AGAGTCGGACACAACTGAAGCAACTTAGCAGCAGCGGCATTAAGATAAGGCCCTCAGCTGAAACAACCTGA

GCTGGCTGGGAGGTCTGTGTACTCTGTCGCTGATGTTGGAAGAGGATTTTCCTTACTGAACTCTCACTGCACA

TCCACGGTCTGCTGCCAGGCTTCATGACTCTGAATTAAGTCCCTCGTCTGTTGGAGCTCCTC

SEQ. ID. NO:383      AW464391
AAAGAAACAAAGGAAAGAAAAAGAGAAGTTTTTACTTCAGAAGCATGAAATCGAGTCCAAGTTATT

TGGGGATCCAGACGAGTTCCCGCTGGCCCATCTCTTGCAGCCTTTCCGGCAGTATTACCTCCAAGCTGAGCAC

TCCCTGCCAGCACTCATCCAGATAAGGCATGATTGGGATCAGTACCTGGTGCCATCTGATCATCCCAAAGGCA

GCTCCATTCCTCAAGGATGGGTCCTTCCCCCGCTCCCCAGCAACGACATCTGGGCAACCGCTGTTAAGCTGCA

TTAGTAAAAGACGTTGCAGGAGTGTCATCCAGCCAAGGCTCCTTCCAGCTCTGAGTATCAGCGATGCTGCCGT

CTTGTACAGTAGACCAAACTCTGTGTGGCATTGCCCTGCCCAGNGGGTACACTTTCCTTCCGTCCTCTGTCTCA

GCC

-continued

SEQ. ID. NO:384    AW465097
GAGCGAGTGGAAGATGAATGCCAGAGGACTTGGATCTCAGCTAAAGGACAGTATTCCAGTTACTGA
GCTGTCAGCAAGTGGACCTTTTGAAAGTCATGATCTTCTTCGAAAAGGTTTCTCTTGTGTGAAAAATGAACTT
CTGCCCAGTCATCCTCTTGAATTATCAGAAAAAAATTTCCAGCTCAACCAAGACAAGATGAACTTCTCCACAC
TGAGAAACATCCAGGGTCTTTTTGCACCACTAAAACTGCAGATGGAATTCAAGGCAGTGCAGCAGGTTCAGC
GTCTTCCATTTCTTCCAAGCTCAAACCTTTCACTGGATATTTTGAGGGGTAACGATGAGACTATTGGATTTGA
AGATATTCTTAATGACCCATCACAAAGTGAACTAATGGGAGAACCGCATTTGATGGTTGAATATAAACTTGG
CTTACTGTAATGCCATGTGCTGTTCATGGAAGTAGNGGGGCTGCGTCTTNNNTATAGTTGTCTTTTTCCTATAA
TTTGATGTGCACAACATTAAAAGTACTAACACATGAG

SEQ. ID. NO:385    AW465151
GGGAAGTTTATTCTCTTCAGCTATTCTACCATCTGCAGCTCCTTCCTTTTCTACCCCACCCAAGAAAG
GTGCCTGGTGCTCTCTGGGCCTGTCTGTGGACACTCTGGGGTAGTGGAGAAAGTCTTGGCTGGCCTGGCTTCT
AGTTACTCTGTTTCTCTTGAGGGCCACTAGCGTTCCTTCTCTGGGCCTTATAGTGTGCTTGGATTACAAATGAG
GACAAGAGGCTTGCCTGCTTCAGAATATATTCCCCATGTGGCTTCGGGCAAGTCAGCCCTCTTTCTGAACTTT
ACTTTTCTGTCAAGTGGGCATTTGGGAGGAATTAGAGCTCACATTTTTAGGGCTGTATGTGAGGGCAAGTGGG
GCTCTGGCAGTGAGAATGCACTTTAGCAAATGATTGAGTTCCCAGAAGTTGAGAAGAAGGAGTGGTTAATAG
TTAGAGTTTCCTAGTTGCCCTAGTGTTGAATCTTGAAG

SEQ. ID. NO:386    AW465276
CCGGCAAGGCGGCTTTTTTCGCGATGCCAGGGGCAGCCGCCAAGGGCTCGGAGCTGTCCGAGAGGAT
CGAGAGTTTCGTGGAGGCGCTGAAGCGGGGCGGCGGGAGGCGCAGCTCCGAGGACATGGCCCGGGAGACTC
TGGGACTGCTTCGCCGCATCATCACGGACCACCGCTGGAGCAATGGAGGGGAGCTGATGGAACTGATCCGGA
GAGAAGGCCGGAGGATGACGGCCGCGCAACCCTCAGAGACCACAGTGGGCAACATGGTGCGGAGAGTGCTC
AGGATCATCCGGGAGGAGTATGGCAGACTCCATGGACGCAGCGACGAGAGCGATCAGCAGGAGTCTCTGCA
CAAACTCTTGACATCCGGGGGCCTGAGCGAGGATTTCCGTTCCCATTATGCTCAACTCCAGTCCAACATCATT

SEQ. ID. NO:387    AW465299
GCTTTCGGCCGCAGTGCCGATGGAGCTGAATGCTTCCCGGCCTGCCACCCTGAAAATGGATTCTGCG
ACGATGACAGTGTGTGCAGGTGCCAGCCTGGCTGGCAGGGTCCCCTGTGTGACCAGTGCGTGACCTTTCCCG
GCTGTGTGAACGGCCTCTGCGTGGAGCCATGGCAGTGCATCTGCAAGGACGGCTGGGACGGACACCTCTGTG
ACCTAGACATCCGGGCTTGCACCTCGACCCCCTGCGCCAACAACGGCACCTGCCTGAACCTCGATGACGGCC
AGTACGAGTGCTCCTGCGCCCCCGGGTTCTCAGGAAAGGATTGTCAGGAAATGGATGGGCCCTGCGTGGTGA
ATGGCTCGCCCTGCCAGCACGGAGGCAGCTGCGTGGACGATGAGGGCCGGGCCCCCACGCTGTCTGCCTGT
GCCCCCCTGGCTTCTCGGGCAACTTCTGCGAGATCGTGACCAACAGCTGCATCCCCAACCCGTGCGAG

SEQ. ID. NO:388    AW465351
AGAAGACTCAAAAGAGCGTGAAGATCGCACCTGGAGCAGTTGTGTGTAGAGAGCGAAATCAGAG
GTGATGTCACTATAGGACCCAGGACAGTGATCCACCCTAAAGCACGAATCATCGCAGAAGCCGGTCCAATAG
TGATCGGCGAAGGCAACCTAATAGAGGAGCAGGCGCTCATCATAAATGCTCACCCTGATAATATCACTCCTG
ATGCAGAAGATCCAGAACCCAAACCTATGATCATTGGCACCAATAATGTGTTTGAAGTTGGCTGTTACTGCCA
AGCCATGAAAATAGGAGATAATAATNNNATCGAGTCAAAAGCGTATGTGGGCAGAAATGTGATACTGA

SEQ. ID. NO:389    AW465482
GCCACAGACCAAACCTGCACCATAAGCCCTGACTCCTTGCCCATACCACCCACCCATGGCCTCCGAA
CCAGGCCCAGCGTCTTGCTGACATGGTAACACAGTGGAGGACCAGCAGATGAATGGAAACCTTGAAGCAGA
GGAGCGGCAGGACCAGAGGCCAGAGCAGGAGCTGACCTGGAGCTGGGGCTACCGGCCTAGAAGCGCCCTGG
ACAGGGTCAAGGCCATGGCCCCCCCACCGCCACTGGCCCCCAGCACCCCACTCCTGCATGGCGAGTTTGGCT

-continued

CCTACCCAGACCGCGGCCCACGCTTCGCCCTCACTCTCACACCACAAGCCCTGCACATACAGCGGTTGCGCCC

AAAGCCCGAGGCCCGGCCCCGGGGTGGCCTGGTCCTGCTGACCGAGGTCTCAGGCTGCTGCACCCTGCGGAG

CCGAAGCCCCCTGGACTCAGCAGCCTACTTCTGCGTCTACACCTACCCC

SEQ. ID. NO:390  AW465514
GAGCGGGTGAGAGGGCAGCGATATGGCTCCTCCGGCTCCTGGTCCGGCTTCTGGCGGCTCCGGGGAG

GTGGACGAGCTGTTCGACGTGAAGAACGCCTTCTACATTGGCAGCTACCAGCAGTGCATCAACGAGGCGCAG

CGGGTGAAGCCATCCAGCCCGGAGAGAGATGTGGAGCGGGATGTCTTCCTGTACAGAGCATACCTGGCCCAG

AGGAAGTACGGCGTGGTGCTGGACGAGATCAAGCCCTCCTCCGCCCCGGAGCTGCAGGCCGTGCGCATGTTT

GCTGAGTACCTGGCCAGCGACAGCCGGCGGGATGCGATCGTGGCCGAGCTGGACCGAGAGATGAGCCGGAG

CGTGGATGTGACCAACACCACCTTCCTGCTCATGGCTGCCTCCATCTATTTCTACGACCAGAACCCAGATGCA

GCCCTGCGCACCCTTCACCAGGGGGACAGCCTGGAGTGCATGGCCATGACAGTGCAG

SEQ. ID. NO:391  AW465560
AGGGGGGCGGCCTTCCATCCTGGGGGCAGCCCCTTGGCGTCCCGGCGTCCTGACAGATCCGTTCCAC

CCCCAGATGGATGGTCTGTTGAGGTCACTGTCGAGCTGTCTCAGAATTCAGGTTCCCTCGGTCTGTCCAAGTA

CTGGCCGCGTGGAGCCGATGGCCGGGCCCTCCCGGTGGAAGGATGGGCCGGCAGCCCTGTCTTCCGACAGCC

CCCTCCCTCCAAAGAAAAATGTCAGTCTTTCTGCTCCGTGTGGTACTATGCAGCTGCTCTTGCAGAAATCACG

GATTTCCTGTGGAATAAAGGTGGTCCCCAAAGTAGGCAGAAAGGAAATATATATATATTTTAGTAATTTATAT

AGATGTCAGCAATTAGGCAGGTCAAGCTGTAGTTTCATTTCCACTGTTAAAATAAAGCTTACATAGTTTCTTT

AAAAGCCTGTGTTGTCCTTTAACAGAGGTTTTTTAAACACTAGGGTGTCGAATGTGAAACACCAGTTTTCATT

GTTCACCTCGAAACCAAAAGTTGTGTGTTGCCAAAGCCAAACCCAGGTTCACGGA

SEQ. ID. NO:392  AW465567
AGGCGTGCGTGGTGACTCTGGAGAACTCGGAACAGGCTCACATCTTCTGGTGGAAAGCTGCTAGGAA

CACGATGAGTCTGCAGTGGACTGCAGTCGCCACCTTCCTCTATGCGGAGGTCTTCGCTGTGCTGCTGCTCTGC

ATTCCCTTCATTTCTCCCAAAAGATGGCAGAAGATTTTCAAGTCCCGCCTTGTGGAGTTGGTAGTGACATATG

GCAACACCTTCTTTGTGGTTCTCATTGTCATCCTTGTGCTACTGGTCATTGATGCTGTTCGTGAGATTCGAAG

TATGATGATGTGACAGAGAAGGTGAACCTCCAGAACAACCCTGGGGCTGTGGAGCACTTCCACATGAAGCTT

TTCCGTGCCCAGAGGAACCTCTACATTGCTGGCTTTTCCTTGCTGCTGTCCTTTCTGCTTANNCGCCTGGTGAC

TCTCATCTCCCAGCAGGCCACGCTGTTGGCCTCCAACGAAGCCTTTAAAAAGCAGGCAGAGAGCGCCAGTGA

TGCA

SEQ. ID. NO:393  AW465831
GTCGGCTGTCTTCCAGTGCCTGGGCCACGGCGGCGGCCCTGGGAGCAGNGGTGGAGCATCCCCATTG

CGTCAAAGATGAAAGGCTGGGGTTGGCTGGCCCTGCTTCTGGGAGCCCTCTTGGGAACTACCTGGGCCCGGA

GGAGCCAGGATCTACACTGTGGAGCTTGCAGGGCTCTGGTGGATGAACTTGAGTGGGAAATTGCCCAGGTGG

ATCCCAAGAAGACCATTCAGATGGGCTCTTTCCGAATCAATCCAGATGGCAGCCAGTCAGTGGTGGAGGTGC

CTTATGCTCGCTCAGAGGCCCACCTCACAGAGCTGCTAGAGGAAGTATGCGACCGGATGAAGGAGTATGGGG

AACAGATCGACCCTTCCACGCACCGCAAGAACTATGTACGTGTCGTGGGCCGATGGAGAATCCAGTGAAC

TGGACCTACAGGGCATTCGAATTGATTCAGACATCAGTGGCACCCTCAAGTTCGCGTGTGAG

-continued

SEQ. ID. NO:394    AW466194
GGATCGGAGGCGACTGTGTGGCCAAGTGGGCGCGGCCGGTACGAGCTGAGGGGCAGGGTGCCCCGG

GCAGGGGGGAGGTGACCCGGGACAGTGCAGGCGGGAGAATAGACCCGCGGACCTCCGAGGGAAATCTGAGC

GTTCAGACCGTGAGCGGATGTAAAATTGACCAAGTCTGGGGGCCAGAAACTGATCAGCGCTGCGGGGCTTAA

CTACGCGGCCGGCGGGAGCGTTCTCCGGTGGCGCGGGGGAGCAGGTGAACAGGTCCTCACTCCCAGCTCCAC

GCCCTCACGCGCTCTCGCCAGGAGCCAGGTTCCCGCCGGCAGCCATGGGCCCCGGCTCCAGCCGTGCCGCCG

GCGTCCTACGCCCGTTGCTCGGCATGCTCGCCTTGATGGTGGCCGCAAGCAACCGCGCCGCCTCCGCCTTCAA

CCTGGACACCCGATTCCT

SEQ. ID. NO:395    BF041753
GCGCCCTGCACTCTGTCCCTCACTCGCCGCCGACGGCCTGTCTCGTCACCCGCACGTCGCGCCGCTGC

CCCGCNGAAATGCTTCGATTACCCGCAGTCCTTCGTCAAATGAGGCCAGTGTCCAGGGCACTGGCTCCTCATC

TCACTCGGGCTTATGCCAAAGATGTAAAATTCGGTGCAGATGCTCGAGCCTTAATGCTTCAAGGTGTNGACCT

TTTAGCCGATGCTGTAGCCGTTACTATGGGGCCAAAGGGAAGGACAGTGATTATTGAACAGAGTTGGGGAAG

TCCCAAAGTGACAAAAGATGGTGTGACTGTTGCAAAGTCTATTGATTTAAAAGATAAATATAAAAATATTGG

CGCTAAACTTGTTCAAGATGTTGCCAATAACACAAATGAAGAGGCGGGGGATGGCACCACTACTGCTACTGT

ACTGGCACGCTCTATTGCCAAGGAAGGCTTCGAGAAG

SEQ. ID. NO:396    BF042071
AGTTGGATGCCTACATGGCTCAGACAGATCCCGAAACCAATGACTGAAGCCTGCCCACCCTCCTGGA

AGACTCTTGTTCAAGTCACACATGTGTAAATAACTTAGGATAACAGATGGGAAGAAAGCTGACTGATACTGA

AAGGACCTATCATAATAGGCTCTGGACTGACTTGCCACCAGTTTGTGCATCTAGTGTGTTCCTTTTACTTTTTG

ATACTATGTTGTATGAAACCCTTTTTTTCCCCTCTGACTGGGGTTTGGTTTTGTTTTGTTATTTGGGGGGGAGGG

SEQ. ID. NO:397    BF043039
CGCGAGCGGCTCCAGGGTGCGAACCGCCGGAGCGGTTCCCAGAAGATGGGCCTCGAAGCGCAGGCC

ATCGGCAGGACCTTCCAGGGCTCGGGCTCCGAGGCCACGTGGCTGGGCGAGGCTATCCCGTGCGTGGCTGAC

ATACTGGGCGAGACTTACAAAGACGACATCGGGCGGCACCTGGAGACGCTCATCAGAAGCTACCCCGACATC

AGGCATTGCGGCATCGGCATCGCGGCCCCTGCTGCCTCCTTCGGTGCACTAGGTTTCCGGAACCTCTGCCTG

GGCCTCAGAGGCCGTTCCCATCAGGCTTGCTTCTTCCCGTCTCCGCCGGTCTTTGCACCCTTCAAGACCCAGG

CACCCCCCCAGGAACGCTGGGTGCCCTAATGCTTCCAGTCCGAGCCCCGGGGTCCCCCTCGCCCTAGGGTCCA

GGGTGTCACTGGAGCTGTCGCGTCTACAGCAGGGGCCCGTGTGTCTCTGCAGGCGGGACCACGTGCCTGCCA

TCCTGGCGCTGCTCCGACTGGGCCGCCGTCGGAACCAGCACTTCNTGCGCCACGCCCAGGCGCTGCTGAGGG

CTG

SEQ. ID. NO:398    BF043954
GTTGGAGCGGCCGCATTTGTTTTTTTTTTTTTTTTTCCTTTTTTACAAAAACATGCATACATACACA

GGGTATAGTCTTGGGGAAGACACACGCACTTGCACGCACACACACTCCCTCTCTTTCACTCGCACACGCGTGC

ATGCACGCGCGCACACACACATACACACAATACTTTCCTTCTTGGCCCCAGGCCTCAACCCCAGAAGCCTCG

AAGACTGTGCCAGGGTAGCCTCCCCCTCCCCCATGTCTTCCATCCACTCTCCCACCCACTCTCCCCTCAGCCA

AGCTAGTCCTATGTAGGGCAAGAGTCAGCTGGGGTCCAGGAGACCCGAAAAAGAGAGAAGGCTCATGGAGG

GGGGCATGGTGACTGAGGGAGCCCTGGGGGGGTCATGCTGTGCTTCTGAGGAGAGATGAAGGGTTTGGCACC

ATTGGATCAGGAAGCACGGAACTCCAAGAGCACCTGTCTGCTCCACCAGGGCACTG

-continued

SEQ. ID. NO:399    BF044362
TGCGGAGACTGCTGGGGCACATCGTTCCCCTGTCCTCTCGGTTCCCTGCGGCCGAAAGGCCTGCTAG

GATTCGGGGATCTGGCCTAGGCTTCCGCGGCGCCCCGCGGGGCGGAATGGCCGCGGAAGAAGAGGACGAG

GTGGAATGGGTGGTGGAGAGCATCGCGGGGTTCCTGCGGGGCCCGGACTGGTCCATCCCCATCTTGGACTT

SEQ. ID. NO:400    BF044484
GCTGGCCTGATGCAGTCAATCAGCCTCACTTTCCGCCTGTGTTGCTGAAGCCTGGTGAGGAGTATGAC

CACACCACTTGGTTCAAGTTTTCTGTGGCCTAAGGAAATGTAAAGATATGTCCTGCTCCAAGGTCAGGCTGGG

AGCCCCTTTAACAGCCTGACTCTCCTATAAAGAGATGAGTTGAAGATTTNNNGGCTTTCAAAGTGATCCTGTG

ATTTAAAATCATACAAATGGTAGCAGTGAGGGTAGTCAGGTCTGAATATTGATTTCCTTCCCAAAGACTGGCT

CCAGGCCAGGTCTAATGACCAGCTCTCCTCTCTGTGAAGTGAAGGGGACTCAACCACCAATGTCACCCATCATC

SEQ. ID. NO:401    BF044941
GACACCCTACTATCCAGTGGGAATGGGAAATGGACACCTTGTAGTTTGAAACAGAACCGGCCCAGAT

CAAGTACTGTGATGTACATATGTCATCCTGAATCTAAGCATGAAATTCTTTCAGTAGCTGAAGTTACAACTTG

TGAATATGAAGTTGTCATTTTGACACCACTCTTGTGCAATCATCCTAAATATAGATTCAGAGCATCTCCCGTG

AATGACATATTTTGCCAGTCACTACCAGGATCGCCGTTTAAACCCCTCACCCTGAGACAGTTGGAACAACAG

GAAGAAATACTAAGGGTGCCTTTTAGGAGAAACAAAGAGGAAGATTTGCAATCAACTAAGGAAGAGAGATT

TCCAGCAATCCACAAACCCATTGCTGTTGGTTCTCAGCCAATGCTCACTGTTGGAACAACCCACATATCCAAA

TTGACAGATGACC

SEQ. ID. NO:402    BF440189
GCAATATGGCAATTTTACTGGGGGTTTAACCCTACCTAGGATGATTGCTTGCTGGGGCTTNGCAACA

GGGTCCAGTTCACACTTAGCACTAATTAAATACTTTATTGAATAAATATAATACCAAACAAAATGCATTCAAA

TGCTAAAAAAAAAATCAATTTTAAAGGCCTTTCTATTCAGGCTAATGACAAACACAATAAAGGCAGATATGC

TAGTTTAACATAATTGGCTGATTTTATACAGCACTTATATCTTTTAGTCCACAAGTATATTATTAAATGATAGA

GAACATCTAATACAACCATTTCTACAGAACTAGGAAATAAATTTCTAAGAAAGAAAGATTTTACAGACCCCA

TCTTTTATACCCACCCCAACAGTCTAACNNNAAAGAGGATAAAGCCAATGCCTTTCCTCACAAGAGCTCACG

ACTAATGTCGCTTTGCTATCAAAATCTGTATTTCTGATCC

SEQ. ID. NO:403    BF440274
TTTTTTTTTTTTTTTACTGTTTAAAACATTTATATTTATATATATAAAAAAATTAAATATATATAATA

TATAGTGTGTTTGAGACTAAAAATATAGTACATAATATTTAAAAAAAAGGAAAATGAAAAAAGGCAGAATA

GGAAAAGTGTGAGGGACACAGATACACATTGCTAAAAATCTACGATGGTCTGTTCTAACAAAAATAATATTT

TTTTCCTCTTAATTATCATCATGGACCCATTTATTATTGGGGCTTGAGTGGAGAAAATTTAACTGGAGCCAGA

AATGGTGGTTGTAATCCCAAGAAGAGTGGGGTTAGAAAACGTGACCACAGGGAGCCCTGGACCTCATTCTGG

TGTGACTGGAGGCAGCCAAATCTCCTGGGTCACTATTGCTAGCAAGATTGTGTC

SEQ. ID. NO:404    BF440607
ACGACGCCAACAACGCCAAGGCCGTGGTGAAGACCTTCCACGAGACGCTTAACTGCTGTGGTTCCAA

CACGCTGATGAGACTGACCACCTCTGTGCTCAAGAACAGCCTGTGTCCCTCCAGCGGCAACGTCNTCACTAAT

TTGTTCAAGGAGGACTGCCATGGGAAGATCGACGAGCTCTTCTCGGGAAAACTGTNCCTCATTGGCATCGCG

-continued

```
GCCATCGTGGTCGCTGTGATCATGATCTTCGAGATGATCCTGANCATGGTGCTCTGCTGTGGCATTCGGAACA

NCTCGGTGTTCTGAAGCTGCCGCCGCTGAAGGCTCCAGGAANGGCCTCAGGGAACCCCGCAGCCCCCCCGAA

TTATCCAAANANTTCCAAAANGGGCCCCCCCACNTTTTTTTTNACCCCTNTTTCNNTGNNACNTTNNNNCTTT

TTTTTAAAGTTTTTTNTTTCNAAACCCCNTTTANTTCCTTTGGGGGATTCCTTGGGGGTCC
```

SEQ. ID. NO:405     BM362313
```
GCACGAGGGTTTGATAGCTCCTGGAGTTCGTGTATCAGGAGATGATGTTATTATAGGCAAAACAGTC

ACCTTGCCTGAAAATGAAGATGAATTGGAGGGCACTAATAGACGCTATACAAAGAGAGACTGTAGCACTTTT

CTCAGGACTAGTGAGACGGGCATTGTGGATCAGGTTATGGTAACTCTCAACCAAGAAGGATATAAATTTTGT

AAAATAAGGGTACGCTCTGTTAGAATTCCACAGATTGGAGACAAATTTGCTAGTCGACATGGTCAAAAGGGT

ACTTGTGGTATTCAGTATAGACAGGAGGATATGCCTTTCACCTGTGAAGGTATCACCCCTGATATCATCATAA

ATCCCCATGGCATCCCCTCTCGTATGACCATTGGTCACTTGATTGAATGTCTTCAAGGGAAGGTATCAGCTAA

CAAGGGTGAAATTGGTGATGCCACTCCATTCAATGATGCTGTTAATGTGCAGAAGNTTTCTAATCTTTTATCT

GATTATGGCTACCATCTC
```

SEQ. ID. NO:406     BM364049
```
GCACGAGCGGCGACGCGGAGCTACCGGATCGGTTCGAGATGGCAGAGGTGGAGGAGACCCTGAAGC

GACTCCAGAGCCAGAAGGGCGTGCAGGGAATCATCGTGGTAAACACAGAAGGNNTTCCCATCAAGAGCACC

ATGGACAATCCCACCACCACACAGTACGCCAACCTCATGGACAACTTCATCTTGAAGGCCCGGAGCACCGTG

CGCGAAATTGACCCCCAGAATGACCTCACTTTCCTTCGAATTCGCTCCAAGAAAAATGAAATTATGGTTGCAC

CAGATAAAGACTATTTCCTGATTGTGATTCAGAATCCAACTGAATAAGCTGCTTTCTTGGCTCCCTGCGTCATT

CCTTAATTTAATGCCCCTCAAGAATAATAGCGTTAATCATGTCCATTGACGGGCACGTGGAAGGCACGTTGGA

GCCCTCCCAGGCTGGTCCGTGACCCG
```

SEQ. ID. NO:407     BM366788
```
GCACGAGGAGAAGCAGATGAATATGAGTCCACCTCCGGGCAATGCTGGCCCAGTGATCATGTCCATT

GAGGAGAAGATGGAGGCTGATGCCCGTTCCATCTATGTTGGCAATGTGGACTATGGTGCAACAGCAGAAGAG

CTAGAAGCACACTTTCATGGCTGTGGTTCAGTCAACCGCGTAACTATACTCTGTGACAAATTTAGTGGCCATC

CGAAAGGGTTTGCGTATATAGAGTTCTCAGACAAAGAGTCAGTGAGGACTTCCCTGGCCTTAGATGAATCCTT

ATTTAGAGGAAGACAGATCAAGGTGATCCCTAAACGAACCAACAGACCAGGCATCAGCACAACAGAGCGAG

GCTTCCCACGAGCCCGATACCGTGCCCGAACCACCAACTACAACAGTTCCCGCTCTCGATTCTAGAGTGGTTT

TAACAGCAGGCCCCGGGGTCGCGTCTACAGGGGCCGGGCTAGAGCGACATCATGGTATTCCCCTTACTAAAA

AAAAGTGTGTATTANGAGGAGAGAGAGGAAAAAAAGAGGAAAGAA
```

SEQ. ID. NO:408     BP22000602103
```
TTTTAAATTGTAATTTTTTTATTGGAAAACAAATATACAACTTGGAATGGATTTGAGGCAAATTGTGC

CATAAGCAGATTTTCTTTAAGTGGCTAAAACAAAGTTTAAAAAGCAAGTTAACAATAAAAGAAAATGTTTCTG

GTATAGGACCAGCAGTACAAAAAAATAGTGTACGAGTACCTGGATAAAACACCCGTTTTGCAATAGTGCAAC

TTTTAAGTACATATTGTTGACTGTCGGTAGTCCACGCAgAGTTACAACTCCACACTTCAACAACAACATGCTGA

CAGTTCCTAAAGAAAACTACTCAAAAAAAAAAAAAAAGGCATAACCCAgATGTTCCCTCATTTGACCAACTC

CATCTAAGTTTAAATGTGCAgAAGGGCTTAAATATATCCAGAGTAAGCCACATGCAACATGTTACTTGATCAA

TTTTCTAAAATAAGGNTTCAGGACAATGAC
```

TABLE I

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 1 | BM362588 | 0.5597 | 7.33E-08 | 0.00058 | upregulated during skeletal muscle growth 5 | USMG5 | BQ276559 | Hs. 171625 |
| 2 | BF440243 | 1.7889 | 9.57E-06 | 0.01434 | Sjogren syndrome antigen B (autoantigen La) | SSB | CA777287 | Hs. 309316 |
| 3 | BM361928 | 0.7393 | 7.73E-06 | 0.01434 | Homo sapiens mRNA; | | BM684505 | Hs. 336425 |
| 4 | BM364471 | 0.6569 | 1.27E-05 | 0.01434 | ribosomal protein L22 | RPL22 | BM046402 | Hs. 326249 |
| 5 | BM365159 | 0.5563 | 4.33E-05 | 0.01434 | pre-mRNA branch site protein p14 | P14 | CD177296 | Hs. 177861 |
| 6 | BM365446 | 0.6692 | 1.15E-05 | 0.01434 | SON DNA binding protein | SON | BU845655 | Hs. 430541 |
| 7 | BM365732 | 0.6456 | 7.14E-06 | 0.01434 | polymerase (RNA) II (DNA directed) polypeptide B, 140 kDa | POLR2B | AA256916 | Hs. 149353 |
| 8 | BF046007 | 0.6706 | 1.962E-05 | 0.01941 | CDC37 cell division cycle 37 homolog (S. cerevisiae) | CDC37 | BM695397 | Hs. 160958 |
| 9 | BF044446 | 0.6752 | 2.36E-05 | 0.02079 | similar to RIKEN cDNA 1700029H17 | na | AI845310 | Mm. 300203 |
| 10 | BF040826 | 0.7727 | 3.61E-05 | 0.02854 | neuropilin 2 | NRP2 | AF280545 | Hs. 368746 |
| 11 | BF039212 | 0.6584 | 4.98E-05 | 0.03585 | asparaginyl-tRNA synthetase | NARS | AJ000334 | Hs. 427212 |
| 12 | AW461477 | 0.7712 | 0.0001041 | 0.04477 | inositol(myo)-1(or 4)-monophosphatase 2 | IMPA2 | AW194846 | Hs. 5753 |
| 13 | AW464361 | 2.3429 | 0.0001041 | 0.04477 | | | | TC186760 |
| 14 | AW466044 | 0.7038 | 9.21E-05 | 0.04477 | Homo sapiens cDNA FLJ11392 fis, clone HEMBA1000575. | | AK021454 | Hs. 435773 |
| 15 | BF039490 | 1.4409 | 0.0001139 | 0.04477 | FK506 binding protein 12-rapamycin associated protein 1 | FRAP1 | BQ440695 | Hs. 338207 |
| 16 | BF042320 | 0.6329 | 0.0001166 | 0.04477 | hypothetical protein FLJ22635 | FLJ22635 | AW024744 | Hs. 353181 |
| 17 | BF043074 | 0.6854 | 0.0001157 | 0.04477 | GLI-Kruppel family member GLI4 | GLI4 | BM931804 | Hs. 404905 |
| 18 | BF044776 | 0.7804 | 9.888E-05 | 0.04477 | ubiquitin-conjugating enzyme E2A (RAD6 homolog) | UBE2A | BU158774 | Hs. 379466 |
| 19 | BF046287 | 1.9876 | 9.685E-05 | 0.04477 | B. taurus mRNA for agouti protein | | BF046287 | Bt. 3352 |
| 20 | BM362351 | 0.6658 | 0.0001188 | 0.04477 | SWI/SNF related, matrix associated, actin dependent regulator of chromatin, subfamily d, member 3 | SMARCD3 | AA844170 | Hs. 444445 |
| 21 | BM366715 | 0.6512 | 8.58E-05 | 0.04477 | translocase of outer mitochondrial membrane 7 homolog (yeast) | TOMM7 | CD385108 | Hs. 112318 |
| 22 | BM366099 | 2.5611 | 0.0001297 | 0.04666 | histone 1, H4i | HIST1H4I | BI837393 | Hs. 248172 |
| 23 | AW464526 | 0.7209 | 0.0001505 | 0.04991 | hypothetical protein similar to RNA-binding protein lark | MGC10871 | AL050172 | Hs. 49994 |
| 24 | BF046202 | 0.3598 | 0.0001513 | 0.04991 | polo-like kinase 2 (Drosophila) | PLK2 | AW996674 | Hs. 398157 |
| 25 | AW466043 | 0.7904 | 0.0001663 | 0.05189 | eukaryotic translation initiation factor 4 gamma, 3 | EIF4G3 | CD513621 | Hs. 402697 |
| 26 | BF040403 | 1.6932 | 0.0001705 | 0.05189 | | | NT_035014.3 | |
| 27 | BF039168 | 0.6360 | 0.0002049 | 0.06005 | low molecular mass ubiquinone-binding protein (9.5 kD) | QP-C | BM548444 | Hs. 146602 |
| 28 | BM362530 | 0.6724 | 0.0002202 | 0.06223 | ribosomal protein L30 | RPL30 | CD173453 | Hs. 400295 |
| 29 | AW461980 | 0.7649 | 0.0002409 | 0.06356 | likely ortholog of mouse hypoxia induced gene 1 | HIG1 | BG700494 | Hs. 7917 |
| 30 | BM364411 | 0.7130 | 0.0002389 | 0.06356 | DNA methyltransferase 1 associated protein 1 | DMAP1 | BI907542 | Hs. 8008 |
| 31 | BF039456 | 2.1686 | 0.0002711 | 0.06684 | ribosomal protein S24 | RPS24 | AA622289 | Hs. 356794 |
| 32 | BF042632 | 1.9846 | 0.0002732 | 0.06684 | Williams Beuren syndrome chromosome region 14 | WBSCR14 | BC012925 | Hs. 285681 |
| 33 | BF044457 | 0.7183 | 0.0002787 | 0.06684 | Homo sapiens cDNA clone IMAGE: 3927795, partial cds | | CD176013 | Hs. 292457 |
| 34 | BF040573 | 2.3798 | 0.0003118 | 0.07238 | ankyrin repeat and SOCS box-containing 9 | ASB9 | BE271724 | Hs. 19404 |
| 35 | BM364731 | 0.6730 | 0.0003201 | 0.07238 | RAS p21 protein activator (GTPase activating protein) 1 | RASA1 | BC033015 | Hs. 758 |
| 36 | BF042198 | 3.4732 | 0.0003324 | 0.07309 | hypothetical protein MGC52057 | MGC52057 | AL831852 | Hs. 21929 |
| 37 | BF045424 | 0.7528 | 0.0003908 | 0.08359 | mitochondrial ribosomal protein L35 | MRPL35 | AL524400 | Hs. 433439 |
| 38 | BF039771 | 0.7461 | 0.0004176 | 0.08370 | NADH dehydrogenase (ubiquinone) 1, alpha/beta subcomplex, 1, 8 kDa | NDUFAB1 | BQ435266 | Hs. 5556 |
| 39 | BF041569 | 0.6950 | 0.000423 | 0.08370 | hypothetical protein LOC285148 | LOC285148 | BX370120 | Hs. 509314 |
| 40 | BM366529 | 0.5912 | 0.0004218 | 0.08370 | ATP-binding cassette, sub-family C (CFTR/MRP), member 3 | ABCC3 | BU177942 | Hs. 90786 |
| 41 | AW465571 | 0.4533 | 0.0004821 | 0.08476 | PRO1073 protein | PRO1073 | BF883638 | Hs. 187199 |
| 42 | BF043043 | 0.6526 | 0.0004937 | 0.08476 | RAB9A, member RAS oncogene family | RAB9A | U44103 | Hs. 444327 |
| 43 | BF043765 | 1.5783 | 0.0004822 | 0.08476 | general transcription factor IIH, polypeptide 2, 44 kDa | GTF2H2 | AF078847 | Hs. 422901 |
| 44 | BF044823 | 0.7903 | 0.000496 | 0.08476 | nuclear receptor coactivator 1 | NCOA1 | NM_147233 | Hs. 386092 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 45 | BF044893 | 0.6222 | 0.0005033 | 0.08476 | serine (or cysteine) proteinase inhibitor, clade E (nexin, plasminogen activator inhibitor type 1), member 1 | SERPINE1 | CA489491 | Hs. 414795 |
| 46 | BF046610 | 1.5839 | 0.0004799 | 0.08476 | v-ski sarcoma viral oncogene homolog (avian) | SK1 | X15218 | Hs. 2969 |
| 47 | BF440261 | 1.6370 | 0.0004687 | 0.08476 | isocitrate dehydrogenase 3 (NAD+) beta | IDH3B | BU680835 | Hs. 436405 |
| 48 | BM362515 | 0.6810 | 0.0005569 | 0.09183 | COX17 homolog, cytochrome c oxidase assembly protein (yeast) | COX17 | BG539943 | Hs. 16297 |
| 49 | AW465165 | 0.7421 | 0.0005733 | 0.09260 | Homo sapiens cDNA FLJ31058 fis, clone HSYRA2000828. | | BQ575646 | Hs. 102495 |
| 50 | AW464987 | 3.0054 | 0.000628 | 0.09941 | | | | TC213565 |
| 51 | AW462906 | 0.7563 | 0.0006993 | 0.10246 | Transcribed sequences | | AW462906 | Bt. 9710 |
| 52 | AW463449 | 1.3041 | 0.0006914 | 0.10246 | polyamine-modulated factor 1 | PMF1 | BM826376 | Hs. 408848 |
| 53 | BF040406 | 1.8294 | 0.000712 | 0.10246 | mitogen-activated protein kinase-activated protein kinase 2 | MAPKAPK2 | AA865261 | Hs. 75074 |
| 54 | BF042130 | 0.6805 | 0.0006681 | 0.10246 | mitochondrial ribosomal protein S18A | Mrps18a | NT_029419.10 | Mm. 287443 |
| 55 | BF043536 | 0.6957 | 0.0006753 | 0.10246 | oxysterol binding protein 2 | OSBP2 | BC004340 | Hs. 7740 |
| 56 | AW464569 | 1.6029 | 0.000759 | 0.10728 | | | | TC214576 |
| 57 | BF040351 | 2.3854 | 0.0007892 | 0.10958 | DKFZP434D146 protein | DKFZP434D146 | AK022655 | Hs. 240845 |
| 58 | BF440195 | 1.6557 | 0.000835 | 0.11255 | no hits | | | |
| 59 | BM362654 | 0.7062 | 0.000839 | 0.11255 | cerebellar degeneration-related protein 1, 34 kDa | CDR1 | BQ222662 | Hs. 370504 |
| 60 | AW462632 | 0.5710 | 0.0008762 | 0.11413 | Homo sapiens cDNA clone IMAGE: 6272440, partial cds | | CA437330 | Hs. 448680 |
| 61 | BF040216 | 1.7157 | 0.0008796 | 0.11413 | | | NT_016297.15 | |
| 62 | BF045874 | 0.6316 | 0.0009077 | 0.11588 | protein BAP28 | FLJ10359 | AW517093 | Hs. 257300 |
| 63 | AW461973 | 0.6999 | 0.0010677 | 0.11658 | Transcribed sequences | | BM105795 | Bt. 3126 |
| 64 | AW461973 | 0.5475 | 0.0006191 | 0.11658 | Transcribed sequences | | BM105795 | Bt. 3126 |
| 65 | AW461973 | 0.8947 | 0.3710353 | 0.11658 | Transcribed sequences | | BM105795 | Bt. 3126 |
| 66 | AW462202 | 0.6132 | 0.0010445 | 0.11658 | UDP-N-acetyl-alpha-D-galactosamine: polypeptide N-acetylgalactosaminyltransferase 12 (GalNAc-T12) | GALNT12 | AJ132365 | Hs. 47099 |
| 67 | AW465524 | 0.7456 | 0.0009858 | 0.11658 | Transcribed sequences | | AW465524 | Bt. 15671 |
| 68 | AW465958 | 0.6437 | 0.001068 | 0.11658 | Homo sapiens cDNA clone IMAGE: 30374935, partial cds | | BM906968 | Hs. 381096 |
| 69 | BF041193 | 0.7937 | 0.0011008 | 0.11658 | translocase of outer mitochondrial membrane 22 homolog (yeast) | TOMM22 | BM554645 | Hs. 285005 |
| 70 | BF042630 | 1.5578 | 0.0010138 | 0.11658 | kelch-like 3 (Drosophila) | KLHL3 | BQ446837 | Hs. 434434 |
| 71 | BF043059 | 2.0344 | 0.0010778 | 0.11658 | | | | TC216947 |
| 72 | BF043236 | 3.0393 | 0.0010698 | 0.11658 | | | | BF043236 |
| 73 | BF043635 | 0.3645 | 0.0010793 | 0.11658 | poliovirus receptor | PVR | BQ678871 | Hs. 171844 |
| 74 | BF043736 | 0.8297 | 0.0010712 | 0.11658 | Transcribed sequences | | BF046146 | Bt. 9988 |
| 75 | BF044851 | 0.7832 | 0.0009527 | 0.11658 | hypothetical protein MGC15677 | MGC15677 | NM_032878 | Hs. 71941 |
| 76 | BF045170 | 0.3654 | 0.001114 | 0.11658 | colony stimulating factor 1 (macrophage) | CSF1 | BF043503 | Bt. 366 |
| 77 | BF045305 | 2.0218 | 0.0009861 | 0.11658 | Mus musculus 2 days neonate thymus thymic cells cDNA, RIKEN full-length enriched library, clone: C920020J23 product: unclassifiable, full insert sequence | | BB667957 | Mm. 260066 |
| 78 | BM362735 | 0.6969 | 0.0011274 | 0.11658 | ribosomal protein S12 | RPS12 | CD390104 | Hs. 380956 |
| 79 | BM366522 | 0.6615 | 0.0011341 | 0.11658 | malate dehydrogenase 2, NAD (mitochondrial) | MDH2 | BX460531 | Hs. 405860 |
| 80 | AW461513 | 0.7629 | 0.0011951 | 0.11715 | Transcribed sequences | | AW461513 | Bt. 12230 |
| 81 | AW462120 | 1.9638 | 0.0012245 | 0.11715 | Homo sapiens, Similar to DNA segment on chromosome X and Y (unique) 155 expressed sequence, clone IMAGE: 4430810, mRNA | | BM684898 | Hs. 21595 |
| 82 | AW463593 | 2.5733 | 0.0011645 | 0.11715 | prolactin | PRL | BG202290 | Hs. 1905 |
| 83 | AW465056 | 0.6840 | 0.0012285 | 0.11715 | keratinocyte associated protein 2 | KRTCAP2 | BQ774375 | Hs. 374854 |
| 84 | BF046404 | 1.5250 | 0.0011851 | 0.11715 | phosphodiesterase 4D, cAMP-specific (phosphodiesterase E3 dunce homolog, Drosophila) | PDE4D | AA481397 | Hs. 28482 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 85 | BM366368 | 2.4188 | 0.0012245 | 0.11715 | integrin, alpha D | ITGAD | U37028 | Hs. 381264 |
| 86 | AW462010 | 0.8053 | 0.0012627 | 0.11758 | ankyrin repeat, family A (RFXANK-like), 2 | ANKRA2 | AA442702 | Hs. 239154 |
| 87 | AW465551 | 1.3113 | 0.0012588 | 0.11758 | mutL homolog 1, colon cancer, nonpolyposis type 2 (*E. coli*) | MLH1 | U07343 | Hs. 433618 |
| 88 | AW465274 | 0.6958 | 0.0012818 | 0.11797 | AP2 associated kinase 1 | AAK1 | NM_014911 | Hs. 135941 |
| 89 | AW462049 | 0.8134 | 0.0013687 | 0.12310 | C-terminal binding protein 1 | CTBP1 | BC011655 | Hs. 196083 |
| 90 | AW463986 | 0.7326 | 0.0013684 | 0.12310 | *Homo sapiens* transducer of erbB-2 2 related gene, mRNA (cDNA clone IMAGE: 5785687), partial cds | | AW297010 | Hs. 161441 |
| 91 | AW462385 | 0.6816 | 0.0015179 | 0.12587 | syntaxin 1A (brain) | STX1A | BU848697 | Hs. 75671 |
| 92 | AW462546 | 1.3394 | 0.0014366 | 0.12587 | coatomer protein complex, subunit zeta 2 | COPZ2 | CA415465 | Hs. 37482 |
| 93 | AW463148 | 2.0428 | 0.0015425 | 0.12587 | pepsinogen 5, group I (pepsinogen A) | PGA5 | NM_014224 | Hs. 432854 |
| 94 | AW464583 | 0.7143 | 0.0015369 | 0.12587 | GTP binding protein 1 | GTPBP1 | BQ050866 | Hs. 283677 |
| 95 | AW465767 | 0.7315 | 0.0014903 | 0.12587 | ubiquitin-conjugating enzyme E2G 2 (UBC7 homolog, yeast) | UBE2G2 | BG323625 | Hs. 250387 |
| 96 | AW466125 | 0.7502 | 0.0015419 | 0.12587 | sorting nexin 2 | SNX2 | BQ937470 | Hs. 11183 |
| 97 | AW466146 | 0.7903 | 0.0015274 | 0.12587 | ribosomal protein L17 | RPL17 | BQ429282 | Hs. 374588 |
| 98 | BF042961 | 0.5447 | 0.0015301 | 0.12587 | KIAA0063 gene product | KIAA0063 | BU197344 | Hs. 3094 |
| 99 | BF043647 | 1.3414 | 0.0014482 | 0.12587 | *Homo sapiens* similar to hypothetical protein MGC32132 (LOC375270), mRNA | | BC016181 | Hs. 444182 |
| 100 | AW462175 | 0.6779 | 0.0016338 | 0.13196 | peroxisomal D3,D2-enoyl-CoA isomerase | PEC1 | BG400978 | Hs. 15250 |
| 101 | AW464554 | 0.7914 | 0.0016507 | 0.13198 | KIAA1181 protein | KIAA1181 | BX410080 | Hs. 180428 |
| 102 | AW464010 | 1.2116 | 0.0017134 | 0.13352 | GATA binding protein 2 | GATA2 | BI518454 | Hs. 367725 |
| 103 | BF045005 | 2.1250 | 0.0016951 | 0.13352 | neutrophil cytosolic factor 4, 40 kDa | NCF4 | BG398359 | Hs. 196352 |
| 104 | BF045561 | 0.6227 | 0.0017206 | 0.13352 | EAP30 subunit of ELL complex | EAP30 | BG685756 | Hs. 127249 |
| 105 | BF046270 | 1.8447 | 0.0017527 | 0.13469 | *Homo sapiens* transcribed sequences | | CA307924 | Hs. 8882 |
| 106 | BF043456 | 1.4696 | 0.0017865 | 0.13596 | carboxypeptidase D | CPD | U65090 | Hs. 5057 |
| 107 | BF040324 | 0.6462 | 0.0018316 | 0.13807 | *Homo sapiens*, clone IMAGE: 6254355, mRNA | | BU741494 | Hs. 133864 |
| 108 | AW462307 | 2.7603 | 0.0019144 | 0.13924 | solute carrier family 11 (proton-coupled divalent metal ion transporters), member 2 | SLC11A2 | AB004857 | Hs. 57435 |
| 109 | BF043382 | 0.7925 | 0.0018925 | 0.13924 | nucleoporin 98 kDa | NUP98 | BQ218203 | Hs. 112255 |
| 110 | BF043624 | 0.6949 | 0.0019175 | 0.13924 | ubiquitin-conjugating enzyme E2H (UBC8 homolog, yeast) | UBE2H | AA939244 | Hs. 372758 |
| 111 | BF440494 | 1.6291 | 0.0018752 | 0.13924 | | | NT_00483615 | |
| 112 | AW461523 | 1.4122 | 0.00196 | 0.13976 | hypothetical protein MGC15716 | MGC15716 | AK074191 | Hs. 282111 |
| 113 | AW461688 | 0.7684 | 0.0019507 | 0.13976 | chromosome 7 open reading frame 11 | C7orf11 | CA418873 | Hs. 129159 |
| 114 | BM362465 | 0.7065 | 0.0019862 | 0.14037 | ubiquinol-cytochrome c reductase (6.4 kD) subunit | UQCR | BF667634 | Hs. 8372 |
| 115 | BF440208 | 1.2735 | 0.0020052 | 0.14045 | deltex 4 homolog (*Drosophila*) | DTX4 | T98251 | Hs. 62264 |
| 116 | AW464711 | 0.5956 | 0.0020555 | 0.14264 | ADP-ribosylation factor-like 1 | ARL1 | AA622011 | Hs. 372616 |
| 117 | AW465606 | 0.7520 | 0.0021085 | 0.14264 | APG7 autophagy 7-like (*S. cerevisiae*) | APG7L | BQ880961 | Hs. 278607 |
| 118 | BF042255 | 1.3021 | 0.0021045 | 0.14264 | DnaJ (Hsp40) homolog, subfamily B, member 1 | DNAJB1 | BX364826 | Hs. 82646 |
| 119 | BF042909 | 0.8137 | 0.0020837 | 0.14264 | *Homo sapiens* hypothetical protein 15E1.2, mRNA (cDNA clone IMAGE: 6200931), partial cds | | AA373890 | Hs. 441127 |
| 120 | BF042997 | 0.7728 | 0.00217 | 0.14556 | hypothetical protein FLJ32954 | FLJ32954 | BC024243 | Hs. 9905 |
| 121 | AW461908 | 0.7908 | 0.0022189 | 0.14667 | glioma tumor suppressor candidate region gene 2 | GLTSCR2 | BM562778 | Hs. 421907 |
| 122 | AW462811 | 0.7074 | 0.0022237 | 0.14667 | CAAX box 1 | CXX1 | BG424569 | Hs. 250708 |
| 123 | AW461534 | 0.6298 | 0.0023319 | 0.14898 | | | NT_011512.9 | |
| 124 | AW461574 | 1.3557 | 0.002363 | 0.14898 | Transcribed sequence with strong similarity to protein ref: NP_056444.1 (*H. sapiens*) pre-mRNA processing factor 31 homolog | | AW461574 | Bt. 1660 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 125 | AW465706 | 0.8093 | 0.0023563 | 0.14898 | topoisomerase I binding, arginine/serine-rich | TOPORS | U82939 | Hs. 446279 |
| 126 | BF041813 | 1.6655 | 0.002378 | 0.14898 | tumor necrosis factor, alpha-induced protein 8 | TNFAIP8 | AA574013 | Hs. 17839 |
| 127 | BF041863 | 0.4895 | 0.0023642 | 0.14898 | | | NT_008705.15 | |
| 128 | BF044557 | 1.5444 | 0.0024093 | 0.14898 | Transcribed sequence | | CB460423 | Bt. 19405 |
| 129 | BF046723 | 2.2140 | 0.0022784 | 0.14898 | | | NT_029419.10 | |
| 130 | BF440382 | 0.6036 | 0.0024066 | 0.14898 | guanine nucleotide binding protein (G protein), gamma 2 | GNG2 | BC020774 | Hs. 112928 |
| 131 | AW463169 | 0.7644 | 0.0024841 | 0.15068 | AD023 protein | AD023 | CA488406 | Hs. 325631 |
| 132 | AW463234 | 0.7692 | 0.0024826 | 0.15068 | NADH dehydrogenase (ubiquinone) flavoprotein 3, 10 kDa | NDUFV3 | AA179564 | Hs. 199471 |
| 133 | BF039617 | 0.8087 | 0.002494 | 0.15068 | hypothetical protein MGC10120 | MGC10120 | AA884267 | Hs. 34906 |
| 134 | BF039493 | 0.7468 | 0.0025265 | 0.15149 | similar to RIKEN cDNA 2410004L22 gene (M. musculus) | MGC20533 | BM909119 | Hs. 69280 |
| 135 | AW461726 | 0.7637 | 0.0027019 | 0.15385 | adenylate cyclase 3 | ADCY3 | BX094242 | Hs. 188402 |
| 136 | AW463524 | 1.6407 | 0.002607 | 0.15385 | myosin, light polypeptide 9, regulatory | MYL9 | BQ717137 | Hs. 433814 |
| 137 | AW465396 | 2.5572 | 0.0027016 | 0.15385 | cytochrome P450, family 4, subfamily A, polypeptide 11 | CYP4A11 | S67581 | Hs. 1645 |
| 138 | AW465666 | 0.6545 | 0.0026717 | 0.15385 | protein tyrosine phosphatase-like (proline instead of catalytic arginine), member b | PTPLB | AK074605 | Hs. 5957 |
| 139 | BF040830 | 2.6732 | 0.0026583 | 0.15385 | MAX dimerization protein 4 | MXD4 | NT_022517.16 | |
| 140 | BF040980 | 0.7352 | 0.0026874 | 0.15385 | Transcribed sequences | | CA308842 | Hs. 511752 |
| 141 | BM364711 | 2.1533 | 0.0026345 | 0.15385 | | | BM364711 | Bt. 11098 |
| 142 | BF039094 | 1.6600 | 0.0027501 | 0.15548 | hypothetical protein KIAA1833 | KIAA1833 | XM_114611 | Hs. 443139 |
| 143 | BM366975 | 0.7709 | 0.0028343 | 0.15910 | chromobox homolog 6 | CBX6 | CA424188 | Hs. 511952 |
| 144 | BF044410 | 2.0975 | 0.0028648 | 0.15968 | testis-specific kinase 2 | TESK2 | AB057597 | Hs. 8980 |
| 145 | AW465824 | 1.3873 | 0.0029221 | 0.16174 | fibrosin 1 | FBS1 | BU196391 | Hs. 247186 |
| 146 | BF045830 | 0.7629 | 0.0030885 | 0.16976 | RelA-associated inhibitor | RAI | BU860065 | Hs. 324051 |
| 147 | BF046712 | 1.3724 | 0.0031245 | 0.17055 | dual-specificity tyrosine-(Y)-phosphorylation regulated kinase 3 | DYRK3 | BC015501 | Hs. 164267 |
| 148 | BF039623 | 1.9607 | 0.0031532 | 0.17094 | plasminogen-related protein A | LOC285189 | XM_351480 | Hs. 449164 |
| 149 | AW465584 | 2.0534 | 0.0031759 | 0.17100 | Transcribed sequence with strong similarity to protein sp: P13995 (H. sapiens) MTDC_HUMAN Bifunctional methylenetetrahydrofolate dehydrogenase/cyclohydrolase, mitochondrial precursor [Includes: NAD-dependent methylenetetrahydrofolate dehydrogenase; Methenyltetrahydrofolate cyclohydrolase] | | | TC214223 |
| 150 | AW462929 | 0.7037 | 0.0032092 | 0.17163 | cyclin-dependent kinase inhibitor 1C (p57, Kip2) | CDKN1C | BU742010 | Hs. 106070 |
| 151 | BM366972 | 0.7576 | 0.0032364 | 0.17192 | splicing factor 3b, subunit 5, 10 kDa | SF3B5 | CA411860 | Hs. 110695 |
| 152 | BF041965 | 0.7803 | 0.0033066 | 0.17342 | Transcribed sequences | | BI774419 | Bt. 22285 |
| 153 | BM365835 | 0.7417 | 0.0033085 | 0.17342 | ribosomal protein S27 (metallopanstimulin 1) | RPS27 | CD248629 | Hs. 337307 |
| 154 | BF045124 | 2.1781 | 0.0033633 | 0.17514 | inositol polyphosphate-4-phosphatase, type II, 105 kDa | INPP4B | BC017924 | Hs. 153687 |
| 155 | BF040256 | 2.8742 | 0.0034738 | 0.17971 | | | CB421959 | Bt. 20862 |
| 156 | BM364415 | 0.7048 | 0.0035667 | 0.18278 | cytochrome c oxidase subunit Vb | COX5B | AA527583 | TC209958 |
| 157 | BM365799 | 0.7019 | 0.0035794 | 0.18278 | transforming growth factor beta 1 induced transcript 1 | TGFB1I1 | BC032545 | Hs. 1342 |
| 158 | AW462329 | 1.4275 | 0.0036045 | 0.18288 | leucine proline-enriched proteoglycan (leprecan) 1 | LEPRE1 | BC004160 | Hs. 25511 |
| 159 | AW462136 | 0.7972 | 0.0036677 | 0.18344 | chromosome 20 open reading frame 7 | C20orf7 | NM_199052 | Hs. 437656 |
| 160 | BF041338 | 2.0406 | 0.0037081 | 0.18344 | cerebroside (3'-phosphoadenylylsulfate: galactosylceramide 3') sulfotransferase | CST | D88667 | Hs. 420282 |
| 161 | BF041765 | 0.7198 | 0.0036978 | 0.18344 | | | | Hs. 17958 |
| 162 | BF045167 | 1.4258 | 0.0036793 | 0.18344 | protein-O-mannosyltransferase 1 | POMT1 | AK074874 | Hs. 209205 |
| 163 | BM362349 | 0.7401 | 0.0037621 | 0.18495 | NADH dehydrogenase (ubiquinone) 1 alpha subcomplex, 2, 8 kDa | NDUFA2 | CA455540 | Hs. 163867 |
| 164 | AW462081 | 0.7895 | 0.003842 | 0.18562 | epithelial membrane protein 1 | EMP1 | AW369615 | Hs. 306692 |
| 165 | BF042546 | 2.4927 | 0.003893 | 0.18562 | KIAA0703 gene product | KIAA0703 | AK091051 | Hs. 6168 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 166 | BF043129 | 2.6616 | 0.0038096 | 0.18562 | Transcribed sequences | | CB432831 | TC192095 |
| 167 | BF043441 | 0.3753 | 0.0038749 | 0.18562 | Transcribed sequences | | CR432831 | Bt. 16982 |
| 168 | BF043441 | 0.1367 | 0.003031 | 0.18562 | Transcribed sequences | | CB432831 | Bt. 16982 |
| 169 | BF043441 | 1.0301 | 0.9404668 | 0.18562 | Transcribed sequences | | CB432831 | Bt. 16982 |
| 170 | BM361957 | 0.7212 | 0.0038832 | 0.18562 | ribosomal protein L34 | RPL34 | BG436845 | Hs. 250895 |
| 171 | BM362618 | 0.7724 | 0.0039316 | 0.18634 | ubiquitin associated domain containing 1 | UBADC1 | BX395764 | Hs. 9194 |
| 172 | AW461418 | 0.7664 | 0.0039726 | 0.18716 | ROD1 regulator of differentiation 1 (*S. pombe*) | ROD1 | NM_005156 | Hs. 374634 |
| 173 | AW461640 | 0.7853 | 0.0041372 | 0.18865 | eukaryotic translation termination factor 1 | ETF1 | AA812738 | Hs. 77324 |
| 174 | AW461984 | 1.2745 | 0.0041471 | 0.18865 | PAK6 (CDKN1A)-activated kinase 6 | PAK6 | BC035596 | Hs. 21420 |
| 175 | BF041453 | 1.5013 | 0.0041268 | 0.18865 | solute carrier family 4, sodium bicarbonate cotransporter, member 5 | SLC4A5 | NM_133478 | Hs. 321127 |
| 176 | BF042148 | 0.6408 | 0.0041056 | 0.18865 | pellino homolog 1 (*Drosophila*) | PELI1 | AA255632 | Hs. 7886 |
| 177 | BF042689 | 1.5422 | 0.0040901 | 0.18865 | hypothetical protein FLJ14494 | FLJ14494 | NM_032795 | Hs. 150458 |
| 178 | BF045165 | 1.2746 | 0.0040777 | 0.18865 | hypothetical protein DKFZp434N2030 | DKFZp434N2030 | BC035136 | Hs. 494204 |
| 179 | AW461802 | 0.7532 | 0.0042274 | 0.18995 | p8 protein (candidate of metastasis 1) | P8 | BG708511 | Hs. 418692 |
| 180 | AW464520 | 1.5809 | 0.0042958 | 0.18995 | low density lipoprotein-related protein 2 | LRP2 | BG399349 | Hs. 252938 |
| 181 | AW465157 | 1.5354 | 0.0042351 | 0.18995 | short stature homeobox 2 | SHOX2 | AK095338 | Hs. 55967 |
| 182 | BF039056 | 3.1018 | 0.0042953 | 0.18995 | Trophoblast Kunitz domain protein 3 (TKDP3) mRNA, partial cds | | BF043269 | Bt. 262 |
| 183 | BF040869 | 2.4647 | 0.0042797 | 0.18995 | leucine-rich repeat-containing G protein-coupled receptor 8 | LGR8 | NM_130806 | Hs. 348481 |
| 184 | BF043917 | 0.8532 | 0.0043968 | 0.19227 | evolutionarily conserved G-patch domain containing | ECGP | AF434677 | Hs. 55014 |
| 185 | BF045154 | 2.0875 | 0.0043767 | 0.19227 | | | NT_004668.16 | |
| 186 | AW461470 | 0.8599 | 0.0045074 | 0.19389 | Transcribed sequences | | AW461470 | Bt. 10716 |
| 187 | AW464274 | 1.6622 | 0.0045045 | 0.19389 | monocarboxylate transporter 13 | SLC16A13 | XM_115484 | Hs. 448010 |
| 188 | BF044013 | 0.7111 | 0.0048622 | 0.19389 | HSPC039 protein | HSPC039 | B1823160 | Hs. 406542 |
| 189 | AW461516 | 1.5622 | 0.0046049 | 0.19683 | G protein-coupled bile acid receptor 1 | GPBAR1 | BG698138 | Hs. 160954 |
| 190 | AW462075 | 0.7630 | 0.0046701 | 0.19683 | serine protease inhibitor, Kunitz type, 2 | SPINT2 | BE899025 | Hs. 31439 |
| 191 | AW462448 | 1.3243 | 0.0049574 | 0.19683 | Transcribed sequences | | AW462448 | Bt. 13259 |
| 192 | AW462519 | 0.7746 | 0.0048382 | 0.19683 | choline kinase-like | CHKL | BU568477 | Hs. 439777 |
| 193 | AW464128 | 0.7198 | 0.0047972 | 0.19683 | vesicle docking protein p115 | VDP | D86326 | Hs. 325948 |
| 194 | AW465040 | 0.5985 | 0.0049117 | 0.19683 | RIKEN cDNA 1110003P22 gene | 1110003P22Rik | CF617508 | Mm. 41420 |
| 195 | AW465639 | 0.7636 | 0.0046489 | 0.19683 | | | NT_010194.16 | |
| 196 | AW465776 | 0.7988 | 0.004949 | 0.19683 | Transcribed sequences | | AW465776 | Bt. 12588 |
| 197 | AW466079 | 3.4285 | 0.0048752 | 0.19683 | glutamyl aminopeptidase (aminopeptidase A) | ENPEP | L14721 | Hs. 435765 |
| 198 | BF039189 | 0.8475 | 0.0047925 | 0.19683 | SH2 domain binding protein 1 (tetratricopeptide repeat containing) | SH2BP1 | B1839172 | Hs. 173288 |
| 199 | BF042267 | 2.0691 | 0.004471 | 0.19683 | | | | BF042267 |
| 200 | BF043458 | 0.6814 | 0.0049295 | 0.19683 | Rab geranylgeranyltransferase, beta subunit | RABGGTB | BC020790 | Hs. 78948 |
| 201 | BF043688 | 1.5270 | 0.0046789 | 0.19683 | KIAA1623 | KIAA1623 | AL567190 | Hs. 421680 |
| 202 | BF044377 | 0.2382 | 0.0049635 | 0.19683 | follistatin-like 1 | FSTL1 | BQ010153 | Hs. 433622 |
| 203 | BM362629 | 0.8571 | 0.0049735 | 0.19683 | thyroid hormone receptor interactor 3 | TRIP3 | CD701615 | Hs. 2210 |
| 204 | BM366480 | 0.7655 | 0.0051562 | 0.19683 | ribosomal protein L27 | RPL27 | BU852832 | Hs. 405528 |
| 205 | AW465210 | 0.7042 | 0.0052193 | 0.20304 | hypothetical protein MGC5306 | MGC5306 | BX416823 | Hs. 355750 |
| 206 | BF043768 | 2.0210 | 0.0052441 | 0.20447 | BRF2, subunit of RNA polymerase III transcription initiation factor, BRF1-like | BRF2 | BQ018062 | Hs. 274136 |
| 207 | BF045850 | 1.3545 | 0.0052441 | 0.20447 | Transcribed sequence with moderate similarity to protein ref: NP_073596.1 (*H. sapiens*) hypothetical protein FLJ21865 [*Homo sapiens*] | | BE664132 | Bt. 6206 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 208 | BM365541 | 1.8091 | 0.0052774 | 0.20476 | choline/ethanolaminephosphotransferase | CEPT1 | AW797250 | Hs. 363572 |
| 209 | BP230001A20G6 | 0.6732 | 0.0053565 | 0.20681 | chromosome 14 open reading frame 170 | C14orf170 | XM_085151 | Hs. 303775 |
| 210 | AW462359 | 0.7978 | 0.0054161 | 0.20810 | Transcribed sequence with weak similarity to protein sp: Q9UKK3 (H. sapiens) PPOV_HUMAN Vault poly | | AW315111 | Bt. 9321 |
| 211 | BF440272 | 1.5176 | 0.0054499 | 0.20839 | regulator of G-protein signalling 5 | RGS5 | BI494221 | Hs. 24950 |
| 212 | AW461819 | 0.4857 | 0.0056347 | 0.21105 | ATPase, Na+/K+ transporting, beta 1 polypeptide | ATP1B1 | AA418647 | Hs. 78629 |
| 213 | AW463150 | 0.7574 | 0.005653 | 0.21105 | Homo sapiens mRNA; cDNA DKFZp434H068 (from clone DKFZp434H068) | | AA148248 | Hs. 506074 |
| 214 | BF039065 | 1.5715 | 0.0056271 | 0.21105 | MLL septin-like fusion | MSF | BU931075 | Hs. 288094 |
| 215 | BM365510 | 0.7674 | 0.0055744 | 0.21105 | kinesin family member 3B | KIF3B | BU690106 | Hs. 301206 |
| 216 | BM365938 | 0.3500 | 0.0055484 | 0.21105 | sestrin 2 | SESN2 | AI700180 | Hs. 8026 |
| 217 | BF039954 | 1.8391 | 0.0058891 | 0.21884 | | | | BF039954 |
| 218 | BF040540 | 1.3105 | 0.0059515 | 0.21990 | neuropathy target esterase | NTE | AJ004832 | Hs. 511760 |
| 219 | BM366584 | 1.1928 | 0.0059732 | 0.21990 | hypothetical protein MGC4238 | MGC4238 | NM_032332 | Hs. 334626 |
| 220 | BF043047 | 1.6391 | 0.0061858 | 0.22667 | similar to Zinc finger protein 136 | LOC199692 | AA214213 | Hs. 14831 |
| 221 | AW461654 | 1.3075 | 0.0063001 | 0.22980 | protein inhibitor of activated STAT protein PIASy | PIASY | T85436 | Hs. 105779 |
| 222 | AW462133 | 1.5404 | 0.0063331 | 0.22994 | echinoderm microtubule associated protein like 5 | EML5 | BF590352 | Hs. 410913 |
| 223 | AW462711 | 0.8294 | 0.0063974 | 0.23104 | Transcribed sequences | | AW462711 | Bt. 7917 |
| 224 | AW466082 | 1.3508 | 0.006451 | 0.23104 | Transcribed sequences | | CB449171 | Bt. 6244 |
| 225 | BF045301 | 0.7722 | 0.0064472 | 0.23104 | methionyl aminopeptidase 2 | METAP2 | CA443908 | Hs. 144906 |
| 226 | AW461425 | 0.7595 | 0.0065455 | 0.23125 | casein kinase 1, alpha 1 | CSNK1A1 | BQ231001 | Hs. 318381 |
| 227 | AW465281 | 0.7778 | 0.0065567 | 0.23125 | Homo sapiens transcribed sequences | | BX483510 | Hs. 105636 |
| 228 | BF045176 | 0.8483 | 0.0065875 | 0.23125 | SET translocation (myeloid leukemia-associated) | SET | M93651 | Hs. 436687 |
| 229 | BF045836 | 0.6667 | 0.006603 | 0.23125 | topoisomerase (DNA) I | TOP1 | BC004475 | Hs. 253536 |
| 230 | BM364051 | 1.4620 | 0.0065546 | 0.23125 | KIAA1836 protein | KIAA1836 | BE888083 | Hs. 318773 |
| 231 | AW464893 | 0.6690 | 0.006645 | 0.23170 | START domain containing 4, sterol regulated | STARD4 | AL832599 | Hs. 93842 |
| 232 | AW465985 | 0.7679 | 0.0068628 | 0.23472 | phosphatidylinositol transfer protein, membrane-associated 2 | PITPNM2 | BC040063 | Hs. 272759 |
| 233 | BF042374 | 0.7915 | 0.0068134 | 0.23472 | necdin-like 2 | NDNL2 | BC041166 | Hs. 512642 |
| 234 | BF043142 | 1.5254 | 0.0068748 | 0.23472 | cyclin M4 | CNNM4 | AA291802 | Hs. 175043 |
| 235 | BF043207 | 0.7376 | 0.0069098 | 0.23472 | hypothetical protein FLJ20244 | FLJ20244 | BC040126 | Hs. 411456 |
| 236 | BF043909 | 0.7258 | 0.0068881 | 0.23472 | bromodomain containing 1 | BRD1 | NM_014577 | Hs. 370880 |
| 237 | BM365156 | 0.8537 | 0.0067749 | 0.23472 | MKI67 (FHA domain) interacting nucleolar phosphoprotein | MKI67IP | AA564737 | Hs. 367842 |
| 238 | BF039394 | 1.4396 | 0.0069435 | 0.23486 | diacylglycerol kinase, eta | DGKH | NM_152910 | Hs. 378969 |
| 239 | BF039014 | 0.7831 | 0.0070139 | 0.23624 | Homo sapiens clone IMAGE: 4815142, mRNA | | BQ326465 | Hs. 349568 |
| 240 | AW465409 | 0.7396 | 0.0070867 | 0.23767 | platelet-activating factor acetylhydrolase, isoform Ib, alpha subunit 45 kDa | PAFAH1B1 | BU072064 | Hs. 77318 |
| 241 | BM366532 | 3.4966 | 0.0071489 | 0.23875 | angiogenin, ribonuclease, RNase A family, 5 | ANG | BQ773604 | Hs. 283749 |
| 242 | AW462090 | 0.7769 | 0.0074169 | 0.24666 | DEAD (Asp-Glu-Ala-Asp) box polypeptide 54 | DDX54 | BM794682 | Hs. 203581 |
| 243 | AW462739 | 0.8437 | 0.0075239 | 0.24735 | chromosome 6 open reading frame 83 | C6orf83 | CA412928 | Hs. 284265 |
| 244 | BF039410 | 0.5371 | 0.0075627 | 0.24735 | RUN and SH3 domain containing 1 | RUSC1 | CA418193 | Hs. 226499 |
| 245 | BF045989 | 0.4548 | 0.0075315 | 0.24735 | chromosome 10 open reading frame 74 | C10orf74 | AA730643 | Hs. 352398 |
| 246 | BF440222 | 1.4891 | 0.0075193 | 0.24735 | coronin, actin binding protein, 1C | CORO1C | CA444755 | Hs. 17377 |
| 247 | AW464311 | 0.8173 | 0.0076248 | 0.24835 | hypothetical protein FLJ20403 | FLJ20403 | BU521884 | Hs. 306221 |
| 248 | BF040466 | 0.7542 | 0.0077081 | 0.25004 | ribosome binding protein 1 homolog 180 kDa (dog) | RRBP1 | AA577671 | Hs. 98614 |
| 249 | AW465742 | 0.8104 | 0.0078784 | 0.25452 | growth hormone inducible transmembrane protein | GHITM | CD701404 | Hs. 352656 |
| 250 | AW463923 | 1.1798 | 0.0081087 | 0.26063 | HLA-B associated transcript 1 | BAT1 | BG675992 | Hs. 254042 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 251 | AW466175 | 0.7750 | 0.0081335 | 0.26063 | ubiquitin specific protease 47 | USP47 | CA944859 | Hs. 441028 |
| 252 | BF044437 | 1.8758 | 0.0081949 | 0.26154 | | | NT_022184.13 | |
| 253 | BF039323 | 0.6587 | 0.0082671 | 0.26279 | | | NT_079592.1 | |
| 254 | AW462705 | 0.7869 | 0.0084481 | 0.26325 | copine III | CPNE3 | BE877797 | Hs. 14158 |
| 255 | BF040988 | 2.1454 | 0.0084317 | 0.26325 | | | NT_011757.13 | |
| 256 | BF044083 | 0.8398 | 0.0083968 | 0.26325 | B-cell linker | Blnk | BB612232 | Mm. 9749 |
| 257 | BF045148 | 0.7724 | 0.0083655 | 0.26325 | Transcribed sequence with strong similarity to protein prf: 2202255A (H. sapiens) 2202255A AT motif-binding factor 1 [Homo sapiens] | | CF767756 | Bt. 6456 |
| 258 | BM363855 | 2.5268 | 0.0083926 | 0.26325 | phospholipase A2, group IID | PLA2G2D | BM153087 | Hs. 189507 |
| 259 | BF044419 | 1.7185 | 0.0085132 | 0.26424 | Homo sapiens cDNA FLJ31099 fis, clone IMR321000230. | | BC020929 | Hs. 177633 |
| 260 | AW465703 | 0.8349 | 0.008612 | 0.26627 | Transcribed sequences | | AW465703 | Bt. 9668 |
| 261 | BF039660 | 0.8068 | 0.0086939 | 0.26650 | dishevelled, dsh homolog 3 (Drosophila) | DVL3 | D86963 | Hs. 381928 |
| 262 | BF039699 | 0.6363 | 0.0087206 | 0.26650 | paraspeckle component 1 | PSPC1 | AF448795 | Hs. 16364 |
| 263 | BF044525 | 0.6176 | 0.0086956 | 0.26650 | KIAA0007 protein | KIAA0007 | CB133931 | Hs. 90315 |
| 264 | BF041013 | 0.7677 | 0.0088577 | 0.26965 | Ran-binding protein 10 | RANBP10 | AL137299 | Hs. 6343 |
| 265 | AW464094 | 0.8308 | 0.0089577 | 0.27089 | programmed cell death 6 interacting protein | PDCD6IP | CA748765 | Hs. 9663 |
| 266 | AW464164 | 0.5096 | 0.0089669 | 0.27089 | fibulin 1 | FBLN1 | BU553419 | Hs. 445240 |
| 267 | BF045865 | 1.4010 | 0.0090141 | 0.27128 | collagen, type VIII, alpha 1 | COL8A1 | CA448060 | Hs. 114599 |
| 268 | AW462758 | 1.5861 | 0.0094557 | 0.27545 | | | | AW462758 |
| 269 | AW462782 | 0.8041 | 0.0092383 | 0.27545 | hypothetical protein DKFZp434K1815 | DKFZp434K1815 | BQ773994 | Hs. 274135 |
| 270 | AW463320 | 1.4604 | 0.0095422 | 0.27545 | mitochondrial ribosomal protein S18A | Mrps18a | NT_009952.14 | Mm. 287443 |
| 271 | AW465653 | 0.7926 | 0.0094217 | 0.27545 | upstream binding transcription factor, RNA polymerase I | UBTF | BQ640761 | Hs. 89781 |
| 272 | AW465738 | 2.4055 | 0.0092567 | 0.27545 | carboxypeptidase A4 | CPA4 | NM_016352 | Hs. 93764 |
| 273 | BF039874 | 1.4597 | 0.0095609 | 0.27545 | prostaglandin F2 receptor negative regulator | PTGFRN | XM_040709 | Hs. 418093 |
| 274 | BF042207 | 0.7473 | 0.009404 | 0.27545 | mitogen-activated protein kinase kinase 1 | MAP2K1 | BM981116 | Hs. 132311 |
| 275 | BF042293 | 0.6981 | 0.0095702 | 0.27545 | | | BE756980 | Bt. 11020 |
| 276 | BF044365 | 2.0515 | 0.0093995 | 0.27545 | cytochrome c oxidase subunit VIII | COX8 | AA442192 | Hs. 433901 |
| 277 | BF045161 | 1.2077 | 0.0095371 | 0.27545 | NADH dehydrogenase (ubiquinone) 1 beta subcomplex, 7, 18 kDa | NDUFB7 | BG574803 | Hs. 433482 |
| 278 | BM361926 | 0.7576 | 0.0094725 | 0.27545 | sorcin | SRI | NM_003130 | Hs. 422340 |
| 279 | BM364516 | 1.8243 | 0.0093859 | 0.27545 | chemokine (C-X-C motif) ligand 12 (stromal cell-derived factor 1) | CXCL12 | BX647204 | Hs. 436042 |
| 280 | AW462100 | 0.7429 | 0.0097767 | 0.27835 | myosin phosphatase-Rho interacting protein | M-RIP | D23673 | Hs. 430725 |
| 281 | BF039681 | 0.7139 | 0.0097685 | 0.27835 | PTK2 protein tyrosine kinase 2 | PTK2 | BG497514 | Hs. 434281 |
| 282 | BM364428 | 0.7728 | 0.0097117 | 0.27835 | chromosome 1 open reading frame 24 | C1orf24 | CA430470 | Hs. 48778 |
| 283 | AW462966 | 1.1930 | 0.0098488 | 0.27940 | nucleolar protein family A, member 3 (H/ACA small nucleolar RNPs) | NOLA3 | AA934691 | Hs. 14317 |
| 284 | AW461868 | 0.7513 | 0.0100302 | 0.27950 | DEAD (Asp-Glu-Ala-Asp) box polypeptide 24 | DDX24 | AU149417 | Hs. 372267 |
| 285 | AW462382 | 0.7440 | 0.0099089 | 0.27950 | malate dehydrogenase 2, NAD (mitochondrial) | MDH2 | BM550823 | Hs. 405860 |
| 286 | AW464067 | 0.7689 | 0.010064 | 0.27950 | bromodomain containing 1 | BRD1 | BU431018 | Hs. 370880 |
| 287 | BF042174 | 0.7999 | 0.0099663 | 0.27950 | Parkinson disease (autosomal recessive, early onset) 7 | PARK7 | BM554785 | Hs. 419640 |
| 288 | BF043744 | 2.8509 | 0.0099637 | 0.27950 | hypothetical protein LOC255743 | LOC255743 | AA449335 | Hs. 282832 |
| 289 | BM365103 | 0.7674 | 0.010005 | 0.27950 | IQ motif containing GTPase activating protein 1 | IQGAP1 | D29640 | Hs. 1742 |
| 290 | AW464273 | 1.6537 | 0.0101655 | 0.28133 | apoptosis(APO-1) antigen 1 (FAS), member 6 | TNFRSF6 | NM_174662 | Bt. 4345 |
| 291 | BM366541 | 0.8137 | 0.0102164 | 0.28175 | NHP2 non-histone chromosome protein 2-like 1 (S. cerevisiae) | NHP2L1 | BU955332 | Hs. 182255 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 292 | AW462227 | 0.8291 | 0.0102891 | 0.28180 | transforming growth factor, beta receptor II (70/80 kDa) | TGFBR2 | CD110077 | Hs. 82028 |
| 293 | AW466159 | 1.4010 | 0.0102895 | 0.28180 | Ran GTPase activating protein 1 | RANGAP1 | BU190935 | Hs. 183800 |
| 294 | BF045523 | 0.7624 | 0.0103369 | 0.28213 | myosin regulatory light chain interacting protein | MYLIP | BQ027638 | Hs. 443793 |
| 295 | BF044848 | 0.8094 | 0.0103891 | 0.28258 | ubiquitin-conjugating enzyme E2 variant 2 | UBE2V2 | X98091 | Hs. 371278 |
| 296 | BF040663 | 2.3303 | 0.0105655 | 0.28541 | | | | BF040663 |
| 297 | BF042477 | 0.7538 | 0.0105356 | 0.28541 | eukaryotic translation initiation factor 5 | EIF5 | BC007728 | Hs. 433702 |
| 298 | BF042245 | 1.5952 | 0.0106039 | 0.28547 | hypothetical protein LOC90850 | LOC90850 | BC050477 | Hs. 343828 |
| 299 | AW463964 | 0.7511 | 0.0106864 | 0.28575 | EF hand domain containing 2 | EFHD2 | AA565855 | Hs. 301342 |
| 300 | BF041775 | 0.7656 | 0.0106543 | 0.28575 | likely ortholog of mouse gene trap locus 3 | GTL3 | BC005152 | Hs. 279818 |
| 301 | BF440363 | 0.7361 | 0.0107527 | 0.28656 | proteasome (prosome, macropain) subunit, alpha type, 3 | PSMA3 | CA431411 | Hs. 246240 |
| 302 | BF040230 | 0.3818 | 0.0108203 | 0.28739 | mitogen-inducible gene 6 | MIG-6 | BQ014845 | Hs. 11169 |
| 303 | AW462792 | 0.8156 | 0.0109467 | 0.28881 | mitochondrial ribosomal protein L32 | MRPL32 | BU927763 | Hs. 50252 |
| 304 | BF046632 | 0.7915 | 0.0109122 | 0.28881 | | | | BF046632 |
| 305 | BF045608 | 0.7502 | 0.0110471 | 0.29049 | LSM8 homolog, U6 small nuclear RNA associated (*S. cerevisiae*) | LSM8 | AA328592 | Hs. 446179 |
| 306 | BF040483 | 0.7404 | 0.0112759 | 0.29553 | | | | TC202969 |
| 307 | AW462063 | 1.3490 | 0.0113454 | 0.29637 | solute carrier family 37 (glycerol-3-phosphate transporter), member 3 | SLC37A3 | BE693370 | Hs. 439590 |
| 308 | AW461912 | 0.8007 | 0.0116025 | 0.29758 | insulin-like growth factor binding protein 7 | IGFBP7 | BC017201 | Hs. 435795 |
| 309 | AW464194 | 0.7571 | 0.0115795 | 0.29758 | PABP1-dependent poly A-specific ribonuclease subunit PAN3 | PAN3 | BC024318 | Hs. 190153 |
| 310 | BF040204 | 0.8016 | 0.0114776 | 0.29758 | Transcribed sequence with weak similarity to protein pir: T14756 (*H. sapiens*) T14756 hypothetical protein DKFZp564F0923.1 - human | | BF040204 | Bt. 12510 |
| 311 | BF041103 | 0.6991 | 0.0116226 | 0.29758 | Transcribed sequences | | BF041103 | Bt. 18264 |
| 312 | BF041164 | 0.8039 | 0.0115809 | 0.29758 | START domain containing 4, sterol regulated | STARD4 | AA807553 | Hs. 93843 |
| 313 | BM362196 | 0.8620 | 0.0114649 | 0.29758 | NADH dehydrogenase (ubiquinone) 1 alpha subcomplex, 10, 42 kDa | NDUFA10 | CA395087 | Hs. 198271 |
| 314 | BM362608 | 0.8057 | 0.0116549 | 0.29758 | hypothetical protein BC004337 | LOC90826 | AA574240 | Hs. 29645 |
| 315 | AW465430 | 0.6830 | 0.0117439 | 0.29758 | | | BAA24106.1 | TC202901 |
| 316 | BF045069 | 0.6399 | 0.0117505 | 0.29809 | splicing factor, arginine/serine-rich 7, 35 kDa | SFRS7 | H12245 | Hs. 309090 |
| 317 | AW461462 | 0.8282 | 0.0126424 | 0.29809 | WD repeat domain 5 | WDR5 | BQ939873 | Hs. 397638 |
| 318 | AW461475 | 0.7230 | 0.0126915 | 0.29938 | AFG3 ATPase family gene 3-like 2 (yeast) | AFG3L2 | BU737481 | Hs. 436683 |
| 319 | AW461535 | 0.8321 | 0.0131623 | 0.29938 | ribonuclease/angiogenin inhibitor | RNH | BX387666 | Hs. 130958 |
| 320 | AW461605 | 1.3591 | 0.0127436 | 0.29938 | prostate cancer antigen-1 | DEPC-1 | BF037645 | Hs. 71917 |
| 321 | AW461982 | 1.2421 | 0.0120911 | 0.29938 | insulin-like growth factor binding protein 3 | IGFBP3 | AW605051 | Hs. 450230 |
| 322 | AW462169 | 0.7422 | 0.0131314 | 0.29938 | chromosome 21 open reading frame 66 | C21orf66 | NM_145328 | Hs. 297559 |
| 323 | AW462456 | 0.8042 | 0.0120082 | 0.29938 | splicing factor proline/glutamine rich (polypyrimidine tract binding protein associated) | SFPQ | CA441964 | Hs. 180610 |
| 324 | AW462702 | 0.8155 | 0.0129927 | 0.29938 | phosphatidylinositol-4-phosphate 5-kinase, type II, gamma | PIP5K2C | AK075553 | Hs. 144502 |
| 325 | AW462838 | 2.2170 | 0.01296 | 0.29938 | pepsinogen F | Pepf | AK004109 | Mm. 34037 |
| 326 | AW463978 | 2.0020 | 0.0126404 | 0.29938 | prolactin | PRL | CD106017 | Hs. 1905 |
| 327 | AW464129 | 1.2890 | 0.0122983 | 0.29938 | integrin-linked kinase | ILK | BC001554 | Hs. 6196 |
| 328 | AW464130 | 0.8240 | 0.0129722 | 0.29938 | protein tyrosine phosphatase-like (proline instead of catalytic arginine), member b | PTPLB | NM_198402 | Hs. 5957 |
| 329 | AW464611 | 1.3071 | 0.0130407 | 0.29938 | transcription factor 7-like 1 (T-cell specific, HMG-box) | TCF7L1 | BU543840 | Hs. 318517 |
| 330 | AW464647 | 0.8230 | 0.013048 | 0.29938 | huntingtin interacting protein 2 | HIP2 | BX427147 | Hs. 246603 |
| 331 | AW464892 | 0.7164 | 0.0124284 | 0.29938 | nucleoporin like 1 | NUPL1 | AB007870 | Hs. 406243 |
| 332 | BF039385 | 0.7836 | 0.0124596 | 0.29938 | transforming, acidic coiled-coil containing protein 1 | TACC1 | BC041391 | Hs. 279245 |
| 333 | BF039551 | 0.8018 | 0.0127349 | 0.29938 | cardiotrophin 1 | CTF1 | BC036787 | Hs. 433319 |

TABLE I-continued

List of differentially expressed genes in blood that predict PTA for milk production

| SEQ ID NO: | GenBank ID (cattle) | Fold Change (hi/lo) | Raw_P | FDR-adj. P | Gene Name | Gene Symbol | GenBank ID Best Hit | UniGene |
|---|---|---|---|---|---|---|---|---|
| 334 | BF039606 | 0.5315 | 0.0129139 | 0.29938 | MAD2 mitotic arrest deficient-like 1 (yeast) | MAD2L1 | U31278 | Hs. 79078 |
| 335 | BF039758 | 1.4410 | 0.0120723 | 0.29938 | aftiphilin protein | AFTIPHILIN | AL833962 | Hs. 7942 |
| 336 | BF041379 | 1.6597 | 0.0127076 | 0.29938 | myosin VB | MYO5B | AL133643 | Hs. 512590 |
| 337 | BF041571 | 0.5919 | 0.0133519 | 0.29938 | CDC42 binding protein kinase beta (DMPK-like) | CDC42BPB | BU845217 | Hs. 436985 |
| 338 | BF041789 | 0.8041 | 0.0122045 | 0.29938 | serine palmitoyltransferase, long chain base subunit 2 | SPTLC2 | AB011098 | Hs. 59403 |
| 339 | BF041797 | 0.8129 | 0.0119381 | 0.29938 | | | | TC219945 |
| 340 | BF041818 | 2.8155 | 0.0122444 | 0.29938 | hypothetical protein FLJ12875 | FLJ12875 | BX334448 | Hs. 10101 |
| 341 | BF041917 | 0.7942 | 0.0127768 | 0.29938 | SEC24 related gene family, member B (S. cerevisiae) | SEC24B | BC040137 | Hs. 7239 |
| 342 | BF041933 | 1.7183 | 0.0133203 | 0.29938 | transient receptor potential cation channel, subfamily M, member 4 | TRPM4 | BU858032 | Hs. 31608 |
| 343 | BF042179 | 1.6954 | 0.0120724 | 0.29938 | transient receptor potential cation channel, subfamily M, member 6 | TRPM6 | AF448232 | Hs. 272225 |
| 344 | BF042480 | 0.6911 | 0.0132416 | 0.29938 | KIAA0020 | KIAA0020 | AI936509 | Hs. 443866 |
| 345 | BF043417 | 0.2095 | 0.0118913 | 0.29938 | phosphofructokinase, liver | PFKL | BI544646 | Hs. 368741 |
| 346 | BF043962 | 0.6835 | 0.0120777 | 0.29938 | BCL2-like 13 (apoptosis facilitator) | BCL2L13 | CA405971 | Hs. 310922 |
| 347 | BF043971 | 0.8269 | 0.0131719 | 0.29938 | F-box only protein 3 | FBXO3 | BC039291 | Hs. 406787 |
| 348 | BF044310 | 0.6726 | 0.0122477 | 0.29938 | lysosomal-associated protein transmembrane 4 alpha | LAPTM4A | BI463546 | Hs. 111894 |
| 349 | BF045055 | 1.8523 | 0.0124084 | 0.29938 | SET domain, bifurcated 1 | SETDB1 | AK095075 | Hs. 345058 |
| 350 | BF045103 | 0.7576 | 0.0132737 | 0.29938 | cyclic AMP phosphoprotein, 19 kD | ARPP-19 | BF794225 | Hs. 7351 |
| 351 | BF045200 | 0.5394 | 0.0132464 | 0.29938 | Transcribed sequences | | BF045200 | Bt. 6459 |
| 352 | BF045261 | 0.7375 | 0.0124415 | 0.29938 | osteocrin | OSTN | NM_198184 | Hs. 526794 |
| 353 | BM364511 | 1.4212 | 0.0133152 | 0.29938 | hypothetical protein FLJ00007 | FLJ00007 | AA766256 | Hs. 120094 |
| 354 | BM364839 | 0.7436 | 0.0130076 | 0.29938 | Homo sapiens similar to protein of fungal metazoan origin like (11.1 kD) (2C514) (LOC374960), mRNA | | BG111067 | Hs. 343588 |
| 355 | BM365207 | 0.2151 | 0.0129951 | 0.29938 | chromosome 9 open reading frame 58 | C9orf58 | AA349673 | Hs. 4944 |
| 356 | BM366035 | 0.8475 | 0.0126785 | 0.29938 | ATP synthase, H+ transporting, mitochondrial F0 complex, subunit e | ATP5I | AA301789 | Hs. 85539 |
| 357 | BM366605 | 2.7408 | 0.0127858 | 0.29938 | ATP synthase, H+ transporting, mitochondrial F0 complex, subunit e | ATP5I | AA301789 | Hs. 85539 |

TABLE II

List of differentially expressed genes in liver that predict PTA for milk production

| SEQ ID NO: | GenBank ID (cattle) | Fold Change | Raw_P | FDR-adj. P | Gene Name | Gene Symbol | GenBank ID Best Hit | Unigene |
|---|---|---|---|---|---|---|---|---|
| 358 | AW464111 | 0.5685 | 0 | 1.32E−07 | | | AAM50023.1 | |
| 359 | AW464166 | 0.3883 | 3.00E−10 | 7.67E−07 | histone 1, H1d | HIST1H1D | NM_005320 | Hs. 136857 |
| 360 | BF045977 | 0.5291 | 4.05E−06 | 0.007977 | epithelial V-like antigen 1 | EVA1 | AF275945 | |
| 361 | BF040267 | 0.5683 | 0.0001496 | 0.220858 | poly(A) binding protein, cytoplasmic 4 (inducible form) | PABPC4 | BQ422891 | Hs. 169900 |
| 362 | BP230002B10 G5 | 0.7223 | 0.0001969 | 0.232606 | ribosomal protein L31 | RPL31 | BQ028654 | Hs. 375921 |
| 363 | BF044279 | 0.7894 | 0.0002679 | 0.263701 | hypothetical protein FLJ13188 | FLJ13188 | BC023577 | Hs. 11859 |
| 364 | AW466058 | 4.1302 | 0.0004149 | 0.350087 | CD14 antigen | CD14 | BG002906 | Hs. 75627 |
| 365 | BF042062 | 4.1572 | 0.0005552 | 0.375487 | solute carrier family 40 (iron-regulated transporter), member 1 | SLC40A1 | AI138761 | Hs. 409875 |
| 366 | AW464065 | 0.6322 | 0.0005722 | 0.375487 | serine/arginine repetitive matrix 2 | SRRM2 | AB002322 | Hs. 433343 |
| 367 | AW464444 | 0.6123 | 0.0006706 | 0.39608 | hypothetical transmembrane protein SBBI54 | SBBI54 | BM010343 | Hs. 116708 |

TABLE III

List of differentially expressed genes in blood and liver that predict PTA for milk production

| SEQ ID NO: | GenBank ID | Contrast Blood | Raw_P Blood | Contrast Liver | Raw_P Liver | Gene Name | Gene Symbol | GenBank ID Best hit | UniGene |
|---|---|---|---|---|---|---|---|---|---|
| 368 | AW461405 | -0.1525 | 0.0542 | -0.3213 | 0.0727 | core promoter element binding protein | COPEB | BU151389 | Hs. 285313 |
| 369 | AW461482 | -0.1409 | 0.0884 | -0.2659 | 0.0171 | low density lipoprotein receptor-related protein 10 | LRP10 | CA488630 | Hs. 28368 |
| 370 | AW461511 | -0.2193 | 0.0495 | -0.2481 | 0.0272 | ubiquitin-conjugating enzyme E2L 3 | UBE2L3 | BU625673 | Hs. 108104 |
| 80 | AW461513 | -0.3904 | 0.0012 | -0.1598 | 0.0968 | Transcribed sequences | | AW461513 | Bt. 12230 |
| 319 | AW461535 | -0.2651 | 0.0132 | -0.2119 | 0.0112 | ribonuclease/angiogenin inhibitor | RNH | BX387666 | Hs. 130958 |
| 371 | AW461572 | -0.1757 | 0.0300 | -0.1998 | 0.0632 | CCAAT/enhancer binding protein (C/EBP), beta | CEBPB | BX417468 | Hs. 99029 |
| 372 | AW461591 | 0.285 | 0.0597 | 0.2631 | 0.0204 | Transcribed sequence with strong similarity to protein prf: 2102256A (H. sapiens) | | AW461591 | Bt. 6019 |
| 373 | AW461600 | 0.3389 | 0.0942 | 0.3447 | 0.0371 | | | | AW461600 |
| 173 | AW461640 | -0.3487 | 0.0041 | -0.3797 | 0.0086 | eukaryotic translation termination factor 1 | ETF1 | AA812738 | Hs. 77324 |
| 374 | AW461650 | -1.4783 | 0.0346 | -0.8129 | 0.0172 | transgelin | TAGLN | D17409 | Hs. 410977 |
| 375 | AW461778 | 0.259 | 0.0943 | 0.5802 | 0.0703 | wingless-type MMTV integration site family, member 6 | WNT6 | NM_006522 | Hs. 29764 |
| 308 | AW461912 | -0.3206 | 0.0116 | -0.3695 | 0.0441 | insulin-like growth factor binding protein 7 | IGFBP7 | BC017201 | Hs. 435795 |
| 29 | AW461980 | -0.3867 | 0.0002 | -0.2313 | 0.0689 | likely ortholog of mouse hypoxia induced gene 1 | HIG1 | BG700494 | Hs. 7917 |
| 321 | AW461982 | 0.3127 | 0.0121 | 0.4021 | 0.0574 | insulin-like growth factor binding protein 3 | IGFBP3 | AW605051 | Hs. 450230 |
| 376 | AW462000 | -0.4442 | 0.0867 | -0.3556 | 0.0237 | CD164 antigen, sialomucin | CD164 | BC040317 | Hs. 43910 |
| 100 | AW462175 | -0.561 | 0.0016 | 0.8753 | 0.0084 | peroxisomal D3,D2-enoyl-CoA isomerase | PECI | BG400978 | Hs. 15250 |
| 377 | AW462221 | 0.668 | 0.0163 | 0.5385 | 0.0508 | Mus musculus adult male medulla oblongata cDNA, RIKEN full-length enriched library, clone: 6330410L21 protein ref: NP_116212.1 (H. sapiens) | | AK031828 | Mm. 252481 |
| 378 | AW462277 | -0.2909 | 0.0643 | -0.1792 | 0.0336 | Transcribed sequence with moderate similarity to protein ref: NP_116212.1 (H. sapiens) | | CF764638 | Bt. 5043 |
| 192 | AW462519 | -0.3685 | 0.0050 | -0.2515 | 0.0686 | choline kinase-like | CHKL | BU568477 | Hs. 439777 |
| 324 | AW462702 | -0.2942 | 0.0130 | -0.213 | 0.0817 | phosphatidylinositol-4-phosphate 5-kinase, type II, | PIP5K2C | AK075553 | Hs. 144502 |
| 379 | AW463060 | -0.185 | 0.0654 | 0.2311 | 0.0498 | calpastatin | CAST | BG208205 | Hs. 440961 |
| 380 | AW463121 | -0.2674 | 0.0332 | -0.2756 | 0.0761 | CD151 antigen | CD151 | BU528765 | Hs. 512867 |
| 381 | AW463263 | 0.4021 | 0.0329 | 0.1067 | 0.0814 | MAD, mothers against decapentaplegic homolog 6 (Drosophila) | MADH6 | AF043640 | Hs. 153863 |
| 382 | AW463937 | 0.525 | 0.0696 | 0.3736 | 0.0217 | Transcribed sequences | | CB452876 | Bt. 18990 |
| 286 | AW464067 | -0.3792 | 0.0101 | -0.3797 | 0.0694 | bromodomain containing 1 | BRD1 | BU431018 | Hs. 370880 |
| 265 | AW464094 | -0.2674 | 0.0090 | -0.2342 | 0.0342 | programmed cell death 6 interacting protein | PDCD6IP | CA748765 | Hs. 9663 |
| 383 | AW464391 | 0.377 | 0.0777 | 0.3149 | 0.0394 | programmed cell death 7 | PDCD7 | NM_005707 | Hs. 143253 |
| 384 | AW465097 | 0.1522 | 0.0646 | 0.2588 | 0.0372 | chromosome 13 open reading frame 12 | C13orf12 | BI463840 | Hs. 268742 |
| 385 | AW465151 | -0.2231 | 0.0242 | 0.2027 | 0.0790 | | | NT_011630.14 | |
| 386 | AW465276 | 0.4732 | 0.0463 | 0.2469 | 0.0792 | eukaryotic translation initiation factor 2B, subunit 2 | EIF2B2 | AF035280 | Hs. 497429 |
| 387 | AW465299 | -0.229 | 0.0668 | 0.3145 | 0.0065 | delta-like 1 homolog (Drosophila) | DLK1 | BX438936 | Hs. 169228 |

TABLE III-continued

List of differentially expressed genes in blood and liver that predict PTA for milk production

| SEQ ID NO: | GenBank ID | Contrast Blood | Raw_P Blood | Contrast Liver | Raw_P Liver | Gene Name | Gene Symbol | GenBank ID Best hit | UniGene |
|---|---|---|---|---|---|---|---|---|---|
| 388 | AW465351 | −0.3094 | 0.0484 | −0.3639 | 0.0849 | dynactin 6 | DCTN6 | D84145 | Hs. 158427 |
| 389 | AW465482 | −0.2549 | 0.0206 | −0.2398 | 0.0320 | sphingosine kinase 2 | SPHK2 | BU542495 | Hs. 444484 |
| 390 | AW465514 | −0.2266 | 0.0584 | −0.3396 | 0.0050 | coatomer protein complex, subunit epsilon | COPE | CA489097 | Hs. 10326 |
| 391 | AW465560 | −1.3432 | 0.0395 | −0.3041 | 0.0682 | collagen, type IV, alpha 1 | COL4A1 | X03963 | Hs. 437173 |
| 392 | AW465567 | 0.212 | 0.0910 | −0.2997 | 0.0866 | B-cell receptor-associated protein 31 | BCAP31 | BM843607 | Hs. 381232 |
| 271 | AW465653 | −0.3354 | 0.0094 | −0.2781 | 0.0610 | transcription factor, RNA polymerase 1 | UBTF | BQ640761 | Hs. 89781 |
| 138 | AW465666 | −0.6116 | 0.0027 | −0.1812 | 0.0502 | protein tyrosine phosphatase-like (proline instead of catalytic arginine), member b | PTPLB | AK074605 | Hs. 5957 |
| 260 | AW465703 | −0.2604 | 0.0086 | 0.366 | 0.0860 | Transcribed sequences | | AW465703 | Bt. 9668 |
| 393 | AW465831 | −0.1632 | 0.0760 | −0.2589 | 0.0435 | transmembrane protein 4 | TMEM4 | BX406238 | Hs. 8752 |
| 394 | AW466194 | 0.4396 | 0.0889 | 0.367 | 0.0645 | integrin, alpha 3 (antigen CD49C, alpha 3 subunit of VLA-3 receptor) | ITGA3 | BC015344 | Hs. 265829 |
| 11 | BF039212 | −0.6029 | 0.0000 | −0.3867 | 0.0241 | asparaginyl-tRNA synthetase | NARS | AJ000334 | Hs. 427212 |
| 69 | BF041193 | −0.3333 | 0.0011 | −0.2739 | 0.0718 | translocase of outer mitochondrial membrane 22 homolog (yeast) | TOMM22 | BM554645 | Hs. 285005 |
| 395 | BF041753 | −0.4868 | 0.0478 | −0.2771 | 0.0633 | heat shock 60 kDa protein 1 (chaperonin) | HSPD1 | AI133536 | Hs. 79037 |
| 338 | BF041789 | −0.3145 | 0.0122 | −0.4083 | 0.0569 | serine palmitoyltransferase, long chain base subunit 2 | SPTLC2 | AB011098 | Hs. 59403 |
| 396 | BF042071 | −0.2126 | 0.0977 | 0.2389 | 0.0678 | DKFZP547E1010 protein | DKFZP547E1010 | AA314101 | Hs. 323817 |
| 297 | BF042477 | −0.4078 | 0.0105 | −0.214 | 0.0895 | eukaryotic translation initiation factor 5 | EIF5 | BC007728 | Hs. 433702 |
| 397 | BF043039 | 0.1179 | 0.0774 | −0.5652 | 0.0377 | chromosome 14 open reading frame 73 | C14orf73 | BU607548 | Hs. 37712 |
| 398 | BF043954 | −0.2387 | 0.0420 | 0.5434 | 0.0113 | histone deacetylase 7A | HDAC7A | BQ646129 | Hs. 200063 |
| 399 | BF044362 | −0.7126 | 0.0144 | 0.3266 | 0.0665 | similar to RIKEN cDNA 4931428D14 gene | MGC15407 | BI603780 | Hs. 23128 |
| 400 | BF044484 | 0.2955 | 0.0732 | −0.3049 | 0.0166 | | | | |
| 401 | BF044941 | −0.3714 | 0.0347 | 0.2297 | 0.0145 | XTP3-transactivated protein B | XTP3TPB | BU929539 | Hs. 438836 |
| 402 | BF440189 | 0.328 | 0.0491 | −0.1995 | 0.0208 | replication factor C (activator 1) 4, 37 kDa | RFC4 | BM979151 | Hs. 35120 |
| 58 | BF440195 | 0.7274 | 0.0008 | 0.2697 | 0.0765 | | | | |
| 403 | BF440274 | 0.1769 | 0.0878 | 0.2317 | 0.0270 | kin of IRRE like (Drosophila) | KIRREL | CA446859 | Hs. 375003 |
| 301 | BF440363 | −0.442 | 0.0108 | −0.1713 | 0.0943 | proteasome (prosome, macropain) subunit, alpha type, 3 | PSMA3 | CA431411 | Hs. 246240 |
| 404 | BF440607 | 0.2531 | 0.0349 | 0.2189 | 0.0341 | CD81 antigen (target of antiproliferative antibody 1) | CD81 | BM920185 | Hs. 54457 |
| 405 | BM362313 | −0.4693 | 0.0620 | −0.4666 | 0.0475 | polymerase (RNA) II (DNA directed) polypeptide B, | POLR2B | AF055028 | Hs. 149353 |
| 406 | BM364049 | −0.382 | 0.0275 | −0.5626 | 0.0366 | dynein, cytoplasmic, light polypeptide 2A | DNCL2A | BU932718 | Hs. 100002 |
| 79 | BM366522 | −0.5962 | 0.0011 | −0.4707 | 0.0191 | malate dehydrogenase 2, NAD (mitochondrial) | MDH2 | BX460531 | Hs. 405860 |
| 407 | BM366788 | −0.2606 | 0.0614 | 0.4313 | 0.0448 | poly(A) binding protein, nuclear 1 | PABPN1 | BU682740 | Hs. 117176 |
| 408 | BP2000602103 | 0.3438 | 0.0164 | −0.2543 | 0.0106 | calmodulin 2 (phosphorylase kinase, delta) | CALM2 | CA441246 | Hs. 425808 |

TABLE IV

Genetic estimates and pedigree information of selected animals used for microarray experiments

| No. | Classification | Barn/Ctrl[2] | Identification | Registration | PTA Milk[1] | PTA Protein | PTA Fat |
|---|---|---|---|---|---|---|---|
| 1 | Low | #7298 | Illini Mason Susan | #60046145 | −68 | 9 | 5 |
| 2 | | #7321 | Illini Leader Lassie | #60046168 | −151 | 4 | −2 |
| 3 | | #7350 | Illini Leader EDI-TW | #60274143 | −203 | 2 | −15 |
| 4 | | #7351 | Illini Leader Edeth TW-TW | #60274144 | −203 | 2 | −15 |
| 5 | | #7355 | Illini Premier Karen | #60274148 | −17 | −2 | 11 |
| 6 | High | #7305 | Illini Marty Glee | #60046152 | 1178 | 34 | 18 |
| 7 | | #7344 | Illini Convincer Suzanne | #60274137 | 1416 | 33 | 42 |
| 8 | | #7361 | Illini Storm Glee | #60274154 | 1108 | 34 | 48 |
| 9 | | #7367 | Illini Emerson Della | #60274160 | 953 | 27 | 31 |
| 10 | | #7368 | Illini Emerson Klara | #60274161 | 1111 | 33 | 35 |
| 11 | Low | #7497 | Illini Progress Edith | #60274290 | −219 | −9 | 15M |
| 12 | | #7556 | Illini Roman Tillie | #60712800 | 304 | 6 | 16 |
| 13 | | #7584 | Illini Outside Milly | #60712828 | 507 | 12 | 24M |
| 14 | | #7589 | Illini Estimate Leota | #60712833 | 194 | 17 | 41M |
| 15 | | #7590 | Illini Luck Tillie | #60712834 | 115 | 12 | 26M |
| 16 | High | #7499 | Illini Marshall Suzanne | #60274292 | 1987 | 49 | 34M |
| 17 | | #7518 | Illini Inquirer Romance | #60274311 | 1536 | 35 | 40M |
| 18 | | #7536 | Illini Kino Joyce | #60712780 | 1569 | 30 | 27M |
| 19 | | #7553 | Illini Emerson Kara | #60712797 | 1257 | 44 | 38 |
| 20 | | #7554 | Illini Jasper Suzanne | #60712798 | 1240 | 33 | 54 |

[1]Herds were selected based on PTA Milk values. Values of PTA protein and fat are cited for reference.
[2]Age - 7298, 7305-13 month; 7321, 7344-11 month; 7350, 7361, 7351, 7367, 7355, 7368-11 month; 7367, 7368-10 month.

PUBLICATIONS CITED

The following documents are incorporated by reference to the extent they relate to the materials and methods of the present disclosure.

Ashburner et al. (2000) Gene ontology: tool for the unification of biology. The Gene Ontology Consortium. *Nature Genetics* 25(1):25-9.

Band et al. (2000) An ordered comparative map of the cattle and human genomes. *Genome Research* 10(9):1359-68.

Band, et al. (2002) A 3,800 gene microarray for cattle functional genomics: comparison of gene expression in spleen, placenta, and brain. *Animal Biotechnology* 13(i): 163-72.

Benjamini, Y. and Hochberg, Y. (1995), "Controlling the False Discovery Rate: a practical and powerful approach to multiple testing," Journal of the Royal Statistical Society. B, 57, 289-300.

Brown and Botstein (1999) Exploring the new world of the genome with DNA microarrays. *Nature Genetics* 21, 33-37.

Cook, R. D. (1977) Detection of influential observations in linear regression. Technometrics, 19, 15-18.

Diehl et al., (2000) Manufacturing DNA microarrays of high spot homogeneity and reduced background signal. *Nucleic Acids Research* 29(7).

Eisen et al. (1998) Cluster analysis and display of genome—wide expression patters. PNAS (USA) 95: 14863-14868.

Hegde et al. (2000) A concise guide to cDNA microarray analysis. *Biotechniques* 29(3):548-50.

Huang and Madan (1999) CAP3: A DNA sequence assembly program. *Genome Research* 9(9):868-77.

Klecka, W. R. (1980), Discriminant Analysis, Sage University Paper Series on Quantitative Applications in the Social Sciences, Series No. 07-019, Beverly Hills: Sage Publications.

Smith and Green (1999) (Unpublished) Repeatmasker, http://ftp.genome.washington.edu/RM/RepeatMasker.html.

U.S. Pat. No. 6,548,740.

http://gowhite.ans.msu.edu.

Yao, J. et al. (2001) Generation of EST and cDNA microarray resources for the study of bovine immunobiology. *Acta Vet. Scand.* 42(3): 391-405.

We claim:

1. A method of determining whether cattle are genetically elite for milk production, the method comprising:
    i) determining a gene expression profile of cattle using as a plurality of genes SEQ ID NOS: 334, 279, 79, 156, 23, 353, 40, 73, 306, 120, 107, 149, 119, 179, 288, 32, 95, 221, 211, 152, 312, 244, 36, 105, 253 and 164;
    ii) comparing the gene expression profile of the cattle with a Gene Expression Index constructed by
        (a) selecting cattle with at least two specific levels of milk production;
        (b) selecting a plurality of genes for which expression can be determined;
        (c) comparing expression levels of the plurality of genes in cattle at each of the two levels of milk production; and
        (d) determining a set of genes predictive of high milk production or with a Reference Expression Profile constructed by
        (a) selecting an optimal subset of genes from the Gene Expression Index that accounts for a significant fraction of the variation in milk production;
        (b) determining a gene expression profile of the cattle for the optimal subset; and
        (c) designating the gene expression profile as a Reference Expression profile for high milk production; and
    (iii) designating the cattle as elite for milk production if their gene expression profile is similar to the Gene Expression Index or the Reference Expression Profile.

2. A method for selecting male or female cattle as genetically elite for milk production, the method comprising:
    i) constructing a Gene Expression Index comprising gene expression values for a plurality of gene sequences set forth in SEQ ID NOS: 334, 279, 79, 156, 23, 353, 40, 73, 306, 120, 107, 149, 119, 179, 288, 32, 95, 221, 211, 152, 312, 244, 36, 105, 253 and 164, wherein the Gene Expression Index is obtained from cattle having high milk production;
    ii) determining a gene expression profile for the cattle to be tested, wherein the gene expression profile comprises gene expression values for the gene sequences set forth in SEQ ID NOS: 334, 279, 79, 156, 23, 353, 40, 73, 306, 120, 107, 149, 119, 179, 288, 32, 95, 221, 211, 152, 312, 244, 36, 105, 253 and 164; and
    iii) designating the male or female cattle as genetically elite for milk production if their gene expression profiles and the gene expression values in the Gene Expression Index are similar.

3. A method for selecting male or female cattle as genetically elite for milk production, the method comprising:
    i) creating a Reference Expression Profile comprising gene expression values for a plurality of genes set forth in SEQ ID NOS: 334, 279, 79, 156, 23, 353, 40, 73, 306, 120, 107, 149, 119, 179, 288, 32, 95, 221, 211, 152, 312, 244, 36, 105, 253 and 164, wherein the Reference Expression Profile is predictive of cattle having high milk production;
    ii) determining a gene expression profile for the cattle to be tested, wherein the gene expression profile comprises gene expression values for the genes set forth in SEQ ID NOS: 334, 279, 79, 156, 23, 353, 40, 73, 306, 120, 107, 149, 119, 179, 288, 32, 95, 221, 211, 152, 312, 244, 36, 105, 253 and 164; and
    iii) designating the male or female cattle as genetically elite for milk production if their gene expression profiles and the gene expression values in the Reference Expression Profile are similar.

4. The method of claim 2, wherein the gene expression profile is obtained by a microarray analysis.

5. The method of claim 2, wherein the gene expression profile is obtained by a quantitative polymerase chain reaction analysis.

6. A method for predicting milk production in a candidate cow, the method comprising:
    i) obtaining a candidate gene expression profile of a candidate cow for a plurality of genes set forth in SEQ ID NOS: 334, 279, 79, 156, 23, 353, 40, 73, 306, 120, 107, 149, 119, 179, 288, 32, 95, 221, 211, 152, 312, 244, 36, 105, 253 and 164;
    ii) comparing the candidate gene expression profile to a Gene Expression Index from cows with known milk production levels; and
    iii) predicting milk production in the candidate cow if the gene expression profile of the candidate cow and the Gene Expression Index are similar.

7. A method for predicting milk production in the daughters of a candidate bull, the method comprising:

i) obtaining a candidate gene expression profile of the candidate bull for a plurality of genes set forth in SEQ ID NOS: 334, 279, 79, 156, 23, 353, 40, 73, 306, 120, 107, 149, 119, 179, 288, 32, 95, 221, 211, 152, 312, 244, 36, 105, 253 and 164;

ii) comparing the candidate gene expression profile to a Gene Expression Index from bulls whose daughters have known milk production levels; and iii) predicting milk production in the daughters of the candidate bull if the gene expression profile of the bull and the Gene Expression Index are similar.

* * * * *